US010668150B2

(12) United States Patent
Cohen et al.

(10) Patent No.: US 10,668,150 B2
(45) Date of Patent: Jun. 2, 2020

(54) IL33 FORM, MUTATED FORMS OF IL33, ANTIBODIES, ASSAYS AND METHODS OF USING THE SAME

(71) Applicant: MedImmune Limited, Cambridge (GB)

(72) Inventors: Emma S. Cohen, Cambridge (GB); David C. Lowe, Cambridge (GB); Robin Butler, Cambridge (GB); Ian C. Scott, Cambridge (GB); Katherine A. Vousden, Cambridge (GB); Martin D. Strain, Cambridge (GB); Sara Carmen, Cambridge (GB); Elizabeth H. England, Cambridge (GB); Benjamin P. Kemp, Cambridge (GB); David G. Rees, Cambridge (GB); Catherine L. Overed-Sayer, Cambridge (GB); Tomas M. Mustelin, Gaithersburg, MD (US); Matthew Sleeman, Cambridge (GB); Kirsty Houslay, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 15/562,228

(22) PCT Filed: Mar. 30, 2016

(86) PCT No.: PCT/EP2016/056973
§ 371 (c)(1),
(2) Date: Sep. 27, 2017

(87) PCT Pub. No.: WO2016/156440
PCT Pub. Date: Oct. 6, 2016

(65) Prior Publication Data
US 2018/0207265 A1    Jul. 26, 2018

Related U.S. Application Data

(60) Provisional application No. 62/140,913, filed on Mar. 31, 2015.

(51) Int. Cl.
*A61K 39/395* (2006.01)
*C07K 16/24* (2006.01)
*A61P 11/06* (2006.01)
*A01K 67/027* (2006.01)
*C07K 14/54* (2006.01)
*A61K 39/00* (2006.01)

(52) U.S. Cl.
CPC ...... *A61K 39/3955* (2013.01); *A01K 67/0278* (2013.01); *A61P 11/06* (2018.01); *C07K 14/54* (2013.01); *C07K 16/244* (2013.01); *A01K 2217/072* (2013.01); *A01K 2227/105* (2013.01); *A01K 2267/03* (2013.01); *A61K 2039/505* (2013.01); *C07K 2317/21* (2013.01); *C07K 2317/33* (2013.01); *C07K 2317/34* (2013.01); *C07K 2317/565* (2013.01); *C07K 2317/567* (2013.01); *C07K 2317/622* (2013.01); *C07K 2317/76* (2013.01); *C07K 2317/92* (2013.01); *C07K 2319/30* (2013.01)

(58) Field of Classification Search
None
See application file for complete search history.

(56) References Cited

FOREIGN PATENT DOCUMENTS

WO    WO 2014/164959 A2    9/2014

OTHER PUBLICATIONS

Goel et al. The Journal of Immunology, 2004; 173(12):7358-7367.*
Edwards et al, Journal of Molecular Biology, 2003, vol. 334, pp. 103-118.*
Lloyd et al Protein Engineering, Design & Selection, 2009, vol. 22, No. 3, pp. 159-168.*
Brummell et al, Biochemistry; 1993; vol. 32, pp. 1180-1187.*
Kobayashi et al. Protein Engineering; 1999; vol. 12, pp. 879-844.*
Casset et al; Biochemical and Biophysical Research Communications, 2003; 307:198-205.*
Paul, Fundamental Immunology, 3rd Edition, 1993, pp. 292-295.*
Cohen, et al., "Oxidation of the alarmin IL-33 regulates ST2-dependent inflammation," Nature Communicatons, vol. 6, Sep. 14, 2015, p. 8327.

* cited by examiner

*Primary Examiner* — Bridget E Bunner
*Assistant Examiner* — Fozia Hamud

(57) ABSTRACT

The present invention provides isolated IL-33 proteins, active fragments thereof and antibodies, antigen binding fragments thereof, against IL-33 proteins. Also provided are methods of modulating cytokine activity, e.g., for the purpose of treating immune and inflammatory disorders.

13 Claims, 58 Drawing Sheets
Specification includes a Sequence Listing.

FIG. 1

% Specific Binding

|   | 1   | 2   | 3   | 4   | 5   | 6   | 7   | 8   | 9   | 10  | 11  | 12  |
|---|-----|-----|-----|-----|-----|-----|-----|-----|-----|-----|-----|-----|
| A | 108 | 108 | 98  | 98  | 102 | 100 | 101 | 104 | 101 | 107 | 96  | 98  |
| B | 109 | 102 | 96  | 81  | 91  | 100 | 97  | 98  | 104 | 101 | 102 | 102 |
| C | 100 | 105 | 96  | 99  | 106 | 106 | 97  | 97  | 107 | 107 | 102 | 100 |
| D | 105 | 107 | 109 | 107 | 104 | 106 | 100 | 105 | 102 | 98  | 100 | 0   |
| E | 107 | 101 | 108 | 91  | 110 | 108 | 112 | 105 | 104 | 107 | 99  | -0  |
| F | 108 | 105 | 104 | 96  | 100 | 106 | 101 | 107 | 98  | 105 | 99  | 0   |
| G | 98  | 106 | 105 | 102 | 105 | 105 | 100 | 104 | 96  | 97  | 105 | 132 |
| H | 102 | 104 | 114 | 108 | 104 | 110 | 102 | 100 | 107 | 100 | 107 | 132 |

Column 12: Rows A–C = Total binding; Rows D–F = Non-specific binding

Well B04 = IL330004

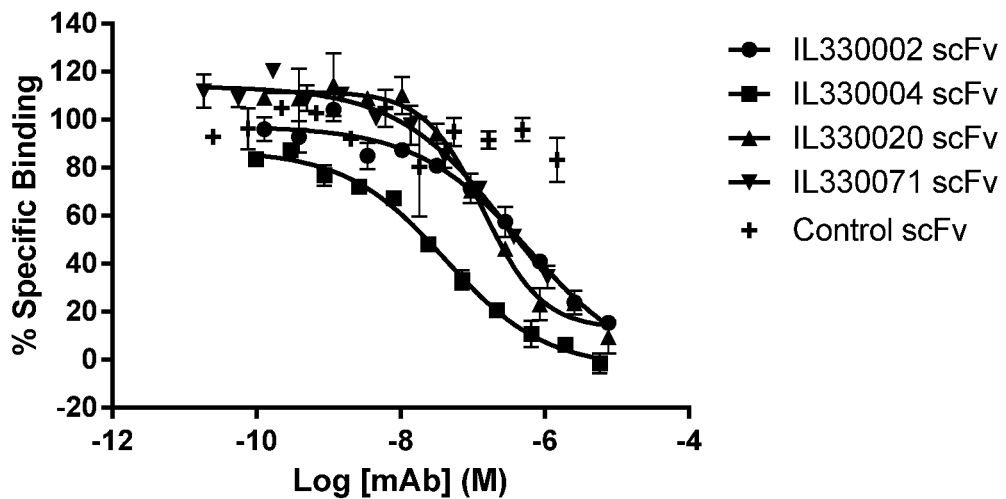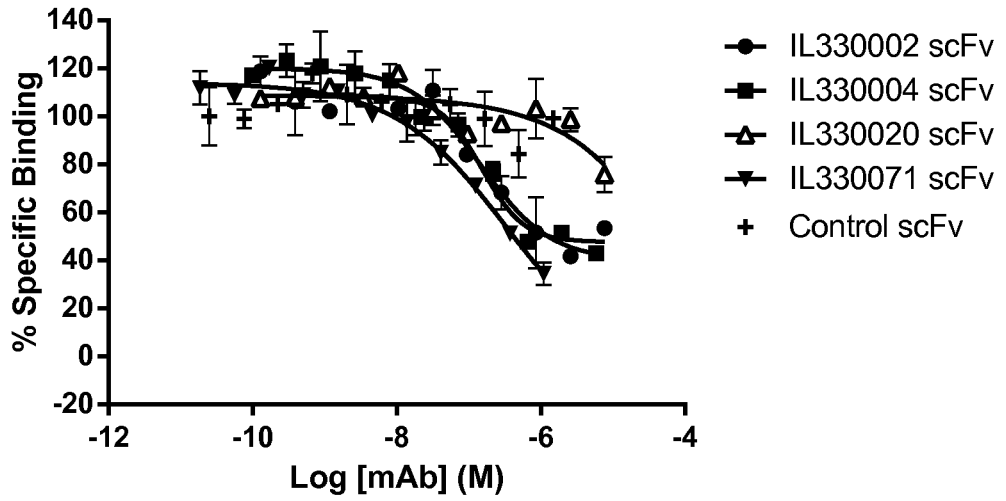
FIGURE 2

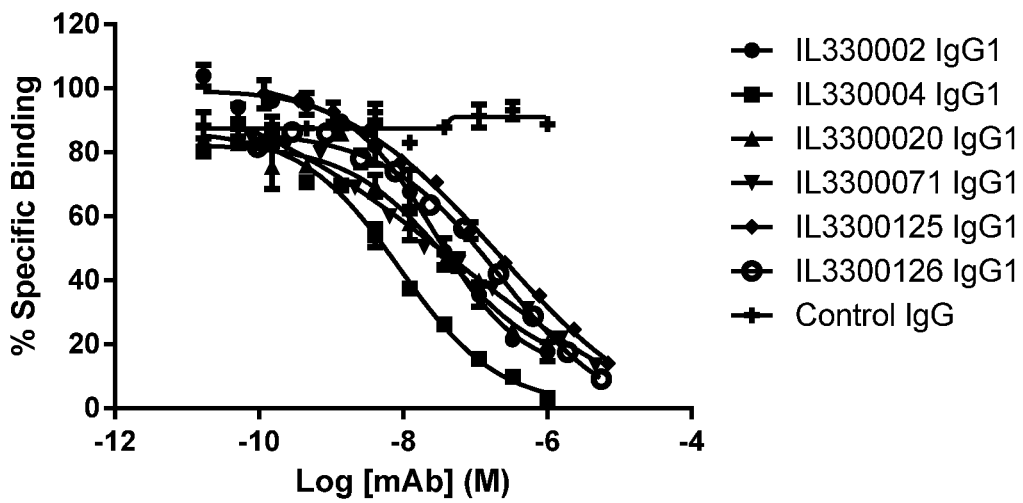
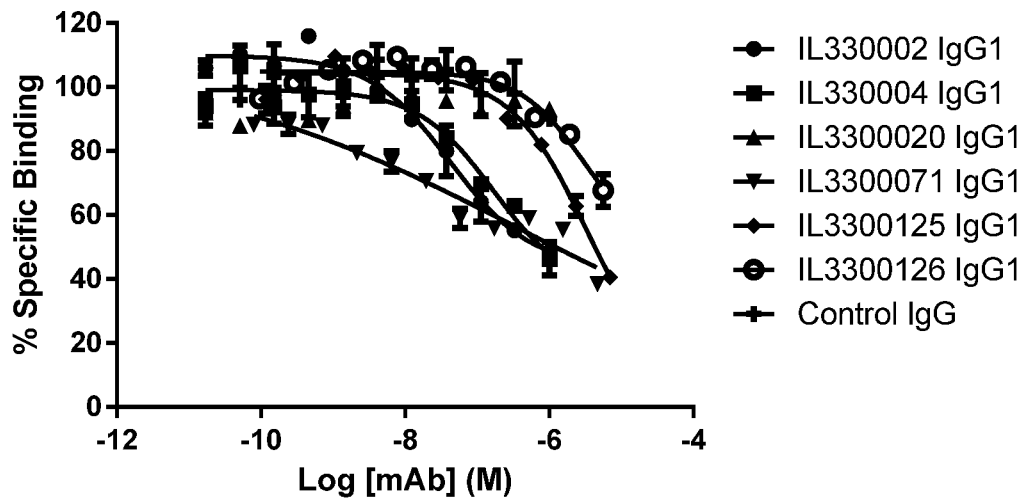
FIGURE 3

Human IL-33

|   | 1 | 2 | 3 | 4 | 5 | 6 | 7 | 8 | 9 | 10 | 11 | 12 |
|---|---|---|---|---|---|---|---|---|---|---|---|---|
| A | 0.059 | 0.046 | 0.041 | 0.042 | 0.046 | 0.043 | 0.045 | 0.046 | 0.047 | 0.056 | 0.054 | 1.246 |
| B | 0.056 | 0.042 | 0.039 | 0.045 | 0.046 | 0.049 | 0.045 | 0.047 | 0.048 | 0.048 | 0.043 | 0.921 |
| C | 0.045 | 0.041 | 0.041 | 1.27 | 0.044 | 0.044 | 0.043 | 0.069 | 0.044 | 0.041 | 0.042 | 0.044 |
| D | 0.051 | 0.039 | 0.038 | 0.039 | 0.039 | 0.041 | 0.04 | 0.04 | 0.041 | 0.04 | 0.043 | 0.033 |
| E | 0.042 | 0.039 | 0.038 | 0.039 | 0.039 | 0.038 | 0.038 | 0.039 | 0.038 | 0.038 | 0.042 | 0.038 |
| F | 0.05 | 0.039 | 0.038 | 0.045 | 0.039 | 0.039 | 0.04 | 0.041 | 0.039 | 0.039 | 0.263 | 0.035 |
| G | 0.037 | 0.04 | 0.04 | 0.04 | 0.04 | 0.039 | 0.04 | 0.043 | 0.04 | 0.042 | 0.052 | 0.037 |
| H | 0.051 | 0.052 | 0.046 | 0.053 | 0.049 | 0.048 | 0.048 | 0.051 | 0.041 | 0.05 | 0.07 | 0.04 |

Cyno IL-33 FH

|   | 1 | 2 | 3 | 4 | 5 | 6 | 7 | 8 | 9 | 10 | 11 | 12 |
|---|---|---|---|---|---|---|---|---|---|---|---|---|
| A | 0.072 | 0.059 | 0.061 | 0.081 | 0.048 | 0.041 | 0.038 | 0.041 | 0.044 | 0.041 | 0.044 | 0.148 |
| B | 0.072 | 0.094 | 0.071 | 0.055 | 0.053 | 0.046 | 0.057 | 0.042 | 0.045 | 0.041 | 0.041 | 0.115 |
| C | 0.074 | 0.098 | 0.076 | 1.193 | 0.08 | 0.042 | 0.041 | 0.066 | 0.1 | 0.062 | 0.045 | 0.064 |
| D | 0.054 | 0.06 | 0.061 | 0.051 | 0.048 | 0.043 | 0.05 | 0.056 | 0.06 | 0.052 | 0.043 | 0.067 |
| E | 0.087 | 0.067 | 0.059 | 0.065 | 0.045 | 0.063 | 0.095 | 0.039 | 0.073 | 0.043 | 0.061 | 0.072 |
| F | 0.072 | 0.065 | 0.085 | 0.064 | 0.065 | 0.058 | 0.058 | 0.075 | 0.05 | 0.057 | 0.276 | 0.058 |
| G | 0.068 | 0.054 | 0.074 | 0.065 | 0.049 | 0.045 | 0.052 | 0.042 | 0.059 | 0.04 | 0.073 | 0.092 |
| H | 0.117 | 0.065 | 0.064 | 0.057 | 0.058 | 0.069 | 0.063 | 0.059 | 0.06 | 0.061 | 0.058 | 0.056 |

Insulin

|   | 1 | 2 | 3 | 4 | 5 | 6 | 7 | 8 | 9 | 10 | 11 | 12 |
|---|---|---|---|---|---|---|---|---|---|---|---|---|
| A | 0.069 | 0.043 | 0.056 | 0.046 | 0.057 | 0.046 | 0.045 | 0.055 | 0.084 | 0.093 | 0.073 | 0.087 |
| B | 0.076 | 0.044 | 0.046 | 0.06 | 0.07 | 0.05 | 0.064 | 0.053 | 0.07 | 0.062 | 0.07 | 0.055 |
| C | 0.071 | 0.079 | 0.074 | 0.052 | 0.058 | 0.059 | 0.066 | 0.059 | 0.079 | 0.062 | 0.065 | 0.056 |
| D | 0.069 | 0.075 | 0.074 | 0.072 | 0.067 | 0.061 | 0.058 | 0.07 | 0.048 | 0.064 | 0.04 | 0.049 |
| E | 0.049 | 0.072 | 0.058 | 0.065 | 0.065 | 0.064 | 0.054 | 0.061 | 0.046 | 0.089 | 0.039 | 0.051 |
| F | 0.1 | 0.058 | 0.06 | 0.052 | 0.065 | 0.061 | 0.076 | 0.069 | 0.057 | 0.043 | 0.375 | 0.061 |
| G | 0.069 | 0.076 | 0.06 | 0.076 | 0.048 | 0.048 | 0.058 | 0.059 | 0.053 | 0.064 | 0.086 | 0.058 |
| H | 0.099 | 0.089 | 0.105 | 0.099 | 0.056 | 0.081 | 0.093 | 0.087 | 0.089 | 0.071 | 0.074 | 0.08 |

FIGURE 6

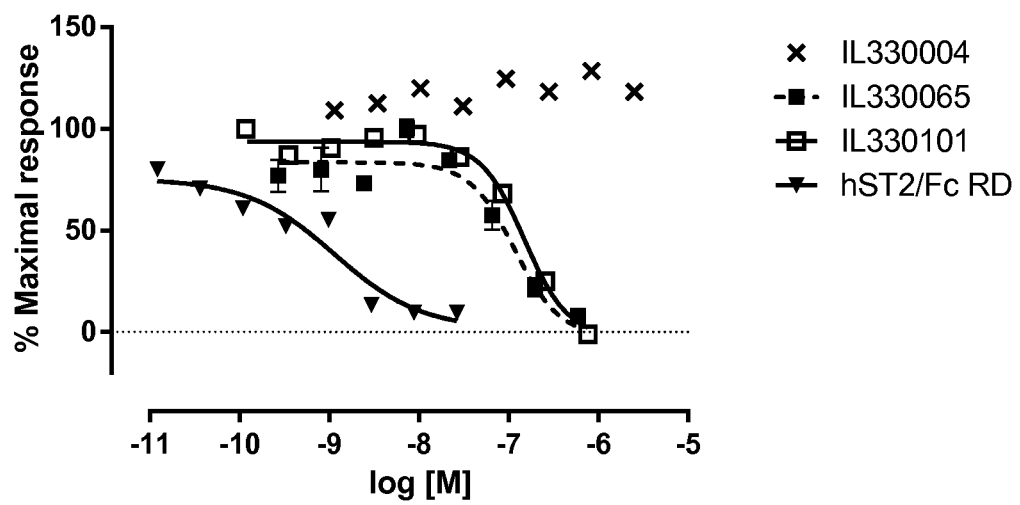
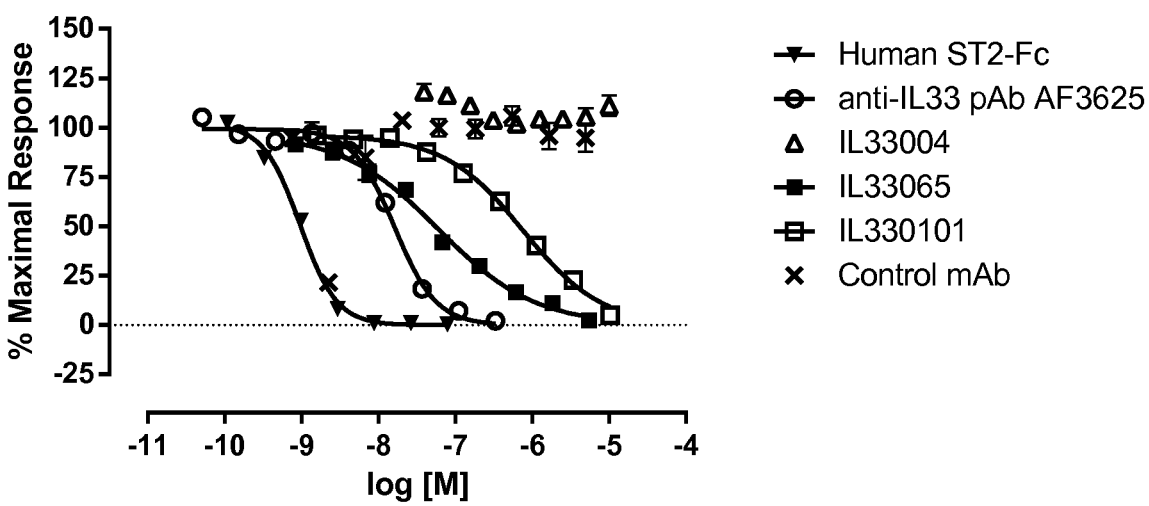
FIGURE 7 m = magic mark XP
a = mock transfected HEK-EBNA
b = FL HuIL33 transfected HEK-EBNA FL HuIL33 predicted MW = 30kDa
Caspase3 cleaved IL33 predicted 10kDa and 20kDa fragments

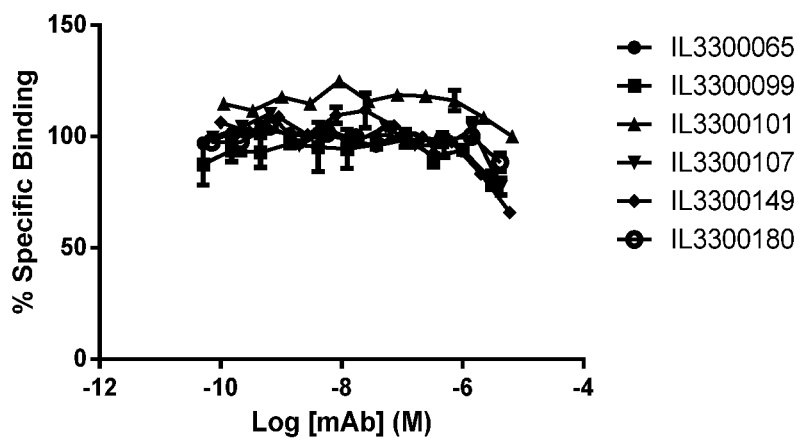
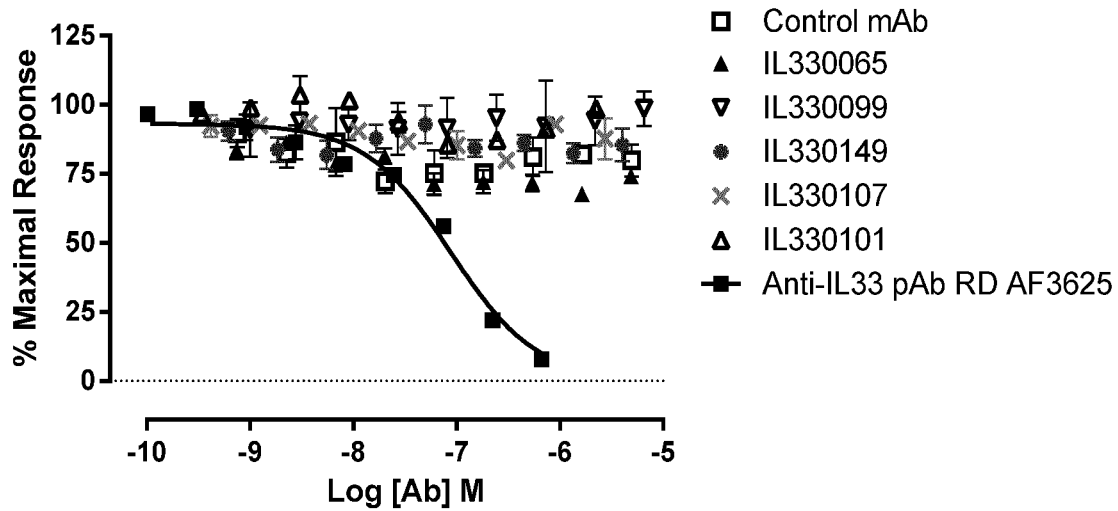
FIGURE 11

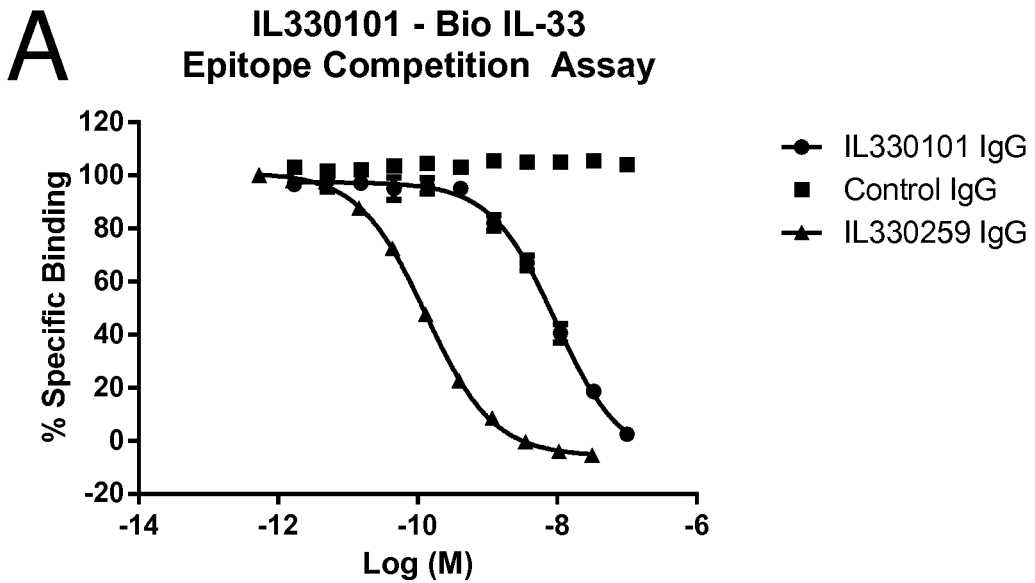
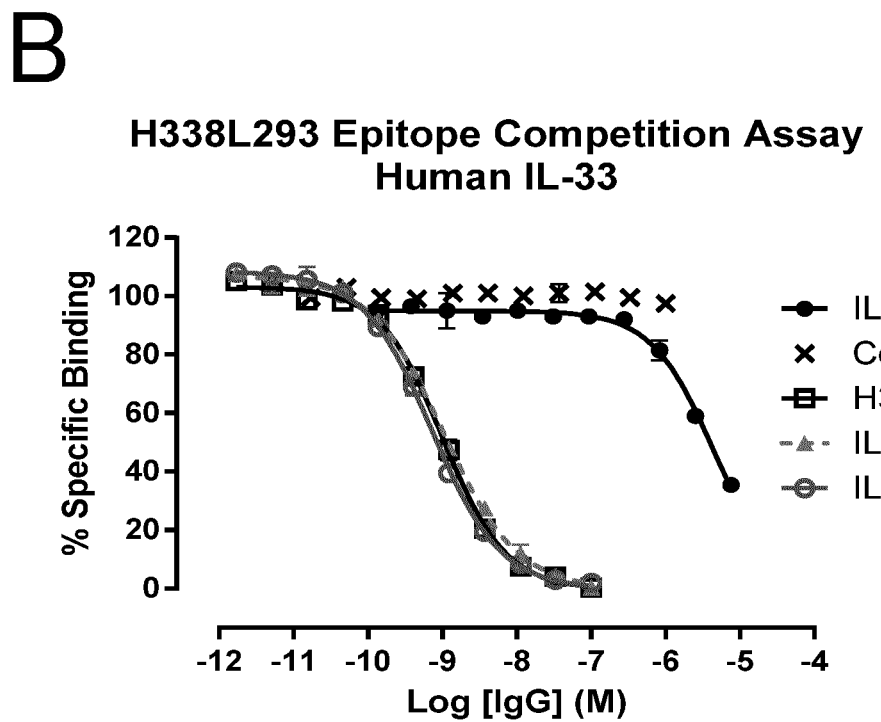
FIGURE 14

Preparation of oxidised IL-33 for mass-spec analysis
Untagged IL-33 (BK349)
18 hour incubation of IL-33 (300ug/ml) in 60% IMDM or PBS (37°C, 5% $CO_2$)
SEC of alternative IL-33 preps
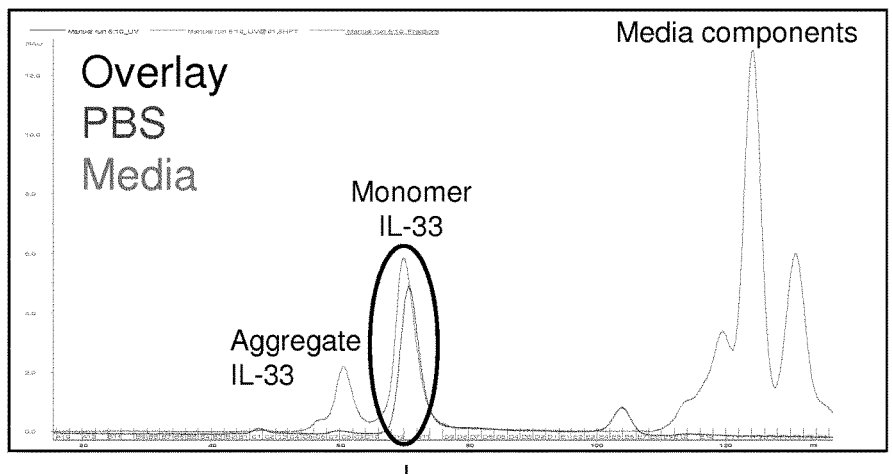
Mass spectrometry analysis
FIGURE 19

Mass Spec analysis – intact mass

FIG. 21A

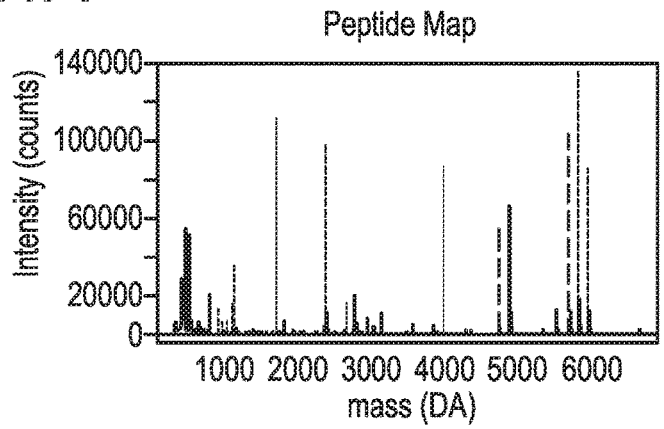

Peptide Map

FIG. 21B

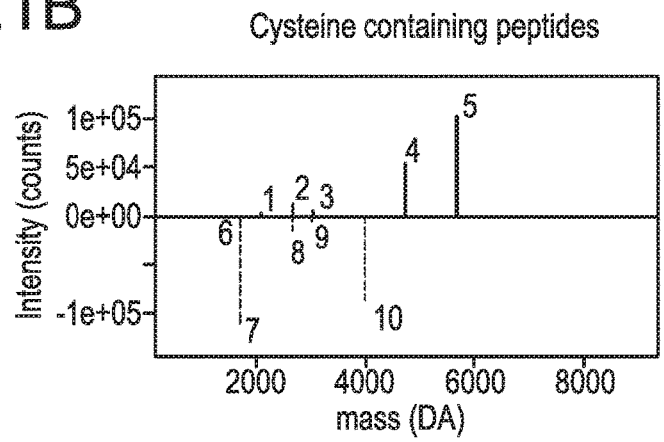

Cysteine containing peptides

FIG. 21C

| Peptides | Sequence | Cys oxidation status |
|---|---|---|
| | Non-reduced Lys-C peptide map | |
| SEQ ID NO:651–SEQ ID NO:652 | 1  $C^{208}$EK–VDSSENI$C^{259}$TENILFK | SS |
| SEQ ID NO:653 | 2  PLPDQAFFVLHNMHSN$C^{227}$VSFE$C^{232}$K | SS |
| SEQ ID NO:654–SEQ ID NO:655 | 3  [EHSVELHK][$C^{208}$EK]–VDSSENI$C^{259}$TENILFK | SS |
| SEQ ID NO:656–SEQ ID NO:657 | 4  [$C^{208}$EK][PLPDQAFFVLHNMHSN$C^{227}$VSFE$C^{232}$K]–VDSSENI$C^{259}$TENILFK | SS |
| SEQ ID NO:658–SEQ ID NO:659 | 5  [EHSVELHK][$C^{208}$EK][PLPDQAFFVLHNMHSN$C^{227}$VSFE$C^{232}$K]–VDSSENI$C^{259}$TENILFK | SS |
| | Reduced Lys-C peptide map | |
| SEQ ID NO:660 | 6  [EHSVELHK][$C^{208}$EK] | SH |
| SEQ ID NO:661 | 7  VDSSENI$C^{259}$TENILFK | SH |
| SEQ ID NO:662 | 8  PLPDQAFFVLHNMHSN$C^{227}$VSFE$C^{232}$K | SH |
| SEQ ID NO:663 | 9  [$C^{208}$EK][PLPDQAFFVLHNMHSN$C^{227}$VSFE$C^{232}$K] | SH |
| SEQ ID NO:664 | 10 [EHSVELHK] [$C^{208}$EK][PLPDQAFFVLHNMHSN$C^{227}$VSFE$C^{232}$K] | SH |

Reduced IL33 binding to ST2
Sensorgrams from 7.8nM to 0.24nM are
shown giving a $K_D$ of 0.2nM,
A
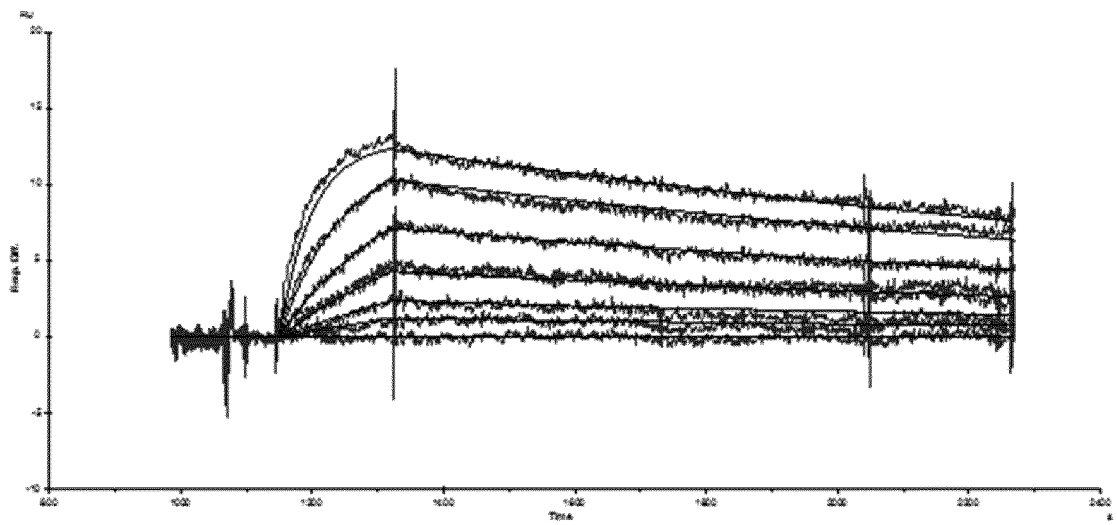
B
DSB IL33 binding to ST2
Sensorgrams from 500nM to 0.24nM
with no obvious binding
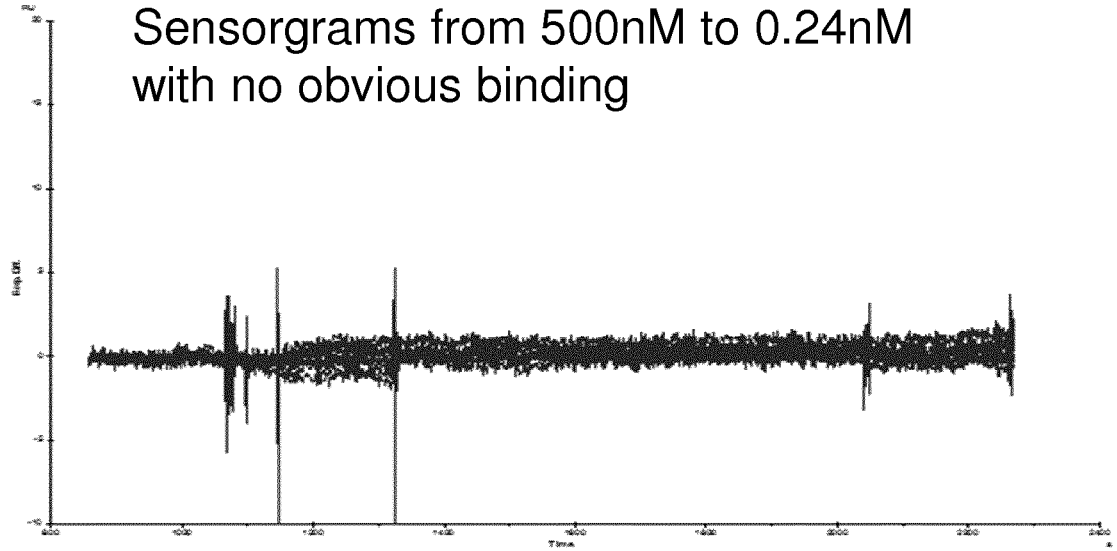
FIGURE 24

A
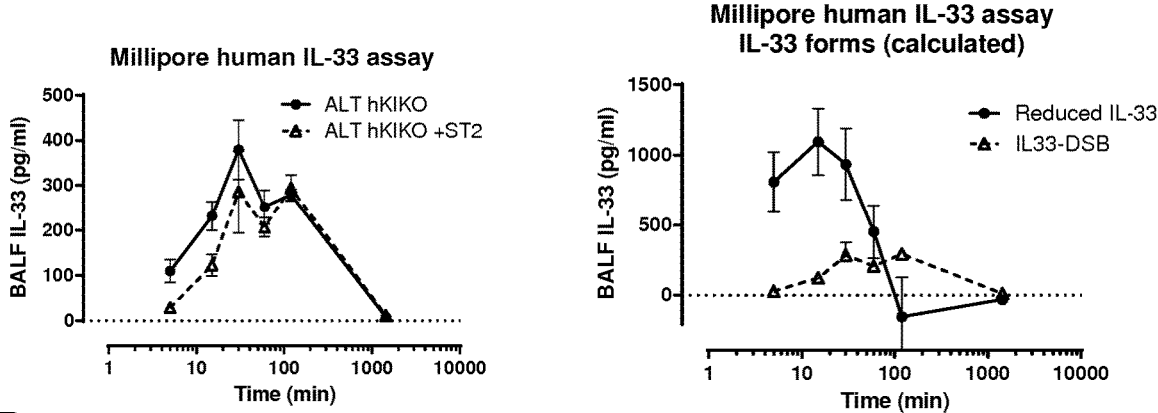
B
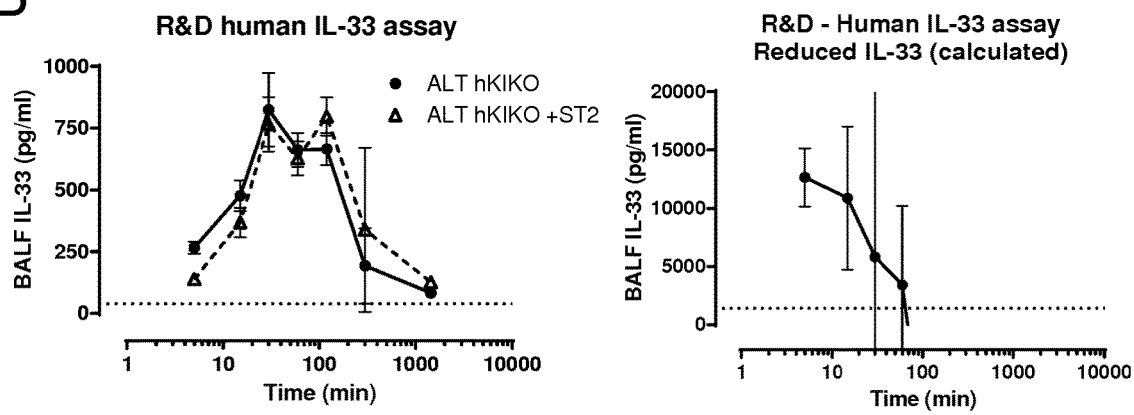
C
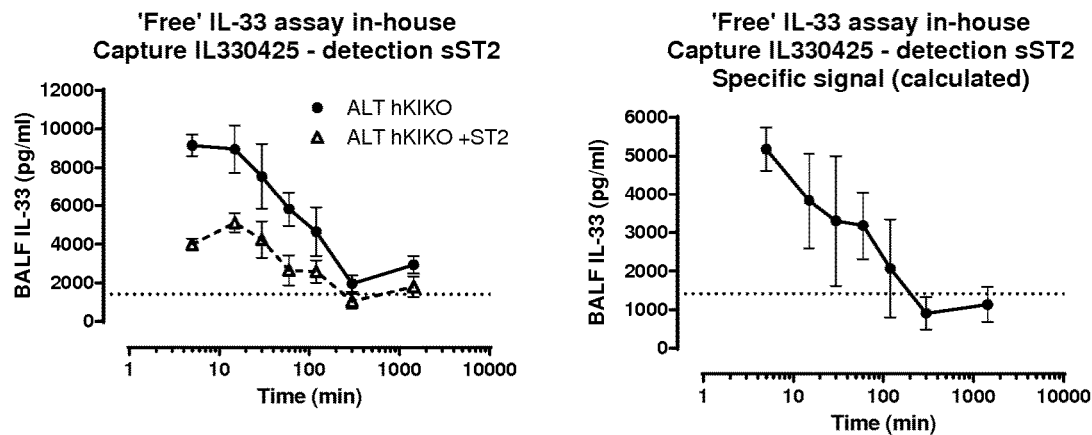
FIGURE 28

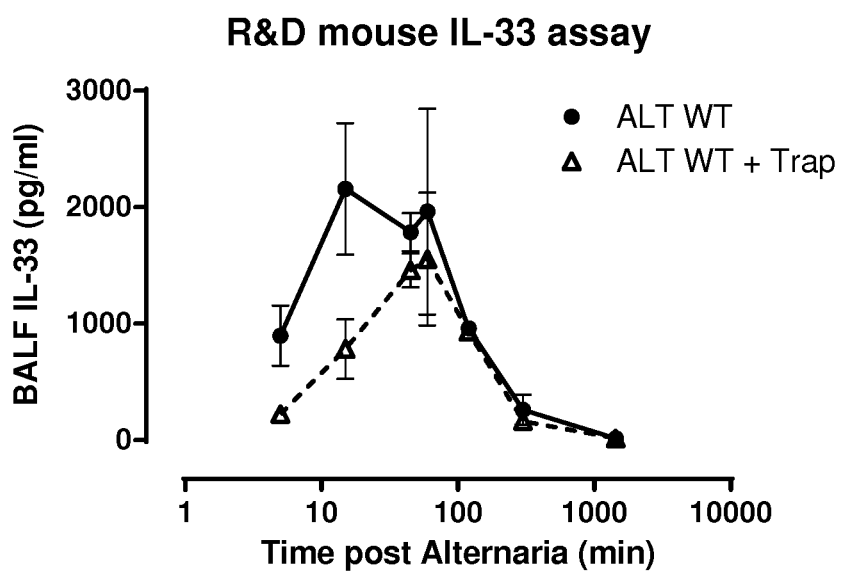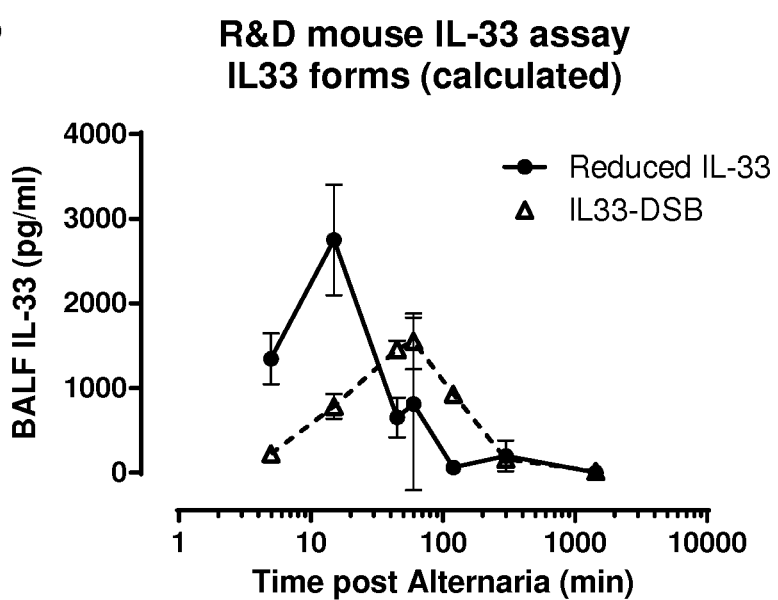
FIGURE 29

A  IL33-ST2 Binding Assay
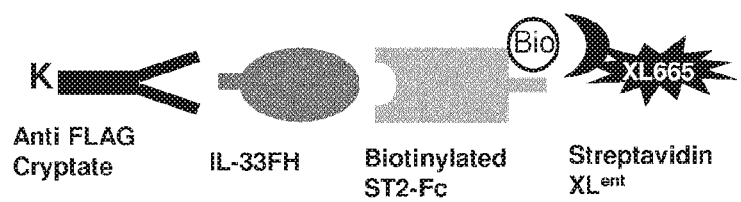
B
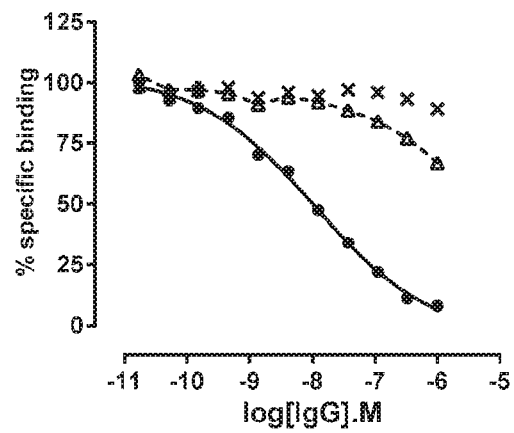
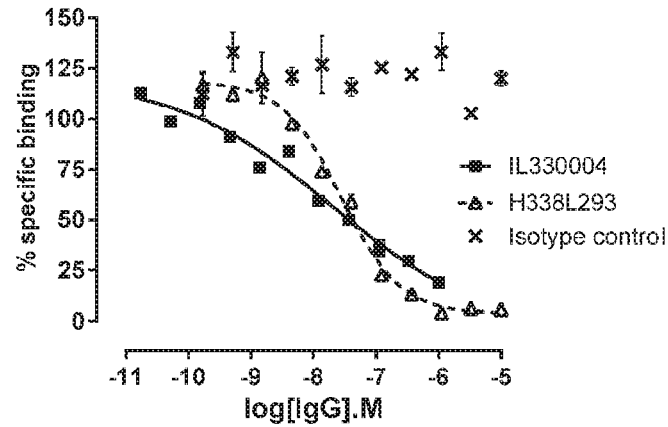
- IL330004
- H338L293
- × Isotype control
FIGURE 32

MALDI-TOF MS-MS fragmentation analysis of 3,206 Da precursor ion

MLMVTLSPTKDFWLHANNKEHSVELHK

| b | | | v | | b | | | v |
|---|---|---|---|---|---|---|---|---|
|  | 1 | M | 27 |  |  |  |  |  |
| 245.1318 | 2 | L | 26 | 3074.5880 | 1800.9175 | 15 | H | 13 | 1542.7772 |
| 376.1723 | 3 | M | 25 | 2961.5040 | 1871.9547 | 16 | A | 12 | 1405.7183 |
| 475.2407 | 4 | V | 24 | 2830.4635 | 1985.9976 | 17 | N | 11 | 1334.6811 |
| 576.2884 | 5 | T | 23 | 2731.3951 | 2100.0405 | 18 | N | 10 | 1220.6382 |
| 689.3725 | 6 | L | 22 | 2630.3474 | 2228.1355 | 19 | K | 9 | 1106.5953 |
| 776.4045 | 7 | S | 21 | 2517.2633 | 2357.1781 | 20 | E | 8 | 978.5003 |
| 873.4573 | 8 | P | 20 | 2430.2313 | 2494.2370 | 21 | H | 7 | 849.4577 |
| 974.5049 | 9 | T | 19 | 2333.1785 | 2581.2690 | 22 | S | 6 | 712.3988 |
| 1102.5999 | 10 | K | 18 | 2232.1309 | 2680.3374 | 23 | V | 5 | 625.3668 |
| 1217.6268 | 11 | D | 17 | 2104.0359 | 2809.3800 | 24 | E | 4 | 526.2984 |
| 1364.6953 | 12 | F | 16 | 1989.0090 | 2922.4641 | 25 | L | 3 | 397.2558 |
| 1550.7746 | 13 | W | 15 | 1841.9405 | 3059.5230 | 26 | H | 2 | 284.1717 |
| 1663.8586 | 14 | L | 14 | 1655.8612 | --- |  | 27 | K | 1 | 147.1128 |

LSPTKDFWLHANNKEHSVELHK

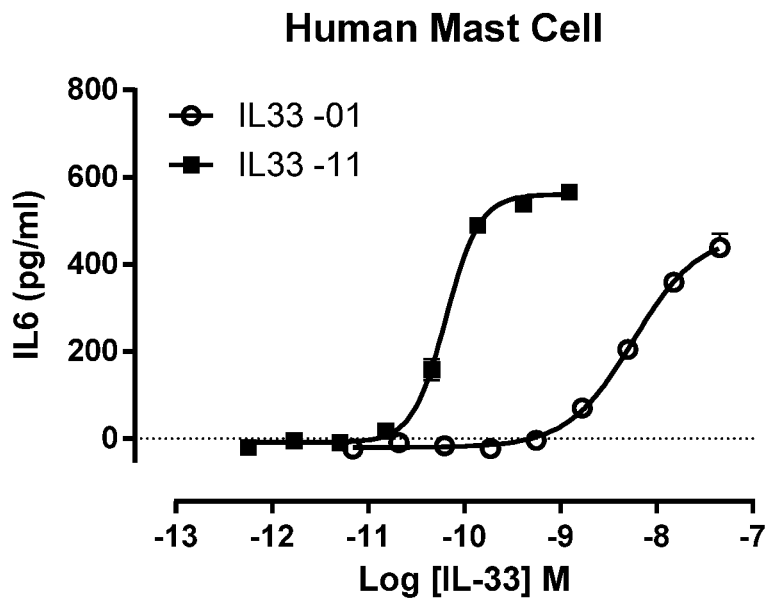
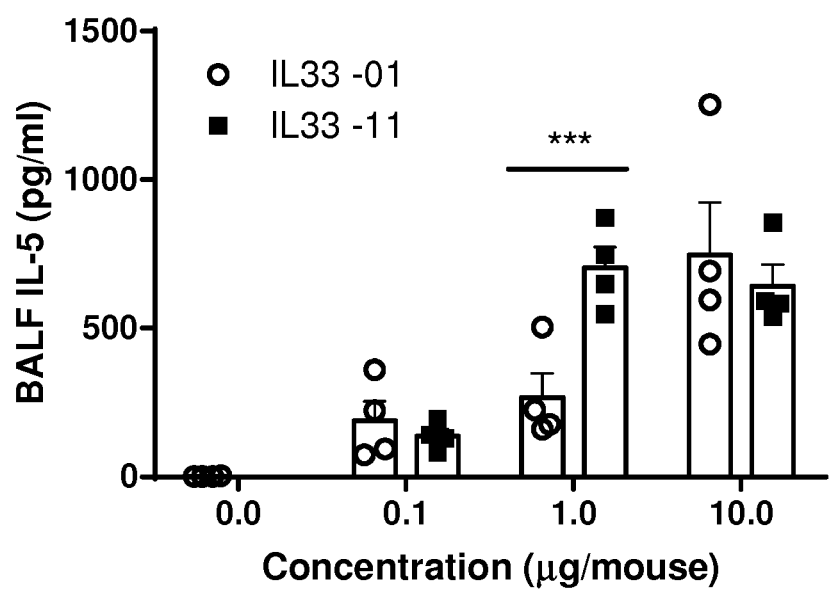
FIGURE 35

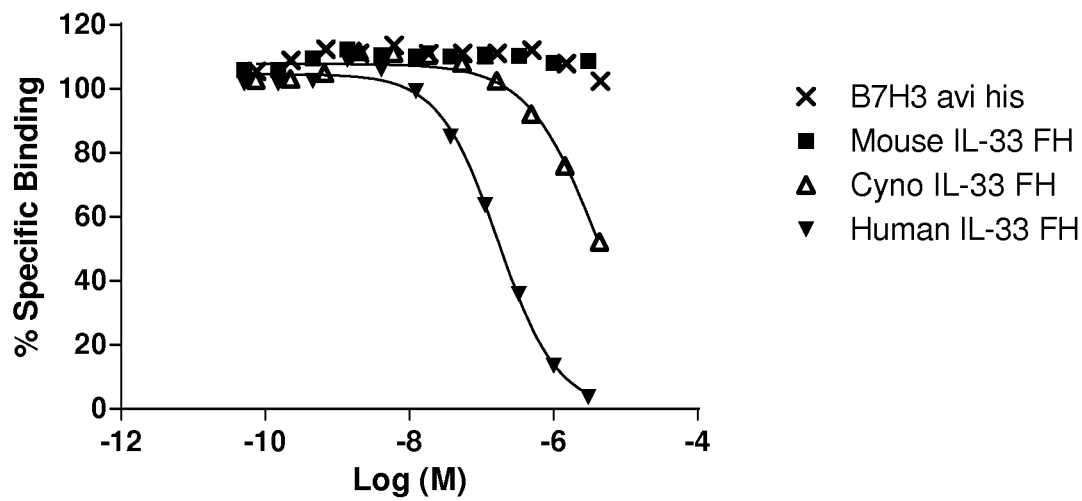
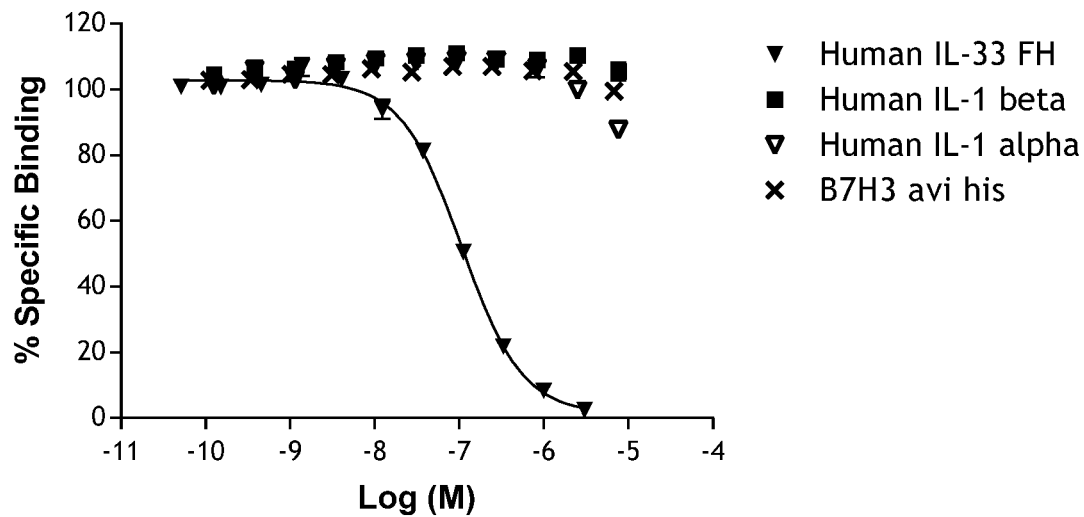
FIGURE 40

A
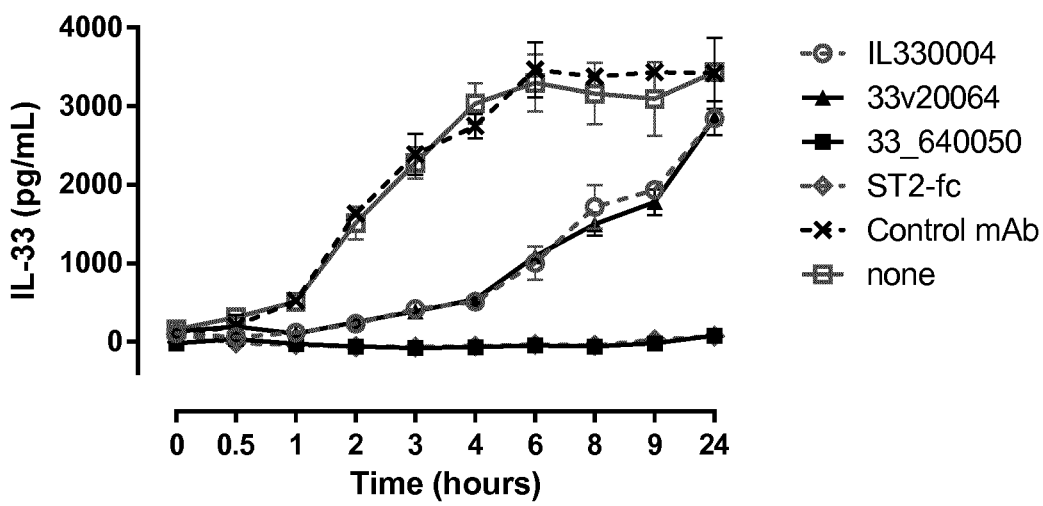
B
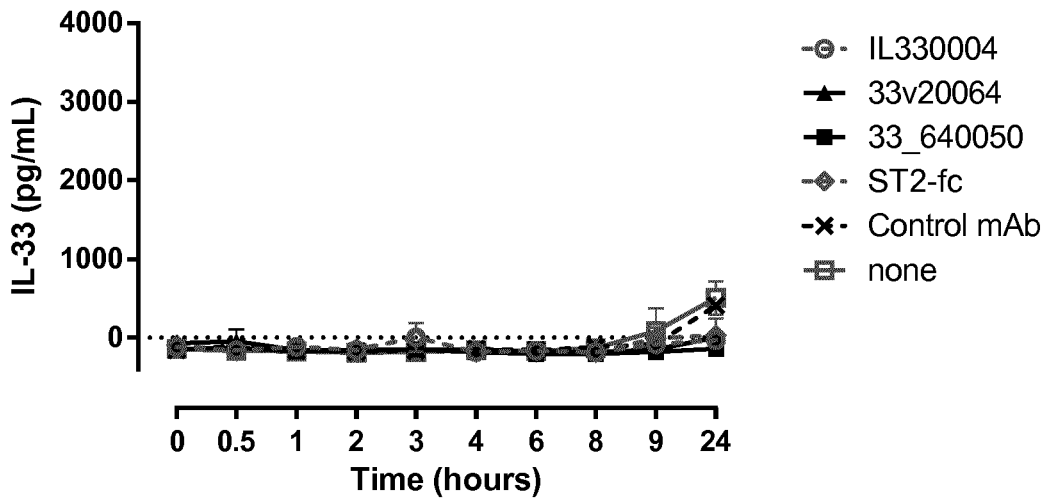
FIGURE 43

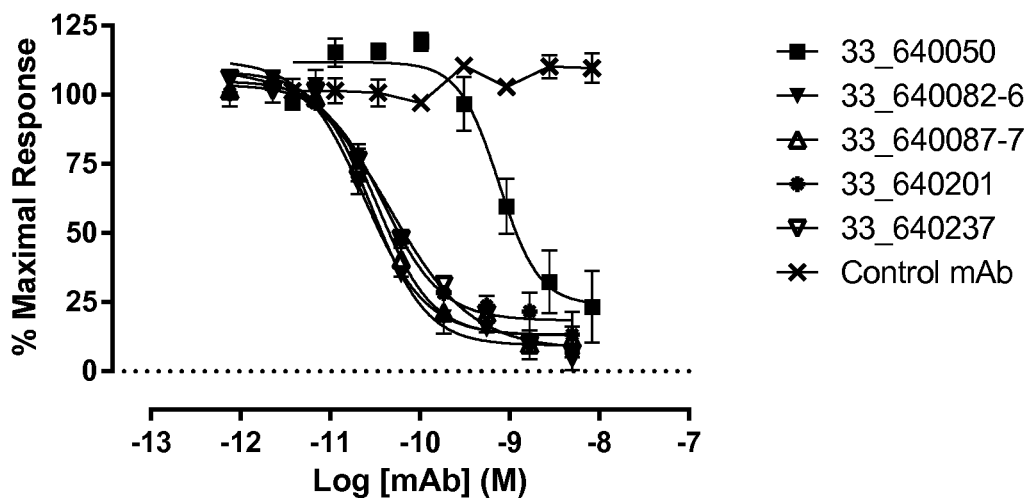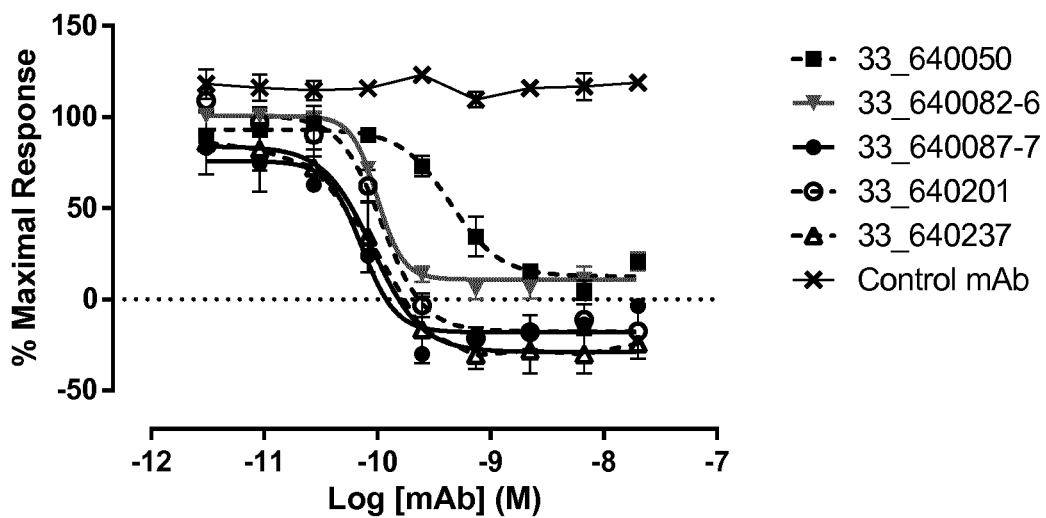
FIGURE 45

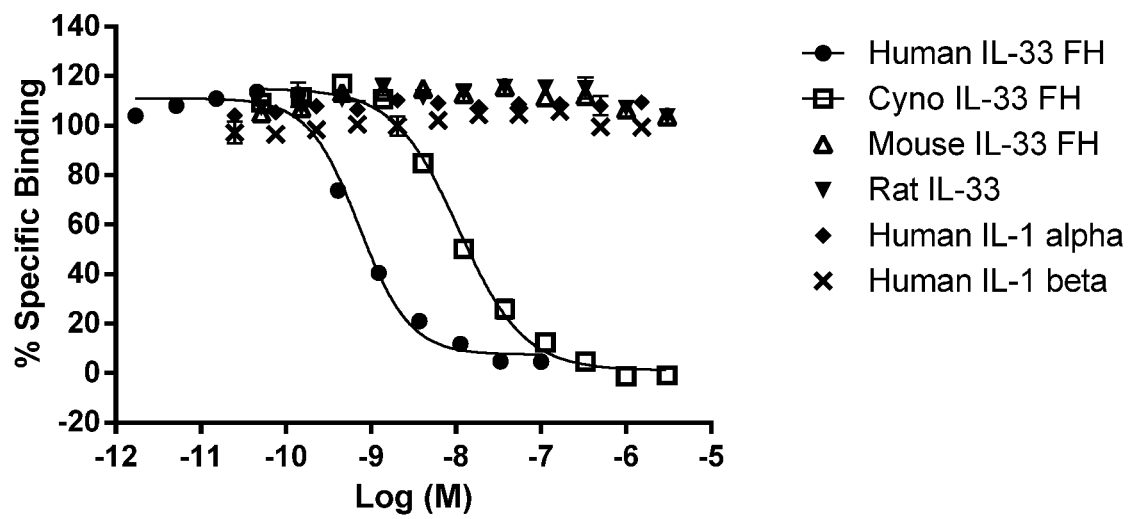
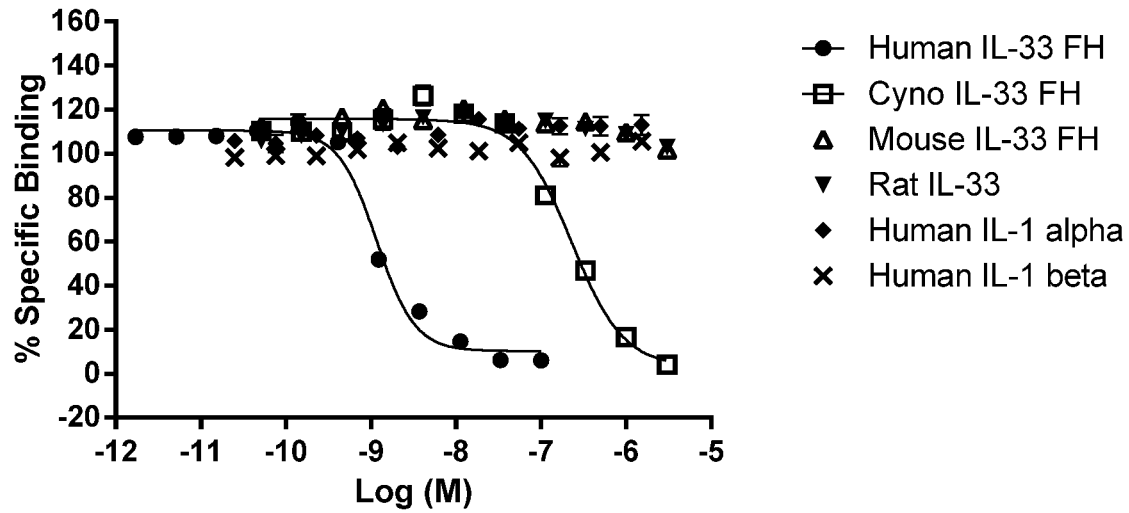
FIGURE 50

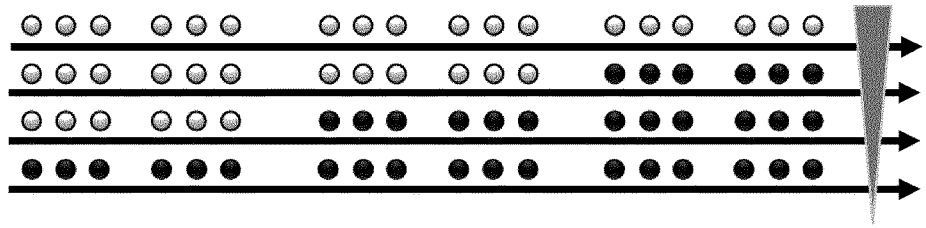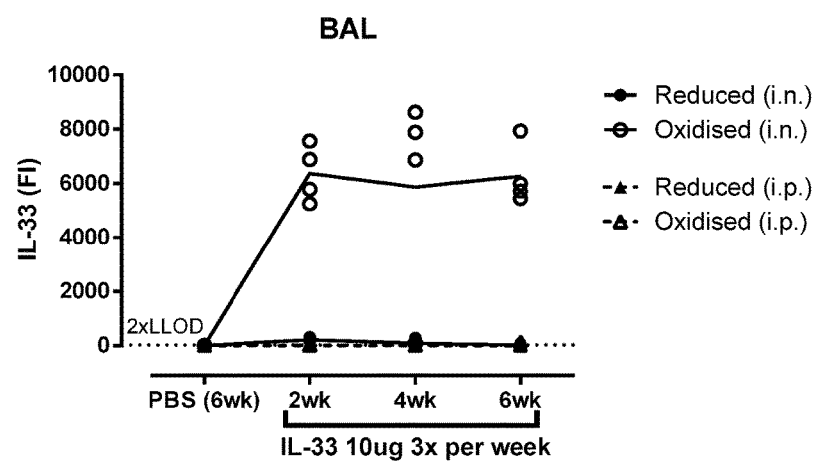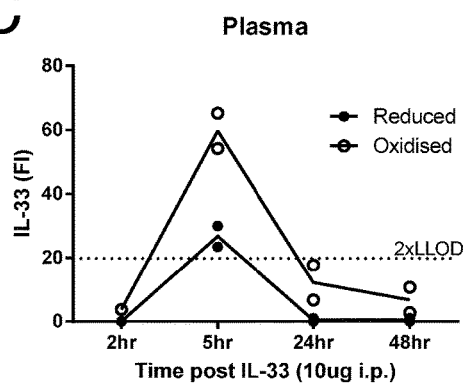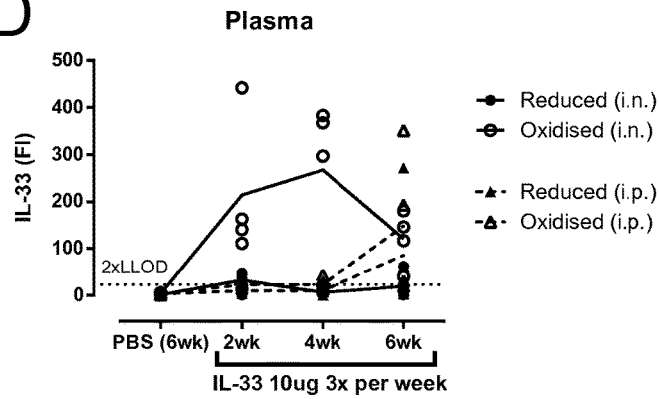
FIGURE 53

A 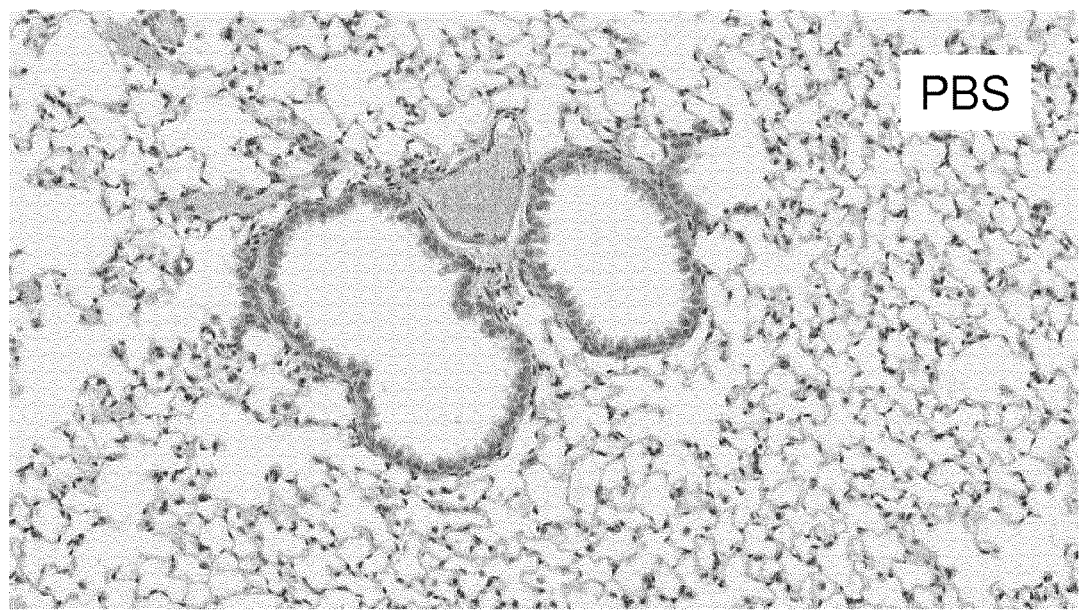
B 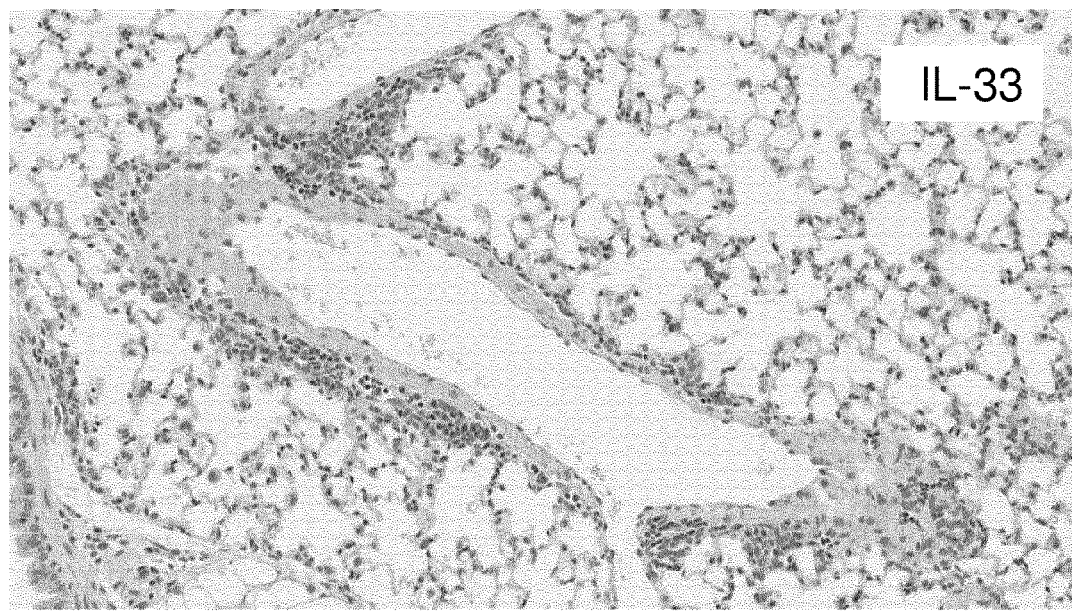
6 week intranasal dosing of IL-33 to ST2-deficient mice leads to perivascular inflammation
FIGURE 54

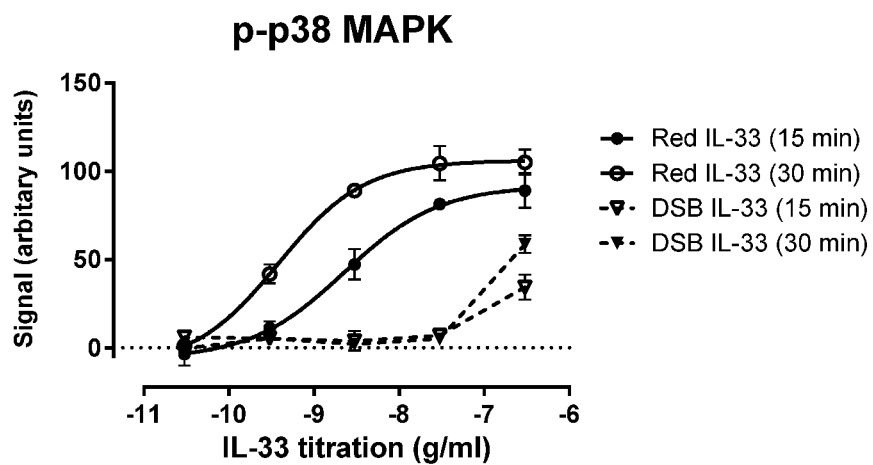
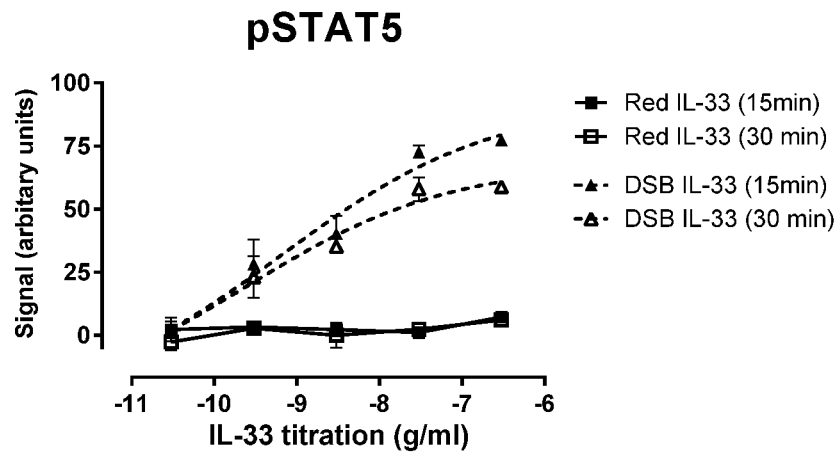
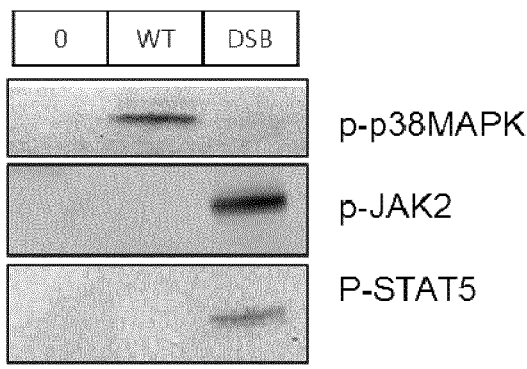
FIGURE 55

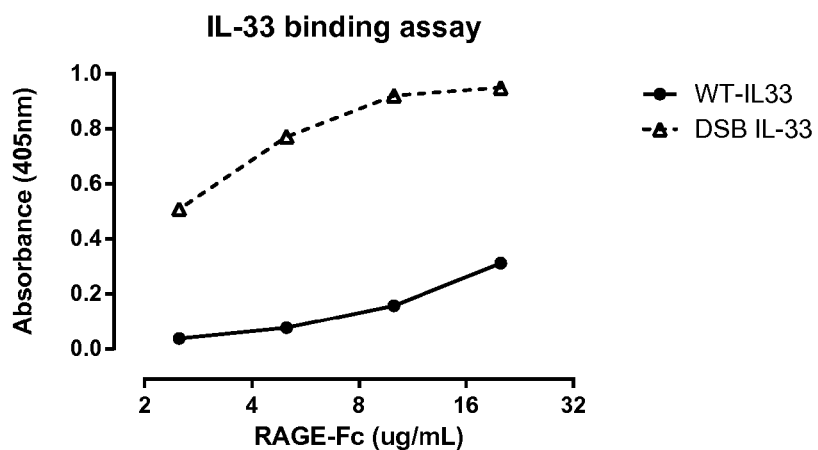
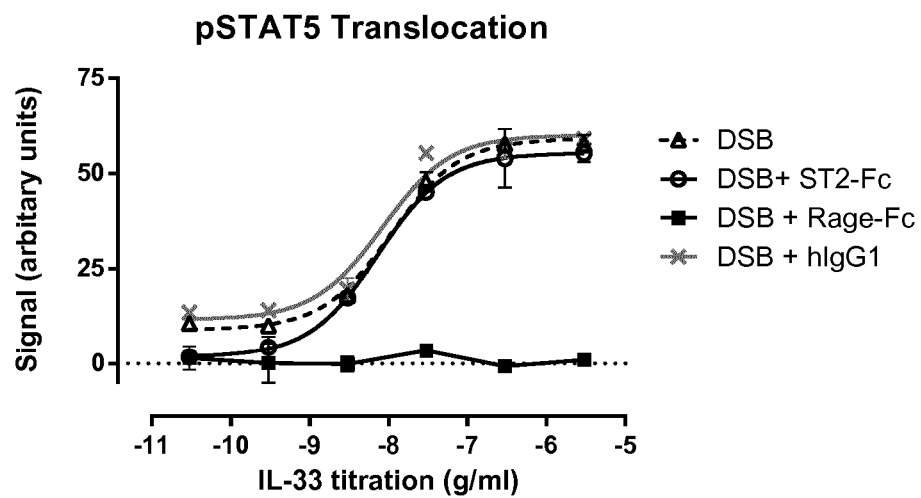
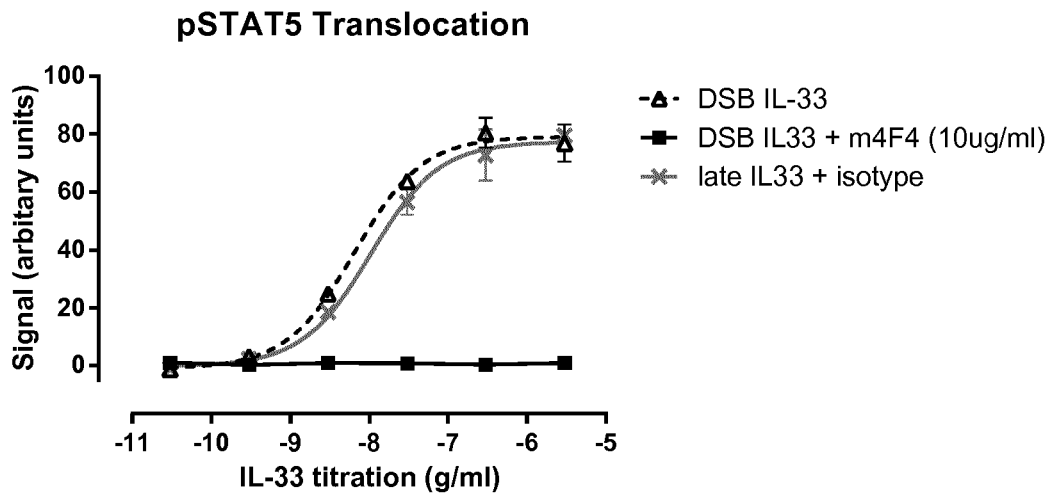
FIGURE 56

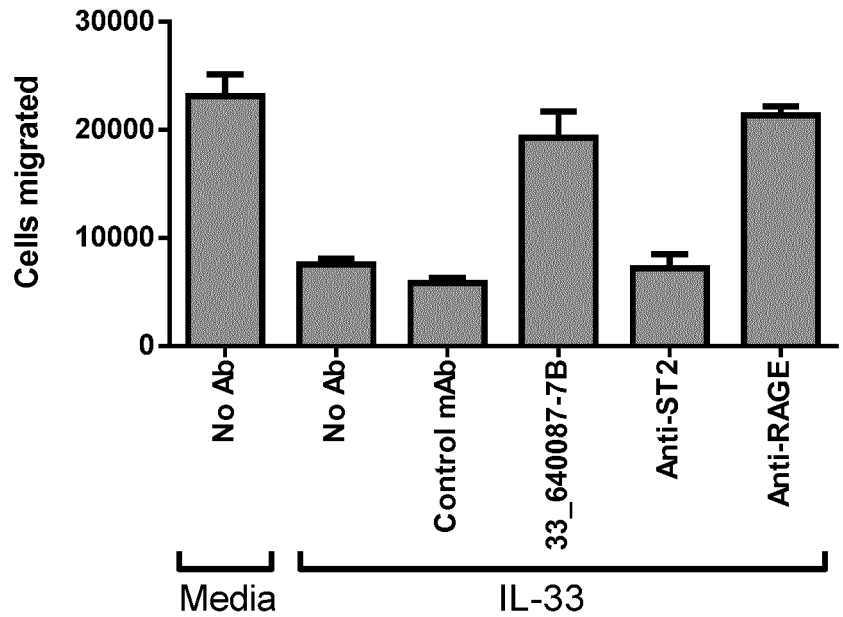
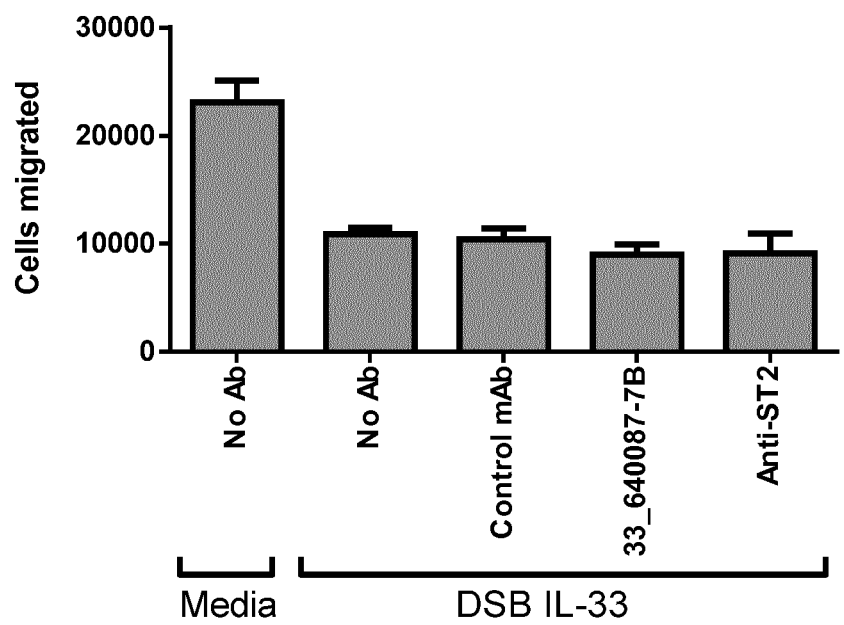
FIGURE 58

SEQUENCE LISTING

```
<160> NUMBER OF SEQ ID NOS: 664

<210> SEQ ID NO 1
<211> LENGTH: 372
<212> TYPE: DNA
<213> ORGANISM: Artificial Sequence
<220> FEATURE:
<223> OTHER INFORMATION: Homo sapiensIL330002 VH DNA

<400> SEQUENCE: 1
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagagtcg    300
tattacgatt tttggagtgg ccaatattac tttgattact ggggcgggg gaccacggtc    360 accgtctcga gt                                                         372

<210> SEQ ID NO 2
<211> LENGTH: 124
<212> TYPE: PRT
<213> ORGANISM: Artificial Sequence
<220> FEATURE:
<223> OTHER INFORMATION: Homo sapiensIL330002 VH PRT

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Ser Tyr Tyr Asp Phe Trp Ser Gly Gln Tyr Tyr Phe Asp
            100                 105                 110
Tyr Trp Gly Arg Gly Thr Thr Val Thr Val Ser Ser
            115                 120
```

<210> SEQ ID NO 3
<211> LENGTH: 5
<212> TYPE: PRT
<213> ORGANISM: Artificial Sequence
<220> FEATURE:
<223> OTHER INFORMATION: Homo sapiensIL330002 VH CDR1 PRT

<400> SEQUENCE: 3

```
Ser Tyr Ala Met Ser
 1               5
```

<210> SEQ ID NO 4
<211> LENGTH: 17
<212> TYPE: PRT
<213> ORGANISM: Artificial Sequence
<220> FEATURE:
<223> OTHER INFORMATION: Homo sapiensIL330002 VH CDR2 PRT

<400> SEQUENCE: 4

```
Ala Ile Ser Gly Ser Gly Gly Ser Thr Tyr Tyr Ala Asp Ser Val Lys
 1               5                  10                  15
Gly
```

<210> SEQ ID NO 5
<211> LENGTH: 15
<212> TYPE: PRT
<213> ORGANISM: Artificial Sequence
<220> FEATURE:
<223> OTHER INFORMATION: Homo sapiensIL330002 VH CDR3 PRT

<400> SEQUENCE: 5

```
Glu Ser Tyr Tyr Asp Phe Trp Ser Gly Gln Tyr Tyr Phe Asp Tyr
 1               5                  10                  15
```

<210> SEQ ID NO 6
<211> LENGTH: 321
<212> TYPE: DNA
<213> ORGANISM: Artificial Sequence
<220> FEATURE:
<223> OTHER INFORMATION: Homo sapiensIL330002 VL DNA

<400> SEQUENCE: 6

```
tcctatgagc tgactcagcc accctcattg tccgtgtccc caggacagac agccagcatc      60
acctgctctg gagataaatt gggagataaa tatgtttcct ggtatcaaca gaagccaggc     120
cagtccccta tcctggtcat ctatcacgat aacaagcggc cctcaggat ccctgagcga      180 ttctctggct ccaactctgg aacacagcc actctgacca tcagcgggac ccaggctatg     240
gatgaggctg actattactg tcaggcgtgg gacagtaacg ctggatatgt cttcggaact    300
gggaccaagg tcaccgtcct a                                               321
```

<210> SEQ ID NO 7
<211> LENGTH: 107
<212> TYPE: PRT
<213> ORGANISM: Artificial Sequence
<220> FEATURE:
<223> OTHER INFORMATION: Homo sapiensIL330002 VL PRT

<400> SEQUENCE: 7

```
Ser Tyr Glu Leu Thr Gln Pro Pro Ser Leu Ser Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Ile Leu Val Ile Tyr
        35                  40                  45

His Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Ala Gly Tyr
                85                  90                  95

Val Phe Gly Thr Gly Thr Lys Val Thr Val Leu
            100                 105
```

<210> SEQ ID NO 8
<211> LENGTH: 11
<212> TYPE: PRT
<213> ORGANISM: Artificial Sequence
<220> FEATURE:
<223> OTHER INFORMATION: Homo sapiensIL330002 VL CDR1 PRT

<400> SEQUENCE: 8

```
Ser Gly Asp Lys Leu Gly Asp Lys Tyr Val Ser
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Homo sapiensIL330002 VL CDR2 PRT

<400> SEQUENCE: 9

```
His Asp Asn Lys Arg Pro Ser
1               5
```

<210> SEQ ID NO 10
<211> LENGTH: 10
<212> TYPE: PRT
<213> ORGANISM: Artificial Sequence
<220> FEATURE:
<223> OTHER INFORMATION: Homo sapiensIL330002 VL CDR3 PRT

<400> SEQUENCE: 10

```
Gln Ala Trp Asp Ser Asn Ala Gly Tyr Val
1               5                   10
```

<210> SEQ ID NO 11
<211> LENGTH: 372
<212> TYPE: DNA
<213> ORGANISM: Artificial Sequence
<220> FEATURE:
<223> OTHER INFORMATION: Homo sapiensIL330004 VH DNA

<400> SEQUENCE: 11

-continued

```
gaggtgcagc tgttggagtc tggggggaggc ttggtacagc ctgggggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagagtcg     300
tattacgatt tttggagtgg ccaatattac tttgattact ggggccaagg gacaatggtc     360
accgtctcga gt                                                         372
```

<210> SEQ ID NO 12
<211> LENGTH: 124
<212> TYPE: PRT
<213> ORGANISM: Artificial Sequence
<220> FEATURE:
<223> OTHER INFORMATION: Homo sapiensIL330004 VH PRT

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Tyr Tyr Asp Phe Trp Ser Gly Gln Tyr Tyr Phe Asp
            100                 105                 110

Tyr Trp Gly Gln Gly Thr Met Val Thr Val Ser Ser
        115                 120
```

<210> SEQ ID NO 13
<211> LENGTH: 5
<212> TYPE: PRT
<213> ORGANISM: Artificial Sequence
<220> FEATURE:
<223> OTHER INFORMATION: Homo sapiensIL330004 VH CDR1 PRT

<400> SEQUENCE: 13

```
Ser Tyr Ala Met Ser
1               5
```

<210> SEQ ID NO 14
<211> LENGTH: 17
<212> TYPE: PRT
<213> ORGANISM: Artificial Sequence
<220> FEATURE:
<223> OTHER INFORMATION: Homo sapiensIL330004 VH CDR2 PRT

<400> SEQUENCE: 14

```
Ala Ile Ser Gly Ser Gly Gly Ser Thr Tyr Tyr Ala Asp Ser Val Lys
1               5                   10                  15

Gly
```

<210> SEQ ID NO 15

```
<211> LENGTH: 15
<212> TYPE: PRT
<213> ORGANISM: Artificial Sequence
<220> FEATURE:
<223> OTHER INFORMATION: Homo sapiensIL330004 VH CDR3 PRT

<400> SEQUENCE: 15

Glu Ser Tyr Tyr Asp Phe Trp Ser Gly Gln Tyr Tyr Phe Asp Tyr
1               5                   10                  15

<210> SEQ ID NO 16
<211> LENGTH: 318
<212> TYPE: DNA
<213> ORGANISM: Artificial Sequence
<220> FEATURE:
<223> OTHER INFORMATION: Homo sapiensIL330004 VL DNA

<400> SEQUENCE: 16
tcctatgagc tgactcagcc accctcagtg tccgtgtccc caggacagac tgccagcatc      60
tcctgctctg gagataaatt gggggataaa tttgcttcct ggtatcagca aaagccaggc     120
cagtcccctg tcttgatcat ctatcaggat aggaagcggc cctcaggaat ccctgagcgg     180
ttctctggct ccaactctgg gaacacagcc actctgacca tcagcgggac ccagactacc     240
gatgaggctg actattactg tcaggcgtgg gacggcagcc tttatgtctt cggaactggg     300
accaagctga ccgtccta                                                   318

<210> SEQ ID NO 17
<211> LENGTH: 106
<212> TYPE: PRT
<213> ORGANISM: Artificial Sequence
<220> FEATURE:
<223> OTHER INFORMATION: Homo sapiensIL330004 VL PRT

<400> SEQUENCE: 17

Ser Tyr Glu Leu Thr Gln Pro Pro Ser Val Ser Val Ser Pro Gly Gln
1               5                   10                  15

Thr Ala Ser Ile Ser Cys Ser Gly Asp Lys Leu Gly Asp Lys Phe Ala
                20                  25                  30

Ser Trp Tyr Gln Gln Lys Pro Gly Gln Ser Pro Val Leu Ile Ile Tyr
            35                  40                  45

Gln Asp Arg Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Thr Thr
65                  70                  75                  80

Asp Glu Ala Asp Tyr Tyr Cys Gln Ala Trp Asp Gly Ser Leu Tyr Val
                85                  90                  95

Phe Gly Thr Gly Thr Lys Leu Thr Val Leu
            100                 105

<210> SEQ ID NO 18
<211> LENGTH: 11
<212> TYPE: PRT
<213> ORGANISM: Artificial Sequence
<220> FEATURE:
<223> OTHER INFORMATION: Homo sapiensIL330004 VL CDR1 PRT

<400> SEQUENCE: 18

Ser Gly Asp Lys Leu Gly Asp Lys Phe Ala Ser
1               5                   10

<210> SEQ ID NO 19
```

<211> LENGTH: 7
<212> TYPE: PRT
<213> ORGANISM: Artificial Sequence
<220> FEATURE:
<223> OTHER INFORMATION: Homo sapiensIL330004 VL CDR2 PRT

<400> SEQUENCE: 19

Gln Asp Arg Lys Arg Pro Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Homo sapiensIL330004 VL CDR3 PRT

<400> SEQUENCE: 20

Gln Ala Trp Asp Gly Ser Leu Tyr Val
1               5

<210> SEQ ID NO 21
<211> LENGTH: 369
<212> TYPE: DNA
<213> ORGANISM: Artificial Sequence
<220> FEATURE:
<223> OTHER INFORMATION: Homo sapiensIL330020 VH DNA

<400> SEQUENCE: 21
caggtgcagc tggtgcagtc tggagctgag gtgaagaagc ctggggcctc agtgaaggtc      60
tcctgcaagg cttctggtta cacctttacc agctacggta tcagctgggt gcgacaggcc     120
cctggacaag gcttgagtg gatgggatgg atcagcgatt accagggtta tacaaagtat      180
gcagagaagt tccagggcag agtcaccatg accacagaca catccacgaa cacagcctac    240
atggagctga ggagcctgag atctgacgac acggccgtgt attactgtgc gagactgtat    300
agcagtggct ggatacgtca gtaccacttt gactattggg gccgaggcac cctggtcacc    360
gtctcgagt                                                            369

<210> SEQ ID NO 22
<211> LENGTH: 123
<212> TYPE: PRT
<213> ORGANISM: Artificial Sequence
<220> FEATURE:
<223> OTHER INFORMATION: Homo sapiensIL330020 VH PRT

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Asp Tyr Gln Gly Tyr Thr Lys Tyr Ala Glu Lys Phe
        50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Tyr Ser Ser Gly Trp Ile Arg Gln Tyr His Phe Asp Tyr
            100                 105                 110

Trp Gly Arg Gly Thr Leu Val Thr Val Ser Ser
        115                 120

<210> SEQ ID NO 23
<211> LENGTH: 5
<212> TYPE: PRT
<213> ORGANISM: Artificial Sequence
<220> FEATURE:
<223> OTHER INFORMATION: Homo sapiensIL330020 VH CDR1 PRT

<400> SEQUENCE: 23

Ser Tyr Gly Ile Ser
1               5

<210> SEQ ID NO 24
<211> LENGTH: 17
<212> TYPE: PRT
<213> ORGANISM: Artificial Sequence
<220> FEATURE:
<223> OTHER INFORMATION: Homo sapiensIL330020 VH CDR2 PRT

<400> SEQUENCE: 24

Trp Ile Ser Asp Tyr Gln Gly Tyr Thr Lys Tyr Ala Glu Lys Phe Gln
1               5                   10                  15

Gly

<210> SEQ ID NO 25
<211> LENGTH: 14
<212> TYPE: PRT
<213> ORGANISM: Artificial Sequence
<220> FEATURE:
<223> OTHER INFORMATION: Homo sapiensIL330020 VH CDR3 PRT

<400> SEQUENCE: 25

Leu Tyr Ser Ser Gly Trp Ile Arg Gln Tyr His Phe Asp Tyr
1               5                   10

<210> SEQ ID NO 26
<211> LENGTH: 315
<212> TYPE: DNA
<213> ORGANISM: Artificial Sequence
<220> FEATURE:
<223> OTHER INFORMATION: Homo sapiensIL330020 VL DNA

<400> SEQUENCE: 26
tcctatgagc tgactcagcc accctcagtg tccgtgtccc caggacagac agccagcatc    60
acctgctcag agataattt gaaagataaa tatgtctcat ggtatcagca gaagccaggg    120
caggcccctg tactggttct ctatcaagat agaaagcggc cctcagggat ccctgagcga    180
ttctctggct ccaactcagg gaacacagcc actctgacca tcagcgggac ccaggctatg    240
gatgaggctg actattattg tcaggcgtgg gacagcggca ctgccttcgg cggagggacc    300
aaggtcaccg tccta                                                    315

<210> SEQ ID NO 27
<211> LENGTH: 105
<212> TYPE: PRT
<213> ORGANISM: Artificial Sequence
<220> FEATURE:
<223> OTHER INFORMATION: Homo sapiensIL330020 VL PRT

<400> SEQUENCE: 27

Ser Tyr Glu Leu Thr Gln Pro Pro Ser Val Ser Val Ser Pro Gly Gln
1               5                   10                  15

-continued

```
Thr Ala Ser Ile Thr Cys Ser Gly Asp Asn Leu Lys Asp Lys Tyr Val
            20                  25                  30
Ser Trp Tyr Gln Gln Lys Pro Gly Gln Ala Pro Val Leu Val Leu Tyr
        35                  40                  45
Gln Asp Arg Lys Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln Ala Trp Asp Ser Gly Thr Ala Phe
                85                  90                  95
Gly Gly Gly Thr Lys Val Thr Val Leu
            100                 105

<210> SEQ ID NO 28
<211> LENGTH: 11
<212> TYPE: PRT
<213> ORGANISM: Artificial Sequence
<220> FEATURE:
<223> OTHER INFORMATION: Homo sapiensIL330020 VL CDR1 PRT

<400> SEQUENCE: 28

Ser Gly Asp Asn Leu Lys Asp Lys Tyr Val Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Homo sapiensIL330020 VL CDR2 PRT

<400> SEQUENCE: 29

Gln Asp Arg Lys Arg Pro Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Homo sapiensIL330020 VL CDR3 PRT

<400> SEQUENCE: 30

Gln Ala Trp Asp Ser Gly Thr Ala
1               5

<210> SEQ ID NO 31
<211> LENGTH: 357
<212> TYPE: DNA
<213> ORGANISM: Artificial Sequence
<220> FEATURE:
<223> OTHER INFORMATION: Homo sapiensIL330071 VH DNA

<400> SEQUENCE: 31
gaggtgcagc tggtggagtc tggagctgag gtgaagcagc ctggggcctc agtgaaggtc      60
tcctgcaagg cttctggtta cacctttacc agctatggta tcagctgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagaaggggt    300
ttctatcatg atgcttttga tatctggggg cgagggacca cggtcaccgt ctcgagt      357
```

```
<210> SEQ ID NO 32
<211> LENGTH: 119
<212> TYPE: PRT
<213> ORGANISM: Artificial Sequence
<220> FEATURE:
<223> OTHER INFORMATION: Homo sapiensIL330071 VH PRT

<400> SEQUENCE: 32

Glu Val Gln Leu Val Glu Ser Gly Ala Glu Val Lys Gln Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gly Phe Tyr His Asp Ala Phe Asp Ile Trp Gly Arg Gly
            100                 105                 110

Thr Thr Val Thr Val Ser Ser
        115

<210> SEQ ID NO 33
<211> LENGTH: 5
<212> TYPE: PRT
<213> ORGANISM: Artificial Sequence
<220> FEATURE:
<223> OTHER INFORMATION: Homo sapiensIL330071 VH CDR1 PRT

<400> SEQUENCE: 33

Ser Tyr Gly Ile Ser
1               5

<210> SEQ ID NO 34
<211> LENGTH: 17
<212> TYPE: PRT
<213> ORGANISM: Artificial Sequence
<220> FEATURE:
<223> OTHER INFORMATION: Homo sapiensIL330071 VH CDR2 PRT

<400> SEQUENCE: 34

Trp Ile Ser Ala Tyr Asn Gly Asn Thr Asn Tyr Ala Gln Lys Leu Gln
1               5                   10                  15

Gly

<210> SEQ ID NO 35
<211> LENGTH: 10
<212> TYPE: PRT
<213> ORGANISM: Artificial Sequence
<220> FEATURE:
<223> OTHER INFORMATION: Homo sapiensIL330071 VH CDR3 PRT

<400> SEQUENCE: 35

Arg Gly Phe Tyr His Asp Ala Phe Asp Ile
1               5                   10

<210> SEQ ID NO 36
<211> LENGTH: 321
<212> TYPE: DNA
```

<213> ORGANISM: Artificial Sequence
<220> FEATURE:
<223> OTHER INFORMATION: Homo sapiensIL330071 VL DNA

<400> SEQUENCE: 36

```
gccatccagt tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctatgct gcatccactt tgcaatcagg ggtcccatct   180
cggttcagcg gcagtggatc tgggacagaa ttcactctca ccatcagcag cctgcagcct   240
gatgattttg caacttatta ctgccaacag tataatagtt attctgtgac gttcggccaa   300
gggaccaagg tggaaatcaa a                                             321
```

<210> SEQ ID NO 37
<211> LENGTH: 107
<212> TYPE: PRT
<213> ORGANISM: Artificial Sequence
<220> FEATURE:
<223> OTHER INFORMATION: Homo sapiensIL330071 VL PRT

<400> SEQUENCE: 37

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Val
                85                  90                  95

Thr Phe Gly Gln Gly Thr Lys Val Glu Ile Lys
            100                 105

<210> SEQ ID NO 38
<211> LENGTH: 11
<212> TYPE: PRT
<213> ORGANISM: Artificial Sequence
<220> FEATURE:
<223> OTHER INFORMATION: Homo sapiensIL330071 VL CDR1 PRT

<400> SEQUENCE: 38

Arg Ala Ser Gln Gly Ile Ser Asn Tyr Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Homo sapiensIL330071 VL CDR2 PRT

<400> SEQUENCE: 39

Ala Ala Ser Thr Leu Gln Ser
1               5

<210> SEQ ID NO 40
<211> LENGTH: 9
<212> TYPE: PRT

<213> ORGANISM: Artificial Sequence
<220> FEATURE:
<223> OTHER INFORMATION: Homo sapiensIL330071 VL CDR3 PRT

<400> SEQUENCE: 40

Gln Gln Tyr Asn Ser Tyr Ser Val Thr
1               5

<210> SEQ ID NO 41
<211> LENGTH: 366
<212> TYPE: DNA
<213> ORGANISM: Artificial Sequence
<220> FEATURE:
<223> OTHER INFORMATION: Homo sapiensIL330125 VH DNA

<400> SEQUENCE: 41
gaagtgcagc tggtgcagtc tggggctgag gtgaagaagc ctggggcctc agtgactgtc    60
tcctgcaagg cttctggata cagcttcacc gactactata tacactgggt gcgacaggcc   120
cctggacaag gtcctgagtg gatgggatgg atcaaccota acagtggtgt cacagacttt   180
gcgcagaagt ttctgggcag ggtcaccatg accagggaca cgtccatcag cacagcctac   240
atggagctga gcagactgac atctgacgac acggccttgt attattgtgc gagagttgcc   300
tttgtatact atgatagtag tgccttccaa tactggggca aggaaccct ggtcaccgtc   360 tcgagt                                                              366

<210> SEQ ID NO 42
<211> LENGTH: 122
<212> TYPE: PRT
<213> ORGANISM: Artificial Sequence
<220> FEATURE:
<223> OTHER INFORMATION: Homo sapiensIL330125 VH PRT

<400> SEQUENCE: 42

Glu Val Gln Leu Val Gln Ser Gly Ala Glu Val Lys Lys Pro Gly Ala
1               5                   10                  15

Ser Val Thr Val Ser Cys Lys Ala Ser Gly Tyr Ser Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Asn Ser Gly Val Thr Asp Phe Ala Gln Lys Phe
    50                  55                  60

Leu Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Leu Tyr Tyr Cys
                85                  90                  95

Ala Arg Val Ala Phe Val Tyr Tyr Asp Ser Ser Ala Phe Gln Tyr Trp
            100                 105                 110

Gly Lys Gly Thr Leu Val Thr Val Ser Ser
        115                 120

<210> SEQ ID NO 43
<211> LENGTH: 5
<212> TYPE: PRT
<213> ORGANISM: Artificial Sequence
<220> FEATURE:
<223> OTHER INFORMATION: Homo sapiensIL330125 VH CDR1 PRT

<400> SEQUENCE: 43

Asp Tyr Tyr Ile His
1               5

```
<210> SEQ ID NO 44
<211> LENGTH: 17
<212> TYPE: PRT
<213> ORGANISM: Artificial Sequence
<220> FEATURE:
<223> OTHER INFORMATION: Homo sapiensIL330125 VH CDR2 PRT

<400> SEQUENCE: 44

Trp Ile Asn Pro Asn Ser Gly Val Thr Asp Phe Ala Gln Lys Phe Leu
1               5                   10                  15

Gly

<210> SEQ ID NO 45
<211> LENGTH: 13
<212> TYPE: PRT
<213> ORGANISM: Artificial Sequence
<220> FEATURE:
<223> OTHER INFORMATION: Homo sapiensIL330125 VH CDR3 PRT

<400> SEQUENCE: 45

Val Ala Phe Val Tyr Tyr Asp Ser Ser Ala Phe Gln Tyr
1               5                   10

<210> SEQ ID NO 46
<211> LENGTH: 324
<212> TYPE: DNA
<213> ORGANISM: Artificial Sequence
<220> FEATURE:
<223> OTHER INFORMATION: Homo sapiensIL330125 VL DNA

<400> SEQUENCE: 46
ctgcctgtgc tgactcagcc accctcagtg tccgtttccc caggacagac agccaccatc      60
acctgctctg cagataagtt gggggataaa tatgctgcct ggtatcagca gaagccaggc     120 cagtccctg tcctggtcat ctatcaagat aggaagcggc cctcaggat ccctgagcga      180 ttctctggct ccaactctgg gaacacagcc actctgatca tcagcgggac ccaggctatg     240
gatgaggctg actattactg tcaggcgtgg gacagcaaca ctggcctta tgtcttcgga     300 actgggacca agctgaccgt ccta                                            324

<210> SEQ ID NO 47
<211> LENGTH: 108
<212> TYPE: PRT
<213> ORGANISM: Artificial Sequence
<220> FEATURE:
<223> OTHER INFORMATION: Homo sapiensIL330125 VL PRT

<400> SEQUENCE: 47

Leu Pro Val Leu Thr Gln Pro Pro Ser Val Ser Val Ser Pro Gly Gln
1               5                   10                  15

Thr Ala Thr Ile Thr Cys Ser Ala Asp Lys Leu Gly Asp Lys Tyr Ala
                20                  25                  30

Ala Trp Tyr Gln Gln Lys Pro Gly Gln Ser Pro Val Leu Val Ile Tyr
            35                  40                  45

Gln Asp Arg Lys Arg Pro Ser Gly Ile Pro Glu Arg Phe Ser Gly Ser
        50                  55                  60

Asn Ser Gly Asn Thr Ala Thr Leu Ile Ile Ser Gly Thr Gln Ala Met
65                  70                  75                  80

Asp Glu Ala Asp Tyr Tyr Cys Gln Ala Trp Asp Ser Asn Thr Gly Leu
                85                  90                  95
```

Tyr Val Phe Gly Thr Gly Thr Lys Leu Thr Val Leu
            100                 105

<210> SEQ ID NO 48
<211> LENGTH: 11
<212> TYPE: PRT
<213> ORGANISM: Artificial Sequence
<220> FEATURE:
<223> OTHER INFORMATION: Homo sapiensIL330125 VL CDR1 PRT

<400> SEQUENCE: 48

Ser Ala Asp Lys Leu Gly Asp Lys Tyr Ala Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Homo sapiensIL330125 VL CDR2 PRT

<400> SEQUENCE: 49

Gln Asp Arg Lys Arg Pro Ser
1               5

<210> SEQ ID NO 50
<211> LENGTH: 11
<212> TYPE: PRT
<213> ORGANISM: Artificial Sequence
<220> FEATURE:
<223> OTHER INFORMATION: Homo sapiensIL330125 VL CDR3 PRT

<400> SEQUENCE: 50

Gln Ala Trp Asp Ser Asn Thr Gly Leu Tyr Val
1               5                   10

<210> SEQ ID NO 51
<211> LENGTH: 378
<212> TYPE: DNA
<213> ORGANISM: Artificial Sequence
<220> FEATURE:
<223> OTHER INFORMATION: Homo sapiensIL330126 VH DNA

<400> SEQUENCE: 51
gaggtccagc tggtacagtc tggggctgaa ctgaagaagc ctggggcctc agtgaaggtc     60
tcctgcaaga cttctggtta cagttttaac acctatggta tcagttgggt gcgacaggcc    120
cctggacaag gcttgagtg gatgggatgg gtcagtggtg acgatggtaa cataaattat    180
gcagagaagt tccagggcag agtcgccatg accacagaca catccacgac cacagcctac    240
atggagctgt ggagcctgac atctgacgac acggccgtct attactgtgc gagagtacgt    300
cgaggcagtg gctggtacaa gaactatcac tactacatgg acgtctgggg ccaagggaca    360
atggtcaccg tctcgagt                                                  378

<210> SEQ ID NO 52
<211> LENGTH: 126
<212> TYPE: PRT
<213> ORGANISM: Artificial Sequence
<220> FEATURE:
<223> OTHER INFORMATION: Homo sapiensIL330126 VH PRT

<400> SEQUENCE: 52

Glu Val Gln Leu Val Gln Ser Gly Ala Glu Leu Lys Lys Pro Gly Ala
1               5                   10                  15

```
Ser Val Lys Val Ser Cys Lys Thr Ser Gly Tyr Ser Phe Asn Thr Tyr
            20                  25                  30

Gly Ile Ser Trp Val Arg Gln Ala Pro Gly Gln Gly Leu Glu Trp Met
        35                  40                  45

Gly Trp Val Ser Gly Asp Asp Gly Asn Ile Asn Tyr Ala Glu Lys Phe
    50                  55                  60

Gln Gly Arg Val Ala Met Thr Thr Asp Thr Ser Thr Thr Thr Ala Tyr
65                  70                  75                  80

Met Glu Leu Trp Ser Leu Thr Ser Asp Asp Thr Ala Val Tyr Tyr Cys
                85                  90                  95

Ala Arg Val Arg Arg Gly Ser Gly Trp Tyr Lys Asn Tyr His Tyr Tyr
            100                 105                 110

Met Asp Val Trp Gly Gln Gly Thr Met Val Thr Val Ser Ser
        115                 120                 125

<210> SEQ ID NO 53
<211> LENGTH: 5
<212> TYPE: PRT
<213> ORGANISM: Artificial Sequence
<220> FEATURE:
<223> OTHER INFORMATION: Homo sapiensIL330126 VH CDR1 PRT

<400> SEQUENCE: 53

Thr Tyr Gly Ile Ser
1               5

<210> SEQ ID NO 54
<211> LENGTH: 17
<212> TYPE: PRT
<213> ORGANISM: Artificial Sequence
<220> FEATURE:
<223> OTHER INFORMATION: Homo sapiensIL330126 VH CDR2 PRT

<400> SEQUENCE: 54

Trp Val Ser Gly Asp Asp Gly Asn Ile Asn Tyr Ala Glu Lys Phe Gln
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: Homo sapiensIL330126 VH CDR3 PRT

<400> SEQUENCE: 55

Val Arg Arg Gly Ser Gly Trp Tyr Lys Asn Tyr His Tyr Tyr Met Asp
1               5                   10                  15

Val

<210> SEQ ID NO 56
<211> LENGTH: 318
<212> TYPE: DNA
<213> ORGANISM: Artificial Sequence
<220> FEATURE:
<223> OTHER INFORMATION: Homo sapiensIL330126 VL DNA

<400> SEQUENCE: 56
cagtctgtgc tgactcagcc accctcagtg tccgtgtccc caggacagac agccagcgtc      60
acctgctctg gagatagatt gggggataaa tatgcttcct ggtatcagca gaagccaggc     120
cagtcccctg tcttggtcat ctatcaagat aggaagcggc cctcagggat ccctgagcga     180
```

```
ttctctggct ccaactctgg gaacacagcc actctgacca tcagcgggac ccaggctatg      240
gatgaggctg actattattg tcaggcgtgg gacggcagta ctgcgctatt cggcggaggg      300
accaagctga ccgtccta                                                    318
```

<210> SEQ ID NO 57
<211> LENGTH: 106
<212> TYPE: PRT
<213> ORGANISM: Artificial Sequence
<220> FEATURE:
<223> OTHER INFORMATION: Homo sapiensIL330126 VL PRT

<400> SEQUENCE: 57

```
Gln Ser Val Leu Thr Gln Pro Pro Ser Val Ser Val Ser Pro Gly Gln
1               5                   10                  15

Thr Ala Ser Val Thr Cys Ser Gly Asp Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Gly Ser Thr Ala Leu
                85                  90                  95

Phe Gly Gly Gly Thr Lys Leu Thr Val Leu
            100                 105
```

<210> SEQ ID NO 58
<211> LENGTH: 11
<212> TYPE: PRT
<213> ORGANISM: Artificial Sequence
<220> FEATURE:
<223> OTHER INFORMATION: Homo sapiensIL330126 VL CDR1 PRT

<400> SEQUENCE: 58

```
Ser Gly Asp Arg Leu Gly Asp Lys Tyr Ala Ser
1               5                   10
```

<210> SEQ ID NO 59
<211> LENGTH: 7
<212> TYPE: PRT
<213> ORGANISM: Artificial Sequence
<220> FEATURE:
<223> OTHER INFORMATION: Homo sapiensIL330126 VL CDR2 PRT

<400> SEQUENCE: 59

```
Gln Asp Arg Lys Arg Pro Ser
1               5
```

<210> SEQ ID NO 60
<211> LENGTH: 9
<212> TYPE: PRT
<213> ORGANISM: Artificial Sequence
<220> FEATURE:
<223> OTHER INFORMATION: Homo sapiensIL330126 VL CDR3 PRT

<400> SEQUENCE: 60

```
Gln Ala Trp Asp Gly Ser Thr Ala Leu
1               5
```

<210> SEQ ID NO 61

<211> LENGTH: 366
<212> TYPE: DNA
<213> ORGANISM: Artificial Sequence
<220> FEATURE:
<223> OTHER INFORMATION: Homo sapiensIL330425 VH DNA

<400> SEQUENCE: 61

```
caggtgcagc tggtgcagtc tgggggaggc gtggtccagc ctggggaggtc cctgagactc      60
tcctgtgcag cctctggatt caccttcagt gaatatagta tgcactgggt ccgccaggct     120
ccagggaagg gactggaata tgtttcaact attagtagta atggggctgg cacatactac     180
gcagactccg tgaagggcag agtcaccatc tccagagaca attccaagaa cacgctgtat     240
gttcaaatga gcagtctgag acctgaggac acggctgtct attactgtgt gaaatcccta     300
actaaatacc cctatggtaa ctactttgac tactggggca gagggaccac ggtcaccgtc     360
tcctca                                                                366
```

<210> SEQ ID NO 62
<211> LENGTH: 122
<212> TYPE: PRT
<213> ORGANISM: Artificial Sequence
<220> FEATURE:
<223> OTHER INFORMATION: Homo sapiensIL330425 VH PRT

<400> SEQUENCE: 62

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Glu Tyr
            20                  25                  30

Ser Met His Trp Val Arg Gln Ala Pro Gly Lys Gly Leu Glu Tyr Val
        35                  40                  45

Ser Thr Ile Ser Ser Asn Gly Ala Gly Thr Tyr Tyr Ala Asp Ser Val
    50                  55                  60

Lys Gly Arg Val Thr Ile Ser Arg Asp Asn Ser Lys Asn Thr Leu Tyr
65                  70                  75                  80

Val Gln Met Ser Ser Leu Arg Pro Glu Asp Thr Ala Val Tyr Tyr Cys
                85                  90                  95

Val Lys Ser Leu Thr Lys Tyr Pro Tyr Gly Asn Tyr Phe Asp Tyr Trp
            100                 105                 110

Gly Arg Gly Thr Thr Val Thr Val Ser Ser
        115                 120

<210> SEQ ID NO 63
<211> LENGTH: 5
<212> TYPE: PRT
<213> ORGANISM: Artificial Sequence
<220> FEATURE:
<223> OTHER INFORMATION: Homo sapiensIL330425 VH CDR1 PRT

<400> SEQUENCE: 63

Glu Tyr Ser Met His
1               5

<210> SEQ ID NO 64
<211> LENGTH: 17
<212> TYPE: PRT
<213> ORGANISM: Artificial Sequence
<220> FEATURE:
<223> OTHER INFORMATION: Homo sapiensIL330425 VH CDR2 PRT

<400> SEQUENCE: 64

```
Thr Ile Ser Ser Asn Gly Ala Gly Thr Tyr Tyr Ala Asp Ser Val Lys
1               5                   10                  15

Gly
```

```
<210> SEQ ID NO 65
<211> LENGTH: 13
<212> TYPE: PRT
<213> ORGANISM: Artificial Sequence
<220> FEATURE:
<223> OTHER INFORMATION: Homo sapiensIL330425 VH CDR3 PRT

<400> SEQUENCE: 65

Ser Leu Thr Lys Tyr Pro Tyr Gly Asn Tyr Phe Asp Tyr
1               5                   10
```

```
<210> SEQ ID NO 66
<211> LENGTH: 324
<212> TYPE: DNA
<213> ORGANISM: Artificial Sequence
<220> FEATURE:
<223> OTHER INFORMATION: Homo sapiensIL330425 VL DNA

<400> SEQUENCE: 66
tcgtctgagc tgactcagga ccctgctgtg tctgtggcct tgggacagac agtcaggatc      60
acatgccaag agacagcct cagaagctat tatgcaagct ggtaccagca gaagccagga     120
caggcccctg tacttgtcat ctatggtaaa acaaccggc cctcaggat cccagaccga      180 ttctctggct ccagctcagg aaacacagct tccttgacca tcactagggc tcaggcggaa     240
gatgaggctg actattactg taactcccgg gacagcagtg gtaaccatgt ggtattcggc     300
ggagggacca agctgaccgt ccta                                            324
```

```
<210> SEQ ID NO 67
<211> LENGTH: 108
<212> TYPE: PRT
<213> ORGANISM: Artificial Sequence
<220> FEATURE:
<223> OTHER INFORMATION: Homo sapiensIL330425 VL PRT

<400> SEQUENCE: 67

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Arg Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105
```

```
<210> SEQ ID NO 68
<211> LENGTH: 11
<212> TYPE: PRT
<213> ORGANISM: Artificial Sequence
<220> FEATURE:
<223> OTHER INFORMATION: Homo sapiensIL330425 VL CDR1 PRT
```

<400> SEQUENCE: 68

Gln Gly Asp Ser Leu Arg Ser Tyr Tyr Ala Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Homo sapiensIL330425 VL CDR2 PRT

<400> SEQUENCE: 69

Gly Lys Asn Asn Arg Pro Ser
1               5

<210> SEQ ID NO 70
<211> LENGTH: 11
<212> TYPE: PRT
<213> ORGANISM: Artificial Sequence
<220> FEATURE:
<223> OTHER INFORMATION: Homo sapiensIL330425 VL CDR3 PRT

<400> SEQUENCE: 70

Asn Ser Arg Asp Ser Ser Gly Asn His Val Val
1               5                   10

<210> SEQ ID NO 71
<211> LENGTH: 375
<212> TYPE: DNA
<213> ORGANISM: Artificial Sequence
<220> FEATURE:
<223> OTHER INFORMATION: Homo sapiensIL330428 VH DNA

<400> SEQUENCE: 71

```
caggtgcagc tggtgcaatc tgggctgag acgaagaagt ctggggcctc agtgaaggtc    60
tcttgcaaga cttctggtta cacctttgat aactttggta tcagttgggt gcgacaggcc   120
cctggacaag gctggagtg ataggatgg atcagcattt acaatggaaa cacagattat    180
gcacagaatc ttcggggcag actcaccttg accacagaca cgtccacgag tacagtccac   240
atggaactga gagcctgag atctgacgac acggccattt attactgtgc gagaggaggg   300
ggtattagca gcagctggac ccctgactac tactttgact actggggcca gggcaccctg   360
gtcaccgtct cctca                                                    375
```

<210> SEQ ID NO 72
<211> LENGTH: 125
<212> TYPE: PRT
<213> ORGANISM: Artificial Sequence
<220> FEATURE:
<223> OTHER INFORMATION: Homo sapiensIL330428 VH PRT

<400> SEQUENCE: 72

Gln Val Gln Leu Val Gln Ser Gly Ala Glu Thr Lys Lys Ser Gly Ala
1               5                   10                  15

Ser Val Lys Val Ser Cys Lys Thr Ser Gly Tyr Thr Phe Asp Asn Phe
                20                  25                  30

Gly Ile Ser Trp Val Arg Gln Ala Pro Gly Gln Gly Leu Glu Trp Ile
            35                  40                  45

Gly Trp Ile Ser Ile Tyr Asn Gly Asn Thr Asp Tyr Ala Gln Asn Leu
        50                  55                  60

Arg Gly Arg Leu Thr Leu Thr Thr Asp Thr Ser Thr Ser Thr Val His
65                  70                  75                  80

-continued

```
Met Glu Leu Lys Ser Leu Arg Ser Asp Asp Thr Ala Ile Tyr Tyr Cys
                 85                  90                  95
Ala Arg Gly Gly Gly Ile Ser Ser Ser Trp Thr Pro Asp Tyr Tyr Phe
            100                 105                 110
Asp Tyr Trp Gly Gln Gly Thr Leu Val Thr Val Ser Ser
        115                 120                 125

<210> SEQ ID NO 73
<211> LENGTH: 5
<212> TYPE: PRT
<213> ORGANISM: Artificial Sequence
<220> FEATURE:
<223> OTHER INFORMATION: Homo sapiensIL330428 VH CDR1 PRT

<400> SEQUENCE: 73

Asn Phe Gly Ile Ser
1               5

<210> SEQ ID NO 74
<211> LENGTH: 17
<212> TYPE: PRT
<213> ORGANISM: Artificial Sequence
<220> FEATURE:
<223> OTHER INFORMATION: Homo sapiensIL330428 VH CDR2 PRT

<400> SEQUENCE: 74

Trp Ile Ser Ile Tyr Asn Gly Asn Thr Asp Tyr Ala Gln Asn Leu Arg
1               5                  10                  15
Gly

<210> SEQ ID NO 75
<211> LENGTH: 16
<212> TYPE: PRT
<213> ORGANISM: Artificial Sequence
<220> FEATURE:
<223> OTHER INFORMATION: Homo sapiensIL330428 VH CDR3 PRT

<400> SEQUENCE: 75

Gly Gly Gly Ile Ser Ser Ser Trp Thr Pro Asp Tyr Tyr Phe Asp Tyr
1               5                  10                  15

<210> SEQ ID NO 76
<211> LENGTH: 324
<212> TYPE: DNA
<213> ORGANISM: Artificial Sequence
<220> FEATURE:
<223> OTHER INFORMATION: Homo sapiensIL330428 VL DNA

<400> SEQUENCE: 76
tcgtctgagc tgactcagga ccctgctgtg tctgtggcct cgggacagac agtccgtctc      60
acatgccaag agacactct cagaaattat tattcaaact ggtaccaaca gaggccagga     120
caggcccccg ttcttgtcct ctacgggaac aacaggcggc cccgggaat cccagctcga     180 ttctctggct cccactcagg aaacacaggt tccctgatca tcactggggc tcaggcggaa     240
gatgaggctg agtatcactg tgccgcccgg gatagcagtg gcgaccatgt tgtcttcggt     300
ggtgggacca aggtcaccgt ccta                                            324

<210> SEQ ID NO 77
<211> LENGTH: 108
<212> TYPE: PRT
<213> ORGANISM: Artificial Sequence
<220> FEATURE:
```

<223> OTHER INFORMATION: Homo sapiensIL330428 VL PRT

<400> SEQUENCE: 77

Ser Ser Glu Leu Thr Gln Asp Pro Ala Val Ser Val Ala Ser Gly Gln
1               5                   10                  15

Thr Val Arg Leu Thr Cys Gln Gly Asp Thr Leu Arg Asn Tyr Tyr Ser
            20                  25                  30

Asn Trp Tyr Gln Gln Arg Pro Gly Gln Ala Pro Val Leu Val Leu Tyr
        35                  40                  45

Gly Asn Asn Arg Arg Pro Pro Gly Ile Pro Ala Arg Phe Ser Gly Ser
    50                  55                  60

His Ser Gly Asn Thr Gly Ser Leu Ile Ile Thr Gly Ala Gln Ala Glu
65                  70                  75                  80

Asp Glu Ala Glu Tyr His Cys Ala Ala Arg Asp Ser Ser Gly Asp His
                85                  90                  95

Val Val Phe Gly Gly Gly Thr Lys Val Thr Val Leu
            100                 105

<210> SEQ ID NO 78
<211> LENGTH: 11
<212> TYPE: PRT
<213> ORGANISM: Artificial Sequence
<220> FEATURE:
<223> OTHER INFORMATION: Homo sapiensIL330428 VL CDR1 PRT

<400> SEQUENCE: 78

Gln Gly Asp Thr Leu Arg Asn Tyr Tyr Ser Asn
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Homo sapiensIL330428 VL CDR2 PRT

<400> SEQUENCE: 79

Gly Asn Asn Arg Arg Pro Pro
1               5

<210> SEQ ID NO 80
<211> LENGTH: 11
<212> TYPE: PRT
<213> ORGANISM: Artificial Sequence
<220> FEATURE:
<223> OTHER INFORMATION: Homo sapiensIL330428 VL CDR3 PRT

<400> SEQUENCE: 80

Ala Ala Arg Asp Ser Ser Gly Asp His Val Val
1               5                   10

<210> SEQ ID NO 81
<211> LENGTH: 339
<212> TYPE: DNA
<213> ORGANISM: Artificial Sequence
<220> FEATURE:
<223> OTHER INFORMATION: Homo sapiensIL330065 VH DNA

<400> SEQUENCE: 81
gaggtccagc tggtgcagtc tggggctgag gtgaagaagc ctgggactgc agtgaagatc      60
tcctgcaagg cttctggata caccttcacc gactactaca ttcattgggt ccaacaggcc    120
cctggaaaag ggcttgagtg gatgggactt gttgatcctg aagacggtga aacaaaatac    180

```
gcagagaaat tccagggccg agtctccata accgcggaca cgtcgactga cacagcctac    240
atggagctga ggagcctgac atctgaggac acggccgtgt atttctgcac aatggggtgg    300
gctcagtggg gccgaggaac cctggtcacc gtctcgagt                           339
```

```
<210> SEQ ID NO 82
<211> LENGTH: 113
<212> TYPE: PRT
<213> ORGANISM: Artificial Sequence
<220> FEATURE:
<223> OTHER INFORMATION: Homo sapiensIL330065 VH PRT

<400> SEQUENCE: 82
```

Glu Val Gln Leu Val Gln Ser Gly Ala Glu Val Lys Lys Pro Gly Thr
1               5                   10                  15

Ala Val Lys Ile Ser Cys Lys Ala Ser Gly Tyr Thr Phe Thr Asp Tyr
            20                  25                  30

Tyr Ile His Trp Val Gln Gln Ala Pro Gly Lys Gly Leu Glu Trp Met
        35                  40                  45

Gly Leu Val Asp Pro Glu Asp Gly Glu Thr Lys Tyr Ala Glu Lys Phe
    50                  55                  60

Gln Gly Arg Val Ser Ile Thr Ala Asp Thr Ser Asp Thr Ala Tyr
65                  70                  75                  80

Met Glu Leu Arg Ser Leu Thr Ser Glu Asp Thr Ala Val Tyr Phe Cys
                85                  90                  95

Thr Met Gly Trp Ala Gln Trp Gly Arg Gly Thr Leu Val Thr Val Ser
            100                 105                 110

Ser

```
<210> SEQ ID NO 83
<211> LENGTH: 5
<212> TYPE: PRT
<213> ORGANISM: Artificial Sequence
<220> FEATURE:
<223> OTHER INFORMATION: Homo sapiensIL330065 VH CDR1 PRT

<400> SEQUENCE: 83
```

Asp Tyr Tyr Ile His
1               5

```
<210> SEQ ID NO 84
<211> LENGTH: 17
<212> TYPE: PRT
<213> ORGANISM: Artificial Sequence
<220> FEATURE:
<223> OTHER INFORMATION: Homo sapiensIL330065 VH CDR2 PRT

<400> SEQUENCE: 84
```

Leu Val Asp Pro Glu Asp Gly Glu Thr Lys Tyr Ala Glu Lys Phe Gln
1               5                   10                  15

Gly

```
<210> SEQ ID NO 85
<211> LENGTH: 4
<212> TYPE: PRT
<213> ORGANISM: Artificial Sequence
<220> FEATURE:
<223> OTHER INFORMATION: Homo sapiensIL330065 VH CDR3 PRT

<400> SEQUENCE: 85
```

Gly Trp Ala Gln

```
<210> SEQ ID NO 86
<211> LENGTH: 330
<212> TYPE: DNA
<213> ORGANISM: Artificial Sequence
<220> FEATURE:
<223> OTHER INFORMATION: Homo sapiensIL330065 VL DNA

<400> SEQUENCE: 86
cagtctgtgt tgacgcagcc gccctcagcg tctgggaccc ccgggcagag ggtcaccatc      60
tcttgttctg gaagcagctc caacatcgga agtaattatg tatactggta ccagcaggtc     120
ccaggaacgg cccccaaact cgtcatctat agggattttc agcggccctc aggggtccct     180
gaccgatttt ccggctccaa gtctggcaac tcagcctccc tggtcatcag tggcctccgg     240
tccgaggatg agggtgaata tgtctgtgca gcatgggatg acagcctgac tggtccaaga     300
ttcggcggag ggaccaaggt caccgtccta                                      330

<210> SEQ ID NO 87
<211> LENGTH: 110
<212> TYPE: PRT
<213> ORGANISM: Artificial Sequence
<220> FEATURE:
<223> OTHER INFORMATION: Homo sapiensIL330065 VL PRT

<400> SEQUENCE: 87

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Val Pro Gly Thr Ala Pro Lys Leu Val
        35                  40                  45

Ile Tyr Arg Asp Phe Gln Arg Pro Ser Gly Val Pro Asp Arg Phe Ser
    50                  55                  60

Gly Ser Lys Ser Gly Asn Ser Ala Ser Leu Val Ile Ser Gly Leu Arg
65                  70                  75                  80

Ser Glu Asp Glu Gly Glu Tyr Val Cys Ala Ala Trp Asp Asp Ser Leu
                85                  90                  95

Thr Gly Pro Arg Phe Gly Gly Gly Thr Lys Val Thr Val Leu
            100                 105                 110

<210> SEQ ID NO 88
<211> LENGTH: 13
<212> TYPE: PRT
<213> ORGANISM: Artificial Sequence
<220> FEATURE:
<223> OTHER INFORMATION: Homo sapiensIL330065 VL CDR1 PRT

<400> SEQUENCE: 88

Ser Gly Ser Ser Ser Asn Ile Gly Ser Asn Tyr Val Tyr
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Homo sapiensIL330065 VL CDR2 PRT

<400> SEQUENCE: 89

Arg Asp Phe Gln Arg Pro Ser
```

<210> SEQ ID NO 90
<211> LENGTH: 11
<212> TYPE: PRT
<213> ORGANISM: Artificial Sequence
<220> FEATURE:
<223> OTHER INFORMATION: Homo sapiensIL330065 VL CDR3 PRT

<400> SEQUENCE: 90

Ala Ala Trp Asp Asp Ser Leu Thr Gly Pro Arg
1               5                   10

<210> SEQ ID NO 91
<211> LENGTH: 393
<212> TYPE: DNA
<213> ORGANISM: Artificial Sequence
<220> FEATURE:
<223> OTHER INFORMATION: Homo sapiensIL330099 VH DNA

<400> SEQUENCE: 91
caggtacagc tgcagcagtc aggggctgag gtgaagaagc ctggggcctc agtgaaggtt      60
tcctgcaagg catctggata caccttcacc agcttctata tgaactgggt gcgacaggcc    120
cccggacaag ggcttgagtg gatgggaata atcagccctc gtggtggtac gacaagttac    180
gcacagaact tccagggcag agtcaccatg accaggaca cgtccacaag cacagtctac     240
atggagctga gtggcctgag atctgacgac acggccgtct attactgtgc gacagagtcc    300
ttttactatg gtcggggac ttattctggc gattattacc tctactccgg tatggccgac     360
tggggcaaag gaaccctggt caccgtctcc tca                                 393

<210> SEQ ID NO 92
<211> LENGTH: 131
<212> TYPE: PRT
<213> ORGANISM: Artificial Sequence
<220> FEATURE:
<223> OTHER INFORMATION: Homo sapiensIL330099 VH PRT

<400> SEQUENCE: 92

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Tyr Met Asn Trp Val Arg Gln Ala Pro Gly Gln Gly Leu Glu Trp Met
        35                  40                  45

Gly Ile Ile Ser Pro Arg Gly Gly Thr Thr Ser Tyr Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Gly Leu Arg Ser Asp Asp Thr Ala Val Tyr Tyr Cys
                85                  90                  95

Ala Thr Glu Ser Phe Tyr Tyr Gly Ser Gly Thr Tyr Ser Gly Asp Tyr
            100                 105                 110

Tyr Leu Tyr Ser Gly Met Ala Asp Trp Gly Lys Gly Thr Leu Val Thr
        115                 120                 125

Val Ser Ser
    130

<210> SEQ ID NO 93
<211> LENGTH: 5

```
<212> TYPE: PRT
<213> ORGANISM: Artificial Sequence
<220> FEATURE:
<223> OTHER INFORMATION: Homo sapiensIL330099 VH CDR1 PRT

<400> SEQUENCE: 93

Ser Phe Tyr Met Asn
1               5

<210> SEQ ID NO 94
<211> LENGTH: 17
<212> TYPE: PRT
<213> ORGANISM: Artificial Sequence
<220> FEATURE:
<223> OTHER INFORMATION: Homo sapiensIL330099 VH CDR2 PRT

<400> SEQUENCE: 94

Ile Ile Ser Pro Arg Gly Gly Thr Thr Ser Tyr Ala Gln Asn Phe Gln
1               5                   10                  15

Gly

<210> SEQ ID NO 95
<211> LENGTH: 22
<212> TYPE: PRT
<213> ORGANISM: Artificial Sequence
<220> FEATURE:
<223> OTHER INFORMATION: Homo sapiensIL330099 VH CDR3 PRT

<400> SEQUENCE: 95

Glu Ser Phe Tyr Tyr Gly Ser Gly Thr Tyr Ser Gly Asp Tyr Tyr Leu
1               5                   10                  15

Tyr Ser Gly Met Ala Asp
            20

<210> SEQ ID NO 96
<211> LENGTH: 324
<212> TYPE: DNA
<213> ORGANISM: Artificial Sequence
<220> FEATURE:
<223> OTHER INFORMATION: Homo sapiensIL330099 VL DNA

<400> SEQUENCE: 96
tcgtctgagc tgactcagga ccctgctgtg tctgcggcct tgggacagac agtcaggatc      60
acatgccaag agacagcct cagaagctat tatgcaagct ggtaccagca gaagccagga     120
caggcccctg tacttgtcat ctatggtaaa acgaccggc cctcagggat cccagaccga     180
ttctctggct ccagctcagg aaacacagct tccttgacca tcactgggc tcaggcggaa     240 gatgaggctg actattactg taactcccgg gacagcagtg gtaaccatgt ggtattcggc     300
ggagggacca agctgaccgt ccta                                            324

<210> SEQ ID NO 97
<211> LENGTH: 108
<212> TYPE: PRT
<213> ORGANISM: Artificial Sequence
<220> FEATURE:
<223> OTHER INFORMATION: Homo sapiensIL330099 VL PRT

<400> SEQUENCE: 97

Ser Ser Glu Leu Thr Gln Asp Pro Ala Val Ser Ala Ala Leu Gly Gln
1               5                   10                  15

Thr Val Arg Ile Thr Cys Gln Gly Asp Ser Leu Arg Ser Tyr Tyr Ala
            20                  25                  30
```

```
Ser Trp Tyr Gln Gln Lys Pro Gly Gln Ala Pro Val Leu Val Ile Tyr
            35                  40                  45

Gly Lys Asn Asp Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu
            100                 105

<210> SEQ ID NO 98
<211> LENGTH: 11
<212> TYPE: PRT
<213> ORGANISM: Artificial Sequence
<220> FEATURE:
<223> OTHER INFORMATION: Homo sapiensIL330099 VL CDR1 PRT

<400> SEQUENCE: 98

Gln Gly Asp Ser Leu Arg Ser Tyr Tyr Ala Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Homo sapiensIL330099 VL CDR2 PRT

<400> SEQUENCE: 99

Gly Lys Asn Asp Arg Pro Ser
1               5

<210> SEQ ID NO 100
<211> LENGTH: 11
<212> TYPE: PRT
<213> ORGANISM: Artificial Sequence
<220> FEATURE:
<223> OTHER INFORMATION: Homo sapiensIL330099 VL CDR3 PRT

<400> SEQUENCE: 100

Asn Ser Arg Asp Ser Ser Gly Asn His Val Val
1               5                   10

<210> SEQ ID NO 101
<211> LENGTH: 351
<212> TYPE: DNA
<213> ORGANISM: Artificial Sequence
<220> FEATURE:
<223> OTHER INFORMATION: Homo sapiensIL330101 VH DNA

<400> SEQUENCE: 101
gaggtgcagc tgttggagtc tgggggaggc ttggtacagc ctgggggtc cctgagactc      60 tcctgtgcag cctctggatt caccttagc agctatgcca tgagctgggt ccgccaggct    120
ccagggaagg ggctggagtg gtctcagct attagtggta gtggtggtag cacatactac    180
gcagactccg tgaagggccg gttcaccatc tccagagaca attccaagaa cacgctgtat   240
ctgcaaatga acagcctgag agccgaggac acggccgtgt attactgtgt gagagtggtg   300
gctggctact ttgactcctg gggccgggga accctggtca ccgtctcgag t            351

<210> SEQ ID NO 102
<211> LENGTH: 117
```

```
<212> TYPE: PRT
<213> ORGANISM: Artificial Sequence
<220> FEATURE:
<223> OTHER INFORMATION: Homo sapiensIL330101 VH PRT

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Val Ala Gly Tyr Phe Asp Ser Trp Gly Arg Gly Thr Leu
            100                 105                 110

Val Thr Val Ser Ser
            115

<210> SEQ ID NO 103
<211> LENGTH: 5
<212> TYPE: PRT
<213> ORGANISM: Artificial Sequence
<220> FEATURE:
<223> OTHER INFORMATION: Homo sapiensIL330101 VH CDR1 PRT

<400> SEQUENCE: 103

Ser Tyr Ala Met Ser
1               5

<210> SEQ ID NO 104
<211> LENGTH: 17
<212> TYPE: PRT
<213> ORGANISM: Artificial Sequence
<220> FEATURE:
<223> OTHER INFORMATION: Homo sapiensIL330101 VH CDR2 PRT

<400> SEQUENCE: 104

Ala Ile Ser Gly Ser Gly Gly Ser Thr Tyr Tyr Ala Asp Ser Val Lys
1               5                   10                  15

Gly

<210> SEQ ID NO 105
<211> LENGTH: 8
<212> TYPE: PRT
<213> ORGANISM: Artificial Sequence
<220> FEATURE:
<223> OTHER INFORMATION: Homo sapiensIL330101 VH CDR3 PRT

<400> SEQUENCE: 105

Val Val Ala Gly Tyr Phe Asp Ser
1               5

<210> SEQ ID NO 106
<211> LENGTH: 324
<212> TYPE: DNA
<213> ORGANISM: Artificial Sequence
<220> FEATURE:
<223> OTHER INFORMATION: Homo sapiensIL330101 VL DNA
```

<400> SEQUENCE: 106

```
tcctatgtgc tgactcagcc accctcggtg tcagtgtccc caggacagac ggccaggatc    60
acctgctctg gcgatgcttt gccaaagcaa tatgctcatt ggtaccagca gaagccaggc   120
caggcccctg cactggtgat atataaagac actgagaggc cctcaggat tcctgagcga   180
ttctctgggt ccagctcagg gacaacagtc acgctgacca tcagtggagt ccaggcagaa   240
gatgaagctg actattactg tcaatcagca gacagtagtg gtgcttcacg ggtgttcggc   300
ggagggacca aggtcaccgt ccta                                          324
```

<210> SEQ ID NO 107
<211> LENGTH: 108
<212> TYPE: PRT
<213> ORGANISM: Artificial Sequence
<220> FEATURE:
<223> OTHER INFORMATION: Homo sapiensIL330101 VL PRT

<400> SEQUENCE: 107

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Ala Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ala Ser
                85                  90                  95

Arg Val Phe Gly Gly Gly Thr Lys Val Thr Val Leu
            100                 105

<210> SEQ ID NO 108
<211> LENGTH: 11
<212> TYPE: PRT
<213> ORGANISM: Artificial Sequence
<220> FEATURE:
<223> OTHER INFORMATION: Homo sapiensIL330101 VL CDR1 PRT

<400> SEQUENCE: 108

Ser Gly Asp Ala Leu Pro Lys Gln Tyr Ala His
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Homo sapiensIL330101 VL CDR2 PRT

<400> SEQUENCE: 109

Lys Asp Thr Glu Arg Pro Ser
1               5

<210> SEQ ID NO 110
<211> LENGTH: 11
<212> TYPE: PRT
<213> ORGANISM: Artificial Sequence
<220> FEATURE:
<223> OTHER INFORMATION: Homo sapiensIL330101 VL CDR3 PRT

<400> SEQUENCE: 110

Gln Ser Ala Asp Ser Ser Gly Ala Ser Arg Val
1               5                   10

<210> SEQ ID NO 111
<211> LENGTH: 351
<212> TYPE: DNA
<213> ORGANISM: Artificial Sequence
<220> FEATURE:
<223> OTHER INFORMATION: Homo sapiensIL330101_fgl VH DNA

<400> SEQUENCE: 111
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgt gagagtggtg   300
gctggctact ttgactcctg gggccgggga accctggtca ccgtctcgag t            351

<210> SEQ ID NO 112
<211> LENGTH: 117
<212> TYPE: PRT
<213> ORGANISM: Artificial Sequence
<220> FEATURE:
<223> OTHER INFORMATION: Homo sapiensIL330101_fgl VH PRT

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Val Ala Gly Tyr Phe Asp Ser Trp Gly Arg Gly Thr Leu
            100                 105                 110

Val Thr Val Ser Ser
        115

<210> SEQ ID NO 113
<211> LENGTH: 5
<212> TYPE: PRT
<213> ORGANISM: Artificial Sequence
<220> FEATURE:
<223> OTHER INFORMATION: Homo sapiensIL330101_fgl VH CDR1 PRT

<400> SEQUENCE: 113

Ser Tyr Ala Met Ser
1               5

<210> SEQ ID NO 114
<211> LENGTH: 17
<212> TYPE: PRT

<213> ORGANISM: Artificial Sequence
<220> FEATURE:
<223> OTHER INFORMATION: Homo sapiensIL330101_fgl VH CDR2 PRT

<400> SEQUENCE: 114

Ala Ile Ser Gly Ser Gly Gly Ser Thr Tyr Tyr Ala Asp Ser Val Lys
1               5                   10                  15

Gly

<210> SEQ ID NO 115
<211> LENGTH: 8
<212> TYPE: PRT
<213> ORGANISM: Artificial Sequence
<220> FEATURE:
<223> OTHER INFORMATION: Homo sapiensIL330101_fgl VH CDR3 PRT

<400> SEQUENCE: 115

Val Val Ala Gly Tyr Phe Asp Ser
1               5

<210> SEQ ID NO 116
<211> LENGTH: 324
<212> TYPE: DNA
<213> ORGANISM: Artificial Sequence
<220> FEATURE:
<223> OTHER INFORMATION: Homo sapiensIL330101_fgl VL DNA

<400> SEQUENCE: 116

```
tcctatgagc tgatgcagcc accctcggtg tcagtgtccc caggacagac ggccaggatc      60
acctgctctg gcgatgcttt gccaaagcaa tatgctcatt ggtaccagca gaagccaggc     120
caggcccctg tgctggtgat atataaagac actgagaggc cctcagggat tcctgagcga     180
ttctctgggt ccagctcagg gacaacagtc acgctgacca tcagtggagt ccaggcagaa     240
gatgaagctg actattactg tcaatcagca gacagtagtg gtgcttcacg ggtgttcggc     300
ggagggacca agctgaccgt ccta                                            324
```

<210> SEQ ID NO 117
<211> LENGTH: 108
<212> TYPE: PRT
<213> ORGANISM: Artificial Sequence
<220> FEATURE:
<223> OTHER INFORMATION: Homo sapiensIL330101_fgl VL PRT

<400> SEQUENCE: 117

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

His Trp Tyr Gln Gln Lys Pro Gly Gln Ala Pro Val Leu Val Ile Tyr
            35                  40                  45

Lys Asp Thr Glu Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ala Ser
                85                  90                  95

Arg Val Phe Gly Gly Gly Thr Lys Leu Thr Val Leu
                100                 105

<210> SEQ ID NO 118

-continued

<210> SEQ ID NO 118
<211> LENGTH: 11
<212> TYPE: PRT
<213> ORGANISM: Artificial Sequence
<220> FEATURE:
<223> OTHER INFORMATION: Homo sapiensIL330101_fgl VL CDR1 PRT

<400> SEQUENCE: 118

Ser Gly Asp Ala Leu Pro Lys Gln Tyr Ala His
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Homo sapiensIL330101_fgl VL CDR2 PRT

<400> SEQUENCE: 119

Lys Asp Thr Glu Arg Pro Ser
1               5

<210> SEQ ID NO 120
<211> LENGTH: 11
<212> TYPE: PRT
<213> ORGANISM: Artificial Sequence
<220> FEATURE:
<223> OTHER INFORMATION: Homo sapiensIL330101_fgl VL CDR3 PRT

<400> SEQUENCE: 120

Gln Ser Ala Asp Ser Ser Gly Ala Ser Arg Val
1               5                   10

<210> SEQ ID NO 121
<211> LENGTH: 357
<212> TYPE: DNA
<213> ORGANISM: Artificial Sequence
<220> FEATURE:
<223> OTHER INFORMATION: Homo sapiensIL330107 VH DNA

<400> SEQUENCE: 121
cagatgcagc tggtgcagtc tgggggaggc gtggtccagc ctggggggtc cctgagactc      60
tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtat attactgtgc gaaaccgttc    300
cccagctact ggtacttcga tctctggggc aaaggcaccc tggtcaccgt ctcgagt       357

<210> SEQ ID NO 122
<211> LENGTH: 119
<212> TYPE: PRT
<213> ORGANISM: Artificial Sequence
<220> FEATURE:
<223> OTHER INFORMATION: Homo sapiensIL330107 VH PRT

<400> SEQUENCE: 122

Gln Met Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Pro Phe Pro Ser Tyr Trp Tyr Phe Asp Leu Trp Gly Lys Gly
                100                 105                 110

Thr Leu Val Thr Val Ser Ser
            115
```

```
<210> SEQ ID NO 123
<211> LENGTH: 5
<212> TYPE: PRT
<213> ORGANISM: Artificial Sequence
<220> FEATURE:
<223> OTHER INFORMATION: Homo sapiensIL330107 VH CDR1 PRT

<400> SEQUENCE: 123

Ser Tyr Ala Met Ser
1               5
```

```
<210> SEQ ID NO 124
<211> LENGTH: 17
<212> TYPE: PRT
<213> ORGANISM: Artificial Sequence
<220> FEATURE:
<223> OTHER INFORMATION: Homo sapiensIL330107 VH CDR2 PRT

<400> SEQUENCE: 124

Ala Ile Ser Gly Ser Gly Gly Ser Thr Tyr Tyr Ala Asp Ser Val Lys
1               5                   10                  15

Gly
```

```
<210> SEQ ID NO 125
<211> LENGTH: 10
<212> TYPE: PRT
<213> ORGANISM: Artificial Sequence
<220> FEATURE:
<223> OTHER INFORMATION: Homo sapiensIL330107 VH CDR3 PRT

<400> SEQUENCE: 125

Pro Phe Pro Ser Tyr Trp Tyr Phe Asp Leu
1               5                   10
```

```
<210> SEQ ID NO 126
<211> LENGTH: 324
<212> TYPE: DNA
<213> ORGANISM: Artificial Sequence
<220> FEATURE:
<223> OTHER INFORMATION: Homo sapiensIL330107 VL DNA

<400> SEQUENCE: 126
tcctatgtgc tgactcagcc accctcggtg tcagtgtccc caggacagac ggccaggatc      60
acctgctctg gagatgcatt gccaaagcaa tatgcttatt ggtaccagca gaagccaggc     120
caggcccctg tgctggtgat atataaagac agtgagaggc cctcagggat ccctgagcga     180
ttctctggct ccagctcagg gacaacagtc acgttgacca tcagtggagt ccaggcagaa     240
gacgaggctg actattactg tcaatcagca gacagcagtg gtacttatcg ggtgttcggc     300
ggagggaccc agctcaccgt ttta                                            324
```

```
<210> SEQ ID NO 127
```

```
<211> LENGTH: 108
<212> TYPE: PRT
<213> ORGANISM: Artificial Sequence
<220> FEATURE:
<223> OTHER INFORMATION: Homo sapiensIL330107 VL PRT

<400> SEQUENCE: 127

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Arg Val Phe Gly Gly Gly Thr Gln Leu Thr Val Leu
            100                 105

<210> SEQ ID NO 128
<211> LENGTH: 11
<212> TYPE: PRT
<213> ORGANISM: Artificial Sequence
<220> FEATURE:
<223> OTHER INFORMATION: Homo sapiensIL330107 VL CDR1 PRT

<400> SEQUENCE: 128

Ser Gly Asp Ala Leu Pro Lys Gln Tyr Ala Tyr
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Homo sapiensIL330107 VL CDR2 PRT

<400> SEQUENCE: 129

Lys Asp Ser Glu Arg Pro Ser
1               5

<210> SEQ ID NO 130
<211> LENGTH: 11
<212> TYPE: PRT
<213> ORGANISM: Artificial Sequence
<220> FEATURE:
<223> OTHER INFORMATION: Homo sapiensIL330107 VL CDR3 PRT

<400> SEQUENCE: 130

Gln Ser Ala Asp Ser Ser Gly Thr Tyr Arg Val
1               5                   10

<210> SEQ ID NO 131
<211> LENGTH: 363
<212> TYPE: DNA
<213> ORGANISM: Artificial Sequence
<220> FEATURE:
<223> OTHER INFORMATION: Homo sapiensIL330149 VH DNA

<400> SEQUENCE: 131
gaggtgcagc tgttggagtc tgggggaggc ttggtacagc ctggggggtc cctgagactc      60
```

```
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgt aagaaccttg    300
gcttacagca cgagctggtt cttgactac tggggcaggg gaaccctggt caccgtctcg    360
agt                                                                  363
```

<210> SEQ ID NO 132
<211> LENGTH: 121
<212> TYPE: PRT
<213> ORGANISM: Artificial Sequence
<220> FEATURE:
<223> OTHER INFORMATION: Homo sapiensIL330149 VH PRT

<400> SEQUENCE: 132

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Thr Leu Ala Tyr Ser Thr Ser Trp Phe Phe Asp Tyr Trp Gly
            100                 105                 110

Arg Gly Thr Leu Val Thr Val Ser Ser
        115                 120
```

<210> SEQ ID NO 133
<211> LENGTH: 5
<212> TYPE: PRT
<213> ORGANISM: Artificial Sequence
<220> FEATURE:
<223> OTHER INFORMATION: Homo sapiensIL330149 VH CDR1 PRT

<400> SEQUENCE: 133

```
Ser Tyr Ala Met Ser
1               5
```

<210> SEQ ID NO 134
<211> LENGTH: 17
<212> TYPE: PRT
<213> ORGANISM: Artificial Sequence
<220> FEATURE:
<223> OTHER INFORMATION: Homo sapiensIL330149 VH CDR2 PRT

<400> SEQUENCE: 134

```
Ala Ile Ser Gly Ser Gly Gly Ser Thr Tyr Tyr Ala Asp Ser Val Lys
1               5                   10                  15

Gly
```

<210> SEQ ID NO 135
<211> LENGTH: 12
<212> TYPE: PRT

<213> ORGANISM: Artificial Sequence
<220> FEATURE:
<223> OTHER INFORMATION: Homo sapiensIL330149 VH CDR3 PRT

<400> SEQUENCE: 135

Thr Leu Ala Tyr Ser Thr Ser Trp Phe Phe Asp Tyr
1               5                   10

<210> SEQ ID NO 136
<211> LENGTH: 318
<212> TYPE: DNA
<213> ORGANISM: Artificial Sequence
<220> FEATURE:
<223> OTHER INFORMATION: Homo sapiensIL330149 VL DNA

<400> SEQUENCE: 136
tcctatgagc tgactcagcc acccgcggtg tcagtgtccc caggacaaac ggccaggatc      60
acctgctctg gagatgcatt gccaaaaaaa tatgcttatt ggtaccagca gaagtcaggc     120
caggcccctg tgctggtcat ctatgaggac gccaaacgac cctccgggat ccctgagaga     180
ttctctggct ccagctcagg gacaatggcc accttgactg taagtggggc ccaggtggag     240
gatgaagctg actactactg ttactcaaca gacagcagtg gtcctgtatt cggcggaggg     300
accaagctga ccgtccta                                                   318

<210> SEQ ID NO 137
<211> LENGTH: 106
<212> TYPE: PRT
<213> ORGANISM: Artificial Sequence
<220> FEATURE:
<223> OTHER INFORMATION: Homo sapiensIL330149 VL PRT

<400> SEQUENCE: 137

Ser Tyr Glu Leu Thr Gln Pro Pro Ala Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ala Lys Arg Pro Ser Gly Ile Pro Glu Arg Phe Ser Gly Ser
    50                  55                  60

Ser Ser Gly Thr Met Ala Thr Leu Thr Val Ser Gly Ala Gln Val Glu
65                  70                  75                  80

Asp Glu Ala Asp Tyr Tyr Cys Tyr Ser Thr Asp Ser Ser Gly Pro Val
                85                  90                  95

Phe Gly Gly Gly Thr Lys Leu Thr Val Leu
            100                 105

<210> SEQ ID NO 138
<211> LENGTH: 11
<212> TYPE: PRT
<213> ORGANISM: Artificial Sequence
<220> FEATURE:
<223> OTHER INFORMATION: Homo sapiensIL330149 VL CDR1 PRT

<400> SEQUENCE: 138

Ser Gly Asp Ala Leu Pro Lys Lys Tyr Ala Tyr
1               5                   10

<210> SEQ ID NO 139
<211> LENGTH: 7
<212> TYPE: PRT

<213> ORGANISM: Artificial Sequence
<220> FEATURE:
<223> OTHER INFORMATION: Homo sapiensIL330149 VL CDR2 PRT

<400> SEQUENCE: 139

Glu Asp Ala Lys Arg Pro Ser
1               5

<210> SEQ ID NO 140
<211> LENGTH: 9
<212> TYPE: PRT
<213> ORGANISM: Artificial Sequence
<220> FEATURE:
<223> OTHER INFORMATION: Homo sapiensIL330149 VL CDR3 PRT

<400> SEQUENCE: 140

Tyr Ser Thr Asp Ser Ser Gly Pro Val
1               5

<210> SEQ ID NO 141
<211> LENGTH: 345
<212> TYPE: DNA
<213> ORGANISM: Artificial Sequence
<220> FEATURE:
<223> OTHER INFORMATION: Homo sapiensIL330180 VH DNA

<400> SEQUENCE: 141

```
caggtacagc tgcagcagtc aggggctgag gtgaagaagc tggggcctc agtgaaggtc      60 tcctgcaagg cttctggata caccttcacc ggctactata tgcactgggt gcgacaggcc    120
cctggacaag gcttgagtg gatgggatgg atcaaccctaa acagtggtgg cacaaactat    180
gcacagaagt tcagggcag agtcaccatg accagggaca cgtccatcag cacagcctac    240
atggagctga gcaggctgag atctgacgac acggccgtgt attactgtgc gagacggaac    300
gcttttgata tctggggcaa gggaaccctg gtcaccgtct cgagt                    345
```

<210> SEQ ID NO 142
<211> LENGTH: 115
<212> TYPE: PRT
<213> ORGANISM: Artificial Sequence
<220> FEATURE:
<223> OTHER INFORMATION: Homo sapiensIL330180 VH PRT

<400> SEQUENCE: 142

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Asn Ala Phe Asp Ile Trp Gly Lys Gly Thr Leu Val Thr
            100                 105                 110

Val Ser Ser
        115

```
<210> SEQ ID NO 143
<211> LENGTH: 5
<212> TYPE: PRT
<213> ORGANISM: Artificial Sequence
<220> FEATURE:
<223> OTHER INFORMATION: Homo sapiensIL330180 VH CDR1 PRT

<400> SEQUENCE: 143

Gly Tyr Tyr Met His
1               5

<210> SEQ ID NO 144
<211> LENGTH: 17
<212> TYPE: PRT
<213> ORGANISM: Artificial Sequence
<220> FEATURE:
<223> OTHER INFORMATION: Homo sapiensIL330180 VH CDR2 PRT

<400> SEQUENCE: 144

Trp Ile Asn Pro Asn Ser Gly Gly Thr Asn Tyr Ala Gln Lys Phe Gln
1               5                   10                  15

Gly

<210> SEQ ID NO 145
<211> LENGTH: 6
<212> TYPE: PRT
<213> ORGANISM: Artificial Sequence
<220> FEATURE:
<223> OTHER INFORMATION: Homo sapiensIL330180 VH CDR3 PRT

<400> SEQUENCE: 145

Arg Asn Ala Phe Asp Ile
1               5

<210> SEQ ID NO 146
<211> LENGTH: 330
<212> TYPE: DNA
<213> ORGANISM: Artificial Sequence
<220> FEATURE:
<223> OTHER INFORMATION: Homo sapiensIL330180 VL DNA

<400> SEQUENCE: 146
cagcctgtgc tgactcagcc accctcggtg tctgaagccc ccaggcagag ggtcaccatc      60
tcctgttctg gaagcagctc aacatcgga aataatgctg taaactggta ccagcagctc     120
ccaggaacgg ccccaaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tggttgggtg    300
ttcggcggag ggaccaaggt caacgtccta                                     330

<210> SEQ ID NO 147
<211> LENGTH: 110
<212> TYPE: PRT
<213> ORGANISM: Artificial Sequence
<220> FEATURE:
<223> OTHER INFORMATION: Homo sapiensIL330180 VL PRT

<400> SEQUENCE: 147

Gln Pro Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
```

```
                35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Val Asn Val Leu
            100                 105                 110
```

<210> SEQ ID NO 148
<211> LENGTH: 13
<212> TYPE: PRT
<213> ORGANISM: Artificial Sequence
<220> FEATURE:
<223> OTHER INFORMATION: Homo sapiensIL330180 VL CDR1 PRT

<400> SEQUENCE: 148

```
Ser Gly Ser Ser Ser Asn Ile Gly Asn Asn Ala Val Asn
1               5                   10
```

<210> SEQ ID NO 149
<211> LENGTH: 7
<212> TYPE: PRT
<213> ORGANISM: Artificial Sequence
<220> FEATURE:
<223> OTHER INFORMATION: Homo sapiensIL330180 VL CDR2 PRT

<400> SEQUENCE: 149

```
Arg Asn Asn Gln Arg Pro Ser
1               5
```

<210> SEQ ID NO 150
<211> LENGTH: 11
<212> TYPE: PRT
<213> ORGANISM: Artificial Sequence
<220> FEATURE:
<223> OTHER INFORMATION: Homo sapiensIL330180 VL CDR3 PRT

<400> SEQUENCE: 150

```
Ala Ala Trp Asp Asp Ser Leu Ser Gly Trp Val
1               5                   10
```

<210> SEQ ID NO 151
<211> LENGTH: 351
<212> TYPE: DNA
<213> ORGANISM: Artificial Sequence
<220> FEATURE:
<223> OTHER INFORMATION: Homo sapiensIL330259 VH DNA

<400> SEQUENCE: 151

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagcg agcacccct ggcagggtag cacatactac        180
gcagactccg tgaagggccg gttcaccatc tccagagaca attccaagaa cacgctgtat     240
ctgcaaatga acagcctgag agccgaggac acggccgtgt attactgtgt gagagtggtg     300
gctggctact tgactcctg gggccgggga accctggtca ccgtctcgag t              351
```

<210> SEQ ID NO 152
<211> LENGTH: 117
<212> TYPE: PRT

-continued

```
<213> ORGANISM: Artificial Sequence
<220> FEATURE:
<223> OTHER INFORMATION: Homo sapiensIL330259 VH PRT

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Val Ala Gly Tyr Phe Asp Ser Trp Gly Arg Gly Thr Leu
            100                 105                 110

Val Thr Val Ser Ser
        115

<210> SEQ ID NO 153
<211> LENGTH: 5
<212> TYPE: PRT
<213> ORGANISM: Artificial Sequence
<220> FEATURE:
<223> OTHER INFORMATION: Homo sapiensIL330259 VH CDR1 PRT

<400> SEQUENCE: 153

Ser Tyr Ala Met Ser
1               5

<210> SEQ ID NO 154
<211> LENGTH: 17
<212> TYPE: PRT
<213> ORGANISM: Artificial Sequence
<220> FEATURE:
<223> OTHER INFORMATION: Homo sapiensIL330259 VH CDR2 PRT

<400> SEQUENCE: 154

Ala Ser Thr Pro Trp Gln Gly Ser Thr Tyr Tyr Ala Asp Ser Val Lys
1               5                   10                  15

Gly

<210> SEQ ID NO 155
<211> LENGTH: 8
<212> TYPE: PRT
<213> ORGANISM: Artificial Sequence
<220> FEATURE:
<223> OTHER INFORMATION: Homo sapiensIL330259 VH CDR3 PRT

<400> SEQUENCE: 155

Val Val Ala Gly Tyr Phe Asp Ser
1               5

<210> SEQ ID NO 156
<211> LENGTH: 324
<212> TYPE: DNA
<213> ORGANISM: Artificial Sequence
<220> FEATURE:
<223> OTHER INFORMATION: Homo sapiensIL330259 VL DNA
```

-continued

<400> SEQUENCE: 156

```
tcctatgtgc tgactcagcc accctcggtg tcagtgtccc caggacagac ggccaggatc    60
acctgctctg gcgatgcttt gccaaagcaa tatgctcatt ggtaccagca gaagccaggc   120
caggcccctg cactggtgat atataaagac actgagaggc cctcagggat tcctgagcga   180
ttctctgggt ccagctcagg gacaacagtc acgctgacca tcagtggagt ccaggcagaa   240
gatgaagctg actattactg tcaatcagca gacagtagtg gtgcttcacg ggtgttcggc   300
ggagggacca aggtcaccgt ccta                                          324
```

<210> SEQ ID NO 157
<211> LENGTH: 108
<212> TYPE: PRT
<213> ORGANISM: Artificial Sequence
<220> FEATURE:
<223> OTHER INFORMATION: Homo sapiensIL330259 VL PRT

<400> SEQUENCE: 157

```
Ser Tyr Val Leu Thr Gln Pro Pro Ser Val Ser Val Ser Pro Gly Gln
1               5                   10                  15
Thr Ala Arg Ile Thr Cys Ser Gly Asp Ala Leu Pro Lys Gln Tyr Ala
            20                  25                  30
His Trp Tyr Gln Gln Lys Pro Gly Gln Ala Pro Ala Leu Val Ile Tyr
        35                  40                  45
Lys Asp Thr Glu Arg Pro Ser Gly Ile Pro Glu Arg Phe Ser Gly Ser
    50                  55                  60
Ser Ser Gly Thr Thr Val Thr Leu Thr Ile Ser Gly Val Gln Ala Glu
65                  70                  75                  80
Asp Glu Ala Asp Tyr Tyr Cys Gln Ser Ala Asp Ser Ser Gly Ala Ser
                85                  90                  95
Arg Val Phe Gly Gly Gly Thr Lys Val Thr Val Leu
            100                 105
```

<210> SEQ ID NO 158
<211> LENGTH: 11
<212> TYPE: PRT
<213> ORGANISM: Artificial Sequence
<220> FEATURE:
<223> OTHER INFORMATION: Homo sapiensIL330259 VL CDR1 PRT

<400> SEQUENCE: 158

```
Ser Gly Asp Ala Leu Pro Lys Gln Tyr Ala His
1               5                   10
```

<210> SEQ ID NO 159
<211> LENGTH: 7
<212> TYPE: PRT
<213> ORGANISM: Artificial Sequence
<220> FEATURE:
<223> OTHER INFORMATION: Homo sapiensIL330259 VL CDR2 PRT

<400> SEQUENCE: 159

```
Lys Asp Thr Glu Arg Pro Ser
1               5
```

<210> SEQ ID NO 160
<211> LENGTH: 11
<212> TYPE: PRT
<213> ORGANISM: Artificial Sequence
<220> FEATURE:
<223> OTHER INFORMATION: Homo sapiensIL330259 VL CDR3 PRT

<400> SEQUENCE: 160

Gln Ser Ala Asp Ser Ser Gly Ala Ser Arg Val
1               5                   10

<210> SEQ ID NO 161
<211> LENGTH: 351
<212> TYPE: DNA
<213> ORGANISM: Artificial Sequence
<220> FEATURE:
<223> OTHER INFORMATION: Homo sapiensIL330259_fgl VH DNA

<400> SEQUENCE: 161

```
gaggtgcagc tgttggagtc tgggggaggc ttggtacagc ctgggggtc cctgagactc      60
tcctgtgcag cctctggatt caccttagc agctatgcca tgagctgggt ccgccaggct     120
ccagggaagg gctggagtg gtctcagcg agcacccct ggcagggtag cacatactac       180
gcagactccg tgaagggccg gttcaccatc tccagagaca attccaagaa cacgctgtat    240
ctgcaaatga acagcctgag agccgaggac acggccgtgt attactgtgt gagagtggtg    300
gctggctact ttgactcctg gggccgggga accctggtca ccgtctcgag t             351
```

<210> SEQ ID NO 162
<211> LENGTH: 117
<212> TYPE: PRT
<213> ORGANISM: Artificial Sequence
<220> FEATURE:
<223> OTHER INFORMATION: Homo sapiensIL330259_fgl VH PRT

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Val Ala Gly Tyr Phe Asp Ser Trp Gly Arg Gly Thr Leu
            100                 105                 110

Val Thr Val Ser Ser
        115

<210> SEQ ID NO 163
<211> LENGTH: 5
<212> TYPE: PRT
<213> ORGANISM: Artificial Sequence
<220> FEATURE:
<223> OTHER INFORMATION: Homo sapiensIL330259_fgl VH CDR1 PRT

<400> SEQUENCE: 163

Ser Tyr Ala Met Ser
1               5

<210> SEQ ID NO 164
<211> LENGTH: 17
<212> TYPE: PRT
<213> ORGANISM: Artificial Sequence
<220> FEATURE:
<223> OTHER INFORMATION: Homo sapiensIL330259_fgl VH CDR2 PRT

<400> SEQUENCE: 164

Ala Ser Thr Pro Trp Gln Gly Ser Thr Tyr Tyr Ala Asp Ser Val Lys
1               5                   10                  15

Gly

<210> SEQ ID NO 165
<211> LENGTH: 8
<212> TYPE: PRT
<213> ORGANISM: Artificial Sequence
<220> FEATURE:
<223> OTHER INFORMATION: Homo sapiensIL330259_fgl VH CDR3 PRT

<400> SEQUENCE: 165

Val Val Ala Gly Tyr Phe Asp Ser
1               5

<210> SEQ ID NO 166
<211> LENGTH: 324
<212> TYPE: DNA
<213> ORGANISM: Artificial Sequence
<220> FEATURE:
<223> OTHER INFORMATION: Homo sapiensIL330259_fgl VL DNA

<400> SEQUENCE: 166
tcctatgagc tgatgcagcc accctcggtg tcagtgtccc caggacagac ggccaggatc      60
acctgctctg gcgatgcttt gccaaagcaa tatgctcatt ggtaccagca gaagccaggc     120
caggcccctg tgctggtgat atataaagac actgagaggc cctcagggat tcctgagcga     180
ttctctgggt ccagctcagg gacaacagtc acgctgacca tcagtggagt ccaggcagaa     240
gatgaagctg actattactg tcaatcagca gacagtagtg gtgcttcacg ggtgttcggc     300
ggagggacca agctgaccgt ccta                                            324

<210> SEQ ID NO 167
<211> LENGTH: 108
<212> TYPE: PRT
<213> ORGANISM: Artificial Sequence
<220> FEATURE:
<223> OTHER INFORMATION: Homo sapiensIL330259_fgl VL PRT

<400> SEQUENCE: 167

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ala Ser
                85                  90                  95

Arg Val Phe Gly Gly Gly Thr Lys Leu Thr Val Leu
            100                 105

<210> SEQ ID NO 168
<211> LENGTH: 11

-continued

```
<212> TYPE: PRT
<213> ORGANISM: Artificial Sequence
<220> FEATURE:
<223> OTHER INFORMATION: Homo sapiensIL330259_fg1 VL CDR1 PRT

<400> SEQUENCE: 168

Ser Gly Asp Ala Leu Pro Lys Gln Tyr Ala His
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Homo sapiensIL330259_fg1 VL CDR2 PRT

<400> SEQUENCE: 169

Lys Asp Thr Glu Arg Pro Ser
1               5

<210> SEQ ID NO 170
<211> LENGTH: 11
<212> TYPE: PRT
<213> ORGANISM: Artificial Sequence
<220> FEATURE:
<223> OTHER INFORMATION: Homo sapiensIL330259_fg1 VL CDR3 PRT

<400> SEQUENCE: 170

Gln Ser Ala Asp Ser Ser Gly Ala Ser Arg Val
1               5                   10

<210> SEQ ID NO 171
<211> LENGTH: 351
<212> TYPE: DNA
<213> ORGANISM: Artificial Sequence
<220> FEATURE:
<223> OTHER INFORMATION: Homo sapiensH338L293 VH DNA

<400> SEQUENCE: 171
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtcccc gggaggggtg gcagtactac     180
gcagactccg tgaagggccg gttcaccatc tccagagaca attccaagaa cacgctgtat     240
ctgcaaatga acagcctgag agccgaggac acggccgtgt attactgtgt gagagtggtg     300
gctggctact ttgactcctg gggccgggga accctggtca ccgtctcgag t              351

<210> SEQ ID NO 172
<211> LENGTH: 117
<212> TYPE: PRT
<213> ORGANISM: Artificial Sequence
<220> FEATURE:
<223> OTHER INFORMATION: Homo sapiensH338L293 VH PRT

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Pro Arg Glu Gly Trp Gln Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Val Ala Gly Tyr Phe Asp Ser Trp Gly Arg Gly Thr Leu
            100                 105                 110

Val Thr Val Ser Ser
        115

<210> SEQ ID NO 173
<211> LENGTH: 5
<212> TYPE: PRT
<213> ORGANISM: Artificial Sequence
<220> FEATURE:
<223> OTHER INFORMATION: Homo sapiensH338L293 VH CDR1 PRT

<400> SEQUENCE: 173

Ser Tyr Ala Met Ser
1               5

<210> SEQ ID NO 174
<211> LENGTH: 17
<212> TYPE: PRT
<213> ORGANISM: Artificial Sequence
<220> FEATURE:
<223> OTHER INFORMATION: Homo sapiensH338L293 VH CDR2 PRT

<400> SEQUENCE: 174

Ala Ile Ser Pro Arg Glu Gly Trp Gln Tyr Tyr Ala Asp Ser Val Lys
1               5                   10                  15

Gly

<210> SEQ ID NO 175
<211> LENGTH: 8
<212> TYPE: PRT
<213> ORGANISM: Artificial Sequence
<220> FEATURE:
<223> OTHER INFORMATION: Homo sapiensH338L293 VH CDR3 PRT

<400> SEQUENCE: 175

Val Val Ala Gly Tyr Phe Asp Ser
1               5

<210> SEQ ID NO 176
<211> LENGTH: 324
<212> TYPE: DNA
<213> ORGANISM: Artificial Sequence
<220> FEATURE:
<223> OTHER INFORMATION: Homo sapiensH338L293 VL DNA

<400> SEQUENCE: 176
tcctatgtgc tgactcagcc accctcggtg tcagtgtccc caggacagac ggccaggatc      60
acctgctctg gcgatgcttt gccaaagcaa tatgctcatt ggtaccagca gaagccaggc     120
caggcccctg cactggtgat atataaagac actgagaggc cctcagggat tcctgagcga     180
ttctctgggt ccagctcagg gacaacagtc acgctgacca tcagtggagt ccaggcagaa     240
gatgaagctg actattactg tatgagcagc gaccccagcg gtgcttcacg ggtgttcggc     300
ggagggacca aggtcaccgt ccta                                            324

<210> SEQ ID NO 177
<211> LENGTH: 108

```
<212> TYPE: PRT
<213> ORGANISM: Artificial Sequence
<220> FEATURE:
<223> OTHER INFORMATION: Homo sapiensH338L293 VL PRT

<400> SEQUENCE: 177

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Ala Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Met Ser Ser Asp Pro Ser Gly Ala Ser
                85                  90                  95

Arg Val Phe Gly Gly Gly Thr Lys Val Thr Val Leu
            100                 105

<210> SEQ ID NO 178
<211> LENGTH: 11
<212> TYPE: PRT
<213> ORGANISM: Artificial Sequence
<220> FEATURE:
<223> OTHER INFORMATION: Homo sapiensH338L293 VL CDR1 PRT

<400> SEQUENCE: 178

Ser Gly Asp Ala Leu Pro Lys Gln Tyr Ala His
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Homo sapiensH338L293 VL CDR2 PRT

<400> SEQUENCE: 179

Lys Asp Thr Glu Arg Pro Ser
1               5

<210> SEQ ID NO 180
<211> LENGTH: 11
<212> TYPE: PRT
<213> ORGANISM: Artificial Sequence
<220> FEATURE:
<223> OTHER INFORMATION: Homo sapiensH338L293 VL CDR3 PRT

<400> SEQUENCE: 180

Met Ser Ser Asp Pro Ser Gly Ala Ser Arg Val
1               5                   10

<210> SEQ ID NO 181
<211> LENGTH: 351
<212> TYPE: DNA
<213> ORGANISM: Artificial Sequence
<220> FEATURE:
<223> OTHER INFORMATION: Homo sapiensH338L293_fgl VH DNA

<400> SEQUENCE: 181
gaggtgcagc tgttggagtc tgggggaggc ttggtacagc ctggggggtc cctgagactc     60
```

```
tcctgtgcag cctctggatt cacctttagc agctatgcca tgagctgggt ccgccaggct    120
ccagggaagg ggctggagtg ggtctcagct attagtcccc gggaggggtg gcagtactac    180
gcagactccg tgaagggccg gttcaccatc tccagagaca attccaagaa cacgctgtat    240
ctgcaaatga acagcctgag agccgaggac acggccgtgt attactgtgt gagagtggtg    300
gctggctact ttgactcctg gggccggggc accctggtca ccgtctcgag t             351
```

```
<210> SEQ ID NO 182
<211> LENGTH: 117
<212> TYPE: PRT
<213> ORGANISM: Artificial Sequence
<220> FEATURE:
<223> OTHER INFORMATION: Homo sapiensH338L293_fgl VH PRT

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Pro Arg Glu Gly Trp Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Val Ala Gly Tyr Phe Asp Ser Trp Gly Arg Gly Thr Leu
            100                 105                 110

Val Thr Val Ser Ser
        115
```

```
<210> SEQ ID NO 183
<211> LENGTH: 5
<212> TYPE: PRT
<213> ORGANISM: Artificial Sequence
<220> FEATURE:
<223> OTHER INFORMATION: Homo sapiensH338L293_fgl VH CDR1 PRT

<400> SEQUENCE: 183

Ser Tyr Ala Met Ser
1               5
```

```
<210> SEQ ID NO 184
<211> LENGTH: 17
<212> TYPE: PRT
<213> ORGANISM: Artificial Sequence
<220> FEATURE:
<223> OTHER INFORMATION: Homo sapiensH338L293_fgl VH CDR2 PRT

<400> SEQUENCE: 184

Ala Ile Ser Pro Arg Glu Gly Trp Gln Tyr Tyr Ala Asp Ser Val Lys
1               5                   10                  15

Gly
```

```
<210> SEQ ID NO 185
<211> LENGTH: 8
<212> TYPE: PRT
<213> ORGANISM: Artificial Sequence
<220> FEATURE:
<223> OTHER INFORMATION: Homo sapiensH338L293_fgl VH CDR3 PRT
```

<400> SEQUENCE: 185

Val Val Ala Gly Tyr Phe Asp Ser
1               5

<210> SEQ ID NO 186
<211> LENGTH: 324
<212> TYPE: DNA
<213> ORGANISM: Artificial Sequence
<220> FEATURE:
<223> OTHER INFORMATION: Homo sapiensH338L293_fg1 VL DNA

<400> SEQUENCE: 186
tcctatgagc tgatgcagcc accctcggtg tcagtgtccc caggacagac ggccaggatc      60
acctgctctg gcgatgcttt gccaaagcaa tatgctcatt ggtaccagca gaagccaggc     120
caggcccctg tgctggtgat atataaagac actgagaggc cctcagggat tcctgagcga     180
ttctctgggt ccagctcagg gacaacagtc acgctgacca tcagtggagt ccaggcagaa     240
gatgaagctg actattactg tatgtcctcg gacccgagcg gtgcttcacg ggtgttcggc     300
ggagggacca agctgaccgt ccta                                            324

<210> SEQ ID NO 187
<211> LENGTH: 108
<212> TYPE: PRT
<213> ORGANISM: Artificial Sequence
<220> FEATURE:
<223> OTHER INFORMATION: Homo sapiensH338L293_fg1 VL PRT

<400> SEQUENCE: 187

Ser Tyr Glu Leu Met Gln Pro Ser Val Ser Val Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Met Ser Ser Asp Pro Ser Gly Ala Ser
                85                  90                  95

Arg Val Phe Gly Gly Gly Thr Lys Leu Thr Val Leu
            100                 105

<210> SEQ ID NO 188
<211> LENGTH: 11
<212> TYPE: PRT
<213> ORGANISM: Artificial Sequence
<220> FEATURE:
<223> OTHER INFORMATION: Homo sapiensH338L293_fg1 VL CDR1 PRT

<400> SEQUENCE: 188

Ser Gly Asp Ala Leu Pro Lys Gln Tyr Ala His
1               5                   10

<210> SEQ ID NO 189
<211> LENGTH: 7
<212> TYPE: PRT
<213> ORGANISM: Artificial Sequence
<220> FEATURE:
<223> OTHER INFORMATION: Homo sapiensH338L293_fg1 VL CDR2 PRT

<400> SEQUENCE: 189

Lys Asp Thr Glu Arg Pro Ser
1               5

<210> SEQ ID NO 190
<211> LENGTH: 11
<212> TYPE: PRT
<213> ORGANISM: Artificial Sequence
<220> FEATURE:
<223> OTHER INFORMATION: Homo sapiensH338L293_fgl VL CDR3 PRT

<400> SEQUENCE: 190

Met Ser Ser Asp Pro Ser Gly Ala Ser Arg Val
1               5                   10

<210> SEQ ID NO 191
<211> LENGTH: 351
<212> TYPE: DNA
<213> ORGANISM: Artificial Sequence
<220> FEATURE:
<223> OTHER INFORMATION: Homo sapiensIL330377 VH DNA

<400> SEQUENCE: 191
gaggtgcagc tgttggagtc tgggggaggc ttggtacagc ctggggggtc cctgagactc        60
tcctgtgcag cctctggatt cacctttagc agctatgcca tgagctgggt ccgccaggct       120
ccagggaagg ggctggagtg ggtctcagcg tccgacatgc tctacggtag cacatactac       180
gcagactccg tgaagggccg gttcaccatc tccagagaca attccaagaa cacgctgtat       240
ctgcaaatga acagcctgag agccgaggac acggccgtgt attactgttc ccagaacatc       300
ctgggctact tgactcctg ggccggggga accctggtca ccgtctcgag t                 351

<210> SEQ ID NO 192
<211> LENGTH: 117
<212> TYPE: PRT
<213> ORGANISM: Artificial Sequence
<220> FEATURE:
<223> OTHER INFORMATION: Homo sapiensIL330377 VH PRT

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Asp Met Leu Tyr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Gln Asn Ile Leu Gly Tyr Phe Asp Ser Trp Gly Arg Gly Thr Leu
            100                 105                 110

Val Thr Val Ser Ser
        115

<210> SEQ ID NO 193
<211> LENGTH: 5
<212> TYPE: PRT

```
<213> ORGANISM: Artificial Sequence
<220> FEATURE:
<223> OTHER INFORMATION: Homo sapiensIL330377 VH CDR1 PRT

<400> SEQUENCE: 193

Ser Tyr Ala Met Ser
1               5

<210> SEQ ID NO 194
<211> LENGTH: 17
<212> TYPE: PRT
<213> ORGANISM: Artificial Sequence
<220> FEATURE:
<223> OTHER INFORMATION: Homo sapiensIL330377 VH CDR2 PRT

<400> SEQUENCE: 194

Ala Ser Asp Met Leu Tyr Gly Ser Thr Tyr Tyr Ala Asp Ser Val Lys
1               5                   10                  15

Gly

<210> SEQ ID NO 195
<211> LENGTH: 8
<212> TYPE: PRT
<213> ORGANISM: Artificial Sequence
<220> FEATURE:
<223> OTHER INFORMATION: Homo sapiensIL330377 VH CDR3 PRT

<400> SEQUENCE: 195

Asn Ile Leu Gly Tyr Phe Asp Ser
1               5

<210> SEQ ID NO 196
<211> LENGTH: 324
<212> TYPE: DNA
<213> ORGANISM: Artificial Sequence
<220> FEATURE:
<223> OTHER INFORMATION: Homo sapiensIL330377 VL DNA

<400> SEQUENCE: 196
tcctatgtgc tgactcagcc accctcggtg tcagtgtccc caggacagac ggccaggatc      60
acctgctctg gcgatgcttt gccaaagcaa tatgctcatt ggtaccagca gaagccaggc     120
caggccsctg cactggtgat atataaagac actgagaggc cctcagggat tcctgagcga     180 ttctctggt ccagctcagg acaacagtc acgctgacca tcagtggagt ccaggcagaa      240
gatgaagctg actattactg tcaatcagca gacagtacgg ggtaccaccg ggtgttcggc     300
ggagggacca aggtcaccgt ctta                                            324

<210> SEQ ID NO 197
<211> LENGTH: 108
<212> TYPE: PRT
<213> ORGANISM: Artificial Sequence
<220> FEATURE:
<223> OTHER INFORMATION: Homo sapiensIL330377 VL PRT

<400> SEQUENCE: 197

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

His Trp Tyr Gln Gln Lys Pro Gly Gln Ala Pro Ala Leu Val Ile Tyr
            35                  40                  45

Lys Asp Thr Glu Arg Pro Ser Gly Ile Pro Glu Arg Phe Ser Gly Ser
```

```
              50                  55                  60
Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Thr Gly Tyr His
                 85                  90                  95

Arg Val Phe Gly Gly Gly Thr Lys Val Thr Val Leu
            100                 105
```

<210> SEQ ID NO 198
<211> LENGTH: 11
<212> TYPE: PRT
<213> ORGANISM: Artificial Sequence
<220> FEATURE:
<223> OTHER INFORMATION: Homo sapiensIL330377 VL CDR1 PRT

<400> SEQUENCE: 198

```
Ser Gly Asp Ala Leu Pro Lys Gln Tyr Ala His
 1               5                  10
```

<210> SEQ ID NO 199
<211> LENGTH: 7
<212> TYPE: PRT
<213> ORGANISM: Artificial Sequence
<220> FEATURE:
<223> OTHER INFORMATION: Homo sapiensIL330377 VL CDR2 PRT

<400> SEQUENCE: 199

```
Lys Asp Thr Glu Arg Pro Ser
 1               5
```

<210> SEQ ID NO 200
<211> LENGTH: 11
<212> TYPE: PRT
<213> ORGANISM: Artificial Sequence
<220> FEATURE:
<223> OTHER INFORMATION: Homo sapiensIL330377 VL CDR3 PRT

<400> SEQUENCE: 200

```
Gln Ser Ala Asp Ser Thr Gly Tyr His Arg Val
 1               5                  10
```

<210> SEQ ID NO 201
<211> LENGTH: 351
<212> TYPE: DNA
<213> ORGANISM: Artificial Sequence
<220> FEATURE:
<223> OTHER INFORMATION: Homo sapiensIL330377_fgl VH DNA

<400> SEQUENCE: 201

```
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg ggctggagtg gtctcagcg tccgacatgc tctacggtag cacatactac     180
gcagactccg tgaagggccg gttcaccatc tccagagaca attccaagaa cacgctgtat    240
ctgcaaatga acagcctgag agccgaggac acggccgtgt attactgttc ccagaacatc    300
ctgggctact tgactcctg gggccgggga accctggtca ccgtctcgag t              351
```

<210> SEQ ID NO 202
<211> LENGTH: 117
<212> TYPE: PRT
<213> ORGANISM: Artificial Sequence
<220> FEATURE:
<223> OTHER INFORMATION: Homo sapiensIL330377_fgl VH PRT

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Asp Met Leu Tyr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Gln Asn Ile Leu Gly Tyr Phe Asp Ser Trp Gly Arg Gly Thr Leu
            100                 105                 110

Val Thr Val Ser Ser
            115

<210> SEQ ID NO 203
<211> LENGTH: 5
<212> TYPE: PRT
<213> ORGANISM: Artificial Sequence
<220> FEATURE:
<223> OTHER INFORMATION: Homo sapiensIL330377_fgl VH CDR1 PRT

<400> SEQUENCE: 203

Ser Tyr Ala Met Ser
1               5

<210> SEQ ID NO 204
<211> LENGTH: 17
<212> TYPE: PRT
<213> ORGANISM: Artificial Sequence
<220> FEATURE:
<223> OTHER INFORMATION: Homo sapiensIL330377_fgl VH CDR2 PRT

<400> SEQUENCE: 204

Ala Ser Asp Met Leu Tyr Gly Ser Thr Tyr Tyr Ala Asp Ser Val Lys
1               5                   10                  15

Gly

<210> SEQ ID NO 205
<211> LENGTH: 8
<212> TYPE: PRT
<213> ORGANISM: Artificial Sequence
<220> FEATURE:
<223> OTHER INFORMATION: Homo sapiensIL330377_fgl VH CDR3 PRT

<400> SEQUENCE: 205

Asn Ile Leu Gly Tyr Phe Asp Ser
1               5

<210> SEQ ID NO 206
<211> LENGTH: 324
<212> TYPE: DNA
<213> ORGANISM: Artificial Sequence
<220> FEATURE:
<223> OTHER INFORMATION: Homo sapiensIL330377_fgl VL DNA

<400> SEQUENCE: 206
tcctatgagc tgatgcagcc accctcggtg tcagtgtccc caggacagac ggccaggatc      60

```
acctgctctg gcgatgcttt gccaaagcaa tatgctcatt ggtaccagca gaagccaggc      120
caggcccctg tgctggtgat atataaagac actgagaggc cctcaggat tcctgagcga       180 ttctctgggt ccagctcagg acaacagtc acgctgacca tcagtggagt ccaggcagaa      240
gatgaagctg actattactg tcaatcagca gacagtacgg ggtaccaccg ggtgttcggc     300
ggagggacca agctgaccgt ccta                                             324
```

<210> SEQ ID NO 207
<211> LENGTH: 108
<212> TYPE: PRT
<213> ORGANISM: Artificial Sequence
<220> FEATURE:
<223> OTHER INFORMATION: Homo sapiensIL330377_fgl VL PRT

<400> SEQUENCE: 207

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Thr Gly Tyr His
                85                  90                  95

Arg Val Phe Gly Gly Gly Thr Lys Leu Thr Val Leu
            100                 105

<210> SEQ ID NO 208
<211> LENGTH: 11
<212> TYPE: PRT
<213> ORGANISM: Artificial Sequence
<220> FEATURE:
<223> OTHER INFORMATION: Homo sapiensIL330377_fgl VL CDR1 PRT

<400> SEQUENCE: 208

Ser Gly Asp Ala Leu Pro Lys Gln Tyr Ala His
1               5                   10

<210> SEQ ID NO 209
<211> LENGTH: 7
<212> TYPE: PRT
<213> ORGANISM: Artificial Sequence
<220> FEATURE:
<223> OTHER INFORMATION: Homo sapiensIL330377_fgl VL CDR2 PRT

<400> SEQUENCE: 209

Lys Asp Thr Glu Arg Pro Ser
1               5

<210> SEQ ID NO 210
<211> LENGTH: 11
<212> TYPE: PRT
<213> ORGANISM: Artificial Sequence
<220> FEATURE:
<223> OTHER INFORMATION: Homo sapiensIL330377_fgl VL CDR3 PRT

<400> SEQUENCE: 210

Gln Ser Ala Asp Ser Thr Gly Tyr His Arg Val

<210> SEQ ID NO 211
<211> LENGTH: 351
<212> TYPE: DNA
<213> ORGANISM: Artificial Sequence
<220> FEATURE:
<223> OTHER INFORMATION: Homo sapiensIL330388 VH DNA

<400> SEQUENCE: 211

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct agcacccccct ggcaaggtag cacatactac   180
gcagactccg tgaagggccg gttcaccatc tccagagaca attccaagaa cacgctgtat   240
ctgcaaatga acagcctgag agccgaggac acggccgtgt attactgtgt gagatggtac   300
tggggggtgga tcgactcctg ggccggggga accctggtca ccgtctcgag t            351
```

<210> SEQ ID NO 212
<211> LENGTH: 117
<212> TYPE: PRT
<213> ORGANISM: Artificial Sequence
<220> FEATURE:
<223> OTHER INFORMATION: Homo sapiensIL330388 VH PRT

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Trp Tyr Trp Gly Trp Ile Asp Ser Trp Gly Arg Gly Thr Leu
            100                 105                 110

Val Thr Val Ser Ser
        115

<210> SEQ ID NO 213
<211> LENGTH: 5
<212> TYPE: PRT
<213> ORGANISM: Artificial Sequence
<220> FEATURE:
<223> OTHER INFORMATION: Homo sapiensIL330388 VH CDR1 PRT

<400> SEQUENCE: 213

Ser Tyr Ala Met Ser
1               5

<210> SEQ ID NO 214
<211> LENGTH: 17
<212> TYPE: PRT
<213> ORGANISM: Artificial Sequence
<220> FEATURE:
<223> OTHER INFORMATION: Homo sapiensIL330388 VH CDR2 PRT -continued

<400> SEQUENCE: 214

Ala Ser Thr Pro Trp Gln Gly Ser Thr Tyr Tyr Ala Asp Ser Val Lys
1               5                   10                  15

Gly

<210> SEQ ID NO 215
<211> LENGTH: 8
<212> TYPE: PRT
<213> ORGANISM: Artificial Sequence
<220> FEATURE:
<223> OTHER INFORMATION: Homo sapiensIL330388 VH CDR3 PRT

<400> SEQUENCE: 215

Trp Tyr Trp Gly Trp Ile Asp Ser
1               5

<210> SEQ ID NO 216
<211> LENGTH: 324
<212> TYPE: DNA
<213> ORGANISM: Artificial Sequence
<220> FEATURE:
<223> OTHER INFORMATION: Homo sapiensIL330388 VL DNA

<400> SEQUENCE: 216
tcctatgtgc tgactcagcc accctcggtg tcagtgtccc caggacagac ggccaggatc      60
acctgctctg gcgatgcttt gccaaagcaa tatgctcatt ggtaccagca gaagccaggc     120
caggcccctg cactggtgat atataaagac actgagaggc cctcagggat tcctgagcga     180
ttctctgggt ccagctcagg gacaacagtc acgctgacca tcagtggagt ccaggcagaa     240
gatgaagctg actattactg tatgtcctcg gacccgagcg gtgcttcacg ggtgttcggc     300
ggagggacca aggtcaccgt ccta                                            324

<210> SEQ ID NO 217
<211> LENGTH: 108
<212> TYPE: PRT
<213> ORGANISM: Artificial Sequence
<220> FEATURE:
<223> OTHER INFORMATION: Homo sapiensIL330388 VL PRT

<400> SEQUENCE: 217

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Ala Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Met Ser Ser Asp Pro Ser Gly Ala Ser
                85                  90                  95

Arg Val Phe Gly Gly Gly Thr Lys Val Thr Val Leu
            100                 105

<210> SEQ ID NO 218
<211> LENGTH: 11
<212> TYPE: PRT
<213> ORGANISM: Artificial Sequence
<220> FEATURE:

<223> OTHER INFORMATION: Homo sapiensIL330388 VL CDR1 PRT

<400> SEQUENCE: 218

Ser Gly Asp Ala Leu Pro Lys Gln Tyr Ala His
1               5                   10

<210> SEQ ID NO 219
<211> LENGTH: 7
<212> TYPE: PRT
<213> ORGANISM: Artificial Sequence
<220> FEATURE:
<223> OTHER INFORMATION: Homo sapiensIL330388 VL CDR2 PRT

<400> SEQUENCE: 219

Lys Asp Thr Glu Arg Pro Ser
1               5

<210> SEQ ID NO 220
<211> LENGTH: 11
<212> TYPE: PRT
<213> ORGANISM: Artificial Sequence
<220> FEATURE:
<223> OTHER INFORMATION: Homo sapiensIL330388 VL CDR3 PRT

<400> SEQUENCE: 220

Met Ser Ser Asp Pro Ser Gly Ala Ser Arg Val
1               5                   10

<210> SEQ ID NO 221
<211> LENGTH: 351
<212> TYPE: DNA
<213> ORGANISM: Artificial Sequence
<220> FEATURE:
<223> OTHER INFORMATION: Homo sapiensIL330388_fgl VH DNA

<400> SEQUENCE: 221
gaggtgcagc tgttggagtc tgggggaggc ttggtacagc ctgggggtc cctgagactc      60 tcctgtgcag cctctggatt caccttagc agctatgcca tgagctgggt ccgccaggct    120
ccagggaagg gctggagtg gtctcagct agcacccct ggcaaggtag cacatactac      180
gcagactccg tgaagggccg gttcaccatc tccagagaca attccaagaa cacgctgtat   240
ctgcaaatga acagcctgag agccgaggac acggccgtgt attactgtgt gagatggtac   300
tgggggtgga tcgactcctg gggccgggga accctggtca ccgtctcctc a            351

<210> SEQ ID NO 222
<211> LENGTH: 117
<212> TYPE: PRT
<213> ORGANISM: Artificial Sequence
<220> FEATURE:
<223> OTHER INFORMATION: Homo sapiensIL330388_fgl VH PRT

<400> SEQUENCE: 222

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
            85                  90                  95

Val Arg Trp Tyr Trp Gly Trp Ile Asp Ser Trp Gly Arg Gly Thr Leu
        100                 105                 110

Val Thr Val Ser Ser
        115

<210> SEQ ID NO 223
<211> LENGTH: 5
<212> TYPE: PRT
<213> ORGANISM: Artificial Sequence
<220> FEATURE:
<223> OTHER INFORMATION: Homo sapiensIL330388_fgl VH CDR1 PRT

<400> SEQUENCE: 223

Ser Tyr Ala Met Ser
1               5

<210> SEQ ID NO 224
<211> LENGTH: 17
<212> TYPE: PRT
<213> ORGANISM: Artificial Sequence
<220> FEATURE:
<223> OTHER INFORMATION: Homo sapiensIL330388_fgl VH CDR2 PRT

<400> SEQUENCE: 224

Ala Ser Thr Pro Trp Gln Gly Ser Thr Tyr Tyr Ala Asp Ser Val Lys
1               5                   10                  15

Gly

<210> SEQ ID NO 225
<211> LENGTH: 8
<212> TYPE: PRT
<213> ORGANISM: Artificial Sequence
<220> FEATURE:
<223> OTHER INFORMATION: Homo sapiensIL330388_fgl VH CDR3 PRT

<400> SEQUENCE: 225

Trp Tyr Trp Gly Trp Ile Asp Ser
1               5

<210> SEQ ID NO 226
<211> LENGTH: 324
<212> TYPE: DNA
<213> ORGANISM: Artificial Sequence
<220> FEATURE:
<223> OTHER INFORMATION: Homo sapiensIL330388_fgl VL DNA

<400> SEQUENCE: 226
tcctatgagc tgatgcagcc accctcggtg tcagtgtccc aggacagac  ggccaggatc    60 acctgctctg gcgatgcttt gccaaagcaa tatgctcatt ggtaccagca gaagccaggc   120
caggcccctg tgctggtgat atataaagac actgagaggc cctcagggat tcctgagcga   180
ttctctgggt ccagctcagg gacaacagtc acgctgacca tcagtggagt ccaggcagaa   240
gatgaagctg actattactg tatgtcctcg gacccgagcg tgcttcacg  ggtgttcggc   300 ggagggacca agctgaccgt ccta                                          324

<210> SEQ ID NO 227
<211> LENGTH: 108
<212> TYPE: PRT
<213> ORGANISM: Artificial Sequence
<220> FEATURE:
```

<223> OTHER INFORMATION: Homo sapiensIL330388_fgl VL PRT

<400> SEQUENCE: 227

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Met Ser Ser Asp Pro Ser Gly Ala Ser
                85                  90                  95

Arg Val Phe Gly Gly Gly Thr Lys Leu Thr Val Leu
            100                 105

<210> SEQ ID NO 228
<211> LENGTH: 11
<212> TYPE: PRT
<213> ORGANISM: Artificial Sequence
<220> FEATURE:
<223> OTHER INFORMATION: Homo sapiensIL330388_fgl VL CDR1 PRT

<400> SEQUENCE: 228

Ser Gly Asp Ala Leu Pro Lys Gln Tyr Ala His
1               5                   10

<210> SEQ ID NO 229
<211> LENGTH: 7
<212> TYPE: PRT
<213> ORGANISM: Artificial Sequence
<220> FEATURE:
<223> OTHER INFORMATION: Homo sapiensIL330388_fgl VL CDR2 PRT

<400> SEQUENCE: 229

Lys Asp Thr Glu Arg Pro Ser
1               5

<210> SEQ ID NO 230
<211> LENGTH: 11
<212> TYPE: PRT
<213> ORGANISM: Artificial Sequence
<220> FEATURE:
<223> OTHER INFORMATION: Homo sapiensIL330388_fgl VL CDR3 PRT

<400> SEQUENCE: 230

Met Ser Ser Asp Pro Ser Gly Ala Ser Arg Val
1               5                   10

<210> SEQ ID NO 231
<211> LENGTH: 351
<212> TYPE: DNA
<213> ORGANISM: Artificial Sequence
<220> FEATURE:
<223> OTHER INFORMATION: Homo sapiensIL330396 VH DNA

<400> SEQUENCE: 231
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct agcacccccct ggcaaggtag cacatactac    180

```
gcagactccg tgaagggccg gttcaccatc tccagagaca attccaagaa cacgctgtat    240
ctgcaaatga acagcctgag agccgaggac acggccgtgt attactgtgt gagatggtac    300
tgggggtgga tcgactcctg gggccgggga accctggtca ccgtctcgag t             351
```

```
<210> SEQ ID NO 232
<211> LENGTH: 117
<212> TYPE: PRT
<213> ORGANISM: Artificial Sequence
<220> FEATURE:
<223> OTHER INFORMATION: Homo sapiensIL330396 VH PRT

<400> SEQUENCE: 232
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Trp Tyr Trp Gly Trp Ile Asp Ser Trp Gly Arg Gly Thr Leu
            100                 105                 110

Val Thr Val Ser Ser
        115

```
<210> SEQ ID NO 233
<211> LENGTH: 5
<212> TYPE: PRT
<213> ORGANISM: Artificial Sequence
<220> FEATURE:
<223> OTHER INFORMATION: Homo sapiensIL330396 VH CDR1 PRT

<400> SEQUENCE: 233
```

Ser Tyr Ala Met Ser
1               5

```
<210> SEQ ID NO 234
<211> LENGTH: 17
<212> TYPE: PRT
<213> ORGANISM: Artificial Sequence
<220> FEATURE:
<223> OTHER INFORMATION: Homo sapiensIL330396 VH CDR2 PRT

<400> SEQUENCE: 234
```

Ala Ser Thr Pro Trp Gln Gly Ser Thr Tyr Tyr Ala Asp Ser Val Lys
1               5                   10                  15

Gly

```
<210> SEQ ID NO 235
<211> LENGTH: 8
<212> TYPE: PRT
<213> ORGANISM: Artificial Sequence
<220> FEATURE:
<223> OTHER INFORMATION: Homo sapiensIL330396 VH CDR3 PRT

<400> SEQUENCE: 235
```

Trp Tyr Trp Gly Trp Ile Asp Ser
1               5

<210> SEQ ID NO 236
<211> LENGTH: 324
<212> TYPE: DNA
<213> ORGANISM: Artificial Sequence
<220> FEATURE:
<223> OTHER INFORMATION: Homo sapiensIL330396 VL DNA

<400> SEQUENCE: 236
tcctatgtgc tgactcagcc accctcggtg tcagtgtccc caggacagac ggccaggatc     60
acctgctctg gcgatgcttt gccaaagcaa tatgctcatt ggtaccagca gaagccaggc    120
caggcccctg cactggtgat atataaagac actgagaggc cctcagggat tcctgagcga    180
ttctctgggt ccagctcagg gacaacagtc acgctgacca tcagtggagt ccaggcagaa    240
gatgaagctg actattactg tatgagcagc gacgacacgg gtgcttcacg ggtgttcggc    300
ggagggacca aggtcaccgt ccta                                           324

<210> SEQ ID NO 237
<211> LENGTH: 108
<212> TYPE: PRT
<213> ORGANISM: Artificial Sequence
<220> FEATURE:
<223> OTHER INFORMATION: Homo sapiensIL330396 VL PRT

<400> SEQUENCE: 237

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Ala Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Met Ser Ser Asp Asp Thr Gly Ala Ser
                85                  90                  95

Arg Val Phe Gly Gly Gly Thr Lys Val Thr Val Leu
            100                 105

<210> SEQ ID NO 238
<211> LENGTH: 11
<212> TYPE: PRT
<213> ORGANISM: Artificial Sequence
<220> FEATURE:
<223> OTHER INFORMATION: Homo sapiensIL330396 VL CDR1 PRT

<400> SEQUENCE: 238

Ser Gly Asp Ala Leu Pro Lys Gln Tyr Ala His
1               5                   10

<210> SEQ ID NO 239
<211> LENGTH: 7
<212> TYPE: PRT
<213> ORGANISM: Artificial Sequence
<220> FEATURE:
<223> OTHER INFORMATION: Homo sapiensIL330396 VL CDR2 PRT

<400> SEQUENCE: 239

Lys Asp Thr Glu Arg Pro Ser
1               5

<210> SEQ ID NO 240
<211> LENGTH: 11
<212> TYPE: PRT
<213> ORGANISM: Artificial Sequence
<220> FEATURE:
<223> OTHER INFORMATION: Homo sapiensIL330396 VL CDR3 PRT

<400> SEQUENCE: 240

Met Ser Ser Asp Asp Thr Gly Ala Ser Arg Val
1               5                   10

<210> SEQ ID NO 241
<211> LENGTH: 351
<212> TYPE: DNA
<213> ORGANISM: Artificial Sequence
<220> FEATURE:
<223> OTHER INFORMATION: Homo sapiensIL330396_fgl VH DNA

<400> SEQUENCE: 241
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg ggctggagtg ggtctcagct agcaccccct ggcaaggtag cacatactac    180
gcagactccg tgaagggccg gttcaccatc tccagagaca attccaagaa cacgctgtat    240
ctgcaaatga acagcctgag agccgaggac acggccgtgt attactgtgt gagatggtac    300
tgggggtgga tcgactcctg gggccgggga accctggtca ccgtctcgag t             351

<210> SEQ ID NO 242
<211> LENGTH: 117
<212> TYPE: PRT
<213> ORGANISM: Artificial Sequence
<220> FEATURE:
<223> OTHER INFORMATION: Homo sapiensIL330396_fgl VH PRT

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Trp Tyr Trp Gly Trp Ile Asp Ser Trp Gly Arg Gly Thr Leu
            100                 105                 110

Val Thr Val Ser Ser
        115

<210> SEQ ID NO 243
<211> LENGTH: 5
<212> TYPE: PRT
<213> ORGANISM: Artificial Sequence
<220> FEATURE:
<223> OTHER INFORMATION: Homo sapiensIL330396_fgl VH CDR1 PRT

<400> SEQUENCE: 243

Ser Tyr Ala Met Ser
1               5

<210> SEQ ID NO 244
<211> LENGTH: 17
<212> TYPE: PRT
<213> ORGANISM: Artificial Sequence
<220> FEATURE:
<223> OTHER INFORMATION: Homo sapiensIL330396_fgl VH CDR2 PRT

<400> SEQUENCE: 244

Ala Ser Thr Pro Trp Gln Gly Ser Thr Tyr Tyr Ala Asp Ser Val Lys
1               5                   10                  15

Gly

<210> SEQ ID NO 245
<211> LENGTH: 8
<212> TYPE: PRT
<213> ORGANISM: Artificial Sequence
<220> FEATURE:
<223> OTHER INFORMATION: Homo sapiensIL330396_fgl VH CDR3 PRT

<400> SEQUENCE: 245

Trp Tyr Trp Gly Trp Ile Asp Ser
1               5

<210> SEQ ID NO 246
<211> LENGTH: 324
<212> TYPE: DNA
<213> ORGANISM: Artificial Sequence
<220> FEATURE:
<223> OTHER INFORMATION: Homo sapiensIL330396_fgl VL DNA

<400> SEQUENCE: 246
tcctatgagc tgatgcagcc accctcggtg tcagtgtccc caggacagac ggccaggatc      60
acctgctctg gcgatgcttt gccaaagcaa tatgctcatt ggtaccagca gaagccaggc     120
caggcccctg tgctggtgat atataaagac actgagaggc cctcagggat tcctgagcga     180
ttctctgggt ccagctcagg gacaacagtc acgctgacca tcagtggagt ccaggcagaa     240
gatgaagctg actattactg tatgagcagc gacgacacgg gtgcttcacg ggtgttcggc     300
ggagggacca agctgaccgt ccta                                            324

<210> SEQ ID NO 247
<211> LENGTH: 108
<212> TYPE: PRT
<213> ORGANISM: Artificial Sequence
<220> FEATURE:
<223> OTHER INFORMATION: Homo sapiensIL330396_fgl VL PRT

<400> SEQUENCE: 247

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

His Trp Tyr Gln Gln Lys Pro Gly Gln Ala Pro Val Leu Val Ile Tyr
            35                  40                  45

Lys Asp Thr Glu Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu

```
                65                  70                  75                  80
Asp Glu Ala Asp Tyr Tyr Cys Met Ser Ser Asp Asp Thr Gly Ala Ser
                    85                  90                  95

Arg Val Phe Gly Gly Gly Thr Lys Leu Thr Val Leu
            100                 105

<210> SEQ ID NO 248
<211> LENGTH: 11
<212> TYPE: PRT
<213> ORGANISM: Artificial Sequence
<220> FEATURE:
<223> OTHER INFORMATION: Homo sapiensIL330396_fgl VL CDR1 PRT

<400> SEQUENCE: 248

Ser Gly Asp Ala Leu Pro Lys Gln Tyr Ala His
1               5                   10

<210> SEQ ID NO 249
<211> LENGTH: 7
<212> TYPE: PRT
<213> ORGANISM: Artificial Sequence
<220> FEATURE:
<223> OTHER INFORMATION: Homo sapiensIL330396_fgl VL CDR2 PRT

<400> SEQUENCE: 249

Lys Asp Thr Glu Arg Pro Ser
1               5

<210> SEQ ID NO 250
<211> LENGTH: 11
<212> TYPE: PRT
<213> ORGANISM: Artificial Sequence
<220> FEATURE:
<223> OTHER INFORMATION: Homo sapiensIL330396_fgl VL CDR3 PRT

<400> SEQUENCE: 250

Met Ser Ser Asp Asp Thr Gly Ala Ser Arg Val
1               5                   10

<210> SEQ ID NO 251
<211> LENGTH: 351
<212> TYPE: DNA
<213> ORGANISM: Artificial Sequence
<220> FEATURE:
<223> OTHER INFORMATION: Homo sapiensIL330398 VH DNA

<400> SEQUENCE: 251
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct agcacccct ggcaaggtag cacatactac        180
gcagactccg tgaagggccg gttcaccatc tccagagaca attccaagaa cacgctgtat    240
ctgcaaatga acagcctgag agccgaggac acggccgtgt attactgtgt gagatggtac    300
tgggggtgga tcgactcctg gggccgggga accctggtca ccgtctcgag t             351

<210> SEQ ID NO 252
<211> LENGTH: 117
<212> TYPE: PRT
<213> ORGANISM: Artificial Sequence
<220> FEATURE:
<223> OTHER INFORMATION: Homo sapiensIL330398 VH PRT

<400> SEQUENCE: 252
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Trp Tyr Trp Gly Trp Ile Asp Ser Trp Gly Arg Gly Thr Leu
            100                 105                 110

Val Thr Val Ser Ser
            115

<210> SEQ ID NO 253
<211> LENGTH: 5
<212> TYPE: PRT
<213> ORGANISM: Artificial Sequence
<220> FEATURE:
<223> OTHER INFORMATION: Homo sapiensIL330398 VH CDR1 PRT

<400> SEQUENCE: 253

Ser Tyr Ala Met Ser
1               5

<210> SEQ ID NO 254
<211> LENGTH: 17
<212> TYPE: PRT
<213> ORGANISM: Artificial Sequence
<220> FEATURE:
<223> OTHER INFORMATION: Homo sapiensIL330398 VH CDR2 PRT

<400> SEQUENCE: 254

Ala Ser Thr Pro Trp Gln Gly Ser Thr Tyr Tyr Ala Asp Ser Val Lys
1               5                   10                  15

Gly

<210> SEQ ID NO 255
<211> LENGTH: 8
<212> TYPE: PRT
<213> ORGANISM: Artificial Sequence
<220> FEATURE:
<223> OTHER INFORMATION: Homo sapiensIL330398 VH CDR3 PRT

<400> SEQUENCE: 255

Trp Tyr Trp Gly Trp Ile Asp Ser
1               5

<210> SEQ ID NO 256
<211> LENGTH: 324
<212> TYPE: DNA
<213> ORGANISM: Artificial Sequence
<220> FEATURE:
<223> OTHER INFORMATION: Homo sapiensIL330398 VL DNA

<400> SEQUENCE: 256
tcctatgtgc tgactcagcc accctcggtg tcagtgtccc caggacagac ggccaggatc      60
acctgctctg gcgatgcttt gccaaagcaa tatgctcatt ggtaccagca gaagccaggc     120

```
caggcccctg cactggtgat atataaagac actgagaggc cctcagggat tcctgagcga      180
ttctctgggt ccagctcagg gacaacagtc acgctgacca tcagtggagt ccaggcagaa      240
gatgaagctg actattactg tttgtccagc gacgcctcgg gtgcttcacg ggtgttcggc      300
ggagggacca aggtcaccgt ccta                                             324
```

<210> SEQ ID NO 257
<211> LENGTH: 108
<212> TYPE: PRT
<213> ORGANISM: Artificial Sequence
<220> FEATURE:
<223> OTHER INFORMATION: Homo sapiensIL330398 VL PRT

<400> SEQUENCE: 257

```
Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Ala Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Leu Ser Ser Asp Ala Ser Gly Ala Ser
                85                  90                  95

Arg Val Phe Gly Gly Gly Thr Lys Val Thr Val Leu
            100                 105
```

<210> SEQ ID NO 258
<211> LENGTH: 11
<212> TYPE: PRT
<213> ORGANISM: Artificial Sequence
<220> FEATURE:
<223> OTHER INFORMATION: Homo sapiensIL330398 VL CDR1 PRT

<400> SEQUENCE: 258

```
Ser Gly Asp Ala Leu Pro Lys Gln Tyr Ala His
1               5                   10
```

<210> SEQ ID NO 259
<211> LENGTH: 7
<212> TYPE: PRT
<213> ORGANISM: Artificial Sequence
<220> FEATURE:
<223> OTHER INFORMATION: Homo sapiensIL330398 VL CDR2 PRT

<400> SEQUENCE: 259

```
Lys Asp Thr Glu Arg Pro Ser
1               5
```

<210> SEQ ID NO 260
<211> LENGTH: 11
<212> TYPE: PRT
<213> ORGANISM: Artificial Sequence
<220> FEATURE:
<223> OTHER INFORMATION: Homo sapiensIL330398 VL CDR3 PRT

<400> SEQUENCE: 260

```
Leu Ser Ser Asp Ala Ser Gly Ala Ser Arg Val
1               5                   10
```

<210> SEQ ID NO 261
<211> LENGTH: 351
<212> TYPE: DNA
<213> ORGANISM: Artificial Sequence
<220> FEATURE:
<223> OTHER INFORMATION: Homo sapiensIL330398_fgl VH DNA

<400> SEQUENCE: 261

```
gaggtgcagc tgttggagtc tgggggaggc ttggtacagc ctgggggtc cctgagactc      60
tcctgtgcag cctctggatt caccttagc agctatgcca tgagctgggt ccgccaggct     120
ccagggaagg ggctggagtg ggtctcagct agcacccct ggcaaggtag cacatactac     180
gcagactccg tgaagggccg gttcaccatc tccagagaca attccaagaa cacgctgtat   240
ctgcaaatga acagcctgag agccgaggac acggccgtgt attactgtgt gagatggtac   300
tgggggtgga tcgactcctg gggccgggga accctggtca ccgtctcgag t            351
```

<210> SEQ ID NO 262
<211> LENGTH: 117
<212> TYPE: PRT
<213> ORGANISM: Artificial Sequence
<220> FEATURE:
<223> OTHER INFORMATION: Homo sapiensIL330398_fgl VH PRT

<400> SEQUENCE: 262

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ser Thr Pro Trp Gln Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Trp Tyr Trp Gly Trp Ile Asp Ser Trp Gly Arg Gly Thr Leu
            100                 105                 110

Val Thr Val Ser Ser
        115

<210> SEQ ID NO 263
<211> LENGTH: 5
<212> TYPE: PRT
<213> ORGANISM: Artificial Sequence
<220> FEATURE:
<223> OTHER INFORMATION: Homo sapiensIL330398_fgl VH CDR1 PRT

<400> SEQUENCE: 263

Ser Tyr Ala Met Ser
1               5

<210> SEQ ID NO 264
<211> LENGTH: 17
<212> TYPE: PRT
<213> ORGANISM: Artificial Sequence
<220> FEATURE:
<223> OTHER INFORMATION: Homo sapiensIL330398_fgl VH CDR2 PRT

<400> SEQUENCE: 264

Ala Ser Thr Pro Trp Gln Gly Ser Thr Tyr Tyr Ala Asp Ser Val Lys

-continued

```
1               5               10              15
Gly
```

<210> SEQ ID NO 265
<211> LENGTH: 8
<212> TYPE: PRT
<213> ORGANISM: Artificial Sequence
<220> FEATURE:
<223> OTHER INFORMATION: Homo sapiensIL330398_fg1 VH CDR3 PRT

<400> SEQUENCE: 265

```
Trp Tyr Trp Gly Trp Ile Asp Ser
1               5
```

<210> SEQ ID NO 266
<211> LENGTH: 324
<212> TYPE: DNA
<213> ORGANISM: Artificial Sequence
<220> FEATURE:
<223> OTHER INFORMATION: Homo sapiensIL330398_fg1 VL DNA

<400> SEQUENCE: 266

```
tcctatgagc tgatgcagcc accctcggtg tcagtgtccc caggacagac ggccaggatc    60
acctgctctg gcgatgcttt gccaaagcaa tatgctcatt ggtaccagca gaagccaggc   120
caggcccctg tgctggtgat atataaagac actgagaggc cctcagggat tcctgagcga   180
ttctctgggt ccagctcagg gacaacagtc acgctgacca tcagtggagt ccaggcagaa   240
gatgaagctg actattactg tttgtccagc gacgcctcgg gtgcttcacg ggtgttcggc   300
ggagggacca agctgaccgt ccta                                          324
```

<210> SEQ ID NO 267
<211> LENGTH: 108
<212> TYPE: PRT
<213> ORGANISM: Artificial Sequence
<220> FEATURE:
<223> OTHER INFORMATION: Homo sapiensIL330398_fg1 VL PRT

<400> SEQUENCE: 267

```
Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

His Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Leu Ser Ser Asp Ala Ser Gly Ala Ser
                85                  90                  95

Arg Val Phe Gly Gly Gly Thr Lys Leu Thr Val Leu
                100                 105
```

<210> SEQ ID NO 268
<211> LENGTH: 11
<212> TYPE: PRT
<213> ORGANISM: Artificial Sequence
<220> FEATURE:
<223> OTHER INFORMATION: Homo sapiensIL330398_fg1 VL CDR1 PRT

<400> SEQUENCE: 268

Ser Gly Asp Ala Leu Pro Lys Gln Tyr Ala His
1               5                   10

<210> SEQ ID NO 269
<211> LENGTH: 7
<212> TYPE: PRT
<213> ORGANISM: Artificial Sequence
<220> FEATURE:
<223> OTHER INFORMATION: Homo sapiensIL330398_fgl VL CDR2 PRT

<400> SEQUENCE: 269

Lys Asp Thr Glu Arg Pro Ser
1               5

<210> SEQ ID NO 270
<211> LENGTH: 11
<212> TYPE: PRT
<213> ORGANISM: Artificial Sequence
<220> FEATURE:
<223> OTHER INFORMATION: Homo sapiensIL330398_fgl VL CDR3 PRT

<400> SEQUENCE: 270

Leu Ser Ser Asp Ala Ser Gly Ala Ser Arg Val
1               5                   10

<210> SEQ ID NO 271
<211> LENGTH: 378
<212> TYPE: DNA
<213> ORGANISM: Artificial Sequence
<220> FEATURE:
<223> OTHER INFORMATION: Homo sapiens33v20064 VH DNA

<400> SEQUENCE: 271
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc gagagatctg     300
tggatacagc tatgggggg gggcttgcgt tatcccttcg gctactgggg ccaagggaca      360
atggtcaccg tctcgagt                                                   378

<210> SEQ ID NO 272
<211> LENGTH: 126
<212> TYPE: PRT
<213> ORGANISM: Artificial Sequence
<220> FEATURE:
<223> OTHER INFORMATION: Homo sapiens33v20064 VH PRT

<400> SEQUENCE: 272

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Leu Trp Ile Gln Leu Trp Gly Gly Gly Leu Arg Tyr Pro
        100                 105                 110

Phe Gly Tyr Trp Gly Gln Gly Thr Met Val Thr Val Ser Ser
        115                 120                 125

<210> SEQ ID NO 273
<211> LENGTH: 5
<212> TYPE: PRT
<213> ORGANISM: Artificial Sequence
<220> FEATURE:
<223> OTHER INFORMATION: Homo sapiens33v20064 VH CDR1 PRT

<400> SEQUENCE: 273

Ser Tyr Ala Met Ser
1               5

<210> SEQ ID NO 274
<211> LENGTH: 17
<212> TYPE: PRT
<213> ORGANISM: Artificial Sequence
<220> FEATURE:
<223> OTHER INFORMATION: Homo sapiens33v20064 VH CDR2 PRT

<400> SEQUENCE: 274

Ala Ile Ser Gly Ser Gly Gly Ser Thr Tyr Tyr Ala Asp Ser Val Lys
1               5                   10                  15

Gly

<210> SEQ ID NO 275
<211> LENGTH: 17
<212> TYPE: PRT
<213> ORGANISM: Artificial Sequence
<220> FEATURE:
<223> OTHER INFORMATION: Homo sapiens33v20064 VH CDR3 PRT

<400> SEQUENCE: 275

Asp Leu Trp Ile Gln Leu Trp Gly Gly Gly Leu Arg Tyr Pro Phe Gly
1               5                   10                  15

Tyr

<210> SEQ ID NO 276
<211> LENGTH: 318
<212> TYPE: DNA
<213> ORGANISM: Artificial Sequence
<220> FEATURE:
<223> OTHER INFORMATION: Homo sapiens33v20064 VL DNA

<400> SEQUENCE: 276
ctgcctgtgc tgactcagcc accctcagtg tccgtgtccc caggacagaa ggccagcatc      60
acctgctctg gagaaagaat gggggataaa tatgctgcct ggtatcagca gaagccaggc     120
cagtcaccta ctggtcat ctatcaagat acaaagcggc cctcagggat ccctgagcga      180
ttctctggct ccaactctgg gaacacagcc acgttgacca tcagcgggac ccaggacatg     240
gatgaggctg actattactg tcaggtgtgg gacagcagca ctggggtatt cggcggaggg     300
accaaggtca ccgtccta                                                   318

<210> SEQ ID NO 277
<211> LENGTH: 106
<212> TYPE: PRT
<213> ORGANISM: Artificial Sequence -continued
<220> FEATURE:
<223> OTHER INFORMATION: Homo sapiens33v20064 VL PRT

<400> SEQUENCE: 277

Leu Pro Val Leu Thr Gln Pro Pro Ser Val Ser Val Ser Pro Gly Gln
1               5                   10                  15

Lys Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Ile Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Asp Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105

<210> SEQ ID NO 278
<211> LENGTH: 11
<212> TYPE: PRT
<213> ORGANISM: Artificial Sequence
<220> FEATURE:
<223> OTHER INFORMATION: Homo sapiens33v20064 VL CDR1 PRT

<400> SEQUENCE: 278

Ser Gly Glu Arg Met Gly Asp Lys Tyr Ala Ala
1               5                   10

<210> SEQ ID NO 279
<211> LENGTH: 7
<212> TYPE: PRT
<213> ORGANISM: Artificial Sequence
<220> FEATURE:
<223> OTHER INFORMATION: Homo sapiens33v20064 VL CDR2 PRT

<400> SEQUENCE: 279

Gln Asp Thr Lys Arg Pro Ser
1               5

<210> SEQ ID NO 280
<211> LENGTH: 9
<212> TYPE: PRT
<213> ORGANISM: Artificial Sequence
<220> FEATURE:
<223> OTHER INFORMATION: Homo sapiens33v20064 VL CDR3 PRT

<400> SEQUENCE: 280

Gln Val Trp Asp Ser Ser Thr Gly Val
1               5

<210> SEQ ID NO 281
<211> LENGTH: 378
<212> TYPE: DNA
<213> ORGANISM: Artificial Sequence
<220> FEATURE:
<223> OTHER INFORMATION: Homo sapiens33_640001 VH DNA

<400> SEQUENCE: 281
gaggtgcagc tgttggagtc tgggggaggc ttggtacagc ctggggggtc cctgagactc      60
tcctgtgcag cctctggatt caccttagc agctatgcca tgagctgggt ccgccaggct     120

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagatctg    300
tggatacagc tatgggggg gggcttgcgt tatcccttcg gctactgggg ccaagggaca    360
atggtcaccg tctcgagt                                                  378
```

<210> SEQ ID NO 282
<211> LENGTH: 126
<212> TYPE: PRT
<213> ORGANISM: Artificial Sequence
<220> FEATURE:
<223> OTHER INFORMATION: Homo sapiens33_640001 VH PRT

<400> SEQUENCE: 282

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Ile Gln Leu Trp Gly Gly Leu Arg Tyr Pro
            100                 105                 110

Phe Gly Tyr Trp Gly Gln Gly Thr Met Val Thr Val Ser Ser
        115                 120                 125
```

<210> SEQ ID NO 283
<211> LENGTH: 5
<212> TYPE: PRT
<213> ORGANISM: Artificial Sequence
<220> FEATURE:
<223> OTHER INFORMATION: Homo sapiens33_640001 VH CDR1 PRT

<400> SEQUENCE: 283

```
Ser Tyr Ala Met Ser
1               5
```

<210> SEQ ID NO 284
<211> LENGTH: 17
<212> TYPE: PRT
<213> ORGANISM: Artificial Sequence
<220> FEATURE:
<223> OTHER INFORMATION: Homo sapiens33_640001 VH CDR2 PRT

<400> SEQUENCE: 284

```
Ala Ile Ser Gly Ser Gly Gly Ser Thr Tyr Tyr Ala Asp Ser Val Lys
1               5                   10                  15

Gly
```

<210> SEQ ID NO 285
<211> LENGTH: 17
<212> TYPE: PRT
<213> ORGANISM: Artificial Sequence
<220> FEATURE:
<223> OTHER INFORMATION: Homo sapiens33_640001 VH CDR3 PRT

<400> SEQUENCE: 285

Asp Leu Trp Ile Gln Leu Trp Gly Gly Gly Leu Arg Tyr Pro Phe Gly
1               5                   10                  15
Tyr

<210> SEQ ID NO 286
<211> LENGTH: 318
<212> TYPE: DNA
<213> ORGANISM: Artificial Sequence
<220> FEATURE:
<223> OTHER INFORMATION: Homo sapiens33_640001 VL DNA

<400> SEQUENCE: 286
tcctacgtgc tgactcagcc accctcagtg tccgtgtccc caggacagac ggccagcatc    60
acctgctctg agaaagaat  gggggataaa tatgctgcct ggtatcagca gaagccaggc   120
cagtcacctg tgctggtcat ctatcaagat acaaagcggc cctcagggat ccctgagcga   180
ttctctggct ccaactctgg gaacacagcc acgttgacca tcagcgggac ccaggccatg   240
gatgaggctg actattactg tcaggtgtgg gacagcagca ctggggtatt cggcggaggg   300
accaaggtca ccgtccta                                                 318

<210> SEQ ID NO 287
<211> LENGTH: 106
<212> TYPE: PRT
<213> ORGANISM: Artificial Sequence
<220> FEATURE:
<223> OTHER INFORMATION: Homo sapiens33_640001 VL PRT

<400> SEQUENCE: 287

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105

<210> SEQ ID NO 288
<211> LENGTH: 11
<212> TYPE: PRT
<213> ORGANISM: Artificial Sequence
<220> FEATURE:
<223> OTHER INFORMATION: Homo sapiens33_640001 VL CDR1 PRT

<400> SEQUENCE: 288

Ser Gly Glu Arg Met Gly Asp Lys Tyr Ala Ala
1               5                   10

<210> SEQ ID NO 289
<211> LENGTH: 7
<212> TYPE: PRT
<213> ORGANISM: Artificial Sequence
<220> FEATURE:
<223> OTHER INFORMATION: Homo sapiens33_640001 VL CDR2 PRT

<400> SEQUENCE: 289

Gln Asp Thr Lys Arg Pro Ser
1               5

<210> SEQ ID NO 290
<211> LENGTH: 9
<212> TYPE: PRT
<213> ORGANISM: Artificial Sequence
<220> FEATURE:
<223> OTHER INFORMATION: Homo sapiens33_640001 VL CDR3 PRT

<400> SEQUENCE: 290

Gln Val Trp Asp Ser Ser Thr Gly Val
1               5

<210> SEQ ID NO 291
<211> LENGTH: 378
<212> TYPE: DNA
<213> ORGANISM: Artificial Sequence
<220> FEATURE:
<223> OTHER INFORMATION: Homo sapiens33_640027 VH DNA

<400> SEQUENCE: 291
gaggtgcagc tgttggagtc tgggggagac ttggtacagc ctggggggtc cctgagactc      60
tcctgtgcag cctctggatt cacctttagc agctatgcca tgagctgggt ccgccaggct     120
ccagggaagg gctggagtg gtctcagct attggtggta gtggtggtag cacatactac       180
gcagactccg tgaagggccg gttcaccatc tccagagaca attccaagaa cacgctgtat     240
ctgcaaatga acagcctgag agccgaggac acggccgtgt attactgtgc gagagatctg     300
tggatgcagc tatgggggggg gggcttgcgt tatcccttcg gctactgggg ccaagggaca   360
atggtcaccg tctcgagt                                                   378

<210> SEQ ID NO 292
<211> LENGTH: 126
<212> TYPE: PRT
<213> ORGANISM: Artificial Sequence
<220> FEATURE:
<223> OTHER INFORMATION: Homo sapiens33_640027 VH PRT

<400> SEQUENCE: 292

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Gln Leu Trp Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 293
<211> LENGTH: 5
<212> TYPE: PRT
<213> ORGANISM: Artificial Sequence
<220> FEATURE:
<223> OTHER INFORMATION: Homo sapiens33_640027 VH CDR1 PRT

<400> SEQUENCE: 293

Ser Tyr Ala Met Ser
1               5

<210> SEQ ID NO 294
<211> LENGTH: 17
<212> TYPE: PRT
<213> ORGANISM: Artificial Sequence
<220> FEATURE:
<223> OTHER INFORMATION: Homo sapiens33_640027 VH CDR2 PRT

<400> SEQUENCE: 294

Ala Ile Gly Gly Ser Gly Gly Ser Thr Tyr Tyr Ala Asp Ser Val Lys
1               5                   10                  15

Gly

<210> SEQ ID NO 295
<211> LENGTH: 17
<212> TYPE: PRT
<213> ORGANISM: Artificial Sequence
<220> FEATURE:
<223> OTHER INFORMATION: Homo sapiens33_640027 VH CDR3 PRT

<400> SEQUENCE: 295

Asp Leu Trp Met Gln Leu Trp Gly Gly Gly Leu Arg Tyr Pro Phe Gly
1               5                   10                  15

Tyr

<210> SEQ ID NO 296
<211> LENGTH: 318
<212> TYPE: DNA
<213> ORGANISM: Artificial Sequence
<220> FEATURE:
<223> OTHER INFORMATION: Homo sapiens33_640027 VL DNA

<400> SEQUENCE: 296
ctgcctgtgc tgactcagcc accctcagtg tccgtgtccc caggacagaa ggccagcatc      60
acctgctctg gagaaagaat agggdataaa tatgccgcct ggtatcagca gaagccgggc     120
cagtcaccta tactggtcat ctatcgagat acaaagcggc cctcagggat ccctgagcga     180
ttctctggct ccaactctgg gaacacagcc acgttgacca tcagcgggac ccaggacatg     240
gatgaggctg actattactg tcaggtgtgg gacagcagca ctggggtatt cggcggaggg     300
accaaggtca ccgtccta                                                   318

<210> SEQ ID NO 297
<211> LENGTH: 106
<212> TYPE: PRT
<213> ORGANISM: Artificial Sequence
<220> FEATURE:
<223> OTHER INFORMATION: Homo sapiens33_640027 VL PRT

<400> SEQUENCE: 297

Leu Pro Val Leu Thr Gln Pro Pro Ser Val Ser Val Ser Pro Gly Gln
1               5                   10                  15

Lys Ala Ser Ile Thr Cys Ser Gly Glu Arg Ile Gly Asp Lys Tyr Ala

```
                20                  25                  30
Ala Trp Tyr Gln Gln Lys Pro Gly Gln Ser Pro Ile Leu Val Ile Tyr
            35                  40                  45
Arg Asp Thr Lys Arg Pro Ser Gly Ile Pro Glu Arg Phe Ser Gly Ser
        50                  55                  60
Asn Ser Gly Asn Thr Ala Thr Leu Thr Ile Ser Gly Thr Gln Asp Met
65                  70                  75                  80
Asp Glu Ala Asp Tyr Tyr Cys Gln Val Trp Asp Ser Ser Thr Gly Val
                85                  90                  95
Phe Gly Gly Gly Thr Lys Val Thr Val Leu
            100                 105

<210> SEQ ID NO 298
<211> LENGTH: 11
<212> TYPE: PRT
<213> ORGANISM: Artificial Sequence
<220> FEATURE:
<223> OTHER INFORMATION: Homo sapiens33_640027 VL CDR1 PRT

<400> SEQUENCE: 298

Ser Gly Glu Arg Ile Gly Asp Lys Tyr Ala Ala
1               5                   10

<210> SEQ ID NO 299
<211> LENGTH: 7
<212> TYPE: PRT
<213> ORGANISM: Artificial Sequence
<220> FEATURE:
<223> OTHER INFORMATION: Homo sapiens33_640027 VL CDR2 PRT

<400> SEQUENCE: 299

Arg Asp Thr Lys Arg Pro Ser
1               5

<210> SEQ ID NO 300
<211> LENGTH: 9
<212> TYPE: PRT
<213> ORGANISM: Artificial Sequence
<220> FEATURE:
<223> OTHER INFORMATION: Homo sapiens33_640027 VL CDR3 PRT

<400> SEQUENCE: 300

Gln Val Trp Asp Ser Ser Thr Gly Val
1               5

<210> SEQ ID NO 301
<211> LENGTH: 378
<212> TYPE: DNA
<213> ORGANISM: Artificial Sequence
<220> FEATURE:
<223> OTHER INFORMATION: Homo sapiens33_640050 VH DNA

<400> SEQUENCE: 301
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtcc gaggcacaag    300
ttcatgcagc tatggggggg gggcttgcgt tatcccttcg gctactgggg ccaagggaca    360
atggtcaccg tctcgagt                                                  378
```

<210> SEQ ID NO 302
<211> LENGTH: 126
<212> TYPE: PRT
<213> ORGANISM: Artificial Sequence
<220> FEATURE:
<223> OTHER INFORMATION: Homo sapiens33_640050 VH PRT

<400> SEQUENCE: 302

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Pro Arg His Lys Phe Met Gln Leu Trp Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 303
<211> LENGTH: 5
<212> TYPE: PRT
<213> ORGANISM: Artificial Sequence
<220> FEATURE:
<223> OTHER INFORMATION: Homo sapiens33_640050 VH CDR1 PRT

<400> SEQUENCE: 303

Ser Tyr Ala Met Ser
1               5

<210> SEQ ID NO 304
<211> LENGTH: 17
<212> TYPE: PRT
<213> ORGANISM: Artificial Sequence
<220> FEATURE:
<223> OTHER INFORMATION: Homo sapiens33_640050 VH CDR2 PRT

<400> SEQUENCE: 304

Ala Ile Ser Gly Ser Gly Gly Ser Thr Tyr Tyr Ala Asp Ser Val Lys
1               5                   10                  15

Gly

<210> SEQ ID NO 305
<211> LENGTH: 17
<212> TYPE: PRT
<213> ORGANISM: Artificial Sequence
<220> FEATURE:
<223> OTHER INFORMATION: Homo sapiens33_640050 VH CDR3 PRT

<400> SEQUENCE: 305

His Lys Phe Met Gln Leu Trp Gly Gly Leu Arg Tyr Pro Phe Gly
1               5                   10                  15

Tyr

```
<210> SEQ ID NO 306
<211> LENGTH: 318
<212> TYPE: DNA
<213> ORGANISM: Artificial Sequence
<220> FEATURE:
<223> OTHER INFORMATION: Homo sapiens33_640050 VL DNA

<400> SEQUENCE: 306
tcctacgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcaagat acaaagcggc cctcagggat ccctgagcga     180
ttctctggct ccaactctgg gaacacagcc acgttgacca tcagcgggac ccaggccatg     240
gatgaggctg actattactg tcaggtgtgg gacagcagca ctggggtatt cggcggaggg     300
accaaggtca ccgtccta                                                   318

<210> SEQ ID NO 307
<211> LENGTH: 106
<212> TYPE: PRT
<213> ORGANISM: Artificial Sequence
<220> FEATURE:
<223> OTHER INFORMATION: Homo sapiens33_640050 VL PRT

<400> SEQUENCE: 307

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105

<210> SEQ ID NO 308
<211> LENGTH: 11
<212> TYPE: PRT
<213> ORGANISM: Artificial Sequence
<220> FEATURE:
<223> OTHER INFORMATION: Homo sapiens33_640050 VL CDR1 PRT

<400> SEQUENCE: 308

Ser Gly Glu Arg Met Gly Asp Lys Tyr Ala Ala
1               5                   10

<210> SEQ ID NO 309
<211> LENGTH: 7
<212> TYPE: PRT
<213> ORGANISM: Artificial Sequence
<220> FEATURE:
<223> OTHER INFORMATION: Homo sapiens33_640050 VL CDR2 PRT

<400> SEQUENCE: 309

Gln Asp Thr Lys Arg Pro Ser
1               5
```

<210> SEQ ID NO 310
<211> LENGTH: 9
<212> TYPE: PRT
<213> ORGANISM: Artificial Sequence
<220> FEATURE:
<223> OTHER INFORMATION: Homo sapiens33_640050 VL CDR3 PRT

<400> SEQUENCE: 310

Gln Val Trp Asp Ser Ser Thr Gly Val
1               5

<210> SEQ ID NO 311
<211> LENGTH: 378
<212> TYPE: DNA
<213> ORGANISM: Artificial Sequence
<220> FEATURE:
<223> OTHER INFORMATION: Homo sapiens33_640047 VH DNA

<400> SEQUENCE: 311
gaggtgcagc tgttggagtc tgggggaggc ttggtacagc ctggggggtc cctgagactc      60
tcctgtgcag cctctggatt caccttttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtac gaggctcaag    300
ttcatgcagc tatggggggg gggcttgcgt tatcccttcg gctactgggg ccaagggaca    360
atggtcaccg tctcgagt                                                   378

<210> SEQ ID NO 312
<211> LENGTH: 126
<212> TYPE: PRT
<213> ORGANISM: Artificial Sequence
<220> FEATURE:
<223> OTHER INFORMATION: Homo sapiens33_640047 VH PRT

<400> SEQUENCE: 312

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Leu Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 313
<211> LENGTH: 5
<212> TYPE: PRT
<213> ORGANISM: Artificial Sequence
<220> FEATURE:
<223> OTHER INFORMATION: Homo sapiens33_640047 VH CDR1 PRT

<400> SEQUENCE: 313

Ser Tyr Ala Met Ser
1               5

<210> SEQ ID NO 314
<211> LENGTH: 17
<212> TYPE: PRT
<213> ORGANISM: Artificial Sequence
<220> FEATURE:
<223> OTHER INFORMATION: Homo sapiens33_640047 VH CDR2 PRT

<400> SEQUENCE: 314

Ala Ile Ser Gly Ser Gly Gly Ser Thr Tyr Tyr Ala Asp Ser Val Lys
1               5                   10                  15

Gly

<210> SEQ ID NO 315
<211> LENGTH: 17
<212> TYPE: PRT
<213> ORGANISM: Artificial Sequence
<220> FEATURE:
<223> OTHER INFORMATION: Homo sapiens33_640047 VH CDR3 PRT

<400> SEQUENCE: 315

Leu Lys Phe Met Gln Leu Trp Gly Gly Gly Leu Arg Tyr Pro Phe Gly
1               5                   10                  15

Tyr

<210> SEQ ID NO 316
<211> LENGTH: 318
<212> TYPE: DNA
<213> ORGANISM: Artificial Sequence
<220> FEATURE:
<223> OTHER INFORMATION: Homo sapiens33_640047 VL DNA

<400> SEQUENCE: 316
tcctacgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcaagat acaaagcggc cctcaggcat ccctgagcga     180
ttctctggct ccaactctgg gaacacagcc acgttgacca tcagcgggac ccaggccatg     240
gatgaggctg actattactg tcaggtgtgg gacagcagca ctggggtatt cggcggaggg     300
accaaggtca ccgtccta                                                   318

<210> SEQ ID NO 317
<211> LENGTH: 106
<212> TYPE: PRT
<213> ORGANISM: Artificial Sequence
<220> FEATURE:
<223> OTHER INFORMATION: Homo sapiens33_640047 VL PRT

<400> SEQUENCE: 317

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met

```
                65                  70                  75                  80
Asp Glu Ala Asp Tyr Tyr Cys Gln Val Trp Asp Ser Ser Thr Gly Val
                        85                  90                  95

Phe Gly Gly Gly Thr Lys Val Thr Val Leu
                100                 105
```

<210> SEQ ID NO 318
<211> LENGTH: 11
<212> TYPE: PRT
<213> ORGANISM: Artificial Sequence
<220> FEATURE:
<223> OTHER INFORMATION: Homo sapiens33_640047 VL CDR1 PRT

<400> SEQUENCE: 318

```
Ser Gly Glu Arg Met Gly Asp Lys Tyr Ala Ala
1               5                   10
```

<210> SEQ ID NO 319
<211> LENGTH: 7
<212> TYPE: PRT
<213> ORGANISM: Artificial Sequence
<220> FEATURE:
<223> OTHER INFORMATION: Homo sapiens33_640047 VL CDR2 PRT

<400> SEQUENCE: 319

```
Gln Asp Thr Lys Arg Pro Ser
1               5
```

<210> SEQ ID NO 320
<211> LENGTH: 9
<212> TYPE: PRT
<213> ORGANISM: Artificial Sequence
<220> FEATURE:
<223> OTHER INFORMATION: Homo sapiens33_640047 VL CDR3 PRT

<400> SEQUENCE: 320

```
Gln Val Trp Asp Ser Ser Thr Gly Val
1               5
```

<210> SEQ ID NO 321
<211> LENGTH: 384
<212> TYPE: DNA
<213> ORGANISM: Artificial Sequence
<220> FEATURE:
<223> OTHER INFORMATION: Homo sapiens33_640166 VH DNA

<400> SEQUENCE: 321

```
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg gctgagtg gtctcagct attaatggtg atggtgatgg tgggcgccca       180
tactacgcag actccgtgaa ggccggttc accatctcca gagacaattc caagaacacg    240
ctgtatctgc aaatgaacag cctgagagcc gaggacacgg ccgtgtatta ctgtgcgaga   300
gatctgtgga tacagctatg gggggggggc ttgcgttatc ccttcggcta ctggggccaa    360
gggacaatgg tcaccgtctc gagt                                           384
```

<210> SEQ ID NO 322
<211> LENGTH: 128
<212> TYPE: PRT
<213> ORGANISM: Artificial Sequence
<220> FEATURE:
<223> OTHER INFORMATION: Homo sapiens33_640166 VH PRT

<400> SEQUENCE: 322

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Gly Asp Gly Asp Gly Gly Arg Pro Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Leu Trp Ile Gln Leu Trp Gly Gly Gly Leu Arg
            100                 105                 110

Tyr Pro Phe Gly Tyr Trp Gly Gln Gly Thr Met Val Thr Val Ser Ser
        115                 120                 125

<210> SEQ ID NO 323
<211> LENGTH: 5
<212> TYPE: PRT
<213> ORGANISM: Artificial Sequence
<220> FEATURE:
<223> OTHER INFORMATION: Homo sapiens33_640166 VH CDR1 PRT

<400> SEQUENCE: 323

Ser Tyr Ala Met Ser
1               5

<210> SEQ ID NO 324
<211> LENGTH: 19
<212> TYPE: PRT
<213> ORGANISM: Artificial Sequence
<220> FEATURE:
<223> OTHER INFORMATION: Homo sapiens33_640166 VH CDR2 PRT

<400> SEQUENCE: 324

Ala Ile Asn Gly Asp Gly Asp Gly Gly Arg Pro Tyr Tyr Ala Asp Ser
1               5                   10                  15

Val Lys Gly

<210> SEQ ID NO 325
<211> LENGTH: 17
<212> TYPE: PRT
<213> ORGANISM: Artificial Sequence
<220> FEATURE:
<223> OTHER INFORMATION: Homo sapiens33_640166 VH CDR3 PRT

<400> SEQUENCE: 325

Asp Leu Trp Ile Gln Leu Trp Gly Gly Gly Leu Arg Tyr Pro Phe Gly
1               5                   10                  15

Tyr

<210> SEQ ID NO 326
<211> LENGTH: 318
<212> TYPE: DNA
<213> ORGANISM: Artificial Sequence
<220> FEATURE:
<223> OTHER INFORMATION: Homo sapiens33_640166 VL DNA

<400> SEQUENCE: 326

```
tcctacgtgc tgactcagcc accctcagtg tccgtgtccc caggacagac ggccagcatc    60
acctgctctg gagaaagaat gggggataaa tatgctgcct ggtatcagca gaagccaggc   120
cagtcacctg tgctggtcat ctatcaagat acaaagcggc cctcagggat ccctgagcga   180
ttctctggct ccaactctgg gaacacagcc acgttgacca tcagcgggac ccaggccatg   240
gatgaggctg actattactg tcaggtgtgg gacagcagca ctggggtatt cggcggaggg   300
accaaggtca ccgtccta                                                 318
```

```
<210> SEQ ID NO 327
<211> LENGTH: 106
<212> TYPE: PRT
<213> ORGANISM: Artificial Sequence
<220> FEATURE:
<223> OTHER INFORMATION: Homo sapiens33_640166 VL PRT

<400> SEQUENCE: 327

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105

<210> SEQ ID NO 328
<211> LENGTH: 11
<212> TYPE: PRT
<213> ORGANISM: Artificial Sequence
<220> FEATURE:
<223> OTHER INFORMATION: Homo sapiens33_640166 VL CDR1 PRT

<400> SEQUENCE: 328

Ser Gly Glu Arg Met Gly Asp Lys Tyr Ala Ala
1               5                   10

<210> SEQ ID NO 329
<211> LENGTH: 7
<212> TYPE: PRT
<213> ORGANISM: Artificial Sequence
<220> FEATURE:
<223> OTHER INFORMATION: Homo sapiens33_640166 VL CDR2 PRT

<400> SEQUENCE: 329

Gln Asp Thr Lys Arg Pro Ser
1               5

<210> SEQ ID NO 330
<211> LENGTH: 9
<212> TYPE: PRT
<213> ORGANISM: Artificial Sequence
<220> FEATURE:
<223> OTHER INFORMATION: Homo sapiens33_640166 VL CDR3 PRT

<400> SEQUENCE: 330
```

Gln Val Trp Asp Ser Ser Thr Gly Val
1               5

<210> SEQ ID NO 331
<211> LENGTH: 378
<212> TYPE: DNA
<213> ORGANISM: Artificial Sequence
<220> FEATURE:
<223> OTHER INFORMATION: Homo sapiens33_640169 VH DNA

<400> SEQUENCE: 331

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcaggt attagtggta tcgacacaag cacatactac   180
gcagactccg tgaagggccg gttcaccatc tccagagaca attccaagaa cacgctgtat   240
ctgcaaatga acagcctgag agccgaggac acggccgtgt attactgtgc gagagatctg   300
tggatacagc tatgggggg gggcttgcgt tatcccttcg gctactgggg ccaagggaca   360
atggtcaccg tctcgagt                                                 378
```

<210> SEQ ID NO 332
<211> LENGTH: 126
<212> TYPE: PRT
<213> ORGANISM: Artificial Sequence
<220> FEATURE:
<223> OTHER INFORMATION: Homo sapiens33_640169 VH PRT

<400> SEQUENCE: 332

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ile Asp Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Ile Gln Leu Trp Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 333
<211> LENGTH: 5
<212> TYPE: PRT
<213> ORGANISM: Artificial Sequence
<220> FEATURE:
<223> OTHER INFORMATION: Homo sapiens33_640169 VH CDR1 PRT

<400> SEQUENCE: 333

Ser Tyr Ala Met Ser
1               5

<210> SEQ ID NO 334
<211> LENGTH: 17
<212> TYPE: PRT
<213> ORGANISM: Artificial Sequence

```
<220> FEATURE:
<223> OTHER INFORMATION: Homo sapiens33_640169 VH CDR2 PRT

<400> SEQUENCE: 334

Gly Ile Ser Gly Ile Asp Thr Ser Thr Tyr Tyr Ala Asp Ser Val Lys
1               5                   10                  15
Gly

<210> SEQ ID NO 335
<211> LENGTH: 17
<212> TYPE: PRT
<213> ORGANISM: Artificial Sequence
<220> FEATURE:
<223> OTHER INFORMATION: Homo sapiens33_640169 VH CDR3 PRT

<400> SEQUENCE: 335

Asp Leu Trp Ile Gln Leu Trp Gly Gly Gly Leu Arg Tyr Pro Phe Gly
1               5                   10                  15
Tyr

<210> SEQ ID NO 336
<211> LENGTH: 318
<212> TYPE: DNA
<213> ORGANISM: Artificial Sequence
<220> FEATURE:
<223> OTHER INFORMATION: Homo sapiens33_640169 VL DNA

<400> SEQUENCE: 336
tcctacgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcaagat acaaagcggc cctcaggat ccctgagcga      180 ttctctggct ccaactctgg gaacacagcc acgttgacca tcagcgggac ccaggccatg     240
gatgaggctg actattactg tcaggtgtgg gacagcagca ctggggtatt cggcggaggg     300
accaaggtca ccgtccta                                                   318

<210> SEQ ID NO 337
<211> LENGTH: 106
<212> TYPE: PRT
<213> ORGANISM: Artificial Sequence
<220> FEATURE:
<223> OTHER INFORMATION: Homo sapiens33_640169 VL PRT

<400> SEQUENCE: 337

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
                20                  25                  30

Ala Trp Tyr Gln Gln Lys Pro Gly Gln Ser Pro Val Leu Val Ile Tyr
            35                  40                  45

Gln Asp Thr Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105
```

<210> SEQ ID NO 338
<211> LENGTH: 11
<212> TYPE: PRT
<213> ORGANISM: Artificial Sequence
<220> FEATURE:
<223> OTHER INFORMATION: Homo sapiens33_640169 VL CDR1 PRT

<400> SEQUENCE: 338

Ser Gly Glu Arg Met Gly Asp Lys Tyr Ala Ala
1               5                   10

<210> SEQ ID NO 339
<211> LENGTH: 7
<212> TYPE: PRT
<213> ORGANISM: Artificial Sequence
<220> FEATURE:
<223> OTHER INFORMATION: Homo sapiens33_640169 VL CDR2 PRT

<400> SEQUENCE: 339

Gln Asp Thr Lys Arg Pro Ser
1               5

<210> SEQ ID NO 340
<211> LENGTH: 9
<212> TYPE: PRT
<213> ORGANISM: Artificial Sequence
<220> FEATURE:
<223> OTHER INFORMATION: Homo sapiens33_640169 VL CDR3 PRT

<400> SEQUENCE: 340

Gln Val Trp Asp Ser Ser Thr Gly Val
1               5

<210> SEQ ID NO 341
<211> LENGTH: 378
<212> TYPE: DNA
<213> ORGANISM: Artificial Sequence
<220> FEATURE:
<223> OTHER INFORMATION: Homo sapiens33_640170 VH DNA

<400> SEQUENCE: 341
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaggc atttctgcaa tagaccaaag cacatactac     180
gcagactccg tgaagggccg gttcaccatc tccagagaca attccaagaa cacgctgtat     240
ctgcaaatga acagcctgag agccgaggac acggccgtgt attactgtgc gagagatctg     300
tggatacagc tatgggggg gggcttgcgt tatcccttcg gctactgggg ccaagggaca     360
atggtcaccg tctcgagt                                                    378

<210> SEQ ID NO 342
<211> LENGTH: 126
<212> TYPE: PRT
<213> ORGANISM: Artificial Sequence
<220> FEATURE:
<223> OTHER INFORMATION: Homo sapiens33_640170 VH PRT

<400> SEQUENCE: 342

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45
Ser Gly Ile Ser Ala Ile Asp Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Ile Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 343
<211> LENGTH: 5
<212> TYPE: PRT
<213> ORGANISM: Artificial Sequence
<220> FEATURE:
<223> OTHER INFORMATION: Homo sapiens33_640170 VH CDR1 PRT

<400> SEQUENCE: 343

Ser Tyr Ala Met Ser
1               5

<210> SEQ ID NO 344
<211> LENGTH: 17
<212> TYPE: PRT
<213> ORGANISM: Artificial Sequence
<220> FEATURE:
<223> OTHER INFORMATION: Homo sapiens33_640170 VH CDR2 PRT

<400> SEQUENCE: 344

Gly Ile Ser Ala Ile Asp Gln Ser Thr Tyr Tyr Ala Asp Ser Val Lys
1               5                   10                  15

Gly

<210> SEQ ID NO 345
<211> LENGTH: 17
<212> TYPE: PRT
<213> ORGANISM: Artificial Sequence
<220> FEATURE:
<223> OTHER INFORMATION: Homo sapiens33_640170 VH CDR3 PRT

<400> SEQUENCE: 345

Asp Leu Trp Ile Gln Leu Trp Gly Gly Gly Leu Arg Tyr Pro Phe Gly
1               5                   10                  15

Tyr

<210> SEQ ID NO 346
<211> LENGTH: 318
<212> TYPE: DNA
<213> ORGANISM: Artificial Sequence
<220> FEATURE:
<223> OTHER INFORMATION: Homo sapiens33_640170 VL DNA

<400> SEQUENCE: 346
tcctacgtgc tgactcagcc accctcagtg tccgtgtccc caggacagac ggccagcatc     60
acctgctctg gagaaagaat ggggataaaa tatgctgcct ggtatcagca gaagccaggc    120
cagtcacctg tgctggtcat ctatcaagat acaaagcggc cctcagggat ccctgagcga    180
ttctctggct ccaactctgg gaacacagcc acgttgacca tcagcgggac ccaggccatg    240
gatgaggctg actattactg tcaggtgtgg gacagcagca ctggggtatt cggcggaggg    300
```
accaaggtca ccgtcccta 318

<210> SEQ ID NO 347
<211> LENGTH: 106
<212> TYPE: PRT
<213> ORGANISM: Artificial Sequence
<220> FEATURE:
<223> OTHER INFORMATION: Homo sapiens33_640170 VL PRT

<400> SEQUENCE: 347

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105

<210> SEQ ID NO 348
<211> LENGTH: 11
<212> TYPE: PRT
<213> ORGANISM: Artificial Sequence
<220> FEATURE:
<223> OTHER INFORMATION: Homo sapiens33_640170 VL CDR1 PRT

<400> SEQUENCE: 348

Ser Gly Glu Arg Met Gly Asp Lys Tyr Ala Ala
1               5                   10

<210> SEQ ID NO 349
<211> LENGTH: 7
<212> TYPE: PRT
<213> ORGANISM: Artificial Sequence
<220> FEATURE:
<223> OTHER INFORMATION: Homo sapiens33_640170 VL CDR2 PRT

<400> SEQUENCE: 349

Gln Asp Thr Lys Arg Pro Ser
1               5

<210> SEQ ID NO 350
<211> LENGTH: 9
<212> TYPE: PRT
<213> ORGANISM: Artificial Sequence
<220> FEATURE:
<223> OTHER INFORMATION: Homo sapiens33_640170 VL CDR3 PRT

<400> SEQUENCE: 350

Gln Val Trp Asp Ser Ser Thr Gly Val
1               5

<210> SEQ ID NO 351
<211> LENGTH: 378
<212> TYPE: DNA
<213> ORGANISM: Artificial Sequence
<220> FEATURE:

<223> OTHER INFORMATION: Homo sapiens33_640036 VH DNA

<400> SEQUENCE: 351

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatctg     300
tggatgcagc tatggggggg gggcttgcgt tatcccttcg gctactgggg ccaagggaca     360
atggtcaccg tctcgagt                                                   378
```

<210> SEQ ID NO 352
<211> LENGTH: 126
<212> TYPE: PRT
<213> ORGANISM: Artificial Sequence
<220> FEATURE:
<223> OTHER INFORMATION: Homo sapiens33_640036 VH PRT

<400> SEQUENCE: 352

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Leu Trp Met Gln Leu Trp Gly Gly Gly Leu Arg Tyr Pro
            100                 105                 110
Phe Gly Tyr Trp Gly Gln Gly Thr Met Val Thr Val Ser Ser
        115                 120                 125
```

<210> SEQ ID NO 353
<211> LENGTH: 5
<212> TYPE: PRT
<213> ORGANISM: Artificial Sequence
<220> FEATURE:
<223> OTHER INFORMATION: Homo sapiens33_640036 VH CDR1 PRT

<400> SEQUENCE: 353

```
Ser Tyr Ala Met Ser
1               5
```

<210> SEQ ID NO 354
<211> LENGTH: 17
<212> TYPE: PRT
<213> ORGANISM: Artificial Sequence
<220> FEATURE:
<223> OTHER INFORMATION: Homo sapiens33_640036 VH CDR2 PRT

<400> SEQUENCE: 354

```
Ala Ile Ser Gly Ser Gly Gly Ser Thr Tyr Tyr Ala Asp Ser Val Lys
1               5                   10                  15
Gly
```

<210> SEQ ID NO 355
<211> LENGTH: 17
<212> TYPE: PRT
<213> ORGANISM: Artificial Sequence
<220> FEATURE:
<223> OTHER INFORMATION: Homo sapiens33_640036 VH CDR3 PRT

<400> SEQUENCE: 355

Asp Leu Trp Met Gln Leu Trp Gly Gly Gly Leu Arg Tyr Pro Phe Gly
1               5                   10                  15

Tyr

<210> SEQ ID NO 356
<211> LENGTH: 318
<212> TYPE: DNA
<213> ORGANISM: Artificial Sequence
<220> FEATURE:
<223> OTHER INFORMATION: Homo sapiens33_640036 VL DNA

<400> SEQUENCE: 356
tcctacgtgc tgactcagcc accctcagtg tccgtgtccc caggacagac ggccagcatc      60
acctgctctg gagaaagaat ggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaggccatg     240
gatgaggctg actattactg tcaggtgtgg gacagcagca ctggggtatt cggcggaggg     300
accaaggtca ccgtccta                                                   318

<210> SEQ ID NO 357
<211> LENGTH: 106
<212> TYPE: PRT
<213> ORGANISM: Artificial Sequence
<220> FEATURE:
<223> OTHER INFORMATION: Homo sapiens33_640036 VL PRT

<400> SEQUENCE: 357

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105

<210> SEQ ID NO 358
<211> LENGTH: 11
<212> TYPE: PRT
<213> ORGANISM: Artificial Sequence
<220> FEATURE:
<223> OTHER INFORMATION: Homo sapiens33_640036 VL CDR1 PRT

<400> SEQUENCE: 358

Ser Gly Glu Arg Met Gly Asp Lys Tyr Ala Ala
1               5                   10

<210> SEQ ID NO 359
<211> LENGTH: 7
<212> TYPE: PRT
<213> ORGANISM: Artificial Sequence
<220> FEATURE:
<223> OTHER INFORMATION: Homo sapiens33_640036 VL CDR2 PRT

<400> SEQUENCE: 359

Arg Asp Thr Lys Arg Pro Ser
1               5

<210> SEQ ID NO 360
<211> LENGTH: 9
<212> TYPE: PRT
<213> ORGANISM: Artificial Sequence
<220> FEATURE:
<223> OTHER INFORMATION: Homo sapiens33_640036 VL CDR3 PRT

<400> SEQUENCE: 360

Gln Val Trp Asp Ser Ser Thr Gly Val
1               5

<210> SEQ ID NO 361
<211> LENGTH: 378
<212> TYPE: DNA
<213> ORGANISM: Artificial Sequence
<220> FEATURE:
<223> OTHER INFORMATION: Homo sapiens33_640117 VH DNA

<400> SEQUENCE: 361
gaggtgcagc tgttggagtc tgggggaggc ttggtacagc ctggggggtc cctgagactc      60
tcctgtgcag cctctggatt caccttttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtac gaggctcaag    300
ttcatgcagc tatgggggggg gggcttgcgt tatcccttcg gctactgggg ccaagggaca    360
atggtcaccg tctcgagt                                                   378

<210> SEQ ID NO 362
<211> LENGTH: 126
<212> TYPE: PRT
<213> ORGANISM: Artificial Sequence
<220> FEATURE:
<223> OTHER INFORMATION: Homo sapiens33_640117 VH PRT

<400> SEQUENCE: 362

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Thr Arg Leu Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 363
<211> LENGTH: 5
<212> TYPE: PRT
<213> ORGANISM: Artificial Sequence
<220> FEATURE:
<223> OTHER INFORMATION: Homo sapiens33_640117 VH CDR1 PRT

<400> SEQUENCE: 363

Ser Tyr Ala Met Ser
1               5

<210> SEQ ID NO 364
<211> LENGTH: 17
<212> TYPE: PRT
<213> ORGANISM: Artificial Sequence
<220> FEATURE:
<223> OTHER INFORMATION: Homo sapiens33_640117 VH CDR2 PRT

<400> SEQUENCE: 364

Ala Ile Ser Gly Ser Gly Gly Ser Thr Tyr Tyr Ala Asp Ser Val Lys
1               5                   10                  15

Gly

<210> SEQ ID NO 365
<211> LENGTH: 17
<212> TYPE: PRT
<213> ORGANISM: Artificial Sequence
<220> FEATURE:
<223> OTHER INFORMATION: Homo sapiens33_640117 VH CDR3 PRT

<400> SEQUENCE: 365

Leu Lys Phe Met Gln Leu Trp Gly Gly Gly Leu Arg Tyr Pro Phe Gly
1               5                   10                  15

Tyr

<210> SEQ ID NO 366
<211> LENGTH: 318
<212> TYPE: DNA
<213> ORGANISM: Artificial Sequence
<220> FEATURE:
<223> OTHER INFORMATION: Homo sapiens33_640117 VL DNA

<400> SEQUENCE: 366
tcctacgtgc tgactcagcc accctcagtg tccgtgtccc caggacagac ggccagcatc     60
acctgctctg gagaaagaat gggggataaa tatgctgcct ggtatcagca gaagccaggc    120
cagtcacctg tgctggtcat ctatcgagat acaaagcggc cctcaggat cccctgagcga    180 ttctctggct ccaactctgg gaacacagcc acgttgacca tcagcgggac ccaggccatg    240
gatgaggctg actattactg tcaggtgtgg gacagcagca ctggggtatt cggcggaggg    300
accaaggtca ccgtccta                                                  318

<210> SEQ ID NO 367
<211> LENGTH: 106
<212> TYPE: PRT
<213> ORGANISM: Artificial Sequence
<220> FEATURE:
```

<223> OTHER INFORMATION: Homo sapiens33_640117 VL PRT

<400> SEQUENCE: 367

Ser Tyr Val Leu Thr Gln Pro Pro Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Ser Ser Thr Gly Val
                85                  90                  95

Phe Gly Gly Gly Thr Lys Val Thr Val Leu
            100                 105

<210> SEQ ID NO 368
<211> LENGTH: 11
<212> TYPE: PRT
<213> ORGANISM: Artificial Sequence
<220> FEATURE:
<223> OTHER INFORMATION: Homo sapiens33_640117 VL CDR1 PRT

<400> SEQUENCE: 368

Ser Gly Glu Arg Met Gly Asp Lys Tyr Ala Ala
1               5                   10

<210> SEQ ID NO 369
<211> LENGTH: 7
<212> TYPE: PRT
<213> ORGANISM: Artificial Sequence
<220> FEATURE:
<223> OTHER INFORMATION: Homo sapiens33_640117 VL CDR2 PRT

<400> SEQUENCE: 369

Arg Asp Thr Lys Arg Pro Ser
1               5

<210> SEQ ID NO 370
<211> LENGTH: 9
<212> TYPE: PRT
<213> ORGANISM: Artificial Sequence
<220> FEATURE:
<223> OTHER INFORMATION: Homo sapiens33_640117 VL CDR3 PRT

<400> SEQUENCE: 370

Gln Val Trp Asp Ser Ser Thr Gly Val
1               5

<210> SEQ ID NO 371
<211> LENGTH: 378
<212> TYPE: DNA
<213> ORGANISM: Artificial Sequence
<220> FEATURE:
<223> OTHER INFORMATION: Homo sapiens33_640076 VH DNA

<400> SEQUENCE: 371
gaggtgcagc tgttggagtc tggggggaggc ttggtacagc ctgggggtc cctgagactc    60 tcctgtgcag cctctggatt caccttagc agctatgcca tgagctgggt ccgccgggct   120
ccagggaagg ggctggagtg ggtctcagct attagtggta gtggtggtag cacatactac   180

```
gcagactccg tgaagggccg gttcaccatc tccagagaca attccaagaa cacgctgtat    240
ctgcaaatga acagcctgag agccgaggac acggccgtgt attactgtgc gagagatctg    300
tggatggaga actgggtggg gggcttgcgt tatcccttcg ctactgggg ccaagggaca    360 atggtcaccg tctcgagt                                                  378
```

```
<210> SEQ ID NO 372
<211> LENGTH: 126
<212> TYPE: PRT
<213> ORGANISM: Artificial Sequence
<220> FEATURE:
<223> OTHER INFORMATION: Homo sapiens33_640076 VH PRT

<400> SEQUENCE: 372
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Glu Asn Trp Val Gly Gly Leu Arg Tyr Pro
            100                 105                 110

Phe Gly Tyr Trp Gly Gln Gly Thr Met Val Thr Val Ser Ser
        115                 120                 125

```
<210> SEQ ID NO 373
<211> LENGTH: 5
<212> TYPE: PRT
<213> ORGANISM: Artificial Sequence
<220> FEATURE:
<223> OTHER INFORMATION: Homo sapiens33_640076 VH CDR1 PRT

<400> SEQUENCE: 373
```

Ser Tyr Ala Met Ser
1               5

```
<210> SEQ ID NO 374
<211> LENGTH: 17
<212> TYPE: PRT
<213> ORGANISM: Artificial Sequence
<220> FEATURE:
<223> OTHER INFORMATION: Homo sapiens33_640076 VH CDR2 PRT

<400> SEQUENCE: 374
```

Ala Ile Ser Gly Ser Gly Gly Ser Thr Tyr Tyr Ala Asp Ser Val Lys
1               5                   10                  15

Gly

```
<210> SEQ ID NO 375
<211> LENGTH: 17
<212> TYPE: PRT
<213> ORGANISM: Artificial Sequence
<220> FEATURE:
<223> OTHER INFORMATION: Homo sapiens33_640076 VH CDR3 PRT
```

<400> SEQUENCE: 375

Asp Leu Trp Met Glu Asn Trp Val Gly Gly Leu Arg Tyr Pro Phe Gly
1               5                   10                  15

Tyr

<210> SEQ ID NO 376
<211> LENGTH: 318
<212> TYPE: DNA
<213> ORGANISM: Artificial Sequence
<220> FEATURE:
<223> OTHER INFORMATION: Homo sapiens33_640076 VL DNA

<400> SEQUENCE: 376
tcctacgtgc tgactcagcc accctcagtg tccgtgtcac caggacagac ggccagcatc     60
acctgctctg gagaaagaat ggggataaa tatgctgcct ggtatcagca gaagccaggc    120
cagtcacctg tgctggtcat ctatcaagat acaaagcggc cctcagggat ccctgagcga    180
ttctctggct ccaactctgg gaacacagcc acgttgacca tcagcgggac ccaggccata    240
gatgaggccg actattactg tgaggtcaag aagtccgaca ctggggtatt cggcggaggg    300
accaaggtca ccgtccta                                                  318

<210> SEQ ID NO 377
<211> LENGTH: 106
<212> TYPE: PRT
<213> ORGANISM: Artificial Sequence
<220> FEATURE:
<223> OTHER INFORMATION: Homo sapiens33_640076 VL PRT

<400> SEQUENCE: 377

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Ile
65                  70                  75                  80

Asp Glu Ala Asp Tyr Tyr Cys Glu Val Lys Lys Ser Asp Thr Gly Val
                85                  90                  95

Phe Gly Gly Gly Thr Lys Val Thr Val Leu
            100                 105

<210> SEQ ID NO 378
<211> LENGTH: 11
<212> TYPE: PRT
<213> ORGANISM: Artificial Sequence
<220> FEATURE:
<223> OTHER INFORMATION: Homo sapiens33_640076 VL CDR1 PRT

<400> SEQUENCE: 378

Ser Gly Glu Arg Met Gly Asp Lys Tyr Ala Ala
1               5                   10

<210> SEQ ID NO 379
<211> LENGTH: 7
<212> TYPE: PRT
<213> ORGANISM: Artificial Sequence
<220> FEATURE:

-continued

<223> OTHER INFORMATION: Homo sapiens33_640076 VL CDR2 PRT

<400> SEQUENCE: 379

Gln Asp Thr Lys Arg Pro Ser
1               5

<210> SEQ ID NO 380
<211> LENGTH: 9
<212> TYPE: PRT
<213> ORGANISM: Artificial Sequence
<220> FEATURE:
<223> OTHER INFORMATION: Homo sapiens33_640076 VL CDR3 PRT

<400> SEQUENCE: 380

Glu Val Lys Lys Ser Asp Thr Gly Val
1               5

<210> SEQ ID NO 381
<211> LENGTH: 378
<212> TYPE: DNA
<213> ORGANISM: Artificial Sequence
<220> FEATURE:
<223> OTHER INFORMATION: Homo sapiens33_640081 VH DNA

<400> SEQUENCE: 381

```
gaggtgcagc tgttggagtc tgggggaggc tcggtacagc ctgggggtc cctgagactc      60 tcctgtgcag cctctggatt cacctttagc agctatgcca tgaactgggt ccgccaggct    120
ccagggaagg ggctggagtg ggtctcagct attagtggta gtggtggtag cacacactac    180
gcagactccg tgaagggccg gttcaccatc tccagagaca attccaagaa cacgctgtat    240
ctgcaaatga acagcctgag agccgaggac acggccgtgt attactgtgg ccgggccaag    300
ttcatgcagc tatggggggg gggcttgcgt tatccctcg gctactgggg ccaagggaca    360
atggtcaccg tctcgagt                                                   378
```

<210> SEQ ID NO 382
<211> LENGTH: 126
<212> TYPE: PRT
<213> ORGANISM: Artificial Sequence
<220> FEATURE:
<223> OTHER INFORMATION: Homo sapiens33_640081 VH PRT

<400> SEQUENCE: 382

Glu Val Gln Leu Leu Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Ala Lys Phe Met Gln Leu Trp Gly Gly Gly Leu Arg Tyr Pro
            100                 105                 110

Leu Gly Tyr Trp Gly Gln Gly Thr Met Val Thr Val Ser Ser
        115                 120                 125

```
<210> SEQ ID NO 383
<211> LENGTH: 5
<212> TYPE: PRT
<213> ORGANISM: Artificial Sequence
<220> FEATURE:
<223> OTHER INFORMATION: Homo sapiens33_640081 VH CDR1 PRT

<400> SEQUENCE: 383

Ser Tyr Ala Met Asn
1               5

<210> SEQ ID NO 384
<211> LENGTH: 17
<212> TYPE: PRT
<213> ORGANISM: Artificial Sequence
<220> FEATURE:
<223> OTHER INFORMATION: Homo sapiens33_640081 VH CDR2 PRT

<400> SEQUENCE: 384

Ala Ile Ser Gly Ser Gly Gly Ser Thr His Tyr Ala Asp Ser Val Lys
1               5                   10                  15

Gly

<210> SEQ ID NO 385
<211> LENGTH: 17
<212> TYPE: PRT
<213> ORGANISM: Artificial Sequence
<220> FEATURE:
<223> OTHER INFORMATION: Homo sapiens33_640081 VH CDR3 PRT

<400> SEQUENCE: 385

Ala Lys Phe Met Gln Leu Trp Gly Gly Gly Leu Arg Tyr Pro Leu Gly
1               5                   10                  15

Tyr

<210> SEQ ID NO 386
<211> LENGTH: 321
<212> TYPE: DNA
<213> ORGANISM: Artificial Sequence
<220> FEATURE:
<223> OTHER INFORMATION: Homo sapiens33_640081 VL DNA

<400> SEQUENCE: 386
tcctacgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcaagat acaaagcggc cctcagggat ccctgagcga     180
ttctctggct ccaactctgg gaacacagcc acgttgacca tcagcgggac ccaggccacg     240
gatgaggctg actattactg tcaggtgtgg gcggccgacg acactggggt attcggcgga     300
gggaccaagg tcaccgtcct a                                                321

<210> SEQ ID NO 387
<211> LENGTH: 107
<212> TYPE: PRT
<213> ORGANISM: Artificial Sequence
<220> FEATURE:
<223> OTHER INFORMATION: Homo sapiens33_640081 VL PRT

<400> SEQUENCE: 387

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30
```

```
Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Thr
65                  70                  75                  80

Asp Glu Ala Asp Tyr Tyr Cys Gln Val Trp Ala Ala Asp Asp Thr Gly
                85                  90                  95

Val Phe Gly Gly Gly Thr Lys Val Thr Val Leu
                100                 105

<210> SEQ ID NO 388
<211> LENGTH: 11
<212> TYPE: PRT
<213> ORGANISM: Artificial Sequence
<220> FEATURE:
<223> OTHER INFORMATION: Homo sapiens33_640081 VL CDR1 PRT

<400> SEQUENCE: 388

Ser Gly Glu Arg Met Gly Asp Lys Tyr Ala Ala
1               5                   10

<210> SEQ ID NO 389
<211> LENGTH: 7
<212> TYPE: PRT
<213> ORGANISM: Artificial Sequence
<220> FEATURE:
<223> OTHER INFORMATION: Homo sapiens33_640081 VL CDR2 PRT

<400> SEQUENCE: 389

Gln Asp Thr Lys Arg Pro Ser
1               5

<210> SEQ ID NO 390
<211> LENGTH: 10
<212> TYPE: PRT
<213> ORGANISM: Artificial Sequence
<220> FEATURE:
<223> OTHER INFORMATION: Homo sapiens33_640081 VL CDR3 PRT

<400> SEQUENCE: 390

Gln Val Trp Ala Ala Asp Asp Thr Gly Val
1               5                   10

<210> SEQ ID NO 391
<211> LENGTH: 378
<212> TYPE: DNA
<213> ORGANISM: Artificial Sequence
<220> FEATURE:
<223> OTHER INFORMATION: Homo sapiens33_640082 VH DNA

<400> SEQUENCE: 391
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc ccggcagaag     300
ttcatgcagc tatgggggg gggcttgcgt tatcccttcg gctactgggg ccaagggaca     360
atggtcaccg tctcgagt                                                   378
```

<210> SEQ ID NO 392
<211> LENGTH: 126
<212> TYPE: PRT
<213> ORGANISM: Artificial Sequence
<220> FEATURE:
<223> OTHER INFORMATION: Homo sapiens33_640082 VH PRT

<400> SEQUENCE: 392

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 393
<211> LENGTH: 5
<212> TYPE: PRT
<213> ORGANISM: Artificial Sequence
<220> FEATURE:
<223> OTHER INFORMATION: Homo sapiens33_640082 VH CDR1 PRT

<400> SEQUENCE: 393

Ser Tyr Ala Met Ser
1               5

<210> SEQ ID NO 394
<211> LENGTH: 17
<212> TYPE: PRT
<213> ORGANISM: Artificial Sequence
<220> FEATURE:
<223> OTHER INFORMATION: Homo sapiens33_640082 VH CDR2 PRT

<400> SEQUENCE: 394

Ala Ile Ser Gly Ser Gly Gly Ser Thr Tyr Tyr Ala Asp Ser Val Lys
1               5                   10                  15

Gly

<210> SEQ ID NO 395
<211> LENGTH: 17
<212> TYPE: PRT
<213> ORGANISM: Artificial Sequence
<220> FEATURE:
<223> OTHER INFORMATION: Homo sapiens33_640082 VH CDR3 PRT

<400> SEQUENCE: 395

Gln Lys Phe Met Gln Leu Trp Gly Gly Gly Leu Arg Tyr Pro Phe Gly
1               5                   10                  15

Tyr

<210> SEQ ID NO 396

<211> LENGTH: 318
<212> TYPE: DNA
<213> ORGANISM: Artificial Sequence
<220> FEATURE:
<223> OTHER INFORMATION: Homo sapiens33_640082 VL DNA

<400> SEQUENCE: 396

```
tcctacgtgc tgactcagcc accctcagtg tccgtgtccc cagggcagac ggccagcatc    60
acctgctctg gagaaagaat gggggataaa tatgctgcct ggtatcagca gaagccaggc   120
cagtcacctg tgctggtcat ctatcaagat acaaagcggc cctcagggat ccctgagcga   180
ttctctggct ccaactctgg gaacacagcc acgttgacca tcagcgggac ccaggccatt   240
gatgaggctg actattactg tggcgtgttg aagcaggaca ctggggtatt cggcggaggg   300
accaaggtca ccgtccta                                                 318
```

<210> SEQ ID NO 397
<211> LENGTH: 106
<212> TYPE: PRT
<213> ORGANISM: Artificial Sequence
<220> FEATURE:
<223> OTHER INFORMATION: Homo sapiens33_640082 VL PRT

<400> SEQUENCE: 397

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Ile
65                  70                  75                  80

Asp Glu Ala Asp Tyr Tyr Cys Gly Val Leu Lys Gln Asp Thr Gly Val
                85                  90                  95

Phe Gly Gly Gly Thr Lys Val Thr Val Leu
            100                 105

<210> SEQ ID NO 398
<211> LENGTH: 11
<212> TYPE: PRT
<213> ORGANISM: Artificial Sequence
<220> FEATURE:
<223> OTHER INFORMATION: Homo sapiens33_640082 VL CDR1 PRT

<400> SEQUENCE: 398

Ser Gly Glu Arg Met Gly Asp Lys Tyr Ala Ala
1               5                   10

<210> SEQ ID NO 399
<211> LENGTH: 7
<212> TYPE: PRT
<213> ORGANISM: Artificial Sequence
<220> FEATURE:
<223> OTHER INFORMATION: Homo sapiens33_640082 VL CDR2 PRT

<400> SEQUENCE: 399

Gln Asp Thr Lys Arg Pro Ser
1               5

<210> SEQ ID NO 400

<211> LENGTH: 9
<212> TYPE: PRT
<213> ORGANISM: Artificial Sequence
<220> FEATURE:
<223> OTHER INFORMATION: Homo sapiens33_640082 VL CDR3 PRT

<400> SEQUENCE: 400

Gly Val Leu Lys Gln Asp Thr Gly Val
1               5

<210> SEQ ID NO 401
<211> LENGTH: 378
<212> TYPE: DNA
<213> ORGANISM: Artificial Sequence
<220> FEATURE:
<223> OTHER INFORMATION: Homo sapiens33_640084 VH DNA

<400> SEQUENCE: 401
gaggtgcagc tgttggagtc tgggggaggc ttggtacagc ctggggggtc cctgagactc      60
tcctgtgcgg cctctggatt cgcctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc ccggcagaag     300
ttcatgcagc tatggggggg gggcttgcgt tatccctttg gctactgggg ccaagggaca     360
atggtcaccg tctcgagt                                                   378

<210> SEQ ID NO 402
<211> LENGTH: 126
<212> TYPE: PRT
<213> ORGANISM: Artificial Sequence
<220> FEATURE:
<223> OTHER INFORMATION: Homo sapiens33_640084 VH PRT

<400> SEQUENCE: 402

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 403
<211> LENGTH: 5
<212> TYPE: PRT
<213> ORGANISM: Artificial Sequence
<220> FEATURE:
<223> OTHER INFORMATION: Homo sapiens33_640084 VH CDR1 PRT

<400> SEQUENCE: 403

Ser Tyr Ala Met Ser
1               5

<210> SEQ ID NO 404
<211> LENGTH: 17
<212> TYPE: PRT
<213> ORGANISM: Artificial Sequence
<220> FEATURE:
<223> OTHER INFORMATION: Homo sapiens33_640084 VH CDR2 PRT

<400> SEQUENCE: 404

Ala Ile Ser Gly Ser Gly Gly Ser Thr Tyr Tyr Ala Asp Ser Val Lys
1               5                   10                  15
Gly

<210> SEQ ID NO 405
<211> LENGTH: 17
<212> TYPE: PRT
<213> ORGANISM: Artificial Sequence
<220> FEATURE:
<223> OTHER INFORMATION: Homo sapiens33_640084 VH CDR3 PRT

<400> SEQUENCE: 405

Gln Lys Phe Met Gln Leu Trp Gly Gly Gly Leu Arg Tyr Pro Phe Gly
1               5                   10                  15
Tyr

<210> SEQ ID NO 406
<211> LENGTH: 318
<212> TYPE: DNA
<213> ORGANISM: Artificial Sequence
<220> FEATURE:
<223> OTHER INFORMATION: Homo sapiens33_640084 VL DNA

<400> SEQUENCE: 406
tcctacgtgc tgactcagcc accctcagtg tccgtgtccc caggacagac ggccagcatc        60
acctgctctg gagaaagaat gggggataaa tatgctgcct ggtatcagca gaagccaggc       120
cagtcacctg tgctggtcat ctatcaagat acaaagcggc cctcagggat ccctgagcga       180
ttctctggct ccaactctgg gaacacagcc acgttgacca tcagcgggac ccaggccgtg       240
gatgaggctg actattactg tcaggtgtgg cgggacgaca gccccatctt cggcggaggg       300
accaaggtca ccgtccta                                                    318

<210> SEQ ID NO 407
<211> LENGTH: 106
<212> TYPE: PRT
<213> ORGANISM: Artificial Sequence
<220> FEATURE:
<223> OTHER INFORMATION: Homo sapiens33_640084 VL PRT

<400> SEQUENCE: 407

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
                20                  25                  30

Ala Trp Tyr Gln Gln Lys Pro Gly Gln Ser Pro Val Leu Val Ile Tyr
            35                  40                  45

Gln Asp Thr Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Val
65                  70                  75                  80

Asp Glu Ala Asp Tyr Tyr Cys Gln Val Trp Arg Asp Ser Pro Ile
             85                  90                  95

Phe Gly Gly Gly Thr Lys Val Thr Val Leu
            100                 105

<210> SEQ ID NO 408
<211> LENGTH: 11
<212> TYPE: PRT
<213> ORGANISM: Artificial Sequence
<220> FEATURE:
<223> OTHER INFORMATION: Homo sapiens33_640084 VL CDR1 PRT

<400> SEQUENCE: 408

Ser Gly Glu Arg Met Gly Asp Lys Tyr Ala Ala
1               5                   10

<210> SEQ ID NO 409
<211> LENGTH: 7
<212> TYPE: PRT
<213> ORGANISM: Artificial Sequence
<220> FEATURE:
<223> OTHER INFORMATION: Homo sapiens33_640084 VL CDR2 PRT

<400> SEQUENCE: 409

Gln Asp Thr Lys Arg Pro Ser
1               5

<210> SEQ ID NO 410
<211> LENGTH: 9
<212> TYPE: PRT
<213> ORGANISM: Artificial Sequence
<220> FEATURE:
<223> OTHER INFORMATION: Homo sapiens33_640084 VL CDR3 PRT

<400> SEQUENCE: 410

Gln Val Trp Arg Asp Asp Ser Pro Ile
1               5

<210> SEQ ID NO 411
<211> LENGTH: 378
<212> TYPE: DNA
<213> ORGANISM: Artificial Sequence
<220> FEATURE:
<223> OTHER INFORMATION: Homo sapiens33_640086 VH DNA

<400> SEQUENCE: 411
gaggtgcagc tgttggagtc tgggggaggc ttggtacagc ctggtgggtc cctgagactc      60
tcctgtgcag cctctggatt cacctttagc agctatgcca tgagctgggt ccgccaggct     120
ccagggaagg ggctggagtg gtctcagct attagtggta gtggtggtag cacatactac     180
gcagactccg tgaagggccg gttcaccatc accagagaca attccaagaa cacgctgtat     240
ctgcaaatga acagcctgag agccgaggac acggccgtgt attactgtgc ccgcgacaag     300
ttcatgcagc tatggggggg gggcttgcgt tatcccttcg gctactgggg ccaagggaca     360
atggtcaccg tctcgagt                                                   378

<210> SEQ ID NO 412
<211> LENGTH: 126
<212> TYPE: PRT
<213> ORGANISM: Artificial Sequence
<220> FEATURE:
<223> OTHER INFORMATION: Homo sapiens33_640086 VH PRT

<400> SEQUENCE: 412

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Thr Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125
```

<210> SEQ ID NO 413
<211> LENGTH: 5
<212> TYPE: PRT
<213> ORGANISM: Artificial Sequence
<220> FEATURE:
<223> OTHER INFORMATION: Homo sapiens33_640086 VH CDR1 PRT

<400> SEQUENCE: 413

```
Ser Tyr Ala Met Ser
1               5
```

<210> SEQ ID NO 414
<211> LENGTH: 17
<212> TYPE: PRT
<213> ORGANISM: Artificial Sequence
<220> FEATURE:
<223> OTHER INFORMATION: Homo sapiens33_640086 VH CDR2 PRT

<400> SEQUENCE: 414

```
Ala Ile Ser Gly Ser Gly Gly Ser Thr Tyr Tyr Ala Asp Ser Val Lys
1               5                   10                  15

Gly
```

<210> SEQ ID NO 415
<211> LENGTH: 17
<212> TYPE: PRT
<213> ORGANISM: Artificial Sequence
<220> FEATURE:
<223> OTHER INFORMATION: Homo sapiens33_640086 VH CDR3 PRT

<400> SEQUENCE: 415

```
Asp Lys Phe Met Gln Leu Trp Gly Gly Gly Leu Arg Tyr Pro Phe Gly
1               5                   10                  15

Tyr
```

<210> SEQ ID NO 416
<211> LENGTH: 318
<212> TYPE: DNA
<213> ORGANISM: Artificial Sequence
<220> FEATURE:
<223> OTHER INFORMATION: Homo sapiens33_640086 VL DNA

<400> SEQUENCE: 416

```
tcctacgtgc tgactcagcc accctcagtg tccgtgtccc caggacagac ggccagcatc    60
```

```
acctgctctg gagaaagaat gggggataaa tatgctgcct ggtatcagca gaagccaggc    120
cagtcacctg tgctggtcat ctatcaagat acaaagcggc cctcaggat ccctgagcga    180 ttctctggct ccaactctgg gaacacagcc acgttgacca tcagcgggac ccaagccatg    240
gatgaggctg actattactg tgaggtcaag gtgaaggaca ctggggtatt cggcggaggg    300
accaaggtca ccgtccta                                                  318
```

<210> SEQ ID NO 417
<211> LENGTH: 106
<212> TYPE: PRT
<213> ORGANISM: Artificial Sequence
<220> FEATURE:
<223> OTHER INFORMATION: Homo sapiens33_640086 VL PRT

<400> SEQUENCE: 417

```
Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Glu Val Lys Val Lys Asp Thr Gly Val
                85                  90                  95

Phe Gly Gly Gly Thr Lys Val Thr Val Leu
            100                 105
```

<210> SEQ ID NO 418
<211> LENGTH: 11
<212> TYPE: PRT
<213> ORGANISM: Artificial Sequence
<220> FEATURE:
<223> OTHER INFORMATION: Homo sapiens33_640086 VL CDR1 PRT

<400> SEQUENCE: 418

```
Ser Gly Glu Arg Met Gly Asp Lys Tyr Ala Ala
1               5                   10
```

<210> SEQ ID NO 419
<211> LENGTH: 7
<212> TYPE: PRT
<213> ORGANISM: Artificial Sequence
<220> FEATURE:
<223> OTHER INFORMATION: Homo sapiens33_640086 VL CDR2 PRT

<400> SEQUENCE: 419

```
Gln Asp Thr Lys Arg Pro Ser
1               5
```

<210> SEQ ID NO 420
<211> LENGTH: 9
<212> TYPE: PRT
<213> ORGANISM: Artificial Sequence
<220> FEATURE:
<223> OTHER INFORMATION: Homo sapiens33_640086 VL CDR3 PRT

<400> SEQUENCE: 420

```
Glu Val Lys Val Lys Asp Thr Gly Val
```

-continued

```
1               5
```

<210> SEQ ID NO 421
<211> LENGTH: 378
<212> TYPE: DNA
<213> ORGANISM: Artificial Sequence
<220> FEATURE:
<223> OTHER INFORMATION: Homo sapiens33_640087 VH DNA

<400> SEQUENCE: 421

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtgatag cacatactac   180
gcagactccg tgaagggccg gttcaccatc tccagagaca attccaagaa cacgctgtat   240
ctgcaaatga acagcctgag agccgaggac acggccgtgt attactgtgc ccggcagaag   300
ttcatgcagc tatgggggggg gggcttgcgt tatcccttcg gctactgggg ccaggggaca   360
atggtcaccg tttcgagt                                                378
```

<210> SEQ ID NO 422
<211> LENGTH: 126
<212> TYPE: PRT
<213> ORGANISM: Artificial Sequence
<220> FEATURE:
<223> OTHER INFORMATION: Homo sapiens33_640087 VH PRT

<400> SEQUENCE: 422

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Leu Arg Tyr Pro
            100                 105                 110

Phe Gly Tyr Trp Gly Gln Gly Thr Met Val Thr Val Ser Ser
        115                 120                 125
```

<210> SEQ ID NO 423
<211> LENGTH: 5
<212> TYPE: PRT
<213> ORGANISM: Artificial Sequence
<220> FEATURE:
<223> OTHER INFORMATION: Homo sapiens33_640087 VH CDR1 PRT

<400> SEQUENCE: 423

```
Ser Tyr Ala Met Ser
1               5
```

<210> SEQ ID NO 424
<211> LENGTH: 17
<212> TYPE: PRT
<213> ORGANISM: Artificial Sequence
<220> FEATURE:

-continued

<223> OTHER INFORMATION: Homo sapiens33_640087 VH CDR2 PRT

<400> SEQUENCE: 424

Ala Ile Ser Gly Ser Gly Asp Ser Thr Tyr Tyr Ala Asp Ser Val Lys
1               5                   10                  15

Gly

<210> SEQ ID NO 425
<211> LENGTH: 17
<212> TYPE: PRT
<213> ORGANISM: Artificial Sequence
<220> FEATURE:
<223> OTHER INFORMATION: Homo sapiens33_640087 VH CDR3 PRT

<400> SEQUENCE: 425

Gln Lys Phe Met Gln Leu Trp Gly Gly Gly Leu Arg Tyr Pro Phe Gly
1               5                   10                  15

Tyr

<210> SEQ ID NO 426
<211> LENGTH: 318
<212> TYPE: DNA
<213> ORGANISM: Artificial Sequence
<220> FEATURE:
<223> OTHER INFORMATION: Homo sapiens33_640087 VL DNA

<400> SEQUENCE: 426
tcctacgtgc tgactcagcc accctcagtg tccgtgtccc caggacaggc ggccagcatc      60
acctgctctg gagaaggaat gggggataaa tatgctgcct ggtatcagca gaagccaggc     120
cagtcacctg tgctggtcat ctatcaagat acaaagcggc cctcagggat ccctgagcga     180
ttctctggct ccaactctgg gaacacagcc acgttgacca tcagcgggac ccaggctatg     240
gatgaggctg actattactg tggggtgatc caggacaaca ctgggggtatt cggcggaggg     300
accaaggtca ccgtccta                                                   318

<210> SEQ ID NO 427
<211> LENGTH: 106
<212> TYPE: PRT
<213> ORGANISM: Artificial Sequence
<220> FEATURE:
<223> OTHER INFORMATION: Homo sapiens33_640087 VL PRT

<400> SEQUENCE: 427

Ser Tyr Val Leu Thr Gln Pro Pro Ser Val Ser Val Ser Pro Gly Gln
1               5                   10                  15

Ala Ala Ser Ile Thr Cys Ser Gly Glu Gly Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Ile Gln Asp Asn Thr Gly Val
                85                  90                  95

Phe Gly Gly Gly Thr Lys Val Thr Val Leu
            100                 105

<210> SEQ ID NO 428

-continued

```
<211> LENGTH: 11
<212> TYPE: PRT
<213> ORGANISM: Artificial Sequence
<220> FEATURE:
<223> OTHER INFORMATION: Homo sapiens33_640087 VL CDR1 PRT

<400> SEQUENCE: 428

Ser Gly Glu Gly Met Gly Asp Lys Tyr Ala Ala
1               5                   10

<210> SEQ ID NO 429
<211> LENGTH: 7
<212> TYPE: PRT
<213> ORGANISM: Artificial Sequence
<220> FEATURE:
<223> OTHER INFORMATION: Homo sapiens33_640087 VL CDR2 PRT

<400> SEQUENCE: 429

Gln Asp Thr Lys Arg Pro Ser
1               5

<210> SEQ ID NO 430
<211> LENGTH: 9
<212> TYPE: PRT
<213> ORGANISM: Artificial Sequence
<220> FEATURE:
<223> OTHER INFORMATION: Homo sapiens33_640087 VL CDR3 PRT

<400> SEQUENCE: 430

Gly Val Ile Gln Asp Asn Thr Gly Val
1               5

<210> SEQ ID NO 431
<211> LENGTH: 378
<212> TYPE: DNA
<213> ORGANISM: Artificial Sequence
<220> FEATURE:
<223> OTHER INFORMATION: Homo sapiens33_640076-1 VH DNA

<400> SEQUENCE: 431
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gagagatctg   300
tggatggaga ctgggtgggg ggcttgcgt tatcccttcg gctactgggg ccaagggaca   360
atggtcaccg tctcctca                                                 378

<210> SEQ ID NO 432
<211> LENGTH: 126
<212> TYPE: PRT
<213> ORGANISM: Artificial Sequence
<220> FEATURE:
<223> OTHER INFORMATION: Homo sapiens33_640076-1 VH PRT

<400> SEQUENCE: 432

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Glu Asn Trp Val Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 433
<211> LENGTH: 5
<212> TYPE: PRT
<213> ORGANISM: Artificial Sequence
<220> FEATURE:
<223> OTHER INFORMATION: Homo sapiens33_640076-1 VH CDR1 PRT

<400> SEQUENCE: 433

Ser Tyr Ala Met Ser
1               5

<210> SEQ ID NO 434
<211> LENGTH: 17
<212> TYPE: PRT
<213> ORGANISM: Artificial Sequence
<220> FEATURE:
<223> OTHER INFORMATION: Homo sapiens33_640076-1 VH CDR2 PRT

<400> SEQUENCE: 434

Ala Ile Ser Gly Ser Gly Gly Ser Thr Tyr Tyr Ala Asp Ser Val Lys
1               5                   10                  15

Gly

<210> SEQ ID NO 435
<211> LENGTH: 17
<212> TYPE: PRT
<213> ORGANISM: Artificial Sequence
<220> FEATURE:
<223> OTHER INFORMATION: Homo sapiens33_640076-1 VH CDR3 PRT

<400> SEQUENCE: 435

Asp Leu Trp Met Glu Asn Trp Val Gly Gly Leu Arg Tyr Pro Phe Gly
1               5                   10                  15

Tyr

<210> SEQ ID NO 436
<211> LENGTH: 318
<212> TYPE: DNA
<213> ORGANISM: Artificial Sequence
<220> FEATURE:
<223> OTHER INFORMATION: Homo sapiens33_640076-1 VL DNA

<400> SEQUENCE: 436
tcctatgtgc tgactcagcc accctcagtg tccgtgtcac caggacagac ggccagcatc      60
acctgctctg gagaaagaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaggccatg     240
gatgaggccg actattactg tgaggtcaag aagtccgaca ctgggggtatt cggcggaggg     300
```
accaaggtca ccgtccta 318

<210> SEQ ID NO 437
<211> LENGTH: 106
<212> TYPE: PRT
<213> ORGANISM: Artificial Sequence
<220> FEATURE:
<223> OTHER INFORMATION: Homo sapiens33_640076-1 VL PRT

<400> SEQUENCE: 437

```
Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Glu Val Lys Lys Ser Asp Thr Gly Val
                85                  90                  95

Phe Gly Gly Gly Thr Lys Val Thr Val Leu
            100                 105
```

<210> SEQ ID NO 438
<211> LENGTH: 11
<212> TYPE: PRT
<213> ORGANISM: Artificial Sequence
<220> FEATURE:
<223> OTHER INFORMATION: Homo sapiens33_640076-1 VL CDR1 PRT

<400> SEQUENCE: 438

```
Ser Gly Glu Arg Met Gly Asp Lys Tyr Ala Ala
1               5                   10
```

<210> SEQ ID NO 439
<211> LENGTH: 7
<212> TYPE: PRT
<213> ORGANISM: Artificial Sequence
<220> FEATURE:
<223> OTHER INFORMATION: Homo sapiens33_640076-1 VL CDR2 PRT

<400> SEQUENCE: 439

```
Arg Asp Thr Lys Arg Pro Ser
1               5
```

<210> SEQ ID NO 440
<211> LENGTH: 9
<212> TYPE: PRT
<213> ORGANISM: Artificial Sequence
<220> FEATURE:
<223> OTHER INFORMATION: Homo sapiens33_640076-1 VL CDR3 PRT

<400> SEQUENCE: 440

```
Glu Val Lys Lys Ser Asp Thr Gly Val
1               5
```

<210> SEQ ID NO 441
<211> LENGTH: 378
<212> TYPE: DNA
<213> ORGANISM: Artificial Sequence
<220> FEATURE:
<223> OTHER INFORMATION: Homo sapiens33_640081-A VH DNA -continued

<400> SEQUENCE: 441

```
gaggtgcagc tgttggagtc tgggggaggc ttggtacagc ctggggggtc cctgagactc      60
tcctgtgcag cctctggatt cacctttagc agctatgcca tgaactgggt ccgccaggct     120
ccagggaagg gctggagtg gtctcagct attagtggta gtggtggtag cacacactac       180
gcagactccg tgaagggccg gttcaccatc tccagagaca attccaagaa cacgctgtat     240
ctgcaaatga acagcctgag agccgaggac acggccgtgt attactgtgg ccgggccaag     300
ttcatgcagc tatgggggg gggcttgcgt tatcccctcg gctactgggg ccaagggaca      360
atggtcaccg tctcctca                                                    378
```

<210> SEQ ID NO 442
<211> LENGTH: 126
<212> TYPE: PRT
<213> ORGANISM: Artificial Sequence
<220> FEATURE:
<223> OTHER INFORMATION: Homo sapiens33_640081-A VH PRT

<400> SEQUENCE: 442

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Ala Lys Phe Met Gln Leu Trp Gly Gly Gly Leu Arg Tyr Pro
            100                 105                 110

Leu Gly Tyr Trp Gly Gln Gly Thr Met Val Thr Val Ser Ser
        115                 120                 125
```

<210> SEQ ID NO 443
<211> LENGTH: 5
<212> TYPE: PRT
<213> ORGANISM: Artificial Sequence
<220> FEATURE:
<223> OTHER INFORMATION: Homo sapiens33_640081-A VH CDR1 PRT

<400> SEQUENCE: 443

```
Ser Tyr Ala Met Asn
1               5
```

<210> SEQ ID NO 444
<211> LENGTH: 17
<212> TYPE: PRT
<213> ORGANISM: Artificial Sequence
<220> FEATURE:
<223> OTHER INFORMATION: Homo sapiens33_640081-A VH CDR2 PRT

<400> SEQUENCE: 444

```
Ala Ile Ser Gly Ser Gly Gly Ser Thr His Tyr Ala Asp Ser Val Lys
1               5                   10                  15

Gly
```

<210> SEQ ID NO 445
<211> LENGTH: 17
<212> TYPE: PRT
<213> ORGANISM: Artificial Sequence
<220> FEATURE:
<223> OTHER INFORMATION: Homo sapiens33_640081-A VH CDR3 PRT

<400> SEQUENCE: 445

Ala Lys Phe Met Gln Leu Trp Gly Gly Gly Leu Arg Tyr Pro Leu Gly
1               5                   10                  15

Tyr

<210> SEQ ID NO 446
<211> LENGTH: 321
<212> TYPE: DNA
<213> ORGANISM: Artificial Sequence
<220> FEATURE:
<223> OTHER INFORMATION: Homo sapiens33_640081-A VL DNA

<400> SEQUENCE: 446
tcctatgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaggccatg     240
gatgaggctg actattactg tcaggtgtgg gcggccgacg acactggggt attcggcgga     300
gggaccaagg tcaccgtcct a                                                321

<210> SEQ ID NO 447
<211> LENGTH: 107
<212> TYPE: PRT
<213> ORGANISM: Artificial Sequence
<220> FEATURE:
<223> OTHER INFORMATION: Homo sapiens33_640081-A VL PRT

<400> SEQUENCE: 447

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
                20                  25                  30

Ala Trp Tyr Gln Gln Lys Pro Gly Gln Ser Pro Val Leu Val Ile Tyr
            35                  40                  45

Arg Asp Thr Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Ala Ala Asp Asp Thr Gly
                85                  90                  95

Val Phe Gly Gly Gly Thr Lys Val Thr Val Leu
            100                 105

<210> SEQ ID NO 448
<211> LENGTH: 11
<212> TYPE: PRT
<213> ORGANISM: Artificial Sequence
<220> FEATURE:
<223> OTHER INFORMATION: Homo sapiens33_640081-A VL CDR1 PRT

<400> SEQUENCE: 448

Ser Gly Glu Arg Met Gly Asp Lys Tyr Ala Ala

<210> SEQ ID NO 449
<211> LENGTH: 7
<212> TYPE: PRT
<213> ORGANISM: Artificial Sequence
<220> FEATURE:
<223> OTHER INFORMATION: Homo sapiens33_640081-A VL CDR2 PRT

<400> SEQUENCE: 449

Arg Asp Thr Lys Arg Pro Ser
1               5

<210> SEQ ID NO 450
<211> LENGTH: 10
<212> TYPE: PRT
<213> ORGANISM: Artificial Sequence
<220> FEATURE:
<223> OTHER INFORMATION: Homo sapiens33_640081-A VL CDR3 PRT

<400> SEQUENCE: 450

Gln Val Trp Ala Ala Asp Asp Thr Gly Val
1               5                   10

<210> SEQ ID NO 451
<211> LENGTH: 378
<212> TYPE: DNA
<213> ORGANISM: Artificial Sequence
<220> FEATURE:
<223> OTHER INFORMATION: Homo sapiens33_640082-2 VH DNA

<400> SEQUENCE: 451
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc ccggcagaag     300
ttcatgcagc tatggggggg gggcttgcgt tatcccttcg gctactgggg ccaagggaca     360
atggtcaccg tctcgagt                                                   378

<210> SEQ ID NO 452
<211> LENGTH: 126
<212> TYPE: PRT
<213> ORGANISM: Artificial Sequence
<220> FEATURE:
<223> OTHER INFORMATION: Homo sapiens33_640082-2 VH PRT

<400> SEQUENCE: 452

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 453
<211> LENGTH: 5
<212> TYPE: PRT
<213> ORGANISM: Artificial Sequence
<220> FEATURE:
<223> OTHER INFORMATION: Homo sapiens33_640082-2 VH CDR1 PRT

<400> SEQUENCE: 453

Ser Tyr Ala Met Ser
1               5

<210> SEQ ID NO 454
<211> LENGTH: 17
<212> TYPE: PRT
<213> ORGANISM: Artificial Sequence
<220> FEATURE:
<223> OTHER INFORMATION: Homo sapiens33_640082-2 VH CDR2 PRT

<400> SEQUENCE: 454

Ala Ile Ser Gly Ser Gly Gly Ser Thr Tyr Tyr Ala Asp Ser Val Lys
1               5                   10                  15

Gly

<210> SEQ ID NO 455
<211> LENGTH: 17
<212> TYPE: PRT
<213> ORGANISM: Artificial Sequence
<220> FEATURE:
<223> OTHER INFORMATION: Homo sapiens33_640082-2 VH CDR3 PRT

<400> SEQUENCE: 455

Gln Lys Phe Met Gln Leu Trp Gly Gly Gly Leu Arg Tyr Pro Phe Gly
1               5                   10                  15

Tyr

<210> SEQ ID NO 456
<211> LENGTH: 318
<212> TYPE: DNA
<213> ORGANISM: Artificial Sequence
<220> FEATURE:
<223> OTHER INFORMATION: Homo sapiens33_640082-2 VL DNA

<400> SEQUENCE: 456
tcctatgtgc tgactcagcc accctcagtg tccgtgtccc cagggcagac ggccagcatc      60
acctgctctg gagaaagaat gggggataaa tatgctgcct ggtatcagca gaagccaggc     120
cagtcacctg tgctggtcat ctatcgagat acaaagcggc cctcaggat ccctgagcga      180 ttctctggct ccaactctgg gaacacagcc acgttgacca tcagcgggac ccaggccatg     240
gatgaggctg actattactg tgcgtgttg aagcaggaca ctgggg tatt cggcggaggg     300 accaaggtca ccgtccta                                                   318

<210> SEQ ID NO 457
<211> LENGTH: 106
<212> TYPE: PRT
<213> ORGANISM: Artificial Sequence
<220> FEATURE:
<223> OTHER INFORMATION: Homo sapiens33_640082-2 VL PRT

<400> SEQUENCE: 457

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Val Thr Val Leu
            100                 105

<210> SEQ ID NO 458
<211> LENGTH: 11
<212> TYPE: PRT
<213> ORGANISM: Artificial Sequence
<220> FEATURE:
<223> OTHER INFORMATION: Homo sapiens33_640082-2 VL CDR1 PRT

<400> SEQUENCE: 458

Ser Gly Glu Arg Met Gly Asp Lys Tyr Ala Ala
1               5                   10

<210> SEQ ID NO 459
<211> LENGTH: 7
<212> TYPE: PRT
<213> ORGANISM: Artificial Sequence
<220> FEATURE:
<223> OTHER INFORMATION: Homo sapiens33_640082-2 VL CDR2 PRT

<400> SEQUENCE: 459

Arg Asp Thr Lys Arg Pro Ser
1               5

<210> SEQ ID NO 460
<211> LENGTH: 9
<212> TYPE: PRT
<213> ORGANISM: Artificial Sequence
<220> FEATURE:
<223> OTHER INFORMATION: Homo sapiens33_640082-2 VL CDR3 PRT

<400> SEQUENCE: 460

Gly Val Leu Lys Gln Asp Thr Gly Val
1               5

<210> SEQ ID NO 461
<211> LENGTH: 378
<212> TYPE: DNA
<213> ORGANISM: Artificial Sequence
<220> FEATURE:
<223> OTHER INFORMATION: Homo sapiens33_640084-2 VH DNA

<400> SEQUENCE: 461
gaggtgcagc tgttggagtc tgggggaggc ttggtacagc ctggggggtc cctgagactc      60
tcctgtgcgg cctctggatt cgcctttagc agctatgcca tgagctgggt ccgccaggct    120
ccagggaagg ggctggagtg gtctcagct attagtggta gtggtggtag cacatactac    180

```
gcagactccg tgaagggccg gttcaccatc tccagagaca attccaagaa cacgctgtat    240
ctgcaaatga acagcctgag agccgaggac acggccgtgt attactgtgc ccggcagaag    300
ttcatgcagc tatgggggg gggcttgcgt tatcccttg gctactgggg ccaagggaca    360
atggtcaccg tctcgagt                                                 378
```

```
<210> SEQ ID NO 462
<211> LENGTH: 126
<212> TYPE: PRT
<213> ORGANISM: Artificial Sequence
<220> FEATURE:
<223> OTHER INFORMATION: Homo sapiens33_640084-2 VH PRT

<400> SEQUENCE: 462

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 463
<211> LENGTH: 5
<212> TYPE: PRT
<213> ORGANISM: Artificial Sequence
<220> FEATURE:
<223> OTHER INFORMATION: Homo sapiens33_640084-2 VH CDR1 PRT

<400> SEQUENCE: 463

Ser Tyr Ala Met Ser
1               5

<210> SEQ ID NO 464
<211> LENGTH: 17
<212> TYPE: PRT
<213> ORGANISM: Artificial Sequence
<220> FEATURE:
<223> OTHER INFORMATION: Homo sapiens33_640084-2 VH CDR2 PRT

<400> SEQUENCE: 464

Ala Ile Ser Gly Ser Gly Gly Ser Thr Tyr Tyr Ala Asp Ser Val Lys
1               5                   10                  15

Gly

<210> SEQ ID NO 465
<211> LENGTH: 17
<212> TYPE: PRT
<213> ORGANISM: Artificial Sequence
<220> FEATURE:
<223> OTHER INFORMATION: Homo sapiens33_640084-2 VH CDR3 PRT

<400> SEQUENCE: 465
```

Gln Lys Phe Met Gln Leu Trp Gly Gly Gly Leu Arg Tyr Pro Phe Gly
1               5                   10                  15

Tyr

<210> SEQ ID NO 466
<211> LENGTH: 318
<212> TYPE: DNA
<213> ORGANISM: Artificial Sequence
<220> FEATURE:
<223> OTHER INFORMATION: Homo sapiens33_640084-2 VL DNA

<400> SEQUENCE: 466
tcctatgtgc tgactcagcc accctcagtg tccgtgtccc caggacagac ggccagcatc        60
acctgctctg gagaaagaat gggggataaa tatgctgcct ggtatcagca gaagccaggc       120
cagtcacctg tgctggtcat ctatcgagat acaaagcggc cctcagggat ccctgagcga       180
ttctctggct ccaactctgg gaacacagcc acgttgacca tcagcgggac ccaggccatg       240
gatgaggctg actattactg tcaggtgtgg cgggacgaca gccccatctt cggcggaggg       300
accaaggtca ccgtccta                                                     318

<210> SEQ ID NO 467
<211> LENGTH: 106
<212> TYPE: PRT
<213> ORGANISM: Artificial Sequence
<220> FEATURE:
<223> OTHER INFORMATION: Homo sapiens33_640084-2 VL PRT

<400> SEQUENCE: 467

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Arg Asp Asp Ser Pro Ile
                85                  90                  95

Phe Gly Gly Gly Thr Lys Val Thr Val Leu
            100                 105

<210> SEQ ID NO 468
<211> LENGTH: 11
<212> TYPE: PRT
<213> ORGANISM: Artificial Sequence
<220> FEATURE:
<223> OTHER INFORMATION: Homo sapiens33_640084-2 VL CDR1 PRT

<400> SEQUENCE: 468

Ser Gly Glu Arg Met Gly Asp Lys Tyr Ala Ala
1               5                   10

<210> SEQ ID NO 469
<211> LENGTH: 7
<212> TYPE: PRT
<213> ORGANISM: Artificial Sequence
<220> FEATURE:
<223> OTHER INFORMATION: Homo sapiens33_640084-2 VL CDR2 PRT

<400> SEQUENCE: 469

Arg Asp Thr Lys Arg Pro Ser
1               5

<210> SEQ ID NO 470
<211> LENGTH: 9
<212> TYPE: PRT
<213> ORGANISM: Artificial Sequence
<220> FEATURE:
<223> OTHER INFORMATION: Homo sapiens33_640084-2 VL CDR3 PRT

<400> SEQUENCE: 470

Gln Val Trp Arg Asp Asp Ser Pro Ile
1               5

<210> SEQ ID NO 471
<211> LENGTH: 378
<212> TYPE: DNA
<213> ORGANISM: Artificial Sequence
<220> FEATURE:
<223> OTHER INFORMATION: Homo sapiens33_640086-2 VH DNA

<400> SEQUENCE: 471
gaggtgcagc tgttggagtc tgggggaggc ttggtacagc ctggtgggtc cctgagactc     60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc agcagagaca attccaagaa cacgctgtat    240
ctgcaaatga acagcctgag agccgaggac acggccgtgt attactgtgc ccgcgacaag    300
ttcatgcagc tatgggggg gggcttgcgt tatcccttcg gctactgggg ccaagggaca    360
atggtcaccg tctcctca                                                   378

<210> SEQ ID NO 472
<211> LENGTH: 126
<212> TYPE: PRT
<213> ORGANISM: Artificial Sequence
<220> FEATURE:
<223> OTHER INFORMATION: Homo sapiens33_640086-2 VH PRT

<400> SEQUENCE: 472

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 473

```
<211> LENGTH: 5
<212> TYPE: PRT
<213> ORGANISM: Artificial Sequence
<220> FEATURE:
<223> OTHER INFORMATION: Homo sapiens33_640086-2 VH CDR1 PRT

<400> SEQUENCE: 473

Ser Tyr Ala Met Ser
1               5

<210> SEQ ID NO 474
<211> LENGTH: 17
<212> TYPE: PRT
<213> ORGANISM: Artificial Sequence
<220> FEATURE:
<223> OTHER INFORMATION: Homo sapiens33_640086-2 VH CDR2 PRT

<400> SEQUENCE: 474

Ala Ile Ser Gly Ser Gly Gly Ser Thr Tyr Tyr Ala Asp Ser Val Lys
1               5                   10                  15
Gly

<210> SEQ ID NO 475
<211> LENGTH: 17
<212> TYPE: PRT
<213> ORGANISM: Artificial Sequence
<220> FEATURE:
<223> OTHER INFORMATION: Homo sapiens33_640086-2 VH CDR3 PRT

<400> SEQUENCE: 475

Asp Lys Phe Met Gln Leu Trp Gly Gly Gly Leu Arg Tyr Pro Phe Gly
1               5                   10                  15
Tyr

<210> SEQ ID NO 476
<211> LENGTH: 318
<212> TYPE: DNA
<213> ORGANISM: Artificial Sequence
<220> FEATURE:
<223> OTHER INFORMATION: Homo sapiens33_640086-2 VL DNA

<400> SEQUENCE: 476
tcctatgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaagccatg     240
gatgaggctg actattactg tgaggtcaag gtgaaggaca ctggggtatt cggcggaggg     300
accaaggtca ccgtccta                                                   318

<210> SEQ ID NO 477
<211> LENGTH: 106
<212> TYPE: PRT
<213> ORGANISM: Artificial Sequence
<220> FEATURE:
<223> OTHER INFORMATION: Homo sapiens33_640086-2 VL PRT

<400> SEQUENCE: 477

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30
```

```
Ala Trp Tyr Gln Gln Lys Pro Gly Gln Ser Pro Val Leu Val Ile Tyr
         35                  40                  45

Arg Asp Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Glu Val Lys Val Lys Asp Thr Gly Val
                 85                  90                  95

Phe Gly Gly Gly Thr Lys Val Thr Val Leu
            100                 105

<210> SEQ ID NO 478
<211> LENGTH: 11
<212> TYPE: PRT
<213> ORGANISM: Artificial Sequence
<220> FEATURE:
<223> OTHER INFORMATION: Homo sapiens33_640086-2 VL CDR1 PRT

<400> SEQUENCE: 478

Ser Gly Glu Arg Met Gly Asp Lys Tyr Ala Ala
1               5                   10

<210> SEQ ID NO 479
<211> LENGTH: 7
<212> TYPE: PRT
<213> ORGANISM: Artificial Sequence
<220> FEATURE:
<223> OTHER INFORMATION: Homo sapiens33_640086-2 VL CDR2 PRT

<400> SEQUENCE: 479

Arg Asp Thr Lys Arg Pro Ser
1               5

<210> SEQ ID NO 480
<211> LENGTH: 9
<212> TYPE: PRT
<213> ORGANISM: Artificial Sequence
<220> FEATURE:
<223> OTHER INFORMATION: Homo sapiens33_640086-2 VL CDR3 PRT

<400> SEQUENCE: 480

Glu Val Lys Val Lys Asp Thr Gly Val
1               5

<210> SEQ ID NO 481
<211> LENGTH: 378
<212> TYPE: DNA
<213> ORGANISM: Artificial Sequence
<220> FEATURE:
<223> OTHER INFORMATION: Homo sapiens33_640087-2 VH DNA

<400> SEQUENCE: 481
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtgatag cacatactac     180
gcagactccg tgaagggccg gttcaccatc tccagagaca attccaagaa cacgctgtat     240
ctgcaaatga acagcctgag agccgaggac acggccgtgt attactgtgc ccggcagaag     300
ttcatgcagc tatgggggg gggcttgcgt tatcccttcg gctactgggg ccaggggaca     360
atggtcaccg tttcgagt                                                   378
```

```
<210> SEQ ID NO 482
<211> LENGTH: 126
<212> TYPE: PRT
<213> ORGANISM: Artificial Sequence
<220> FEATURE:
<223> OTHER INFORMATION: Homo sapiens33_640087-2 VH PRT

<400> SEQUENCE: 482

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 483
<211> LENGTH: 5
<212> TYPE: PRT
<213> ORGANISM: Artificial Sequence
<220> FEATURE:
<223> OTHER INFORMATION: Homo sapiens33_640087-2 VH CDR1 PRT

<400> SEQUENCE: 483

Ser Tyr Ala Met Ser
1               5

<210> SEQ ID NO 484
<211> LENGTH: 17
<212> TYPE: PRT
<213> ORGANISM: Artificial Sequence
<220> FEATURE:
<223> OTHER INFORMATION: Homo sapiens33_640087-2 VH CDR2 PRT

<400> SEQUENCE: 484

Ala Ile Ser Gly Ser Gly Asp Ser Thr Tyr Tyr Ala Asp Ser Val Lys
1               5                   10                  15

Gly

<210> SEQ ID NO 485
<211> LENGTH: 17
<212> TYPE: PRT
<213> ORGANISM: Artificial Sequence
<220> FEATURE:
<223> OTHER INFORMATION: Homo sapiens33_640087-2 VH CDR3 PRT

<400> SEQUENCE: 485

Gln Lys Phe Met Gln Leu Trp Gly Gly Gly Leu Arg Tyr Pro Phe Gly
1               5                   10                  15

Tyr

<210> SEQ ID NO 486
<211> LENGTH: 318
```

<212> TYPE: DNA
<213> ORGANISM: Artificial Sequence
<220> FEATURE:
<223> OTHER INFORMATION: Homo sapiens33_640087-2 VL DNA

<400> SEQUENCE: 486

```
tcctatgtgc tgactcagcc accctcagtg tccgtgtccc caggacagac ggccagcatc    60
acctgctctg agaaggaat gggggataaa tatgctgcct ggtatcagca gaagccaggc   120
cagtcacctg tgctggtcat ctatcgagat acaaagcggc cctcaggat ccctgagcga   180
ttctctggct ccaactctgg gaacacagcc acgttgacca tcagcgggac ccaggctatg   240
gatgaggctg actattactg tggggtgatc caggacaaca ctggggtatt cggcggaggg   300
accaaggtca ccgtccta                                                 318
```

<210> SEQ ID NO 487
<211> LENGTH: 106
<212> TYPE: PRT
<213> ORGANISM: Artificial Sequence
<220> FEATURE:
<223> OTHER INFORMATION: Homo sapiens33_640087-2 VL PRT

<400> SEQUENCE: 487

Ser Tyr Val Leu Thr Gln Pro Pro Ser Val Ser Val Ser Pro Gly Gln
1               5                   10                  15
Thr Ala Ser Ile Thr Cys Ser Gly Glu Gly Met Gly Asp Lys Tyr Ala
            20                  25                  30
Ala Trp Tyr Gln Gln Lys Pro Gly Gln Ser Pro Val Leu Val Ile Tyr
        35                  40                  45
Arg Asp Thr Lys Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gly Val Ile Gln Asp Asn Thr Gly Val
                85                  90                  95
Phe Gly Gly Gly Thr Lys Val Thr Val Leu
            100                 105

<210> SEQ ID NO 488
<211> LENGTH: 11
<212> TYPE: PRT
<213> ORGANISM: Artificial Sequence
<220> FEATURE:
<223> OTHER INFORMATION: Homo sapiens33_640087-2 VL CDR1 PRT

<400> SEQUENCE: 488

Ser Gly Glu Gly Met Gly Asp Lys Tyr Ala Ala
1               5                   10

<210> SEQ ID NO 489
<211> LENGTH: 7
<212> TYPE: PRT
<213> ORGANISM: Artificial Sequence
<220> FEATURE:
<223> OTHER INFORMATION: Homo sapiens33_640087-2 VL CDR2 PRT

<400> SEQUENCE: 489

Arg Asp Thr Lys Arg Pro Ser
1               5

<210> SEQ ID NO 490
<211> LENGTH: 9

```
<212> TYPE: PRT
<213> ORGANISM: Artificial Sequence
<220> FEATURE:
<223> OTHER INFORMATION: Homo sapiens33_640087-2 VL CDR3 PRT

<400> SEQUENCE: 490

Gly Val Ile Gln Asp Asn Thr Gly Val
1               5

<210> SEQ ID NO 491
<211> LENGTH: 378
<212> TYPE: DNA
<213> ORGANISM: Artificial Sequence
<220> FEATURE:
<223> OTHER INFORMATION: Homo sapiens33_640076-4 VH DNA

<400> SEQUENCE: 491
gaggtgcagc tgttggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg ggtctcaggc atttctgcaa tagaccaaag cacatactac      180
gcagactccg tgaagggccg gttcaccatc tccagagaca attccaagaa cacgctgtat      240
ctgcaaatga acagcctgag agccgaggac acggccgtgt attactgtgc gagagatctg      300
tggatggaga ctgggtgggg ggcttgcgt tatcccttcg gctactgggg ccaagggaca      360
atggtcaccg tctcctca                                                    378

<210> SEQ ID NO 492
<211> LENGTH: 126
<212> TYPE: PRT
<213> ORGANISM: Artificial Sequence
<220> FEATURE:
<223> OTHER INFORMATION: Homo sapiens33_640076-4 VH PRT

<400> SEQUENCE: 492

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ile Asp Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Glu Asn Trp Val Gly Leu Arg Tyr Pro
            100                 105                 110

Phe Gly Tyr Trp Gly Gln Gly Thr Met Val Thr Val Ser Ser
        115                 120                 125

<210> SEQ ID NO 493
<211> LENGTH: 5
<212> TYPE: PRT
<213> ORGANISM: Artificial Sequence
<220> FEATURE:
<223> OTHER INFORMATION: Homo sapiens33_640076-4 VH CDR1 PRT

<400> SEQUENCE: 493

Ser Tyr Ala Met Ser
```

<210> SEQ ID NO 494
<211> LENGTH: 17
<212> TYPE: PRT
<213> ORGANISM: Artificial Sequence
<220> FEATURE:
<223> OTHER INFORMATION: Homo sapiens33_640076-4 VH CDR2 PRT

<400> SEQUENCE: 494

Gly Ile Ser Ala Ile Asp Gln Ser Thr Tyr Tyr Ala Asp Ser Val Lys
1               5                   10                  15

Gly

<210> SEQ ID NO 495
<211> LENGTH: 17
<212> TYPE: PRT
<213> ORGANISM: Artificial Sequence
<220> FEATURE:
<223> OTHER INFORMATION: Homo sapiens33_640076-4 VH CDR3 PRT

<400> SEQUENCE: 495

Asp Leu Trp Met Glu Asn Trp Val Gly Gly Leu Arg Tyr Pro Phe Gly
1               5                   10                  15

Tyr

<210> SEQ ID NO 496
<211> LENGTH: 318
<212> TYPE: DNA
<213> ORGANISM: Artificial Sequence
<220> FEATURE:
<223> OTHER INFORMATION: Homo sapiens33_640076-4 VL DNA

<400> SEQUENCE: 496
tcctatgtgc tgactcagcc accctcagtg tccgtgtcac caggacagac ggccagcatc    60
acctgctctg agaaagaat ggggataaa tatgctgcct ggtatcagca aaagccaggc    120
cagtcacctg tgctggtcat ctatcgagat acaaagcggc cctcagggat ccctgagcga    180
ttctctggct ccaactctgg gaacacagcc acgttgacca tcagcgggac ccaggccatg    240
gatgaggccg actattactg tgaggtcaag aagtccgaca ctggggtatt cggcggaggg    300
accaaggtca ccgtccta                                                  318

<210> SEQ ID NO 497
<211> LENGTH: 106
<212> TYPE: PRT
<213> ORGANISM: Artificial Sequence
<220> FEATURE:
<223> OTHER INFORMATION: Homo sapiens33_640076-4 VL PRT

<400> SEQUENCE: 497

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
                20                  25                  30

Ala Trp Tyr Gln Gln Lys Pro Gly Gln Ser Pro Val Leu Val Ile Tyr
            35                  40                  45

Arg Asp Thr Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Glu Val Lys Lys Ser Asp Thr Gly Val
            85                  90                  95

Phe Gly Gly Gly Thr Lys Val Thr Val Leu
            100                 105

<210> SEQ ID NO 498
<211> LENGTH: 11
<212> TYPE: PRT
<213> ORGANISM: Artificial Sequence
<220> FEATURE:
<223> OTHER INFORMATION: Homo sapiens33_640076-4 VL CDR1 PRT

<400> SEQUENCE: 498

Ser Gly Glu Arg Met Gly Asp Lys Tyr Ala Ala
1               5                   10

<210> SEQ ID NO 499
<211> LENGTH: 7
<212> TYPE: PRT
<213> ORGANISM: Artificial Sequence
<220> FEATURE:
<223> OTHER INFORMATION: Homo sapiens33_640076-4 VL CDR2 PRT

<400> SEQUENCE: 499

Arg Asp Thr Lys Arg Pro Ser
1               5

<210> SEQ ID NO 500
<211> LENGTH: 9
<212> TYPE: PRT
<213> ORGANISM: Artificial Sequence
<220> FEATURE:
<223> OTHER INFORMATION: Homo sapiens33_640076-4 VL CDR3 PRT

<400> SEQUENCE: 500

Glu Val Lys Lys Ser Asp Thr Gly Val
1               5

<210> SEQ ID NO 501
<211> LENGTH: 384
<212> TYPE: DNA
<213> ORGANISM: Artificial Sequence
<220> FEATURE:
<223> OTHER INFORMATION: Homo sapiens33_640082-4 VH DNA

<400> SEQUENCE: 501
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attaatggtg atggtgatgg tgggcgccca     180
tactacgcag actccgtgaa ggccggttc accatctcca gagacaattc caagaacacg      240
ctgtatctgc aaatgaacag cctgagagcc gaggacacgg ccgtgtatta ctgtgcccgg     300
cagaagttca tgcagctatg ggggggggc ttgcgttatc ccttcggcta ctggggccaa      360
gggacaatgg tcaccgtctc ctca                                            384

<210> SEQ ID NO 502
<211> LENGTH: 128
<212> TYPE: PRT
<213> ORGANISM: Artificial Sequence
<220> FEATURE:
<223> OTHER INFORMATION: Homo sapiens33_640082-4 VH PRT

<400> SEQUENCE: 502

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Gly Asp Gly Asp Gly Gly Arg Pro Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gln Lys Phe Met Gln Leu Trp Gly Gly Gly Leu Arg
            100                 105                 110

Tyr Pro Phe Gly Tyr Trp Gly Gln Gly Thr Met Val Thr Val Ser Ser
            115                 120                 125
```

<210> SEQ ID NO 503
<211> LENGTH: 5
<212> TYPE: PRT
<213> ORGANISM: Artificial Sequence
<220> FEATURE:
<223> OTHER INFORMATION: Homo sapiens33_640082-4 VH CDR1 PRT

<400> SEQUENCE: 503

```
Ser Tyr Ala Met Ser
1               5
```

<210> SEQ ID NO 504
<211> LENGTH: 19
<212> TYPE: PRT
<213> ORGANISM: Artificial Sequence
<220> FEATURE:
<223> OTHER INFORMATION: Homo sapiens33_640082-4 VH CDR2 PRT

<400> SEQUENCE: 504

```
Ala Ile Asn Gly Asp Gly Asp Gly Gly Arg Pro Tyr Tyr Ala Asp Ser
1               5                   10                  15

Val Lys Gly
```

<210> SEQ ID NO 505
<211> LENGTH: 17
<212> TYPE: PRT
<213> ORGANISM: Artificial Sequence
<220> FEATURE:
<223> OTHER INFORMATION: Homo sapiens33_640082-4 VH CDR3 PRT

<400> SEQUENCE: 505

```
Gln Lys Phe Met Gln Leu Trp Gly Gly Gly Leu Arg Tyr Pro Phe Gly
1               5                   10                  15

Tyr
```

<210> SEQ ID NO 506
<211> LENGTH: 318
<212> TYPE: DNA
<213> ORGANISM: Artificial Sequence
<220> FEATURE:
<223> OTHER INFORMATION: Homo sapiens33_640082-4 VL DNA

<400> SEQUENCE: 506

```
tcctatgtgc tgactcagcc accctcagtg tccgtgtccc cagggcagac ggccagcatc    60
```

```
acctgctctg gagaaagaat gggggataaa tatgctgcct ggtatcagca gaagccaggc   120
cagtcacctg tgctggtcat ctatcgagat acaaagcggc cctcagggat ccctgagcga   180
ttctctggct ccaactctgg gaacacagcc acgttgacca tcagcgggac ccaggccatg   240
gatgaggctg actattactg tggcgtgttg aagcaggaca ctggggtatt cggcggaggg   300
accaaggtca ccgtccta                                                 318
```

```
<210> SEQ ID NO 507
<211> LENGTH: 106
<212> TYPE: PRT
<213> ORGANISM: Artificial Sequence
<220> FEATURE:
<223> OTHER INFORMATION: Homo sapiens33_640082-4 VL PRT

<400> SEQUENCE: 507

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Val Thr Val Leu
            100                 105

<210> SEQ ID NO 508
<211> LENGTH: 11
<212> TYPE: PRT
<213> ORGANISM: Artificial Sequence
<220> FEATURE:
<223> OTHER INFORMATION: Homo sapiens33_640082-4 VL CDR1 PRT

<400> SEQUENCE: 508

Ser Gly Glu Arg Met Gly Asp Lys Tyr Ala Ala
1               5                   10

<210> SEQ ID NO 509
<211> LENGTH: 7
<212> TYPE: PRT
<213> ORGANISM: Artificial Sequence
<220> FEATURE:
<223> OTHER INFORMATION: Homo sapiens33_640082-4 VL CDR2 PRT

<400> SEQUENCE: 509

Arg Asp Thr Lys Arg Pro Ser
1               5

<210> SEQ ID NO 510
<211> LENGTH: 9
<212> TYPE: PRT
<213> ORGANISM: Artificial Sequence
<220> FEATURE:
<223> OTHER INFORMATION: Homo sapiens33_640082-4 VL CDR3 PRT

<400> SEQUENCE: 510

Gly Val Leu Lys Gln Asp Thr Gly Val
1               5
```

<210> SEQ ID NO 511
<211> LENGTH: 378
<212> TYPE: DNA
<213> ORGANISM: Artificial Sequence
<220> FEATURE:
<223> OTHER INFORMATION: Homo sapiens33_640082-6 VH DNA

<400> SEQUENCE: 511

```
gaggtgcagc tgttggagtc tgggggaggc ttggtacagc ctgggggtc cctgagactc      60
tcctgtgcag cctctggatt caccttagc agctatgcca tgagctgggt ccgccaggct    120
ccagggaagg ggctggagtg gtctcaggt attagtggta tcgacacaag cacatactac    180
gcagactccg tgaagggccg gttcaccatc tccagagaca attccaagaa cacgctgtat    240
ctgcaaatga acagcctgag agccgaggac acggccgtgt attactgtgc ccggcagaag    300
ttcatgcagc tatggggggg gggcttgcgt tatcccttcg gctactgggg ccaagggaca    360
atggtcaccg tctcctca                                                   378
```

<210> SEQ ID NO 512
<211> LENGTH: 126
<212> TYPE: PRT
<213> ORGANISM: Artificial Sequence
<220> FEATURE:
<223> OTHER INFORMATION: Homo sapiens33_640082-6 VH PRT

<400> SEQUENCE: 512

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ile Asp Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 513
<211> LENGTH: 5
<212> TYPE: PRT
<213> ORGANISM: Artificial Sequence
<220> FEATURE:
<223> OTHER INFORMATION: Homo sapiens33_640082-6 VH CDR1 PRT

<400> SEQUENCE: 513

Ser Tyr Ala Met Ser
1               5

<210> SEQ ID NO 514
<211> LENGTH: 17
<212> TYPE: PRT
<213> ORGANISM: Artificial Sequence
<220> FEATURE:
<223> OTHER INFORMATION: Homo sapiens33_640082-6 VH CDR2 PRT

<400> SEQUENCE: 514

Gly Ile Ser Gly Ile Asp Thr Ser Thr Tyr Tyr Ala Asp Ser Val Lys
1               5                   10                  15

Gly

<210> SEQ ID NO 515
<211> LENGTH: 17
<212> TYPE: PRT
<213> ORGANISM: Artificial Sequence
<220> FEATURE:
<223> OTHER INFORMATION: Homo sapiens33_640082-6 VH CDR3 PRT

<400> SEQUENCE: 515

Gln Lys Phe Met Gln Leu Trp Gly Gly Gly Leu Arg Tyr Pro Phe Gly
1               5                   10                  15

Tyr

<210> SEQ ID NO 516
<211> LENGTH: 318
<212> TYPE: DNA
<213> ORGANISM: Artificial Sequence
<220> FEATURE:
<223> OTHER INFORMATION: Homo sapiens33_640082-6 VL DNA

<400> SEQUENCE: 516
tcctatgtgc tgactcagcc accctcagtg tccgtgtccc cagggcagac ggccagcatc      60
acctgctctg gagaaagaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaggccatg     240
gatgaggctg actattactg tggcgtgttg aagcaggaca ctggggtatt cggcggaggg     300
accaaggtca ccgtccta                                                   318

<210> SEQ ID NO 517
<211> LENGTH: 106
<212> TYPE: PRT
<213> ORGANISM: Artificial Sequence
<220> FEATURE:
<223> OTHER INFORMATION: Homo sapiens33_640082-6 VL PRT

<400> SEQUENCE: 517

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Val Thr Val Leu
            100                 105

<210> SEQ ID NO 518
<211> LENGTH: 11

```
<212> TYPE: PRT
<213> ORGANISM: Artificial Sequence
<220> FEATURE:
<223> OTHER INFORMATION: Homo sapiens33_640082-6 VL CDR1 PRT

<400> SEQUENCE: 518

Ser Gly Glu Arg Met Gly Asp Lys Tyr Ala Ala
1               5                   10

<210> SEQ ID NO 519
<211> LENGTH: 7
<212> TYPE: PRT
<213> ORGANISM: Artificial Sequence
<220> FEATURE:
<223> OTHER INFORMATION: Homo sapiens33_640082-6 VL CDR2 PRT

<400> SEQUENCE: 519

Arg Asp Thr Lys Arg Pro Ser
1               5

<210> SEQ ID NO 520
<211> LENGTH: 9
<212> TYPE: PRT
<213> ORGANISM: Artificial Sequence
<220> FEATURE:
<223> OTHER INFORMATION: Homo sapiens33_640082-6 VL CDR3 PRT

<400> SEQUENCE: 520

Gly Val Leu Lys Gln Asp Thr Gly Val
1               5

<210> SEQ ID NO 521
<211> LENGTH: 378
<212> TYPE: DNA
<213> ORGANISM: Artificial Sequence
<220> FEATURE:
<223> OTHER INFORMATION: Homo sapiens33_640082-7 VH DNA

<400> SEQUENCE: 521
gaggtgcagc tgttggagtc tgggggaggc ttggtacagc ctggggggtc cctgagactc      60
tcctgtgcag cctctggatt caccttagc agctatgcca tgagctgggt ccgccaggct     120
ccagggaagg ggctggagtg ggtctcaggc atttctgcaa tagaccaaag cacatactac    180
gcagactccg tgaagggccg gttcaccatc tccagagaca attccaagaa cacgctgtat    240
ctgcaaatga acagcctgag agccgaggac acggccgtgt attactgtgc ccggcagaag    300
ttcatgcagc tatgggggggg gggcttgcgt tatcccttcg gctactgggg ccaagggaca    360
atggtcaccg tctcctca                                                  378

<210> SEQ ID NO 522
<211> LENGTH: 126
<212> TYPE: PRT
<213> ORGANISM: Artificial Sequence
<220> FEATURE:
<223> OTHER INFORMATION: Homo sapiens33_640082-7 VH PRT

<400> SEQUENCE: 522

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Gly Ile Ser Ala Ile Asp Gln Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Lys Phe Met Gln Leu Trp Gly Gly Leu Arg Tyr Pro
            100                 105                 110

Phe Gly Tyr Trp Gly Gln Gly Thr Met Val Thr Val Ser Ser
            115                 120                 125

<210> SEQ ID NO 523
<211> LENGTH: 5
<212> TYPE: PRT
<213> ORGANISM: Artificial Sequence
<220> FEATURE:
<223> OTHER INFORMATION: Homo sapiens33_640082-7 VH CDR1 PRT

<400> SEQUENCE: 523

Ser Tyr Ala Met Ser
1               5

<210> SEQ ID NO 524
<211> LENGTH: 17
<212> TYPE: PRT
<213> ORGANISM: Artificial Sequence
<220> FEATURE:
<223> OTHER INFORMATION: Homo sapiens33_640082-7 VH CDR2 PRT

<400> SEQUENCE: 524

Gly Ile Ser Ala Ile Asp Gln Ser Thr Tyr Tyr Ala Asp Ser Val Lys
1               5                   10                  15
Gly

<210> SEQ ID NO 525
<211> LENGTH: 17
<212> TYPE: PRT
<213> ORGANISM: Artificial Sequence
<220> FEATURE:
<223> OTHER INFORMATION: Homo sapiens33_640082-7 VH CDR3 PRT

<400> SEQUENCE: 525

Gln Lys Phe Met Gln Leu Trp Gly Gly Leu Arg Tyr Pro Phe Gly
1               5                   10                  15
Tyr

<210> SEQ ID NO 526
<211> LENGTH: 318
<212> TYPE: DNA
<213> ORGANISM: Artificial Sequence
<220> FEATURE:
<223> OTHER INFORMATION: Homo sapiens33_640082-7 VL DNA

<400> SEQUENCE: 526
tcctatgtgc tgactcagcc accctcagtg tccgtgtccc cagggcagac ggccagcatc      60
acctgctctg gagaaagaat gggggataaa tatgctgcct ggtatcagca gaagccaggc    120
cagtcacctg tgctggtcat ctatcgagat acaaagcggc cctcagggat ccctgagcga    180
ttctctggct ccaactctgg gaacacagcc acgttgacca tcagcgggac ccaggccatg    240
gatgaggctg actattactg tggcgtgttg aagcaggaca ctggggtatt cggcggaggg    300
accaaggtca ccgtccta                                                  318
```

```
<210> SEQ ID NO 527
<211> LENGTH: 106
<212> TYPE: PRT
<213> ORGANISM: Artificial Sequence
<220> FEATURE:
<223> OTHER INFORMATION: Homo sapiens33_640082-7 VL PRT

<400> SEQUENCE: 527

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Val Thr Val Leu
            100                 105

<210> SEQ ID NO 528
<211> LENGTH: 11
<212> TYPE: PRT
<213> ORGANISM: Artificial Sequence
<220> FEATURE:
<223> OTHER INFORMATION: Homo sapiens33_640082-7 VL CDR1 PRT

<400> SEQUENCE: 528

Ser Gly Glu Arg Met Gly Asp Lys Tyr Ala Ala
1               5                   10

<210> SEQ ID NO 529
<211> LENGTH: 7
<212> TYPE: PRT
<213> ORGANISM: Artificial Sequence
<220> FEATURE:
<223> OTHER INFORMATION: Homo sapiens33_640082-7 VL CDR2 PRT

<400> SEQUENCE: 529

Arg Asp Thr Lys Arg Pro Ser
1               5

<210> SEQ ID NO 530
<211> LENGTH: 9
<212> TYPE: PRT
<213> ORGANISM: Artificial Sequence
<220> FEATURE:
<223> OTHER INFORMATION: Homo sapiens33_640082-7 VL CDR3 PRT

<400> SEQUENCE: 530

Gly Val Leu Lys Gln Asp Thr Gly Val
1               5

<210> SEQ ID NO 531
<211> LENGTH: 378
<212> TYPE: DNA
<213> ORGANISM: Artificial Sequence
<220> FEATURE:
<223> OTHER INFORMATION: Homo sapiens33_640086-6 VH DNA
```

<400> SEQUENCE: 531

```
gaggtgcagc tgttggagtc tgggggaggc ttggtacagc ctggtgggtc cctgagactc      60
tcctgtgcag cctctggatt cacctttagc agctatgcca tgagctgggt ccgccaggct     120
ccagggaagg ggctggagtg ggtctcaggt attagtggta tcgacacaag cacatactac     180
gcagactccg tgaagggccg gttcaccatc agcagagaca attccaagaa cacgctgtat     240
ctgcaaatga acagcctgag agccgaggac acggccgtgt attactgtgc ccgcgacaag     300
ttcatgcagc tatggggggg gggcttgcgt tatcccttcg gctactgggg ccaagggaca     360
atggtcaccg tctcctca                                                   378
```

<210> SEQ ID NO 532
<211> LENGTH: 126
<212> TYPE: PRT
<213> ORGANISM: Artificial Sequence
<220> FEATURE:
<223> OTHER INFORMATION: Homo sapiens33_640086-6 VH PRT

<400> SEQUENCE: 532

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ile Asp Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 533
<211> LENGTH: 5
<212> TYPE: PRT
<213> ORGANISM: Artificial Sequence
<220> FEATURE:
<223> OTHER INFORMATION: Homo sapiens33_640086-6 VH CDR1 PRT

<400> SEQUENCE: 533

Ser Tyr Ala Met Ser
1               5

<210> SEQ ID NO 534
<211> LENGTH: 17
<212> TYPE: PRT
<213> ORGANISM: Artificial Sequence
<220> FEATURE:
<223> OTHER INFORMATION: Homo sapiens33_640086-6 VH CDR2 PRT

<400> SEQUENCE: 534

Gly Ile Ser Gly Ile Asp Thr Ser Thr Tyr Tyr Ala Asp Ser Val Lys
1               5                   10                  15

Gly

```
<210> SEQ ID NO 535
<211> LENGTH: 17
<212> TYPE: PRT
<213> ORGANISM: Artificial Sequence
<220> FEATURE:
<223> OTHER INFORMATION: Homo sapiens33_640086-6 VH CDR3 PRT

<400> SEQUENCE: 535

Asp Lys Phe Met Gln Leu Trp Gly Gly Gly Leu Arg Tyr Pro Phe Gly
1               5                   10                  15
Tyr

<210> SEQ ID NO 536
<211> LENGTH: 318
<212> TYPE: DNA
<213> ORGANISM: Artificial Sequence
<220> FEATURE:
<223> OTHER INFORMATION: Homo sapiens33_640086-6 VL DNA

<400> SEQUENCE: 536
tcctatgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaagccatg     240
gatgaggctg actattactg tgaggtcaag gtgaaggaca ctggggtatt cggcggaggg     300
accaaggtca ccgtccta                                                   318

<210> SEQ ID NO 537
<211> LENGTH: 106
<212> TYPE: PRT
<213> ORGANISM: Artificial Sequence
<220> FEATURE:
<223> OTHER INFORMATION: Homo sapiens33_640086-6 VL PRT

<400> SEQUENCE: 537

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Glu Val Lys Val Lys Asp Thr Gly Val
                85                  90                  95

Phe Gly Gly Gly Thr Lys Val Thr Val Leu
            100                 105

<210> SEQ ID NO 538
<211> LENGTH: 11
<212> TYPE: PRT
<213> ORGANISM: Artificial Sequence
<220> FEATURE:
<223> OTHER INFORMATION: Homo sapiens33_640086-6 VL CDR1 PRT

<400> SEQUENCE: 538

Ser Gly Glu Arg Met Gly Asp Lys Tyr Ala Ala
1               5                   10
```

<210> SEQ ID NO 539
<211> LENGTH: 7
<212> TYPE: PRT
<213> ORGANISM: Artificial Sequence
<220> FEATURE:
<223> OTHER INFORMATION: Homo sapiens33_640086-6 VL CDR2 PRT

<400> SEQUENCE: 539

Arg Asp Thr Lys Arg Pro Ser
1               5

<210> SEQ ID NO 540
<211> LENGTH: 9
<212> TYPE: PRT
<213> ORGANISM: Artificial Sequence
<220> FEATURE:
<223> OTHER INFORMATION: Homo sapiens33_640086-6 VL CDR3 PRT

<400> SEQUENCE: 540

Glu Val Lys Val Lys Asp Thr Gly Val
1               5

<210> SEQ ID NO 541
<211> LENGTH: 378
<212> TYPE: DNA
<213> ORGANISM: Artificial Sequence
<220> FEATURE:
<223> OTHER INFORMATION: Homo sapiens33_640087-7 VH DNA

<400> SEQUENCE: 541
gaggtgcagc tgttggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg ggtctcaggc atttctgcaa tagaccaaag cacatactac      180
gcagactccg tgaagggccg gttcaccatc tccagagaca attccaagaa cacgctgtat      240
ctgcaaatga acagcctgag agccgaggac acggccgtgt attactgtgc ccggcagaag      300
ttcatgcagc tatgggggg gggcttgcgt tatcccttcg gctactgggg ccaggggaca      360
atggtcaccg tctcctca                                                   378

<210> SEQ ID NO 542
<211> LENGTH: 126
<212> TYPE: PRT
<213> ORGANISM: Artificial Sequence
<220> FEATURE:
<223> OTHER INFORMATION: Homo sapiens33_640087-7 VH PRT

<400> SEQUENCE: 542

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ile Asp Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 543
<211> LENGTH: 5
<212> TYPE: PRT
<213> ORGANISM: Artificial Sequence
<220> FEATURE:
<223> OTHER INFORMATION: Homo sapiens33_640087-7 VH CDR1 PRT

<400> SEQUENCE: 543

Ser Tyr Ala Met Ser
1               5

<210> SEQ ID NO 544
<211> LENGTH: 17
<212> TYPE: PRT
<213> ORGANISM: Artificial Sequence
<220> FEATURE:
<223> OTHER INFORMATION: Homo sapiens33_640087-7 VH CDR2 PRT

<400> SEQUENCE: 544

Gly Ile Ser Ala Ile Asp Gln Ser Thr Tyr Tyr Ala Asp Ser Val Lys
1               5                   10                  15

Gly

<210> SEQ ID NO 545
<211> LENGTH: 17
<212> TYPE: PRT
<213> ORGANISM: Artificial Sequence
<220> FEATURE:
<223> OTHER INFORMATION: Homo sapiens33_640087-7 VH CDR3 PRT

<400> SEQUENCE: 545

Gln Lys Phe Met Gln Leu Trp Gly Gly Gly Leu Arg Tyr Pro Phe Gly
1               5                   10                  15

Tyr

<210> SEQ ID NO 546
<211> LENGTH: 318
<212> TYPE: DNA
<213> ORGANISM: Artificial Sequence
<220> FEATURE:
<223> OTHER INFORMATION: Homo sapiens33_640087-7 VL DNA

<400> SEQUENCE: 546
tcctatgtgc tgactcagcc accctcagtg tccgtgtccc caggacagac ggccagcatc      60
acctgctctg gagaaggaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaggctatg     240
gatgaggctg actattactg tggggtgatc caggacaaca ctgggggtatt cggcggaggg     300 accaaggtca ccgtccta                                                   318

<210> SEQ ID NO 547
<211> LENGTH: 106
<212> TYPE: PRT
<213> ORGANISM: Artificial Sequence
<220> FEATURE:
<223> OTHER INFORMATION: Homo sapiens33_640087-7 VL PRT

<400> SEQUENCE: 547

Ser Tyr Val Leu Thr Gln Pro Pro Ser Val Ser Val Ser Pro Gly Gln
1               5                   10                  15

Thr Ala Ser Ile Thr Cys Ser Gly Glu Gly Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65              70                  75                  80

Asp Glu Ala Asp Tyr Tyr Cys Gly Val Ile Gln Asp Asn Thr Gly Val
                85                  90                  95

Phe Gly Gly Gly Thr Lys Val Thr Val Leu
            100                 105

<210> SEQ ID NO 548
<211> LENGTH: 11
<212> TYPE: PRT
<213> ORGANISM: Artificial Sequence
<220> FEATURE:
<223> OTHER INFORMATION: Homo sapiens33_640087-7 VL CDR1 PRT

<400> SEQUENCE: 548

Ser Gly Glu Gly Met Gly Asp Lys Tyr Ala Ala
1               5                   10

<210> SEQ ID NO 549
<211> LENGTH: 7
<212> TYPE: PRT
<213> ORGANISM: Artificial Sequence
<220> FEATURE:
<223> OTHER INFORMATION: Homo sapiens33_640087-7 VL CDR2 PRT

<400> SEQUENCE: 549

Arg Asp Thr Lys Arg Pro Ser
1               5

<210> SEQ ID NO 550
<211> LENGTH: 9
<212> TYPE: PRT
<213> ORGANISM: Artificial Sequence
<220> FEATURE:
<223> OTHER INFORMATION: Homo sapiens33_640087-7 VL CDR3 PRT

<400> SEQUENCE: 550

Gly Val Ile Gln Asp Asn Thr Gly Val
1               5

<210> SEQ ID NO 551
<211> LENGTH: 378
<212> TYPE: DNA
<213> ORGANISM: Artificial Sequence
<220> FEATURE:
<223> OTHER INFORMATION: Homo sapiens33_640201 VH DNA

<400> SEQUENCE: 551
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctctcatca attgacgcca ttagttcaag cacatactac     180
gcagactccg tgaagggccg gttcaccatc tccagagaca attccaagaa cacgctgtat     240

```
ctgcaaatga acagcctgag agccgaggac acggccgtgt attactgttc ccgccagaag    300
ttcatgcagc tatgggggg  gggcttgcgt tatcccttcg gctactgggg ccaagggaca    360
atggtcaccg tctcgagt                                                  378
```

<210> SEQ ID NO 552
<211> LENGTH: 126
<212> TYPE: PRT
<213> ORGANISM: Artificial Sequence
<220> FEATURE:
<223> OTHER INFORMATION: Homo sapiens33_640201 VH PRT

<400> SEQUENCE: 552

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Ala Ile Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Lys Phe Met Gln Leu Trp Gly Gly Leu Arg Tyr Pro
            100                 105                 110

Phe Gly Tyr Trp Gly Gln Gly Thr Met Val Thr Val Ser Ser
        115                 120                 125
```

<210> SEQ ID NO 553
<211> LENGTH: 5
<212> TYPE: PRT
<213> ORGANISM: Artificial Sequence
<220> FEATURE:
<223> OTHER INFORMATION: Homo sapiens33_640201 VH CDR1 PRT

<400> SEQUENCE: 553

```
Ser Tyr Ala Met Ser
1               5
```

<210> SEQ ID NO 554
<211> LENGTH: 17
<212> TYPE: PRT
<213> ORGANISM: Artificial Sequence
<220> FEATURE:
<223> OTHER INFORMATION: Homo sapiens33_640201 VH CDR2 PRT

<400> SEQUENCE: 554

```
Ser Ile Asp Ala Ile Ser Ser Ser Thr Tyr Tyr Ala Asp Ser Val Lys
1               5                   10                  15

Gly
```

<210> SEQ ID NO 555
<211> LENGTH: 17
<212> TYPE: PRT
<213> ORGANISM: Artificial Sequence
<220> FEATURE:
<223> OTHER INFORMATION: Homo sapiens33_640201 VH CDR3 PRT

<400> SEQUENCE: 555

Gln Lys Phe Met Gln Leu Trp Gly Gly Gly Leu Arg Tyr Pro Phe Gly
1               5                   10                  15

Tyr

<210> SEQ ID NO 556
<211> LENGTH: 318
<212> TYPE: DNA
<213> ORGANISM: Artificial Sequence
<220> FEATURE:
<223> OTHER INFORMATION: Homo sapiens33_640201 VL DNA

<400> SEQUENCE: 556
tcctacgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcaagat acaaagcggc cctcagggat ccctgagcga     180
ttctctggct ccaactctgg gaacacagcc acgttgacca tcagcgggac ccaggccgtg     240
gatgaggctg actattactg tggcgtgttg aagcaggaca ctggggtatt cggcggaggg     300
accaaggtca ccgtcccta                                                 318

<210> SEQ ID NO 557
<211> LENGTH: 106
<212> TYPE: PRT
<213> ORGANISM: Artificial Sequence
<220> FEATURE:
<223> OTHER INFORMATION: Homo sapiens33_640201 VL PRT

<400> SEQUENCE: 557

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Val
65                  70                  75                  80

Asp Glu Ala Asp Tyr Tyr Cys Gly Val Leu Lys Gln Asp Thr Gly Val
                85                  90                  95

Phe Gly Gly Gly Thr Lys Val Thr Val Leu
            100                 105

<210> SEQ ID NO 558
<211> LENGTH: 11
<212> TYPE: PRT
<213> ORGANISM: Artificial Sequence
<220> FEATURE:
<223> OTHER INFORMATION: Homo sapiens33_640201 VL CDR1 PRT

<400> SEQUENCE: 558

Ser Gly Glu Arg Met Gly Asp Lys Tyr Ala Ala
1               5                   10

<210> SEQ ID NO 559
<211> LENGTH: 7
<212> TYPE: PRT
<213> ORGANISM: Artificial Sequence
<220> FEATURE:
<223> OTHER INFORMATION: Homo sapiens33_640201 VL CDR2 PRT

<400> SEQUENCE: 559

Gln Asp Thr Lys Arg Pro Ser
1               5

<210> SEQ ID NO 560
<211> LENGTH: 9
<212> TYPE: PRT
<213> ORGANISM: Artificial Sequence
<220> FEATURE:
<223> OTHER INFORMATION: Homo sapiens33_640201 VL CDR3 PRT

<400> SEQUENCE: 560

Gly Val Leu Lys Gln Asp Thr Gly Val
1               5

<210> SEQ ID NO 561
<211> LENGTH: 378
<212> TYPE: DNA
<213> ORGANISM: Artificial Sequence
<220> FEATURE:
<223> OTHER INFORMATION: Homo sapiens33_640237 VH DNA

<400> SEQUENCE: 561
gaggtgcagc tgttggaatc tggggggaggc ttggtacagc ctggggggtc cctgagactc      60
tcctgtgcag cctctggatt cacctttagc agctatgcca tgagctgggt ccgccaggct     120
ccagggaagg gctggagtg gtctcaggc attgcagacg atttcaccag cacatactac       180
gcagaccccg tgaagggccg gttcaccatc tccagagaca attccaagaa cacgctgtat     240
ctgcaaatga acagcctgag agccgaggac acggccgtgt attactgtgc gagagatctg    300
tggatgatga actacgcggg cggcttgcgt tatcccttcg gctactgggg ccaagggaca    360
acggtcaccg tctcgagt                                                   378

<210> SEQ ID NO 562
<211> LENGTH: 126
<212> TYPE: PRT
<213> ORGANISM: Artificial Sequence
<220> FEATURE:
<223> OTHER INFORMATION: Homo sapiens33_640237 VH PRT

<400> SEQUENCE: 562

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ala Asp Asp Phe Thr Ser Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Met Asn Tyr Ala Gly Gly Leu Arg Tyr Pro
            100                 105                 110

Phe Gly Tyr Trp Gly Gln Gly Thr Thr Val Thr Val Ser Ser
        115                 120                 125

<210> SEQ ID NO 563
<211> LENGTH: 5

```
<212> TYPE: PRT
<213> ORGANISM: Artificial Sequence
<220> FEATURE:
<223> OTHER INFORMATION: Homo sapiens33_640237 VH CDR1 PRT

<400> SEQUENCE: 563

Ser Tyr Ala Met Ser
1               5

<210> SEQ ID NO 564
<211> LENGTH: 17
<212> TYPE: PRT
<213> ORGANISM: Artificial Sequence
<220> FEATURE:
<223> OTHER INFORMATION: Homo sapiens33_640237 VH CDR2 PRT

<400> SEQUENCE: 564

Gly Ile Ala Asp Asp Phe Thr Ser Thr Tyr Tyr Ala Asp Pro Val Lys
1               5                   10                  15
Gly

<210> SEQ ID NO 565
<211> LENGTH: 17
<212> TYPE: PRT
<213> ORGANISM: Artificial Sequence
<220> FEATURE:
<223> OTHER INFORMATION: Homo sapiens33_640237 VH CDR3 PRT

<400> SEQUENCE: 565

Asp Leu Trp Met Met Asn Tyr Ala Gly Gly Leu Arg Tyr Pro Phe Gly
1               5                   10                  15
Tyr

<210> SEQ ID NO 566
<211> LENGTH: 318
<212> TYPE: DNA
<213> ORGANISM: Artificial Sequence
<220> FEATURE:
<223> OTHER INFORMATION: Homo sapiens33_640237 VL DNA

<400> SEQUENCE: 566
tcctacgtgc tgactcagcc accctcagtg tccgtgtccc caggacagac ggccagcatc      60
acctgctctg gagaaagaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaggccatt     240
gatgaggctg actattactg tgcgtgttg aagcaggaca ctggggtatt cggcggaggg     300
accaaggtca ccgtccta                                                  318

<210> SEQ ID NO 567
<211> LENGTH: 106
<212> TYPE: PRT
<213> ORGANISM: Artificial Sequence
<220> FEATURE:
<223> OTHER INFORMATION: Homo sapiens33_640237 VL PRT

<400> SEQUENCE: 567

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
```

```
                35                  40                  45
Arg Asp Thr Lys Arg Pro Ser Gly Ile Pro Glu Arg Phe Ser Gly Ser
                50                  55                  60

Asn Ser Gly Asn Thr Ala Thr Leu Thr Ile Ser Gly Thr Gln Ala Ile
 65                  70                  75                  80

Asp Glu Ala Asp Tyr Tyr Cys Gly Val Leu Lys Gln Asp Thr Gly Val
                85                  90                  95

Phe Gly Gly Gly Thr Lys Val Thr Val Leu
                100                 105

<210> SEQ ID NO 568
<211> LENGTH: 11
<212> TYPE: PRT
<213> ORGANISM: Artificial Sequence
<220> FEATURE:
<223> OTHER INFORMATION: Homo sapiens33_640237 VL CDR1 PRT

<400> SEQUENCE: 568

Ser Gly Glu Arg Met Gly Asp Lys Tyr Ala Ala
 1               5                   10

<210> SEQ ID NO 569
<211> LENGTH: 7
<212> TYPE: PRT
<213> ORGANISM: Artificial Sequence
<220> FEATURE:
<223> OTHER INFORMATION: Homo sapiens33_640237 VL CDR2 PRT

<400> SEQUENCE: 569

Arg Asp Thr Lys Arg Pro Ser
 1               5

<210> SEQ ID NO 570
<211> LENGTH: 9
<212> TYPE: PRT
<213> ORGANISM: Artificial Sequence
<220> FEATURE:
<223> OTHER INFORMATION: Homo sapiens33_640237 VL CDR3 PRT

<400> SEQUENCE: 570

Gly Val Leu Lys Gln Asp Thr Gly Val
 1               5

<210> SEQ ID NO 571
<211> LENGTH: 378
<212> TYPE: DNA
<213> ORGANISM: Artificial Sequence
<220> FEATURE:
<223> OTHER INFORMATION: Homo sapiens33_640201-2 VH DNA

<400> SEQUENCE: 571
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcatca attgacgcca ttagttcaag cacatactac    180
gcagactccg tgaagggccg gttcaccatc tccagagaca attccaagaa cacgctgtat    240
ctgcaaatga acagcctgag agccgaggac acggccgtgt attactgttc ccgccagaag    300
ttcatgcagc tatgggggg gggcttgcgt tatcccttcg gctactgggg ccaagggaca    360
atggtcaccg tctcgagt                                                  378

<210> SEQ ID NO 572
```

```
<211> LENGTH: 126
<212> TYPE: PRT
<213> ORGANISM: Artificial Sequence
<220> FEATURE:
<223> OTHER INFORMATION: Homo sapiens33_640201-2 VH PRT

<400> SEQUENCE: 572

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Ala Ile Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 573
<211> LENGTH: 5
<212> TYPE: PRT
<213> ORGANISM: Artificial Sequence
<220> FEATURE:
<223> OTHER INFORMATION: Homo sapiens33_640201-2 VH CDR1 PRT

<400> SEQUENCE: 573

Ser Tyr Ala Met Ser
 1               5

<210> SEQ ID NO 574
<211> LENGTH: 17
<212> TYPE: PRT
<213> ORGANISM: Artificial Sequence
<220> FEATURE:
<223> OTHER INFORMATION: Homo sapiens33_640201-2 VH CDR2 PRT

<400> SEQUENCE: 574

Ser Ile Asp Ala Ile Ser Ser Ser Thr Tyr Tyr Ala Asp Ser Val Lys
 1               5                   10                  15

Gly

<210> SEQ ID NO 575
<211> LENGTH: 17
<212> TYPE: PRT
<213> ORGANISM: Artificial Sequence
<220> FEATURE:
<223> OTHER INFORMATION: Homo sapiens33_640201-2 VH CDR3 PRT

<400> SEQUENCE: 575

Gln Lys Phe Met Gln Leu Trp Gly Gly Gly Leu Arg Tyr Pro Phe Gly
 1               5                   10                  15

Tyr

<210> SEQ ID NO 576
<211> LENGTH: 318
<212> TYPE: DNA
```

<213> ORGANISM: Artificial Sequence
<220> FEATURE:
<223> OTHER INFORMATION: Homo sapiens33_640201-2 VL DNA

<400> SEQUENCE: 576

```
tcctatgtgc tgactcagcc accctcagtg tccgtgtccc caggacagac ggccagcatc    60
acctgctctg gagaaagaat ggggggataaa tatgctgcct ggtatcagca aaagccaggc   120
cagtcacctg tgctggtcat ctatcgagat acaaagcggc cctcaggat  ccctgagcga   180
ttctctggct ccaactctgg aacacagcc  acgttgacca tcagcgggac ccaggccatg   240
gatgaggctg actattactg tggcgtgttg aagcaggaca ctggggtatt cggcggaggg   300
accaaggtca ccgtccta                                                 318
```

<210> SEQ ID NO 577
<211> LENGTH: 106
<212> TYPE: PRT
<213> ORGANISM: Artificial Sequence
<220> FEATURE:
<223> OTHER INFORMATION: Homo sapiens33_640201-2 VL PRT

<400> SEQUENCE: 577

```
Ser Tyr Val Leu Thr Gln Pro Pro Ser Val Ser Val Ser Pro Gly Gln
  1               5                  10                  15

Thr Ala Ser Ile Thr Cys Ser Gly Glu Arg Met Gly Asp Lys Tyr Ala
             20                  25                  30

Ala Trp Tyr Gln Gln Lys Pro Gly Gln Ser Pro Val Leu Val Ile Tyr
         35                  40                  45

Arg Asp Thr Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gly Val Leu Lys Gln Asp Thr Gly Val
                 85                  90                  95

Phe Gly Gly Gly Thr Lys Val Thr Val Leu
            100                 105
```

<210> SEQ ID NO 578
<211> LENGTH: 11
<212> TYPE: PRT
<213> ORGANISM: Artificial Sequence
<220> FEATURE:
<223> OTHER INFORMATION: Homo sapiens33_640201-2 VL CDR1 PRT

<400> SEQUENCE: 578

```
Ser Gly Glu Arg Met Gly Asp Lys Tyr Ala Ala
  1               5                  10
```

<210> SEQ ID NO 579
<211> LENGTH: 7
<212> TYPE: PRT
<213> ORGANISM: Artificial Sequence
<220> FEATURE:
<223> OTHER INFORMATION: Homo sapiens33_640201-2 VL CDR2 PRT

<400> SEQUENCE: 579

```
Arg Asp Thr Lys Arg Pro Ser
  1               5
```

<210> SEQ ID NO 580
<211> LENGTH: 9
<212> TYPE: PRT

<213> ORGANISM: Artificial Sequence
<220> FEATURE:
<223> OTHER INFORMATION: Homo sapiens33_640201-2 VL CDR3 PRT

<400> SEQUENCE: 580

Gly Val Leu Lys Gln Asp Thr Gly Val
1               5

<210> SEQ ID NO 581
<211> LENGTH: 378
<212> TYPE: DNA
<213> ORGANISM: Artificial Sequence
<220> FEATURE:
<223> OTHER INFORMATION: Homo sapiens33_640237-2 VH DNA

<400> SEQUENCE: 581

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaggc attgcagacg atttcaccag cacatactac     180
gcagaccccg tgaagggccg gttcaccatc tccagagaca attccaagaa cacgctgtat     240
ctgcaaatga acagcctgag agccgaggac acggccgtgt attactgtgc gagagatctg     300
tggatgatga actacgcggg cggcttgcgt tatcccttcg gctactgggg ccaagggacc     360
atggtcaccg tctcctca                                                    378
```

<210> SEQ ID NO 582
<211> LENGTH: 126
<212> TYPE: PRT
<213> ORGANISM: Artificial Sequence
<220> FEATURE:
<223> OTHER INFORMATION: Homo sapiens33_640237-2 VH PRT

<400> SEQUENCE: 582

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ala Asp Asp Phe Thr Ser Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Met Asn Tyr Ala Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 583
<211> LENGTH: 5
<212> TYPE: PRT
<213> ORGANISM: Artificial Sequence
<220> FEATURE:
<223> OTHER INFORMATION: Homo sapiens33_640237-2 VH CDR1 PRT

<400> SEQUENCE: 583

Ser Tyr Ala Met Ser
1               5

<210> SEQ ID NO 584
<211> LENGTH: 17
<212> TYPE: PRT
<213> ORGANISM: Artificial Sequence
<220> FEATURE:
<223> OTHER INFORMATION: Homo sapiens33_640237-2 VH CDR2 PRT

<400> SEQUENCE: 584

Gly Ile Ala Asp Asp Phe Thr Ser Thr Tyr Tyr Ala Asp Pro Val Lys
1               5                   10                  15

Gly

<210> SEQ ID NO 585
<211> LENGTH: 17
<212> TYPE: PRT
<213> ORGANISM: Artificial Sequence
<220> FEATURE:
<223> OTHER INFORMATION: Homo sapiens33_640237-2 VH CDR3 PRT

<400> SEQUENCE: 585

Asp Leu Trp Met Met Asn Tyr Ala Gly Gly Leu Arg Tyr Pro Phe Gly
1               5                   10                  15

Tyr

<210> SEQ ID NO 586
<211> LENGTH: 318
<212> TYPE: DNA
<213> ORGANISM: Artificial Sequence
<220> FEATURE:
<223> OTHER INFORMATION: Homo sapiens33_640237-2 VL DNA

<400> SEQUENCE: 586
tcctatgtgc tgactcagcc accctcagtg tccgtgtccc caggacagac ggccagcatc    60
acctgctctg gagaaagaat gggggataaa tatgctgcct ggtatcagca gaagccaggc   120
cagtcacctg tgctggtcat ctatcgagat acaaagcggc cctcagggat ccctgagcga   180
ttctctggct ccaactctgg gaacacagcc acgttgacca tcagcgggac ccaggccatg   240
gatgaggctg actattactg tggcgtgttg aagcaggaca ctggggtatt cggcggaggg   300
accaaggtca ccgtccta                                                318

<210> SEQ ID NO 587
<211> LENGTH: 106
<212> TYPE: PRT
<213> ORGANISM: Artificial Sequence
<220> FEATURE:
<223> OTHER INFORMATION: Homo sapiens33_640237-2 VL PRT

<400> SEQUENCE: 587

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val

```
                85                  90                  95

Phe Gly Gly Gly Thr Lys Val Thr Val Leu
            100                 105

<210> SEQ ID NO 588
<211> LENGTH: 11
<212> TYPE: PRT
<213> ORGANISM: Artificial Sequence
<220> FEATURE:
<223> OTHER INFORMATION: Homo sapiens33_640237-2 VL CDR1 PRT

<400> SEQUENCE: 588

Ser Gly Glu Arg Met Gly Asp Lys Tyr Ala Ala
1               5                   10

<210> SEQ ID NO 589
<211> LENGTH: 7
<212> TYPE: PRT
<213> ORGANISM: Artificial Sequence
<220> FEATURE:
<223> OTHER INFORMATION: Homo sapiens33_640237-2 VL CDR2 PRT

<400> SEQUENCE: 589

Arg Asp Thr Lys Arg Pro Ser
1               5

<210> SEQ ID NO 590
<211> LENGTH: 9
<212> TYPE: PRT
<213> ORGANISM: Artificial Sequence
<220> FEATURE:
<223> OTHER INFORMATION: Homo sapiens33_640237-2 VL CDR3 PRT

<400> SEQUENCE: 590

Gly Val Leu Lys Gln Asp Thr Gly Val
1               5

<210> SEQ ID NO 591
<211> LENGTH: 378
<212> TYPE: DNA
<213> ORGANISM: Artificial Sequence
<220> FEATURE:
<223> OTHER INFORMATION: Homo sapiens33_640076-4B VH DNA

<400> SEQUENCE: 591
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaggc atttctgcaa tagaccaaag cacatactac     180
gcagactccg tgaagggccg gttcaccatc tccagagaca attccaagaa cacgctgtat     240
ctgcaaatga acagcctgag agccgaggac acggccgtgt attactgtgc gagagatctg     300
tggatggaga ctgggtgggg ggcttgcgt tatcccttcg gctactgggg ccaagggaca     360
atggtcaccg tctcctca                                                   378

<210> SEQ ID NO 592
<211> LENGTH: 126
<212> TYPE: PRT
<213> ORGANISM: Artificial Sequence
<220> FEATURE:
<223> OTHER INFORMATION: Homo sapiens33_640076-4B VH PRT

<400> SEQUENCE: 592

Glu Val Gln Leu Leu Glu Ser Gly Gly Gly Leu Val Gln Pro Gly Gly
```

```
1               5                   10                  15
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Gly Ile Ser Ala Ile Asp Gln Ser Thr Tyr Tyr Ala Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
            85                  90                  95

Ala Arg Asp Leu Trp Met Glu Asn Trp Val Gly Gly Leu Arg Tyr Pro
            100                 105                 110

Phe Gly Tyr Trp Gly Gln Gly Thr Met Val Thr Val Ser Ser
            115                 120                 125
```

<210> SEQ ID NO 593
<211> LENGTH: 318
<212> TYPE: DNA
<213> ORGANISM: Artificial Sequence
<220> FEATURE:
<223> OTHER INFORMATION: Homo sapiens33_640076-4B VL DNA

<400> SEQUENCE: 593

```
tcctatgtgc tgactcagcc accctcagtg tccgtgtcac caggacagac ggccagcatc    60
acctgctctg gagaaagaat ggggataaa tatgctgcct ggtatcagca gaagccaggc   120
cagtcacctg tgctggtcat ctatcgagat acaaagcggc cctcagggat ccctgagcga   180
ttctctggct ccaactctgg gaacacagcc acgttgacca tcagcgggac ccaggccatg   240
gatgaggccg actattactg tgaggtcaag aagtccgaca ctggggtatt cggcggaggg   300
accaagctca ccgtccta                                                 318
```

<210> SEQ ID NO 594
<211> LENGTH: 106
<212> TYPE: PRT
<213> ORGANISM: Artificial Sequence
<220> FEATURE:
<223> OTHER INFORMATION: Homo sapiens33_640076-4B VL PRT

<400> SEQUENCE: 594

```
Ser Tyr Val Leu Thr Gln Pro Pro Ser Val Ser Val Ser Pro Gly Gln
 1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
            35                  40                  45

Arg Asp Thr Lys Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
 65                 70                  75                  80

Asp Glu Ala Asp Tyr Tyr Cys Glu Val Lys Lys Ser Asp Thr Gly Val
            85                  90                  95

Phe Gly Gly Gly Thr Lys Leu Thr Val Leu
            100                 105
```

<210> SEQ ID NO 595
<211> LENGTH: 378

<212> TYPE: DNA
<213> ORGANISM: Artificial Sequence
<220> FEATURE:
<223> OTHER INFORMATION: Homo sapiens33_640081-AB VH DNA

<400> SEQUENCE: 595

| | |
|---|---|
| gaggtgcagc tgttggagtc tgggggaggc ttggtacagc ctggggggtc cctgagactc | 60 |
| tcctgtgcag cctctggatt cacctttagc agctatgcca tgaactgggt ccgccaggct | 120 |
| ccagggaagg ggctggagtg ggtctcagct attagtggta gtggtggtag cacacactac | 180 |
| gcagactccg tgaagggccg gttcaccatc tccagagaca attccaagaa cacgctgtat | 240 |
| ctgcaaatga acagcctgag agccgaggac acggccgtgt attactgtgg ccgggccaag | 300 |
| ttcatgcagc tatggggggg gggcttgcgt tatcccctcg gctactgggg ccaagggaca | 360 |
| atggtcaccg tctcctca | 378 |

<210> SEQ ID NO 596
<211> LENGTH: 126
<212> TYPE: PRT
<213> ORGANISM: Artificial Sequence
<220> FEATURE:
<223> OTHER INFORMATION: Homo sapiens33_640081-AB VH PRT

<400> SEQUENCE: 596

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Ala Lys Phe Met Gln Leu Trp Gly Gly Gly Leu Arg Tyr Pro
            100                 105                 110

Leu Gly Tyr Trp Gly Gln Gly Thr Met Val Thr Val Ser Ser
        115                 120                 125
```

<210> SEQ ID NO 597
<211> LENGTH: 321
<212> TYPE: DNA
<213> ORGANISM: Artificial Sequence
<220> FEATURE:
<223> OTHER INFORMATION: Homo sapiens33_640081-AB VL DNA

<400> SEQUENCE: 597

| | |
|---|---|
| tcctatgtgc tgactcagcc accctcagtg tccgtgtccc caggacagac ggccagcatc | 60 |
| acctgctctg gagaaagaat gggggataaa tatgctgcct ggtatcagca gaagccaggc | 120 |
| cagtcacctg tgctggtcat ctatcgagat acaaagcggc cctcagggat ccctgagcga | 180 |
| ttctctggct ccaactctgg gaacacagcc acgttgacca tcagcgggac ccaggccatg | 240 |
| gatgaggctg actattactg tcaggtgtgg cggccgacg acactggggt attcggcgga | 300 |
| gggaccaagc tcaccgtcct a | 321 |

<210> SEQ ID NO 598

<211> LENGTH: 107
<212> TYPE: PRT
<213> ORGANISM: Artificial Sequence
<220> FEATURE:
<223> OTHER INFORMATION: Homo sapiens33_640081-AB VL PRT

<400> SEQUENCE: 598

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Ala Ala Asp Asp Thr Gly
                85                  90                  95

Val Phe Gly Gly Gly Thr Lys Leu Thr Val Leu
            100                 105

<210> SEQ ID NO 599
<211> LENGTH: 378
<212> TYPE: DNA
<213> ORGANISM: Artificial Sequence
<220> FEATURE:
<223> OTHER INFORMATION: Homo sapiens33_640082-6B VH DNA

<400> SEQUENCE: 599
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaggt attagtggta tcgacacaag cacatactac     180
gcagactccg tgaagggccg gttcaccatc tccagagaca attccaagaa cacgctgtat     240
ctgcaaatga acagcctgag agccgaggac acggccgtgt attactgtgc ccggcagaag     300
ttcatgcagc tatggggggg gggcttgcgt tatcccttcg ctactgggg ccaagggaca     360 atggtcaccg tctcctca                                                    378

<210> SEQ ID NO 600
<211> LENGTH: 126
<212> TYPE: PRT
<213> ORGANISM: Artificial Sequence
<220> FEATURE:
<223> OTHER INFORMATION: Homo sapiens33_640082-6B VH PRT

<400> SEQUENCE: 600

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ile Asp Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Arg Gln Lys Phe Met Gln Leu Trp Gly Gly Gly Leu Arg Tyr Pro
                100                 105                 110

Phe Gly Tyr Trp Gly Gln Gly Thr Met Val Thr Val Ser Ser
            115                 120                 125

<210> SEQ ID NO 601
<211> LENGTH: 318
<212> TYPE: DNA
<213> ORGANISM: Artificial Sequence
<220> FEATURE:
<223> OTHER INFORMATION: Homo sapiens33_640082-6B VL DNA

<400> SEQUENCE: 601
tcctatgtgc tgactcagcc accctcagtg tccgtgtccc cagggcagac ggccagcatc    60
acctgctctg gagaaagaat gggggataaa tatgctgcct ggtatcagca gaagccaggc   120
cagtcacctg tgctggtcat ctatcgagat acaaagcggc cctcagggat ccctgagcga   180
ttctctggct ccaactctgg gaacacagcc acgttgacca tcagcgggac ccaggccatg   240
gatgaggctg actattactg tggcgtgttg aagcaggaca ctggggtatt cggcggaggg   300
accaagctca ccgtccta                                                 318

<210> SEQ ID NO 602
<211> LENGTH: 106
<212> TYPE: PRT
<213> ORGANISM: Artificial Sequence
<220> FEATURE:
<223> OTHER INFORMATION: Homo sapiens33_640082-6B VL PRT

<400> SEQUENCE: 602

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Leu Thr Val Leu
            100                 105

<210> SEQ ID NO 603
<211> LENGTH: 378
<212> TYPE: DNA
<213> ORGANISM: Artificial Sequence
<220> FEATURE:
<223> OTHER INFORMATION: Homo sapiens33_640082-7B VH DNA

<400> SEQUENCE: 603
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg gtctcaggc atttctgcaa tagaccaaag cacatactac   180
gcagactccg tgaagggccg gttcaccatc tccagagaca attccaagaa cacgctgtat   240
```

```
ctgcaaatga acagcctgag agccgaggac acggccgtgt attactgtgc ccggcagaag    300
ttcatgcagc tatgggggg gggcttgcgt tatcccttcg gctactgggg ccaagggaca    360
atggtcaccg tctcctca                                                  378
```

<210> SEQ ID NO 604
<211> LENGTH: 126
<212> TYPE: PRT
<213> ORGANISM: Artificial Sequence
<220> FEATURE:
<223> OTHER INFORMATION: Homo sapiens33_640082-7B VH PRT

<400> SEQUENCE: 604

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ile Asp Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Leu Arg Tyr Pro
            100                 105                 110

Phe Gly Tyr Trp Gly Gln Gly Thr Met Val Thr Val Ser Ser
        115                 120                 125
```

<210> SEQ ID NO 605
<211> LENGTH: 318
<212> TYPE: DNA
<213> ORGANISM: Artificial Sequence
<220> FEATURE:
<223> OTHER INFORMATION: Homo sapiens33_640082-7B VL DNA

<400> SEQUENCE: 605

```
tcctatgtgc tgactcagcc accctcagtg tccgtgtccc cagggcagac ggccagcatc    60
acctgctctg gagaaagaat gggggataaa tatgctgcct ggtatcagca gaagccaggc   120
cagtcacctg tgctggtcat ctatcgagat acaaagcggc cctcagggat ccctgagcga   180
ttctctggct ccaactctgg gaacacagcc acgttgacca tcagcgggac ccaggccatg   240
gatgaggctg actattactg tggcgtgttg aagcaggaca ctggggtatt cggcggaggg   300
accaagctca ccgtccta                                                 318
```

<210> SEQ ID NO 606
<211> LENGTH: 106
<212> TYPE: PRT
<213> ORGANISM: Artificial Sequence
<220> FEATURE:
<223> OTHER INFORMATION: Homo sapiens33_640082-7B VL PRT

<400> SEQUENCE: 606

```
Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
```

```
                 35                  40                  45
Arg Asp Thr Lys Arg Pro Ser Gly Ile Pro Glu Arg Phe Ser Gly Ser
             50                  55                  60
Asn Ser Gly Asn Thr Ala Thr Leu Thr Ile Ser Gly Thr Gln Ala Met
 65                  70                  75                  80
Asp Glu Ala Asp Tyr Tyr Cys Gly Val Leu Lys Gln Asp Thr Gly Val
                 85                  90                  95
Phe Gly Gly Gly Thr Lys Leu Thr Val Leu
            100                 105
```

<210> SEQ ID NO 607
<211> LENGTH: 378
<212> TYPE: DNA
<213> ORGANISM: Artificial Sequence
<220> FEATURE:
<223> OTHER INFORMATION: Homo sapiens33_640084-2B VH DNA

<400> SEQUENCE: 607

```
gaggtgcagc tgttggagtc tgggggaggc ttggtacagc ctggggggtc cctgagactc      60
tcctgtgcgg cctctggatt cgcctttagc agctatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc ccggcagaag     300
ttcatgcagc tatggggggg gggcttgcgt tatccctttg gctactgggg ccaagggaca     360
atggtcaccg tctcgagt                                                   378
```

<210> SEQ ID NO 608
<211> LENGTH: 126
<212> TYPE: PRT
<213> ORGANISM: Artificial Sequence
<220> FEATURE:
<223> OTHER INFORMATION: Homo sapiens33_640084-2B VH PRT

<400> SEQUENCE: 608

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Ala Phe Ser Ser Tyr
             20                  25                  30
Ala Met Ser Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gln Lys Phe Met Gln Leu Trp Gly Gly Gly Leu Arg Tyr Pro
            100                 105                 110
Phe Gly Tyr Trp Gly Gln Gly Thr Met Val Thr Val Ser Ser
            115                 120                 125
```

<210> SEQ ID NO 609
<211> LENGTH: 318
<212> TYPE: DNA
<213> ORGANISM: Artificial Sequence
<220> FEATURE:
<223> OTHER INFORMATION: Homo sapiens33_640084-2B VL DNA

<400> SEQUENCE: 609

```
tcctatgtgc tgactcagcc acactcagtg tccgtgtccc caggacagac ggccagcatc    60
acctgctctg gagaaagaat gggggataaa tatgctgcct ggtatcagca gaagccaggc   120
cagtcacctg tgctggtcat ctatcgagat acaaagcggc cctcaggat  ccctgagcga   180
ttctctggct ccaactctgg gaacacagcc acgttgacca tcagcgggac ccaggccatg   240
gatgaggctg actattactg tcaggtgtgg cgggacgaca gccccatctt cggcggaggg   300
accaagctca ccgtccta                                                  318
```

<210> SEQ ID NO 610
<211> LENGTH: 106
<212> TYPE: PRT
<213> ORGANISM: Artificial Sequence
<220> FEATURE:
<223> OTHER INFORMATION: Homo sapiens33_640084-2B VL PRT

<400> SEQUENCE: 610

```
Ser Tyr Val Leu Thr Gln Pro Pro Ser Val Ser Val Ser Pro Gly Gln
  1               5                  10                  15

Thr Ala Ser Ile Thr Cys Ser Gly Glu Arg Met Gly Asp Lys Tyr Ala
             20                  25                  30

Ala Trp Tyr Gln Gln Lys Pro Gly Gln Ser Pro Val Leu Val Ile Tyr
         35                  40                  45

Arg Asp Thr Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Arg Asp Asp Ser Pro Ile
                 85                  90                  95

Phe Gly Gly Gly Thr Lys Leu Thr Val Leu
            100                 105
```

<210> SEQ ID NO 611
<211> LENGTH: 378
<212> TYPE: DNA
<213> ORGANISM: Artificial Sequence
<220> FEATURE:
<223> OTHER INFORMATION: Homo sapiens33_640086-6B VH DNA

<400> SEQUENCE: 611

```
gaggtgcagc tgttggagtc tgggggaggc ttggtacagc ctggtgggtc cctgagactc    60
tcctgtgcag cctctggatt cacctttagc agctatgcca tgagctgggt ccgccaggct   120
ccagggaagg ggctggagtg gtctcaggt  attagtggta tcgacacaag cacatactac   180
gcagactccg tgaagggccg gttcaccatc agcagagaca attccaagaa cacgctgtat   240
ctgcaaatga acagcctgag agccgaggac acggccgtgt attactgtgc ccgcgacaag   300
ttcatgcagc tatgggggg  gggcttgcgt tatccttcg  gctactgggg ccaagggaca   360
atggtcaccg tctcctca                                                  378
```

<210> SEQ ID NO 612
<211> LENGTH: 126
<212> TYPE: PRT
<213> ORGANISM: Artificial Sequence
<220> FEATURE:
<223> OTHER INFORMATION: Homo sapiens33_640086-6B VH PRT

<400> SEQUENCE: 612

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ile Asp Thr Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Asp Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 613
<211> LENGTH: 318
<212> TYPE: DNA
<213> ORGANISM: Artificial Sequence
<220> FEATURE:
<223> OTHER INFORMATION: Homo sapiens33_640086-6B VL DNA

<400> SEQUENCE: 613
tcctatgtgc tgactcagcc accctcagtg tccgtgtccc caggacagac ggccagcatc    60
acctgctctg agaaagaat ggggataaa tatgctgcct ggtatcagca gaagccaggc   120
cagtcacctg tgctggtcat ctatcgagat acaaagcggc cctcagggat ccctgagcga   180
ttctctggct ccaactctgg gaacacagcc acgttgacca tcagcgggac ccaagccatg   240
gatgaggctg actattactg tgaggtcaag gtgaaggaca ctggggtatt cggcggaggg   300
accaagctca ccgtccta                                                 318

<210> SEQ ID NO 614
<211> LENGTH: 106
<212> TYPE: PRT
<213> ORGANISM: Artificial Sequence
<220> FEATURE:
<223> OTHER INFORMATION: Homo sapiens33_640086-6B VL PRT

<400> SEQUENCE: 614

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65              70                  75                  80

Asp Glu Ala Asp Tyr Tyr Cys Glu Val Lys Val Lys Asp Thr Gly Val
                85                  90                  95

Phe Gly Gly Gly Thr Lys Leu Thr Val Leu
            100                 105

```
<210> SEQ ID NO 615
<211> LENGTH: 378
<212> TYPE: DNA
<213> ORGANISM: Artificial Sequence
<220> FEATURE:
<223> OTHER INFORMATION: Homo sapiens33_640087-7B VH DNA

<400> SEQUENCE: 615
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaggc atttctgcaa tagaccaaag cacatactac     180
gcagactccg tgaagggccg gttcaccatc tccagagaca attccaagaa cacgctgtat     240
ctgcaaatga acagcctgag agccgaggac acggccgtgt attactgtgc ccggcagaag     300
ttcatgcagc tatgggggg gggcttgcgt tatcccttcg gctactgggg ccaggggaca     360
atggtcaccg tctcctca                                                   378

<210> SEQ ID NO 616
<211> LENGTH: 126
<212> TYPE: PRT
<213> ORGANISM: Artificial Sequence
<220> FEATURE:
<223> OTHER INFORMATION: Homo sapiens33_640087-7B VH PRT

<400> SEQUENCE: 616

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ile Asp Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 617
<211> LENGTH: 318
<212> TYPE: DNA
<213> ORGANISM: Artificial Sequence
<220> FEATURE:
<223> OTHER INFORMATION: Homo sapiens33_640087-7B VL DNA

<400> SEQUENCE: 617
tcctatgtgc tgactcagcc accctcagtg tccgtgtccc caggacagac ggccagcatc      60
acctgctctg gagaaggaat gggggataaa tatgctgcct ggtatcagca gaagccaggc     120
cagtcacctg tgctggtcat ctatcgagat acaaagcggc cctcagggat ccctgagcga     180
ttctctggct ccaactctgg gaacacagcc acgttgacca tcagcgggac ccaggctatg     240
gatgaggctg actattactg tggggtgatc caggacaaca ctggggtatt cggcggaggg     300
accaagctca ccgtcccta                                                  318
```

<210> SEQ ID NO 618
<211> LENGTH: 106
<212> TYPE: PRT
<213> ORGANISM: Artificial Sequence
<220> FEATURE:
<223> OTHER INFORMATION: Homo sapiens33_640087-7B VL PRT

<400> SEQUENCE: 618

Ser Tyr Val Leu Thr Gln Pro Pro Ser Val Ser Val Ser Pro Gly Gln
1               5                   10                  15

Thr Ala Ser Ile Thr Cys Ser Gly Glu Gly Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Ile Gln Asp Asn Thr Gly Val
                85                  90                  95

Phe Gly Gly Gly Thr Lys Leu Thr Val Leu
            100                 105

<210> SEQ ID NO 619
<211> LENGTH: 378
<212> TYPE: DNA
<213> ORGANISM: Artificial Sequence
<220> FEATURE:
<223> OTHER INFORMATION: Homo sapiens33_640201-2B VH DNA

<400> SEQUENCE: 619
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctcatca attgacgcca ttagttcaag cacatactac      180
gcagactccg tgaagggccg gttcaccatc tccagagaca attccaagaa cacgctgtat     240
ctgcaaatga acagcctgag agccgaggac acggccgtgt attactgttc ccgccagaag     300
ttcatgcagc tatgggggg gggcttgcgt tatcccttcg gctactgggg ccaagggaca      360
atggtcaccg tctcgagt                                                  378

<210> SEQ ID NO 620
<211> LENGTH: 126
<212> TYPE: PRT
<213> ORGANISM: Artificial Sequence
<220> FEATURE:
<223> OTHER INFORMATION: Homo sapiens33_640201-2B VH PRT

<400> SEQUENCE: 620

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Ala Ile Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ser Arg Gln Lys Phe Met Gln Leu Trp Gly Gly Leu Arg Tyr Pro
            100                 105                 110

Phe Gly Tyr Trp Gly Gln Gly Thr Met Val Thr Val Ser Ser
        115                 120                 125

<210> SEQ ID NO 621
<211> LENGTH: 318
<212> TYPE: DNA
<213> ORGANISM: Artificial Sequence
<220> FEATURE:
<223> OTHER INFORMATION: Homo sapiens33_640201-2B VL DNA

<400> SEQUENCE: 621
tcctatgtgc tgactcagcc acccteagtg tccgtgtccc caggacagac ggccagcatc    60
acctgctctg gagaaagaat gggggataaa tatgctgcct ggtatcagca gaagccaggc   120
cagtcacctg tgctggtcat ctatcgagat acaaagcggc cctcaggat  ccctgagcga   180 ttctctggct ccaactctgg gaacacagcc acgttgacca tcagcgggac ccaggccatg   240
gatgaggctg actattactg tggcgtgttg aagcaggaca ctggggtatt cggcggaggg   300
accaagctca ccgtccta                                                 318

<210> SEQ ID NO 622
<211> LENGTH: 106
<212> TYPE: PRT
<213> ORGANISM: Artificial Sequence
<220> FEATURE:
<223> OTHER INFORMATION: Homo sapiens33_640201-2B VL PRT

<400> SEQUENCE: 622

Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Leu Thr Val Leu
            100                 105

<210> SEQ ID NO 623
<211> LENGTH: 378
<212> TYPE: DNA
<213> ORGANISM: Artificial Sequence
<220> FEATURE:
<223> OTHER INFORMATION: Homo sapiens33_640237-2B VH DNA

<400> SEQUENCE: 623
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcaggc attgcagacg atttcaccag cacatactac   180
```

-continued

```
gcagaccccg tgaagggccg gttcaccatc tccagagaca attccaagaa cacgctgtat    240
ctgcaaatga acagcctgag agccgaggac acggccgtgt attactgtgc gagagatctg    300
tggatgatga actacgcggg cggcttgcgt tatcccttcg gctactgggg ccaagggacc    360
atggtcaccg tctcctca                                                  378
```

<210> SEQ ID NO 624
<211> LENGTH: 126
<212> TYPE: PRT
<213> ORGANISM: Artificial Sequence
<220> FEATURE:
<223> OTHER INFORMATION: Homo sapiens33_640237-2B VH PRT

<400> SEQUENCE: 624

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ala Asp Asp Phe Thr Ser Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Met Asn Tyr Ala Gly Gly Leu Arg Tyr Pro
            100                 105                 110

Phe Gly Tyr Trp Gly Gln Gly Thr Met Val Thr Val Ser Ser
        115                 120                 125
```

<210> SEQ ID NO 625
<211> LENGTH: 318
<212> TYPE: DNA
<213> ORGANISM: Artificial Sequence
<220> FEATURE:
<223> OTHER INFORMATION: Homo sapiens33_640237-2B VL DNA

<400> SEQUENCE: 625

```
tcctatgtgc tgactcagcc accctcagtg tccgtgtccc caggacagac ggccagcatc    60
acctgctctg gagaaagaat gggggataaa tatgctgcct ggtatcagca gaagccaggc    120
cagtcacctg tgctggtcat ctatcgagat acaaagcggc cctcagggat ccctgagcga    180
ttctctggct ccaactctgg gaacacagcc acgttgacca tcagcgggac ccaggccatg    240
gatgaggctg actattactg tgcgtgttg aagcaggaca ctggggtatt cggcggaggg    300
accaagctca ccgtcccta                                                 318
```

<210> SEQ ID NO 626
<211> LENGTH: 106
<212> TYPE: PRT
<213> ORGANISM: Artificial Sequence
<220> FEATURE:
<223> OTHER INFORMATION: Homo sapiens33_640237-2B VL PRT

<400> SEQUENCE: 626

```
Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30
```

```
Ala Trp Tyr Gln Gln Lys Pro Gly Gln Ser Pro Val Leu Val Ile Tyr
            35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Leu Thr Val Leu
            100                 105

<210> SEQ ID NO 627
<211> LENGTH: 191
<212> TYPE: PRT
<213> ORGANISM: Artificial Sequence
<220> FEATURE:
<223> OTHER INFORMATION: Mature Human IL-33 aa 112-270 c-terminal FLAG
      10His

<400> SEQUENCE: 627

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
            35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
            115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr Asn
145                 150                 155                 160

Pro Ala Phe Leu Tyr Lys Val Val Gly Ala Ala Asp Tyr Lys Asp Asp
                165                 170                 175

Asp Asp Lys Ala Ala His His His His His His His His His His
            180                 185                 190

<210> SEQ ID NO 628
<211> LENGTH: 190
<212> TYPE: PRT
<213> ORGANISM: Artificial Sequence
<220> FEATURE:
<223> OTHER INFORMATION: Mature Mouse IL-33 aa 109-266 c-terminal FLAG
      10His

<400> SEQUENCE: 628

Ser Ile Gln Gly Thr Ser Leu Leu Thr Gln Ser Pro Ala Ser Leu Ser
1               5                   10                  15

Thr Tyr Asn Asp Gln Ser Val Ser Phe Val Leu Glu Asn Gly Cys Tyr
            20                  25                  30
```

```
Val Ile Asn Val Asp Asp Ser Gly Lys Asp Gln Glu Gln Asp Gln Val
            35                  40                  45

Leu Leu Arg Tyr Tyr Glu Ser Pro Cys Pro Ala Ser Gln Ser Gly Asp
    50                  55                  60

Gly Val Asp Gly Lys Lys Leu Met Val Asn Met Ser Pro Ile Lys Asp
65                  70                  75                  80

Thr Asp Ile Trp Leu His Ala Asn Asp Lys Asp Tyr Ser Val Glu Leu
                85                  90                  95

Gln Arg Gly Asp Val Ser Pro Pro Glu Gln Ala Phe Phe Val Leu His
                100                 105                 110

Lys Lys Ser Ser Asp Phe Val Ser Phe Glu Cys Lys Asn Leu Pro Gly
            115                 120                 125

Thr Tyr Ile Gly Val Lys Asp Asn Gln Leu Ala Leu Val Glu Glu Lys
            130                 135                 140

Asp Glu Ser Cys Asn Asn Ile Met Phe Lys Leu Ser Lys Ile Asn Pro
145                 150                 155                 160

Ala Phe Leu Tyr Lys Val Val Gly Ala Ala Asp Tyr Lys Asp Asp Asp
                165                 170                 175

Asp Lys Ala Ala His His His His His His His His His His
            180                 185                 190

<210> SEQ ID NO 629
<211> LENGTH: 191
<212> TYPE: PRT
<213> ORGANISM: Artificial Sequence
<220> FEATURE:
<223> OTHER INFORMATION: Mature cynomolgus IL-33 aa 112-270 c-terminal
      FLAG 10His

<400> SEQUENCE: 629

Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
            35                  40                  45

Leu Leu Ser Tyr Tyr Glu Ser Gln His Pro Ser Ser Glu Ser Gly Asp
    50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
            100                 105                 110

Ser Phe Asn Cys Val Ser Phe Glu Cys Lys Thr Asp Pro Gly Val Phe
            115                 120                 125

Ile Gly Val Lys Asp Asn His Leu Ala Leu Ile Lys Val Asp Tyr Ser
            130                 135                 140

Glu Asn Leu Gly Ser Glu Asn Ile Leu Phe Lys Leu Ser Glu Ile Asn
145                 150                 155                 160

Pro Ala Phe Leu Tyr Lys Val Val Gly Ala Ala Asp Tyr Lys Asp Asp
                165                 170                 175

Asp Asp Lys Ala Ala His His His His His His His His His His
            180                 185                 190
```

```
<210> SEQ ID NO 630
<211> LENGTH: 577
<212> TYPE: PRT
<213> ORGANISM: Artificial Sequence
<220> FEATURE:
<223> OTHER INFORMATION: Human ST2 ECD-Fc/His6

<400> SEQUENCE: 630

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ile Asp His His Ser Asp Pro Ala Phe Leu Tyr Lys Val
                325                 330                 335

Val Gly Ala Ala Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
```

```
                370                 375                 380
Cys Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
                435                 440                 445

Asn Lys Ala Leu Pro Ala Pro Ile Glu Lys Thr Ile Ser Lys Ala Lys
                450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
                515                 520                 525

Phe Leu Tyr Ser Lys Leu Thr Val Asp Lys Ser Arg Trp Gln Gln Gly
                530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys His His His His His
                565                 570                 575

His

<210> SEQ ID NO 631
<211> LENGTH: 581
<212> TYPE: PRT
<213> ORGANISM: Artificial Sequence
<220> FEATURE:
<223> OTHER INFORMATION: Mouse ST2 ECD-Fc/His

<400> SEQUENCE: 631

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
                20                  25                  30

Leu Glu Asn Glu Ala Leu Ile Val Arg Cys Pro Gln Arg Gly Arg Ser
                35                  40                  45

Thr Tyr Pro Val Glu Trp Tyr Tyr Ser Asp Thr Asn Glu Ser Ile Pro
                50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
                100                 105                 110

Lys Pro Pro Ser Cys Asn Ile Pro Asp Tyr Leu Met Tyr Ser Thr Val
                115                 120                 125

Arg Gly Ser Asp Lys Asn Phe Lys Ile Thr Cys Pro Thr Ile Asp Leu
                130                 135                 140

Tyr Asn Trp Thr Ala Pro Val Gln Trp Phe Lys Asn Cys Lys Ala Leu
145                 150                 155                 160
```

-continued

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
            180                 185                 190

Glu Asn Gly Thr Asn Tyr Ile Val Thr Ala Thr Arg Ser Phe Thr Val
        195                 200                 205

Glu Glu Lys Gly Phe Ser Met Phe Pro Val Ile Thr Asn Pro Pro Tyr
    210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
            260                 265                 270

Glu Glu Glu Gly Arg Asn Glu Ser Ser Ser Asn Asp Met Asp Cys Leu
        275                 280                 285

Thr Ser Val Leu Arg Ile Thr Gly Val Thr Glu Lys Asp Leu Ser Leu
    290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ile Asp His Arg Asp Pro Ala Phe
                325                 330                 335

Leu Tyr Lys Val Val Gly Ala Ala Pro Lys Ser Cys Asp Lys Thr His
            340                 345                 350

Thr Cys Pro Pro Cys Pro Ala Pro Glu Leu Leu Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
    435                 440                 445

Cys Lys Val Ser Asn Lys Ala Leu Pro Ala Pro Ile Glu Lys Thr Ile
450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys His
                565                 570                 575

His His His His His
            580

<210> SEQ ID NO 632
<211> LENGTH: 193
<212> TYPE: PRT
<213> ORGANISM: Artificial Sequence
<220> FEATURE:
<223> OTHER INFORMATION: IL33-01 - Human IL33 with N-terminal 10His,
      avitag, Factor-Xa protease cleavage site

<400> SEQUENCE: 632

Met His His His His His His His His His Ala Ala Gly Leu Asn
1               5                   10                  15

Asp Ile Phe Glu Ala Gln Lys Ile Glu Trp His Glu Ala Ala Ile Glu
            20                  25                  30

Gly Arg Ser Ile Thr Gly Ile Ser Pro Ile Thr Glu Tyr Leu Ala Ser
        35                  40                  45

Leu Ser Thr Tyr Asn Asp Gln Ser Ile Thr Phe Ala Leu Glu Asp Glu
    50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Cys Glu Lys Pro Leu Pro Asp Gln Ala Phe Phe Val Leu His
    130                 135                 140

Asn Met His Ser Asn Cys Val Ser Phe Glu Cys Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Cys Thr Glu Asn Ile Leu Phe Lys Leu Ser Glu
            180                 185                 190

Thr

<210> SEQ ID NO 633
<211> LENGTH: 178
<212> TYPE: PRT
<213> ORGANISM: Artificial Sequence
<220> FEATURE:
<223> OTHER INFORMATION: Human IL33 with N-terminal 6His tag and TEV
      protease cleavage site

<400> SEQUENCE: 633

Met Gly His His His His His His Gly Gly Gly Glu Asn Leu Tyr Phe
1               5                   10                  15

Gln Gly Ser Ser Ile Thr Gly Ile Ser Pro Ile Thr Glu Tyr Leu Ala
            20                  25                  30

Ser Leu Ser Thr Tyr Asn Asp Gln Ser Ile Thr Phe Ala Leu Glu Asp
        35                  40                  45

Glu Ser Tyr Glu Ile Tyr Val Glu Asp Leu Lys Lys Asp Glu Lys Lys
    50                  55                  60

Asp Lys Val Leu Leu Ser Tyr Tyr Glu Ser Gln His Pro Ser Asn Glu
65                  70                  75                  80

Ser Gly Asp Gly Val Asp Gly Lys Met Leu Met Val Thr Leu Ser Pro

-continued

```
                85                  90                  95
Thr Lys Asp Phe Trp Leu His Ala Asn Asn Lys Glu His Ser Val Glu
                100                 105                 110

Leu His Lys Cys Glu Lys Pro Leu Pro Asp Gln Ala Phe Phe Val Leu
            115                 120                 125

His Asn Met His Ser Asn Cys Val Ser Phe Glu Cys Lys Thr Asp Pro
        130                 135                 140

Gly Val Phe Ile Gly Val Lys Asp Asn His Leu Ala Leu Ile Lys Val
145                 150                 155                 160

Asp Ser Ser Glu Asn Leu Cys Thr Glu Asn Ile Leu Phe Lys Leu Ser
                165                 170                 175

Glu Thr

<210> SEQ ID NO 634
<211> LENGTH: 193
<212> TYPE: PRT
<213> ORGANISM: Artificial Sequence
<220> FEATURE:
<223> OTHER INFORMATION: IL33-02

<400> SEQUENCE: 634

Met His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
        50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
                100                 105                 110

Lys Asp Phe Trp Leu His Ala Asn Asn Lys Glu His Ser Val Glu Leu
            115                 120                 125

His Lys Ser Glu Lys Pro Leu Pro Asp Gln Ala Phe Phe Val Leu His
        130                 135                 140

Asn Met His Ser Asn Cys Val Ser Phe Glu Cys Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Cys Thr Glu Asn Ile Leu Phe Lys Leu Ser Glu
                180                 185                 190

Thr

<210> SEQ ID NO 635
<211> LENGTH: 193
<212> TYPE: PRT
<213> ORGANISM: Artificial Sequence
<220> FEATURE:
<223> OTHER INFORMATION: IL33-03

<400> SEQUENCE: 635

Met His His His His His His His His Ala Ala Gly Leu Asn
1               5                   10                  15
```

```
Asp Ile Phe Glu Ala Gln Lys Ile Glu Trp His Glu Ala Ala Ile Glu
            20                  25                  30

Gly Arg Ser Ile Thr Gly Ile Ser Pro Ile Thr Glu Tyr Leu Ala Ser
        35                  40                  45

Leu Ser Thr Tyr Asn Asp Gln Ser Ile Thr Phe Ala Leu Glu Asp Glu
 50                  55                  60

Ser Tyr Glu Ile Tyr Val Glu Asp Leu Lys Lys Asp Glu Lys Lys Asp
 65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Cys Glu Lys Pro Leu Pro Asp Gln Ala Phe Phe Val Leu His
130                 135                 140

Asn Met His Ser Asn Ser Val Ser Phe Glu Cys Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Cys Thr Glu Asn Ile Leu Phe Lys Leu Ser Glu
            180                 185                 190

Thr

<210> SEQ ID NO 636
<211> LENGTH: 193
<212> TYPE: PRT
<213> ORGANISM: Artificial Sequence
<220> FEATURE:
<223> OTHER INFORMATION: IL33-04

<400> SEQUENCE: 636

Met His His His His His His His His Ala Ala Gly Leu Asn
1               5                   10                  15

Asp Ile Phe Glu Ala Gln Lys Ile Glu Trp His Glu Ala Ala Ile Glu
            20                  25                  30

Gly Arg Ser Ile Thr Gly Ile Ser Pro Ile Thr Glu Tyr Leu Ala Ser
        35                  40                  45

Leu Ser Thr Tyr Asn Asp Gln Ser Ile Thr Phe Ala Leu Glu Asp Glu
 50                  55                  60

Ser Tyr Glu Ile Tyr Val Glu Asp Leu Lys Lys Asp Glu Lys Lys Asp
 65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Cys Glu Lys Pro Leu Pro Asp Gln Ala Phe Phe Val Leu His
130                 135                 140

Asn Met His Ser Asn Cys Val Ser Phe Glu Ser Lys Thr Asp Pro Gly
145                 150                 155                 160

Val Phe Ile Gly Val Lys Asp Asn His Leu Ala Leu Ile Lys Val Asp
                165                 170                 175
```

```
Ser Ser Glu Asn Leu Cys Thr Glu Asn Ile Leu Phe Lys Leu Ser Glu
            180                 185                 190

Thr

<210> SEQ ID NO 637
<211> LENGTH: 193
<212> TYPE: PRT
<213> ORGANISM: Artificial Sequence
<220> FEATURE:
<223> OTHER INFORMATION: IL33-05

<400> SEQUENCE: 637

Met His His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
        50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Cys Glu Lys Pro Leu Pro Asp Gln Ala Phe Phe Val Leu His
130                 135                 140

Asn Met His Ser Asn Cys Val Ser Phe Glu Cys Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Ser Thr Glu Asn Ile Leu Phe Lys Leu Ser Glu
            180                 185                 190

Thr

<210> SEQ ID NO 638
<211> LENGTH: 193
<212> TYPE: PRT
<213> ORGANISM: Artificial Sequence
<220> FEATURE:
<223> OTHER INFORMATION: IL33-06

<400> SEQUENCE: 638

Met His His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
        50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
```

```
                    85                  90                  95
Gly Asp Gly Val Asp Gly Lys Met Leu Met Val Thr Leu Ser Pro Thr
                100                 105                 110
Lys Asp Phe Trp Leu His Ala Asn Asn Lys Glu His Ser Val Glu Leu
                115                 120                 125
His Lys Ser Glu Lys Pro Leu Pro Asp Gln Ala Phe Phe Val Leu His
            130                 135                 140
Asn Met His Ser Asn Ser Val Ser Phe Glu Cys Lys Thr Asp Pro Gly
145                 150                 155                 160
Val Phe Ile Gly Val Lys Asp Asn His Leu Ala Leu Ile Lys Val Asp
                165                 170                 175
Ser Ser Glu Asn Leu Cys Thr Glu Asn Ile Leu Phe Lys Leu Ser Glu
                180                 185                 190
Thr

<210> SEQ ID NO 639
<211> LENGTH: 193
<212> TYPE: PRT
<213> ORGANISM: Artificial Sequence
<220> FEATURE:
<223> OTHER INFORMATION: IL33-07

<400> SEQUENCE: 639

Met His His His His His His His His Ala Ala Gly Leu Asn
1               5                   10                  15
Asp Ile Phe Glu Ala Gln Lys Ile Glu Trp His Glu Ala Ala Ile Glu
                20                  25                  30
Gly Arg Ser Ile Thr Gly Ile Ser Pro Ile Thr Glu Tyr Leu Ala Ser
            35                  40                  45
Leu Ser Thr Tyr Asn Asp Gln Ser Ile Thr Phe Ala Leu Glu Asp Glu
    50                  55                  60
Ser Tyr Glu Ile Tyr Val Glu Asp Leu Lys Lys Asp Glu Lys Lys Asp
65                  70                  75                  80
Lys Val Leu Leu Ser Tyr Tyr Glu Ser Gln His Pro Ser Asn Glu Ser
                85                  90                  95
Gly Asp Gly Val Asp Gly Lys Met Leu Met Val Thr Leu Ser Pro Thr
                100                 105                 110
Lys Asp Phe Trp Leu His Ala Asn Asn Lys Glu His Ser Val Glu Leu
                115                 120                 125
His Lys Cys Glu Lys Pro Leu Pro Asp Gln Ala Phe Phe Val Leu His
            130                 135                 140
Asn Met His Ser Asn Cys Val Ser Phe Glu Ser Lys Thr Asp Pro Gly
145                 150                 155                 160
Val Phe Ile Gly Val Lys Asp Asn His Leu Ala Leu Ile Lys Val Asp
                165                 170                 175
Ser Ser Glu Asn Leu Ser Thr Glu Asn Ile Leu Phe Lys Leu Ser Glu
                180                 185                 190
Thr

<210> SEQ ID NO 640
<211> LENGTH: 193
<212> TYPE: PRT
<213> ORGANISM: Artificial Sequence
<220> FEATURE:
<223> OTHER INFORMATION: IL33-08

<400> SEQUENCE: 640
```

Met His His His His His His His His Ala Ala Gly Leu Asn
1               5                   10                  15

Asp Ile Phe Glu Ala Gln Lys Ile Glu Trp His Glu Ala Ala Ile Glu
            20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
    50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
            115                 120                 125

His Lys Ser Glu Lys Pro Leu Pro Asp Gln Ala Phe Phe Val Leu His
    130                 135                 140

Asn Met His Ser Asn Cys Val Ser Phe Glu Ser Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Cys Thr Glu Asn Ile Leu Phe Lys Leu Ser Glu
            180                 185                 190

Thr

<210> SEQ ID NO 641
<211> LENGTH: 193
<212> TYPE: PRT
<213> ORGANISM: Artificial Sequence
<220> FEATURE:
<223> OTHER INFORMATION: IL33-09

<400> SEQUENCE: 641

Met His His His His His His His His Ala Ala Gly Leu Asn
1               5                   10                  15

Asp Ile Phe Glu Ala Gln Lys Ile Glu Trp His Glu Ala Ala Ile Glu
            20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
    50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
            115                 120                 125

His Lys Cys Glu Lys Pro Leu Pro Asp Gln Ala Phe Phe Val Leu His
    130                 135                 140

Asn Met His Ser Asn Ser Val Ser Phe Glu Cys Lys Thr Asp Pro Gly
145                 150                 155                 160

```
Val Phe Ile Gly Val Lys Asp Asn His Leu Ala Leu Ile Lys Val Asp
                165                 170                 175

Ser Ser Glu Asn Leu Ser Thr Glu Asn Ile Leu Phe Lys Leu Ser Glu
            180                 185                 190

Thr
```

<210> SEQ ID NO 642
<211> LENGTH: 193
<212> TYPE: PRT
<213> ORGANISM: Artificial Sequence
<220> FEATURE:
<223> OTHER INFORMATION: IL33-10

<400> SEQUENCE: 642

```
Met His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Cys Glu Lys Pro Leu Pro Asp Gln Ala Phe Phe Val Leu His
130                 135                 140

Asn Met His Ser Asn Ser Val Ser Phe Glu Ser Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Cys Thr Glu Asn Ile Leu Phe Lys Leu Ser Glu
            180                 185                 190

Thr
```

<210> SEQ ID NO 643
<211> LENGTH: 193
<212> TYPE: PRT
<213> ORGANISM: Artificial Sequence
<220> FEATURE:
<223> OTHER INFORMATION: IL33-11

<400> SEQUENCE: 643

```
Met His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
50                  55                  60

Ser Tyr Glu Ile Tyr Val Glu Asp Leu Lys Lys Asp Glu Lys Lys Asp
```

-continued

```
                65                  70                  75                  80
Lys Val Leu Leu Ser Tyr Tyr Glu Ser Gln His Pro Ser Asn Glu Ser
                    85                  90                  95

Gly Asp Gly Val Asp Gly Lys Met Leu Met Val Thr Leu Ser Pro Thr
                100                 105                 110

Lys Asp Phe Trp Leu His Ala Asn Asn Lys Glu His Ser Val Glu Leu
                115                 120                 125

His Lys Ser Glu Lys Pro Leu Pro Asp Gln Ala Phe Phe Val Leu His
            130                 135                 140

Asn Met His Ser Asn Cys Val Ser Phe Glu Cys Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Ser Thr Glu Asn Ile Leu Phe Lys Leu Ser Glu
                180                 185                 190

Thr
```

<210> SEQ ID NO 644
<211> LENGTH: 193
<212> TYPE: PRT
<213> ORGANISM: Artificial Sequence
<220> FEATURE:
<223> OTHER INFORMATION: IL33-12

<400> SEQUENCE: 644

```
Met His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
        50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                    85                  90                  95

Gly Asp Gly Val Asp Gly Lys Met Leu Met Val Thr Leu Ser Pro Thr
                100                 105                 110

Lys Asp Phe Trp Leu His Ala Asn Asn Lys Glu His Ser Val Glu Leu
                115                 120                 125

His Lys Ser Glu Lys Pro Leu Pro Asp Gln Ala Phe Phe Val Leu His
            130                 135                 140

Asn Met His Ser Asn Ser Val Ser Phe Glu Ser Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Cys Thr Glu Asn Ile Leu Phe Lys Leu Ser Glu
                180                 185                 190

Thr
```

<210> SEQ ID NO 645
<211> LENGTH: 193
<212> TYPE: PRT
<213> ORGANISM: Artificial Sequence
<220> FEATURE:

<223> OTHER INFORMATION: IL33-13

<400> SEQUENCE: 645

Met His His His His His His His His Ala Ala Gly Leu Asn
1               5                   10                  15

Asp Ile Phe Glu Ala Gln Lys Ile Glu Trp His Glu Ala Ala Ile Glu
            20                  25                  30

Gly Arg Ser Ile Thr Gly Ile Ser Pro Ile Thr Glu Tyr Leu Ala Ser
        35                  40                  45

Leu Ser Thr Tyr Asn Asp Gln Ser Ile Thr Phe Ala Leu Glu Asp Glu
    50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Ser Glu Lys Pro Leu Pro Asp Gln Ala Phe Phe Val Leu His
    130                 135                 140

Asn Met His Ser Asn Ser Val Ser Phe Glu Cys Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Ser Thr Glu Asn Ile Leu Phe Lys Leu Ser Glu
            180                 185                 190

Thr

<210> SEQ ID NO 646
<211> LENGTH: 193
<212> TYPE: PRT
<213> ORGANISM: Artificial Sequence
<220> FEATURE:
<223> OTHER INFORMATION: IL33-14

<400> SEQUENCE: 646

Met His His His His His His His His Ala Ala Gly Leu Asn
1               5                   10                  15

Asp Ile Phe Glu Ala Gln Lys Ile Glu Trp His Glu Ala Ala Ile Glu
            20                  25                  30

Gly Arg Ser Ile Thr Gly Ile Ser Pro Ile Thr Glu Tyr Leu Ala Ser
        35                  40                  45

Leu Ser Thr Tyr Asn Asp Gln Ser Ile Thr Phe Ala Leu Glu Asp Glu
    50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Ser Glu Lys Pro Leu Pro Asp Gln Ala Phe Phe Val Leu His
    130                 135                 140

-continued

Asn Met His Ser Asn Cys Val Ser Phe Glu Ser Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Ser Thr Glu Asn Ile Leu Phe Lys Leu Ser Glu
                180                 185                 190

Thr

<210> SEQ ID NO 647
<211> LENGTH: 193
<212> TYPE: PRT
<213> ORGANISM: Artificial Sequence
<220> FEATURE:
<223> OTHER INFORMATION: IL33-15

<400> SEQUENCE: 647

Met His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
50                  55                  60

Ser Tyr Glu Ile Tyr Val Glu Asp Leu Lys Lys Asp Glu Lys Lys Asp
65                  70                  75                  80

Lys Val Leu Leu Ser Tyr Tyr Glu Ser Gln His Pro Ser Asn Glu Ser
                85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
        115                 120                 125

His Lys Cys Glu Lys Pro Leu Pro Asp Gln Ala Phe Phe Val Leu His
    130                 135                 140

Asn Met His Ser Asn Ser Val Ser Phe Glu Ser Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Ser Thr Glu Asn Ile Leu Phe Lys Leu Ser Glu
                180                 185                 190

Thr

<210> SEQ ID NO 648
<211> LENGTH: 193
<212> TYPE: PRT
<213> ORGANISM: Artificial Sequence
<220> FEATURE:
<223> OTHER INFORMATION: IL33-16

<400> SEQUENCE: 648

Met His His His His His His His His Ala Ala Gly Leu Asn
1               5                   10                  15

Asp Ile Phe Glu Ala Gln Lys Ile Glu Trp His Glu Ala Ala Ile Glu
                20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu

```
                    50                  55                  60
Ser Tyr Glu Ile Tyr Val Glu Asp Leu Lys Lys Asp Glu Lys Lys Asp
 65                  70                  75                  80

Lys Val Leu Leu Ser Tyr Tyr Glu Ser Gln His Pro Ser Asn Glu Ser
                     85                  90                  95

Gly Asp Gly Val Asp Gly Lys Met Leu Met Val Thr Leu Ser Pro Thr
            100                 105                 110

Lys Asp Phe Trp Leu His Ala Asn Asn Lys Glu His Ser Val Glu Leu
                115                 120                 125

His Lys Ser Glu Lys Pro Leu Pro Asp Gln Ala Phe Phe Val Leu His
    130                 135                 140

Asn Met His Ser Asn Ser Val Ser Phe Glu Ser Lys Thr Asp Pro Gly
145                 150                 155                 160

Val Phe Ile Gly Val Lys Asp Asn His Leu Ala Leu Ile Lys Val Asp
                165                 170                 175

Ser Ser Glu Asn Leu Ser Thr Glu Asn Ile Leu Phe Lys Leu Ser Glu
                180                 185                 190

Thr

<210> SEQ ID NO 649
<211> LENGTH: 193
<212> TYPE: PRT
<213> ORGANISM: Artificial Sequence
<220> FEATURE:
<223> OTHER INFORMATION: Cyno HisAvi_IL-33

<400> SEQUENCE: 649

Met His His His His His His His His Ala Ala Gly Leu Asn
 1               5                  10                  15

Asp Ile Phe Glu Ala Gln Lys Ile Glu Trp His Glu Ala Ile Glu
                 20                  25                  30

Gly Arg Ser Ile Thr Gly Ile Ser Pro Ile Thr Glu Tyr Leu Ala Ser
            35                  40                  45

Leu Ser Thr Tyr Asn Asp Gln Ser Ile Thr Phe Ala Leu Glu Asp Glu
 50                  55                  60

Ser Tyr Glu Ile Tyr Val Glu Asp Leu Lys Lys Asp Lys Lys Lys Asp
 65                  70                  75                  80

Lys Val Leu Leu Ser Tyr Tyr Glu Ser Gln His Pro Ser Ser Glu Ser
                     85                  90                  95

Gly Asp Gly Val Asp Gly Lys Met Leu Met Val Thr Leu Ser Pro Thr
            100                 105                 110

Lys Asp Phe Trp Leu Gln Ala Asn Asn Lys Glu His Ser Val Glu Leu
                115                 120                 125

His Lys Cys Glu Lys Pro Leu Pro Asp Gln Ala Phe Phe Val Leu His
    130                 135                 140

Asn Arg Ser Phe Asn Cys Val Ser Phe Glu Cys Lys Thr Asp Pro Gly
145                 150                 155                 160

Val Phe Ile Gly Val Lys Asp Asn His Leu Ala Leu Ile Lys Val Asp
                165                 170                 175

Tyr Ser Glu Asn Leu Gly Ser Glu Asn Ile Leu Phe Lys Leu Ser Glu
                180                 185                 190

Ile

<210> SEQ ID NO 650
<211> LENGTH: 360
```

<212> TYPE: PRT
<213> ORGANISM: Artificial Sequence
<220> FEATURE:
<223> OTHER INFORMATION: Human ST2 ECD-Flag-his10

<400> SEQUENCE: 650

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ile Asp His His Ser Asp Pro Ala Phe Leu Tyr Lys Val
                325                 330                 335

Val Gly Ala Ala Asp Tyr Lys Asp Asp Asp Lys Ala Ala His His
            340                 345                 350

His His His His His His
        355                 360
```

<210> SEQ ID NO 651
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Cys Glu Lys
1

<210> SEQ ID NO 652
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Val Asp Ser Ser Glu Asn Ile Cys Thr Glu Asn Ile Leu Phe Lys
1               5                   10                  15

<210> SEQ ID NO 653
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Pro Leu Pro Asp Gln Ala Phe Phe Val Leu His Asn Met His Ser Asn
1               5                   10                  15

Cys Val Ser Phe Glu Cys Lys
            20

<210> SEQ ID NO 654
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Glu His Ser Val Glu Leu His Lys Cys Glu Lys
1               5                   10

<210> SEQ ID NO 655
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Val Asp Ser Ser Glu Asn Ile Cys Thr Glu Asn Ile Leu Phe Lys
1               5                   10                  15

<210> SEQ ID NO 656
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 656

Cys Glu Lys Pro Leu Pro Asp Gln Ala Phe Phe Val Leu His Asn Met
1               5                   10                  15

His Ser Asn Cys Val Ser Phe Glu Cys Lys
            20                  25

<210> SEQ ID NO 657
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Val Asp Ser Ser Glu Asn Ile Cys Thr Glu Asn Ile Leu Phe Lys
1               5                   10                  15

<210> SEQ ID NO 658
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 658

Glu His Ser Val Glu Leu His Lys Cys Glu Lys Pro Leu Pro Asp Gln
1               5                   10                  15

Ala Phe Phe Val Leu His Asn Met His Ser Asn Cys Val Ser Phe Glu
            20                  25                  30

Cys Lys

<210> SEQ ID NO 659
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Val Asp Ser Ser Glu Asn Ile Cys Thr Glu Asn Ile Leu Phe Lys
1               5                   10                  15

<210> SEQ ID NO 660
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Glu His Ser Val Glu Leu His Lys Cys Glu Lys
1               5                   10

<210> SEQ ID NO 661
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661
```

```
Val Asp Ser Ser Glu Asn Ile Cys Thr Glu Asn Ile Leu Phe Lys
1               5                   10                  15

<210> SEQ ID NO 662
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Pro Leu Pro Asp Gln Ala Phe Phe Val Leu His Asn Met His Ser Asn
1               5                   10                  15

Cys Val Ser Phe Glu Cys Lys
            20

<210> SEQ ID NO 663
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Cys Glu Lys Pro Leu Pro Asp Gln Ala Phe Phe Val Leu His Asn Met
1               5                   10                  15

His Ser Asn Cys Val Ser Phe Glu Cys Lys
            20                  25

<210> SEQ ID NO 664
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 664

Glu His Ser Val Glu Leu His Lys Cys Glu Lys Pro Leu Pro Asp Gln
1               5                   10                  15

Ala Phe Phe Val Leu His Asn Met His Ser Asn Cys Val Ser Phe Glu
            20                  25                  30

Cys Lys
```

IL33 FORM, MUTATED FORMS OF IL33, ANTIBODIES, ASSAYS AND METHODS OF USING THE SAME

CROSS-REFERENCE TO RELATED APPLICATIONS

This application is a U.S. National Stage application of International Application No. PCT/EP2016/056973, filed on Mar. 30, 2016, said International Application No. PCT/EP2016/056973 claims benefit under 35 U.S.C. § 119(e) of the U.S. Provisional Application No. 62/140,913, filed Mar. 31, 2015. Each of the above listed applications is incorporated by reference herein in its entirety for all purposes.

REFERENCE TO THE SEQUENCE LISTING

The application incorporates by reference a Sequence Listing submitted with this application as text file entitled IL33-105-US-PCT_SL.txt, created on Oct. 29, 2019, and having a size of 364,949 bytes.

The present disclosure relates to novel forms of IL-33; novel mutants of IL-33; binding proteins, such as antibodies specific to any one of said proteins, in particular binding proteins able to modulate the amount of said form present; compositions comprising a protein or a binding protein, such as an antibody according to the present disclosure; and use of any one of the same, particularly in therapy, for example in the treatment of prevention of inflammatory disease. The disclosure herein also extends to assays for identifying and/or quantifying the different forms of IL-33.

BACKGROUND OF THE INVENTION

Interleukin-33 (IL-33), also called IL-1F11, is a member of the IL-1 family of cytokines that stimulates the generation of cells, cytokines, and immunoglobulins characteristic of a type two immune response. IL-33 is a 270 amino acid protein, consisting of two domains: a homeodomain and a cytokine (IL-1-like) domain. The homeodomain contains a nuclear localization signal (NLS). IL-33 mediates signal transduction through ST2, a receptor expressed on Th2 cells, mast cells and a wide variety of other cell types.

Schmitz et al. first identified IL-33 as the ligand for the orphan receptor ST2 (also called IL-1R4) (Schmitz et al., *Immunity* 23(5)479-90 (2005)). IL-33 receptor is formed from heterodimeric molecules. ST2 and IL-1R accessory protein (IL-1RAcP) dimerize to form an IL-33 receptor (ST2:IL-1RAcP). IL-1RAcP is a shared component of receptors for IL-1α, IL-1β, IL-1F6, IL1F8, and IL1F9. IL-1RAcP is not required for binding, but is critical for signaling. The TIR-domain of the IL-33 receptor recruits MyD88 and TRAF6, and the receptor signal results in activation of NFκB and MAP Kinase pathways (Oboki et al., *Allergology International* 59:143-160 (2010)). IL-33 receptor may potentially associate with other receptors and has been reported to interact with c-kit on mast cells (Drube et al., *Blood* 115:3899-3906 (2010))

Recently, IL-33 has been shown to bind a second IL-33 receptor heterodimeric complex: ST2 also forms a complex with another IL-1R family molecule, "single Ig IL-1R-related molecule" (SIGIRR) (also called Toll IL-1R8 (TIR8)) to form ST2:SIGIRR. SIGIRR/TIR8 is considered to act as a negative regulator of IL-1R and Toll-like receptor (TLR)-mediated immune responses (Garlanda et al., *Trends Immunol.* 30:439-46 (2009)). In contrast to ST2:IL-1RAcP, ST2:SIGIRR seems to act as a negative regulator of IL-33 (Oboki et al. (2010)).

The only known ligand of the ST2 receptor is IL-33 (see, e.g., Schmitz et al., *Immunity* 23(5)479-90 (2005); Chackerian et al., *J. Immunol.* 179(4):2551-5 (2007)). The ST2 receptor is expressed at baseline by Th2 cells and mast cells, both cell types are known to be important mediators of allergic asthma. The extracellular form of IL-33 stimulates target cells by binding to ST2 and subsequently activates NFκB and MAP Kinase pathways, leading to a range of functional responses including production of cytokines and chemokines. Soluble ST2 (sST2) is thought to be a decoy receptor, preventing IL-33 signaling.

In humans, IL-33 was found to be expressed constitutively in smooth muscle and in bronchial epithelia. Expression can be induced by IL-1β and TNF-α in lung and dermal fibroblasts (Schmitz et al. (2005)). The levels of soluble ST2 protein and IL-33 mRNA/protein are increased in sera and tissues from patients with asthma (Oboki et al., *Allergology International* 59:143-160 (2010)).

In vivo, IL-33 induces the expression of IL-4, IL-5, and IL-13 and leads to severe pathological changes in mucosal organs. Administration of IL-33 to mice has potent inflammatory effects, including massive blood eosinophilia, increased IL-5 and IgE serum levels, and goblet cell hyperplasia at mucosal surfaces (Schmitz et al. (2005)). Intraperitoneal or intranasal administration of IL-33 to mice led to induction of eosinophilic inflammation in the pulmonary and intestinal mucosa through the IL-13 and STAT6-dependent pathways (Oboki et al. (2010)). Accordingly, IL-33 may play a role in allergic diseases such as asthma and other inflammatory airway diseases.

Some reports in the literature suggest that goblet cells secrete CXCL8/IL-8, and this is increased by IL-33 through ST2R-ERK pathway, suggesting a mechanism for enhanced airway inflammation in the asthmatic airway with goblet cell metaplasia (Clin Exp Allergy. 2014 April; 44(4):540-52)

Therefore there has been interest in IL-33 as a therapeutic target. However, to date the therapeutic benefits of blocking this therapeutic target have yet to be fully realised. The present inventors have established for the first time that IL-33 exists in a reduced form (also referred to herein as redIL-33) and an oxidized form. The inventors have characterized the oxidized form of IL-33 for the first time as described herein. In vitro and in vivo studies by the inventors have shown that disappearance of redIL-33 (the reduced form) correlated with the appearance of oxidised IL-33. In physiological fluids in vitro, redIL-33 is rapidly oxidised to form a disulphide bonded form. The oxidized form (also referred to herein as IL-33-DSB) has at least one (e.g. two) disulfide bonds, in between the cysteines selected from the group Cys208, Cys 227, Cys 232 and Cys259, (numbered with reference to full length human IL-33 as disclosed in UniProt O97560, residues 112 to 270 of which are recited within SEQ ID NO. 632). It has previously been unappreciated that the commercially available assays seem to predominantly detect this oxidized form. The present inventors therefore needed to devise assays to selectively detect the redIL-33 that is responsible for interacting with ST2 and driving biological activity associated with IL-33 release.

The reduced form appears to be the active form of the protein which generates the signal cascade and in fact in vivo it appears that the reduced form is converted into the oxidized form as a mechanism for terminating the signaling through ST2. The present inventors have found that redIL-33 binds ST2 (FIG. 24A). In contrast, IL-33-DSB showed no ST2 binding (FIG. 24B). This has lead the inventors to hypothesize that in vivo oxidation could be a mechanism to turn off IL-33-ST2 activity. In addition, the present inventors have established for the first time that the oxidized form of IL-33 (IL-33-DSB) binds to receptor for advanced glycation end products (RAGE) and signals through this alternative pathway (FIG. 56).

The present inventors believe that this understanding may be utilized to generate more effective therapeutic agents. In one embodiment, the present inventors have identified an antibody that preferentially binds the oxidized form but surprisingly attenuates the activity of the reduced form by essentially catalyzing the conversion of the reduced form to the oxidized form. Advantageously this mechanism simply augments the in vivo mechanism for terminating the signaling through ST2.

In another embodiment, the inventors have identified an antibody that preferentially binds the reduced form of IL-33 (redIL-33), with femtomolar affinity, and attenuates and/or inhibits IL-33 mediated signaling through ST2. This antibody provides for the first time a mechanism for treating or preventing IL-33/ST2 mediated inflammatory responses.

In a yet further embodiment, the antibodies of the present invention can attenuate or inhibit the previously unrecognized signaling pathway for IL-33-DSB through RAGE, and any IL-33/RAGE mediated effects. The antibodies of the present invention may act by directly binding of IL-33-DSB and attenuating or inhibiting the ligand/receptor interaction with RAGE or alternatively may bind to redIL-33 and prevent or reduce its conversion to the IL-33-DSB thereby indirectly attenuating or inhibiting the ligand/receptor interaction with RAGE.

BRIEF SUMMARY OF THE INVENTION

Thus in a first aspect there is provided isolated IL-33 in a reduced from (redIL-33) or a binding fragment thereof.

In one aspect there is provided an isolated IL-33 protein stabilized in a reduced form by a modification that prevents the formation of disulphide bridges between the native cysteines. Such modifications may comprise deletion of one or more cysteine residues, mutations which replace one or more native cysteines with an alternative amino acid and/or conjugation to a chemical entity.

In one embodiment there is provided a mutated form of IL-33 as described herein, in particular as shown in SEQ ID NO: 634 to 648.

In one embodiment the chemical entity is biotin, which reduces or eliminates the ability of redIL-33 to be converted to IL-33-DSB.

In one aspect there is provided a mutant IL-33 wherein one or more cysteines are replaced with a non-cysteine amino acid, for example wherein one, two, three, four or more cysteines selected from Cys-208, Cys-227, Cys-232 and Cys-259 are replaced, for example with an amino acid such as serine. In one embodiment the cysteine residue is independently selected from Cys-208, Cys-227, Cys-232 and Cys-259. Thus in one embodiment a mutant according to the present disclosure is unable to form one or both of the disulfide bonds in the IL-33-DSB.

In one embodiment the present disclosure is directed to an isolated binding molecule which attenuates the activity of redIL-33, including a stabilized form thereof according to the present disclosure, for example inhibits said activity. In one embodiment the attenuation is through specifically binding redIL-33. In one embodiment the attenuation is through binding IL-33-DSB and, for example catalyzing or accelerating the conversion of redIL-33 to IL-33-DSB.

In one embodiment the attenuation down-regulates or turns off ST2-dependent signaling.

In certain embodiments, the binding molecule or the antibody or antigen-binding fragment thereof of the present disclosure inhibits IL-33 driven cytokine production, for example in mast cells.

In one embodiment the attenuation down-regulates or prevents IL-5 release from the ST2 pathway.

In one embodiment the attenuation down-regulates or prevents eosinophil activation.

In one embodiment the attenuation down-regulates or prevents NFκB release. In one embodiment the attenuation down-regulates or prevents IL-4 release. In one embodiment the attenuation down-regulates or prevents IL-6 release. In one embodiment the attenuation down-regulates or prevents IL-8 release. In one embodiment the attenuation down-regulates or prevents IL-13 release.

In certain embodiments, the binding molecule or the antibody or antigen-binding fragment thereof of the present disclosure attenuates or inhibits IL-33/RAGE mediated signaling. Attenuation or inhibition of RAGE-mediated signaling can enhance epithelial migration relative to that seen in an unmodulated IL-33 driven inflammatory response (see FIG. 58). Such enhanced epithelial migration may play a role in tissue repair and wound healing, particularly in lung tissue, such as lung epithelium.

In one embodiment, the present disclosure is directed to an isolated binding molecule which specifically binds to redIL-33 or a binding fragment of redIL-33.

In one embodiment, the present disclosure is directed to an isolated binding molecule which specifically binds to redIL-33 and inhibits binding of the same to ST2.

In one embodiment, the present disclosure is directed to an isolated binding molecule which specifically binds to redIL-33 and inhibits signaling of redIL-33 by physically blocking the interaction of IL-33 with its receptor.

In one embodiment the present disclosure is directed to a molecule which s binds IL-33 and catalyses the conversion of redIL-33 to IL-33-DSB thereby down-regulating or turning off ST-2 signaling.

In one embodiment the present disclosure is directed to a binding molecule with an competitive mode of action.

In one embodiment the present disclosure is directed to a binding molecule with an allosteric mode of action.

In some embodiments, the binding molecule of the invention comprises an antibody or antigen-binding fragment thereof.

The following formula employs the single letter amino acid code.

In one embodiment the binding molecule, such as an antibody or binding fragment thereof comprises a CDRH1 of formula (I):

$$SYAMX \qquad (I)$$

wherein X is an amino acid, for example S or N, such as S.

In one embodiment the binding molecule, such as an antibody or binding fragment thereof comprises a CDRH2 of formula (II):

$$X_1IX_2X_3X_4X_5X_6X_7X_8X_9X_{10}X_{11}YADX_{12}VKG \qquad (II)$$

wherein:

$X_1$ is A, G or S in particular A or G, such as A;

$X_2$ is A, D, G, N, S in particular A, D or S, such as S;

$X_3$ is A, D or G in particular A or G, such as G $X_4$ is absent or D in particular absent;

$X_5$ is absent or G in particular absent;
$X_6$ is D, I or S in particular I or S, such as S;
$X_7$ is D, F, G or S in particular D or G, such as G;
$X_8$ is D, G, Q, S, T in particular G, Q or T, such as G;
$X_9$ is R or S in particular S;
$X_{10}$ is P or T in particular P;
$X_{11}$ is H or Y in particular Y; and
X12 is P or S in particular S.

In one embodiment the binding molecule, such as an antibody or binding fragment thereof comprises a CDRH3 of formula (III):

$$X_{13}X_{14}X_{15}X_{16}X_{17}X_{18}X_{19}X_{20}X_{21}GGLRYPX_{22} \quad \text{(III)}$$

wherein:
$X_{13}$ is A, D, H, L or Q in particular D or Q, such as D;
$X_{14}$ is K or L in particular K;
$X_{15}$ is F or W in particular F;
$X_{16}$ is I or M in particular M;
$X_{17}$ is Q or E in particular Q;
$X_{18}$ is L or N in particular L;
$X_{19}$ is W or Y in particular W;
$X_{20}$ is A, G or V in particular G; and
$X_{21}$ is F or L in particular F.

In one embodiment the binding molecule, such as an antibody or binding fragment thereof comprises a CDRH1 of formula (I) and a CDRH2 of formula (II), as defined above.

In one embodiment the binding molecule, such as an antibody or binding fragment thereof comprises a CDRH1 of formula (I) and a CDRH3 of formula (III), as defined above.

In one embodiment the binding molecule, such as an antibody or binding fragment thereof comprises a CDRH2 of formula (II) and a CDRH3 of formula (III), as defined above.

In one embodiment the binding molecule, such as an antibody or binding fragment thereof comprises a CDRH1 of formula (I) and a CDRH2 of formula (II), and a CDRH3 of formula (III) as defined above.

In one embodiment the binding molecule, such as an antibody or binding fragment thereof comprises a CDRL1 of formula (IV):

$$SGEX_{22}X_{23}GDKYAA \quad \text{(IV)}$$

wherein:
$X_{22}$ is an amino acid, for example R or G, in particular R; and
$X_{23}$ is an amino acid, for example M or I, in particular M.

In one embodiment the binding molecule, such as an antibody or binding fragment thereof comprises a CDRL2 of formula (V):

$$X_{24}DTKRPS \quad \text{(V)}$$

wherein:
$X_{24}$ is an amino acid, for example Q or R, in particular R.

In one embodiment the binding molecule, such as an antibody or binding fragment thereof comprises a CDRL3 of formula (VI):

$$X_{25}VX_{26}X_{27}X_{28}X_{29}X_{30}X_{31}X_{32}X_{33} \quad \text{(VI)}$$

wherein:
$X_{25}$ is E, G or Q in particular G or Q, such as G;
$X_{26}$ is I, K, L or W in particular L or W, such as W;
$X_{27}$ is A, D, K, Q, R or V in particular D or K, such as K;
$X_{28}$ is A, D, K, Q or S in particular Q or S, such as S;
$X_{29}$ is D, N or S in particular D or S, such as D;
$X_{30}$ is D, S or T in particular D or S, such as D;
$X_{31}$ is absent or T in particular absent;
$X_{32}$ is G or P in particular G; and
$X_{33}$ is I or V in particular V.

In one embodiment the binding molecule, such as an antibody or binding fragment thereof comprises a CDRL1 of formula (IV) and a CDRL2 of formula (V), as defined above.

In one embodiment the binding molecule, such as an antibody or binding fragment thereof comprises a CDRL1 of formula (IV) and a CDRL3 of formula (VI), as defined above.

In one embodiment the binding molecule, such as an antibody or binding fragment thereof comprises a CDRL2 of formula (V) and a CDRL3 of formula (VI), as defined above.

In one embodiment the binding molecule, such as an antibody or binding fragment thereof comprises a CDRL1 of formula (IV) and a CDRL2 of formula (V), and a CDRL3 of formula (VI) as defined above.

In one embodiment the binding molecule, such as an antibody or binding fragment thereof comprises CDRH1 of formula (I) and CDRL1 of formula (IV).

In one embodiment the binding molecule, such as an antibody or binding fragment thereof comprises CDRH1 of formula (I) and CDRL2 of formula (V).

In one embodiment the binding molecule, such as an antibody or binding fragment thereof comprises CDRH1 of formula (I) and CDRL3 of formula (VI).

In one embodiment the binding molecule, such as an antibody or binding fragment thereof comprises CDRH2 of formula (II) and CDRL1 of formula (IV).

In one embodiment the binding molecule, such as an antibody or binding fragment thereof comprises CDRH2 of formula (II) and CDRL2 of formula (V).

In one embodiment the binding molecule, such as an antibody or binding fragment thereof comprises CDRH2 of formula (II) and CDRL3 of formula (VI).

In one embodiment the binding molecule, such as an antibody or binding fragment thereof comprises CDRH3 of formula (III) and CDRL1 of formula (IV).

In one embodiment the binding molecule, such as an antibody or binding fragment thereof comprises CDRH3 of formula (III) and CDRL2 of formula (V).

In one embodiment the binding molecule, such as an antibody or binding fragment thereof comprises CDRH3 of formula (III) and CDRL3 of formula (VI).

In one embodiment the binding molecule, such as an antibody or binding fragment thereof comprises CDRH1 of formula (I), CDRH2 of formula (II) and CDRL1 of formula (IV).

In one embodiment the binding molecule, such as an antibody or binding fragment thereof comprises CDRH1 of formula (I), CDRH2 of formula (II) and CDRL2 of formula (V).

In one embodiment the binding molecule, such as an antibody or binding fragment thereof comprises CDRH1 of formula (I), CDRH2 of formula (II) and CDRL3 of formula (VI).

In one embodiment the binding molecule, such as an antibody or binding fragment thereof comprises CDRH1 of formula (I), CDRH3 of formula (III) and CDRL1 of formula (IV).

In one embodiment the binding molecule, such as an antibody or binding fragment thereof comprises CDRH1 of formula (I), CDRH3 of formula (III) and CDRL2 of formula (V).

In one embodiment the binding molecule, such as an antibody or binding fragment thereof comprises CDRH1 of formula (I), CDRH3 of formula (II) and CDRL3 of formula (VI).

In one embodiment the binding molecule, such as an antibody or binding fragment thereof comprises CDRH2 of formula (II), CDRH3 of formula (III) and CDRL1 of formula (IV).

In one embodiment the binding molecule, such as an antibody or binding fragment thereof comprises CDRH2 of formula (II), CDRH3 of formula (III) and CDRL2 of formula (V).

In one embodiment the binding molecule, such as an antibody or binding fragment thereof comprises CDRH2 of formula (II), CDRH3 of formula (II) and CDRL3 of formula (VI).

In one embodiment the binding molecule, such as an antibody or binding fragment thereof comprises CDRH1 of formula (I), CDRH2 of formula (II), CDRH3 of formula (III) and CDRL1 of formula (IV).

In one embodiment the binding molecule, such as an antibody or binding fragment thereof comprises CDRH1 of formula (I), CDRH2 of formula (II), CDRH3 of formula (III) and CDRL2 of formula (V).

In one embodiment the binding molecule, such as an antibody or binding fragment thereof comprises CDRH1 of formula (I), CDRH2 of formula (II), CDRH3 of formula (II) and CDRL3 of formula (VI).

In one embodiment the binding molecule, such as an antibody or binding fragment thereof comprises CDRH1 of formula (I), CDRH2 of formula (II), CDRH3 of formula (III), CDRL1 of formula (IV) and CDRL2 of formula (V).

In one embodiment the binding molecule, such as an antibody or binding fragment thereof comprises CDRH1 of formula (I), CDRH2 of formula (II), CDRH3 of formula (III), CDRL1 of formula (IV) and CDRL3 of formula (VI).

In one embodiment the binding molecule, such as an antibody or binding fragment thereof comprises CDRH1 of formula (I), CDRH2 of formula (II), CDRH3 of formula (II), CDRL2 of formula (V) and CDRL3 of formula (VI).

In one embodiment the binding molecule, such as an antibody or binding fragment thereof comprises CDRH1 of formula (I), CDRH2 of formula (II), CDRH3 of formula (II), CDRL1 of formula (IV), CDRL2 of formula (V) and CDRL3 of formula (VI).

In one embodiment the binding molecule of the disclosure comprises 3 CDRs, for example in a heavy chain variable region independently selected from SEQ ID NO: 3, 4, 5, 13, 14, 15, 23, 24, 25, 33, 34, 35, 43, 44, 45, 53, 54, 55, 63, 64, 65, 73, 74, 75, 83, 84, 85, 93, 94, 95, 103, 104, 105, 113, 114, 115, 153, 154, 155, 163, 164, 165, 173, 174, 175, 183, 184, 185, 193, 194, 195, 203, 204, 205, 213, 214, 215, 223, 224, 225, 233, 234, 235, 243, 244, 245, 253, 254, 255, 263, 264, 265, 273, 274, 275, 283, 284, 285, 293, 294, 295, 303, 304, 305, 313, 314, 315, 353, 354, 355, 363, 364, 365, 373, 374, 375, 383, 384, 385, 393, 394, 395, 403, 404, 405, 413, 414, 415, 453, 454, 455, 463, 464, 465, 473, 474, 475, 483, 484, 485, 493, 494, 495, 503, 504, 505, 513, 514, 515, 553, 554, 555, 563, 564, 565, 573, 574, 575, 583, 584 and 585.

In one embodiment the binding molecule of the disclosure comprises 3 CDRs, for example in a light chain variable region independently selected from SEQ ID NO: 8, 9, 10, 18, 19, 20, 28, 29, 30, 38, 39, 40, 48, 49, 50, 58, 59, 60, 68, 69, 70, 78, 79, 80, 88, 89, 90, 98, 99, 100, 108, 109, 118, 119, 120, 158, 159, 160, 168, 169, 170, 178, 179, 180, 188, 189, 190, 198, 199, 200, 208, 209, 210, 218, 219, 220, 228, 229, 230, 238, 239, 240, 248, 249, 250, 258, 259, 260, 268, 269, 270, 278, 279, 280, 288, 289, 290, 298, 299, 300 308, 309, 310, 318, 319, 320, 328, 329, 330, 338, 339, 340, 348, 349, 350, 358, 359, 360, 368, 369 370 378, 379, 380, 388, 389, 390, 398, 399, 400, 408, 409, 410, 418, 419, 420, 428, 429, 430, 438, 439, 440, 448, 449, 450, 458, 459, 460, 468, 469, 470, 478, 479, 480, 488, 489, 490, 498, 499, 500 508, 509, 510, 518, 519, 520, 528, 529, 530, 538, 539, 540, 548, 549, 550, 558, 559, 560, 568, 569, 570, 578, 579, 580, 588, 589, and 590.

In one embodiment the binding molecule of the disclosure comprises 3 CDRs, for example in a heavy chain variable region independently selected from SEQ ID NO: 3, 4, 5, 13, 14, 15, 23, 24, 25, 33, 34, 35, 43, 44, 45, 53, 54, 55, 63, 64, 65, 73, 74, 75, 83, 84, 85, 93, 94, 95, 103, 104, 105, 113, 114, 115, 153, 154, 155, 163, 164, 165, 173, 174, 175, 183, 184, 185, 193, 194, 195, 203, 204, 205, 213, 214, 215, 223, 224, 225, 233, 234, 235, 243, 244, 245, 253, 254, 255, 263, 264, 265, 273, 274, 275, 283, 284, 285, 293, 294, 295, 303, 304, 305, 313, 314, 315, 353, 354, 355, 363, 364, 365, 373, 374, 375, 383, 384, 385, 393, 394, 395, 403, 404, 405, 413, 414, 415, 453, 454, 455, 463, 464, 465, 473, 474, 475, 483, 484, 485, 493, 494, 495, 503, 504, 505, 513, 514, 515, 553, 554, 555, 563, 564, 565, 573, 574, 575, 583, 584 and 585, and 3 CDRs, for example in a light chain variable region independently selected from SEQ ID NO: 8, 9, 10, 18, 19, 20, 28, 29, 30, 38, 39, 40, 48, 49, 50, 58, 59, 60, 68, 69, 70, 78, 79, 80, 88, 89, 90, 98, 99, 100, 108, 109, 118, 119, 120, 158, 159, 160, 168, 169, 170, 178, 179, 180, 188, 189, 190, 198, 199, 200, 208, 209, 210, 218, 219, 220, 228, 229, 230, 238, 239, 240, 248, 249, 250, 258, 259, 260, 268, 269, 270, 278, 279, 280, 288, 289, 290, 298, 299, 300 308, 309, 310, 318, 319, 320, 328, 329, 330, 338, 339, 340, 348, 349, 350, 358, 359, 360, 368, 369 370 378, 379, 380, 388, 389, 390, 398, 399, 400, 408, 409, 410, 418, 419, 420, 428, 429, 430, 438, 439, 440, 448, 449, 450, 458, 459, 460, 468, 469, 470, 478, 479, 480, 488, 489, 490, 498, 499, 500 508, 509, 510, 518, 519, 520, 528, 529, 530, 538, 539, 540, 548, 549, 550, 558, 559, 560, 568, 569, 570, 578, 579, 580, 588, 589, and 590.

In one embodiment the binding molecule of the disclosure comprises at least one CDR selected from SEQ ID NO: 3, 4 and 5, for example SEQ ID NO: 3 and 4, SEQ ID NO: 3 and 5, or SEQ ID NO: 4 and 5, such as a heavy variable region comprising SEQ ID NO: 3 for CDRH1, SEQ ID NO: 4 for CDRH2 and SEQ ID NO: 5 for CDRH3.

In one embodiment the binding molecule of the disclosure comprises at least one CDR selected from SEQ ID NO: 13, 14 and 15, for example SEQ ID NO: 13 and 14, SEQ ID NO: 13 and 15, or SEQ ID NO: 14 and 15, such as a heavy variable region comprising SEQ ID NO: 13 for CDRH1, SEQ ID NO: 14 for CDRH2 and SEQ ID NO: 15 for CDRH3.

In one embodiment the binding molecule of the disclosure comprises at least one CDR selected from SEQ ID NO: 23, 24 and 25, for example SEQ ID NO: 23 and 24, SEQ ID NO: 23 and 25, or SEQ ID NO: 24 and 25, such as a heavy variable region comprising SEQ ID NO: 23 for CDRH1, SEQ ID NO: 24 for CDRH2 and SEQ ID NO: 25 for CDRH3.

In one embodiment the binding molecule of the disclosure comprises at least one CDR selected from SEQ ID NO: 33, 34 and 35, for example SEQ ID NO: 33 and 34, SEQ ID NO: 33 and 35, or SEQ ID NO: 34 and 35, such as a heavy variable region comprising SEQ ID NO: 33 for CDRH1, SEQ ID NO: 34 for CDRH2 and SEQ ID NO: 35 for CDRH3.

In one embodiment the binding molecule of the disclosure comprises at least one CDR selected from SEQ ID NO: 43, 44 and 45, for example SEQ ID NO: 43 and 44, SEQ ID NO: 43 and 45, or SEQ ID NO: 44 and 45, such as a heavy variable region comprising SEQ ID NO: 43 for CDRH1, SEQ ID NO: 44 for CDRH2 and SEQ ID NO: 45 for CDRH3.

In one embodiment the binding molecule of the disclosure comprises at least one CDR selected from SEQ ID NO: 53, 54 and 55, for example SEQ ID NO: 53 and 54, SEQ ID NO: 53 and 55, or SEQ ID NO: 54 and 55, such as a heavy variable region comprising SEQ ID NO: 53 for CDRH1, SEQ ID NO: 54 for CDRH2 and SEQ ID NO: 55 for CDRH3.

In one embodiment the binding molecule of the disclosure comprises at least one CDR selected from SEQ ID NO: 63, 64 and 65, for example SEQ ID NO: 63 and 64, SEQ ID NO: 63 and 65, or SEQ ID NO: 64 and 65, such as a heavy variable region comprising SEQ ID NO: 63 for CDRH1, SEQ ID NO: 64 for CDRH2 and SEQ ID NO: 65 for CDRH3.

In one embodiment the binding molecule of the disclosure comprises at least one CDR selected from SEQ ID NO: 73, 74 and 75, for example SEQ ID NO: 73 and 74, SEQ ID NO: 73 and 75, or SEQ ID NO: 74 and 75, such as a heavy variable region comprising SEQ ID NO: 73 for CDRH1, SEQ ID NO: 74 for CDRH2 and SEQ ID NO: 75 for CDRH3.

In one embodiment the binding molecule of the disclosure comprises at least one CDR selected from SEQ ID NO: 83, 84 and 85, for example SEQ ID NO: 83 and 84, SEQ ID NO: 83 and 85, or SEQ ID NO: 84 and 85, such as a heavy variable region comprising SEQ ID NO: 83 for CDRH1, SEQ ID NO: 84 for CDRH2 and SEQ ID NO: 85 for CDRH3.

In one embodiment the binding molecule of the disclosure comprises at least one CDR selected from SEQ ID NO: 93, 94 and 95, for example SEQ ID NO: 93 and 94, SEQ ID NO: 93 and 95, or SEQ ID NO: 94 and 95, such as a heavy variable region comprising SEQ ID NO: 93 for CDRH1, SEQ ID NO: 94 for CDRH2 and SEQ ID NO: 95 for CDRH3.

In one embodiment the binding molecule of the disclosure comprises at least one CDR selected from SEQ ID NO: 103, 104 and 105, for example SEQ ID NO: 103 and 104, SEQ ID NO: 103 and 105, or SEQ ID NO: 104 and 105, such as a heavy variable region comprising SEQ ID NO: 103 for CDRH1, SEQ ID NO: 104 for CDRH2 and SEQ ID NO: 105 for CDRH3.

In one embodiment the binding molecule of the disclosure comprises at least one CDR selected from SEQ ID NO: 113, 114 and 115, for example SEQ ID NO: 113 and 114, SEQ ID NO: 113 and 115, or SEQ ID NO: 114 and 115, such as a heavy variable region comprising SEQ ID NO: 113 for CDRH1, SEQ ID NO: 114 for CDRH2 and SEQ ID NO: 115 for CDRH3.

In one embodiment the binding molecule of the disclosure comprises at least one CDR selected from SEQ ID NO: 123, 124 and 125, for example SEQ ID NO: 123 and 124, SEQ ID NO: 123 and 125, or SEQ ID NO: 124 and 25, such as a heavy variable region comprising SEQ ID NO: 123 for CDRH1, SEQ ID NO: 124 for CDRH2 and SEQ ID NO: 125 for CDRH3.

In one embodiment the binding molecule of the disclosure comprises at least one CDR selected from SEQ ID NO: 133, 134 and 135, for example SEQ ID NO: 133 and 134, SEQ ID NO: 133 and 135, or SEQ ID NO: 134 and 135, such as a heavy variable region comprising SEQ ID NO: 133 for CDRH1, SEQ ID NO: 134 for CDRH2 and SEQ ID NO: 135 for CDRH3.

In one embodiment the binding molecule of the disclosure comprises at least one CDR selected from SEQ ID NO: 143, 144 and 145, for example SEQ ID NO: 143 and 144, SEQ ID NO: 143 and 145, or SEQ ID NO: 144 and 145, such as a heavy variable region comprising SEQ ID NO: 143 for CDRH1, SEQ ID NO: 144 for CDRH2 and SEQ ID NO: 145 for CDRH3.

In one embodiment the binding molecule of the disclosure comprises at least one CDR selected from SEQ ID NO: 153, 154 and 155, for example SEQ ID NO: 153 and 154, SEQ ID NO: 153 and 155, or SEQ ID NO: 154 and 155, such as a heavy variable region comprising SEQ ID NO: 153 for CDRH1, SEQ ID NO: 154 for CDRH2 and SEQ ID NO: 155 for CDRH3.

In one embodiment the binding molecule of the disclosure comprises at least one CDR selected from SEQ ID NO: 163, 164 and 165, for example SEQ ID NO: 163 and 164, SEQ ID NO: 163 and 165, or SEQ ID NO: 164 and 165, such as a heavy variable region comprising SEQ ID NO: 163 for CDRH1, SEQ ID NO: 164 for CDRH2 and SEQ ID NO: 165 for CDRH3.

In one embodiment the binding molecule of the disclosure comprises at least one CDR selected from SEQ ID NO: 173, 174 and 175, for example SEQ ID NO: 173 and 174, SEQ ID NO: 173 and 175, or SEQ ID NO: 174 and 175, such as a heavy variable region comprising SEQ ID NO: 173 for CDRH1, SEQ ID NO: 174 for CDRH2 and SEQ ID NO: 175 for CDRH3.

In one embodiment the binding molecule of the disclosure comprises at least one CDR selected from SEQ ID NO: 183, 184 and 185, for example SEQ ID NO: 183 and 184, SEQ ID NO: 183 and 185, or SEQ ID NO: 184 and 185, such as a heavy variable region comprising SEQ ID NO: 183 for CDRH1, SEQ ID NO: 184 for CDRH2 and SEQ ID NO: 185 for CDRH3

In one embodiment the binding molecule of the disclosure comprises at least one CDR selected from SEQ ID NO: 193, 194 and 195, for example SEQ ID NO: 193 and 194, SEQ ID NO: 193 and 95, or SEQ ID NO: 194 and 195, such as a heavy variable region comprising SEQ ID NO: 193 for CDRH1, SEQ ID NO: 194 for CDRH2 and SEQ ID NO: 195 for CDRH3.

In one embodiment the binding molecule of the disclosure comprises at least one CDR selected from SEQ ID NO: 203, 204 and 205, for example SEQ ID NO: 203 and 204, SEQ ID NO: 203 and 205, or SEQ ID NO: 204 and 205, such as a heavy variable region comprising SEQ ID NO: 203 for CDRH1, SEQ ID NO: 204 for CDRH2 and SEQ ID NO: 205 for CDRH3.

In one embodiment the binding molecule of the disclosure comprises at least one CDR selected from SEQ ID NO: 213, 214 and 215, for example SEQ ID NO: 213 and 214, SEQ ID NO: 213 and 215, or SEQ ID NO: 214 and 215, such as a heavy variable region comprising SEQ ID NO: 213 for CDRH1, SEQ ID NO: 214 for CDRH2 and SEQ ID NO: 215 for CDRH3.

In one embodiment the binding molecule of the disclosure comprises at least one CDR selected from SEQ ID NO: 223, 224 and 225, for example SEQ ID NO: 223 and 224, SEQ ID NO: 223 and 225, or SEQ ID NO: 224 and 225, such as a heavy variable region comprising SEQ ID NO: 223 for CDRH1, SEQ ID NO: 224 for CDRH2 and SEQ ID NO: 225 for CDRH3.

In one embodiment the binding molecule of the disclosure comprises at least one CDR selected from SEQ ID NO: 233, 234 and 235, for example SEQ ID NO: 233 and 234, SEQ ID NO: 233 and 235, or SEQ ID NO: 234 and 235, such as a heavy variable region comprising SEQ ID NO: 233 for CDRH1, SEQ ID NO: 234 for CDRH2 and SEQ ID NO: 235 for CDRH3.

In one embodiment the binding molecule of the disclosure comprises at least one CDR selected from SEQ ID NO: 243, 244 and 245, for example SEQ ID NO: 243 and 244, SEQ ID NO: 243 and 245, or SEQ ID NO: 244 and 245, such as a heavy variable region comprising SEQ ID NO: 243 for CDRH1, SEQ ID NO: 244 for CDRH2 and SEQ ID NO: 245 for CDRH3.

In one embodiment the binding molecule of the disclosure comprises at least one CDR selected from SEQ ID NO: 253, 254 and 255, for example SEQ ID NO: 253 and 254, SEQ ID NO: 253 and 255, or SEQ ID NO: 254 and 255, such as a heavy variable region comprising SEQ ID NO: 253 for CDRH1, SEQ ID NO: 254 for CDRH2 and SEQ ID NO: 255 for CDRH3.

In one embodiment the binding molecule of the disclosure comprises at least one CDR selected from SEQ ID NO: 263, 264 and 265, for example SEQ ID NO: 263 and 264, SEQ ID NO: 263 and 265, or SEQ ID NO: 264 and 265, such as a heavy variable region comprising SEQ ID NO: 263 for CDRH1, SEQ ID NO: 264 for CDRH2 and SEQ ID NO: 265 for CDRH3.

In one embodiment the binding molecule of the disclosure comprises at least one CDR selected from SEQ ID NO: 273, 274 and 275, for example SEQ ID NO: 273 and 274, SEQ ID NO: 273 and 275, or SEQ ID NO: 274 and 275, such as a heavy variable region comprising SEQ ID NO: 273 for CDRH1, SEQ ID NO: 274 for CDRH2 and SEQ ID NO: 275 for CDRH3.

In one embodiment the binding molecule of the disclosure comprises at least one CDR selected from SEQ ID NO: 283, 284 and 285, for example SEQ ID NO: 283 and 284, SEQ ID NO: 283 and 285, or SEQ ID NO: 284 and 285, such as a heavy variable region comprising SEQ ID NO: 283 for CDRH1, SEQ ID NO: 284 for CDRH2 and SEQ ID NO: 285 for CDRH3

In one embodiment the binding molecule of the disclosure comprises at least one CDR selected from SEQ ID NO: 293, 294 and 295, for example SEQ ID NO: 293 and 294, SEQ ID NO: 293 and 295, or SEQ ID NO: 294 and 295, such as a heavy variable region comprising SEQ ID NO: 293 for CDRH1, SEQ ID NO: 294 for CDRH2 and SEQ ID NO: 295 for CDRH3.

In one embodiment the binding molecule of the disclosure comprises at least one CDR selected from SEQ ID NO: 303, 304 and 305, for example SEQ ID NO: 303 and 304, SEQ ID NO: 303 and 305, or SEQ ID NO: 304 and 305, such as a heavy variable region comprising SEQ ID NO: 303 for CDRH1, SEQ ID NO: 304 for CDRH2 and SEQ ID NO: 305 for CDRH3.

In one embodiment the binding molecule of the disclosure comprises at least one CDR selected from SEQ ID NO: 313, 314 and 315, for example SEQ ID NO: 313 and 314, SEQ ID NO: 313 and 315, or SEQ ID NO: 314 and 315, such as a heavy variable region comprising SEQ ID NO: 313 for CDRH1, SEQ ID NO: 314 for CDRH2 and SEQ ID NO: 315 for CDRH3.

In one embodiment the binding molecule of the disclosure comprises at least one CDR selected from SEQ ID NO: 323, 324 and 325, for example SEQ ID NO: 323 and 324, SEQ ID NO: 323 and 325, or SEQ ID NO: 324 and 325, such as a heavy variable region comprising SEQ ID NO: 323 for CDRH1, SEQ ID NO: 324 for CDRH2 and SEQ ID NO: 325 for CDRH3.

In one embodiment the binding molecule of the disclosure comprises at least one CDR selected from SEQ ID NO: 333, 334 and 335, for example SEQ ID NO: 333 and 334, SEQ ID NO: 333 and 335, or SEQ ID NO: 334 and 335, such as a heavy variable region comprising SEQ ID NO: 333 for CDRH1, SEQ ID NO: 334 for CDRH2 and SEQ ID NO: 335 for CDRH3.

In one embodiment the binding molecule of the disclosure comprises at least one CDR selected from SEQ ID NO: 343, 344 and 345, for example SEQ ID NO: 343 and 344, SEQ ID NO: 343 and 345, or SEQ ID NO: 344 and 345, such as a heavy variable region comprising SEQ ID NO: 343 for CDRH1, SEQ ID NO: 344 for CDRH2 and SEQ ID NO: 345 for CDRH3.

In one embodiment the binding molecule of the disclosure comprises at least one CDR selected from SEQ ID NO: 353, 354 and 355, for example SEQ ID NO: 353 and 354, SEQ ID NO: 353 and 355, or SEQ ID NO: 354 and 355, such as a heavy variable region comprising SEQ ID NO: 353 for CDRH1, SEQ ID NO: 354 for CDRH2 and SEQ ID NO: 355 for CDRH3.

In one embodiment the binding molecule of the disclosure comprises at least one CDR selected from SEQ ID NO: 363, 364 and 365, for example SEQ ID NO: 363 and 364, SEQ ID NO: 363 and 365, or SEQ ID NO: 364 and 365, such as a heavy variable region comprising SEQ ID NO: 363 for CDRH1, SEQ ID NO: 364 for CDRH2 and SEQ ID NO: 365 for CDRH3.

In one embodiment the binding molecule of the disclosure comprises at least one CDR selected from SEQ ID NO: 373, 374 and 375, for example SEQ ID NO: 373 and 374, SEQ ID NO: 373 and 375, or SEQ ID NO: 374 and 375, such as a heavy variable region comprising SEQ ID NO: 373 for CDRH1, SEQ ID NO: 374 for CDRH2 and SEQ ID NO: 375 for CDRH3.

In one embodiment the binding molecule of the disclosure comprises at least one CDR selected from SEQ ID NO: 383, 384 and 385, for example SEQ ID NO: 383 and 384, SEQ ID NO: 383 and 385, or SEQ ID NO: 384 and 385, such as a heavy variable region comprising SEQ ID NO: 383 for CDRH1, SEQ ID NO: 384 for CDRH2 and SEQ ID NO: 385 for CDRH3

In one embodiment the binding molecule of the disclosure comprises at least one CDR selected from SEQ ID NO: 393, 394 and 395, for example SEQ ID NO: 393 and 394, SEQ ID NO: 393 and 395, or SEQ ID NO: 394 and 395, such as a heavy variable region comprising SEQ ID NO: 393 for CDRH1, SEQ ID NO: 394 for CDRH2 and SEQ ID NO: 395 for CDRH3.

In one embodiment the binding molecule of the disclosure comprises at least one CDR selected from SEQ ID NO: 403, 404 and 405, for example SEQ ID NO: 403 and 404, SEQ ID NO: 403 and 405, or SEQ ID NO: 404 and 405, such as a heavy variable region comprising SEQ ID NO: 403 for CDRH1, SEQ ID NO: 404 for CDRH2 and SEQ ID NO: 405 for CDRH3.

In one embodiment the binding molecule of the disclosure comprises at least one CDR selected from SEQ ID NO: 413, 414 and 415, for example SEQ ID NO: 413 and 414, SEQ ID NO: 413 and 415, or SEQ ID NO: 414 and 415, such as a heavy variable region comprising SEQ ID NO: 413 for CDRH1, SEQ ID NO: 414 for CDRH2 and SEQ ID NO: 415 for CDRH3.

In one embodiment the binding molecule of the disclosure comprises at least one CDR selected from SEQ ID NO: 423, 424 and 425, for example SEQ ID NO: 423 and 424, SEQ ID NO: 423 and 425, or SEQ ID NO: 424 and 425, such as a heavy variable region comprising SEQ ID NO: 423 for CDRH1, SEQ ID NO: 424 for CDRH2 and SEQ ID NO: 425 for CDRH3.

In one embodiment the binding molecule of the disclosure comprises at least one CDR selected from SEQ ID NO: 433, 434 and 435, for example SEQ ID NO: 433 and 434, SEQ ID NO: 433 and 435, or SEQ ID NO: 434 and 435, such as a heavy variable region comprising SEQ ID NO: 433 for CDRH1, SEQ ID NO: 434 for CDRH2 and SEQ ID NO: 435 for CDRH3.

In one embodiment the binding molecule of the disclosure comprises at least one CDR selected from SEQ ID NO: 443, 444 and 445, for example SEQ ID NO: 443 and 444, SEQ ID NO: 443 and 445, or SEQ ID NO: 444 and 445, such as a heavy variable region comprising SEQ ID NO: 443 for CDRH1, SEQ ID NO: 444 for CDRH2 and SEQ ID NO: 445 for CDRH3.

In one embodiment the binding molecule of the disclosure comprises at least one CDR selected from SEQ ID NO: 453, 454 and 455, for example SEQ ID NO: 453 and 454, SEQ ID NO: 453 and 455, or SEQ ID NO: 454 and 455, such as a heavy variable region comprising SEQ ID NO: 453 for CDRH1, SEQ ID NO: 454 for CDRH2 and SEQ ID NO: 455 for CDRH3.

In one embodiment the binding molecule of the disclosure comprises at least one CDR selected from SEQ ID NO: 463, 464 and 465, for example SEQ ID NO: 463 and 464, SEQ ID NO: 463 and 465, or SEQ ID NO: 464 and 465, such as a heavy variable region comprising SEQ ID NO: 463 for CDRH1, SEQ ID NO: 464 for CDRH2 and SEQ ID NO: 465 for CDRH3.

In one embodiment the binding molecule of the disclosure comprises at least one CDR selected from SEQ ID NO: 473, 474 and 475, for example SEQ ID NO: 473 and 474, SEQ ID NO: 473 and 475, or SEQ ID NO: 474 and 475, such as a heavy variable region comprising SEQ ID NO: 473 for CDRH1, SEQ ID NO: 474 for CDRH2 and SEQ ID NO: 475 for CDRH3.

In one embodiment the binding molecule of the disclosure comprises at least one CDR selected from SEQ ID NO: 483, 484 and 485, for example SEQ ID NO: 483 and 484, SEQ ID NO: 483 and 485, or SEQ ID NO: 484 and 485, such as a heavy variable region comprising SEQ ID NO: 483 for CDRH1, SEQ ID NO: 484 for CDRH2 and SEQ ID NO: 485 for CDRH3

In one embodiment the binding molecule of the disclosure comprises at least one CDR selected from SEQ ID NO: 493, 494 and 495, for example SEQ ID NO: 493 and 494, SEQ ID NO: 493 and 495, or SEQ ID NO: 494 and 495, such as a heavy variable region comprising SEQ ID NO: 493 for CDRH1, SEQ ID NO: 494 for CDRH2 and SEQ ID NO: 495 for CDRH3.

In one embodiment the binding molecule of the disclosure comprises at least one CDR selected from SEQ ID NO: 503, 504 and 505, for example SEQ ID NO: 503 and 504, SEQ ID NO: 503 and 505, or SEQ ID NO: 504 and 505, such as a heavy variable region comprising SEQ ID NO: 503 for CDRH1, SEQ ID NO: 504 for CDRH2 and SEQ ID NO: 505 for CDRH3.

In one embodiment the binding molecule of the disclosure comprises at least one CDR selected from SEQ ID NO: 513, 514 and 515, for example SEQ ID NO: 513 and 514, SEQ ID NO: 513 and 515, or SEQ ID NO: 514 and 515, such as a heavy variable region comprising SEQ ID NO: 513 for CDRH1, SEQ ID NO: 514 for CDRH2 and SEQ ID NO: 515 for CDRH3.

In one embodiment the binding molecule of the disclosure comprises at least one CDR selected from SEQ ID NO: 523, 524 and 525, for example SEQ ID NO: 523 and 524, SEQ ID NO: 523 and 525, or SEQ ID NO: 524 and 525, such as a heavy variable region comprising SEQ ID NO: 523 for CDRH1, SEQ ID NO: 524 for CDRH2 and SEQ ID NO: 525 for CDRH3.

In one embodiment the binding molecule of the disclosure comprises at least one CDR selected from SEQ ID NO: 533, 534 and 535, for example SEQ ID NO: 533 and 534, SEQ ID NO: 533 and 535, or SEQ ID NO: 534 and 535, such as a heavy variable region comprising SEQ ID NO: 533 for CDRH1, SEQ ID NO: 534 for CDRH2 and SEQ ID NO: 535 for CDRH3.

In one embodiment the binding molecule of the disclosure comprises at least one CDR selected from SEQ ID NO: 543, 544 and 545, for example SEQ ID NO: 543 and 544, SEQ ID NO: 543 and 545, or SEQ ID NO: 544 and 545, such as a heavy variable region comprising SEQ ID NO: 543 for CDRH1, SEQ ID NO: 544 for CDRH2 and SEQ ID NO: 545 for CDRH3.

In one embodiment the binding molecule of the disclosure comprises at least one CDR selected from SEQ ID NO: 553, 554 and 555, for example SEQ ID NO: 553 and 554, SEQ ID NO: 553 and 555, or SEQ ID NO: 554 and 555, such as a heavy variable region comprising SEQ ID NO: 553 for CDRH1, SEQ ID NO: 554 for CDRH2 and SEQ ID NO: 555 for CDRH3.

In one embodiment the binding molecule of the disclosure comprises at least one CDR selected from SEQ ID NO: 563, 564 and 565, for example SEQ ID NO: 563 and 564, SEQ ID NO: 563 and 565, or SEQ ID NO: 564 and 565, such as a heavy variable region comprising SEQ ID NO: 563 for CDRH1, SEQ ID NO: 564 for CDRH2 and SEQ ID NO: 565 for CDRH3.

In one embodiment the binding molecule of the disclosure comprises at least one CDR selected from SEQ ID NO: 573, 574 and 575, for example SEQ ID NO: 573 and 574, SEQ ID NO: 573 and 575, or SEQ ID NO: 574 and 575, such as a heavy variable region comprising SEQ ID NO: 573 for CDRH1, SEQ ID NO: 574 for CDRH2 and SEQ ID NO: 575 for CDRH3.

In one embodiment the binding molecule of the disclosure comprises at least one CDR selected from SEQ ID NO: 583, 584 and 585, for example SEQ ID NO: 583 and 584, SEQ ID NO: 583 and 585, or SEQ ID NO: 584 and 585, such as a heavy variable region comprising SEQ ID NO: 583 for CDRH1, SEQ ID NO: 584 for CDRH2 and SEQ ID NO: 585 for CDRH3

In one embodiment the binding molecule of the disclosure comprises at least one CDR selected from SEQ ID NO: 8, 9 and 10, for example SEQ ID NO: 8 and 9, SEQ ID NO: 8 and 10, or SEQ ID NO: 9 and 10, such as a light variable region comprising SEQ ID NO: 8 for CDRL1, SEQ ID NO: 9 for CDRL2 and SEQ ID NO: 10 for CDRL3.

In one embodiment the binding molecule of the disclosure comprises at least one CDR selected from SEQ ID NO: 18, 19 and 20, for example SEQ ID NO: 18 and 19, SEQ ID NO: 18 and 20, or SEQ ID NO: 19 and 20, such as a light variable region comprising SEQ ID NO: 18 for CDRL1, SEQ ID NO: 19 for CDRL2 and SEQ ID NO: 20 for CDRL3.

In one embodiment the binding molecule of the disclosure comprises at least one CDR selected from SEQ ID NO: 28, 29 and 30, for example SEQ ID NO: 28 and 29, SEQ ID NO:

28 and 30, or SEQ ID NO: 29 and 30, such as a light variable region comprising SEQ ID NO: 28 for CDRL1, SEQ ID NO: 29 for CDRL2 and SEQ ID NO: 30 for CDRL3.

In one embodiment the binding molecule of the disclosure comprises at least one CDR selected from SEQ ID NO: 38, 39 and 40, for example SEQ ID NO: 38 and 39, SEQ ID NO: 38 and 40, or SEQ ID NO: 39 and 40, such as a light variable region comprising SEQ ID NO: 38 for CDRL1, SEQ ID NO: 39 for CDRL2 and SEQ ID NO: 40 for CDRL3.

In one embodiment the binding molecule of the disclosure comprises at least one CDR selected from SEQ ID NO: 48, 49 and 50, for example SEQ ID NO: 48 and 49, SEQ ID NO: 48 and 50, or SEQ ID NO: 49 and 50, such as a light variable region comprising SEQ ID NO: 48 for CDRL1, SEQ ID NO: 49 for CDRL2 and SEQ ID NO: 50 for CDRL3.

In one embodiment the binding molecule of the disclosure comprises at least one CDR selected from SEQ ID NO: 58, 59 and 60, for example SEQ ID NO: 58 and 59, SEQ ID NO: 58 and 60, or SEQ ID NO: 59 and 60, such as a light variable region comprising SEQ ID NO: 58 for CDRL1, SEQ ID NO: 59 for CDRL2 and SEQ ID NO: 60 for CDRL3.

In one embodiment the binding molecule of the disclosure comprises at least one CDR selected from SEQ ID NO: 68, 69 and 70, for example SEQ ID NO: 68 and 69, SEQ ID NO: 68 and 70, or SEQ ID NO: 69 and 70, such as a light variable region comprising SEQ ID NO: 68 for CDRL1, SEQ ID NO: 69 for CDRL2 and SEQ ID NO: 70 for CDRL3.

In one embodiment the binding molecule of the disclosure comprises at least one CDR selected from SEQ ID NO: 78, 79 and 80, for example SEQ ID NO: 78 and 79, SEQ ID NO: 78 and 80, or SEQ ID NO: 79 and 80, such as a light variable region comprising SEQ ID NO: 78 for CDRL1, SEQ ID NO: 79 for CDRL2 and SEQ ID NO: 80 for CDRL3.

In one embodiment the binding molecule of the disclosure comprises at least one CDR selected from SEQ ID NO: 88, 89 and 90, for example SEQ ID NO: 88 and 89, SEQ ID NO: 88 and 90, or SEQ ID NO: 89 and 90, such as a light variable region comprising SEQ ID NO: 88 for CDRL1, SEQ ID NO: 89 for CDRL2 and SEQ ID NO: 90 for CDRL3.

In one embodiment the binding molecule of the disclosure comprises at least one CDR selected from SEQ ID NO: 98, 99 and 100, for example SEQ ID NO: 98 and 99, SEQ ID NO: 98 and 100, or SEQ ID NO: 99 and 100, such as a light variable region comprising SEQ ID NO: 98 for CDRL1, SEQ ID NO: 99 for CDRL2 and SEQ ID NO: 100 for CDRL3.

In one embodiment the binding molecule of the disclosure comprises at least one CDR selected from SEQ ID NO: 108, 109 and 110, for example SEQ ID NO: 108 and 109, SEQ ID NO: 108 and 110, or SEQ ID NO: 109 and 110, such as a light variable region comprising SEQ ID NO: 108 for CDRL1, SEQ ID NO: 109 for CDRL2 and SEQ ID NO: 110 for CDRL3.

In one embodiment the binding molecule of the disclosure comprises at least one CDR selected from SEQ ID NO: 118, 119 and 120, for example SEQ ID NO: 118 and 119, SEQ ID NO: 118 and 120, or SEQ ID NO: 119 and 120, such as a light variable region comprising SEQ ID NO: 118 for CDRL1, SEQ ID NO: 119 for CDRL2 and SEQ ID NO: 120 for CDRL3.

In one embodiment the binding molecule of the disclosure comprises at least one CDR selected from SEQ ID NO: 128, 129 and 130, for example SEQ ID NO: 128 and 129, SEQ ID NO: 128 and 130, or SEQ ID NO: 129 and 130, such as a light variable region comprising SEQ ID NO: 128 for CDRL1, SEQ ID NO: 129 for CDRL2 and SEQ ID NO: 130 for CDRL3.

In one embodiment the binding molecule of the disclosure comprises at least one CDR selected from SEQ ID NO: 138, 139 and 140, for example SEQ ID NO: 138 and 139, SEQ ID NO: 138 and 140, or SEQ ID NO: 139 and 140, such as a light variable region comprising SEQ ID NO: 138 for CDRL1, SEQ ID NO: 139 for CDRL2 and SEQ ID NO: 140 for CDRL3.

In one embodiment the binding molecule of the disclosure comprises at least one CDR selected from SEQ ID NO: 148, 149 and 150, for example SEQ ID NO: 148 and 149, SEQ ID NO: 148 and 150, or SEQ ID NO: 149 and 150, such as a light variable region comprising SEQ ID NO: 148 for CDRL1, SEQ ID NO: 149 for CDRL2 and SEQ ID NO: 120 for CDRL3.

In one embodiment the binding molecule of the disclosure comprises at least one CDR selected from SEQ ID NO: 158, 159 and 160, for example SEQ ID NO: 158 and 159, SEQ ID NO: 158 and 160, or SEQ ID NO: 159 and 160, such as a light variable region comprising SEQ ID NO: 158 for CDRL1, SEQ ID NO: 159 for CDRL2 and SEQ ID NO: 160 for CDRL3.

In one embodiment the binding molecule of the disclosure comprises at least one CDR selected from SEQ ID NO: 168, 169 and 170, for example SEQ ID NO: 168 and 169, SEQ ID NO: 168 and 170, or SEQ ID NO: 169 and 170, such as a light variable region comprising SEQ ID NO: 168 for CDRL1, SEQ ID NO: 169 for CDRL2 and SEQ ID NO: 170 for CDRL3.

In one embodiment the binding molecule of the disclosure comprises at least one CDR selected from SEQ ID NO: 178, 179 and 180, for example SEQ ID NO: 178 and 179, SEQ ID NO: 178 and 180, or SEQ ID NO: 179 and 180, such as a light variable region comprising SEQ ID NO: 178 for CDRL1, SEQ ID NO: 179 for CDRL2 and SEQ ID NO: 180 for CDRL3.

In one embodiment the binding molecule of the disclosure comprises at least one CDR selected from SEQ ID NO: 188, 189 and 190, for example SEQ ID NO: 188 and 189, SEQ ID NO: 188 and 190, or SEQ ID NO: 189 and 190, such as a light variable region comprising SEQ ID NO: 188 for CDRL1, SEQ ID NO: 189 for CDRL2 and SEQ ID NO: 190 for CDRL3.

In one embodiment the binding molecule of the disclosure comprises at least one CDR selected from SEQ ID NO: 198, 199 and 200, for example SEQ ID NO: 198 and 199, SEQ ID NO: 198 and 200, or SEQ ID NO: 199 and 200, such as a light variable region comprising SEQ ID NO: 198 for CDRL1, SEQ ID NO: 199 for CDRL2 and SEQ ID NO: 200 for CDRL3.

In one embodiment the binding molecule of the disclosure comprises at least one CDR selected from SEQ ID NO: 208, 209 and 210, for example SEQ ID NO: 208 and 209, SEQ ID NO: 208 and 210, or SEQ ID NO: 209 and 210, such as a light variable region comprising SEQ ID NO: 208 for CDRL1, SEQ ID NO: 209 for CDRL2 and SEQ ID NO: 210 for CDRL3.

In one embodiment the binding molecule of the disclosure comprises at least one CDR selected from SEQ ID NO: 218, 219 and 220, for example SEQ ID NO: 218 and 219, SEQ ID NO: 218 and 220, or SEQ ID NO: 219 and 220, such as a light variable region comprising SEQ ID NO: 218 for CDRL1, SEQ ID NO: 219 for CDRL2 and SEQ ID NO: 220 for CDRL3.

In one embodiment the binding molecule of the disclosure comprises at least one CDR selected from SEQ ID NO: 228, 229 and 230, for example SEQ ID NO: 228 and 229, SEQ ID NO: 228 and 230, or SEQ ID NO: 229 and 230, such as a light variable region comprising SEQ ID NO: 228 for CDRL1, SEQ ID NO: 229 for CDRL2 and SEQ ID NO: 230 for CDRL3.

In one embodiment the binding molecule of the disclosure comprises at least one CDR selected from SEQ ID NO: 238, 239 and 240, for example SEQ ID NO: 238 and 239, SEQ ID NO: 238 and 240, or SEQ ID NO: 239 and 240, such as a light variable region comprising SEQ ID NO: 238 for CDRL1, SEQ ID NO: 239 for CDRL2 and SEQ ID NO: 240 for CDRL3.

In one embodiment the binding molecule of the disclosure comprises at least one CDR selected from SEQ ID NO: 248, 249 and 250, for example SEQ ID NO: 248 and 249, SEQ ID NO: 248 and 250, or SEQ ID NO: 249 and 250, such as a light variable region comprising SEQ ID NO: 248 for CDRL1, SEQ ID NO: 249 for CDRL2 and SEQ ID NO: 220 for CDRL3.

In one embodiment the binding molecule of the disclosure comprises at least one CDR selected from SEQ ID NO: 258, 259 and 260, for example SEQ ID NO: 258 and 259, SEQ ID NO: 258 and 260, or SEQ ID NO: 259 and 260, such as a light variable region comprising SEQ ID NO: 258 for CDRL1, SEQ ID NO: 259 for CDRL2 and SEQ ID NO: 260 for CDRL3.

In one embodiment the binding molecule of the disclosure comprises at least one CDR selected from SEQ ID NO: 268, 269 and 270, for example SEQ ID NO: 268 and 269, SEQ ID NO: 268 and 270, or SEQ ID NO: 269 and 270, such as a light variable region comprising SEQ ID NO: 268 for CDRL1, SEQ ID NO: 269 for CDRL2 and SEQ ID NO: 270 for CDRL3.

In one embodiment the binding molecule of the disclosure comprises at least one CDR selected from SEQ ID NO: 278, 279 and 280, for example SEQ ID NO: 278 and 279, SEQ ID NO: 278 and 280, or SEQ ID NO: 279 and 280, such as a light variable region comprising SEQ ID NO: 278 for CDRL1, SEQ ID NO: 279 for CDRL2 and SEQ ID NO: 280 for CDRL3.

In one embodiment the binding molecule of the disclosure comprises at least one CDR selected from SEQ ID NO: 288, 289 and 290, for example SEQ ID NO: 288 and 289, SEQ ID NO: 288 and 290, or SEQ ID NO: 289 and 290, such as a light variable region comprising SEQ ID NO: 288 for CDRL1, SEQ ID NO: 289 for CDRL2 and SEQ ID NO: 290 for CDRL3.

In one embodiment the binding molecule of the disclosure comprises at least one CDR selected from SEQ ID NO: 298, 299 and 300, for example SEQ ID NO: 298 and 299, SEQ ID NO: 298 and 300, or SEQ ID NO: 299 and 300, such as a light variable region comprising SEQ ID NO: 298 for CDRL1, SEQ ID NO: 299 for CDRL2 and SEQ ID NO: 300 for CDRL3.

In one embodiment the binding molecule of the disclosure comprises at least one CDR selected from SEQ ID NO: 308, 309 and 310, for example SEQ ID NO: 308 and 309, SEQ ID NO: 308 and 310, or SEQ ID NO: 309 and 310, such as a light variable region comprising SEQ ID NO: 308 for CDRL1, SEQ ID NO: 309 for CDRL2 and SEQ ID NO: 310 for CDRL3.

In one embodiment the binding molecule of the disclosure comprises at least one CDR selected from SEQ ID NO: 318, 319 and 320, for example SEQ ID NO: 318 and 319, SEQ ID NO: 318 and 320, or SEQ ID NO: 319 and 320, such as a light variable region comprising SEQ ID NO: 318 for CDRL1, SEQ ID NO: 319 for CDRL2 and SEQ ID NO: 320 for CDRL3.

In one embodiment the binding molecule of the disclosure comprises at least one CDR selected from SEQ ID NO: 328, 329 and 330, for example SEQ ID NO: 328 and 329, SEQ ID NO: 328 and 330, or SEQ ID NO: 329 and 330, such as a light variable region comprising SEQ ID NO: 328 for CDRL1, SEQ ID NO: 329 for CDRL2 and SEQ ID NO: 330 for CDRL3.

In one embodiment the binding molecule of the disclosure comprises at least one CDR selected from SEQ ID NO: 338, 339 and 340, for example SEQ ID NO: 338 and 339, SEQ ID NO: 338 and 340, or SEQ ID NO: 339 and 340, such as a light variable region comprising SEQ ID NO: 338 for CDRL1, SEQ ID NO: 339 for CDRL2 and SEQ ID NO: 340 for CDRL3.

In one embodiment the binding molecule of the disclosure comprises at least one CDR selected from SEQ ID NO: 348, 349 and 350, for example SEQ ID NO: 348 and 349, SEQ ID NO: 348 and 350, or SEQ ID NO: 349 and 350, such as a light variable region comprising SEQ ID NO: 348 for CDRL1, SEQ ID NO: 349 for CDRL2 and SEQ ID NO: 320 for CDRL3.

In one embodiment the binding molecule of the disclosure comprises at least one CDR selected from SEQ ID NO: 358, 359 and 360, for example SEQ ID NO: 358 and 359, SEQ ID NO: 358 and 360, or SEQ ID NO: 359 and 360, such as a light variable region comprising SEQ ID NO: 358 for CDRL1, SEQ ID NO: 359 for CDRL2 and SEQ ID NO: 360 for CDRL3.

In one embodiment the binding molecule of the disclosure comprises at least one CDR selected from SEQ ID NO: 368, 369 and 370, for example SEQ ID NO: 368 and 369, SEQ ID NO: 368 and 370, or SEQ ID NO: 369 and 370, such as a light variable region comprising SEQ ID NO: 368 for CDRL1, SEQ ID NO: 369 for CDRL2 and SEQ ID NO: 370 for CDRL3.

In one embodiment the binding molecule of the disclosure comprises at least one CDR selected from SEQ ID NO: 378, 379 and 380, for example SEQ ID NO: 378 and 379, SEQ ID NO: 378 and 380, or SEQ ID NO: 379 and 380, such as a light variable region comprising SEQ ID NO: 378 for CDRL1, SEQ ID NO: 379 for CDRL2 and SEQ ID NO: 380 for CDRL3.

In one embodiment the binding molecule of the disclosure comprises at least one CDR selected from SEQ ID NO: 388, 389 and 390, for example SEQ ID NO: 388 and 389, SEQ ID NO: 388 and 390, or SEQ ID NO: 389 and 390, such as a light variable region comprising SEQ ID NO: 388 for CDRL1, SEQ ID NO: 389 for CDRL2 and SEQ ID NO: 390 for CDRL3.

In one embodiment the binding molecule of the disclosure comprises at least one CDR selected from SEQ ID NO: 398, 399 and 400, for example SEQ ID NO: 398 and 399, SEQ ID NO: 398 and 400, or SEQ ID NO: 399 and 400, such as a light variable region comprising SEQ ID NO: 398 for CDRL1, SEQ ID NO: 399 for CDRL2 and SEQ ID NO: 400 for CDRL3.

In one embodiment the binding molecule of the disclosure comprises at least one CDR selected from SEQ ID NO: 408, 409 and 410, for example SEQ ID NO: 408 and 409, SEQ ID NO: 408 and 410, or SEQ ID NO: 409 and 410, such as a light variable region comprising SEQ ID NO: 408 for CDRL1, SEQ ID NO: 409 for CDRL2 and SEQ ID NO: 410 for CDRL3.

In one embodiment the binding molecule of the disclosure comprises at least one CDR selected from SEQ ID NO: 418, 419 and 420, for example SEQ ID NO: 418 and 419, SEQ ID NO: 418 and 420, or SEQ ID NO: 419 and 420, such as a light variable region comprising SEQ ID NO: 418 for CDRL1, SEQ ID NO: 419 for CDRL2 and SEQ ID NO: 420 for CDRL3.

In one embodiment the binding molecule of the disclosure comprises at least one CDR selected from SEQ ID NO: 428, 429 and 430, for example SEQ ID NO: 428 and 429, SEQ ID NO: 428 and 430, or SEQ ID NO: 429 and 430, such as a light variable region comprising SEQ ID NO: 428 for CDRL1, SEQ ID NO: 429 for CDRL2 and SEQ ID NO: 430 for CDRL3.

In one embodiment the binding molecule of the disclosure comprises at least one CDR selected from SEQ ID NO: 438, 439 and 440, for example SEQ ID NO: 438 and 439, SEQ ID NO: 438 and 440, or SEQ ID NO: 439 and 440, such as a light variable region comprising SEQ ID NO: 438 for CDRL1, SEQ ID NO: 439 for CDRL2 and SEQ ID NO: 440 for CDRL3.

In one embodiment the binding molecule of the disclosure comprises at least one CDR selected from SEQ ID NO: 448, 449 and 450, for example SEQ ID NO: 448 and 449, SEQ ID NO: 448 and 450, or SEQ ID NO: 449 and 450, such as a light variable region comprising SEQ ID NO: 448 for CDRL1, SEQ ID NO: 449 for CDRL2 and SEQ ID NO: 420 for CDRL3.

In one embodiment the binding molecule of the disclosure comprises at least one CDR selected from SEQ ID NO: 458, 459 and 460, for example SEQ ID NO: 458 and 459, SEQ ID NO: 458 and 460, or SEQ ID NO: 459 and 460, such as a light variable region comprising SEQ ID NO: 458 for CDRL1, SEQ ID NO: 459 for CDRL2 and SEQ ID NO: 460 for CDRL3.

In one embodiment the binding molecule of the disclosure comprises at least one CDR selected from SEQ ID NO: 468, 469 and 470, for example SEQ ID NO: 468 and 469, SEQ ID NO: 468 and 470, or SEQ ID NO: 469 and 470, such as a light variable region comprising SEQ ID NO: 468 for CDRL1, SEQ ID NO: 469 for CDRL2 and SEQ ID NO: 470 for CDRL3.

In one embodiment the binding molecule of the disclosure comprises at least one CDR selected from SEQ ID NO: 478, 479 and 480, for example SEQ ID NO: 478 and 479, SEQ ID NO: 478 and 480, or SEQ ID NO: 479 and 480, such as a light variable region comprising SEQ ID NO: 478 for CDRL1, SEQ ID NO: 479 for CDRL2 and SEQ ID NO: 480 for CDRL3.

In one embodiment the binding molecule of the disclosure comprises at least one CDR selected from SEQ ID NO: 488, 489 and 490, for example SEQ ID NO: 488 and 489, SEQ ID NO: 488 and 490, or SEQ ID NO: 489 and 490, such as a light variable region comprising SEQ ID NO: 488 for CDRL1, SEQ ID NO: 489 for CDRL2 and SEQ ID NO: 490 for CDRL3.

In one embodiment the binding molecule of the disclosure comprises at least one CDR selected from SEQ ID NO: 498, 499 and 500, for example SEQ ID NO: 498 and 499, SEQ ID NO: 498 and 500, or SEQ ID NO: 499 and 500, such as a light variable region comprising SEQ ID NO: 498 for CDRL1, SEQ ID NO: 499 for CDRL2 and SEQ ID NO: 500 for CDRL3.

In one embodiment the binding molecule of the disclosure comprises at least one CDR selected from SEQ ID NO: 508, 509 and 510, for example SEQ ID NO: 508 and 509, SEQ ID NO: 508 and 510, or SEQ ID NO: 509 and 510, such as a light variable region comprising SEQ ID NO: 508 for CDRL1, SEQ ID NO: 509 for CDRL2 and SEQ ID NO: 510 for CDRL3.

In one embodiment the binding molecule of the disclosure comprises at least one CDR selected from SEQ ID NO: 518, 519 and 520, for example SEQ ID NO: 518 and 519, SEQ ID NO: 518 and 520, or SEQ ID NO: 519 and 520, such as a light variable region comprising SEQ ID NO: 518 for CDRL1, SEQ ID NO: 519 for CDRL2 and SEQ ID NO: 520 for CDRL3.

In one embodiment the binding molecule of the disclosure comprises at least one CDR selected from SEQ ID NO: 528, 529 and 530, for example SEQ ID NO: 528 and 529, SEQ ID NO: 528 and 530, or SEQ ID NO: 529 and 530, such as a light variable region comprising SEQ ID NO: 528 for CDRL1, SEQ ID NO: 529 for CDRL2 and SEQ ID NO: 530 for CDRL3.

In one embodiment the binding molecule of the disclosure comprises at least one CDR selected from SEQ ID NO: 538, 539 and 540, for example SEQ ID NO: 538 and 539, SEQ ID NO: 538 and 540, or SEQ ID NO: 539 and 540, such as a light variable region comprising SEQ ID NO: 538 for CDRL1, SEQ ID NO: 539 for CDRL2 and SEQ ID NO: 540 for CDRL3.

In one embodiment the binding molecule of the disclosure comprises at least one CDR selected from SEQ ID NO: 548, 549 and 550, for example SEQ ID NO: 548 and 549, SEQ ID NO: 548 and 550, or SEQ ID NO: 549 and 550, such as a light variable region comprising SEQ ID NO: 548 for CDRL1, SEQ ID NO: 549 for CDRL2 and SEQ ID NO: 520 for CDRL3.

In one embodiment the binding molecule of the disclosure comprises at least one CDR selected from SEQ ID NO: 558, 559 and 560, for example SEQ ID NO: 558 and 559, SEQ ID NO: 558 and 560, or SEQ ID NO: 559 and 560, such as a light variable region comprising SEQ ID NO: 558 for CDRL1, SEQ ID NO: 559 for CDRL2 and SEQ ID NO: 560 for CDRL3.

In one embodiment the binding molecule of the disclosure comprises at least one CDR selected from SEQ ID NO: 568, 569 and 570, for example SEQ ID NO: 568 and 569, SEQ ID NO: 568 and 570, or SEQ ID NO: 569 and 570, such as a light variable region comprising SEQ ID NO: 568 for CDRL1, SEQ ID NO: 569 for CDRL2 and SEQ ID NO: 570 for CDRL3.

In one embodiment the binding molecule of the disclosure comprises at least one CDR selected from SEQ ID NO: 578, 579 and 580, for example SEQ ID NO: 578 and 579, SEQ ID NO: 578 and 580, or SEQ ID NO: 579 and 580, such as a light variable region comprising SEQ ID NO: 578 for CDRL1, SEQ ID NO: 579 for CDRL2 and SEQ ID NO: 580 for CDRL3.

In one embodiment the binding molecule of the disclosure comprises at least one CDR selected from SEQ ID NO: 588, 589 and 590, for example SEQ ID NO: 588 and 589, SEQ ID NO: 588 and 590, or SEQ ID NO: 589 and 590, such as a light variable region comprising SEQ ID NO: 588 for CDRL1, SEQ ID NO: 589 for CDRL2 and SEQ ID NO: 590 for CDRL3.

In one embodiment a binding molecule of the disclosure comprises a heavy variable region comprising SEQ ID NO: 103 for CDRH1, SEQ ID NO: 104 for CDRH2 and SEQ ID NO: 105 for CDRH3 and at least one CDR in a light chain variable region independently selected from SEQ ID NO: 108, 109 and 120, in particular a light variable region comprising SEQ ID NO: 108 for CDRL1, SEQ ID NO: 109 for CDRL2 and SEQ ID NO: 120 for CDRL3.

In one embodiment a binding molecule of the disclosure comprises a heavy variable region comprising SEQ ID NO: 113 for CDRH1, SEQ ID NO: 114 for CDRH2 and SEQ ID NO: 115 for CDRH3 and at least one CDR in a light chain variable region independently selected from SEQ ID NO: 118, 119 and 120, in particular a light variable region comprising SEQ ID NO: 118 for CDRL1, SEQ ID NO: 119 for CDRL2 and SEQ ID NO: 120 for CDRL3.

In one embodiment a binding molecule of the disclosure comprises a heavy variable region comprising SEQ ID NO: 123 for CDRH1, SEQ ID NO: 124 for CDRH2 and SEQ ID NO: 125 for CDRH3 and at least one CDR in a light chain variable region independently selected from SEQ ID NO: 128, 129 and 130, in particular a light variable region comprising SEQ ID NO: 128 for CDRL1, SEQ ID NO: 129 for CDRL2 and SEQ ID NO: 130 for CDRL3.

In one embodiment a binding molecule of the disclosure comprises a heavy variable region comprising SEQ ID NO: 133 for CDRH1, SEQ ID NO: 134 for CDRH2 and SEQ ID NO: 135 for CDRH3 and at least one CDR in a light chain variable region independently selected from SEQ ID NO: 138, 139 and 140, in particular a light variable region comprising SEQ ID NO: 138 for CDRL1, SEQ ID NO: 139 for CDRL2 and SEQ ID NO: 140 for CDRL3.

In one embodiment a binding molecule of the disclosure comprises a heavy variable region comprising SEQ ID NO: 143 for CDRH1, SEQ ID NO: 144 for CDRH2 and SEQ ID NO: 145 for CDRH3 and at least one CDR in a light chain variable region independently selected from SEQ ID NO: 148, 149 and 150, in particular a light variable region comprising SEQ ID NO: 148 for CDRL1, SEQ ID NO: 149 for CDRL2 and SEQ ID NO: 150 for CDRL3.

In one embodiment a binding molecule of the disclosure comprises a heavy variable region comprising SEQ ID NO: 153 for CDRH1, SEQ ID NO: 154 for CDRH2 and SEQ ID NO: 155 for CDRH3 and at least one CDR in a light chain variable region independently selected from SEQ ID NO: 158, 159 and 160, in particular a light variable region comprising SEQ ID NO: 158 for CDRL1, SEQ ID NO: 159 for CDRL2 and SEQ ID NO: 160 for CDRL3.

In one embodiment a binding molecule of the disclosure comprises a heavy variable region comprising SEQ ID NO: 163 for CDRH1, SEQ ID NO: 164 for CDRH2 and SEQ ID NO: 165 for CDRH3 and at least one CDR in a light chain variable region independently selected from SEQ ID NO: 168, 169 and 170, in particular a light variable region comprising SEQ ID NO: 168 for CDRL1, SEQ ID NO: 169 for CDRL2 and SEQ ID NO: 170 for CDRL3.

In one embodiment a binding molecule of the disclosure comprises a heavy variable region comprising SEQ ID NO: 173 for CDRH1, SEQ ID NO: 174 for CDRH2 and SEQ ID NO: 175 for CDRH3 and at least one CDR in a light chain variable region independently selected from SEQ ID NO: 178, 179 and 180, in particular a light variable region comprising SEQ ID NO: 178 for CDRL1, SEQ ID NO: 179 for CDRL2 and SEQ ID NO: 180 for CDRL3.

In one embodiment a binding molecule of the disclosure comprises a heavy variable region comprising SEQ ID NO: 183 for CDRH1, SEQ ID NO: 184 for CDRH2 and SEQ ID NO: 185 for CDRH3 and at least one CDR in a light chain variable region independently selected from SEQ ID NO: 188, 189 and 190, in particular a light variable region comprising SEQ ID NO: 188 for CDRL1, SEQ ID NO: 189 for CDRL2 and SEQ ID NO: 190 for CDRL3.

In one embodiment a binding molecule of the disclosure comprises a heavy variable region comprising SEQ ID NO: 193 for CDRH1, SEQ ID NO: 194 for CDRH2 and SEQ ID NO: 195 for CDRH3 and at least one CDR in a light chain variable region independently selected from SEQ ID NO: 198, 199 and 200, in particular a light variable region comprising SEQ ID NO: 198 for CDRL1, SEQ ID NO: 199 for CDRL2 and SEQ ID NO: 200 for CDRL3.

In one embodiment a binding molecule of the disclosure comprises a heavy variable region comprising SEQ ID NO: 203 for CDRH1, SEQ ID NO: 204 for CDRH2 and SEQ ID NO: 205 for CDRH3 and at least one CDR in a light chain variable region independently selected from SEQ ID NO: 208, 209 and 220, in particular a light variable region comprising SEQ ID NO: 208 for CDRL1, SEQ ID NO: 209 for CDRL2 and SEQ ID NO: 220 for CDRL3.

In one embodiment a binding molecule of the disclosure comprises a heavy variable region comprising SEQ ID NO: 213 for CDRH1, SEQ ID NO: 214 for CDRH2 and SEQ ID NO: 215 for CDRH3 and at least one CDR in a light chain variable region independently selected from SEQ ID NO: 218, 219 and 220, in particular a light variable region comprising SEQ ID NO: 218 for CDRL1, SEQ ID NO: 219 for CDRL2 and SEQ ID NO: 220 for CDRL3.

In one embodiment a binding molecule of the disclosure comprises a heavy variable region comprising SEQ ID NO: 223 for CDRH1, SEQ ID NO: 224 for CDRH2 and SEQ ID NO: 225 for CDRH3 and at least one CDR in a light chain variable region independently selected from SEQ ID NO: 228, 229 and 230, in particular a light variable region comprising SEQ ID NO: 228 for CDRL1, SEQ ID NO: 229 for CDRL2 and SEQ ID NO: 230 for CDRL3.

In one embodiment a binding molecule of the disclosure comprises a heavy variable region comprising SEQ ID NO: 233 for CDRH1, SEQ ID NO: 234 for CDRH2 and SEQ ID NO: 235 for CDRH3 and at least one CDR in a light chain variable region independently selected from SEQ ID NO: 238, 239 and 240, in particular a light variable region comprising SEQ ID NO: 238 for CDRL1, SEQ ID NO: 239 for CDRL2 and SEQ ID NO: 240 for CDRL3.

In one embodiment a binding molecule of the disclosure comprises a heavy variable region comprising SEQ ID NO: 243 for CDRH1, SEQ ID NO: 244 for CDRH2 and SEQ ID NO: 245 for CDRH3 and at least one CDR in a light chain variable region independently selected from SEQ ID NO: 248, 249 and 250, in particular a light variable region comprising SEQ ID NO: 248 for CDRL1, SEQ ID NO: 249 for CDRL2 and SEQ ID NO: 250 for CDRL3.

In one embodiment a binding molecule of the disclosure comprises a heavy variable region comprising SEQ ID NO: 253 for CDRH1, SEQ ID NO: 254 for CDRH2 and SEQ ID NO: 255 for CDRH3 and at least one CDR in a light chain variable region independently selected from SEQ ID NO: 258, 259 and 260, in particular a light variable region comprising SEQ ID NO: 258 for CDRL1, SEQ ID NO: 259 for CDRL2 and SEQ ID NO: 260 for CDRL3.

In one embodiment a binding molecule of the disclosure comprises a heavy variable region comprising SEQ ID NO: 263 for CDRH1, SEQ ID NO: 264 for CDRH2 and SEQ ID NO: 265 for CDRH3 and at least one CDR in a light chain variable region independently selected from SEQ ID NO: 268, 269 and 270, in particular a light variable region comprising SEQ ID NO: 268 for CDRL1, SEQ ID NO: 269 for CDRL2 and SEQ ID NO: 270 for CDRL3.

In one embodiment a binding molecule of the disclosure comprises a heavy variable region comprising SEQ ID NO: 273 for CDRH1, SEQ ID NO: 274 for CDRH2 and SEQ ID NO: 275 for CDRH3 and at least one CDR in a light chain variable region independently selected from SEQ ID NO: 278, 279 and 280, in particular a light variable region comprising SEQ ID NO: 278 for CDRL1, SEQ ID NO: 279 for CDRL2 and SEQ ID NO: 280 for CDRL3.

In one embodiment a binding molecule of the disclosure comprises a heavy variable region comprising SEQ ID NO: 283 for CDRH1, SEQ ID NO: 284 for CDRH2 and SEQ ID NO: 285 for CDRH3 and at least one CDR in a light chain variable region independently selected from SEQ ID NO: 288, 289 and 290, in particular a light variable region comprising SEQ ID NO: 288 for CDRL1, SEQ ID NO: 289 for CDRL2 and SEQ ID NO: 290 for CDRL3.

In one embodiment a binding molecule of the disclosure comprises a heavy variable region comprising SEQ ID NO: 293 for CDRH1, SEQ ID NO: 294 for CDRH2 and SEQ ID NO: 295 for CDRH3 and at least one CDR in a light chain variable region independently selected from SEQ ID NO: 298, 299 and 300, in particular a light variable region comprising SEQ ID NO: 298 for CDRL1, SEQ ID NO: 299 for CDRL2 and SEQ ID NO: 300 for CDRL3.

In one embodiment a binding molecule of the disclosure comprises a heavy variable region comprising SEQ ID NO: 303 for CDRH1, SEQ ID NO: 304 for CDRH2 and SEQ ID NO: 305 for CDRH3 and at least one CDR in a light chain variable region independently selected from SEQ ID NO: 308, 309 and 320, in particular a light variable region comprising SEQ ID NO: 308 for CDRL1, SEQ ID NO: 309 for CDRL2 and SEQ ID NO: 320 for CDRL3.

In one embodiment a binding molecule of the disclosure comprises a heavy variable region comprising SEQ ID NO: 313 for CDRH1, SEQ ID NO: 314 for CDRH2 and SEQ ID NO: 315 for CDRH3 and at least one CDR in a light chain variable region independently selected from SEQ ID NO: 318, 319 and 320, in particular a light variable region comprising SEQ ID NO: 318 for CDRL1, SEQ ID NO: 319 for CDRL2 and SEQ ID NO: 320 for CDRL3.

In one embodiment a binding molecule of the disclosure comprises a heavy variable region comprising SEQ ID NO: 323 for CDRH1, SEQ ID NO: 324 for CDRH2 and SEQ ID NO: 325 for CDRH3 and at least one CDR in a light chain variable region independently selected from SEQ ID NO: 328, 329 and 330, in particular a light variable region comprising SEQ ID NO: 328 for CDRL1, SEQ ID NO: 329 for CDRL2 and SEQ ID NO: 330 for CDRL3.

In one embodiment a binding molecule of the disclosure comprises a heavy variable region comprising SEQ ID NO: 333 for CDRH1, SEQ ID NO: 334 for CDRH2 and SEQ ID NO: 335 for CDRH3 and at least one CDR in a light chain variable region independently selected from SEQ ID NO: 338, 339 and 340, in particular a light variable region comprising SEQ ID NO: 338 for CDRL1, SEQ ID NO: 339 for CDRL2 and SEQ ID NO: 340 for CDRL3.

In one embodiment a binding molecule of the disclosure comprises a heavy variable region comprising SEQ ID NO: 343 for CDRH1, SEQ ID NO: 344 for CDRH2 and SEQ ID NO: 345 for CDRH3 and at least one CDR in a light chain variable region independently selected from SEQ ID NO: 348, 349 and 350, in particular a light variable region comprising SEQ ID NO: 348 for CDRL1, SEQ ID NO: 349 for CDRL2 and SEQ ID NO: 350 for CDRL3.

In one embodiment a binding molecule of the disclosure comprises a heavy variable region comprising SEQ ID NO: 353 for CDRH1, SEQ ID NO: 354 for CDRH2 and SEQ ID NO: 355 for CDRH3 and at least one CDR in a light chain variable region independently selected from SEQ ID NO: 358, 359 and 360, in particular a light variable region comprising SEQ ID NO: 358 for CDRL1, SEQ ID NO: 359 for CDRL2 and SEQ ID NO: 360 for CDRL3.

In one embodiment a binding molecule of the disclosure comprises a heavy variable region comprising SEQ ID NO: 363 for CDRH1, SEQ ID NO: 364 for CDRH2 and SEQ ID NO: 365 for CDRH3 and at least one CDR in a light chain variable region independently selected from SEQ ID NO: 368, 369 and 370, in particular a light variable region comprising SEQ ID NO: 368 for CDRL1, SEQ ID NO: 369 for CDRL2 and SEQ ID NO: 370 for CDRL3.

In one embodiment a binding molecule of the disclosure comprises a heavy variable region comprising SEQ ID NO: 373 for CDRH1, SEQ ID NO: 374 for CDRH2 and SEQ ID NO: 375 for CDRH3 and at least one CDR in a light chain variable region independently selected from SEQ ID NO: 378, 379 and 380, in particular a light variable region comprising SEQ ID NO: 378 for CDRL1, SEQ ID NO: 379 for CDRL2 and SEQ ID NO: 380 for CDRL3.

In one embodiment a binding molecule of the disclosure comprises a heavy variable region comprising SEQ ID NO: 383 for CDRH1, SEQ ID NO: 384 for CDRH2 and SEQ ID NO: 385 for CDRH3 and at least one CDR in a light chain variable region independently selected from SEQ ID NO: 388, 389 and 390, in particular a light variable region comprising SEQ ID NO: 388 for CDRL1, SEQ ID NO: 389 for CDRL2 and SEQ ID NO: 390 for CDRL3.

In one embodiment a binding molecule of the disclosure comprises a heavy variable region comprising SEQ ID NO: 393 for CDRH1, SEQ ID NO: 394 for CDRH2 and SEQ ID NO: 395 for CDRH3 and at least one CDR in a light chain variable region independently selected from SEQ ID NO: 398, 399 and 400, in particular a light variable region comprising SEQ ID NO: 398 for CDRL1, SEQ ID NO: 399 for CDRL2 and SEQ ID NO: 400 for CDRL3.

In one embodiment a binding molecule of the disclosure comprises a heavy variable region comprising SEQ ID NO: 403 for CDRH1, SEQ ID NO: 404 for CDRH2 and SEQ ID NO: 405 for CDRH3 and at least one CDR in a light chain variable region independently selected from SEQ ID NO: 408, 409 and 420, in particular a light variable region comprising SEQ ID NO: 408 for CDRL1, SEQ ID NO: 409 for CDRL2 and SEQ ID NO: 420 for CDRL3.

In one embodiment a binding molecule of the disclosure comprises a heavy variable region comprising SEQ ID NO: 413 for CDRH1, SEQ ID NO: 414 for CDRH2 and SEQ ID NO: 415 for CDRH3 and at least one CDR in a light chain variable region independently selected from SEQ ID NO: 418, 419 and 420, in particular a light variable region comprising SEQ ID NO: 418 for CDRL1, SEQ ID NO: 419 for CDRL2 and SEQ ID NO: 420 for CDRL3.

In one embodiment a binding molecule of the disclosure comprises a heavy variable region comprising SEQ ID NO: 423 for CDRH1, SEQ ID NO: 424 for CDRH2 and SEQ ID NO: 425 for CDRH3 and at least one CDR in a light chain variable region independently selected from SEQ ID NO: 428, 429 and 430, in particular a light variable region comprising SEQ ID NO: 428 for CDRL1, SEQ ID NO: 429 for CDRL2 and SEQ ID NO: 430 for CDRL3.

In one embodiment a binding molecule of the disclosure comprises a heavy variable region comprising SEQ ID NO: 433 for CDRH1, SEQ ID NO: 434 for CDRH2 and SEQ ID NO: 435 for CDRH3 and at least one CDR in a light chain variable region independently selected from SEQ ID NO: 438, 439 and 440, in particular a light variable region comprising SEQ ID NO: 438 for CDRL1, SEQ ID NO: 439 for CDRL2 and SEQ ID NO: 440 for CDRL3.

In one embodiment a binding molecule of the disclosure comprises a heavy variable region comprising SEQ ID NO: 443 for CDRH1, SEQ ID NO: 444 for CDRH2 and SEQ ID NO: 445 for CDRH3 and at least one CDR in a light chain variable region independently selected from SEQ ID NO: 448, 449 and 450, in particular a light variable region comprising SEQ ID NO: 448 for CDRL1, SEQ ID NO: 449 for CDRL2 and SEQ ID NO: 450 for CDRL3.

In one embodiment a binding molecule of the disclosure comprises a heavy variable region comprising SEQ ID NO: 453 for CDRH1, SEQ ID NO: 454 for CDRH2 and SEQ ID NO: 455 for CDRH3 and at least one CDR in a light chain variable region independently selected from SEQ ID NO: 458, 459 and 460, in particular a light variable region comprising SEQ ID NO: 458 for CDRL1, SEQ ID NO: 459 for CDRL2 and SEQ ID NO: 460 for CDRL3.

In one embodiment a binding molecule of the disclosure comprises a heavy variable region comprising SEQ ID NO: 463 for CDRH1, SEQ ID NO: 464 for CDRH2 and SEQ ID NO: 465 for CDRH3 and at least one CDR in a light chain variable region independently selected from SEQ ID NO: 468, 469 and 470, in particular a light variable region comprising SEQ ID NO: 468 for CDRL1, SEQ ID NO: 469 for CDRL2 and SEQ ID NO: 470 for CDRL3.

In one embodiment a binding molecule of the disclosure comprises a heavy variable region comprising SEQ ID NO: 473 for CDRH1, SEQ ID NO: 474 for CDRH2 and SEQ ID NO: 475 for CDRH3 and at least one CDR in a light chain variable region independently selected from SEQ ID NO: 478, 479 and 480, in particular a light variable region comprising SEQ ID NO: 478 for CDRL1, SEQ ID NO: 479 for CDRL2 and SEQ ID NO: 480 for CDRL3.

In one embodiment a binding molecule of the disclosure comprises a heavy variable region comprising SEQ ID NO: 483 for CDRH1, SEQ ID NO: 484 for CDRH2 and SEQ ID NO: 485 for CDRH3 and at least one CDR in a light chain variable region independently selected from SEQ ID NO: 488, 489 and 490, in particular a light variable region comprising SEQ ID NO: 488 for CDRL1, SEQ ID NO: 489 for CDRL2 and SEQ ID NO: 490 for CDRL3.

In one embodiment a binding molecule of the disclosure comprises a heavy variable region comprising SEQ ID NO: 493 for CDRH1, SEQ ID NO: 494 for CDRH2 and SEQ ID NO: 495 for CDRH3 and at least one CDR in a light chain variable region independently selected from SEQ ID NO: 498, 499 and 500, in particular a light variable region comprising SEQ ID NO: 498 for CDRL1, SEQ ID NO: 499 for CDRL2 and SEQ ID NO: 500 for CDRL3.

In one embodiment a binding molecule of the disclosure comprises a heavy variable region comprising SEQ ID NO: 503 for CDRH1, SEQ ID NO: 504 for CDRH2 and SEQ ID NO: 505 for CDRH3 and at least one CDR in a light chain variable region independently selected from SEQ ID NO: 508, 509 and 520, in particular a light variable region comprising SEQ ID NO: 508 for CDRL1, SEQ ID NO: 509 for CDRL2 and SEQ ID NO: 520 for CDRL3.

In one embodiment a binding molecule of the disclosure comprises a heavy variable region comprising SEQ ID NO: 513 for CDRH1, SEQ ID NO: 514 for CDRH2 and SEQ ID NO: 515 for CDRH3 and at least one CDR in a light chain variable region independently selected from SEQ ID NO: 518, 519 and 520, in particular a light variable region comprising SEQ ID NO: 518 for CDRL1, SEQ ID NO: 519 for CDRL2 and SEQ ID NO: 520 for CDRL3.

In one embodiment a binding molecule of the disclosure comprises a heavy variable region comprising SEQ ID NO: 523 for CDRH1, SEQ ID NO: 524 for CDRH2 and SEQ ID NO: 525 for CDRH3 and at least one CDR in a light chain variable region independently selected from SEQ ID NO: 528, 529 and 530, in particular a light variable region comprising SEQ ID NO: 528 for CDRL1, SEQ ID NO: 529 for CDRL2 and SEQ ID NO: 530 for CDRL3.

In one embodiment a binding molecule of the disclosure comprises a heavy variable region comprising SEQ ID NO: 533 for CDRH1, SEQ ID NO: 534 for CDRH2 and SEQ ID NO: 535 for CDRH3 and at least one CDR in a light chain variable region independently selected from SEQ ID NO: 538, 539 and 540, in particular a light variable region comprising SEQ ID NO: 538 for CDRL1, SEQ ID NO: 539 for CDRL2 and SEQ ID NO: 540 for CDRL3.

In one embodiment a binding molecule of the disclosure comprises a heavy variable region comprising SEQ ID NO: 543 for CDRH1, SEQ ID NO: 544 for CDRH2 and SEQ ID NO: 545 for CDRH3 and at least one CDR in a light chain variable region independently selected from SEQ ID NO: 548, 549 and 550, in particular a light variable region comprising SEQ ID NO: 548 for CDRL1, SEQ ID NO: 549 for CDRL2 and SEQ ID NO: 550 for CDRL3.

In one embodiment a binding molecule of the disclosure comprises a heavy variable region comprising SEQ ID NO: 553 for CDRH1, SEQ ID NO: 554 for CDRH2 and SEQ ID NO: 555 for CDRH3 and at least one CDR in a light chain variable region independently selected from SEQ ID NO: 558, 559 and 560, in particular a light variable region comprising SEQ ID NO: 558 for CDRL1, SEQ ID NO: 559 for CDRL2 and SEQ ID NO: 560 for CDRL3.

In one embodiment a binding molecule of the disclosure comprises a heavy variable region comprising SEQ ID NO: 563 for CDRH1, SEQ ID NO: 564 for CDRH2 and SEQ ID NO: 565 for CDRH3 and at least one CDR in a light chain variable region independently selected from SEQ ID NO: 568, 569 and 570, in particular a light variable region comprising SEQ ID NO: 568 for CDRL1, SEQ ID NO: 569 for CDRL2 and SEQ ID NO: 570 for CDRL3.

In one embodiment a binding molecule of the disclosure comprises a heavy variable region comprising SEQ ID NO: 573 for CDRH1, SEQ ID NO: 574 for CDRH2 and SEQ ID NO: 575 for CDRH3 and at least one CDR in a light chain variable region independently selected from SEQ ID NO: 578, 579 and 580, in particular a light variable region comprising SEQ ID NO: 578 for CDRL1, SEQ ID NO: 579 for CDRL2 and SEQ ID NO: 580 for CDRL3.

In one embodiment a binding molecule of the disclosure comprises a heavy variable region comprising SEQ ID NO: 583 for CDRH1, SEQ ID NO: 584 for CDRH2 and SEQ ID NO: 585 for CDRH3 and at least one CDR in a light chain variable region independently selected from SEQ ID NO: 588, 589 and 590, in particular a light variable region comprising SEQ ID NO: 588 for CDRL1, SEQ ID NO: 589 for CDRL2 and SEQ ID NO: 590 for CDRL3.

In one embodiment the binding molecule of the present disclosure comprises a variable region of SEQ ID NO: 2, for example as a variable region in a heavy chain.

In one embodiment the binding molecule of the present disclosure comprises a variable region of SEQ ID NO: 7 for example as a variable region in a light chain.

In one embodiment the binding molecule of the present disclosure comprises a variable heavy region of SEQ ID NO: 2 and a variable light region of SEQ ID NO: 7.

In one embodiment the binding molecule of the present disclosure comprises a variable region of SEQ ID NO: 12, for example as a variable region in a heavy chain.

In one embodiment the binding molecule of the present disclosure comprises a variable region of SEQ ID NO: 17 for example as a variable region in a light chain.

In one embodiment the binding molecule of the present disclosure comprises a variable heavy region of SEQ ID NO: 12 and a variable light region of SEQ ID NO: 17.

In one embodiment the binding molecule of the present disclosure comprises a variable region of SEQ ID NO: 22, for example as a variable region in a heavy chain.

In one embodiment the binding molecule of the present disclosure comprises a variable region of SEQ ID NO: 27 for example as a variable region in a light chain.

In one embodiment the binding molecule of the present disclosure comprises a variable heavy region of SEQ ID NO: 22 and a variable light region of SEQ ID NO: 27.

In one embodiment the binding molecule of the present disclosure comprises a variable region of SEQ ID NO: 32, for example as a variable region in a heavy chain.

In one embodiment the binding molecule of the present disclosure comprises a variable region of SEQ ID NO: 37 for example as a variable region in a light chain.

In one embodiment the binding molecule of the present disclosure comprises a variable heavy region of SEQ ID NO: 32 and a variable light region of SEQ ID NO: 37.

In one embodiment the binding molecule of the present disclosure comprises a variable region of SEQ ID NO: 52, for example as a variable region in a heavy chain.

In one embodiment the binding molecule of the present disclosure comprises a variable region of SEQ ID NO: 57, for example as a variable region in a light chain.

In one embodiment the binding molecule of the present disclosure comprises a variable heavy region of SEQ ID NO: 52 and a variable light region of SEQ ID NO: 57.

In one embodiment the binding molecule of the present disclosure comprises a variable region of SEQ ID NO: 62, for example as a variable region in a heavy chain.

In one embodiment the binding molecule of the present disclosure comprises a variable region of SEQ ID NO: 67, for example as a variable region in a light chain.

In one embodiment the binding molecule of the present disclosure comprises a variable heavy region of SEQ ID NO: 62 and a variable light region of SEQ ID NO: 67.

In one embodiment the binding molecule of the present disclosure comprises a variable region of SEQ ID NO: 72, for example as a variable region in a heavy chain.

In one embodiment the binding molecule of the present disclosure comprises a variable region of SEQ ID NO: 77, for example as a variable region in a light chain.

In one embodiment the binding molecule of the present disclosure comprises a variable heavy region of SEQ ID NO: 72 and a variable light region of SEQ ID NO: 77.

In one embodiment the binding molecule of the present disclosure comprises a variable region of SEQ ID NO: 82, for example as a variable region in a heavy chain.

In one embodiment the binding molecule of the present disclosure comprises a variable region of SEQ ID NO: 87, for example as a variable region in a light chain.

In one embodiment the binding molecule of the present disclosure comprises a variable heavy region of SEQ ID NO: 82 and a variable light region of SEQ ID NO: 87.

In one embodiment the binding molecule of the present disclosure comprises a variable region of SEQ ID NO: 92, for example as a variable region in a heavy chain.

In one embodiment the binding molecule of the present disclosure comprises a variable region of SEQ ID NO: 97, for example as a variable region in a light chain.

In one embodiment the binding molecule of the present disclosure comprises a variable heavy region of SEQ ID NO: 92 and a variable light region of SEQ ID NO: 97.

In one embodiment the binding molecule of the present disclosure comprises a variable region of SEQ ID NO: 102, for example as a variable region in a heavy chain.

In one embodiment the binding molecule of the present disclosure comprises a variable region of SEQ ID NO: 107 for example as a variable region in a light chain.

In one embodiment the binding molecule of the present disclosure comprises a variable heavy region of SEQ ID NO: 102 and a variable light region of SEQ ID NO: 107.

In one embodiment the binding molecule of the present disclosure comprises a variable region of SEQ ID NO: 112, for example as a variable region in a heavy chain.

In one embodiment the binding molecule of the present disclosure comprises a variable region of SEQ ID NO: 117 for example as a variable region in a light chain.

In one embodiment the binding molecule of the present disclosure comprises a variable heavy region of SEQ ID NO: 112 and a variable light region of SEQ ID NO: 117.

In one embodiment the binding molecule of the present disclosure comprises a variable region of SEQ ID NO: 122, for example as a variable region in a heavy chain.

In one embodiment the binding molecule of the present disclosure comprises a variable region of SEQ ID NO: 127 for example as a variable region in a light chain.

In one embodiment the binding molecule of the present disclosure comprises a variable heavy region of SEQ ID NO: 122 and a variable light region of SEQ ID NO: 127.

In one embodiment the binding molecule of the present disclosure comprises a variable region of SEQ ID NO: 132, for example as a variable region in a heavy chain.

In one embodiment the binding molecule of the present disclosure comprises a variable region of SEQ ID NO: 137 for example as a variable region in a light chain.

In one embodiment the binding molecule of the present disclosure comprises a variable heavy region of SEQ ID NO: 132 and a variable light region of SEQ ID NO: 137.

In one embodiment the binding molecule of the present disclosure comprises a variable region of SEQ ID NO: 152, for example as a variable region in a heavy chain.

In one embodiment the binding molecule of the present disclosure comprises a variable region of SEQ ID NO: 157, for example as a variable region in a light chain.

In one embodiment the binding molecule of the present disclosure comprises a variable heavy region of SEQ ID NO: 152 and a variable light region of SEQ ID NO: 157.

In one embodiment the binding molecule of the present disclosure comprises a variable region of SEQ ID NO: 162, for example as a variable region in a heavy chain.

In one embodiment the binding molecule of the present disclosure comprises a variable region of SEQ ID NO: 167, for example as a variable region in a light chain.

In one embodiment the binding molecule of the present disclosure comprises a variable heavy region of SEQ ID NO: 162 and a variable light region of SEQ ID NO: 167.

In one embodiment the binding molecule of the present disclosure comprises a variable region of SEQ ID NO: 172, for example as a variable region in a heavy chain.

In one embodiment the binding molecule of the present disclosure comprises a variable region of SEQ ID NO: 177, for example as a variable region in a light chain.

In one embodiment the binding molecule of the present disclosure comprises a variable heavy region of SEQ ID NO: 172 and a variable light region of SEQ ID NO: 177.

In one embodiment the binding molecule of the present disclosure comprises a variable region of SEQ ID NO: 182, for example as a variable region in a heavy chain.

In one embodiment the binding molecule of the present disclosure comprises a variable region of SEQ ID NO: 187, for example as a variable region in a light chain.

In one embodiment the binding molecule of the present disclosure comprises a variable heavy region of SEQ ID NO: 182 and a variable light region of SEQ ID NO: 187.

In one embodiment the binding molecule of the present disclosure comprises a variable region of SEQ ID NO: 192, for example as a variable region in a heavy chain.

In one embodiment the binding molecule of the present disclosure comprises a variable region of SEQ ID NO: 197, for example as a variable region in a light chain.

In one embodiment the binding molecule of the present disclosure comprises a variable heavy region of SEQ ID NO: 192 and a variable light region of SEQ ID NO: 197.

In one embodiment the binding molecule of the present disclosure comprises a variable region of SEQ ID NO: 202, for example as a variable region in a heavy chain.

In one embodiment the binding molecule of the present disclosure comprises a variable region of SEQ ID NO: 207, for example as a variable region in a light chain.

In one embodiment the binding molecule of the present disclosure comprises a variable heavy region of SEQ ID NO: 202 and a variable light region of SEQ ID NO: 207.

In one embodiment the binding molecule of the present disclosure comprises a variable region of SEQ ID NO: 212, for example as a variable region in a heavy chain.

In one embodiment the binding molecule of the present disclosure comprises a variable region of SEQ ID NO: 217, for example as a variable region in a light chain.

In one embodiment the binding molecule of the present disclosure comprises a variable heavy region of SEQ ID NO: 212 and a variable light region of SEQ ID NO: 217.

In one embodiment the binding molecule of the present disclosure comprises a variable region of SEQ ID NO: 222, for example as a variable region in a heavy chain.

In one embodiment the binding molecule of the present disclosure comprises a variable region of SEQ ID NO: 227, for example as a variable region in a light chain.

In one embodiment the binding molecule of the present disclosure comprises a variable heavy region of SEQ ID NO: 222 and a variable light region of SEQ ID NO: 227.

In one embodiment the binding molecule of the present disclosure comprises a variable region of SEQ ID NO: 232, for example as a variable region in a heavy chain.

In one embodiment the binding molecule of the present disclosure comprises a variable region of SEQ ID NO: 237, for example as a variable region in a light chain.

In one embodiment the binding molecule of the present disclosure comprises a variable heavy region of SEQ ID NO: 232 and a variable light region of SEQ ID NO: 237.

In one embodiment the binding molecule of the present disclosure comprises a variable region of SEQ ID NO: 242, for example as a variable region in a heavy chain.

In one embodiment the binding molecule of the present disclosure comprises a variable region of SEQ ID NO: 247, for example as a variable region in a light chain.

In one embodiment the binding molecule of the present disclosure comprises a variable heavy region of SEQ ID NO: 242 and a variable light region of SEQ ID NO: 247.

In one embodiment the binding molecule of the present disclosure comprises a variable region of SEQ ID NO: 252, for example as a variable region in a heavy chain.

In one embodiment the binding molecule of the present disclosure comprises a variable region of SEQ ID NO: 257, for example as a variable region in a light chain.

In one embodiment the binding molecule of the present disclosure comprises a variable heavy region of SEQ ID NO: 252 and a variable light region of SEQ ID NO: 257.

In one embodiment the binding molecule of the present disclosure comprises a variable region of SEQ ID NO: 262, for example as a variable region in a heavy chain.

In one embodiment the binding molecule of the present disclosure comprises a variable region of SEQ ID NO: 267, for example as a variable region in a light chain.

In one embodiment the binding molecule of the present disclosure comprises a variable heavy region of SEQ ID NO: 262 and a variable light region of SEQ ID NO: 267.

In one embodiment the binding molecule of the present disclosure comprises a variable region of SEQ ID NO: 272, for example as a variable region in a heavy chain.

In one embodiment the binding molecule of the present disclosure comprises a variable region of SEQ ID NO: 277, for example as a variable region in a light chain.

In one embodiment the binding molecule of the present disclosure comprises a variable heavy region of SEQ ID NO: 272 and a variable light region of SEQ ID NO: 277.

In one embodiment the binding molecule of the present disclosure comprises a variable region of SEQ ID NO: 282, for example as a variable region in a heavy chain.

In one embodiment the binding molecule of the present disclosure comprises a variable region of SEQ ID NO: 287, for example as a variable region in a light chain.

In one embodiment the binding molecule of the present disclosure comprises a variable heavy region of SEQ ID NO: 282 and a variable light region of SEQ ID NO: 287.

In one embodiment the binding molecule of the present disclosure comprises a variable region of SEQ ID NO: 292, for example as a variable region in a heavy chain.

In one embodiment the binding molecule of the present disclosure comprises a variable region of SEQ ID NO: 297, for example as a variable region in a light chain.

In one embodiment the binding molecule of the present disclosure comprises a variable heavy region of SEQ ID NO: 292 and a variable light region of SEQ ID NO: 297.

In one embodiment the binding molecule of the present disclosure comprises a variable region of SEQ ID NO: 302, for example as a variable region in a heavy chain.

In one embodiment the binding molecule of the present disclosure comprises a variable region of SEQ ID NO: 307 for example as a variable region in a light chain.

In one embodiment the binding molecule of the present disclosure comprises a variable heavy region of SEQ ID NO: 302 and a variable light region of SEQ ID NO: 307.

In one embodiment the binding molecule of the present disclosure comprises a variable region of SEQ ID NO: 312, for example as a variable region in a heavy chain.

In one embodiment the binding molecule of the present disclosure comprises a variable region of SEQ ID NO: 317 for example as a variable region in a light chain.

In one embodiment the binding molecule of the present disclosure comprises a variable heavy region of SEQ ID NO: 312 and a variable light region of SEQ ID NO: 317.

In one embodiment the binding molecule of the present disclosure comprises a variable region of SEQ ID NO: 322, for example as a variable region in a heavy chain.

In one embodiment the binding molecule of the present disclosure comprises a variable region of SEQ ID NO: 327 for example as a variable region in a light chain.

In one embodiment the binding molecule of the present disclosure comprises a variable heavy region of SEQ ID NO: 322 and a variable light region of SEQ ID NO: 327.

In one embodiment the binding molecule of the present disclosure comprises a variable region of SEQ ID NO: 332, for example as a variable region in a heavy chain.

In one embodiment the binding molecule of the present disclosure comprises a variable region of SEQ ID NO: 337 for example as a variable region in a light chain.

In one embodiment the binding molecule of the present disclosure comprises a variable heavy region of SEQ ID NO: 332 and a variable light region of SEQ ID NO: 337.

In one embodiment the binding molecule of the present disclosure comprises a variable region of SEQ ID NO: 352, for example as a variable region in a heavy chain.

In one embodiment the binding molecule of the present disclosure comprises a variable region of SEQ ID NO: 357, for example as a variable region in a light chain.

In one embodiment the binding molecule of the present disclosure comprises a variable heavy region of SEQ ID NO: 352 and a variable light region of SEQ ID NO: 357.

In one embodiment the binding molecule of the present disclosure comprises a variable region of SEQ ID NO: 362, for example as a variable region in a heavy chain.

In one embodiment the binding molecule of the present disclosure comprises a variable region of SEQ ID NO: 367, for example as a variable region in a light chain.

In one embodiment the binding molecule of the present disclosure comprises a variable heavy region of SEQ ID NO: 362 and a variable light region of SEQ ID NO: 367.

In one embodiment the binding molecule of the present disclosure comprises a variable region of SEQ ID NO: 372, for example as a variable region in a heavy chain.

In one embodiment the binding molecule of the present disclosure comprises a variable region of SEQ ID NO: 377, for example as a variable region in a light chain.

In one embodiment the binding molecule of the present disclosure comprises a variable heavy region of SEQ ID NO: 372 and a variable light region of SEQ ID NO: 377.

In one embodiment the binding molecule of the present disclosure comprises a variable region of SEQ ID NO: 382, for example as a variable region in a heavy chain.

In one embodiment the binding molecule of the present disclosure comprises a variable region of SEQ ID NO: 387, for example as a variable region in a light chain.

In one embodiment the binding molecule of the present disclosure comprises a variable heavy region of SEQ ID NO: 382 and a variable light region of SEQ ID NO: 387.

In one embodiment the binding molecule of the present disclosure comprises a variable region of SEQ ID NO: 392, for example as a variable region in a heavy chain.

In one embodiment the binding molecule of the present disclosure comprises a variable region of SEQ ID NO: 397, for example as a variable region in a light chain.

In one embodiment the binding molecule of the present disclosure comprises a variable heavy region of SEQ ID NO: 392 and a variable light region of SEQ ID NO: 397.

In one embodiment the binding molecule of the present disclosure comprises a variable region of SEQ ID NO: 402, for example as a variable region in a heavy chain.

In one embodiment the binding molecule of the present disclosure comprises a variable region of SEQ ID NO: 407 for example as a variable region in a light chain.

In one embodiment the binding molecule of the present disclosure comprises a variable heavy region of SEQ ID NO: 402 and a variable light region of SEQ ID NO: 407.

In one embodiment the binding molecule of the present disclosure comprises a variable region of SEQ ID NO: 412, for example as a variable region in a heavy chain.

In one embodiment the binding molecule of the present disclosure comprises a variable region of SEQ ID NO: 417 for example as a variable region in a light chain.

In one embodiment the binding molecule of the present disclosure comprises a variable heavy region of SEQ ID NO: 412 and a variable light region of SEQ ID NO: 417.

In one embodiment the binding molecule of the present disclosure comprises a variable region of SEQ ID NO: 422, for example as a variable region in a heavy chain.

In one embodiment the binding molecule of the present disclosure comprises a variable region of SEQ ID NO: 427 for example as a variable region in a light chain.

In one embodiment the binding molecule of the present disclosure comprises a variable heavy region of SEQ ID NO: 422 and a variable light region of SEQ ID NO: 427.

In one embodiment the binding molecule of the present disclosure comprises a variable region of SEQ ID NO: 432, for example as a variable region in a heavy chain.

In one embodiment the binding molecule of the present disclosure comprises a variable region of SEQ ID NO: 437 for example as a variable region in a light chain.

In one embodiment the binding molecule of the present disclosure comprises a variable heavy region of SEQ ID NO: 432 and a variable light region of SEQ ID NO: 437.

In one embodiment the binding molecule of the present disclosure comprises a variable region of SEQ ID NO: 452, for example as a variable region in a heavy chain.

In one embodiment the binding molecule of the present disclosure comprises a variable region of SEQ ID NO: 457, for example as a variable region in a light chain.

In one embodiment the binding molecule of the present disclosure comprises a variable heavy region of SEQ ID NO: 452 and a variable light region of SEQ ID NO: 457.

In one embodiment the binding molecule of the present disclosure comprises a variable region of SEQ ID NO: 462, for example as a variable region in a heavy chain.

In one embodiment the binding molecule of the present disclosure comprises a variable region of SEQ ID NO: 467, for example as a variable region in a light chain.

In one embodiment the binding molecule of the present disclosure comprises a variable heavy region of SEQ ID NO: 462 and a variable light region of SEQ ID NO: 467.

In one embodiment the binding molecule of the present disclosure comprises a variable region of SEQ ID NO: 472, for example as a variable region in a heavy chain.

In one embodiment the binding molecule of the present disclosure comprises a variable region of SEQ ID NO: 477, for example as a variable region in a light chain.

In one embodiment the binding molecule of the present disclosure comprises a variable heavy region of SEQ ID NO: 472 and a variable light region of SEQ ID NO: 477.

In one embodiment the binding molecule of the present disclosure comprises a variable region of SEQ ID NO: 482, for example as a variable region in a heavy chain.

In one embodiment the binding molecule of the present disclosure comprises a variable region of SEQ ID NO: 487, for example as a variable region in a light chain.

In one embodiment the binding molecule of the present disclosure comprises a variable heavy region of SEQ ID NO: 482 and a variable light region of SEQ ID NO: 487.

In one embodiment the binding molecule of the present disclosure comprises a variable region of SEQ ID NO: 492, for example as a variable region in a heavy chain.

In one embodiment the binding molecule of the present disclosure comprises a variable region of SEQ ID NO: 497, for example as a variable region in a light chain.

In one embodiment the binding molecule of the present disclosure comprises a variable heavy region of SEQ ID NO: 492 and a variable light region of SEQ ID NO: 497.

In one embodiment the binding molecule of the present disclosure comprises a variable region of SEQ ID NO: 502, for example as a variable region in a heavy chain.

In one embodiment the binding molecule of the present disclosure comprises a variable region of SEQ ID NO: 507 for example as a variable region in a light chain.

In one embodiment the binding molecule of the present disclosure comprises a variable heavy region of SEQ ID NO: 502 and a variable light region of SEQ ID NO: 507.

In one embodiment the binding molecule of the present disclosure comprises a variable region of SEQ ID NO: 512, for example as a variable region in a heavy chain.

In one embodiment the binding molecule of the present disclosure comprises a variable region of SEQ ID NO: 517 for example as a variable region in a light chain.

In one embodiment the binding molecule of the present disclosure comprises a variable heavy region of SEQ ID NO: 512 and a variable light region of SEQ ID NO: 517.

In one embodiment the binding molecule of the present disclosure comprises a variable region of SEQ ID NO: 522, for example as a variable region in a heavy chain.

In one embodiment the binding molecule of the present disclosure comprises a variable region of SEQ ID NO: 527 for example as a variable region in a light chain.

In one embodiment the binding molecule of the present disclosure comprises a variable heavy region of SEQ ID NO: 522 and a variable light region of SEQ ID NO: 527.

In one embodiment the binding molecule of the present disclosure comprises a variable region of SEQ ID NO: 532, for example as a variable region in a heavy chain.

In one embodiment the binding molecule of the present disclosure comprises a variable region of SEQ ID NO: 537 for example as a variable region in a light chain.

In one embodiment the binding molecule of the present disclosure comprises a variable heavy region of SEQ ID NO: 532 and a variable light region of SEQ ID NO: 537.

In one embodiment the binding molecule of the present disclosure comprises a variable region of SEQ ID NO: 552, for example as a variable region in a heavy chain.

In one embodiment the binding molecule of the present disclosure comprises a variable region of SEQ ID NO: 557, for example as a variable region in a light chain.

In one embodiment the binding molecule of the present disclosure comprises a variable heavy region of SEQ ID NO: 552 and a variable light region of SEQ ID NO: 557.

In one embodiment the binding molecule of the present disclosure comprises a variable region of SEQ ID NO: 562, for example as a variable region in a heavy chain.

In one embodiment the binding molecule of the present disclosure comprises a variable region of SEQ ID NO: 567, for example as a variable region in a light chain.

In one embodiment the binding molecule of the present disclosure comprises a variable heavy region of SEQ ID NO: 562 and a variable light region of SEQ ID NO: 567.

In one embodiment the binding molecule of the present disclosure comprises a variable region of SEQ ID NO: 572, for example as a variable region in a heavy chain.

In one embodiment the binding molecule of the present disclosure comprises a variable region of SEQ ID NO: 577, for example as a variable region in a light chain.

In one embodiment the binding molecule of the present disclosure comprises a variable heavy region of SEQ ID NO: 572 and a variable light region of SEQ ID NO: 577.

In one embodiment the binding molecule of the present disclosure comprises a variable region of SEQ ID NO: 582, for example as a variable region in a heavy chain.

In one embodiment the binding molecule of the present disclosure comprises a variable region of SEQ ID NO: 587, for example as a variable region in a light chain.

In one embodiment the binding molecule of the present disclosure comprises a variable heavy region of SEQ ID NO: 582 and a variable light region of SEQ ID NO: 587.

In one embodiment the binding molecule of the present disclosure comprises a variable region of SEQ ID NO: 592, for example as a variable region in a heavy chain.

In one embodiment the binding molecule of the present disclosure comprises a variable region of SEQ ID NO: 594, for example as a variable region in a light chain.

In one embodiment the binding molecule of the present disclosure comprises a variable heavy region of SEQ ID NO: 592 and a variable light region of SEQ ID NO: 59.

In one embodiment the binding molecule of the present disclosure comprises a variable region of SEQ ID NO: 596, for example as a variable region in a heavy chain.

In one embodiment the binding molecule of the present disclosure comprises a variable region of SEQ ID NO: 598, for example as a variable region in a light chain.

In one embodiment the binding molecule of the present disclosure comprises a variable heavy region of SEQ ID NO: 596 and a variable light region of SEQ ID NO: 598.

In one embodiment the binding molecule of the present disclosure comprises a variable region of SEQ ID NO: 600, for example as a variable region in a heavy chain.

In one embodiment the binding molecule of the present disclosure comprises a variable region of SEQ ID NO: 602, for example as a variable region in a light chain.

In one embodiment the binding molecule of the present disclosure comprises a variable heavy region of SEQ ID NO: 600 and a variable light region of SEQ ID NO: 602.

In one embodiment the binding molecule of the present disclosure comprises a variable region of SEQ ID NO: 604, for example as a variable region in a heavy chain.

In one embodiment the binding molecule of the present disclosure comprises a variable region of SEQ ID NO: 606, for example as a variable region in a light chain.

In one embodiment the binding molecule of the present disclosure comprises a variable heavy region of SEQ ID NO: 604 and a variable light region of SEQ ID NO: 606.

In one embodiment the binding molecule of the present disclosure comprises a variable region of SEQ ID NO: 608, for example as a variable region in a heavy chain.

In one embodiment the binding molecule of the present disclosure comprises a variable region of SEQ ID NO: 610, for example as a variable region in a light chain.

In one embodiment the binding molecule of the present disclosure comprises a variable heavy region of SEQ ID NO: 608 and a variable light region of SEQ ID NO: 610.

In one embodiment the binding molecule of the present disclosure comprises a variable region of SEQ ID NO: 612, for example as a variable region in a heavy chain.

In one embodiment the binding molecule of the present disclosure comprises a variable region of SEQ ID NO: 614, for example as a variable region in a light chain.

In one embodiment the binding molecule of the present disclosure comprises a variable heavy region of SEQ ID NO: 612 and a variable light region of SEQ ID NO: 614.

In one embodiment the binding molecule of the present disclosure comprises a variable region of SEQ ID NO: 616, for example as a variable region in a heavy chain.

In one embodiment the binding molecule of the present disclosure comprises a variable region of SEQ ID NO: 618, for example as a variable region in a light chain.

In one embodiment the binding molecule of the present disclosure comprises a variable heavy region of SEQ ID NO: 616 and a variable light region of SEQ ID NO: 618.

In one embodiment the binding molecule of the present disclosure comprises a variable region of SEQ ID NO: 620, for example as a variable region in a heavy chain.

In one embodiment the binding molecule of the present disclosure comprises a variable region of SEQ ID NO: 622, for example as a variable region in a light chain.

In one embodiment the binding molecule of the present disclosure comprises a variable heavy region of SEQ ID NO: 620 and a variable light region of SEQ ID NO: 622.

In one embodiment the binding molecule of the present disclosure comprises a variable region of SEQ ID NO: 624, for example as a variable region in a heavy chain.

In one embodiment the binding molecule of the present disclosure comprises a variable region of SEQ ID NO: 626, for example as a variable region in a light chain.

In one embodiment the binding molecule of the present disclosure comprises a variable heavy region of SEQ ID NO: 624 and a variable light region of SEQ ID NO: 626.

In another embodiment, the present disclosure is directed to an isolated antibody or antigen-binding fragment thereof which specifically binds to IL-33, comprising a VH and VL, wherein the VH has an amino acid sequence at least 90%, for example 91, 92, 93, 94, 95, 96, 97, 98, 99 or 100% identical to a VH as disclosed above e.g. SEQ ID NO: 182 or SEQ ID NO 616

In another embodiment, the present disclosure is directed to an isolated antibody or antigen-binding fragment thereof which specifically binds to IL-33, comprising a VH and VL, wherein a VH as disclosed above, e.g. in SEQ ID NO: 182 or SEQ ID NO 616, has a sequence with 1, 2, 3 or 4 amino acids in the framework independently replaced with a different amino acid or deleted.

In another embodiment, the present disclosure is directed to an isolated antibody or antigen-binding fragment thereof which specifically binds to IL-33, comprising a VH and VL, wherein the VL has an amino acid sequence at least 90%, for example 91, 92, 93, 94, 95, 96, 97, 98, 99 or 100% identical to a VL as disclosed above, e.g. SEQ ID NO: 187 or SEQ ID NO 618.

In another embodiment, the present disclosure is directed to an isolated antibody or antigen-binding fragment thereof which specifically binds to IL-33, comprising a VH and VL, wherein a VL disclosed above, e.g. in SEQ ID NO: 187 or SEQ ID NO 618, has a sequence with 1, 2, 3 or 4 amino acids in the framework independently replaced with a different amino acid or deleted.

In another embodiment, the present disclosure is directed to an isolated antibody or antigen-binding fragment thereof which specifically binds to IL-33, comprising a VH and VL, wherein the VH has an amino acid sequence at least 90%, for example 91, 92, 93, 94, 95, 96, 97, 98, 99 or 100% identical to a VH as disclosed above, e.g. SEQ ID NO: 182 or SEQ ID NO. 616, and VL has an amino acid sequence at least 90%, for example 91, 92, 93, 94, 95, 96, 97, 98, 99 or 100% identical to a VL as disclosed above, e.g. SEQ ID NO: 187 or SEQ ID NO 618.

In another embodiment, the present disclosure is directed to an isolated antibody or antigen-binding fragment thereof which specifically binds to IL-33, comprising a VH and VL, wherein a VH a VH as disclosed above e.g. SEQ ID NO: 182 or SEQ ID NO 616 has a sequence with 1, 2, 3 or 4 amino acids in the framework are independently replaced with a different amino acid or deleted a VL disclosed above, e.g. in SEQ ID NO: 187 or SEQ ID NO 618 has a sequence with 1, 2, 3 or 4 amino acids in the framework are independently replaced with a different amino acid or deleted.

In one embodiment there is provided an antibody or binding fragment which cross-blocks a binding molecule, for example an antibody or binding fragment according to the present disclosure, in particular wherein said antibody or binding fragment binds the same epitope as a molecule disclosed herein.

In some embodiments, the binding molecule or the antibody or antigen-binding fragment thereof is a human antibody, a chimeric antibody, or a humanized antibody. In some embodiments, the binding molecule or the antibody or antigen-binding fragment thereof is a naturally-occurring antibody, an scFv fragment, an Fab fragment, an F(ab')2 fragment, a minibody, a diabody, a triabody, a tetrabody, or a single chain antibody. In some embodiments, the binding molecule or the antibody or antigen-binding fragment thereof is a monoclonal antibody.

In another embodiment, the present disclosure is directed to a polynucleotide encoding the binding molecule or the antibody or antigen-binding fragment thereof of the disclosure, in particular as described herein. In certain embodiments, the polynucleotide encodes the VH of an antibody or antigen-binding fragment thereof of the disclosure. In certain embodiments, the polynucleotide encodes a VL of an antibody or antigen-binding fragment thereof of the disclosure.

In some embodiments, the disclosure is directed to a vector comprising the polynucleotide of the disclosure.

In some embodiments, the disclosure is directed to a composition comprising the polynucleotide or a vector of the disclosure.

In another embodiment, there is provided a host cell comprising the polynucleotide or a vector of the disclosure.

In another embodiment, the disclosure herein is directed to a method of producing an anti-IL-33 antibody or antigen-binding fragment thereof, comprising culturing the host cell of the disclosure, and recovering said antibody or antigen-binding fragment thereof. In some embodiments, the disclosure is directed to an anti-IL-33 antibody or antigen-binding fragment thereof produced by a method of the disclosure.

In another embodiment, the disclosure is directed to a pharmaceutical composition comprising a binding molecule or an antibody or antigen-binding fragment thereof of the disclosure and a carrier.

In another embodiment, the disclosure is directed to a method for treating a subject with an inflammatory condition comprising administering to said subject an effective amount of an antibody or antigen-binding fragment according to the present disclosure that inhibits IL-33 driven cytokine production.

In another embodiment, there is provided a method of treating a subject with an inflammatory condition comprising administering a binding molecule of the present disclosure or a composition comprising the same.

In one aspect there is provided a binding molecule of the present disclosure or a composition comprising the same for use in treatment, for example an inflammatory condition, in particular as described herein.

In one embodiment there is provided the use of a binding molecule of the present disclosure or a composition comprising the same in the manufacture of a medication for the treatment or prevention of an inflammatory condition.

In one embodiment the inflammatory condition is selected from asthma, chronic obstructive pulmonary disease (COPD), chronic rhinosinusitis, a fibroproliferative disease (for example pulmonary fibrosis), pulmonary eosinophilia, pleural malignancy, rheumatoid arthritis, collagen vascular disease, atherosclerotic vascular disease, uticaria, inflammatory bowel disease (for example Crohn's disease or Coeliac disease), systemic lupus erythematosus, progressive systemic sclerosis, Wegner's granulomatosis, septic shock and Bechet's disease.

In some embodiments, the inflammatory condition is an allergic disorder, for example asthma, chronic rhinosinusitis, food allergy, eczema or dermatitis, in particular asthma, such as refractory asthma (also referred to as severe asthma).

In some embodiments the inflammatory response or condition is in the airway of said subject.

In one embodiment the inflammatory response or condition is in smooth muscle.

In another embodiment, the disclosure is directed to a method for preventing an inflammatory response in a subject comprising administering to said subject an effective amount of an antibody or antigen-binding fragment thereof that binds IL-33 and does not block IL-33 from binding to ST2 wherein ST2 signaling is reduced.

In another embodiment, the disclosure is directed to a method for preventing an inflammatory response in a subject comprising administering to said subject an effective amount of an antibody or antigen-binding fragment according to the present disclosure that inhibits IL-33 driven cytokine production.

In another embodiment, the disclosure is directed to a method for preventing an inflammatory response in a subject comprising administering to said subject an effective amount of a binding molecule or an antibody or antigen-binding fragment thereof of the disclosure.

In another embodiment, the disclosure is directed to a method of identifying a therapeutic antibody or antigen-binding fragment thereof comprising selecting for an antibody or antigen-binding fragment thereof that binds to IL-33, wherein said antibody or antigen-binding fragment thereof does not block IL-33 from binding to ST2 and inhibits IL-33 driven cytokine production.

In one embodiment there is provided immunizing a host with redIL-33, for example stabilized in the reduced form, a or mutant thereof which has a reduced capacity to form disulfide bonds, in particular a reduced capacity to form a disulfide bond at one or more locations independently selected from Cys-208, Cys-227, Cys-232 and Cys-259. In one embodiment the method further comprises the steps of screen antibodies from the host, for example employing functional assays and isolating and/or replicating at least the variable regions from at least one of the said antibodies.

In embodiment there is provided use of redIL-33, for example stabilized in the reduced form, a or mutant thereof which has a reduced capacity to form disulfide bonds, in particular a reduced capacity to form a disulfide bond at one or more locations independently selected from Cys-208, Cys-227, Cys-232 and Cys-259, to identify an inhibitor of the ST2 signaling, in particular an antibody or binding fragment thereof specific to redIL-33. In one embodiment the use employs interrogating a library, for example a phage display antibody library employing said protein or active fragment thereof.

In some embodiments, the antibody or antigen-binding fragment thereof of the disclosure does not inhibit NFκB signaling.

In one embodiment there is provided a method of identifying or generating a binding molecule of the present disclosure employing redIL-33 or a mutant of the present disclosure (referred herein collectively as a protein of the present disclosure). In one embodiment the method comprises the step of interrogating a library with proteins of the present disclosure to identify a binding molecule. In one embodiment the method comprises immunizing a host with a protein of the present disclosure.

In one embodiment there is provided an epitope from IL-33, which is bound by a binding molecule, such as an antibody or binding fragment thereof, as disclosed herein, in particular a catalytic epitope, i.e. an epitope the binding of which augments the rate of conversion of the IL-33 reduced form to the oxidized form.

In another embodiment, the disclosure is directed to a method for detecting redIL-33 expression in a sample.

DETAILED DESCRIPTION OF THE INVENTION

I. Definitions

"Isolated" as employed herein refers to a protein in a non-natural environment in particular isolated from nature, for example the term does not include the protein in vivo, nor the protein in a sample taken from a human or animal body. Generally proteins will be in a carrier such as a liquid or media, or may be formulated, frozen or freeze dried and all of these forms may be encompassed by "isolated" as appropriate. In one embodiment isolated does not refer to protein in a gel, for example a gel employed in Western blot analysis or similar.

IL-33 protein as employed herein refers to interleukin 33, in particular a mammalian interleukin 33 protein, for example human protein deposited with UniProt number O95760. However, given the present inventors findings, it clear that this entity is not a single species but instead exists as reduced and oxidized form. Given the rapid oxidation of the reduced form in vivo, for example in the period 5 minutes to 40 minutes, and in vitro, generally prior art references to IL-33 are in fact references to the oxidized form. Furthermore, commercial assays appear to quantify this oxidized form.

Oxidized IL-33, IL-33-DSB (disulfide bonded) and DSB IL-33 are employed interchangeably herein.

Oxidized IL-33 as employed herein refers to a protein visible as a distinct band, for example by western blot analysis under non-reducing conditions, in particular with a mass 4 Da less than the corresponding reduced from. In particular, it refers to a protein with one or two disulphide bonds between the cysteines independently selected from cysteines 208, 227, 232 and 259. In one embodiment the oxidized IL-33 shows no binding to ST2.

Reduced IL-33 and redIL-33 are employed interchangeably herein.

Reduced IL-33 as employed herein refers to form of the IL-33 that binds to ST2 and triggers ST2 dependent signaling. In particular cysteines 208, 227, 232 and 259 of the reduced form are not disulfide bonded. An active fragment of redIL-33 as employed herein refers to a fragment with comparable activity to redIL-33, for example a similar extent of ST2-dependent signaling. In one embodiment an active fragment is 20, 30 40, 50, 60, 70, 75, 80, 85, 90, 95, 96, 97, 98 or 99% of the activity of the full length redIL-33.

ST-2 dependent signaling as employed herein refers to the IL-33/ST2 system where IL-33 recognition by ST2 promotes dimerization with IL1-RAcP on the cell surface and within the cell recruitment of receptor complex components MyD88, TRAF6 and IRAK1-4 to intracellular TIR domain. Thus ST-2 dependent signaling may be interrupted by perturbing the interaction of IL-33 with ST2 or alternatively by interrupting the interaction with IL-1RAcP.

"Stabilized in a reduced form" as employed herein refers to a modification which encourages the proteins to adopt or stay in the reduced from or prevents the formation of oxidized IL-33.

In one embodiment the stabilization is by conjugation to a chemical entity, for example biotinylation. redIL-33 has a tendency to be mono-biotinylated when exposed at neutral pH to the —SH reactive reagent biotin-BMCC (Available from Thermo scientific). The analysis performed by the present inventors suggests that the biotinylation occurs at Cys208. Biotinylation at this location appears to block and/or reduce oxidation of the protein. Whilst not wishing to be bound by theory the in silico analysis performed by the inventors suggests that Cys208 is a potential initiator of the activities required for conformational changes and oxidation of the protein.

In one embodiment the stabilization is biotinylation at Cys208.

In one embodiment Cys208 is replaced by an amino acid, such as serine. In one embodiment Cys227 is replaced by an amino acid, such as serine. In one embodiment Cys232 is replaced by an amino acid, such as serine. In one embodiment Cys259 is replaced by an amino acid, such as serine. In one embodiment Cys208 and 227 are independently replaced by an amino acid, such as serine. In one embodiment Cys208 and 232 are independently replaced by an amino acid, such as serine. In one embodiment Cys208 and 259 are independently replaced by an amino acid, such as serine. In one embodiment Cys208, 227 and 232 are independently replaced by an amino acid, such as serine. In one embodiment Cys208, 227 and 259 are independently replaced by an amino acid, such as serine. In one embodiment Cys208, 232 and 259 are independently replaced by an amino acid, such as serine. In one embodiment Cys227, 232 and 259 are independently replaced by an amino acid, such as serine. In one embodiment Cys208, 227, 232 and 259 are independently replaced by an amino acid, such as serine.

Mutation as employed herein refers to a change in the amino acid sequence or a change in a polynucleotide sequence such that the amino acid encoded by the polynucleotide is different or some other tangible, for example functional difference is achieved. In particular the change may comprise the deletion or substitution of an amino residue. Codon optimization or redundancy in the genetic code is not a mutation in the context of the present application.

Mutation will generally be employed herein wherein there is an amino acid or polynucleotide sequence change to the native or wild-type protein, whereas variant will be employed when discussing changes to novel sequences.

Native as employed herein refers to an entity, such as an amino acid which is found in the wild-type sequence or is otherwise naturally occurring.

Conjugated as employed herein refers to a connection joining two entities or fragments, for example a bond, such as a con-valent bond.

An entity as employed herein refers to an "element", molecule, fragment, atom, component or the like.

A chemical entity is a molecule or fragment of the type prepared by synthetic chemical processes.

In one embodiment the stabilization is by mutation of the IL-33 protein, for example a point mutation, in particular replacing one or more cysteine amino acids with an alternative amino acid, for example serine. An alternative amino acid as employed in this context refers to a non-cysteine amino acid. In one embodiment the amino acid is a non-naturally occurring amino acid. In one embodiment the amino acid is a naturally occurring amino acid. In one embodiment the amino acid is proteinaceous. In one embodiment the amino acid is serine, which is advantageous because it is a conservative substitution and generally activity of the protein is retained, after this substitution.

Stabilization of the redIL-33 is important because it fixes the form of IL-33 in the active conformation, which can in turn be used as a tool to find binding molecules that attenuate the protein's activity. In one embodiment the stabilized protein is employed to interrogate a library of molecules such as a phage library of antibodies or synthetic libraries of antibodies. In one embodiment the stabilized protein is employed to immunize a host, thereby providing for the first time an opportunity to generate antibodies specific to the reduced form.

"Attenuates the activity of" as employed herein refers to reducing the relevant activity or stopping the relevant activity. Generally attenuation and inhibition are employed interchangeably herein unless the context indicates otherwise.

In one embodiment the attenuation is by binding redIL-33. In one embodiment the binding molecule, such as an antibody or binding fragment thereof is specific to redIL-33, that is to say it has a greater affinity for redIL-33 than for oxidized form, for example 1, 2, 3, 4, 5 greater affinity or more. This is referred to herein as a redIL-33 specific antibody.

In one embodiment a redIL-33 specific antibody binds such that it sterically blocks binding to the receptor ST2.

In one embodiment a redIL-33 specific antibody binds such that it sterically blocks binding to the receptor IL-1RAcP.

In one embodiment a redIL-33 specific antibody binds such that it allosterically blocks binding to the receptor ST2.

In one embodiment a redIL-33 specific antibody binds such that it allosterically blocks binding to the receptor IL-1RAcP.

In one embodiment a redIL-33 specific antibody binds such that it allosterically blocks signaling through the receptor ST2, but may bind ST2 and/or IL-1RAcP.

In one embodiment the antibody binds the oxidized form of IL-33 and catalyses conversion of the reduced form to the oxidized form. Whilst not wishing to be bound by theory it may be that by binding the oxidized form, the equilibrium of the process is changed in favour of conversion to the oxidized form.

It is to be noted that the term "a" or "an" entity refers to one or more of that entity; for example, "an anti-IL-33 antibody" is understood to represent one or more anti-IL-33 antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

An "isolated" polypeptide or a fragment, variant, or derivative thereof is intended to refer to a polypeptide that is not in its natural milieu. No particular level of purification is required. For example, an isolated polypeptide can be removed from its native or natural environment. Recombinantly produced polypeptides and proteins expressed in host cells are considered isolated for purpose of the disclosure, as are native or recombinant polypeptides that have been separated, fractionated, or partially or substantially purified by any suitable technique.

Protein as employed herein refers to a polypeptide with secondary and tertiary structure.

Also included as polypeptides of the present disclosure are fragments, derivatives, analogs, or variants of the foregoing polypeptides, and any combination thereof.

The terms "fragment," "variant," "derivative," and "analog", for example when referring to a protein or polypeptide of the present disclosure, such as a anti-IL-33 antibodies or antibody polypeptides of the present disclosure include any polypeptides that retain at least some of the antigen-binding properties of the corresponding antibody or antibody polypeptide of the disclosure. Fragments of polypeptides of the present disclosure include proteolytic fragments, as well as deletion fragments, in addition to specific antibody fragments discussed elsewhere herein. Variants of anti-IL-33 antibodies and antibody polypeptides of the present disclosure include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques.

Variant polypeptides may comprise conservative or non-conservative amino acid substitutions, deletions, or additions. Variant polypeptides may also be referred to herein as "polypeptide analogs." As used herein a "derivative" of, for example an anti-IL-33 antibody or antibody polypeptide, refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Derivatives of anti-IL-33 antibodies and antibody polypeptides of the present disclosure, may include polypeptides that have been altered so as to exhibit additional features not found on the reference antibody or antibody polypeptide of the disclosure.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-IL-33 binding molecule, e.g., an antibody or antigen binding fragment thereof, contained in a vector is considered isolated for the purposes of the present disclosure. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present disclosure can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the disclosure may encode heterologous coding regions, either fused or unfused to a nucleic acid encoding an anti-IL-33 antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide of the present disclosure is RNA, for example, in the form of messenger RNA (mRNA).

Polynucleotide and nucleic acid coding regions of the present disclosure may be associated with additional coding regions that encode secretory or signal peptides, which direct the secretion of a polypeptide encoded by a polynucleotide of the present disclosure. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" or "antigen binding molecule" of the present disclosure refers in its broadest sense to a molecule that specifically binds an antigenic determinant. In one embodiment, the binding molecule specifically binds to IL-33, in particular redIL-33 or IL-33-DSB. In another embodiment, a binding molecule of the disclosure is an antibody or an antigen-binding fragment thereof.

In another embodiment, a binding molecule of the disclosure comprises at least one heavy or light chain CDR of a reference antibody molecule. In another embodiment, a binding molecule of the disclosure comprises at least six CDRs from one or more reference antibody molecules.

The present disclosure is directed to certain anti-IL-33 antibodies, or antigen-binding fragments, variants, or derivatives thereof.

Antibody as employed herein refers to an immunoglobulin molecule as discussed below in more detail, in particular a full-length antibody or a molecule comprising a full-length antibody, for example a DVD-Ig mole and the like.

A binding fragment is an epitope/antigen binding fragment of an antibody fragment, for example comprising a binding, in particular comprising 6 CDRs, such as 3 CDRs in heavy variable region and 3 CDRs in light variable region.

Unless specifically referring to full-sized antibodies such as naturally occurring antibodies, the term "anti-IL-33 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins. Completely human antibodies are particularly desirable for therapeutic treatment of human patients. Human antibodies can be made by a variety of methods known in the art including phage display methods using antibody libraries derived from human immunoglobulin sequences as described in Vaughan et al., *Nat. Biotech.* 14:309-314 (1996), Sheets et al., *Proc. Nat'l. Acad. Sci.* 95:6157-6162 (1998), Hoogenboom and Winter, *J. Mol. Biol.* 227:381 (1992), and Marks et al., *J. Mol. Biol.* 222:581 (1991)). Techniques for the generation and use of antibody phage libraries are also described in, e.g., U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., *J. Mol. Biol.*, 376:1382 (2008) (each of which is incorporated by reference in its entirety). In addition, as known in the art, human antibodies can be produced using transgenic mice which are incapable of expressing functional endogenous immunoglobulins, but which can express human immunoglobulin genes. For an overview of this technology, see Lonberg and Huszar, *Int. Rev. Immunol.* 13:65-93 (1995). "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a IL-33 polypeptide or fragment or variant thereof according to the present disclosure.

Standard techniques known to those of skill in the art can be used to introduce mutations in the nucleotide sequence encoding a human anti-IL-33 antibody, including, but not limited to, site-directed mutagenesis and PCR-mediated mutagenesis which result in amino acid substitutions. In one embodiment the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, CDRH1, CDRH2, CDRH3, VL region, CDRL1, CDRL2, or CDRL3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind an IL-33 polypeptide, e.g., human, primate, murine, or any combination of human, primate and murine IL-33). Such variants (or derivatives thereof) of "human" or "fully human" antibodies can also be referred to as human or fully human antibodies that are "optimized" or "optimized for antigen binding" and include, but are not limited to, antibodies that have improved affinity to antigen, antibodies with altered antigen specificity, or antibodies with reduced potential structural liabilities.

Basic immunoglobulin structures in vertebrate systems are relatively well understood. See, e.g., Harlow et al. (1988) Antibodies: A Laboratory Manual (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma$1-$\gamma$4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. While the following discussion will generally be directed to the IgG class of immunoglobulin molecules, all immunoglobulin classes are clearly within the scope of the present disclosure. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

The base of the antibody "Y" is called the Fc (Fragment, crystallizable) region, and is composed of two heavy chains that contribute two or three constant domains depending on the class of the antibody. Thus, the Fc region binds to a specific class of Fc receptors, and other immune molecules, such as complement proteins. Both the light and heavy chains are divided into regions of structural and functional homology. The terms "constant" and "variable" are used functionally. In this regard, it will be appreciated that the variable domains of both the light (V$\lambda$ or V$\kappa$) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a $\beta$-sheet conformation and the CDRs form loops that connect, and in some cases form part of, the $\beta$-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-IL-33 antibody or antigen-binding fragment, variant, or derivative thereof of the present disclosure are according to the Kabat numbering system.

Antibodies or antigen-binding fragments, variants, or derivatives thereof of the disclosure include, but are not limited to, polyclonal, monoclonal, multispecific, mouse, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-IL-33 antibodies disclosed herein). ScFv molecules are known in the art and are described, e.g., in U.S. Pat. No. 5,892,019. Immunoglobulin or antibody molecules of the disclosure can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, a binding polypeptide for use in the disclosure may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-IL-33 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the disclosure are not identical. For example, each monomer may comprise a different target binding site, forming, for example, a bispecific antibody.

The heavy chain portions of a binding molecule for use in the diagnostic and treatment methods disclosed herein may be derived from different immunoglobulin molecules. For example, a heavy chain portion of a polypeptide may comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-IL-33 antibodies, or antigen-binding fragments, variants, or derivatives thereof disclosed herein may be described or specified in terms of the epitope(s) or portion(s) of an antigen, e.g., a target polypeptide disclosed herein (e.g., full length or mature IL-33) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-IL-33 antibodies of the present disclosure may contain a sequence of at least 4, at least 5, at least 6, at least 7, more preferably at least 8, at least 9, at least 10, at least 15, at least 20, at least 25, or between about 15 to about 30 contiguous or non-contiguous amino acids of IL-33.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

In one embodiment an antibody or binding fragment thereof preferentially binds IL-33. By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

In one embodiment an antibody or antigen-binding fragment, variant, or derivative thereof according to the present disclosure may be said to bind a target polypeptide disclosed herein (e.g., IL-33, e.g., human, primate, murine, or any combination of human, primate and murine IL-33) or a fragment or variant thereof with an off rate (k(off)) of less than or equal to $5 \times 10^{-1}$ sec$^{-1}$, $10^{-1}$ sec$^{-1}$, $5 \times 10^{-2}$ sec$^{-1}$, $10^{-2}$ sec$^{-1}$, $5 \times 10^{-3}$ sec$^{-1}$ or $10^{-3}$ sec$^{-1}$. For example, an antibody of the disclosure may be said to bind a target polypeptide disclosed herein (e.g., IL-33, e.g., human, primate, murine, or any combination of human, primate and murine IL-33) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

In one embodiment an antibody or antigen-binding fragment, variant, or derivative thereof disclosed herein may be said to bind a target polypeptide disclosed herein (e.g., IL-33, e.g., human, primate, murine, or any combination of human, primate and murine IL-33) or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. For example, an antibody of the disclosure may be said to bind a target polypeptide disclosed herein (e.g., IL-33, e.g., human, primate, murine, or any combination of human, primate and murine IL-33) or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$.

Cross-reactivity as employed herein intended to refer to where binding molecules, for example antibodies or binding fragments thereof bind the same epitope or overlapping epitopes. Competitively inhibiting binding as employed herein is a form of cross-reactivity.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, solid phase assays such as competition ELISA assays, Dissociation-Enhanced Lanthanide Fluorescent Immunoassays (DELFIA®, Perkin Elmer), and radioligand binding assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-IL-33 antibodies or antigen-binding fragments, variants, or derivatives thereof of the disclosure may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-IL-33 binding molecules, e.g., antibodies or antigen-binding fragments, variants or derivatives thereof of the disclosure may also be described or specified in terms of their binding affinity to a polypeptide of the disclosure, e.g., IL-33, e.g., human, primate, murine, or any combination of human, primate and murine IL-33. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Anti-IL-33 antibodies or antigen-binding fragments, variants or derivatives thereof of the disclosure may be "multispecific," e.g., bispecific, trispecific, or of greater multispecificity, meaning that it recognizes and binds to two or more different epitopes present on one or more different antigens (e.g., proteins) at the same time. Thus, whether an anti-IL-33 antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains present in a binding polypeptide or IL-33 binding molecule, e.g., an antibody or antigen binding fragment thereof. Each binding domain specifically binds one epitope. When a binding polypeptide or IL-33 binding molecule comprises more than one binding domain, each binding domain may specifically bind the same epitope, for an antibody with two binding domains, termed "bivalent monospecific," or to different epitopes, for an antibody with two binding domains, termed "bivalent bispecific." An antibody or antigen binding fragment thereof may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Patent Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., *J. Immunol.* 147:60-69 (1991); U.S. Pat. Nos. 4,474,893; 4,714,681; 4,925,648; 5,573,920; 5,601,819; Kostelny et al., *J. Immunol.* 148: 1547-1553 (1992).

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

As used herein, the term "engineered antibody" will refer to a human antibody in which the variable domain in either the heavy or light chain or both is altered by at least one amino acid replacement. In one embodiment amino acid replacement of framework residues will reduce potential immunogenicity by changing the framework residue to germline. In another embodiment, amino acid replacement of either framework or CDR residues may remove potential structural liabilities that may result in instability, aggregation or heterogeneity of product. Examples of undesirable liabilities include unpaired cysteines (which may lead to disulfide bond scrambling, or variable sulfhydryl adduct formation), N-linked glycosylation sites (resulting in heterogeneity of structure and activity), as well as deamidation (e.g. NG, NS), isomerization (DG), oxidation (exposed methionine), and hydrolysis (DP) sites. In another embodiment, amino acid replacement of CDR and framework residues by either a targeted or random mutagenesis approach may result in antibodies with enhanced binding, potency or specificity characteristics. In another embodiment, "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species.

As used herein, the term "humanized antibody" will refer to an antibody molecule derived from a non-human species antibody (also referred to herein as a donor antibody) that bind the desired antigen having one or more complementarity determining regions (CDRs) from the non-human species and a framework region from a human immunoglobulin molecule (also referred to herein as an acceptor antibody). It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the IL-33 antigen. A human framework region that has been engineered in this manner would thus comprise a mixture of human and donor framework residues, and is referred to herein as a "partially human framework region."

For example, humanization of an anti-IL-33 antibody can be essentially performed by methods known in the art (e.g., the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-IL-33 antibody. See also U.S. Pat. Nos. 5,225,539; 5,585,089; 5,693,761; 5,693,762; 5,859,205; herein incorporated by reference. The resulting humanized anti-IL-33 antibody would comprise at least one rodent or mutant rodent CDR within the fully human framework regions of the variable domain of the heavy and/or light chain of the humanized antibody. In some instances, residues within the framework regions of one or more variable domains of the humanized anti-IL-33 antibody are replaced by corresponding non-human (for example, rodent) residues (see, for example, U.S. Pat. Nos. 5,585,089; 5,693,761; 5,693,762; and 6,180,370), in which case the resulting humanized anti-IL-33 antibody would comprise partially human framework regions within the variable domain of the heavy and/or light chain.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 321:522-525 (1986); Riechmann et al., Nature 332:323-329 (1988); and Presta, Curr. Op. Struct. Biol. 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of an inflammatory condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans; domestic animals; farm animals; and zoo, sports, or pet animals such as dogs, cats, guinea pigs, rabbits, rats, mice, horses, cattle, cows, and so on.

As used herein, phrases such as "a subject that would benefit from administration of an anti-IL-33 antibody" and "an animal in need of treatment" includes subjects, such as mammalian subjects, that would benefit from administration of an anti-IL-33 antibody used, e.g., for detection of an anti-IL-33 polypeptide (e.g., for a diagnostic procedure) and/or from treatment, i.e., palliation or prevention of a disease, with an anti-IL-33 antibody.

II. Target Polypeptide Description

As used herein, the terms "IL-33" and "IL-33 polypeptide" are used interchangeably. In certain embodiments, IL-33 is full length. In another embodiment, IL-33 is mature, truncated IL-33 (amino acids 112-270). Recent studies suggest full length IL-33 is active (Cayrol and Girard, *Proc Natl Acad Sci USA* 106(22):9021-6 (2009); Hayakawa et al., *Biochem Biophys Res Commun* 387(1):218-22 (2009); Talabot-Ayer et al., *J Biol Chem.* 284(29):19420-6 (2009)). However, N-terminally processed or truncated IL-33 including but not limited to aa 72-270, 79-270, 95-270, 99-270, 107-270, 109-270, 111-270, 112-270 may have enhanced activity (Lefrancais 2012, 2014). In another embodiments, IL-33 may include a full length IL-33, a fragment thereof, or an IL-33 mutant or variant polypeptide, wherein the fragment of IL-33 or IL-33 variant polypeptide retains some or all functional properties of active IL-33.

Human IL-33 is a 270 amino acid protein (Accession No. O95760), consisting of two domains: a homeodomain and a cytokine (IL-1-like) domain. The homeodomain contains a nuclear localization signal (NLS). IL-33 was originally identified as "DVS27" gene which was upregulated in vasospastic cerebral arteries after subarachnoid hemorrhage (Onda et al., *J. Cereb. Blood Flow Metab.* 19:1279-88 (1999)), and as a "nuclear factor from high endothelial venules (NF-HEV)," which is expressed in endothelial cell nuclei (Baekkevold et al., *Am. J. Pathol* 163:69-79 (2003)). IL-33 (also called IL-1F11) is now regarded as the 11$^{th}$ member in the IL-1 family for cytokines, which also includes IL-α, IL1β, and IL-18. See Oboki et al., *Allergology International* 59:143-160 (2010).

Schmitz et al. first identified IL-33 as the ligand for the orphan receptor ST2 (also called IL-1R4) (Schmitz et al., *Immunity* 23(5):479-90 (2005)). The only known ligand of the ST2 receptor is IL-33 (Schmitz et al. (2005)). IL-33 receptor is formed from heterodimeric molecules, consisting of ST2 and IL-1R accessory protein (IL-1RAcP). IL-1RAcP is a shared component of receptors for IL-1α, IL-1β, IL-1F6, IL1F8, and IL1F9. IL-33 binds to IL-33 receptor, which is a dimer of ST2 and IL-1RAcP. IL-1RAcP is not required for binding, but is critical for signaling. The TIR-domain of IL-33 receptor recruits MyD88 and TRAF6, and the receptor signal results in activation of NFκB and MAP Kinase pathways (Oboki et al. (2010)). The IL-33 receptor may potentially associate with other receptors and has been reported to cross activate the receptor tyrosine kinase c-Kit in human and mouse mast cells (Drube et al., *Blood* 115: 3899-906 (2010)). The structural basis for this cross-activation is the complex formation between c-Kit, ST2, and IL-1RAcP. C-Kit and IL-1RAcP interact constitutively and ST2 joins this complex upon ligand binding.

Recently, IL-33 has been shown to bind a second IL-33 receptor heterodimeric complex. ST2 forms a complex with another IL1R family molecule, "single Ig IL-1R-related molecule" (SIGIRR) (also called Toll IL-1R8 (TIR8)). SIGIRR/TIR8 is considered to act as a negative regulator of IL-1R and Toll-like receptor (TLR)-mediated immune responses (Garlanda et al., *Trends Immunol.* 30:439-46 (2009)). In contrast to ST2:IL-1RAcP, ST2:SIGIRR seems to act as a negative regulator of IL-33.

ST2 is expressed at baseline by Th2 cells and mast cells, both cell types known to be important mediators of allergic asthma. IL-33 is able to stimulate these (and various other cells) to produce a range of functional responses including cytokines and chemokines.

Anti-IL-33 Antibodies

In certain embodiments, the binding molecules, e.g., antibodies or antigen-binding fragments, variants, or derivatives thereof, of the disclosure, e.g., antibodies IL330065, IL330099, IL330101, IL330107, IL33149, and IL330180, and 33_640076-4B, 33_640081-AB; 33_640082-6B, 33_640082-7B, 33_640084-2B, 33_640086-6B, 33_640087-7B, 33_640201-2B, and 33_640237-2B, bind to IL-33 and inhibit the IL-33-driven cytokine release from mast cells, endothelial cells and proliferation of TF-1 cells.

In certain embodiments, the antibodies of the disclosure comprise anti-IL-33 antibodies or antigen-binding fragments, variants, or derivatives thereof that bind to IL-33, e.g., antibodies IL330065, IL330099, IL330101, IL330107, IL33149, and IL330180 and 33_640076-4B, 33_640081-AB; 33_640082-6B, 33_640082-7B, 33_640084-2B, 33_640086-6B, 33_640087-7B, 33_640201-2B, and 33_640237-2B. In certain embodiments the anti-IL-33 antibodies bind human, primate, murine, or any combination of human, primate and murine IL-33. In certain embodiments, the anti-IL-33 antibodies inhibit IL-33 driven cytokine production.

In one embodiment, the present disclosure provides an isolated binding molecule, e.g., an antibody or antigen-binding fragment thereof, which specifically binds to the same IL-33 epitope as antibody IL330065, IL330099, IL330101, IL330107, IL33149, or IL330180 and 33_640076-4B, 33_640081-AB; 33_640082-6B, 33_640082-7B, 33_640084-2B, 33_640086-6B, 33_640087-7B, 33_640201-2B, and 33_640237-2B. In another embodiment, the present disclosure provides an isolated binding molecule, e.g., an antibody or antigen-binding fragment thereof, which specifically binds to IL-33, and competitively inhibits antibody IL330065, IL330099, IL330101, IL330107, IL33149, or IL330180 and 33_640076-4B, 33_640081-AB; 33_640082-6B, 33_640082-7B, 33_640084-2B, 33_640086-6B, 33_640087-7B, 33_640201-2B, and 33_640237-2B from specifically binding to IL-33, e.g., human, primate, murine, or any combination of human, primate, and murine IL-33.

In certain embodiments, the binding molecule of the disclosure has an amino acid sequence that has at least 75%, 80%, 85%, 88%, 89%, 90%, 91%, 92%, 93%, 94%, or 95% sequence identity to the amino acid sequence for the reference anti-IL-33 antibody molecule. In a further embodiment, the binding molecule shares at least 96%, 97%, 98%, 99%, or 100% sequence identity to the reference antibody. In certain embodiments, the reference antibody is IL330065, IL330099, IL330101, IL330107, IL33149, or IL330180 and 33_640076-4B, 33_640081-AB; 33_640082-6B, 33_640082-7B, 33_640084-2B, 33_640086-6B, 33_640087-7B, 33_640201-2B, and 33_640237-2B.

In another embodiment, the present disclosure provides an isolated antibody or antigen-binding fragment thereof comprising, consisting essentially of, or consisting of an immunoglobulin heavy chain variable domain (VH domain), where at least one of the CDRs of the VH domain has an amino acid sequence that is at least 75%, 80%, 85%, 90%, 95%, 96%, 97%, 98%, 99%, or identical to a CDR1, CDR2 or CDR3 region from to the VH CDRs disclosed above, wherein an antibody or antigen-binding fragment thereof comprising the encoded VH domain specifically or preferentially binds to IL-33. In certain embodiments, the antibody or antigen-binding fragment thereof inhibits IL-33 driven cytokine production.

In another embodiment, the present disclosure provides an isolated antibody or antigen-binding fragment thereof comprising, consisting essentially of, or consisting of an immunoglobulin heavy chain variable domain (VH domain), where at least one of the CDRs of the VH domain has an amino acid sequence that is at least 75%, 80%, 85%, 90%, 95%, 96%, 97%, 98%, 99%, or identical to the VH CDRs disclosed above, wherein an antibody or antigen-binding fragment thereof comprising the encoded VH domain specifically or preferentially binds to IL-33. In certain embodiments, the isolated antibody further comprises a immunoglobulin light chain variable domain (VL domain). In certain embodiments, the antibody or antigen-binding fragment thereof inhibits IL-33 driven cytokine production.

In another embodiment, the present disclosure provides an isolated antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to the VH CDRs disclosed above, wherein an antibody or antigen-binding fragment thereof comprising the encoded VH domain specifically or preferentially binds to IL-33. In certain embodiments, the isolated antibody further comprises a VL domain. In certain embodiments, the antibody or antigen-binding fragment thereof inhibits IL-33 driven cytokine production.

In another embodiment, the present disclosure provides an isolated antibody or antigen-binding fragment thereof comprising, consisting essentially of, or consisting of a VH domain that has an amino acid sequence that is at least 75%, 80%, 85%, 90%, 91%, 92%, 93%, 94%, 95%, 96%, 97%, 98%, 99%, or 100% identical to a VH amino acid sequence of SEQ ID NO: 2, 12, 22, 32, 42, or 52, wherein an antibody or antigen-binding fragment thereof comprising the encoded VH domain specifically or preferentially binds to IL-33. In certain embodiments, the isolated antibody further comprises a VL domain. In certain embodiments, the antibody or antigen-binding fragment thereof inhibits IL-33 driven cytokine production.

In another embodiment, the present disclosure provides an isolated antibody or antigen-binding fragment thereof comprising, consisting essentially of, or consisting of an immunoglobulin light chain variable domain (VL domain), where at least one of the CDRs of the VL domain has an amino acid sequence that is at least 75%, 80%, 85%, 90%, 95%, 96%, 97%, 98%, 99%, or identical to a CDR1, CDR2 or CDR3 region from VH amino acid sequences SEQ disclosed above, wherein an antibody or antigen-binding fragment thereof comprising the encoded VL domain specifically or preferentially binds to IL-33. In certain embodiments, the isolated antibody further comprises a VH domain. In certain embodiments, the antibody or antigen-binding fragment thereof inhibits IL-33 driven cytokine production.

In another embodiment, the present disclosure provides an isolated antibody or antigen-binding fragment thereof comprising, consisting essentially of, or consisting of an immunoglobulin light chain variable domain (VL domain), where at least one of the CDRs of the VL domain has an amino acid sequence that is at least 75%, 80%, 85%, 90%, 95%, 96%, 97%, 98%, 99%, or identical to the VL CDRs disclosed above, wherein an antibody or antigen-binding fragment thereof comprising the encoded VL domain specifically or preferentially binds to IL-33. In certain embodiments, the isolated antibody further comprises a VH domain. In certain embodiments, the antibody or antigen-binding fragment thereof inhibits IL-33 driven cytokine production.

In another embodiment, the present disclosure provides an isolated antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to the VL CDRs disclosed above, wherein an antibody or antigen-binding fragment thereof comprising the encoded VL domain specifically or preferentially binds to IL-33. In certain embodiments, the isolated antibody further comprises a VH domain. In certain embodiments, the antibody or antigen-binding fragment thereof inhibits IL-33 driven cytokine production.

In a further embodiment, the present disclosure includes an isolated antibody or antigen-binding fragment thereof comprising, consisting essentially of, or consisting of a VL domain that has an amino acid sequence that is at least 75%, 80%, 85%, 90%, 91%, 92%, 93%, 94%, 95%, 96%, 97%, 98%, 99%, or 100% identical to a VL amino acid sequence disclosed above, wherein an antibody or antigen-binding fragment thereof comprising the encoded VL domain specifically or preferentially binds to IL-33. In certain embodiments, the isolated antibody further comprises a VH domain. In certain embodiments, the antibody or antigen-binding fragment thereof inhibits IL-33 driven cytokine production.

Suitable biologically active variants of the anti-IL-33 antibodies of the disclosure can be used in the methods of the present disclosure. Such variants will retain the desired binding properties of the parent anti-IL-33 antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res.

Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of an anti-IL-33 binding molecule, e.g., an antibody or antigen-binding fragment thereof, polypeptides of interest, modifications are made such that variants continue to possess the desired properties, e.g., being capable of specifically binding to a IL-33, and in certain embodiments not blocking binding of IL-33 to ST2. Obviously, any mutations made in the DNA encoding the variant polypeptide must not place the sequence out of reading frame and preferably will not create complementary regions that could produce secondary mRNA structure.

Methods for measuring anti-IL-33 binding molecule, e.g., an antibody or antigen-binding fragment thereof, binding specificity include, but are not limited to, standard competitive binding assays, ELISA assays, BIACORE assays, functional assays such as proliferation or factor release and the like. See, for example, such assays disclosed in WO 93/14125; Shi et al., *Immunity* 13:633-642 (2000); Kumanogoh et al., *J Immunol* 169:1375-1381 (2002); Watanabe et al., *J Immunol* 167:4321-4328 (2001); Wang et al., *Blood* 97:3498-3504 (2001); and Giraudon et al., *J Immunol* 172(2):1246-1255 (2004), all of which are herein incorporated by reference.

As discussed herein, where any particular polypeptide, including the constant regions, CDRs, VH domains, or VL domains disclosed herein, is at least 65%, 70%, 75%, 80%, 85%, 90%, 91%, 92%, 93%, 94%, 95%, 96%, 97%, 98%, 99%, or even 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53713). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present disclosure, the parameters are set, of course, such that the percentage of identity is calculated over the full length of the reference polypeptide sequence and that gaps in homology of up to 5% of the total number of amino acids in the reference sequence are allowed.

For the purposes of the present disclosure, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from a reference anti-IL-33 antibody (e.g., IL330065, IL330099, IL330101, IL330107, IL33149, or IL330180) by as few as 1 to 30 amino acid residues, as few as 1 to 15 amino acid residues, as few as 1 to 10 amino acid residues, such as 6-10, as few as 5, as few as 4, 3, 2, or even 1 amino acid residue.

The precise chemical structure of a polypeptide capable of specifically binding IL-33 and retaining the desired activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-IL-33 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-IL-33 antibody used herein so long as the desired properties of the anti-IL-33 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (e.g., binding specificity for IL-33, binding affinity, and associated activity, e.g., ability to inhibit the IL-33-driven cytokine release from mast cells, endothelial cells and proliferation of TF-1 cells) do not remove the polypeptide sequence from the definition of anti-IL-33 antibodies of interest as used herein.

The art provides substantial guidance regarding the preparation and use of polypeptide variants. In preparing the anti-IL-33 binding molecule, e.g., an antibody or antigen-binding fragment thereof, variants, one of skill in the art can readily determine which modifications to the native protein's nucleotide or amino acid sequence will result in a variant that is suitable for use as a therapeutically active component of a pharmaceutical composition used in the methods of the present disclosure.

It is known that variants of the Fc region (e.g., amino acid substitutions and/or additions and/or deletions) can enhance or diminish effector function of an antibody and may alter the pharmacokinetic properties (e.g., half-life) of the antibody. For example, see U.S. Pat. No. 6,737,056B1 and U.S. Patent Application Publication No. 2004/0132101A1, which disclose Fc mutations that optimize antibody binding to Fc receptors.

In certain anti-IL-33 antibodies, the Fc portion may be mutated to decrease effector function using techniques known in the art. For example, alteration of a constant region domain e.g. by point mutations or amino acid substitutions may reduce Fc receptor binding of the circulating modified antibody thereby minimizing effector cell or complement-mediated clearance or damage to cells expressing or presenting the target. For example, one particular set of substitutions, the triple mutation L234F/L235E/P331S ('TM') causes a profound decrease in the binding activity of human IgG1 molecules to human C1q, CD64, CD32A and CD16. See, e.g., Oganesyan et al., *Acta Crystallogr D Biol Crystallogr.* 64:700-704 (2008).

In other cases it may be that constant region modifications consistent with the instant disclosure increases serum half-life. The serum half-life of proteins comprising Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time in circulation for the antibody administered.

An increase in half-life allows for the reduction in amount of drug given to a patient as well as reducing the frequency of administration. To increase the serum half life of the antibody, one may incorporate a salvage receptor binding epitope into the antibody (especially an antibody fragment) as known in the art. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Antibodies with increased half-lives may also be generated by modifying amino acid residues identified as involved in the interaction between the Fc and the FcRn receptor. For example, the introduction of the triple mutation M252Y/S254T/T256E ('YTE') into the CH2 domain of human immunoglobulin G (IgG) molecules causes an increase in their binding to the human neonatal Fc receptor (FcRn). See U.S. Pat. No. 7,083,784, the contents of which are herein incorporated by reference in its entirety.

In addition, in some embodiments, the Fc region comprises a modification (e.g., amino acid substitutions, amino acid insertions, amino acid deletions) at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the Fc region may comprise a non naturally occurring amino acid residue at additional and/or alternative positions known in the art.

In other embodiments, the Fc region comprises at least one substitution selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241R, 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non-naturally occurring amino acid residues known in the art.

In additional embodiments, the Fc region comprises at least one modification (e.g., amino acid substitutions, amino acid insertions, amino acid deletions) at one or more positions selected from the group consisting of 234, 235 and 331. In some embodiments, the non-naturally occurring amino acids are selected from the group consisting of 234F, 235F, 235Y, and 331S. Provided herein is an Fc variant, where the Fc region comprises at least one non-naturally occurring amino acid at one or more positions selected from the group consisting of 239, 330 and 332. In some embodiments, the non-naturally occurring amino acids are selected from the group consisting of 239D, 330L and 332E.

In other embodiments, the Fc region comprises at least one non-naturally occurring amino acid at one or more positions selected from the group consisting of 252, 254, and 256. In certain embodiments, the non-naturally occurring amino acids are selected from the group consisting of 252Y, 254T and 256E, described in U.S. Pat. No. 7,083,784, the contents of which are herein incorporated by reference in its entirety.

Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as biodistribution and serum half-life, may easily be measured and quantified using well known immunological techniques without undue experimentation.

Anti-IL-33 antibodies of the disclosure also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-IL-33 polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind an antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity or enhanced stability/homogeneity of the final molecule). Following mutagenesis, the encoded protein may routinely be expressed and the functional and/or biological activity of the encoded protein, (e.g., ability to immunospecifically bind at least one epitope of an IL-33 polypeptide) can be determined using techniques described herein or by routinely modifying techniques known in the art.

In certain embodiments, antibodies of the disclosure can be optimized by modifying framework residues located in the vernier region/zone or residues proposed to support the structure of the CDR regions (see, e.g., Foote, J. and G. Winter, *J Mol. Biol.* 224.2: 487-99 (1992); Padlan, E. A., *Mol. Immunol* 31.3: 169-217 (1994)). In some embodiments, these modifications may be constructed by using PCR mediated site-directed mutagenesis using standard molecular biology methods. The modified antibodies can be tested for binding affinity as disclosed herein. In another embodiment, further optimization, e.g., back mutations or affinity maturation by introducing amino acid substitutions in the CDR regions or by site directed mutagenesis can also be performed.

In certain embodiments, the anti-IL-33 antibodies of the disclosure comprise at least one optimized complementarity-determining region (CDR). By "optimized CDR" is intended that the CDR has been modified and optimized sequences selected based on the sustained or improved binding affinity and/or anti-IL-33 activity that is imparted to an anti-IL-33 antibody comprising the optimized CDR. "Anti-IL-33 activity" can include, for example activity which modulates one or more of the following activities associated with IL-33, e.g., IL-33-driven cytokine release from mast cells, endothelial cells, and proliferation of TF-1 cells; mediator (e.g., cytokine or chemokine) release from basophils, eosinophils, Th2 cells, NK, NKT cells, macrophages, or dendritic cells; modulation of cell surface receptors; modulation of antigen presentation; or any other activity association with IL-33. Anti-IL-33 activity can also be attributed to a decrease in incidence or severity of diseases associated with IL-33 expression and/or release, including, but not limited to, certain types of inflammatory conditions, e.g., an allergic disorder such as asthma or other inflammatory response in the airway of a subject. The modifications may involve replacement of amino acid residues within the CDR such that an anti-IL-33 antibody retains specificity for the IL-33 antigen and has improved binding affinity and/or improved anti-IL-33 activity.

IV. Polynucleotides Encoding Anti-IL-33 Antibodies

The present disclosure also provides for nucleic acid molecules encoding anti-IL-33 antibodies of the disclosure, or antigen-binding fragments, variants, or derivatives thereof.

In one embodiment, the present disclosure provides an isolated polynucleotide comprising, consisting essentially of, or consisting of a nucleic acid encoding an immunoglobulin heavy chain variable domain (VH domain), where at least one of the CDRs of the VH domain is encoded by a nucleic acid sequence that is at least 75%, 80%, 85%, 90%, 95%, 96%, 97%, 98%, 99%, or identical to a CDRH 1, 2, or 3 polynucleotide sequence of a VH-encoding sequence selected from the group consisting of SEQ ID NO: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 5421, 531, 541, 551, 561, 571, and 581. In certain embodiments, the antibody or antigen-binding fragment thereof inhibits IL-33 driven cytokine production.

In other embodiments, the present disclosure provides an isolated polynucleotide comprising, consisting essentially of, or consisting of a nucleic acid encoding an immunoglobulin VH domain, where the sequence of at least one of the CDRs of the VH domain is selected from the group consisting of: (a) a CDRH1 sequence comprising the amino acid sequence set forth in SEQ ID NO: 3, 13, 23, 33, 43, 53, 63, 73, 83, 93, 103, 113, 123, 133, 143, 153, 163, 173, 183, 193, 203, 213, 223, 233, 243, 253, 263, 273, 283, 293, 303, 313, 323, 333, 343, 353, 363, 373, 383, 393, 403, 413, 423, 433, 443, 453, 463, 473, 483, 493, 503, 513, 5423, 533, 543, 553, 563, 573 and 583; (b) a CDRH2 sequence comprising the amino acid sequence set forth in SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 384, 394, 404, 414, 424, 434, 444, 454, 464, 474, 484, 494, 504, 514, 5424, 534, 544, 554, 564, 574; and 584, and (c) a CDRH3 sequence comprising the amino acid sequence set forth in SEQ ID NO: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 5425, 535, 545, 555, 565, 575 and 585. In certain embodiments, the antibody or antigen-binding fragment thereof inhibits IL-33 driven cytokine production.

In a further embodiment, the present disclosure includes an isolated polynucleotide comprising, consisting essentially of, or consisting of a nucleic acid encoding a VH domain that has an amino acid sequence that is at least 75%, 80%, 85%, 90%, 91%, 92%, 93%, 94%, 95%, 96%, 97%, 98%, 99%, or 100% identical to a reference VH domain polypeptide sequence comprising SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 382, 392, 402, 412, 422, 432, 442, 452, 462, 472, 482, 492, 502, 512, 5422, 532, 542, 552, 562, 572, and 582, wherein an anti-IL-33 antibody comprising the encoded VH domain specifically or preferentially binds to IL-33. In certain embodiments, the antibody or antigen-binding fragment thereof inhibits IL-33 driven cytokine production.

In one embodiment, the present disclosure provides an isolated polynucleotide comprising, consisting essentially of, or consisting of a nucleic acid encoding an immunoglobulin light chain variable domain (VL domain), where at least one of the CDRs of the VL domain is encoded by a nucleic acid sequence that is at least 75%, 80%, 85%, 90%, 95%, 96%, 97%, 98%, 99%, or identical to a CDRL 1, 2, or 3 polynucleotide sequence of a VL-encoding sequence selected from the group consisting of SEQ ID NO: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 5426, 536, 546, 556, 566, 576, and 586. In certain embodiments, the antibody or antigen-binding fragment thereof inhibits IL-33 driven cytokine production.

In other embodiments, the present disclosure provides an isolated polynucleotide comprising, consisting essentially of, or consisting of a nucleic acid encoding an immunoglobulin VL domain, where the sequence of at least one of the CDRs of the VL domain is selected from the group consisting of: (a) a CDRL1 sequence comprising the amino acid sequence set forth in SEQ ID NO: 8, 18, 28, 38, 48, 58, 68, 78, 88, 98, 108, 118, 128, 138, 148, 158, 168, 178, 188, 198, 208, 218, 228, 238, 248, 258, 268, 278, 288, 298, 308, 318, 328, 338, 348, 358, 368, 378, 388, 398, 408, 418, 428, 438, 448, 458, 468, 478, 488, 498, 508, 518, 5428, 538, 548, 558, 568, 578, and 588, (b) a CDRL2 sequence comprising the amino acid sequence set forth in SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 389, 399, 409, 419, 429, 439, 449, 459, 469, 479, 489, 499, 509, 519, 5429, 539, 549, 559, 569, 579, and 589, and (c) a CDRL3 sequence comprising the amino acid sequence set forth in SEQ ID NO: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 5420, 530, 540, 550, 560, 570, 580 and 590. In certain embodiments, the antibody or antigen-binding fragment thereof inhibits IL-33 driven cytokine production.

In a further embodiment, the present disclosure includes an isolated polynucleotide comprising, consisting essentially of, or consisting of a nucleic acid encoding a VL domain that has an amino acid sequence that is at least 75%, 80%, 85%, 90%, 91%, 92%, 93%, 94%, 95%, 96%, 97%, 98%, 99%, or 100% identical to a reference VL domain polypeptide sequence comprising SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 387, 397, 407, 417, 427, 437, 447, 457, 467, 477, 487, 497, 507, 517, 5427, 537, 547, 557, 567, 577, and 587, wherein an anti-IL-33 antibody comprising the encoded VL domain specifically or preferentially binds to IL-33. In certain embodiments, the antibody or antigen-binding fragment thereof inhibits IL-33 driven cytokine production.

Any of the polynucleotides described above may further include additional nucleic acids, encoding, e.g., a signal peptide to direct secretion of the encoded polypeptide, antibody constant regions as described herein, or other heterologous polypeptides as described herein. Also, as described in more detail elsewhere herein, the present disclosure includes compositions comprising one or more of the polynucleotides described above.

In one embodiment, the disclosure includes compositions comprising a first polynucleotide and second polynucleotide wherein said first polynucleotide encodes a VH domain as described herein and wherein said second polynucleotide encodes a VL domain as described herein. Specifically a composition which comprises, consists essentially of, or consists of a VH domain-encoding polynucleotide, as set forth in SEQ ID NO: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 5421, 531, 541, 551, 561, 571, or 581, and a VL domain-encoding polynucleotide, for example, a polynucleotide encoding the VL domain as set forth in SEQ ID NO: 66, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 5426, 536, 546, 556, 566, 576, or 586.

The present disclosure also includes fragments of the polynucleotides of the disclosure, as described elsewhere. Additionally polynucleotides that encode fusion polypolypeptides, Fab fragments, and other derivatives, as described herein, are also contemplated by the disclosure.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *Bio Techniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-IL-33 antibody, or antigen-binding fragment, variant, or derivative thereof of the disclosure, may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other anti-IL-33 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-IL-33 antibody. Amplified nucleic acids generated by PCR may then be cloned into replicable cloning vectors using any method well known in the art.

Once the nucleotide sequence and corresponding amino acid sequence of the anti-IL-33 antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual (2nd ed.; Cold Spring Harbor Laboratory, Cold Spring Harbor, N.Y.) and Ausubel et al., eds. (1998) Current Protocols in Molecular Biology (John Wiley & Sons, NY), which are both incorporated by reference herein in their entireties), to generate antibodies having a different amino acid sequence, for example to create amino acid substitutions, deletions, and/or insertions.

A polynucleotide encoding an anti-IL-33 binding molecule, e.g., an antibody, or antigen-binding fragment, variant, or derivative thereof, can be composed of any polyribonucleotide or polydeoxyribonucleotide, which may be unmodified RNA or DNA or modified RNA or DNA. For example, a polynucleotide encoding anti-IL-33 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an anti-IL-33 binding molecule, e.g., an antibody, or antigen-binding fragment, variant, or derivative thereof can be composed of triple-stranded regions comprising RNA or DNA or both RNA and DNA. A polynucleotide encoding an anti-IL-33 binding molecule, e.g., antibody, or antigen-binding fragment, variant, or derivative thereof, may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. Fusion Proteins and Antibody Conjugates

As discussed in more detail elsewhere herein, anti-IL-33 binding molecules, e.g., antibodies of the disclosure, or antigen-binding fragments, variants, or derivatives thereof, may further be recombinantly fused to a heterologous polypeptide at the N- or C-terminus or chemically conjugated (including covalent and non-covalent conjugations) to polypeptides or other compositions. For example, anti-IL-33 antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-IL-33 antibodies of the disclosure, or antigen-binding fragments, variants, or derivatives thereof, may include derivatives that are modified, i.e., by the covalent attachment of any type of molecule to the antibody such that covalent attachment does not prevent the antibody from binding to IL-33. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Anti-IL-33 binding molecules, e.g., antibodies of the disclosure, or antigen-binding fragments, variants, or derivatives thereof, can be composed of amino acids joined to each other by peptide bonds or modified peptide bonds, i.e., peptide isosteres, and may contain amino acids other than the 20 gene-encoded amino acids. For example, anti-IL-33 antibodies may be modified by natural processes, such as post-translational processing, or by chemical modification techniques that are well known in the art. Such modifications are well described in basic texts and in more detailed monographs, as well as in a voluminous research literature. Modifications can occur anywhere in the anti-IL-33 binding molecule, including the peptide backbone, the amino acid side-chains and the amino or carboxyl termini, or on moieties such as carbohydrates. It will be appreciated that the same type of modification may be present in the same or varying degrees at several sites in a given anti-IL-33 binding molecule. Also, a given anti-IL-33 binding molecule may contain many types of modifications. Anti-IL-33 binding molecules may be branched, for example, as a result of ubiquitination, and they may be cyclic, with or without branching. Cyclic, branched, and branched cyclic anti-IL-33 binding molecule may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, T. E. Creighton, W. H. Freeman and Company, NY; 2nd ed. (1993); Johnson, ed. (1983) Posttranslational Covalent Modification of Proteins (Academic Press, NY), pgs. 1-12; Seifter et al., Meth. Enzymol. 182:626-646 (1990); Rattan et al., Ann. NY Acad. Sci. 663:48-62 (1992)).

The present disclosure also provides for fusion proteins comprising an anti-IL-33 antibody, or antigen-binding fragment, variant, or derivative thereof, and a heterologous polypeptide. The heterologous polypeptide to which the antibody is fused may be useful for function or is useful to target the anti-IL-33 polypeptide expressing cells.

In one embodiment, a fusion protein of the disclosure comprises, consists essentially of, or consists of, a polypeptide having the amino acid sequence of any one or more of the VH domains of an antibody of the disclosure or the amino acid sequence of any one or more of the VL domains of an antibody of the disclosure or fragments or variants thereof, and a heterologous polypeptide sequence.

In another embodiment, a fusion protein for use in the diagnostic and treatment methods disclosed herein comprises, consists essentially of, or consists of a polypeptide having the amino acid sequence of any one, two, three of the CDRs of the VH domain of an anti-IL-33 antibody, or fragments, variants, or derivatives thereof, or the amino acid sequence of any one, two, three of the CDRs of the VL domain an anti-IL-33 antibody, or fragments, variants, or derivatives thereof, and a heterologous polypeptide sequence.

In one embodiment, a fusion protein comprises a polypeptide having the amino acid sequence of at least one VH domain of an anti-IL-33 antibody of the disclosure and the amino acid sequence of at least one VL domain of an anti-IL-33 antibody of the disclosure or fragments, derivatives or variants thereof, and a heterologous polypeptide sequence. Preferably, the VH and VL domains of the fusion protein correspond to a single source antibody (or scFv or Fab fragment) that specifically binds at least one epitope of IL-33.

In yet another embodiment, a fusion protein for use in the diagnostic and treatment methods disclosed herein comprises a polypeptide having the amino acid sequence of any one, two, three or more of the CDRs of the VH domain of an anti-IL-33 antibody and the amino acid sequence of any one, two, three or more of the CDRs of the VL domain of an anti-IL-33 antibody, or fragments or variants thereof, and a heterologous polypeptide sequence. Preferably, two, three, four, five, six, or more of the CDR(s) of the VH domain or VL domain correspond to single source antibody (or scFv or Fab fragment) of the disclosure. Nucleic acid molecules encoding these fusion proteins are also encompassed by the disclosure.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 130:2221-2229 (1990); and Watson et al., *Nature* 349:164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1333-1344 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, J. Cell. Biol. Vol. 135, Abstract No. 1448 (1991)).

As discussed elsewhere herein, anti-IL-33 binding molecules, e.g., antibodies of the disclosure, or antigen-binding fragments, variants, or derivatives thereof, may be fused to heterologous polypeptides to increase the in vivo half life of the polypeptides or for use in immunoassays using methods known in the art. For example, in one embodiment, PEG can be conjugated to the anti-IL-33 antibodies of the disclosure to increase their half-life in vivo. See Leong et al., *Cytokine* 16:106 (2001); Adv. in Drug Deliv. Rev. 54:531 (2002); or Weir et al., *Biochem. Soc. Transactions* 30:512 (2002).

Moreover, anti-IL-33 binding molecules, e.g., antibodies of the disclosure, or antigen-binding fragments, variants, or derivatives thereof, can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91313), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,136,964 and 5,225,538). The precise site at which the fusion is made may be selected empirically to optimize the secretion or binding characteristics of the fusion protein. DNA encoding the fusion protein is then transfected into a host cell for expression.

Anti-IL-33 binding molecules, e.g., antibodies of the present disclosure, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of the patient. Anti-IL-33 binding molecules, e.g., antibodies of the disclosure, or antigen-binding fragments, variants, or derivatives thereof, can be labeled or conjugated either before or after purification, or when purification is performed.

In particular, anti-IL-33 antibodies of the disclosure, or antigen-binding fragments, variants, or derivatives thereof, may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker may be prepared in the presence of a coupling agent, e.g., those listed herein, or by reaction with an isothiocyanate, preferably fluorescein-isothiocyanate. Conjugates of the anti-IL-33 antibodies of the disclosure, or antigen-binding fragments, variants, or derivatives thereof, are prepared in an analogous manner.

The present disclosure further encompasses anti-IL-33 binding molecules, e.g., antibodies of the disclosure, or antigen-binding fragments, variants, or derivatives thereof, conjugated to a diagnostic or therapeutic agent. The anti-IL-33 antibodies, including antigen-binding fragments, variants, and derivatives thereof, can be used diagnostically to, for example, monitor the development or progression of a disease as part of a clinical testing procedure to, e.g., determine the efficacy of a given treatment and/or prevention regimen. For example, detection can be facilitated by coupling the anti-IL-33 antibody, or antigen-binding fragment, variant, or derivative thereof, to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present disclosure. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{131}$In, $^{90}$Y, or $^{99}$Tc.

An anti-IL-33 binding molecule, e.g., an antibody, or antigen-binding fragment, variant, or derivative thereof, also can be detectably labeled by coupling it to a chemiluminescent compound. The presence of the chemiluminescent-tagged anti-IL-33 binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-IL-33 antibody, or antigen-binding fragment, variant, or derivative thereof, can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md.; Diagnostic Horizons 2:1-7 (1978); Voller et al., J. Clin. Pathol. 31:507-520 (1978); Butler, Meth. Enzymol. 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the anti-IL-33 antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Additionally, the detection can be accomplished by fluorescent methods, whereby a fluorescence emitting metals such as 152Eu, or others of the lanthanide series is bound directly or indirectly to the anti-IL-33 antibody. Detection may also be accomplished by visual comparison of the extent of enzymatic reaction of a substrate in comparison with similarly prepared standards.

Detection may also be accomplished using any of a variety of other immunoassays. For example, by radioactively labeling the anti-IL-33 binding molecule, e.g., antibody, or antigen-binding fragment, variant, or derivative thereof, it is possible to detect the binding molecule through the use of a radioimmunoassay (RIA) (see, for example, Weintraub (March, 1986) Principles of Radioimmunoassays, Seventh Training Course on Radioligand Assay Techniques (The Endocrine Society), which is incorporated by reference herein). The radioactive isotope can be detected by means including, but not limited to, a gamma counter, a scintillation counter, or autoradiography.

An anti-IL-33 binding molecule, e.g., antibody, or antigen-binding fragment, variant, or derivative thereof, can also be detectably labeled using fluorescence emitting metals such as 152Eu, or others of the lanthanide series. These metals can be attached to the binding molecule using such metal chelating groups as diethylenetriaminepentacetic acid (DTPA) or ethylenediaminetetraacetic acid (EDTA).

Techniques for conjugating various moieties to an antibody (e.g., an anti-IL-33 antibody), or antigen-binding fragment, variant, or derivative thereof, are well known, see, e.g., Amon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-56; Hellstrom et al. (1987) "Antibodies for Drug Delivery," in Controlled Drug Delivery, ed. Robinson et al. (2nd ed.; Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al. (1982) "The Preparation and Cytotoxic Properties of Antibody-Toxin Conjugates," Immunol. Rev. 62:139-58.

VI. Expression of Antibody Polypeptides

DNA sequences that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present disclosure at any point during the isolation process or subsequent analysis.

Following manipulation of the isolated genetic material to provide anti-IL-33 antibodies, or antigen-binding fragments, variants, or derivatives thereof, of the disclosure, the polynucleotides encoding the anti-IL-33 antibodies are typically inserted in an expression vector for introduction into host cells that may be used to produce the desired quantity of anti-IL-33 antibody.

Recombinant expression of an antibody, or fragment, derivative or analog thereof, e.g., a heavy or light chain of an antibody that binds to a target molecule described herein, e.g., IL-33, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the disclosure has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The disclosure, thus, provides replicable vectors comprising a nucleotide sequence encoding an antibody molecule of the disclosure, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present disclosure as a vehicle for introducing into and expressing a desired gene in a host cell. As known to those skilled in the art, such vectors may easily be selected from the group consisting of plasmids, phages, viruses and retroviruses. In general, vectors compatible with the instant disclosure will comprise a selection marker, appropriate restriction sites to facilitate cloning of the desired gene and the ability to enter and/or replicate in eukaryotic or prokaryotic cells.

For the purposes of this disclosure, numerous expression vector systems may be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthesized as discussed above. Of course, any expression vector that is capable of eliciting expression in eukaryotic cells may be used in the present disclosure. Examples of suitable vectors include, but are not limited to, plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels of immunoglobulin heavy and light chains is routine experimentation that can be carried out, for example, by robotic systems.

More generally, once the vector or DNA sequence encoding a monomeric subunit of the anti-IL-33 antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the disclosure includes host cells containing a polynucleotide encoding an antibody of the disclosure, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells that may, when transformed or transfected with the appropriate nucleotide coding sequences, express an antibody molecule of the disclosure in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., *Bio/Technology* 8:2 (1990)).

The host cell line used for protein expression is often of mammalian origin; those skilled in the art are credited with ability to preferentially determine particular host cell lines that are best suited for the desired gene product to be expressed therein. Exemplary host cell lines include, but are not limited to, CHO (Chinese Hamster Ovary), DG44 and DUXB13 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including, but not limited to, the herpes simplex virus thymidine kinase (Wigler et al., *Cell* 13:223 (1977)), hypoxanthine-guanine phosphoribosyltransferase (Szybalska and Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan and Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); TIB TECH 13(5):155-215 (May, 1993); and hygro, which confers resistance to hygromycin (Santerre et al., *Gene* 30:147 (1984). Methods commonly known in the art of recombinant DNA technology which can be used are described in Ausubel et al. (1993) Current Protocols in Molecular Biology (John Wiley & Sons, NY); Kriegler (1990) "Gene Transfer and Expression" in A Laboratory Manual (Stockton Press, NY); Dracopoli et al. (eds) (1994) Current Protocols in Human Genetics (John Wiley & Sons, NY) Chapters 12 and 13; Colberre-Garapin et al. (1981) J. Mol. Biol. 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-IL-33 antibodies, or antigen-binding fragments, variants, or derivatives thereof of the disclosure can also be expressed in non-mammalian cells such as insect, bacteria or yeast or plant cells. Bacteria that readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye and Inouye, *Nucleic Acids Res.* 13:3101-3109 (1985); Van Heeke and Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., *Nature* 282:39 (1979); Kingsman et al., *Gene* 7:141 (1979); Tschemper et al., *Gene* 10:157 (1980)) is commonly used. This plasmid already contains the TRP1 gene, which provides a selection marker for a mutant strain of yeast lacking the ability to grow in tryptophan, for example ATCC No. 44076 or PEN-1 (Jones, *Genetics* 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once a binding molecule of the disclosure has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the disclosure is disclosed in U.S. Patent Application Publication No. 2002 0123057 A1.

VII. Treatment Methods Using Therapeutic Anti-IL-33 Antibodies

Methods of the disclosure are directed to the use of anti-IL-33 binding molecules, e.g., antibodies, including antigen-binding fragments, variants, and derivatives thereof, to treat patients having a disease associated with IL-33 expression or IL-33-expressing cells. By "IL-33-expressing cell" is intended cells expressing IL-33 antigen. Methods for detecting IL-33 expression in cells are well known in the art and include, but are not limited to, PCR techniques, immunohistochemistry, flow cytometry, Western blot, ELISA, and the like.

Though the following discussion refers to diagnostic methods and treatment of various diseases and disorders with an anti-IL-33 antibody of the disclosure, the methods described herein are also applicable to the antigen-binding fragments, variants, and derivatives of these anti-IL-33 antibodies that retain the desired properties of the anti-IL-33 antibodies of the disclosure, e.g., capable of specifically binding IL-33 and neutralizing IL-33 pathogenic activity.

In one embodiment, treatment includes the application or administration of an anti-IL-33 binding molecule, e.g., an antibody or antigen binding fragment thereof, of the current disclosure to a subject or patient, or application or administration of the anti-IL-33 binding molecule to an isolated tissue or cell line from a subject or patient, where the subject or patient has a disease, a symptom of a disease, or a predisposition toward a disease. In another embodiment, treatment is also intended to include the application or administration of a pharmaceutical composition comprising the anti-IL-33 binding molecule, e.g., an antibody or antigen binding fragment thereof, of the current disclosure to a subject or patient, or application or administration of a pharmaceutical composition comprising the anti-IL-33 binding molecule to an isolated tissue or cell line from a subject or patient, who has a disease, a symptom of a disease, or a predisposition toward a disease.

The anti-IL-33 binding molecules, e.g., antibodies or binding fragments thereof, of the present disclosure are useful for the treatment of various inflammatory conditions. By "anti-inflammatory activity" is intended a reduction in the rate of inflammatory response in an IL-33-expressing cell, and hence a decline in inflammation in a tissue that arises during therapy. For example, therapy with at least one anti-IL-33 antibody causes a physiological response, for example, a reduction in inflammatory response that is beneficial with respect to treatment of disease states associated with IL-33-expressing cells in a human.

In one embodiment, the disclosure relates to anti-IL-33 binding molecules, e.g., antibodies or binding fragments thereof, according to the present disclosure for use as a medicament, in particular for use in the treatment or prophylaxis of an inflammatory response or for use in treatment of an inflammatory condition e.g., asthma or COPD. In certain embodiments, an anti-IL-33 binding molecule, e.g., an antibody or binding-fragment thereof, of the disclosure is used for the treatment of an allergic disorder. In certain embodiments, an anti-IL-33 binding molecule, e.g., an antibody or binding-fragment thereof, of the disclosure is used for the treatment of an inflammatory response in the airway of a subject or patient.

In accordance with the methods of the present disclosure, at least one anti-IL-33 binding molecule, e.g., an antibody or antigen binding fragment thereof, as defined elsewhere herein is used to promote a positive therapeutic response with respect to an inflammatory response. By "positive therapeutic response" with respect to inflammation treatment is intended an improvement in the disease in association with the anti-inflammatory activity of these binding molecules, e.g., antibodies or fragments thereof, and/or an improvement in the symptoms associated with the disease. That is, an anti-inflammatory effect, the prevention of further inflammation and/or a reduction in existing inflammation, and/or a decrease in one or more symptoms associated with the disease can be observed. Thus, for example, an improvement in the disease may be characterized as a complete response. By "complete response" is intended an absence of clinically detectable disease with normalization of any previous test results. Such a response must persist for at least one month following treatment according to the methods of the disclosure. Alternatively, an improvement in the disease may be categorized as being a partial response.

The anti-IL-33 binding molecules, e.g., antibodies or antigen binding fragments thereof, described herein may also find use in the treatment of inflammatory diseases and deficiencies or disorders of the immune system that are associated with IL-33 expressing cells. Inflammatory diseases are characterized by inflammation and tissue destruction, or a combination thereof. By "anti-inflammatory activity" is intended a reduction or prevention of inflammation. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens. In one embodiment, the inflammatory disease is an inflammatory disorder of the airway, e.g., asthma or COPD.

Asthma is considered a common inflammatory disease of the airways characterized, e.g., by variable and recurring symptoms, reversible airflow obstruction, and bronchospasm. Asthma symptoms can include wheezing, coughing, chest tightness, and shortness of breath. Symptoms can be triggered by exposure to allergens or irritants. Asthma may be classified as atopic (extrinsic) or non-atopic (intrinsic), based on whether symptoms are precipitated by allergens (atopic) or not (non-atopic). An acute asthma exacerbation is commonly referred to as an "asthma attack". Further signs which can occur during an asthma attack include the use of accessory muscles of respiration (sternocleidomastoid and scalene muscles of the neck), there may be a paradoxical pulse (a pulse that is weaker during inhalation and stronger during exhalation), and over-inflation of the chest. A blue color of the skin and nails may occur from lack of oxygen.

In accordance with the methods of the present disclosure, at least one anti-IL-33 binding molecule, e.g., an antibody or antigen binding fragment thereof, as defined elsewhere herein is used to promote a positive therapeutic response with respect to treatment or prevention of an inflammatory disease. By "positive therapeutic response" with respect to an inflammatory disease is intended an improvement in the disease in association with the anti-inflammatory activity, or the like, of these antibodies, and/or an improvement in the symptoms associated with the disease. That is, a reduction in the inflammatory response including but not limited to reduced secretion of inflammatory cytokines, adhesion molecules, proteases, immunoglobulins, combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in and/or a decrease in one or more symptoms mediated by stimulation of IL-33-expressing cells can be observed. Such positive therapeutic responses are not limited to the route of administration.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-IL-33 binding molecule, e.g., an antibody or antigen-binding fragment thereof, may experience the beneficial effect of an improvement in the symptoms associated with the disease.

The anti-IL-33 binding molecules, e.g., antibodies or binding fragments thereof, of the disclosure can be used in combination with any known therapies for inflammatory diseases, including any agent or combination of agents that are known to be useful, or which have been used or are currently in use, for treatment of inflammatory diseases, e.g., asthma or COPD. Agents used to treat asthma are divided into two general classes: quick-relief medications used to treat acute symptoms; and long-term control medications used to prevent further exacerbation. Fast acting treatments include, e.g., short-acting beta-2 adrenoceptor agonist (SABA) (e.g., salbutamol); anticholerginic medications (e.g., ipratropium bromide), adrenergic agonists (e.g., epinephrine). Long term control treatments include, e.g., glucocorticoids (e.g., fluticasone propionate); long-acting beta-2 adrenoceptor agonist (LABA); leukotriene antagonists (e.g., zafirlukast); and mast cell stabilizers (e.g., cromolyn sodium). Fast acting and long term control treatments are often administered by inhalation.

Thus, where the combined therapies comprise administration of an anti-IL-33 binding molecule in combination with administration of another therapeutic agent, the methods of the disclosure encompass coadministration, using separate formulations or a single pharmaceutical formulation, and consecutive administration in either order. In some embodiments of the disclosure, the anti-IL-33 antibodies described herein are administered in combination with anti-inflammatory drugs, wherein the antibody or antigen-binding fragment thereof and the therapeutic agent(s) may be administered sequentially, in either order, or simultaneously (i.e., concurrently or within the same time frame).

A further embodiment of the disclosure is the use of anti-IL-33 binding molecule, e.g., antibodies or antigen binding fragments thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

VIII. Pharmaceutical Compositions and Administration Methods

Methods of preparing and administering the anti-IL-33 binding molecule, e.g., antibodies, or antigen-binding fragments, variants, or derivatives thereof, of the disclosure to a subject in need thereof are well known to or are readily determined by those skilled in the art. The route of administration of the anti-IL-33 binding molecule, e.g., antibody, or antigen-binding fragment, variant, or derivative thereof, may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the disclosure, another example of a form for administration would be a solution for injection, in particular for intravenous or intraarterial injection or drip. Usually, a suitable pharmaceutical composition of the disclosure may comprise a buffer (e.g. acetate, phosphate or citrate buffer), a surfactant (e.g. a polysorbate), optionally a stabilizer agent (e.g. human albumin), etc. However, in other methods compatible with the teachings herein, anti-IL-33 binding molecules, e.g., antibodies, or antigen-binding fragments, variants, or derivatives thereof, of the disclosure can be delivered directly to the site of the adverse cellular population thereby increasing the exposure of the diseased tissue to the therapeutic agent. In one embodiment, the administration is directly to the airway, e.g., by inhalation or intranasal administration.

As discussed herein, anti-IL-33 binding molecules, e.g., antibodies, or antigen-binding fragments, variants, or derivatives thereof, of the disclosure may be administered in a pharmaceutically effective amount for the in vivo treatment of IL-33-expressing cell-mediated diseases such as certain types of inflammatory diseases. In this regard, it will be appreciated that the disclosed binding molecules of the disclosure will be formulated so as to facilitate administration and promote stability of the active agent. Preferably, pharmaceutical compositions in accordance with the present disclosure comprise a pharmaceutically acceptable, non-toxic, sterile carrier such as physiological saline, non-toxic buffers, preservatives and the like. For the purposes of the instant application, a pharmaceutically effective amount of an anti-IL-33 binding molecule, e.g., an antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or condition or to detect a substance or a cell.

The pharmaceutical compositions used in this disclosure may comprise pharmaceutically acceptable carriers, including, e.g., water, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the present disclosure, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-IL-33 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this disclosure may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an anti-IL-33 binding molecule, e.g., antibody, or fragment, variant, or derivative thereof that may be combined with the carrier materials to produce a single dosage form will vary depending upon the subject treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, anti-IL-33 antibodies, or antigen-binding fragments, variants, or derivatives thereof of the disclosure may be administered to a human or other animal in accordance with the aforementioned methods of treatment in an amount sufficient to produce a therapeutic effect. The anti-IL-33 antibodies, or antigen-binding fragments, variants or derivatives thereof of the disclosure can be administered to such human or other animal in a conventional dosage form prepared by combining the antibody or antigen-binding fragment thereof of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-IL-33 binding molecules, e.g., antibodies, or antigen-binding fragments, variants, or derivatives thereof, of the disclosure may prove to be particularly effective.

By "therapeutically effective dose or amount" or "effective amount" is intended an amount of anti-IL-33 binding molecule, e.g., antibody or antigen binding fragment thereof, that when administered brings about a positive therapeutic response with respect to treatment of a patient with a disease or condition to be treated.

The present disclosure also provides for the use of an anti-IL-33 binding molecule, e.g., an antibody or antigen-binding fragment, variant, or derivative thereof, in the manufacture of a medicament for treating an inflammatory disease, including, e.g., asthma or COPD.

The disclosure also provides for the use of an anti-IL-33 binding molecule, e.g., antibody of the disclosure, or antigen-binding fragment, variant, or derivative thereof, in the manufacture of a medicament for treating a subject for treating an inflammatory disease, wherein the medicament is used in a subject that has been pretreated with at least one other therapy. By "pretreated" or "pretreatment" is intended the subject has received one or more other therapies (e.g., been treated with at least one other anti-inflammatory therapy) prior to receiving the medicament comprising the anti-IL-33 binding molecule, e.g., antibody or antigen-binding fragment, variant, or derivative thereof. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-IL-33 binding molecule, for example, an antibody or antigen-binding fragment, variant, or derivative thereof. It is not necessary that the subject was a responder to pretreatment with the prior therapy or therapies. Thus, the subject that receives the medicament comprising the anti-IL-33 binding molecule, e.g., an antibody or antigen-binding fragment, variant, or derivative thereof could have responded, or could have failed to respond to pretreatment with the prior therapy, or to one or more of the prior therapies where pretreatment comprised multiple therapies.

IX. Diagnostics

The disclosure further provides a diagnostic method useful during diagnosis of IL-33-expressing cell-mediated diseases such as certain types of inflammatory diseases including, e.g., asthma, which involves measuring the expression level of IL-33 protein or transcript in tissue or other cells or body fluid from an individual and comparing the measured expression level with a standard IL-33 expression level in normal tissue or body fluid, whereby an increase in the expression level compared to the standard is indicative of a disorder.

The anti-IL-33 antibodies of the disclosure and antigen-binding fragments, variants, and derivatives thereof, can be used to assay IL-33 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting IL-33 protein expression include immunoassays, such as the enzyme linked immunosorbent assay (ELISA), immunoprecipitation, or Western blotting. Suitable assays are described in more detail elsewhere herein.

By "assaying the expression level of IL-33 polypeptide" is intended qualitatively or quantitatively measuring or estimating the level of IL-33 polypeptide in a first biological sample either directly (e.g., by determining or estimating absolute protein level) or relatively (e.g., by comparing to the disease associated polypeptide level in a second biological sample). Preferably, IL-33 polypeptide expression level in the first biological sample is measured or estimated and compared to a standard IL-33 polypeptide level, the standard being taken from a second biological sample obtained from an individual not having the disorder or being determined by averaging levels from a population of individuals not having the disorder. As will be appreciated in the art, once the "standard" IL-33 polypeptide level is known, it can be used repeatedly as a standard for comparison.

By "biological sample" is intended any biological sample obtained from an individual, cell line, tissue culture, or other source of cells potentially expressing IL-33. Methods for obtaining tissue biopsies and body fluids from mammals are well known in the art.

X. Immunoassays

Anti-IL-33 binding molecules, e.g., antibodies, or antigen-binding fragments, variants, or derivatives thereof of the disclosure may be assayed for immunospecific binding by any method known in the art. Binding assays may be performed as direct binding assays or as competition-binding assays. Immunoassays that can be used include but are not limited to ELISA (enzyme linked immunosorbent assay), western blotting, immunocytochemistry, immunoprecipitation, affinity chromatography, Bio-Layer Interferometry, Octet, ForteBio) and biochemical assays such as Dissociation-Enhanced Lanthanide Fluorescent Immunoassays (DELFIA®, Perkin Elmer), Förster resonance energy transfer (FRET) assays (e.g. homogeneous time resolved fluorescence (HTRF®, Cis Biointernational), and radioligand binding assays to name but a few. Binding can also be detected in cell assays, for example, by flow cytometry and Fluorescent Microvolumetric Assay Technology (FMAT®, Applied Biosystems). In a direct binding assay, a candidate antibody is tested for binding to IL-33 antigen. Competition binding assays, on the other hand, assess the ability of a candidate antibody to compete with a known anti-IL-33 antibody or fragment or other compound, such as ST2, that binds to IL-33. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipation protocols see, e.g., Ausubel et al., eds, (1994) Current Protocols in Molecular Biology (John Wiley & Sons, Inc., NY) Vol. 1 at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding Western blot protocols see, e.g., Ausubel et al., eds, (1994) Current Protocols in Molecular Biology (John Wiley & Sons, Inc., NY) Vol. 1 at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, (1994) Current Protocols in Molecular Biology (John Wiley & Sons, Inc., NY) Vol. 1 at 13.2.1.

Anti-IL-33 antibodies, or antigen-binding fragments, variants, or derivatives thereof of the disclosure, additionally, can be employed histologically, as in immunofluorescence, immunoelectron microscopy or non-immunological assays, for in situ detection of IL-33 protein or conserved variants or peptide fragments thereof. In situ detection may be accomplished by removing a histological specimen from a patient, and applying thereto a labeled anti-IL-33 antibody, or antigen-binding fragment, variant, or derivative thereof, preferably applied by overlaying the labeled antibody (or fragment) onto a biological sample. Through the use of such a procedure, it is possible to determine not only the presence of IL-33 protein, or conserved variants or peptide fragments, but also its distribution in the examined tissue. Using the present disclosure, those of ordinary skill will readily perceive that any of a wide variety of histological methods (such as staining procedures) can be modified in order to achieve such in situ detection.

Immunoassays and non-immunoassays for IL-33 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to IL-33 or conserved variants or peptide fragments thereof, and detecting the bound antibody by any of a number of techniques well known in the art.

The biological sample can be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-IL-33 antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present disclosure. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Solution phase binding assays may also be performed using suitable methods known in the art, by way of example but not limited to Förster resonance energy transfer (FRET) assays (e.g. homogeneous time resolved fluorescence (HTRF®, Cis Biointernational). An HTRF® assay is a homogeneous assay technology that utilizes fluorescence resonance energy transfer between a donor and acceptor fluorophore that are in close proximity (Mathis, G., *Clin Chem* 41(9):1391-7 (1995)). The assay can be used to measure macromolecular interactions by directly or indirectly coupling one of the molecules of interest to a donor fluorophore, e.g. europium (Eu3+) cryptate, and coupling the other molecule of interest to an acceptor fluorophore, e.g.

XL665 (a stable cross linked allophycocyanin). Excitation of the donor molecule results in fluorescence emission. The energy from this emission can be transferred to the acceptor fluorophore, when in close proximity to the donor fluorophore, resulting in the emission of a specific long-lived fluorescence.

The binding activity of a given lot of anti-IL-33 antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody Surface plasmon reasonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When an analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Another example of such a method includes measuring the equilibrium dissociation constant "$K_D$" using a Kinetic Exclusion Assay, which can be carried out, for example, using a KinExa instrument (Sapidyne Instruments). Briefly, the solution phase equilibrium dissociation constant $K_D$ of anti-IL33 antibodies can be determined by pre-mixing varying concentrations of the antibody with IL-33 until equilibrium is reached. The amount of free antibody is then measured using the KinExa by capturing free antibody using IL-33 coated beads, washing away unbound material and detecting bound antibody using a fluorescently labelled species specific antibody. The amount of free antibody detected at each IL-33 concentration is plotted against the concentration of IL-33 and the KinExa software is used to calculate the equilibrium dissociation constant ($K_D$).

Methods and reagents suitable for determination of binding characteristics of an isolated antibody or antigen-binding fragment thereof presented, or an altered/mutant derivative thereof (discussed below), are known in the art and/or are commercially available. Equipment and software designed for such kinetic analyses are commercially available (e.g., BIAcore, BIAevaluation software, GE Healthcare; KinExa Software, Sapidyne Instruments).

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to hind the first Mab, followed by addition of antigen and second MAb sequentially. The sensorgrams will reveal: (1) how much of the antigen binds to first Mab, (2) to what extent the second MAb binds to the surface-attached antigen, (3) if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides that interfere with binding of a given MAb are assumed to be structurally related to the epitope defined by that MAb.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature.

All of the references cited herein, are incorporated herein by reference in their entireties.

The following examples are offered by way of illustration and not by way of limitation.

DESCRIPTION OF THE FIGURES

FIG. 1 Shows a HTRF assay for human IL33-ST2 binding in the presence of unpurified scFv periplasmic preparations. A well containing antibody IL330004 is highlighted.

FIG. 2 Shows neutralization of human (FIG. 2A) and cynomolgus (FIG. 2B) IL33 by purified scFv preparations in an IL33-ST2 HTRF assay.

FIG. 3 Shows neutralization of human (FIG. 3A) and cynomolgus (FIG. 3B) IL33 by purified IgG preparations in an IL33-ST2 HTRF assay.

FIG. 6 Shows binding data from a single plate screened against human IL-33, cynomolgus IL-33 and insulin. One specific human/cynomolgus cross-reactive IL-33 binder is shown in well C4, and wells A12 and B12 contain control IL-33 binding clone.

FIG. 7A Shows neutralizing activity of antibodies in a TF-1 proliferation assay.

FIG. 7B Shows neutralizing activity of antibodies in a HUVEC IL-6 production assay.

FIG. 11A Shows a HTRF® receptor-ligand competition assay in the presence of antibodies IL330065, IL330099, IL330101, IL330107, IL33149, and IL330180.

FIG. 11B Shows Huvec NFkB (p65/RelA) translocation assay in the presence of antibodies IL330065, IL330099, IL330101, IL330107, and IL330149.

FIG. 14A Shows competitive binding IL330259 IgG with mAb IL330101 for binding to biotinylated human IL-33.

FIG. 14B Shows competitive binding antibodies with mAb H338L293 for binding to biotinylated human IL-33.

FIG. 19 Shows the purification of cell culture media-treated human IL-33 by SEC.

FIG. 21 Shows the disulphide mapping of media-treated human IL-33. Data were consistent with the formation of two disulphide bridges. FIG. 21A shows combined, deconvoluted mass spectra from non-reduced and reduced Lys-C peptide mapping analysis of DSB IL-33. FIG. 21B shows isolated spectra for cysteine containing peptides. FIG. 21C shows sequences of disulphide bonded peptides identified by non-reduced and reduced Lys-C peptide mapping analysis of disulphide bonded IL-33. Disulphide linkages are represented by two hyphens (- -). Lys-C miscleavages are represented by square brackets.

FIG. 23A shows the comparison of fractional hydrogen exchange (for deuterium) in reduced IL-33 (left panel) and DSB IL-33 (right panel). FIG. 23B shows a structural model of differential HX-MS data overlaid with the ST2 binding site (red and magenta).

FIG. 24 Shows redIL-33 (FIG. 24A) or DSB IL-33 (FIG. 24B) binding to ST2.

FIGS. 25A and B shows that two commercial human IL-33 assays predominantly detect the disulphide-bonded form of IL-33 (IL33-DSB). FIG. 25C shows that the mouse IL-33 assay detects both reduced and oxidized forms of mouse IL-33.

FIG. 26A shows signal intensity as a function of DSB IL-33 or red-IL-33 concentration using IL330004 as a capture probe and IL330425 as a detection probe. FIG. 26B shows signal intensity as a function of DSB IL-33 or red-IL-33 concentration using IL330425 as a capture probe and biotinylated sST2.Fc as a detection probe.

FIG. 28 Shows analysis of BALF from humanized IL-33 mice collected at varying timepoints following *Alternaria* intranasal challenge, using a combination of multiple ELISA assays. (FIG. 28A) Millipore, (FIG. 28B) R&D systems and (FIG. 28C) IL330425/sST2-biotin assays were used to measure IL-33 in the presence or absence of sST2 (left hand graphs). Signals in the presence of sST2 (signal from the reduced IL-33 fraction eliminated) were compared with a disulphide bonded IL-33 standard to quantify the levels of disulphide bonded IL-33. The reduced IL-33 signal was calculated as the difference in signal between IL-33 measurements in the presence and absence of ST2, quantified against a reduced IL-33 standard. Estimations for reduced IL-33 are shown on the right hand graphs.

FIG. 29 Shows analysis of BALF from wild type BALB/c mice collected at varying timepoints following *Alternaria* intranasal challenge. Mouse IL-33 ELISA (R&D systems) was used to measure IL-33 in the presence or absence of sST2 (media-treated mouse IL-33 used as standard curve) (FIG. 29A). Signals in the presence of sST2 (signal from the reduced IL-33 fraction eliminated) were compared with a media-treated mouse IL-33 standard to quantify the levels of oxidised IL-33. The reduced IL-33 signal was calculated as the difference in signal between IL-33 measurements in the presence and absence of ST2, quantified against a reduced mouse IL-33 standard, (FIG. 29B).

FIG. 31A shows NFkB signaling 30 minutes following stimulation. FIG. 31B shows NFkB signaling 6 hours following stimulation.

FIG. 32 Shows the inhibition of the FRET signal, produced by human IL-33 binding to human ST2 with increasing concentrations of H338L293 under directly competitive conditions (FIG. 32B) or following preincubation with IL-33 (FIG. 32C). FIG. 32A shows a schematic representation of the assay.

FIG. 33 Shows epitope mapping of H338L293.

FIG. 35 Shows that IL33-11 has greater potency than IL33-01 (WT) in vitro (FIG. 35A) and in vivo (FIG. 35B).

FIG. 37A shows the inhibition of the FRET signal after 1 hour incubation produced by human IL-33-01 binding to human ST2 with increasing concentrations of IL-33 scFv antibody 33v20064. FIG. 37B shows the inhibition of the FRET signal after 1 hour incubation produced by human IL-33-11 binding to human ST2 with increasing concentrations of IL-33 scFv antibody 33v20064. FIG. 37C shows the inhibition of the FRET signal after overnight incubation produced by human IL-33-01 binding to human ST2 with increasing concentrations of IL-33 scFv antibody 33v20064. FIG. 37D shows the inhibition of the FRET signal after overnight incubation produced by human IL-33-11 binding to human ST2 with increasing concentrations of IL-33 scFv antibody 33v20064.

FIG. 38A shows the inhibition of the FRET signal after 1 hour incubation, produced by human IL-33 binding to human ST2 with increasing concentrations of 33v20064 IgG1 antibody. FIG. 38B shows the inhibition of the FRET signal after overnight incubation, produced by human IL-33 binding to human ST2 with increasing concentrations of 33v20064 IgG1 antibody.

FIG. 40 Shows the inhibition of the FRET signal, produced by biotinylated human IL-33-01 binding to DyLight labelled 33v20064, with increasing concentrations of mouse IL-33 FH and cyno IL-33 FH (FIG. 40A), human IL-33 FH and B7H3 avi his (FIGS. 40A and 40B), and human IL-1 beta and human IL-1 alpha (FIG. 40B). Inhibition of the signal corresponds with relative binding affinity of 33v20064 to the test protein.

FIG. 41A shows the inhibition of the FRET signal after 1 hour incubation. FIG. 41B shows the inhibition of the FRET signal after overnight incubation.

FIG. 43 Shows the effect of IL-33 binding proteins on conversion from redIL-33 to DSB IL-33, in IMDM+1% BSA (FIG. 43A) or PBS+1% BSA (FIG. 43B).

FIG. 45 Shows antibody neutralization of IL-8 production in HUVECs stimulated by truncated (112-270) (FIG. 45A) or full length (1-270) IL-33 (FIG. 45B).

FIG. 50 Shows mAb specificity for IL-33 from various species or other IL-1 family members using a FRET assay based on (A) IL33/33_640087-7B or (B) 33_640237-2B.

FIG. 53A Experimental design of a pilot in vivo study to investigate the potential for activity IL-33 independent of ST2.

FIG. 53B Analysis of human IL-33 exposure in BAL fluid following repeated administration of human IL-33 to BALB/c mice.

FIG. 53C Analysis of IL-33 exposure in plasma following a single intraperitoneal administration of human IL-33 (10 ug).

FIG. 53D Analysis of IL-33 exposure in plasma following repeated administration of human IL-33 to BALB/c mice.

FIG. 54 Shows representative H&E stained paraffin sections of lung tissue from mice administered (FIG. 54A) PBS or (FIG. 54B) IL-33 intranasally for 6 weeks.

FIG. 55 Shows (FIG. 55A) p-p38 MAPK or (FIG. 55B) p-STAT5 nuclear translocation activity in Huvecs in response to reduced IL-33 or DSB IL-33.

FIG. 55C Western blot analysis of for p-p38 MAPK, p-JAK2 and p-STAT5 in Huvecs stimulated for 15 minutes with reduced IL-33 or DSB IL-33.

FIG. 56A Shows binding of RAGE-Fc to reduced or DSB IL-33 by ELISA.

FIG. 56B Shows inhibition of the Huvec pSTAT5 response to DSB IL-33 with RAGE-Fc or anti-RAGE mAb.

FIG. 56C Shows inhibition of the Huvec pSTAT5 response to DSB IL-33 with anti-RAGE mAb.

FIG. 58 Shows the effect of anti-IL-33, anti-ST2 or anti-RAGE mAbs on IL-33 induced inhibition of A549 cell migration versus (A) reduced IL-33 (B) DSB IL-33.

SUMMARY OF THE SEQUENCES

Figure 4:
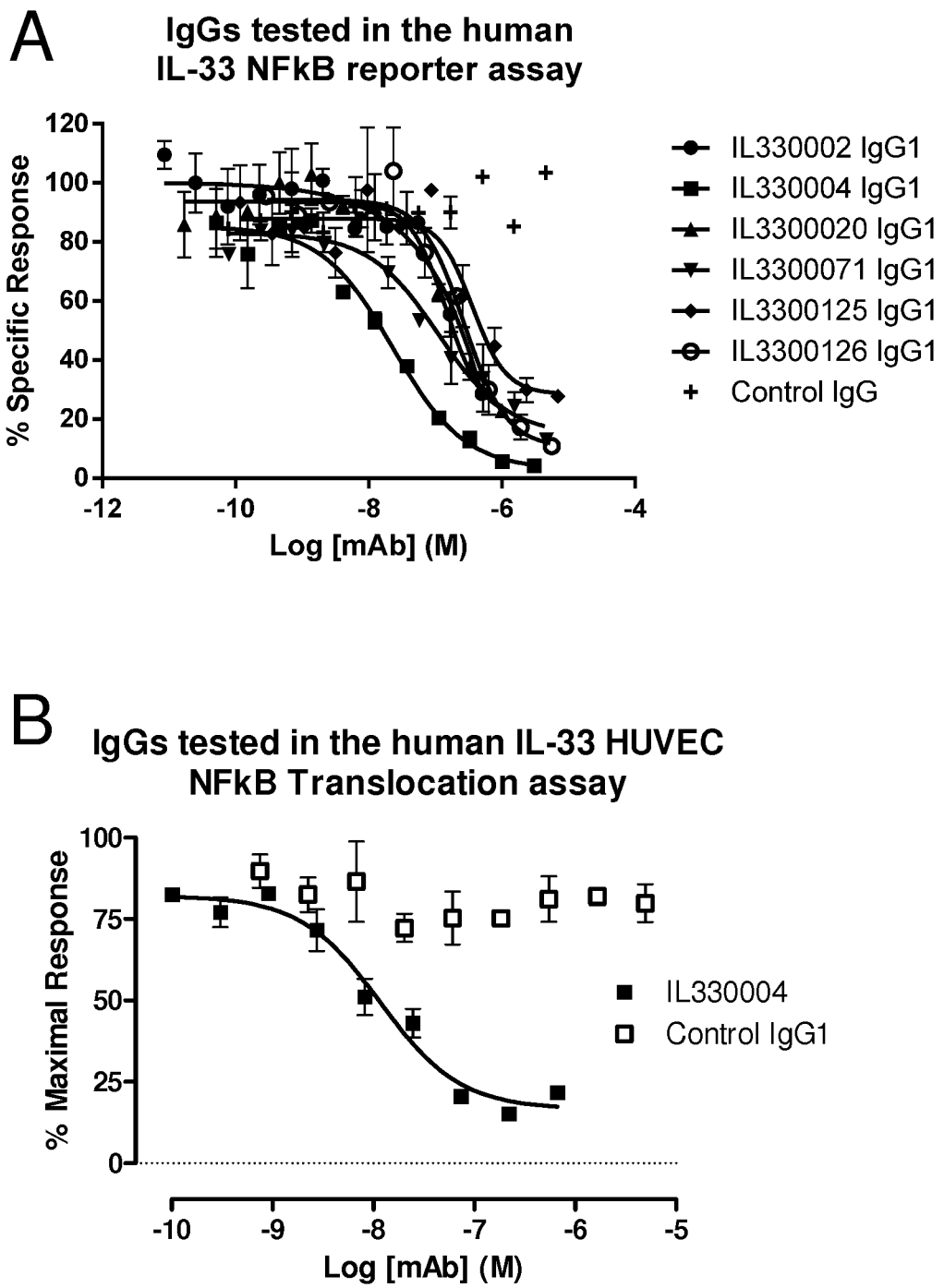
FIG. 4 Shows neutralization of human IL33 by purified IgG preparations in a luciferase NFκB reporter assay (FIG. 4A) and a HUVEC NFκB translocation assay (FIG. 4B).

| SEQ ID NO: | Reference/Antibody Name | Description |
| --- | --- | --- |
| 1 | IL330002 | VH DNA |
| 2 | IL330002 | VH PRT |
| 3 | IL330002 | VH CDR1 PRT |
| 4 | IL330002 | VH CDR2 PRT |
| 5 | IL330002 | VH CDR3 PRT |
| 6 | IL330002 | VL DNA |
| 7 | IL330002 | VL PRT |
| 8 | IL330002 | VL CDR1 PRT |
| 9 | IL330002 | VL CDR2 PRT |
| 10 | IL330002 | VL CDR3 PRT |
| 11 | IL330004 | VH DNA |
| 12 | IL330004 | VH PRT |
| 13 | IL330004 | VH CDR1 PRT |
| 14 | IL330004 | VH CDR2 PRT |
| 15 | IL330004 | VH CDR3 PRT |
| 16 | IL330004 | VL DNA |
| 17 | IL330004 | VL PRT |
| 18 | IL330004 | VL CDR1 PRT |
| 19 | IL330004 | VL CDR2 PRT |
| 20 | IL330004 | VL CDR3 PRT |
| 21 | IL330020 | VH DNA |
| 22 | IL330020 | VH PRT |
| 23 | IL330020 | VH CDR1 PRT |
| 24 | IL330020 | VH CDR2 PRT |
| 25 | IL330020 | VH CDR3 PRT |
| 26 | IL330020 | VL DNA |
| 27 | IL330020 | VL PRT |
| 28 | IL330020 | VL CDR1 PRT |
| 29 | IL330020 | VL CDR2 PRT |
| 30 | IL330020 | VL CDR3 PRT |
| 31 | IL330071 | VH DNA |
| 32 | IL330071 | VH PRT |
| 33 | IL330071 | VH CDR1 PRT |
| 34 | IL330071 | VH CDR2 PRT |
| 35 | IL330071 | VH CDR3 PRT |
| 36 | IL330071 | VL DNA |
| 37 | IL330071 | VL PRT |
| 38 | IL330071 | VL CDR1 PRT |
| 39 | IL330071 | VL CDR2 PRT |
| 40 | IL330071 | VL CDR3 PRT |
| 41 | IL330125 | VH DNA |
| 42 | IL330125 | VH PRT |
| 43 | IL330125 | VH CDR1 PRT |
| 44 | IL330125 | VH CDR2 PRT |
| 45 | IL330125 | VH CDR3 PRT |
| 46 | IL330125 | VL DNA |
| 47 | IL330125 | VL PRT |
| 48 | IL330125 | VL CDR1 PRT |
| 49 | IL330125 | VL CDR2 PRT |

| SEQ ID NO: | Reference/Antibody Name | Description |
|---|---|---|
| 50 | IL330125 | VL CDR3 PRT |
| 51 | IL330126 | VH DNA |
| 52 | IL330126 | VH PRT |
| 53 | IL330126 | VH CDR1 PRT |
| 54 | IL330126 | VH CDR2 PRT |
| 55 | IL330126 | VH CDR3 PRT |
| 56 | IL330126 | VL DNA |
| 57 | IL330126 | VL PRT |
| 58 | IL330126 | VL CDR1 PRT |
| 59 | IL330126 | VL CDR2 PRT |
| 60 | IL330126 | VL CDR3 PRT |
| 61 | IL330425 | VH DNA |
| 62 | IL330425 | VH PRT |
| 63 | IL330425 | VH CDR1 PRT |
| 64 | IL330425 | VH CDR2 PRT |
| 65 | IL330425 | VH CDR3 PRT |
| 66 | IL330425 | VL DNA |
| 67 | IL330425 | VL PRT |
| 68 | IL330425 | VL CDR1 PRT |
| 69 | IL330425 | VL CDR2 PRT |
| 70 | IL330425 | VL CDR3 PRT |
| 71 | IL330428 | VH DNA |
| 72 | IL330428 | VH PRT |
| 73 | IL330428 | VH CDR1 PRT |
| 74 | IL330428 | VH CDR2 PRT |
| 75 | IL330428 | VH CDR3 PRT |
| 76 | IL330428 | VL DNA |
| 77 | IL330428 | VL PRT |
| 78 | IL330428 | VL CDR1 PRT |
| 79 | IL330428 | VL CDR2 PRT |
| 80 | IL330428 | VL CDR3 PRT |
| 81 | IL330065 | VH DNA |
| 82 | IL330065 | VH PRT |
| 83 | IL330065 | VH CDR1 PRT |
| 84 | IL330065 | VH CDR2 PRT |
| 85 | IL330065 | VH CDR3 PRT |
| 86 | IL330065 | VL DNA |
| 87 | IL330065 | VL PRT |
| 88 | IL330065 | VL CDR1 PRT |
| 89 | IL330065 | VL CDR2 PRT |
| 90 | IL330065 | VL CDR3 PRT |
| 91 | IL330099 | VH DNA |
| 92 | IL330099 | VH PRT |
| 93 | IL330099 | VH CDR1 PRT |
| 94 | IL330099 | VH CDR2 PRT |
| 95 | IL330099 | VH CDR3 PRT |
| 96 | IL330099 | VL DNA |
| 97 | IL330099 | VL PRT |
| 98 | IL330099 | VL CDR1 PRT |
| 99 | IL330099 | VL CDR2 PRT |
| 100 | IL330099 | VL CDR3 PRT |
| 101 | IL330101 | VH DNA |
| 102 | IL330101 | VH PRT |
| 103 | IL330101 | VH CDR1 PRT |
| 104 | IL330101 | VH CDR2 PRT |
| 105 | IL330101 | VH CDR3 PRT |
| 106 | IL330101 | VL DNA |
| 107 | IL330101 | VL PRT |
| 108 | IL330101 | VL CDR1 PRT |
| 109 | IL330101 | VL CDR2 PRT |
| 110 | IL330101 | VL CDR3 PRT |
| 111 | IL330101_fgl | VH DNA |
| 112 | IL330101_fgl | VH PRT |
| 113 | IL330101_fgl | VH CDR1 PRT |
| 114 | IL330101_fgl | VH CDR2 PRT |
| 115 | IL330101_fgl | VH CDR3 PRT |
| 116 | IL330101_fgl | VL DNA |
| 117 | IL330101_fgl | VL PRT |
| 118 | IL330101_fgl | VL CDR1 PRT |
| 119 | IL330101_fgl | VL CDR2 PRT |
| 120 | IL330101_fgl | VL CDR3 PRT |
| 121 | IL330107 | VH DNA |
| 122 | IL330107 | VH PRT |
| 123 | IL330107 | VH CDR1 PRT |
| 124 | IL330107 | VH CDR2 PRT |
| 125 | IL330107 | VH CDR3 PRT |
| 126 | IL330107 | VL DNA |
| 127 | IL330107 | VL PRT |
| 128 | IL330107 | VL CDR1 PRT |
| 129 | IL330107 | VL CDR2 PRT |
| 130 | IL330107 | VL CDR3 PRT |
| 131 | IL330149 | VH DNA |
| 132 | IL330149 | VH PRT |
| 133 | IL330149 | VH CDR1 PRT |
| 134 | IL330149 | VH CDR2 PRT |
| 135 | IL330149 | VH CDR3 PRT |
| 136 | IL330149 | VL DNA |
| 137 | IL330149 | VL PRT |
| 138 | IL330149 | VL CDR1 PRT |
| 139 | IL330149 | VL CDR2 PRT |
| 140 | IL330149 | VL CDR3 PRT |
| 141 | IL330180 | VH DNA |
| 142 | IL330180 | VH PRT |
| 143 | IL330180 | VH CDR1 PRT |
| 144 | IL330180 | VH CDR2 PRT |
| 145 | IL330180 | VH CDR3 PRT |
| 146 | IL330180 | VL DNA |
| 147 | IL330180 | VL PRT |
| 148 | IL330180 | VL CDR1 PRT |
| 149 | IL330180 | VL CDR2 PRT |
| 150 | IL330180 | VL CDR3 PRT |
| 151 | IL330259 | VH DNA |
| 152 | IL330259 | VH PRT |
| 153 | IL330259 | VH CDR1 PRT |
| 154 | IL330259 | VH CDR2 PRT |
| 155 | IL330259 | VH CDR3 PRT |
| 156 | IL330259 | VL DNA |
| 157 | IL330259 | VL PRT |
| 158 | IL330259 | VL CDR1 PRT |
| 159 | IL330259 | VL CDR2 PRT |
| 160 | IL330259 | VL CDR3 PRT |
| 161 | IL330259_fgl | VH DNA |
| 162 | IL330259_fgl | VH PRT |
| 163 | IL330259_fgl | VH CDR1 PRT |
| 164 | IL330259_fgl | VH CDR2 PRT |
| 165 | IL330259_fgl | VH CDR3 PRT |
| 166 | IL330259_fgl | VL DNA |
| 167 | IL330259_fgl | VL PRT |
| 168 | IL330259_fgl | VL CDR1 PRT |
| 169 | IL330259_fgl | VL CDR2 PRT |
| 170 | IL330259_fgl | VL CDR3 PRT |
| 171 | H338L293 | VH DNA |
| 172 | H338L293 | VH PRT |
| 173 | H338L293 | VH CDR1 PRT |
| 174 | H338L293 | VH CDR2 PRT |
| 175 | H338L293 | VH CDR3 PRT |
| 176 | H338L293 | VL DNA |
| 177 | H338L293 | VL PRT |
| 178 | H338L293 | VL CDR1 PRT |
| 179 | H338L293 | VL CDR2 PRT |
| 180 | H338L293 | VL CDR3 PRT |
| 181 | H338L293_fgl | VH DNA |
| 182 | H338L293_fgl | VH PRT |
| 183 | H338L293_fgl | VH CDR1 PRT |
| 184 | H338L293_fgl | VH CDR2 PRT |
| 185 | H338L293_fgl | VH CDR3 PRT |
| 186 | H338L293_fgl | VL DNA |
| 187 | H338L293_fgl | VL PRT |
| 188 | H338L293_fgl | VL CDR1 PRT |
| 189 | H338L293_fgl | VL CDR2 PRT |
| 190 | H338L293_fgl | VL CDR3 PRT |
| 191 | IL330377 | VH DNA |
| 192 | IL330377 | VH PRT |
| 193 | IL330377 | VH CDR1 PRT |
| 194 | IL330377 | VH CDR2 PRT |
| 195 | IL330377 | VH CDR3 PRT |
| 196 | IL330377 | VL DNA |
| 197 | IL330377 | VL PRT |
| 198 | IL330377 | VL CDR1 PRT |
| 199 | IL330377 | VL CDR2 PRT |
| 200 | IL330377 | VL CDR3 PRT |
| 201 | IL330377_fgl | VH DNA |
| 202 | IL330377_fgl | VH PRT |
| 203 | IL330377_fgl | VH CDR1 PRT |

-continued

| SEQ ID NO: | Reference/Antibody Name | Description |
|---|---|---|
| 204 | IL330377_fgl | VH CDR2 PRT |
| 205 | IL330377_fgl | VH CDR3 PRT |
| 206 | IL330377_fgl | VL DNA |
| 207 | IL330377_fgl | VL PRT |
| 208 | IL330377_fgl | VL CDR1 PRT |
| 209 | IL330377_fgl | VL CDR2 PRT |
| 210 | IL330377_fgl | VL CDR3 PRT |
| 211 | IL330388 | VH DNA |
| 212 | IL330388 | VH PRT |
| 213 | IL330388 | VH CDR1 PRT |
| 214 | IL330388 | VH CDR2 PRT |
| 215 | IL330388 | VH CDR3 PRT |
| 216 | IL330388 | VL DNA |
| 217 | IL330388 | VL PRT |
| 218 | IL330388 | VL CDR1 PRT |
| 219 | IL330388 | VL CDR2 PRT |
| 220 | IL330388 | VL CDR3 PRT |
| 221 | IL330388_fgl | VH DNA |
| 222 | IL330388_fgl | VH PRT |
| 223 | IL330388_fgl | VH CDR1 PRT |
| 224 | IL330388_fgl | VH CDR2 PRT |
| 225 | IL330388_fgl | VH CDR3 PRT |
| 226 | IL330388_fgl | VL DNA |
| 227 | IL330388_fgl | VL PRT |
| 228 | IL330388_fgl | VL CDR1 PRT |
| 229 | IL330388_fgl | VL CDR2 PRT |
| 230 | IL330388_fgl | VL CDR3 PRT |
| 231 | IL330396 | VH DNA |
| 232 | IL330396 | VH PRT |
| 233 | IL330396 | VH CDR1 PRT |
| 234 | IL330396 | VH CDR2 PRT |
| 235 | IL330396 | VH CDR3 PRT |
| 236 | IL330396 | VL DNA |
| 237 | IL330396 | VL PRT |
| 238 | IL330396 | VL CDR1 PRT |
| 239 | IL330396 | VL CDR2 PRT |
| 240 | IL330396 | VL CDR3 PRT |
| 241 | IL330396_fgl | VH DNA |
| 242 | IL330396_fgl | VH PRT |
| 243 | IL330396_fgl | VH CDR1 PRT |
| 244 | IL330396_fgl | VH CDR2 PRT |
| 245 | IL330396_fgl | VH CDR3 PRT |
| 246 | IL330396_fgl | VL DNA |
| 247 | IL330396_fgl | VL PRT |
| 248 | IL330396_fgl | VL CDR1 PRT |
| 249 | IL330396_fgl | VL CDR2 PRT |
| 250 | IL330396_fgl | VL CDR3 PRT |
| 251 | IL330398 | VH DNA |
| 252 | IL330398 | VH PRT |
| 253 | IL330398 | VH CDR1 PRT |
| 254 | IL330398 | VH CDR2 PRT |
| 255 | IL330398 | VH CDR3 PRT |
| 256 | IL330398 | VL DNA |
| 257 | IL330398 | VL PRT |
| 258 | IL330398 | VL CDR1 PRT |
| 259 | IL330398 | VL CDR2 PRT |
| 260 | IL330398 | VL CDR3 PRT |
| 261 | IL330398_fgl | VH DNA |
| 262 | IL330398_fgl | VH PRT |
| 263 | IL330398_fgl | VH CDR1 PRT |
| 264 | IL330398_fgl | VH CDR2 PRT |
| 265 | IL330398_fgl | VH CDR3 PRT |
| 266 | IL330398_fgl | VL DNA |
| 267 | IL330398_fgl | VL PRT |
| 268 | IL330398_fgl | VL CDR1 PRT |
| 269 | IL330398_fgl | VL CDR2 PRT |
| 270 | IL330398_fgl | VL CDR3 PRT |
| 271 | ZZ1EBX-E05 (33v20064) | VH DNA |
| 272 | ZZ1EBX-E05 (33v20064) | VH PRT |
| 273 | ZZ1EBX-E05 (33v20064) | VH CDR1 PRT |
| 274 | ZZ1EBX-E05 (33v20064) | VH CDR2 PRT |
| 275 | ZZ1EBX-E05 (33v20064) | VH CDR3 PRT |
| 276 | ZZ1EBX-E05 (33v20064) | VL DNA |
| 277 | ZZ1EBX-E05 (33v20064) | VL PRT |
| 278 | ZZ1EBX-E05 (33v20064) | VL CDR1 PRT |
| 279 | ZZ1EBX-E05 (33v20064) | VL CDR2 PRT |
| 280 | ZZ1EBX-E05 (33v20064) | VL CDR3 PRT |
| 281 | ZZ1I6V-H02 (33_640001) | VH DNA |
| 282 | ZZ1I6V-H02 (33_640001) | VH PRT |
| 283 | ZZ1I6V-H02 (33_640001) | VH CDR1 PRT |
| 284 | ZZ1I6V-H02 (33_640001) | VH CDR2 PRT |
| 285 | ZZ1I6V-H02 (33_640001) | VH CDR3 PRT |
| 286 | ZZ1I6V-H02 (33_640001) | VL DNA |
| 287 | ZZ1I6V-H02 (33_640001) | VL PRT |
| 288 | ZZ1I6V-H02 (33_640001) | VL CDR1 PRT |
| 289 | ZZ1I6V-H02 (33_640001) | VL CDR2 PRT |
| 290 | ZZ1I6V-H02 (33_640001) | VL CDR3 PRT |
| 291 | ZZ1JRB-A03 (33_640027) | VH DNA |
| 292 | ZZ1JRB-A03 (33_640027) | VH PRT |
| 293 | ZZ1JRB-A03 (33_640027) | VH CDR1 PRT |
| 294 | ZZ1JRB-A03 (33_640027) | VH CDR2 PRT |
| 295 | ZZ1JRB-A03 (33_640027) | VH CDR3 PRT |
| 296 | ZZ1JRB-A03 (33_640027) | VL DNA |
| 297 | ZZ1JRB-A03 (33_640027) | VL PRT |
| 298 | ZZ1JRB-A03 (33_640027) | VL CDR1 PRT |
| 299 | ZZ1JRB-A03 (33_640027) | VL CDR2 PRT |
| 300 | ZZ1JRB-A03 (33_640027) | VL CDR3 PRT |
| 301 | ZZ1F7Q-D10 (33_640050) | VH DNA |
| 302 | ZZ1F7Q-D10 (33_640050) | VH PRT |
| 303 | ZZ1F7Q-D10 (33_640050) | VH CDR1 PRT |
| 304 | ZZ1F7Q-D10 (33_640050) | VH CDR2 PRT |
| 305 | ZZ1F7Q-D10 (33_640050) | VH CDR3 PRT |
| 306 | ZZ1F7Q-D10 (33_640050) | VL DNA |
| 307 | ZZ1F7Q-D10 (33_640050) | VL PRT |
| 308 | ZZ1F7Q-D10 (33_640050) | VL CDR1 PRT |
| 309 | ZZ1F7Q-D10 (33_640050) | VL CDR2 PRT |
| 310 | ZZ1F7Q-D10 (33_640050) | VL CDR3 PRT |
| 311 | ZZ1F7P-E01 (33_640047) | VH DNA |
| 312 | ZZ1F7P-E01 (33_640047) | VH PRT |
| 313 | ZZ1F7P-E01 (33_640047) | VH CDR1 PRT |
| 314 | ZZ1F7P-E01 (33_640047) | VH CDR2 PRT |
| 315 | ZZ1F7P-E01 (33_640047) | VH CDR3 PRT |
| 316 | ZZ1F7P-E01 (33_640047) | VL DNA |
| 317 | ZZ1F7P-E01 (33_640047) | VL PRT |
| 318 | ZZ1F7P-E01 (33_640047) | VL CDR1 PRT |
| 319 | ZZ1F7P-E01 (33_640047) | VL CDR2 PRT |
| 320 | ZZ1F7P-E01 (33_640047) | VL CDR3 PRT |
| 321 | ZZ1IV4-H06 (33_640166) | VH DNA |
| 322 | ZZ1IV4-H06 (33_640166) | VH PRT |
| 323 | ZZ1IV4-H06 (33_640166) | VH CDR1 PRT |
| 324 | ZZ1IV4-H06 (33_640166) | VH CDR2 PRT |
| 325 | ZZ1IV4-H06 (33_640166) | VH CDR3 PRT |
| 326 | ZZ1IV4-H06 (33_640166) | VL DNA |
| 327 | ZZ1IV4-H06 (33_640166) | VL PRT |
| 328 | ZZ1IV4-H06 (33_640166) | VL CDR1 PRT |
| 329 | ZZ1IV4-H06 (33_640166) | VL CDR2 PRT |
| 330 | ZZ1IV4-H06 (33_640166) | VL CDR3 PRT |
| 331 | ZZ1IV4-G09 (33_640169) | VH DNA |
| 332 | ZZ1IV4-G09 (33_640169) | VH PRT |
| 333 | ZZ1IV4-G09 (33_640169) | VH CDR1 PRT |
| 334 | ZZ1IV4-G09 (33_640169) | VH CDR2 PRT |
| 335 | ZZ1IV4-G09 (33_640169) | VH CDR3 PRT |
| 336 | ZZ1IV4-G09 (33_640169) | VL DNA |
| 337 | ZZ1IV4-G09 (33_640169) | VL PRT |
| 338 | ZZ1IV4-G09 (33_640169) | VL CDR1 PRT |
| 339 | ZZ1IV4-G09 (33_640169) | VL CDR2 PRT |
| 340 | ZZ1IV4-G09 (33_640169) | VL CDR3 PRT |
| 341 | ZZ1K7Q-B11 (33_640170) | VH DNA |
| 342 | ZZ1K7Q-B11 (33_640170) | VH PRT |
| 343 | ZZ1K7Q-B11 (33_640170) | VH CDR1 PRT |
| 344 | ZZ1K7Q-B11 (33_640170) | VH CDR2 PRT |
| 345 | ZZ1K7Q-B11 (33_640170) | VH CDR3 PRT |
| 346 | ZZ1K7Q-B11 (33_640170) | VL DNA |
| 347 | ZZ1K7Q-B11 (33_640170) | VL PRT |
| 348 | ZZ1K7Q-B11 (33_640170) | VL CDR1 PRT |
| 349 | ZZ1K7Q-B11 (33_640170) | VL CDR2 PRT |
| 350 | ZZ1K7Q-B11 (33_640170) | VL CDR3 PRT |
| 351 | ZZ1KAD-C04 (33_640036) | VH DNA |
| 352 | ZZ1KAD-C04 (33_640036) | VH PRT |
| 353 | ZZ1KAD-C04 (33_640036) | VH CDR1 PRT |
| 354 | ZZ1KAD-C04 (33_640036) | VH CDR2 PRT |
| 355 | ZZ1KAD-C04 (33_640036) | VH CDR3 PRT |
| 356 | ZZ1KAD-C04 (33_640036) | VL DNA |
| 357 | ZZ1KAD-C04 (33_640036) | VL PRT |

| SEQ ID NO: | Reference/Antibody Name | Description |
|---|---|---|
| 358 | ZZ1KAD-C04 (33_640036) | VL CDR1 PRT |
| 359 | ZZ1KAD-C04 (33_640036) | VL CDR2 PRT |
| 360 | ZZ1KAD-C04 (33_640036) | VL CDR3 PRT |
| 361 | 33_640117 | VH DNA |
| 362 | 33_640117 | VH PRT |
| 363 | 33_640117 | VH CDR1 PRT |
| 364 | 33_640117 | VH CDR2 PRT |
| 365 | 33_640117 | VH CDR3 PRT |
| 366 | 33_640117 | VL DNA |
| 367 | 33_640117 | VL PRT |
| 368 | 33_640117 | VL CDR1 PRT |
| 369 | 33_640117 | VL CDR2 PRT |
| 370 | 33_640117 | VL CDR3 PRT |
| 371 | ZZ1JLT-F06 (33_640076) | VH DNA |
| 372 | ZZ1JLT-F06 (33_640076) | VH PRT |
| 373 | ZZ1JLT-F06 (33_640076) | VH CDR1 PRT |
| 374 | ZZ1JLT-F06 (33_640076) | VH CDR2 PRT |
| 375 | ZZ1JLT-F06 (33_640076) | VH CDR3 PRT |
| 376 | ZZ1JLT-F06 (33_640076) | VL DNA |
| 377 | ZZ1JLT-F06 (33_640076) | VL PRT |
| 378 | ZZ1JLT-F06 (33_640076) | VL CDR1 PRT |
| 379 | ZZ1JLT-F06 (33_640076) | VL CDR2 PRT |
| 380 | ZZ1JLT-F06 (33_640076) | VL CDR3 PRT |
| 381 | ZZ1JMB-H05 (33_640081) | VH DNA |
| 382 | ZZ1JMB-H05 (33_640081) | VH PRT |
| 383 | ZZ1JMB-H05 (33_640081) | VH CDR1 PRT |
| 384 | ZZ1JMB-H05 (33_640081) | VH CDR2 PRT |
| 385 | ZZ1JMB-H05 (33_640081) | VH CDR3 PRT |
| 386 | ZZ1JMB-H05 (33_640081) | VL DNA |
| 387 | ZZ1JMB-H05 (33_640081) | VL PRT |
| 388 | ZZ1JMB-H05 (33_640081) | VL CDR1 PRT |
| 389 | ZZ1JMB-H05 (33_640081) | VL CDR2 PRT |
| 390 | ZZ1JMB-H05 (33_640081) | VL CDR3 PRT |
| 391 | ZZ1JMA-B04 (33_640082) | VH DNA |
| 392 | ZZ1JMA-B04 (33_640082) | VH PRT |
| 393 | ZZ1JMA-B04 (33_640082) | VH CDR1 PRT |
| 394 | ZZ1JMA-B04 (33_640082) | VH CDR2 PRT |
| 395 | ZZ1JMA-B04 (33_640082) | VH CDR3 PRT |
| 396 | ZZ1JMA-B04 (33_640082) | VL DNA |
| 397 | ZZ1JMA-B04 (33_640082) | VL PRT |
| 398 | ZZ1JMA-B04 (33_640082) | VL CDR1 PRT |
| 399 | ZZ1JMA-B04 (33_640082) | VL CDR2 PRT |
| 400 | ZZ1JMA-B04 (33_640082) | VL CDR3 PRT |
| 401 | ZZ1JLR-D06 (33_640084) | VH DNA |
| 402 | ZZ1JLR-D06 (33_640084) | VH PRT |
| 403 | ZZ1JLR-D06 (33_640084) | VH CDR1 PRT |
| 404 | ZZ1JLR-D06 (33_640084) | VH CDR2 PRT |
| 405 | ZZ1JLR-D06 (33_640084) | VH CDR3 PRT |
| 406 | ZZ1JLR-D06 (33_640084) | VL DNA |
| 407 | ZZ1JLR-D06 (33_640084) | VL PRT |
| 408 | ZZ1JLR-D06 (33_640084) | VL CDR1 PRT |
| 409 | ZZ1JLR-D06 (33_640084) | VL CDR2 PRT |
| 410 | ZZ1JLR-D06 (33_640084) | VL CDR3 PRT |
| 411 | ZZ1JMC-H09 (33_640086) | VH DNA |
| 412 | ZZ1JMC-H09 (33_640086) | VH PRT |
| 413 | ZZ1JMC-H09 (33_640086) | VH CDR1 PRT |
| 414 | ZZ1JMC-H09 (33_640086) | VH CDR2 PRT |
| 415 | ZZ1JMC-H09 (33_640086) | VH CDR3 PRT |
| 416 | ZZ1JMC-H09 (33_640086) | VL DNA |
| 417 | ZZ1JMC-H09 (33_640086) | VL PRT |
| 418 | ZZ1JMC-H09 (33_640086) | VL CDR1 PRT |
| 419 | ZZ1JMC-H09 (33_640086) | VL CDR2 PRT |
| 420 | ZZ1JMC-H09 (33_640086) | VL CDR3 PRT |
| 421 | ZZ1JMF-G02 (33_640087) | VH DNA |
| 422 | ZZ1JMF-G02 (33_640087) | VH PRT |
| 423 | ZZ1JMF-G02 (33_640087) | VH CDR1 PRT |
| 424 | ZZ1JMF-G02 (33_640087) | VH CDR2 PRT |
| 425 | ZZ1JMF-G02 (33_640087) | VH CDR3 PRT |
| 426 | ZZ1JMF-G02 (33_640087) | VL DNA |
| 427 | ZZ1JMF-G02 (33_640087) | VL PRT |
| 428 | ZZ1JMF-G02 (33_640087) | VL CDR1 PRT |
| 429 | ZZ1JMF-G02 (33_640087) | VL CDR2 PRT |
| 430 | ZZ1JMF-G02 (33_640087) | VL CDR3 PRT |
| 431 | 33_640076_1 | VH DNA |
| 432 | 33_640076_1 | VH PRT |
| 433 | 33_640076_1 | VH CDR1 PRT |
| 434 | 33_640076_1 | VH CDR2 PRT |
| 435 | 33_640076_1 | VH CDR3 PRT |
| 436 | 33_640076_1 | VL DNA |
| 437 | 33_640076_1 | VL PRT |
| 438 | 33_640076_1 | VL CDR1 PRT |
| 439 | 33_640076_1 | VL CDR2 PRT |
| 440 | 33_640076_1 | VL CDR3 PRT |
| 441 | 33_640081_A | VH DNA |
| 442 | 33_640081_A | VH PRT |
| 443 | 33_640081_A | VH CDR1 PRT |
| 444 | 33_640081_A | VH CDR2 PRT |
| 445 | 33_640081_A | VH CDR3 PRT |
| 446 | 33_640081_A | VL DNA |
| 447 | 33_640081_A | VL PRT |
| 448 | 33_640081_A | VL CDR1 PRT |
| 449 | 33_640081_A | VL CDR2 PRT |
| 450 | 33_640081_A | VL CDR3 PRT |
| 451 | 33_640082_2 | VH DNA |
| 452 | 33_640082_2 | VH PRT |
| 453 | 33_640082_2 | VH CDR1 PRT |
| 454 | 33_640082_2 | VH CDR2 PRT |
| 455 | 33_640082_2 | VH CDR3 PRT |
| 456 | 33_640082_2 | VL DNA |
| 457 | 33_640082_2 | VL PRT |
| 458 | 33_640082_2 | VL CDR1 PRT |
| 459 | 33_640082_2 | VL CDR2 PRT |
| 460 | 33_640082_2 | VL CDR3 PRT |
| 461 | 33_640084_2 | VH DNA |
| 462 | 33_640084_2 | VH PRT |
| 463 | 33_640084_2 | VH CDR1 PRT |
| 464 | 33_640084_2 | VH CDR2 PRT |
| 465 | 33_640084_2 | VH CDR3 PRT |
| 466 | 33_640084_2 | VL DNA |
| 467 | 33_640084_2 | VL PRT |
| 468 | 33_640084_2 | VL CDR1 PRT |
| 469 | 33_640084_2 | VL CDR2 PRT |
| 470 | 33_640084_2 | VL CDR3 PRT |
| 471 | 33_640086_2 | VH DNA |
| 472 | 33_640086_2 | VH PRT |
| 473 | 33_640086_2 | VH CDR1 PRT |
| 474 | 33_640086_2 | VH CDR2 PRT |
| 475 | 33_640086_2 | VH CDR3 PRT |
| 476 | 33_640086_2 | VL DNA |
| 477 | 33_640086_2 | VL PRT |
| 478 | 33_640086_2 | VL CDR1 PRT |
| 479 | 33_640086_2 | VL CDR2 PRT |
| 480 | 33_640086_2 | VL CDR3 PRT |
| 481 | 33_640087_2 | VH DNA |
| 482 | 33_640087_2 | VH PRT |
| 483 | 33_640087_2 | VH CDR1 PRT |
| 484 | 33_640087_2 | VH CDR2 PRT |
| 485 | 33_640087_2 | VH CDR3 PRT |
| 486 | 33_640087_2 | VL DNA |
| 487 | 33_640087_2 | VL PRT |
| 488 | 33_640087_2 | VL CDR1 PRT |
| 489 | 33_640087_2 | VL CDR2 PRT |
| 490 | 33_640087_2 | VL CDR3 PRT |
| 491 | 33_640076_4 | VH DNA |
| 492 | 33_640076_4 | VH PRT |
| 493 | 33_640076_4 | VH CDR1 PRT |
| 494 | 33_640076_4 | VH CDR2 PRT |
| 495 | 33_640076_4 | VH CDR3 PRT |
| 496 | 33_640076_4 | VL DNA |
| 497 | 33_640076_4 | VL PRT |
| 498 | 33_640076_4 | VL CDR1 PRT |
| 499 | 33_640076_4 | VL CDR2 PRT |
| 500 | 33_640076_4 | VL CDR3 PRT |
| 501 | 33_640082_4 | VH DNA |
| 502 | 33_640082_4 | VH PRT |
| 503 | 33_640082_4 | VH CDR1 PRT |
| 504 | 33_640082_4 | VH CDR2 PRT |
| 505 | 33_640082_4 | VH CDR3 PRT |
| 506 | 33_640082_4 | VL DNA |
| 507 | 33_640082_4 | VL PRT |
| 508 | 33_640082_4 | VL CDR1 PRT |
| 509 | 33_640082_4 | VL CDR2 PRT |
| 510 | 33_640082_4 | VL CDR3 PRT |
| 511 | 33_640082_6 | VH DNA |

-continued

| SEQ ID NO: | Reference/Antibody Name | Description |
|---|---|---|
| 512 | 33_640082_6 | VH PRT |
| 513 | 33_640082_6 | VH CDR1 PRT |
| 514 | 33_640082_6 | VH CDR2 PRT |
| 515 | 33_640082_6 | VH CDR3 PRT |
| 516 | 33_640082_6 | VL DNA |
| 517 | 33_640082_6 | VL PRT |
| 518 | 33_640082_6 | VL CDR1 PRT |
| 519 | 33_640082_6 | VL CDR2 PRT |
| 520 | 33_640082_6 | VL CDR3 PRT |
| 521 | 33_640082_7 | VH DNA |
| 522 | 33_640082_7 | VH PRT |
| 523 | 33_640082_7 | VH CDR1 PRT |
| 524 | 33_640082_7 | VH CDR2 PRT |
| 525 | 33_640082_7 | VH CDR3 PRT |
| 526 | 33_640082_7 | VL DNA |
| 527 | 33_640082_7 | VL PRT |
| 528 | 33_640082_7 | VL CDR1 PRT |
| 529 | 33_640082_7 | VL CDR2 PRT |
| 530 | 33_640082_7 | VL CDR3 PRT |
| 531 | 33_640086_6 | VH DNA |
| 532 | 33_640086_6 | VH PRT |
| 533 | 33_640086_6 | VH CDR1 PRT |
| 534 | 33_640086_6 | VH CDR2 PRT |
| 535 | 33_640086_6 | VH CDR3 PRT |
| 536 | 33_640086_6 | VL DNA |
| 537 | 33_640086_6 | VL PRT |
| 538 | 33_640086_6 | VL CDR1 PRT |
| 539 | 33_640086_6 | VL CDR2 PRT |
| 540 | 33_640086_6 | VL CDR3 PRT |
| 541 | 33_640087_7 | VH DNA |
| 542 | 33_640087_7 | VH PRT |
| 543 | 33_640087_7 | VH CDR1 PRT |
| 544 | 33_640087_7 | VH CDR2 PRT |
| 545 | 33_640087_7 | VH CDR3 PRT |
| 546 | 33_640087_7 | VL DNA |
| 547 | 33_640087_7 | VL PRT |
| 548 | 33_640087_7 | VL CDR1 PRT |
| 549 | 33_640087_7 | VL CDR2 PRT |
| 550 | 33_640087_7 | VL CDR3 PRT |
| 551 | ZZ1JMY-H09 (33_640201) | VH DNA |
| 552 | ZZ1JMY-H09 (33_640201) | VH PRT |
| 553 | ZZ1JMY-H09 (33_640201) | VH CDR1 PRT |
| 554 | ZZ1JMY-H09 (33_640201) | VH CDR2 PRT |
| 555 | ZZ1JMY-H09 (33_640201) | VH CDR3 PRT |
| 556 | ZZ1JMY-H09 (33_640201) | VL DNA |
| 557 | ZZ1JMY-H09 (33_640201) | VL PRT |
| 558 | ZZ1JMY-H09 (33_640201) | VL CDR1 PRT |
| 559 | ZZ1JMY-H09 (33_640201) | VL CDR2 PRT |
| 560 | ZZ1JMY-H09 (33_640201) | VL CDR3 PRT |
| 561 | ZZ1M37-E06 (33_640237) | VH DNA |
| 562 | ZZ1M37-E06 (33_640237) | VH PRT |
| 563 | ZZ1M37-E06 (33_640237) | VH CDR1 PRT |
| 564 | ZZ1M37-E06 (33_640237) | VH CDR2 PRT |
| 565 | ZZ1M37-E06 (33_640237) | VH CDR3 PRT |
| 566 | ZZ1M37-E06 (33_640237) | VL DNA |
| 567 | ZZ1M37-E06 (33_640237) | VL PRT |
| 568 | ZZ1M37-E06 (33_640237) | VL CDR1 PRT |
| 569 | ZZ1M37-E06 (33_640237) | VL CDR2 PRT |
| 570 | ZZ1M37-E06 (33_640237) | VL CDR3 PRT |
| 571 | 33_640201_2 | VH DNA |
| 572 | 33_640201_2 | VH PRT |
| 573 | 33_640201_2 | VH CDR1 PRT |
| 574 | 33_640201_2 | VH CDR2 PRT |
| 575 | 33_640201_2 | VH CDR3 PRT |
| 576 | 33_640201_2 | VL DNA |
| 577 | 33_640201_2 | VL PRT |
| 578 | 33_640201_2 | VL CDR1 PRT |
| 579 | 33_640201_2 | VL CDR2 PRT |
| 580 | 33_640201_2 | VL CDR3 PRT |
| 581 | 33_640237_2 | VH DNA |
| 582 | 33_640237_2 | VH PRT |
| 583 | 33_640237_2 | VH CDR1 PRT |
| 584 | 33_640237_2 | VH CDR2 PRT |
| 585 | 33_640237_2 | VH CDR3 PRT |
| 586 | 33_640237_2 | VL DNA |
| 587 | 33_640237_2 | VL PRT |
| 588 | 33_640237_2 | VL CDR1 PRT |
| 589 | 33_640237_2 | VL CDR2 PRT |
| 590 | 33_640237_2 | VL CDR3 PRT |
| 591 | 33_640076_4B | VH DNA |
| 592 | 33_640076_4B | VH PRT |
| 593 | 33_640076_4B | VL DNA |
| 594 | 33_640076_4B | VL PRT |
| 595 | 33_640081_AB | VH DNA |
| 596 | 33_640081_AB | VH PRT |
| 597 | 33_640081_AB | VL DNA |
| 598 | 33_640081_AB | VL PRT |
| 599 | 33_640082_6B | VH DNA |
| 600 | 33_640082_6B | VH PRT |
| 601 | 33_640082_6B | VL DNA |
| 602 | 33_640082_6B | VL PRT |
| 603 | 33_640082_7B | VH DNA |
| 604 | 33_640082_7B | VH PRT |
| 605 | 33_640082_7B | VL DNA |
| 606 | 33_640082_7B | VL PRT |
| 607 | 33_640084_2B | VH DNA |
| 608 | 33_640084_2B | VH PRT |
| 609 | 33_640084_2B | VL DNA |
| 610 | 33_640084_2B | VL PRT |
| 611 | 33_640086_6B | VH DNA |
| 612 | 33_640086_6B | VH PRT |
| 613 | 33_640086_6B | VL DNA |
| 614 | 33_640086_6B | VL PRT |
| 615 | 33_640087_7B | VH DNA |
| 616 | 33_640087_7B | VH PRT |
| 617 | 33_640087_7B | VL DNA |
| 618 | 33_640087_7B | VL PRT |
| 619 | 33_640201_2B | VH DNA |
| 620 | 33_640201_2B | VH PRT |
| 621 | 33_640201_2B | VL DNA |
| 622 | 33_640201_2B | VL PRT |
| 623 | 33_640237_2B | VH DNA |
| 624 | 33_640237_2B | VH PRT |
| 625 | 33_640237_2B | VL DNA |
| 626 | 33_640237_2B | VL PRT |
| 627 | Mature Human IL-33_FH | a.a. 112-270 PRT |
| 628 | Mature Mouse IL-33_FH | a.a. 109-266 PRT |
| 629 | Mature Cynomolugus IL-33 | a.a. 112-270 PRT |
| 630 | Human ST2 ECD-Fc/his6 | a.a. 1-328 PRT |
| 631 | Mouse ST2 ECD-Fc/His6 | a.a. 1-332 PRT |
| 632 | IL33-01 | a.a. 112-270 PRT |
| 633 | Human 6His TEV mature IL-33 WT | a.a. 112-270 PRT |
| 634 | IL33-02 | a.a. 112-270 PRT |
| 635 | IL33-03 | a.a. 112-270 PRT |
| 636 | IL33-04 | a.a. 112-270 PRT |
| 637 | IL33-05 | a.a. 112-270 PRT |
| 638 | IL33-06 | a.a. 112-270 PRT |
| 639 | IL33-07 | a.a. 112-270 PRT |
| 640 | IL33-08 | a.a. 112-270 PRT |
| 641 | IL33-09 | a.a. 112-270 PRT |
| 642 | IL33-10 | a.a. 112-270 PRT |
| 643 | IL33-11 | a.a. 112-270 PRT |
| 644 | IL33-12 | a.a. 112-270 PRT |
| 645 | IL33-13 | a.a. 112-270 PRT |
| 646 | IL33-14 | a.a. 112-270 PRT |
| 647 | IL33-15 | a.a. 112-270 PRT |
| 648 | IL33-16 | a.a. 112-270 PRT |
| 649 | Cynomolgus 10His Avitag IL-33 | a.a. 112-270 PRT |
| 650 | Human ST2 ECD-Flag-his10 | a.a. 1-328 PRT |

EXAMPLES

Example 1 Isolation of Antibodies to IL-33

Cloning, Expression and Purification of Mature IL-33 from Human, Mouse and Cynomolgus Monkey Protein sequences for IL-1RAcP and ST2 were obtained from Swiss Prot. Isolation and identification of anti-IL-33 scFv antibodies cDNA molecules encoding the mature component of IL-33 were synthesized by primer extension PCR and cloned into pJexpress404 (DNA 2.0). Accession numbers corresponding to database sequence information for human and mouse IL-33 are shown in Table 2. No Cynomologus monkey sequences were available so based on the high homology between Cynomolgus monkey and Rhesus monkey, the sequence of Rhesus monkey (Accession No. ENSMMUT00000030043) was used to design primers capable of amplifying the coding sequence of the IL-33 gene in Cynomolgus monkey. The Rhesus gene sequence was aligned to the Humans IL-33 cDNA sequence (Accession No. NM_033439), this demonstrated that the Rhesus sequence was mis-assembled and was missing exon 1. A BLAST search was performed against the Rhesus genomic sequence using the human exon 1, and the Rhesus sequence matching exon 1 was identified. Additional primers were designed to amplify exon 1.

The mature IL-33 coding sequence was modified to contain a FLAG® 10× his epitope tag (DYKDDDDKAAH-HHHHHHHHH; SEQ ID NO. 627) at the C-terminus of the protein. SEQ ID NOs corresponding to mature Flag®His-tagged human, cynomolgus and mouse IL-33 are shown in Table 2.

TABLE 2

Sequences for human, mouse and cynomolgus monkey mature IL-33

| Species | Amino acids | Accession No. (Swiss-Prot) | Flag ®His-tagged IL-33 Sequences |
|---|---|---|---|
| Human | 112-270 | O95760 | SEQ ID NO. 627 |
| Mouse | 109-266 | Q8BVZ5 | SEQ ID NO. 628 |
| Cynomolgus | 112-270 | Not Available | SEQ ID NO. 629 |

Vectors were transformed into BL21(DE3) competent cells (Merck Biosciences, 69450) and expression induced with 1 mM IPTG. Harvested cells were lysed with Bugbuster (Merck Biosciences, 70584) and expressed protein was purified using Ni-NTA affinity chromatography (Histrap HP column: GE Healthcare, 17-5248-02) followed by Size Exclusion chromatography (Superdex 75 column: GE Healthcare, 17-1068-01).

Protein Modifications

IgGs and modified receptor proteins used herein were biotinylated via free amines using EZ link Sulfo-NHS-LC-Biotin (Thermo/Pierce, 21335) The biotin reagent was dissolved in anhydrous dimethylformamide and PBS based protein solutions were adjusted to pH ~8 with 1 M NaHCO$_3$ in D-PBS (Dulbecco's phosphate buffered saline). IL-33 proteins used herein were biotinylated via free cysteines using EZ link Biotin-BMCC (Perbio/Pierce, product no. 21900). The biotin reagent was dissolved in anhydrous dimethylformamide and mixed PBS protein solutions. Label incorporations were assessed by MALDI-TOF mass spectrometry in all cases and unreacted reagents were cleared by buffer exchange using PBS equilibrated disposable Sephadex G25 columns. For biotinylation, the final protein concentrations were determined by 280 nm absorbance using extinction coefficients calculated from amino acid sequences.

Selections

A large single chain Fv (scFv) human antibody library, based upon variable (V) genes isolated from human B-cells from adult naïve donors and cloned into a phagemid vector based on filamentous phage M13 was used for selections (Hutchings, C., "Generation of Naïve Human Antibody Libraries" in Antibody Engineering, Dubel. Berlin, Springer Laboratory Manuals: p. 93 (2001); Lloyd et al., Protein Eng. Des. Sel. 22(3):159-68 (2009)). IL-33-specific scFv antibodies were isolated from the phage display library in a series of repeated selection cycles on recombinant human and/or mouse IL-33 essentially as described in Vaughan et al. (Nat. Biotechnol. 14(3):309-14 (1996)). A list of IL-33 reagents used herein is shown in Table 3.

TABLE 3

ELISA Binding Assay Reagents

| Reagent | Supplier | Catalogue Number/ Designation | ELISA assay |
|---|---|---|---|
| Human IL-33 | Axxora/Adipogen | AG-40B-0038 | Phage/IgG |
| Human IL-33 | Axxora/Alexis | ALX-522-098 | Phage |
| Human IL-33 Flag ®His | In house | PS-295 | Phage/IgG |
| Human IL-33 | Peprotech | 200-33 | Phage |
| Mouse IL-33 | Peprotech | 210-33 | Phage |
| Mouse IL-33 | Axxora/Alexis | ALX-522-101 | Phage |
| Mouse IL-33 Flag ®His | In house | PS-296 | Phage/IgG |
| Cynomologus IL-33 Flag ®His | In house | PS-368 | Phage/IgG |
| IL-4Rα Flag ®His | In house | 020629080 | Phage/IgG |
| Bovine insulin - biotin | Sigma | I2258 | Phage/IgG |

In brief, the scFv-phage particles were incubated with biotinylated recombinant IL-33 in solution (biotinylated via free cysteines using EZ link Biotin-BMCC (Perbio/Pierce, product no. 21900)). Particles were incubated with 100 nM biotinylated recombinant IL-33 for 2 hours. ScFv bound to antigen were then captured on streptavidin-coated paramagnetic beads (Dynabeads®, M-280) following manufacturer's recommendations. Unbound phage was washed away in a series of wash cycles using PBS-Tween. The phage particles retained on the antigen were eluted, infected into bacteria and rescued for the next round of selection. Typically two or three rounds of selection were performed in this way.

Identification of IL-33 Specific Binders by Phage ELISA

A representative number of individual clones from the selection outputs after two or three rounds of selection described above were grown up in 96-well plates. Single-chain Fv fragments were displayed on phage particles and tested in a binding assay to determine cross-reactivity and specificity to a panel of recombinant human, mouse and cynomolgus IL-33 antigens. Phage-displayed scFv supernatant samples were generated in 96-well deep well plates as follows. 5 µl of culture from each well of a 96-well master plate was transferred into a Greiner deep well culture plate containing 500 µl of 2TYAG (2TY+100 µg/ml ampicillin+ 2% glucose) media and incubated for 5 hours at 37° C., 280 rpm. K07 M13 helper phage (diluted to 1.5×10$^{11}$ pfu/ml in 2TYAG) was then added at 100 µl/well and the plate incubated at 37° C., 150 rpm to allow infection. The plate was spun down at 3200 rpm for 10 minutes and the supernatant removed. Bacterial pellets were resuspended in 500 µl/well 2TYAK (2TY+100 µg/ml ampicillin+50 µg/ml kanamycin) and the plate incubated overnight at 25° C., 280 rpm. In the morning, 500 µl of 6% (w/v) skimmed milk powder in 2×PBS was added to each well and the plate incubated for 1 hour at room temperature. The plate was then centrifuged at 3200 rpm for 10 minutes and the blocked phage-displayed scFv supernatants were used directly in ELISA experiments.

For EC50 determinations, typically purified IgGs were diluted 3-fold in 3% (w/v) dried-milk powder in PBS (PBS-M), to give 11 concentration points. 96-well Greiner polypropylene plates (Greiner, 650201) were used for dilution preparation. Generally, each dilution was prepared in duplicate. IgG dilutions were allowed to block in PBS-M for 1 hour at room temperature before being used directly in ELISA experiments.

The IL-33 binding assays were plate-based ELISAs performed essentially as follows. Table 3 above shows the antigens used for these experiments. Not all antigens were used in every experiment, but in all cases a human, a mouse, and a cynomolgus IL-33 antigen was tested. Relevant control antigens (bovine insulin plus IL-4Rα FLAG®His, if appropriate) were also used to test for non-specific binding. With the exception of bovine insulin, all antigens were biotinylated (see subsection 1.1. above) and all were generated using bacterial expression. The method for generation of IL-4Rα FLAG®His, which was used as a control antigen, is described in WO/2010/070346.

Streptavidin plates (Thermo Scientific, AB-1226) were coated with biotinylated antigen at 0.5 μg/ml in PBS and incubated overnight at 4° C. Plates were washed 3× with PBS and blocked with 300 μl/well blocking buffer (PBS-M) for 1 hour. Plates were washed 1× with PBS and blocked samples added, 50 μl/well for 1 hour at room temperature. Plates were washed 3× with PBS-T (PBS+1% (v/v) Tween-20) and detection reagents [anti-human IgG HRP (Sigma, A0170) or anti-M13-HRP antibody (Amersham, 27-9421-01) for detection of IgG or phage-displayed scFv, respectively] at 1:5000 dilutions were added at 50 μl/well in PBS-M for 1 hour at room temperature. Plates were washed 3× with PBS-T and developed with TMB, 50 μl/well (Sigma, T0440). The reaction was quenched with 50 μl/well 0.1M $H_2SO_4$ before reading on an EnVision™ plate reader, or similar equipment, at 450 nm.

Dose response curves were plotted for IgG titrations using Prism (Graphpad) curve-fitting software. Phage-displayed scFv were considered to bind the IL-33 antigen if the absorbance 450 nm was >0.5, and <0.2 for the same sample on controls (insulin and IL-4Rα Flag®His).

Cloning, Expression and Purification of ST2 ECD from Human and Mouse cDNA molecules encoding the extracellular domains (ECDs) of ST2 from human and mouse were synthesized by primer extension PCR cloning and cloned into pDONR221 (Invitrogen, 12536-017). Database sequences for human and mouse ST2 were used (see Table 4). ST2 ECD cDNA clones in pDONR221 were transferred to mammalian expression vector pDEST12.2 using LR Gateway Clonase II enzyme according to the manufacturer's instructions. The pDEST12.2 vector had been modified to contain the human IgG1 Fc coding region, polyhistidine (His6) tag in-frame with the inserted gene of interest, and also by insertion of the oriP origin of replication from the pCEP4 vector allowing episomal plasmid replication upon transfection into cell lines expressing the EBNA-1 gene product (such as HEK293-EBNA cells).

TABLE 4

Amino acids and accession numbers for human and mouse ST2 extracellular domain

| Species | Amino acids | Accession number (Swiss-Prot) | EDC-Fc-His6 Sequences |
|---|---|---|---|
| Human | 1-328 | Q01638 | SEQ ID NO: 630 |
| Mouse | 1-332 | P14719 | SEQ ID NO: 631 |

Expressed ST2.Fc proteins in HEK293-EBNA supernatants were purified using Protein A affinity chromatography (HiTrap Protein A column (GE Healthcare, 17-0402-01)) followed by Size Exclusion chromatography (Superdex 200 column (GE Healthcare, 17-1069-01)).

Inhibition of IL-33 Binding to ST2 by Unpurified scFv

A representative number of individual clones from the selection outputs after two or three rounds of selection described above were grown up in 96-well plates. ScFv were expressed in the bacterial periplasm (Kipriyanov, et al. *J Immunol Methods* 200(1-2): 69-77 (1997)) and screened for their inhibitory activity in a homogeneous FRET (fluorescence resonance energy transfer) HTRF® (Homogeneous Time-Resolved Fluorescence, Cisbio International) based IL-33:ST2-binding assay. In this assay, samples competed with human or mouse ST2.Fc for binding to FLAG®His-tagged human, cynomolgus or mouse IL-33.

An HTRF® assay is a homogeneous assay technology that utilises fluorescence resonance energy transfer between a donor and acceptor fluorophore that are in close proximity (Mathis, et al. *Clin Chem* 41(9):1391-7 (1995)). This assay was used to measure macromolecular interactions by directly or indirectly coupling one of the molecules of interest to a donor fluorophore, europium (Eu3+) cryptate, and coupling the other molecule of interest to an acceptor fluorophore XL665, (a stable cross linked allophycocyanin). Excitation of the cryptate molecule (at 337 nm) resulted in fluorescence emission at 620 nm. The energy from this emission was transferred to XL665 in close proximity to the cryptate, resulting in the emission of a specific long-lived fluorescence (at 665 nm) from the XL665. The specific signals of both the donor (at 620 nm) and the acceptor (at 665 nm) were measured, allowing the calculation of a 665/620 nm ratio that compensates for the presence of colored compounds in the assay.

Unpurified anti-IL-33 scFv samples were tested for inhibition of FLAG®-His tagged IL-33 binding ST2-Fc by adding 10 microlitres of each dilution of antibody test sample to a 384 well low volume assay plate (Costar, 3676). Next, a solution containing 2 nM human or mouse ST2-Fc and 3 nM anti-human Fc cryptate detection (Cisbio International, 61HFCKLB) was prepared and 5 microlitres of the mix added to the assay plate. This was followed by the addition of 5 microlitres of a solution containing 1.2 nM FLAG®-His tagged human, cynomolgus or mouse IL-33 combined with 20 nM anti-FLAG® XL665 detection (Cisbio International, 61FG2XLB). All dilutions were performed in assay buffer containing 0.8 M potassium fluoride (BDH 103444T) and 0.1% bovine serum albumin (BSA, Sigma A9576) in Dulbeccos PBS (Invitrogen, 14190185). Assay plates were incubated for 1 hour at room temperature followed by 16 hour at 4° C. before reading time resolved fluorescence at 620 nm and 665 nm emission wavelengths using an EnVision plate reader (Perkin Elmer).

Data were analysed by calculating the 665/620 nm ratio followed by the % Delta F values for each sample. The 665/620 nm ratio was used to correct for sample interference using Equation 1:

$$665/620 \text{ nm ratio} = \left(\frac{665 \text{ nm signal}}{620 \text{ nm signal}}\right) \times 10{,}000$$

The % Delta F for each sample was then calculated using Equation 2:

$$\text{Delta } F \text{ (\%)} = \left(\frac{\text{sample } 665/620 \text{ nm ratio} - \text{negative control } 665/620 \text{ nm ratio}}{\text{negative control } 665/620 \text{ nm ratio}}\right) \times 100$$

The negative control (non-specific binding) was defined by replacing test sample with 150 nM non-tagged human or mouse IL-33 (Axxora, human ALX522-098, mouse ALX-522-101) prepared in a dilution buffer comprised of Dulbeccos PBS (Invitrogen, 14190185) containing 0.1% bovine serum albumin (BSA, Sigma A9576).

The % Delta F values were subsequently used to calculate % specific binding as described in Equation 3:

$$\% \text{ specific binding} = \left( \frac{(\text{Sample Delta } F \% - NSB \text{ Delta } F \%)}{(\text{Total binding Delta } F \% - NSB \text{ Delta } F \%)} \right) \times 100$$

$IC_{50}$ values were determined using GraphPad Prism software by curve fitting using a four-parameter logistic equation (Equation 4).

$Y = \text{Bottom} + (\text{Top} - \text{Bottom})/(1+10^{((\text{Log EC50}-X)*\text{HillSlope})})$   Equation 4

X is the logarithm of concentration.
Y is specific binding
Y starts at Bottom and goes to Top with a sigmoid shape.

FIG. 1 shows the inhibition of the FRET signal, produced by human IL-33 binding to human ST2, by unpurified scFv periplasmic extracts in a single point screen. The final concentration of the periplasmic extract was 50% v/v. Well B04 (unpurified IL330004 scFv) shows an example 'hit' and column 12 contains control wells as indicated.

Inhibition of IL-33 Binding to ST2 by Purified scFv

Single chain Fv clones which showed an inhibitory effect on IL-33:ST2 interaction as unpurified periplasmic extracts or demonstrated a desirable species cross-reactivity and specificity profile by phage binding experiments above, were subjected to DNA sequencing (Osbourn, et al. *Immunotechnology* 2(3):181-96 (1996); Vaughan, et al. *Nat Biotechnol* 14(3):309-14 (1996).). Unique scFv were expressed again in bacteria and purified by affinity chromatography (as described in WO01/66754). The potencies of these samples were determined by competing a dilution series of the purified preparation against human or mouse ST2.Fc for binding to FLAG®His-tagged human, cynomolgus or mouse IL-33 as described above. Purified scFv preparations that were capable of inhibiting the IL-33:ST2 interaction to a greater extent than the negative control were selected for conversion to IgG format (e.g., scFv antibodies IL330002, IL330004, IL330020 and IL330071

FIG. 2A: shows the inhibition of the FRET signal, produced by human IL-33 binding to human ST2 with increasing concentrations of IL-33 scFv antibodies IL330002, IL330004, IL330020 and IL330071, wherein the x-axis is the concentration of antibody in molar concentration and the y-axis is percent specific binding.

FIG. 2B: shows the inhibition of the FRET signal, produced by cynomolgus monkey IL-33 binding to human ST2 with increasing concentrations of IL-33 scFv antibodies IL330002, IL330004, IL330020 and IL330071, wherein the x-axis is the concentration of antibody in molar concentration and the y-axis is percent specific binding.

Identification of Partner Antibodies for IL330004 scFv periplasmic extracts of those clones that demonstrated positive binding to human IL-33 by Phage ELISA were screened by Octet assay (Octet RED 384 system) to identify an antibody that bound IL-33 simultaneously with IL330004. Neat periprep samples were captured on a Nickel NTA biosensor and sequential binding of IL-33 (200 nM) followed by IL330004 (200 nM) was performed. Biosensors were regenerated to minimise use. Sensors are regenerated in glycine (10 mM, pH 1.7), neutralised in buffer (PBS+1 mg/ml (0.1%) BSA+0.02% Tween20) and reloaded with NiSO4 (10 mM) to replenish the nickel on the biosensor surface. IL330425 and IL330428 were identified and converted to whole immunoglobulin G1 (IgG1) antibody format.

Reformatting of scFv to IgG1

Single chain Fv clones with desirable properties from the IL-33:ST2 binding assays, plus a panel of phage-displayed scFv with desirable specificities by binding experiments were converted to whole immunoglobulin G1 (IgG1) antibody format essentially as described by Persic et al. (*Gene* 187(1):9-18 (1997)) with the following modifications. An OriP fragment was included in the expression vectors to facilitate use with CHO-transient cells and to allow episomal replication. The variable heavy (VH) domain was cloned into a vector (pEU1.3) containing the human heavy chain constant domains and regulatory elements to express whole IgG1 heavy chain in mammalian cells. Similarly, the variable light (VL) domain was cloned into a vector (pEU4.4) for the expression of the human light chain (lambda) constant domains and regulatory elements to express whole IgG light chain in mammalian cells. To obtain IgGs, the heavy and light chain IgG expressing vectors were transfected into CHO-transient mammalian cells (Daramola et al. *Biotechnol Prog* 30(1):132-41 (2014)). IgGs were expressed and secreted into the medium. Harvests were filtered prior to purification, then IgG was purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralized by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG (Mach et al., *Anal. Biochem.* 200(1): 74-80 (1992)). The purified IgG were analyzed for aggregation and degradation purity using SEC-HPLC and by SDS-PAGE. SEQ ID NOs corresponding to the various regions of antibodies IL330002, IL330004, IL330020, IL330071, IL330125, and IL330126 are shown in Table 5.

TABLE 5

Anti-IL-33 Antibody Sequences

| IgG1 | VH Sequence | VL Sequence | VH CDRs 1, 2, 3 | VL CDRs 1, 2, 3 |
|---|---|---|---|---|
| IL330002 | SEQ ID NO: 2 | SEQ ID NO: 7 | SEQ ID NO: 3 | SEQ ID NO: 8 |
|  |  |  | SEQ ID NO: 4 | SEQ ID NO: 9 |
|  |  |  | SEQ ID NO: 5 | SEQ ID NO: 10 |
| IL330004 | SEQ ID NO: 12 | SEQ ID NO: 17 | SEQ ID NO: 13 | SEQ ID NO: 18 |
|  |  |  | SEQ ID NO: 14 | SEQ ID NO: 19 |
|  |  |  | SEQ ID NO: 15 | SEQ ID NO: 20 |
| IL330020 | SEQ ID NO: 22 | SEQ ID NO: 27 | SEQ ID NO: 23 | SEQ ID NO: 28 |
|  |  |  | SEQ ID NO: 24 | SEQ ID NO: 29 |

TABLE 5-continued

Anti-IL-33 Antibody Sequences

| IgG1 | VH Sequence | VL Sequence | VH CDRs 1, 2, 3 | VL CDRs 1, 2, 3 |
|---|---|---|---|---|
| IL330071 | SEQ ID NO: 32 | SEQ ID NO: 37 | SEQ ID NO: 25<br>SEQ ID NO: 33<br>SEQ ID NO: 34<br>SEQ ID NO: 35 | SEQ ID NO: 30<br>SEQ ID NO: 38<br>SEQ ID NO: 39<br>SEQ ID NO: 40 |
| IL330125 | SEQ ID NO: 42 | SEQ ID NO: 47 | SEQ ID NO: 43<br>SEQ ID NO: 44<br>SEQ ID NO: 45 | SEQ ID NO: 48<br>SEQ ID NO: 49<br>SEQ ID NO: 50 |
| IL330126 | SEQ ID NO: 52 | SEQ ID NO: 57 | SEQ ID NO: 53<br>SEQ ID NO: 54<br>SEQ ID NO: 55 | SEQ ID NO: 58<br>SEQ ID NO: 59<br>SEQ ID NO: 60 |
| IL330425 | SEQ ID NO: 62 | SEQ ID NO: 67 | SEQ ID NO: 63<br>SEQ ID NO: 64<br>SEQ ID NO: 65 | SEQ ID NO: 68<br>SEQ ID NO: 69<br>SEQ ID NO: 70 |
| IL330428 | SEQ ID NO: 72 | SEQ ID NO: 77 | SEQ ID NO: 73<br>SEQ ID NO: 74<br>SEQ ID NO: 75 | SEQ ID NO: 78<br>SEQ ID NO: 79<br>SEQ ID NO: 80 |

Inhibition of IL-33 Binding to ST2 by Purified IgG

The ability of anti-IL-33 antibodies to inhibit the binding of FLAG®-His tagged IL-33 to the ST2 receptor was assessed in a biochemical HTRF® (Homogeneous Time-Resolved Fluorescence, Cisbio International) competition assay, the principles of which are described above.

Activity of purified IgG preparations were determined by competing a dilution series of the purified IgG against biotinylated human or mouse ST2.Fc for binding to FLAG®His-tagged human, cynomolgus or mouse IL-33.

Purified or unpurified anti-IL-33 antibody samples were tested for inhibition of FLAG®-His tagged IL-33 binding ST2-Fc by adding 10 microlitres of each dilution of antibody test sample to a 384 well low volume assay plate (Costar 3676). Next, a solution containing 4 nM biotinylated human or mouse ST2-Fc and 20 nM streptavidin XL665 detection (Cisbio International, 611SAXLB) was prepared and 5 microlitres of the mix added to the assay plate. This was followed by the addition of 5 microlitres of a solution containing 1.2 nM FLAG®-His tagged human, cynomolgus or mouse IL-33 combined with 1.72 nM anti-FLAG® cryptate detection (Cisbio International, 61FG2KLB). All dilutions were performed in assay buffer comprised of Dulbeccos PBS (Invitrogen, 14190185) containing 0.8 M potassium fluoride (BDH 103444T) and 0.1% BSA (Sigma A9576). Assay plates were incubated for 2 hour at room temperature followed by 16 hour at 4° C. before reading time resolved fluorescence at 620 nm and 665 nm emission wavelengths using an EnVision plate reader (Perkin Elmer).

Data were analyzed as described above using Equations 1 to 3.

The negative control (non-specific binding) was defined by replacing test sample with 100 nM non-biotinylated ST2 prepared in a dilution buffer comprised of Dulbecco's PBS (Invitrogen, 14190185) containing 0.1% bovine serum albumin (BSA, Sigma A9576).

The representative potencies ($IC_{50}$) for purified IgG antibodies IL330002, IL330004, IL330020, IL330071, IL330125, and IL330126 are shown in Table 6.

TABLE 6

$IC_{50}$ results in the IL-33 FLAG ®-His/ST2-Fc competition assay

| IgG | Human IL-33 FLAG ® + Human ST2-Fc | Cynomolgus IL-33 FLAG ® + Human ST2-Fc |
|---|---|---|
| IL330002 | 27 nM | 42 nM |
| IL330004 | 9 nM | 170 nM |
| IL330020 | 40 nM | No inhibition |
| IL330071 | 59 nM | 375 nM |
| IL330125 | 210 nM | No inhibition |
| IL330126 | 226 nM | No inhibition |

All of the purified IgG preparations (i.e., IL330002, IL330004, IL330020, IL330071, IL330125, and IL330126) were shown to inhibit the human IL-33: human ST2 interaction. FIG. 3A: shows the inhibition of the FRET signal, produced by human IL-33 binding to human ST2 with increasing concentrations of IL-33 IgG1 antibodies IL330002, IL330004, IL330020, IL330071, IL330125 and IL330126, wherein the x-axis is the concentration of antibody in molar concentration and the y-axis is percent specific binding.

The IL330002, IL330004, and IL330071 IgG preparations were also shown to inhibit the cynomolgus IL-33: human ST2 interaction. FIG. 3B: shows the inhibition of the FRET signal, produced by cynomolgus monkey IL-33 binding to human ST2 with increasing concentrations of IL-33 IgG1 antibodies IL330002, IL330004, IL330020 and IL330071, IL330125 and IL330126, wherein the x-axis is the concentration of antibody in molar concentration and the y-axis is percent specific binding. No inhibition was detected in the mouse IL-33 FLAG®-His+mouse ST2-Fc competition assay by any of the above tested antibodies.

Inhibition of NFκB Signaling in Hela-ST2 Reporter Cells by IgG

A reporter assay was used to assess the inhibition of IL-33 induced NFκB signaling by anti-IL-33 antibodies IL330002, IL330004, IL330020, IL330071, IL330125, and IL330126, using Hela cells co-transfected with ST2 and an NFκB responsive luciferase reporter construct. Cells were exposed to IL-33 in the presence or absence of test antibody, and NFκB signaling was detected by measuring the activity of the luciferase subsequently produced. Hela cells containing luciferase reporter construct were sourced from Panomics. Human ST2 sequence was cloned into a lentiviral vector from System Biosciences. Lentiviral particles were generated in Ad293 cells (Stratagene) and used to transduce the Hela-luciferase reporter cells.

In the reporter assay, stimulation of the ST2 receptor with IL-33 resulted in activation of the NFκB signaling pathway and through the NFκB promoter, initiated the expression of the enzyme luciferase. Following lysis of the cells, a luciferase substrate was added, which underwent a chemical reaction in the presence of luciferase to produce a luminescent product. The amount of light detected from the cell lysate was quantified using an Envision plate reader (PerkinElmer) and used as a direct measure of IL-33 mediated NFκB signaling.

Hela transfected cells were maintained in media containing hygromycin B to maintain stable receptor expression.

Cells were exposed to IL-33 in the presence or absence of test antibody, and NFκB signaling detected by measuring the activity of the luciferase subsequently produced.

Transfected Hela cells were seeded at $1\times10^4$ cells/well (50 microlitres per well) in DMEM culture medium (Invitrogen, 41966) containing 10% v/v Fetal Bovine Serum (heat inactivated) and 100 microgram per mL Hygromycin B (Invitrogen 10687-010) into 384 well black-walled, Poly-D-Lysine coated plates (Greiner, 781946). Plates were incubated at 37 degrees Celsius, 5% $CO_2$ for 18-24 hours, and then cell medium was gently aspirated from the wells prior to addition of test samples.

Serial dilutions of samples were prepared by dilution in DMEM culture medium (Invitrogen 41966) containing 10% v/v FBS (heat inactivated) and 100 microgram per mL Hygromycin B (Invitrogen, 10687-010). Fifteen microlitres of test sample was added to cells in duplicate. IL-33 FLAG®-His was diluted to 0.6 nM in DMEM culture medium (Invitrogen, 41966) containing 10% v/v FBS (heat inactivated) and 100 microgram per mL Hygromycin B (Invitrogen 10687-010) and 15 microlitres added to the cells and test samples. This concentration represented the $EC_{50}$ value of the reporter cell response to IL-33 FLAG®-His (Geomean 0.32 nM, 95% confidence intervals 0.25-0.40 nM, n=5). Background response was defined by the addition of 30 microlitres DMEM culture medium (Invitrogen, 41966) containing 10% v/v FBS (heat inactivated) and 100 microgram per mL Hygromycin B (Invitrogen, 10687-010). Plates were incubated at 37 degrees Celsius, 5% $CO_2$ for 4 hours and at room temperature for 1 hour.

To measure production of luciferase in response to NFκB signaling, 30 microlitres of Bright Glo® lysis buffer combined with luciferase substrate (Promega, E2620) was added to the plate and incubated at room temperature for 5 minutes. Luminescence produced as a result of oxidation of the substrate by luciferase is read using an EnVision plate reader (PerkinElmer).

The relative light unit (RLU) values were subsequently used to calculate % specific response as described in equation 5:

$$\% \text{ specific response} = \left( \frac{(\text{Sample } RLU - BackgroundRLU)}{(\text{Total } RLU - BackgroundRLU)} \right) \times 100$$

$IC_{50}$ values were determined using GraphPad Prism software by curve fitting using a four-parameter logistic equation (Equation 4):

Purified IgG preparations of antibodies IL330002, IL330004, IL330020, IL330071, IL330125, and IL330126 were shown to inhibit the NFκB-driven luciferase activity with representative potencies (IC50) shown in Table 7.

TABLE 7

$IC_{50}$ results in the human ST2 transfected HeLa NFkB reporter assay

| IgG | Human IL-33 FLAG®-His |
|---|---|
| IL330002 | 226 nM |
| IL330004 | 23 nM |
| IL330020 | 147 nM |
| IL330125 | 332 nM |
| IL330126 | 245 nM |
| IL330071 | 226 nM |

FIG. 4A shows the inhibition of NFκB activity in luciferase NFκB reporter assay by IL-33 antibodies IL330002, IL330004 IL330020, IL330071, IL330125, and IL330126 compared to a negative control IgG.

Inhibition of NFκB Signaling in Huvec by IgG

NFκB signaling in Human umbilical vein endothelial cells (Huvecs) in response to IL-33 was assessed by nuclear translocation of the p65/RelA NFkB subunit detected by immunofluorecence staining. Imaging and quantification of the nuclear staining intensity was performed on ArrayScan VTi HCS Reader (Cellomics).

Huvecs were obtained from Cambrex and maintained in complete EBM-2 media (Lonza) according to recommended protocol. Huvecs were harvested from flasks with accutase (PAA, # L11-007) and seeded at $1\times10^4/100$ μl/well in culture media [EBM-2 (Lonza, # CC-3156) with EGM-2 Single-Quot Kit Suppl. & Growth Factors (Lonza, # CC-4176)] into 96-well black walled, clear flat-bottomed Collagen I coated plates (Greiner) and incubated at 37° C., 5% $CO_2$ for 18-24 hours. After this time, media was aspirated, leaving cell monolayer intact, and replaced with assays test samples as prepared below.

Test samples of purified IgG (in duplicate) were diluted to the desired concentration in complete culture media in 96 well U-bottom polypropylene plates (Greiner, 650201). IL-33 (Adipogen) was prepared in complete culture media mixed with appropriate test antibody to give a final IL-33 concentration of 1 ng/mL in a total volume of 120 μl/well. All samples were incubated for 30 mins at 37° C., prior to transfer of 100 μl of IL-33/antibody mixture to the assay plate. Following 30 minute incubation at 37° C., media were aspirated, leaving the cell monolayer intact and cells were fixed for 15 minutes with 3.7% formaldehyde solution that had been pre-warmed to 37° C. Fixative was aspirated and cells were washed twice with 100 μL/well of PBS.

Cells were stained for NFκB using a Cellomics NFκB assay kit (Thermo Scientific, #8400492) according to manufacturer's instructions. Briefly, cells were permeabilised for 15 minutes at room temperature, blocked for 15 minutes and stained for 1 hour with primary antibody solution in a volume of 50 μL. Plates were washed ×2 in blocking buffer and stained for 1 hour at room temperature with secondary antibody solution, which included Hoechst nuclear stain as well as secondary antibody. Plates were washed ×2 in PBS. Cells were stored in a final volume of 150 μL/well PBS and covered with a black, light-blocking seal (Perkin Elmer, #6005189) before reading on ArrayScan VTi HCS Reader. The intensity of nuclear staining was calculated using a suitable algorithm. Data were analysed using Graphpad Prism software. $IC_{50}$ values were determined by curve fitting using a four-parameter logistic equation (Equation 4).

FIG. 4B shows the inhibition of NFκB activity in Huvec NFκB translocation assay by IL-33 antibody IL330004 compared to Anti-NIP IgG1 negative control antibody, NIP228. Nuclear translocation of p65/RelA NFκB was inhibited by antibody IL330004. When tested as a purified IgG, the IC50 for antibody IL330004 was calculated as being 12 nM.

Binding Affinity Calculation for IL-33 Antibodies using BIAcore

The binding affinity of purified IgG samples of exemplary binding members to human and cynomolgus IL-33 was determined by surface plasmon resonance using BIAcore 2000 biosensor (BIAcore AB) essentially as described by Karlsson et al., *J Immunol Methods* 145(1-2):229-40 (1991). In brief, Protein G' (Sigma Aldrich, P4689) was covalently coupled to the surface of a CM5 sensor chip using standard amine coupling reagents according to manufacturer's instructions (BIAcore). The protein G' surface was used to capture purified anti-IL-33 antibodies via the Fc domain to provide a surface density of approximately 290RU per cycle. Human or cynomolgus IL-33 prepared in HBS-EP buffer (BIAcore AB), at a range of concentrations, between 600 nM and 18.75 nM, were passed over the sensor chip surface. The surface was regenerated using two 10 mM Glycine washes of pH 1.7 and pH 1.5 between each injection of antibody. The resulting sensorgrams were evaluated using BIA evaluation 3.1 software and fitted to a 1:1 Langmuir binding model, to provide relative binding data. The binding results (KD, Ka, and Kd) for antibodies IL330002 and IL330004 binding to human or cynomolgus IL-33 are shown in Table 8.

TABLE 8

BIAcore binding affinity of exemplary binding members

| Antibody | Antigen | KD (nM) | Ka (1/Ms) | Kd (1/s) |
|---|---|---|---|---|
| IL330002 | Human IL-33 FLAG®-His | 35 | 6.16E+04 | 2.18E−03 |
| IL330002 | Cynomolgus IL-33 FLAG®-His | 189 | 2.34E+04 | 4.42E−03 |
| IL330004 | Human IL-33 FLAG®-His | 6 | 1.96E+05 | 1.10E−03 |
| IL330004 | Cynomolgus IL-33 FLAG®-His | 365 | 1.25E+04 | 4.58E−03 |

Binding of IL-33 Antibodies to Intracellular IL-33

Selection and activity studies described above used recombinant or commercial sources of mature IL-33 (amino acids 112-270). Studies suggest full length IL-33 may also be active (Cayrol et al., *Proc Natl Acad Sci USA* 106(22): 9021-6 (2009); Hayakawa et al., *Biochem Biophys Res Commun* 387(1):218-22 (2009); Talabot-Ayer et al., *J Biol Chem.* 284(29):19420-6 (2009)). The binding of antibodies to full length ("native") IL-33 was determined by immunofluorescence staining of primary bronchial smooth muscle cells (BSMC).

BSMC were obtained from Cambrex and maintained in complete smooth muscle growth media (SmBM®, Lonza) according to manufacturer's instructions. Cells were harvested from flasks with accutase (PAA # L11-007) and seeded at $2\times10^4/100$ µl/well in culture media [SMBM (Lonza # CC-3181) with SMGM SingleQuot Kit Suppl. & Growth Factors (Lonza # CC-4149)] into 96-well black walled, clear flat-bottomed Collagen I coated plates (Greiner) and incubated at 37° C., 5% $CO_2$ for 18-24 hours. After this time, media was aspirated, leaving cell monolayer intact, and cells were fixed for 15 minutes with 3.7% formaldehyde solution that had been pre-warmed to 37° C. Fixative was aspirated and cells were washed twice with 100 µL/well of PBS. Cells were permeabilised for 15 minutes at room temperature using permeabilisation buffer (Thermo Scientific, #8400492), washed ×2 in PBS and blocked with 100 µL/well of PBS/1% BSA (Sigma, # A9576) for 30-60 minutes at room temperature. Blocking buffer was flicked out and replaced with a titration of anti-IL-33 or suitable isotype control antibodies, that had been diluted in blocking buffer, for 1 hour at room temperature.

Plates were washed ×2 in PBS and stained for 1 hour at room temperature with secondary antibody solution, which included Hoechst dye (10 mg/mL; Thermo Scientific) diluted 1:10000 as well as secondary antibody (Anti-Human IgG (H+L), Alexa Fluor® 488 conjugate 2 mg/mL; Invitrogen, # A11013) diluted 1:1000. Plates were washed three times in PBS. Cells were stored in a final volume of 150 µL/well PBS and covered with a black, light-blocking seal (Perkin Elmer, #6005189) before imaging on ArrayScan VTi HCS Reader.

Figure 5:
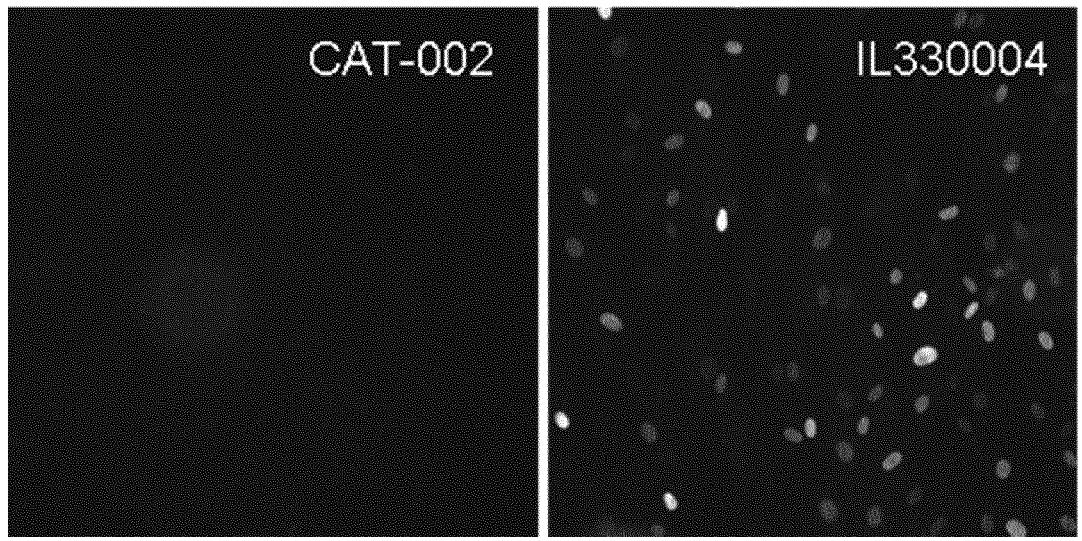
FIG. 5 Shows detection of endogenous IL-33 in bronchial smooth muscle cells by immunofluorescence staining by IL-33 antibody IL330004 (right panel) compared to CAT-002 negative control (left panel).

IL-33 expression by cultured BSMC was confirmed with a commercial polyclonal antibody (R&D Systems, # AF3625), detected with anti-Goat IgG (H+L), Alexa Fluor® 488 conjugate 2 mg/mL; Invitrogen, # A11055). FIG. 5 shows detection of endogenous IL-33 in bronchial smooth muscle cells by immunofluorescence staining by IL-33 antibody IL330004 (right panel) compared to CAT-002 negative control (left panel). Antibody IL330004 showed a clear nuclear staining of BSMC, corresponding with the expected localization of full length IL-33, and that detected with the commercial pAb.

Example 2 Isolation and Identification of Anti-IL-33 scFv Antibodies

Identification of IL-33 Specific Binders by Phage ELISA

Reagents and selections were as described in Example 1. Single-chain Fv fragments were displayed on phage particles and tested as unpurified preparations in a single point ELISA screen. Phage-displayed scFv were considered to bind the IL-33 antigen if the absorbance 450 nm was >0.5, and <0.1-0.2 for the same sample on controls (insulin and IL-4Rα Flag®His).

FIG. 6 shows data from a single plate screened against human IL-33, cynomolgus IL-33 and insulin. One specific human/cynomolgus cross-reactive IL-33 binder is shown in well C4, and wells A12 and B12 contain control IL-33 binding clone.

Identification of IL-33 Binders by Axxora IL33305B Competition

The Axxora IL33305B Competition Assay is a homogeneous assay that utilizes Fluorescence Microvolume Assay Technology (FMAT). The assay assessed the inhibition of Axxora IL33305B mAb (Axxora/Adipogen, # AG-20A-0041-0050) binding to recombinant biotinylated human IL-33 Flag®His in the presence of crude scFv supernatant samples or purified scFv and IgG in a 384-well format.

ScFv were expressed in the bacterial periplasm and screened for their inhibitory activity in an FMAT epitope competition assay against a known biologically active IL33305B mAb. Biotinylated IL-33 was immobilized on streptavidin coated beads (Spherotec, # SVP-60-5) and the interaction with Axxora IL33305B Ab was detected using a goat anti-mouse Alexafluor®-647 labeled antibody (Molecular Probes A21236). The FMAT system is a macroconfocalimager, which measures the red fluorescence associated with the beads.

Plates were read on the Applied Biosystems Cellular Detection system 8200 reader. The Helium neon excitation laser focuses within 100 µm depth of the bottom of the well scanning an area 1 $mm^2$. The beads settle at the bottom of the well and upon laser excitation at 633 nm those beads with fluorophore bound (where the local concentration of fluorophore is relatively high compared to unbound fluorophore) emit a signal at 650-685 nm that is measured using PMT1. Unbound fluorophore in solution is outside the excitation depth or at a relatively low local concentration and thus does not emit a significant signal. ScFv or IgG samples that effectively block IL33305B binding to IL-33 will therefore cause a reduction in the amount of bead:IL-33:IL33305B:anti-mouse Alexafluor®-647 labeled antibody complexes at the bottom of the well which results in a reduction in measured fluorescence.

For the assay setup, the following were prepared:

(1) IL33305B and anti-mouse AF647 mix, IL33305B was diluted to 2.25 nM in assay buffer [PBS (Gibco, 14190-094) containing 0.1% BSA (Sigma, # A9576) and 0.1% Tween-20 (Sigma, P2287)] and mixed with anti-mouse AF647 diluted to 2 μg/ml (final 400 ng/ml) in assay buffer.

(2) IL-33 and bead mix, 2.5 nM biotinylated human IL-33 FLAG®His was added to 0.0095% w/v streptavidin beads in assay buffer and incubated with rotation at room temperature for 1 hour—before use these particles were spun down at 2000 rpm for 15 minutes and resuspended in original volume assay buffer.

(3) Sample Preparation, crude scFv supernatant samples were generated in 96 deep well plates. 5 μl culture from each well of a 96-well master plate was transferred into a Greiner deep well culture plate containing 900 μl of 2TY+100 μg/ml ampicillin+0.1% glucose media and incubated for 5 hours at 37° C., 280 rpm. 10 mM IPTG in TY was then added at 100 ul/well and the plate incubated overnight at 30° C., 280 rpm. The next morning, the plate was spun down at 3200 rpm for 15 minutes. For high-throughput screening, scFv supernatants from the deep well plate were transferred directly to the assay plate to achieve a final concentration of 20%.

For IC50 determinations, typically purified scFv or IgGs were diluted 3-fold in assay buffer, in duplicate, to give 11 concentration points. 96 well Greiner polypropylene (Greiner, 650201) plates are used for dilution preparation.

Into columns 1-22 of a 384-well clear bottomed non-binding surface black plate (Costar, #3655), the following were added: 10 μl sample, 20 μl IL33305B/anti-mouse AF647 mix, and 20 μl IL-33/bead mix. In all cases, total well volume was 40 μl. Controls typically used in these experiments included: IL-33/bead mix plus anti-mouse AF647 was added (non-specific binding); IL330305B/anti-mouse AF647 mix plus IL-33/bead mix (total binding). The plates were sealed and incubated for four hours at room temperature in the dark and then read on the Applied Biosystems Cellular Detection system 8200 reader. Data was analyzed with the Velocity algorithm, with gating set as color ratio<0.4, size<15 and minute count 20. Hits from the crude scFv supernatant samples were defined as showing 50% or greater inhibition of signal compared to the total binding control wells. Dose response curves were plotted for purified scFv and IgG titrations using Prism (Graphpad) curve-fitting software.

Reformatting of scFv to IgG1 scFv that displayed a desirable species cross-reactivity and specificity profile as determined by phage-displayed scFv binding experiments or showed an inhibitory effect in the epitope competition assay against Axxora Il33305B (as described above), were subjected to DNA sequencing (Osbourn et al., *Immunotechnology* 2(3):181-96 (1996); Vaughan et al., *Nat. Biotechnol.* 14(3):309-14 (1996)). First, scFv with desirable properties were converted to whole immunoglobulin G1 (IgG1), or an effector-null isotype IgG1 TM (IgG1 Fc sequence incorporating mutations L234F, L235E and P331S), antibody format as described in Example 1. SEQ ID NOs corresponding to the various regions of antibodies IL330065, IL330099, IL330101, IL330107, IL33149, and IL330180 are shown in Table 9.

TABLE 9

Anti-IL-33 Antibody Sequences

| IgG1 | VH Sequence | VL Sequence | VH CDRs 1, 2, 3 | VL CDRs 1, 2, 3 |
|---|---|---|---|---|
| IL330065 | SEQ ID NO: 82 | SEQ ID NO: 87 | SEQ ID NO: 83 SEQ ID NO: 84 SEQ ID NO: 85 | SEQ ID NO: 88 SEQ ID NO: 89 SEQ ID NO: 90 |
| IL330099 | SEQ ID NO: 92 | SEQ ID NO: 97 | SEQ ID NO: 93 SEQ ID NO: 94 SEQ ID NO: 95 | SEQ ID NO: 98 SEQ ID NO: 99 SEQ ID NO: 100 |
| IL330101 | SEQ ID NO: 102 | SEQ ID NO: 107 | SEQ ID NO: 103 SEQ ID NO: 104 SEQ ID NO: 105 | SEQ ID NO: 108 SEQ ID NO: 109 SEQ ID NO: 110 |
| IL330107 | SEQ ID NO: 122 | SEQ ID NO: 127 | SEQ ID NO: 123 SEQ ID NO: 124 SEQ ID NO: 125 | SEQ ID NO: 128 SEQ ID NO: 129 SEQ ID NO: 130 |
| IL330149 | SEQ ID NO: 132 | SEQ ID NO: 137 | SEQ ID NO: 133 SEQ ID NO: 134 SEQ ID NO: 135 | SEQ ID NO: 138 SEQ ID NO: 139 SEQ ID NO: 140 |
| IL330180 | SEQ ID NO: 142 | SEQ ID NO: 147 | SEQ ID NO: 143 SEQ ID NO: 144 SEQ ID NO: 145 | SEQ ID NO: 148 SEQ ID NO: 149 SEQ ID NO: 150 |

Binding Assay for IgGs

Species cross-reactivity of anti-IL-33 antibodies was determined using a plate-based ELISA. Streptavidin plates (Thermo Scientific, AB-1226) were coated with biotinylated antigen at 0.5 μg/ml in PBS. Binding of purified IgG preparations was detected with anti-human IgG HRP (Sigma, A0170). EC50 data for binding curves are shown in Table 10.

TABLE 10

Binding of IL-33 antibodies to Flag ®His-tagged human, cynomolgus or mouse IL-33

| | EC50 (nM) | | |
|---|---|---|---|
| Antibody | Human IL-33 Flag ®His | Cynomolgus IL-33 Flag ®His | Mouse IL-33 Flag ®His |
| IL330065 | 0.65 | 0.66 | No binding |
| IL330099 | 0.40 | 0.35 | 0.38 |
| IL330101 | 1.19 | 1.20 | 0.85 |
| IL330107 | 0.86 | 1.09 | 0.83 |
| IL330149 | 0.23 | 0.35 | 0.17 |
| IL330180 | Not determined* | Not determined* | Not determined* |

IL330180 was determined to bind to human IL-33, but not Cynomolgus or mouse IL-33 in phage-displayed scFv format.

Inhibition of IL-33 Functional Responses by Anti-IL-33 Antibodies

Inhibition of TF-1 Cell Proliferation by IgG

A cell viability assay was used to assess the inhibition of IL-33 induced proliferation/survival from TF-1 cells by anti-IL-33 antibodies. The CellTiter-Glo® Luminescent Cell Viability Assay (Promega) is a homogeneous method to determine the number of viable cells in culture based on quantitation of the ATP present, which signals the presence of metabolically active cells. Cells were exposed to IL-33 in the presence or absence of test antibody. Cell viability was measured by CellTiter-Glo following 72 hour stimulation with IL-33.

In particular, the proliferation assay was used to assess the inhibition of IL-33 induced proliferation from TF-1 cells by anti-IL-33 antibodies. TF-1 cells were a gift from R&D Systems and maintained according to manufacturer's instructions. The assay media comprised RPMI-1640 with GLUTAMAX I (Invitrogen, 61870) containing 5% fetal bovine serum (heat inactivated, gamma-irradiated), 1% sodium pyruvate (Sigma, S8636), 1-2% Penicillin/streptomycin (Invitrogen, 15140-122). Prior to each assay, TF-1 cells were pelleted by centrifugation at 300×g for 5 minutes, the media were removed by aspiration, and the cells were then re-suspended in assay media. This process was repeated twice with cells re-suspended at a final concentration of $2 \times 10^5$ cells/ml in assay media. Test solutions of IgG (in duplicate) were titrated to the desired concentration range in assay media in 96 well U-bottom polypropylene plates (Greiner, 650201) and 504, transferred to 96-well flat-bottomed tissue culture-treated plates (Costar, #3598). Recombinant human IL-33 (Alexis, ALX-522-098-3010) was added to the appropriate test antibody titrations to give a total volume of 100 µl/well. 100 µl of cell suspension was then added to 100 µl of IL-33 or IL-33 and antibody mixture to give a total assay volume of 200 µl/well and total cell number of 20,000 per well. A final assay concentration of 100 ng/mL IL-33 was used in the assay, which was selected as the dose that gave approximately 80% of maximal proliferative response. Plates were incubated for 72 hours at 37° C. and 5% $CO_2$. 100 µL of supernatant was carefully removed from the assay plates. 100 µL of CellTiter-Glo (Promega, G7571), reconstituted according to manufacturers instructions, was added per well. Plates were shaken on a plate shaker at 500 rpm for 5 minutes and luminescence read on EnVision plate reader (PerkinElmer). Data were analyzed using Graphpad Prism software. IC50 values were determined by curve fitting using a three or four-parameter logistic equation.

For those antibodies that achieved full inhibition curves, IC50 values were calculated and are summarized in Table 11 below. Purified IgG preparations were capable of inhibiting TF-1 proliferation in response to IL-33. FIG. 7A shows percent inhibition for IL330065 and IL330101 (compared to control mAb and hST2/Fc) for the TF-1 proliferation assay, wherein the x-axis is the concentration of antibody in molar concentration and the y-axis is a percentage of the maximum response.

Inhibition of Huvec IL-6 Release by IL-33 Antibodies

A cytokine release assay was used to assess the inhibition of IL-33 induced IL-6 production from human umbilical vein endothelial cells (Huvec) by anti-IL-33 antibodies. Cells were exposed to IL-33 in the presence or absence of test antibody.

Huvecs were obtained from Cambrex and maintained in complete EBM-2 media (Lonza) according to manufacturer's protocol. Cells were harvested from flasks with accutase (PAA, # L11-007) and seeded at $1 \times 10^4$/100 µl/well in culture media (EBM-2 (Lonza, # CC-3156) with EGM-2 SingleQuot Kit Suppl. & Growth Factors (Lonza, # CC-4176)) into 96-well flat-bottomed tissue-culture treated plates (Costar, #3598) and incubated at 37° C., 5% $CO_2$ for 18-24 hours. After this time, media was aspirated, leaving cell monolayer intact, and replaced with assay test samples as discussed below.

Test solutions of purified IgG (in duplicate) were diluted to the desired concentration in complete culture media in 96 well U-bottom polypropylene plates (Greiner, 650201). IL-33 (Adipogen) was prepared in complete culture media mixed with appropriate test antibody to give a final IL-33 concentration of 30 ng/mL. All samples were incubated for 30 minutes at room temperature, prior to transfer of 120 µl of IL-33/antibody mixture to the assay plate. Following 18-24 hour incubation, IL-6 was measured in cell supernatants by ELISA (R&D Systems, DY206) adapted for europium readout. Black Fluro-Nunc Maxisorp plates (VWR, #437111) were coated with 50 µL capture antibody, washed three times with PBS-Tween (0.01%) using an automated plate washer (Biotek) and blocked with 250 µL/well of PBS/1% BSA (Sigma, # A9576) for 1-2 hours at room temperature. Plates were washed as above and incubated with 50 uL mast cell assay supernatants for 1-2 hours at room temperature. Following 3× wash with PBS-Tween, plates were incubated with detection antibody (50 uL/well) according to manufacturer's instructions. ELISA plates were washed three times in PBS-Tween, and Streptavidin-Europium (PerkinElmer, 1244-360) was diluted 1:1000 in DELFIA® assay buffer (PerkinElmer, 4002-0010) and added at 50 µl/well for 45-60 minutes at room temperature. Plates were then washed 7 times in DELFIA wash buffer before the addition of 50 µl/well of enhancement solution (PerkinElmer, 4001-0010) and analyzed using time resolved fluorometry (Excitation 340 nM, Emission 615 nM). Data were analyzed using Graphpad Prism software. IC50 values were determined by curve fitting using a three or four-parameter logistic equation. For those antibodies that achieved full inhibition curves, IC50 values were calculated and are summarized in Table 11 below. Purified IgG preparations (IgG1 or IgG1-TM) of antibodies IL330065, IL330099, IL330101, IL330107, IL330149, and IL330180 inhibited IL-6 production in comparison with control antibodies. Potency of exemplary binding members was essentially unaffected by the presence of IgG1-TM Fc sequence mutations (L234F, L235E and P331S), and the data as shown combines information for both formats. FIG. 7B shows percent maximal IL-6 release for IL330065 and IL330101 (compared to human ST2-Fc, anti-IL33 pAb AF3625 (R & D Systems), and control mAb), wherein the x-axis is the concentration of antibody in molar concentration and the y-axis is a percentage of the maximum response.

Inhibition of Human Mast Cell Cytokine Release

A cytokine release assay was used to assess the inhibition of IL-33 induced IL-6 production by anti-IL-33 antibodies from human mast cells. In addition to IL-6, other cytokines (IL-5, IL-6, IL-8, IL-10, IL-13, GM-CSF and TNFα) in cell supernatants were measured using alternative duoset ELISAs or Mesoscale Discovery multiplex analysis.

Human mast cells were produced by in vitro differentiation of cord blood CD133+ progenitor cells (Lonza, #2C-108) essentially as described in Andersen et al. (*J Immunol Methods* 336:166-174 (2008)). Progenitor cells were thawed according to manufacturer's instructions and cultured in vitro in Serum Free Expansion Media (StemSpan, #09650) supplemented with 1% Penicillin/streptomycin (Invitrogen, 15140-122) and growth factors: 100 ng/mL Stem Cell Factor (Peprotech, # AF-300-07) and 50 ng/mL IL-6 (Peprotech, # AF-200-6) for 8 weeks. In addition, 1 ng/mL IL-3 (R&D Systems, #203-IL) was included in the culture media during the first three weeks. Cells were maintained throughout at <5×10$^5$/mL.

Mast cells were cultured overnight in assay media (StemSpan, #09650; 1% Penicillin/streptomycin (Invitrogen, 15140-122) and 100 ng/mL Stem Cell Factor (Peprotech, # AF-300-07)), prior to exposure to IL-33 in the presence or absence of test antibody.

For cytokine release assays, cells were removed, pelleted (150 g for 10 minutes) and resuspended in assay media (StemSpan, #09650, 1% Penicillin/streptomycin (Invitrogen, 15140-122) and 100 ng/mL Stem Cell Factor (Peprotech, # AF-300-07)). Cells were returned to a flask and cultured for 18-24 hours prior to assay setup. For sample assessment, test solutions of IgG (in duplicate) were titrated to the desired concentration range in assay media in 96 well U-bottom polypropylene plates (Greiner, 650201) and 50 μL of test solutions transferred to 96-well flat-bottomed tissue-culture treated plates (Costar, #3598). 50 μL of recombinant human IL-33 (Adipogen, #522-098-3010), diluted in assay media to 90 ng/mL was added to the appropriate test antibody titrations to give a total volume of 100 μl/well. 50 μl of cell suspension (1.5×10$^5$) was then added to 100 μl of IL-33 or IL-33 and antibody mixture to give a total assay volume of 150 μl/well and total cell number of 5×10$^4$ per well. A final assay concentration of 30 ng/mL IL-33 was used in the assay, selected as the dose that gave approximately 50-80% of maximal cytokine response. Plates were incubated for 18-24 hours at 37° C. and 5% $CO_2$.

IL-6 was measured in cell supernatants by ELISA (R&D Systems, DY206) adapted for europium readout. Black Fluro-Nunc Maxisorp plates (VWR, #437111) were coated with 50 μL capture antibody, washed three times with PBS-Tween (0.01%) using an automated plate washer (Biotek) and blocked with 250 μL/well of PBS/1% BSA (Sigma, # A9576) for 1-2 hours at room temperature. Plates were washed as above and incubated with 50 μL mast cell assay supernatants for 1-2 hours at room temperature. Following 3× wash with PBS-Tween, plates were incubated with detection antibody (50 μL/well) according to manufacturer's instructions. ELISA plates were washed three times in PBS-Tween, and Streptavidin-Europium (PerkinElmer, 1244-360) was diluted 1:1000 in DELFIA assay buffer (PerkinElmer, 4002-0010) and added at 50 μl/well for 45-60 minutes at room temperature. Plates were then washed 7 times in DELFIA wash buffer before the addition of 50 μl/well of enhancement solution (PerkinElmer, 4001-0010) and analyzed using time resolved fluorometry (Excitation 340 nM, Emission 615 nM). Data were analyzed using Graphpad Prism software. IC50 values were determined by curve fitting using a three or four-parameter logistic equation.

Figure 8:
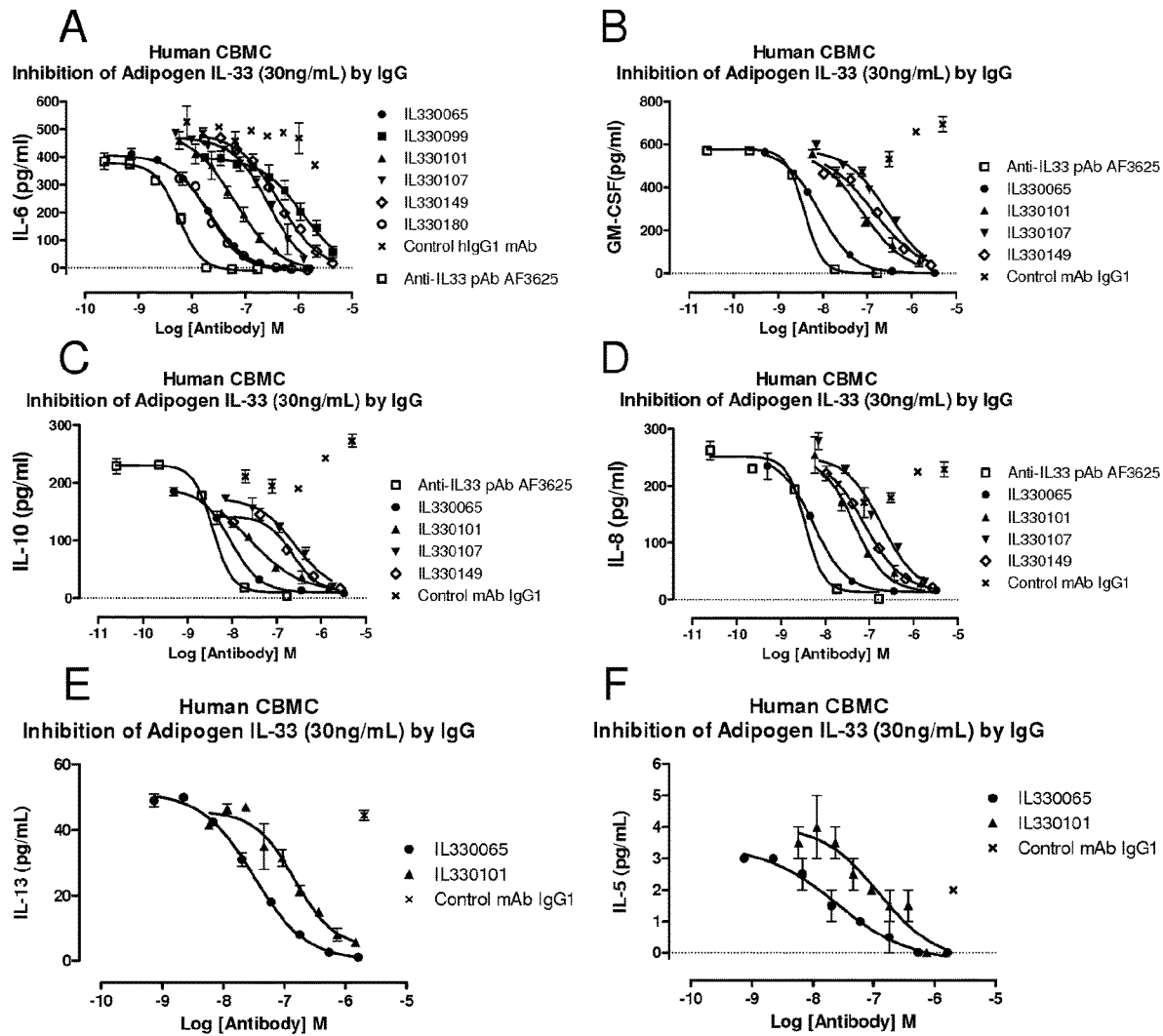
FIG. 8 Shows neutralizing activity of antibodies in a mast cell IL-6 (FIG. 8A), GM-CSF (FIG. 8B), IL-10 (FIG. 8C), IL-8 (FIG. 8D), IL-13 (FIG. 8E) and IL-5 (FIG. 8F) cytokine production assay.

FIG. 8A shows the reduction of IL-6 production by increasing concentrations of antibodies IL330065, IL330099, IL330101, IL330107, IL33149, and IL330180, wherein the x-axis is the concentration of antibody in molar concentration and the y-axis is % maximum response. Purified IgG preparations of test antibodies were capable of inhibiting the IL-6 activity in comparison with control antibodies. Potency of exemplary binding members was essentially unaffected by the presence of IgG1-TM Fc sequence mutations (L234F, L235E and P331S) and the data combines information for both formats. IC50 results for TF-1 proliferation assay, HUVEC IL-6 production, and mast cell IL-6 production are shown in Table 11.

TABLE 11

Example potencies of clones identified from naïve human scFv phage display libraries

| | IgG1 Geomean (95% CI) IC50 (nM) | | |
|---|---|---|---|
| Antibody | TF-1 proliferation | Huvec IL-6 production | Mast cell IL-6 production |
| IL330065 | 81 (19-345) | 87 (60-129) | 12 (4-40) |
| IL330099 | Incomplete curve | Incomplete curve | 1221 (n = 1) |
| IL330101 | 149 (n = 1) | 497 (167-1474) | 49 (31-75) |
| IL330107 | 94 (n = 1) | Incomplete curve | 283 (154-522) |
| IL330149 | Incomplete curve | Incomplete curve | 298 (n = 2) |
| IL330180 | Not Determined | Not Determined | 22 (n = 1) |

Additional cytokines (IL-5, IL-6, IL-8, IL-10, IL-13, and GM-CSF) in cell supernatants were detected using Meso-Scale Diagnostics Demonstration 10-plex human cytokine assay (# K15002B-1) according to manufacturer's instructions. Cytokines were measured in cell supernatants by ELISA adapted for europium readout using a similar protocol to the IL-6 ELISA described above.

Mast cells were shown to produce a range of cytokines after stimulation with IL-33 (Meso-Scale Diagnostics Demonstration 10-plex human cytokine assay # K15002B-1; R&D Systems, # DY213). FIGS. 8B-F show the inhibition of IL-33-driven production of GM-CSF, IL10, IL-8, IL-13 and IL-5, respectively. These results show that antibodies IL330065, IL330101, IL330107, and IL330149 were able to inhibit IL-33-driven production of all cytokines measured.

Binding and Neutralization of Native Full Length IL-33

Selection and activity studies described above used recombinant in house or commercial sources of mature IL-33 (amino acids 112-270). Full length IL-33 may also be active (Cayrol et al., *Proc Natl Acad Sci USA* 106(22): 9021-6 (2009); Hayakawa et al., *Biochem Biophys Res Commun* 387(1):218-22 (2009); Talabot-Ayer et al., *J Biol Chem.* 284(29):19420-6 (2009)). To assess binding of antibodies to full length IL-33, full length IL-33 was cloned and expressed in HEK293-EBNA cells. As described below, selected antibodies were shown to bind to full length IL-33 as determined by Western blot.

Cloning and Expression of Full-Length Human IL-33

The cDNA molecule encoding full-length (FL) IL-33 from human (Swiss Prot accession number O95760 amino acids 1-270) was synthesized by primer extension PCR cloning and cloned into pDONR221 (Invitrogen, 12536-017) and was transferred to the mammalian expression vector pDEST12.2 (Invitrogen) using LR Gateway Clonase II enzyme according to the manufacturer's instructions (Invitrogen, 12538-120). The pDEST12.2 vector had been modified to contain the oriP origin of replication from the pCEP4 vector (Invitrogen) allowing episomal plasmid replication upon transfection into cell lines expressing the EBNA-1 gene product (such as HEK293-EBNA cells). HEK293-EBNA cells were transfected with Lipofectamine 2000 (Invitrogen, 11668-019). Cells expressing FL HuIL-33 (and mock-transfected controls) were lysed using sonication in the presence of protease inhibitors (Roche, 05892791001).

Western Blot Analysis of Cell Lysates Expressing Full-Length Human IL-33

Figure 9:
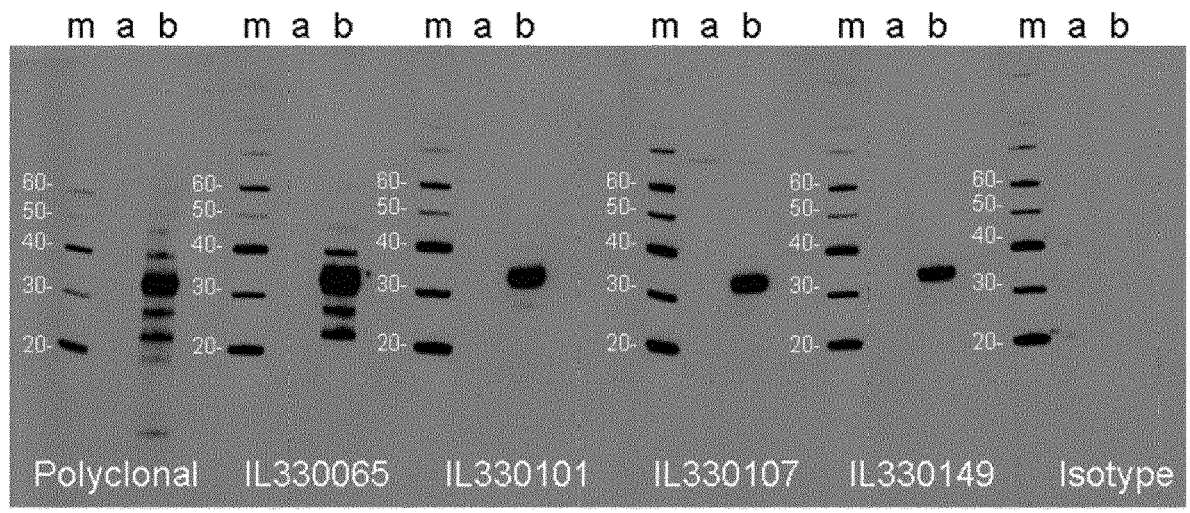
FIG. 9 Shows binding of IL-33 antibodies (IL330065, IL330101, IL330107, and IL330149) to full length human IL-33 by Western blot.

Proteins from cell lysates were denatured and reduced with SDS sample buffer and DTT prior to separation by SDS-PAGE electrophoresis and transfer to Nitrocellulose membranes. Membranes were blocked with 5% non-fat dried milk in PBS-T for 1 h, incubated with primary antibody (0.5 μg per ml) for 1 h, washed three times in PBS-T, then incubated for 1 h with HRP-conjugated secondary antibody (1 in 10,000 dilution of goat anti-human IgG (Sigma, A0170)) and washed three times in PBS-T. HRP was detected with Amersham ECL plus detection reagent (GE healthcare, RPN2132). Sizes were estimated by comparing migration to that of Magic Mark XP (Invitrogen, LC5602). FIG. 9 shows binding of IL-33 antibodies (IL330065, IL330101, IL330107, and IL330149) to full length human IL-33 by Western blot.

Neutralization of Mast Cell Cytokine Responses to Full Length IL-33 Cell Lysate

HEK293-EBNA cells expressing full length (FL) HuIL-33 (and mock-transfected controls) were harvested 24 hours following transfection with accutase (PAA, # L11-007). Cells were diluted to $5\times10^7$/mL with PBS and homogenized for 30 seconds using a tissue homogenizer. Cell debris was removed by centrifugation. Mast cells were stimulated with cell lysates at varying concentrations. Stimulation of cytokine production was only observed with full length IL-33-transfected cell lysate and not with mock transfected cell lysate. A concentration of lysate that stimulated a sub-maximal cytokine release (approx EC50) was selected for antibody neutralization studies.

For cytokine release assays, mast cells were cultured overnight in assay media (StemSpan, #09650; 1% Penicillin/streptomycin (Invitrogen, 15140-122) and 100 ng/mL Stem Cell Factor (Peprotech, # AF-300-07)), prior to exposure to FL HuIL-33 in the presence or absence of test antibody. IL-6 and IL-13 production was detected by ELISA of assay supernatants after 18-24 hours. A detailed description of the protocol was described above (Example 2-0007).

Figure 10:
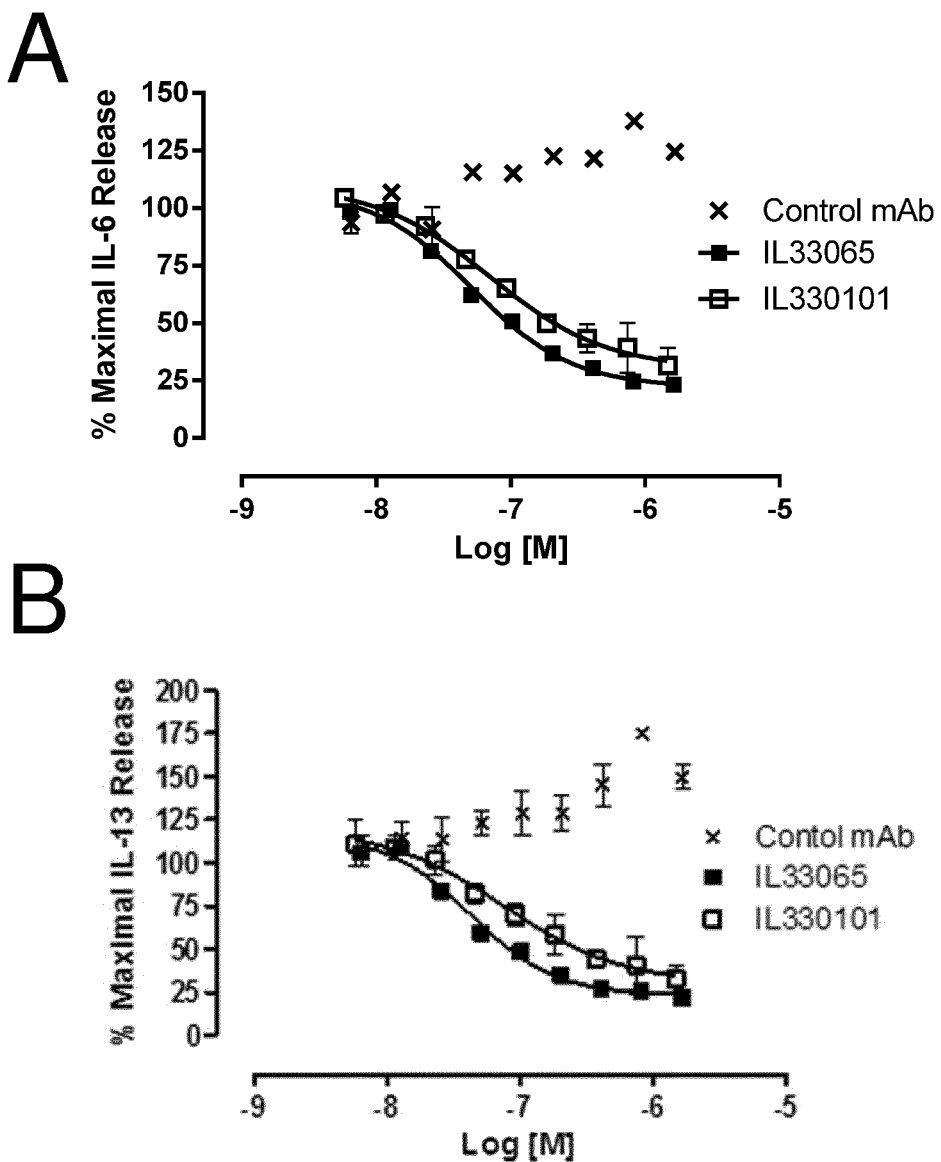
FIG. 10 Shows neutralizing activity of anti-IL-33 antibodies IL330065 and IL330101 on mast cell IL-6 (FIG. 10A) and IL-13 (FIG. 10B) production stimulated by full length IL-33 cell lysates.

FIG. 10 shows the effect of anti-IL-33 antibodies IL330065 and IL330101 on mast cell IL-6 and IL-13 production stimulated by cell lysates of full length IL-33-transfected cells. Purified IgG preparations were capable of inhibiting IL-6 (FIG. 10A) and IL-13 (FIG. 10B) production induced by full length IL-33 cell lysates.

Non-Competitive Mode of Action of IL-33 Antibodies
Inhibition of IL-33 Binding to ST2 by Purified IgG The ability of anti-IL-33 antibodies to inhibit the binding of Flag®-His tagged IL-33 to the ST2 receptor was assessed in a biochemical HTRF® (Homogeneous Time-Resolved Fluorescence, Cisbio International) competition assay the full methods of which are described in Example 1.

FIG. 11A shows specific binding results for HTRF® receptor-ligand competition assay with increasing concentrations of antibodies IL330065, IL330099, IL330101, IL330107, IL33149, and IL330180. These results show that antibodies IL330065, IL330099, IL330101, IL330107, IL33149, and IL330180 are not competitive inhibitors of the IL-33:ST2 interaction.

Inhibition of NFkB Signaling in Huvec by IgG

NFkB signaling in Huvecs in response to IL-33 was assessed by nuclear translocation of the p65/RelA NFkB subunit, detected by immunofluorecence staining as described in Example 1.

FIG. 11B shows Huvec NFkB translocation with increasing concentrations of antibodies IL330065, IL330099, IL330101, IL330107, and IL330149. These results show that IL330065, IL330099, IL330101, IL330107, and IL330149 did not inhibit nuclear translocation of p65/RelA NFkB in IL-33-stimulated Huvecs 30 minutes following stimulation. The results are consistent with failure of antibodies IL330065, IL330099, IL330101, IL330107, IL33149, and IL330180 to inhibit IL-33 binding to ST2.

Epitope Binning of IL-33 Antibodies in HTRF® Epitope Competition Assays

The ability of antibodies to compete with mAb IL330101 or mAb IL330180 for binding to biotinylated human IL-33 was assessed in a biochemical HTRF® (Homogeneous Time-Resolved Fluorescence, Cisbio International) epitope competition assay.

The HTRF® epitope competition assays, described below, were used to measure the binding of a lead antibody in IgG format to biotinylated IL-33. Test scFv samples which recognize a similar epitope to the lead antibody, will compete with the lead antibody for binding to IL-33, leading to a reduction in assay signal.

Purified anti-IL-33 scFv antibody samples were tested for inhibition of biotinylated human IL-33 binding the lead antibody by adding 5 microliters of each dilution of antibody test sample to a 384 well low volume assay plate (Costar, 3673). Next, a solution containing 8 nM IL330180 IgG1 or 12 nM IL330101 IgG1 and 40 nM anti human Fc detection (Cisbio International, 61HFXLB) was prepared and 2.5 microliters added to the assay plate. This was followed by the addition of 2.5 microliters of a solution containing 4 nM (for IL330180 epitope competition assay) or 18 nM (for IL330101 epitope competition assay) biotinylated human IL-33 (Axxora, AG-40B-0038; biotinylated) and 4.65 nM streptavidin cryptate detection (Cisbio International, 610SAKLB). All dilutions were performed in assay buffer comprised of Dulbeccos PBS (Invitrogen, 14190185) containing 0.8 M potassium fluoride (BDH, 103444T) and 0.1% bovine serum albumin (BSA, Sigma A9576). Assay plates were incubated for 2 hour at room temperature followed by 16 hour at 4° C. before reading time resolved fluorescence at 620 nm and 665 nm emission wavelengths using an EnVision plate reader (Perkin Elmer). Data were analyzed using Equations 1 to 3 as described previously. The negative control (non-specific binding) is defined by replacing biotinylated IL-33/streptavidin cryptate combination with streptavidin cryptate detection only.

Figure 12:
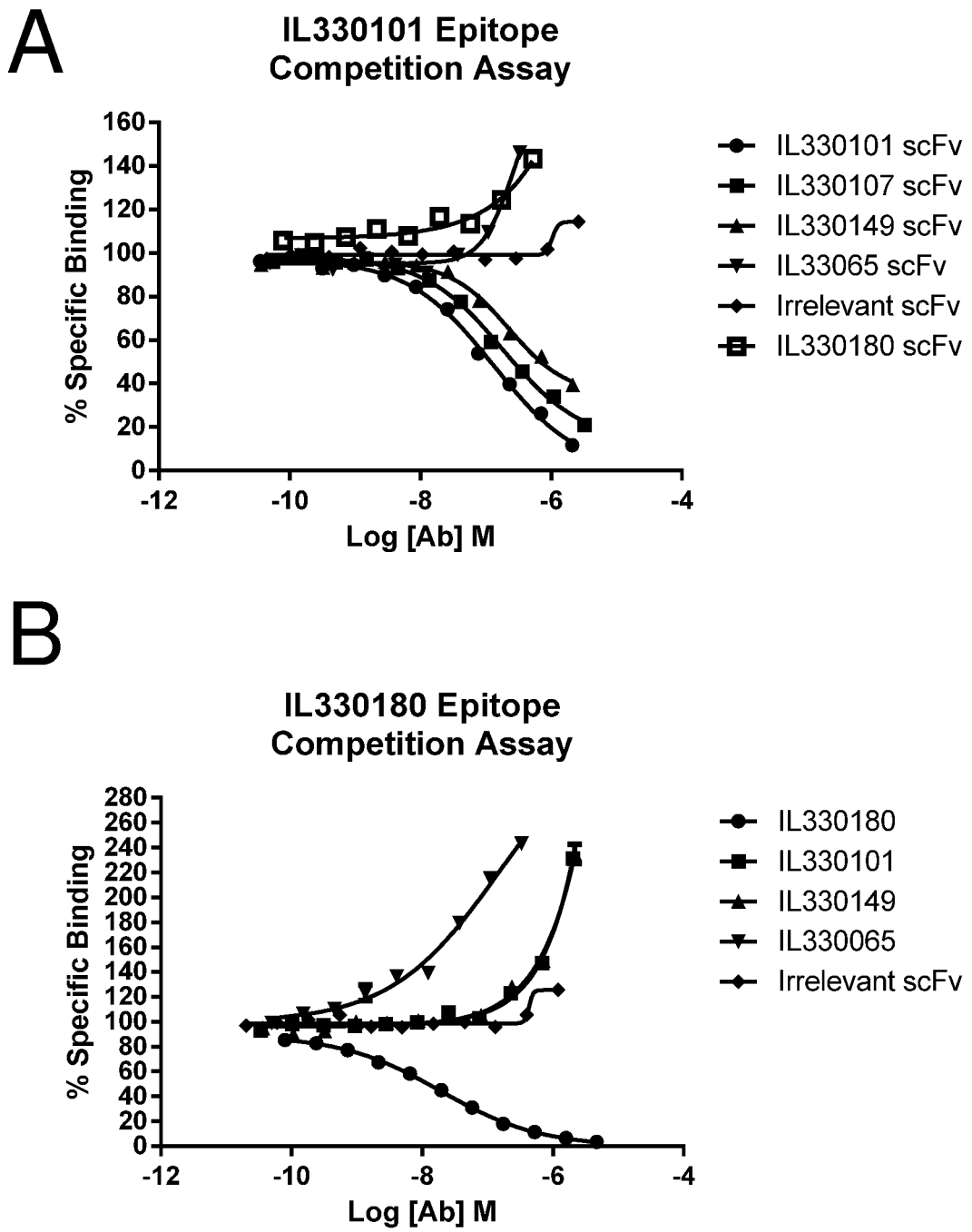
FIG. 12A Shows competitive binding of purified scFv preparations with mAb IL330101 for binding to biotinylated human IL-33.
FIG. 12B Shows competitive binding of purified scFv preparations with mAb IL330180 for binding to biotinylated human IL-33.

Results for IL330101 and IL330180 epitope competition assay are shown in FIGS. 8A and 8B, respectively. FIG. 12A shows the competitive binding of IL330101 scFv, IL330107 scFv, IL330149 scFv, IL330065 scFv, Irrelevant scFv, and IL330180 scFv with mAb IL330101 for binding to biotinylated human IL-33. These results show that IL330101 scFv, IL330107 scFv, IL330149 scFv competitively inhibited IL330101 binding to biotinylated human IL-33.

FIG. 12B shows the competitive binding of IL330180, IL330101, IL330149, IL330065, and Irrelevant scFv with mAb IL330180 for binding to biotinylated human IL-33 assessed in a biochemical HTRF®. These results show that IL330101, IL330149, and IL330065 do not competitively inhibit IL330180 binding to biotinylated human IL-33.

Epitope binning using this method shows three panels of antibodies comprising IL330101, IL330107 and IL330149 in panel 1, IL330065 in panel 2 and IL330180 in panel 3, as detailed in Table 12.

TABLE 12

Epitope Binning Panels

|  | Inhibition in IL330101 Epitope Competition Assay | Inhibition in IL330180 Epitope Competition Assay |
| --- | --- | --- |
| IL330101 | ✓ | X |
| IL330107 | ✓ | X |
| IL330149 | ✓ | X |

TABLE 12-continued

Epitope Binning Panels

| | Inhibition in IL330101 Epitope Competition Assay | Inhibition in IL330180 Epitope Competition Assay |
|---|---|---|
| IL330065 | X | X |
| IL330180 | X | ✓ |

Example 3 Optimization of Anti-IL-33 Ab IL330101

Affinity Maturation

IL330101 was optimised using a targeted mutagenesis approach and affinity-based phage display selections. Large scFv-phage libraries derived from the lead clone were created by oligonucleotide-directed mutagenesis of the variable heavy (VH) complementarity determining regions 2 and 3 (CDR2 and CDR3) and light (VL) chain CDR3 using standard molecular biology techniques as described (Clackson, T. and Lowman, H. B. *Phage Display—A Practical Approach*, 2004. Oxford University Press). The libraries were subjected to affinity-based phage display selections in order to select variants with higher affinity for human and mouse IL-33. The selections were performed essentially as described previously (Thompson, J et al. *J Mol Biol*, 1996. 256: p. 77-88) using reagents as described in Examples 1 and 2. In brief, the scFv-phage particles were incubated with recombinant biotinylated human IL-33 in solution (Adipogen; biotinylated as described in Protein Modifications within Example 1). ScFv-phage bound to antigen were then captured on streptavidin-coated paramagnetic beads (Dynabeads® M-280) following the manufacturer's recommendations. The selected scFv-phage particles were then rescued as described previously (Osbourn, J. K., et al. *Immunotechnology*, 1996. 2(3): p. 181-96), and the selection process was repeated in the presence of alternating and decreasing concentrations of human or mouse biotinylated IL-33—typically from 500 nM to 500 pM over four rounds of selection.

Inhibition of IL-33 Binding to mAb by Unpurified scFv

A representative number of individual clones from the selection outputs were grown up in 96-well plates. ScFv were expressed in the bacterial periplasm (Kipriyanov, et al. *J Immunol Methods* 200(1-2): 69-77 (1997)) and screened for their inhibitory activity in a homogeneous FRET (fluorescence resonance energy transfer) HTRF® (Homogeneous Time-Resolved Fluorescence, Cisbio International) based IL-33:mAb-binding assay. In this assay, samples competed with IL330101 IgG for binding to biotinylated human IL-33 or mouse IL-33 FLAG®His. Such epitope competition assays are based on the principle that a test antibody sample, which recognizes a similar epitope to the anti-IL-33 IgG, will compete with the IgG for binding to biotinylated IL-33 resulting in a reduction in assay signal.

Unpurified anti-IL-33 scFv samples were tested for inhibition of biotinylated human or mouse IL-33 FLAG®His binding to IL330101 by adding 5 microlitres of sample to a 384 well low volume assay plate (Costar, 3673). Next, a solution containing 12 nM IL330101 combined with 40 nM anti human Fc XL665 detection (Cisbio International, 61HFCXLB) was prepared for the human IL-33 assay and 2 nM IL330101 combined with 40 nM anti human Fc XL665 detection (Cisbio International, 61HFCXLB) was prepared for the mouse assay. 2.5 microlitres was added to the assay plates. This was followed by the addition of 2.5 microlitres of a solution containing 18 nM biotinylated human IL-33 (Adipogen, AG-40B-0038) combined with 4.6 nM streptavidin cryptate detection (Cisbio International, 610SAKLB) for the human assay or a solution containing 2 nM biotinylated mouse IL-33 FLAG®His combined with 4.6 nM streptavidin cryptate detection (Cisbio International, 610SAKLB) for the cynomolgus assay. All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 4 hour at room temperature followed by 16 hour at 4 degrees Celsius and time resolved fluorescence was read at 620 nm and 665 nm emission wavelengths using an EnVision plate reader (Perkin Elmer). Data were analysed by calculating the 665/620 nm ratio followed by the % Delta F values for each sample. The 665/620 nm ratio was used to correct for sample interference using Equation 1. The % Delta F for each sample was then calculated using Equation 2. The negative control (non-specific binding) was defined by replacing biotinylated IL-33 combined with streptavidin cryptate detection with streptavidin cryptate detection only. The % Delta F values were subsequently used to calculate % specific binding as described in Equation 3.

As the epitope competition assay reached its limit of sensitivity, an assay using an intermediate optimised mAb IL330259 was used for testing unpurified scFv samples. Unpurified anti-IL-33 antibody samples were tested for inhibition of biotinylated human IL-33 or biotinylated mouse IL-33 FLAG®His binding DyLight labelled IL330259 by adding 5 microlitres of each sample to a 384 well low volume assay plate (Costar, 3673). Next, a solution containing 20 nM DyLight labelled IL330259 was prepared for the human IL-33 assay and 4 nM DyLight labelled IL330259 was prepared for the mouse assay and 2.5 microlitres added to the assay plates (IgG labelled using kit (Thermo Scientific, 53051) as per manufacturer's instructions). This was followed by the addition of 2.5 microlitres of a solution containing 20 nM biotinylated human IL-33 (Adipogen, AG-40B-0038) or 1.6 nM biotinylated mouse IL-33 FLAG®His combined with 6 nM streptavidin cryptate detection (Cisbio International, 610SAKLB). All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 4 hour at room temperature followed by 16 hour at 4 degrees Celsius and time resolved fluorescence was read at 620 nm and 665 nm emission wavelengths using an EnVision plate reader (Perkin Elmer). Data were analysed by calculating the 665/620 nm ratio followed by the % Delta F values for each sample. The 665/620 nm ratio was used to correct for sample interference using Equation 1. The % Delta F for each sample was then calculated using Equation 2. The negative control (non-specific binding) was defined by replacing biotinylated IL-33 combined with streptavidin cryptate detection with streptavidin cryptate detection only. The % Delta F values were subsequently used to calculate % specific binding as described in Equation 3.

Inhibition of IL-33 Binding to mAb by Purified scFv

Single chain Fv clones which showed a greater inhibitory effect on IL-33:mAb interaction as unpurified periplasmic extracts compared to IL330101 were subjected to DNA sequencing (Osbourn, et al. *Immunotechnology* 2(3): 181-96 (1996); Vaughan, et al. *Nat Biotechnol* 14(3):309-14 (1996)). Unique scFv were expressed again in bacteria and purified by affinity chromatography (as described in WO01/66754). The potencies of these samples were determined by competing a dilution series of the purified preparation against IL330101 IgG for binding to biotinylated human IL-33, biotinylated mouse IL-33 FLAG®His or biotinylated cynomolgus IL-33 FLAG®His as described above but with the addition of the biotinylated cynomolgus IL-33 FLAG®His assay (biotinylated cynomolgus IL-33 FLAG®His was added at 12 nM concentration).

Figure 13:
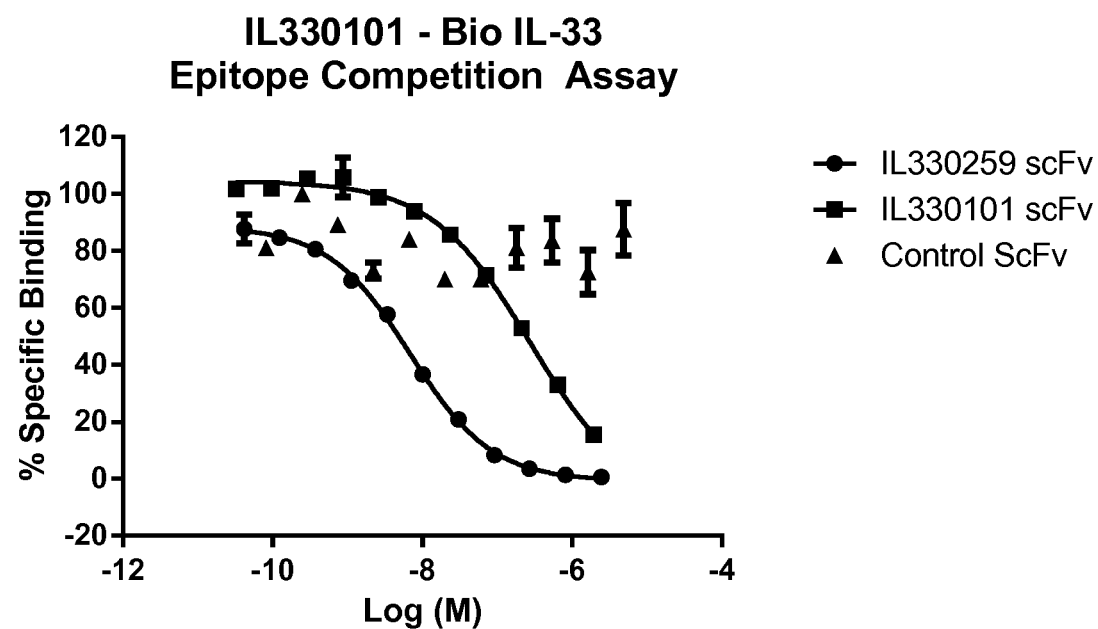
FIG. 13 Shows competitive binding IL330259 scFv with mAb IL330101 for binding to biotinylated human IL-33.

FIG. 13: shows inhibition of the FRET signal, produced by biotinylated human IL-33 binding to IL330101 with increasing concentrations of IL-33 scFv antibodies IL330101, IL330259, wherein the x-axis is the concentration of antibody in molar concentration and the y-axis is percent specific binding.

Purified scFv preparations that were capable of inhibiting the IL-33:mAb interaction to a greater extent than IL330101 were selected for conversion to IgG format. The method of IgG expression and purification is described in Example 1.

As the epitope competition assay reached its limit of sensitivity, an assay using an intermediate optimised mAb (IL330259) was used for testing purified scFv samples. Purified anti-IL-33 antibody samples were tested for inhibition of biotinylated human IL-33, biotinylated mouse IL-33 FLAG®His or biotinylated cynomolgus FLAG®His IL-33 binding IL330259 as described above with the addition of the biotinylated cynomolgus IL-33 FLAG®His assay (biotinylated cynomolgus IL-33 FLAG®His was added at 12 nM concentration).

Based on sequence and epitope competition data, selected VH and VL outputs were recombined by standard molecular biology techniques to form libraries in which clones contained randomly paired VH and VL sequences (for example, VH CDR2/VL CDR3 and VH CDR3/VL CDR3 libraries). Alternatively, VH CDR3 and VL CDR3 sequences were randomly paired and recombined with specific VH CDR2 sequences selected from a pool of improved variants, to generate libraries in which all three CDRs were non-parental. Typically five rounds of affinity selection using decreasing and alternating concentrations of human and mouse biotinylated IL-33, from 10 nM to 10 pM, were performed on all recombination libraries to identify scFv sequences with improved kinetics. Alternatively, recombination libraries were selected using a fixed concentration of biotinylated IL-33 (for example, 1 nM, 100 pM or 300 pM) in the presence of 1000× unbiotinylated IL-33 for increasing amounts of time (for example 30 minutes, 1 hour, 2 hours or 4 hours) over four rounds of selection—a process known in the art as 'off rate' or 'competition' selection—to identify scFv's with improved kinetics.

Samples were again screened in an HTRF® epitope competition assay for the ability to inhibit the binding of labelled-huIL-33 to IL330101 parent antibody or VH CDR2 optimized antibody IL330259 as described previously. ScFv's which showed a significantly improved inhibitory effect when compared to IL330101, were subjected to DNA sequencing, and unique variants were produced as purified scFv for further characterisation. Inhibitory scFv's were converted to whole immunoglobulin G1 (IgG1) antibody format as described in Example 1.

Alternatively, individual unique VH CDR2, VH CDR3 and VL CDR3 sequences were specifically and rationally recombined and produced as IgG directly. In this example, IgGs were tested for improved kinetics without any additional affinity selection.

Antibodies with improved kinetics were identified from all strategies and are exemplified by IL330259, IL330377, IL330388, IL330396, IL330398 and H338L293.

The amino acid sequences of the $V_H$ and $V_L$ domains of IL330101 parent and the optimised anti-IL-33 antibodies were aligned to the known human germline sequences in the IMGT database (Lefranc, M. P. et al. *Nucl. Acids Res.* 2009. 37(Database issue): D1006-D1012), and the closest germline was identified by sequence similarity. For the $V_H$ domain of the IL330101 antibody lineage this was IGHV3-21/IGHJ2. For the $V_L$ domain it was IGLV3-25/IGLJ3. Without considering the Vernier residues (Foote, J., et al. *J Mol Biol*, 1992. 224: p. 487), which were left unchanged, there were no changes required in the frameworks of the $V_H$ domains and 4 changes in the $V_L$ frameworks (V3E, T5M, A45V and V104L; Kabat numbering). These positions were changed as indicated using standard site directed mutagenesis techniques with appropriate mutagenic primers. Antibodies that were germlined in this way appear in the sequence listings with the 'fgl' suffix.SEQ ID NOs corresponding to the various regions of antibodies IL330259, H338L293, IL330377, IL330388, IL330396, and IL330398 are shown in Table 13.

TABLE 13

Anti-IL-33 Antibody Sequences

| IgG1 | VH SEQ ID NO: | VL SEQ ID NO: | VH CDRs 1, 2, 3 | VL CDRs 1, 2, 3 |
|---|---|---|---|---|
| IL330101_fgl | 112 | 117 | SEQ ID NO: 113 | SEQ ID NO: 118 |
| | | | SEQ ID NO: 114 | SEQ ID NO: 119 |
| | | | SEQ ID NO: 115 | SEQ ID NO: 120 |
| IL330259 | 152 | 157 | SEQ ID NO: 153 | SEQ ID NO: 158 |
| | | | SEQ ID NO: 154 | SEQ ID NO: 159 |
| | | | SEQ ID NO: 155 | SEQ ID NO: 160 |
| IL330259_fgl | 162 | 167 | SEQ ID NO: 163 | SEQ ID NO: 168 |
| | | | SEQ ID NO: 164 | SEQ ID NO: 169 |
| | | | SEQ ID NO: 165 | SEQ ID NO: 170 |
| H338L293 | 172 | 177 | SEQ ID NO: 173 | SEQ ID NO: 178 |
| | | | SEQ ID NO: 174 | SEQ ID NO: 179 |
| | | | SEQ ID NO: 175 | SEQ ID NO: 180 |
| H338L293_fgl | 182 | 187 | SEQ ID NO: 183 | SEQ ID NO: 188 |
| | | | SEQ ID NO: 184 | SEQ ID NO: 189 |
| | | | SEQ ID NO: 185 | SEQ ID NO: 190 |
| IL330377 | 192 | 197 | SEQ ID NO: 193 | SEQ ID NO: 198 |
| | | | SEQ ID NO: 194 | SEQ ID NO: 199 |
| | | | SEQ ID NO: 195 | SEQ ID NO: 200 |
| IL330377_fgl | 202 | 207 | SEQ ID NO: 203 | SEQ ID NO: 208 |
| | | | SEQ ID NO: 204 | SEQ ID NO: 209 |
| | | | SEQ ID NO: 205 | SEQ ID NO: 210 |
| IL330388 | 212 | 217 | SEQ ID NO: 213 | SEQ ID NO: 218 |
| | | | SEQ ID NO: 214 | SEQ ID NO: 219 |
| | | | SEQ ID NO: 215 | SEQ ID NO: 220 |

TABLE 13-continued

Anti-IL-33 Antibody Sequences

| IgG1 | VH SEQ ID NO: | VL SEQ ID NO: | VH CDRs 1, 2, 3 | VL CDRs 1, 2, 3 |
|---|---|---|---|---|
| IL330388_fgl | 222 | 227 | SEQ ID NO: 223<br>SEQ ID NO: 224<br>SEQ ID NO: 225 | SEQ ID NO: 228<br>SEQ ID NO: 229<br>SEQ ID NO: 230 |
| IL330396 | 232 | 237 | SEQ ID NO: 233<br>SEQ ID NO: 234<br>SEQ ID NO: 235 | SEQ ID NO: 238<br>SEQ ID NO: 239<br>SEQ ID NO: 240 |
| IL330396_fgl | 242 | 247 | SEQ ID NO: 243<br>SEQ ID NO: 244<br>SEQ ID NO: 245 | SEQ ID NO: 248<br>SEQ ID NO: 249<br>SEQ ID NO: 250 |
| IL330398 | 252 | 257 | SEQ ID NO: 253<br>SEQ ID NO: 254<br>SEQ ID NO: 255 | SEQ ID NO: 258<br>SEQ ID NO: 259<br>SEQ ID NO: 260 |
| IL330398_fgl | 262 | 267 | SEQ ID NO: 263<br>SEQ ID NO: 264<br>SEQ ID NO: 265 | SEQ ID NO: 268<br>SEQ ID NO: 269<br>SEQ ID NO: 270 |

Inhibition of IL-33 Binding to mAb by Purified IgG

The ability of anti-IL-33 antibodies to inhibit the binding of biotinylated human IL-33, biotinylated mouse IL-33 FLAG®His or cynomolgus IL-33 FLAG®His to the DyLight labelled IL330101 IgG was assessed in a biochemical HTRF® (Homogeneous Time-Resolved Fluorescence, Cisbio International) competition assay.

Purified anti-IL-33 antibody samples were tested for inhibition of biotinylated human IL-33, biotinylated mouse IL-33 FLAG®His or biotinylated cynomolgus FLAG®His IL-33 binding DyLight labelled IL330101 by adding 5 microlitres of each concentration of sample to a 384 well low volume assay plate (Costar, 3673). Next, a solution containing 40 nM DyLight labelled IL330101 was prepared and 2.5 microlitres added to the assay plates (labelled using kit (Thermo Scientific, 53051) as per manufacturer's instructions). This was followed by the addition of 2.5 microlitres of a solution containing 40 nM biotinylated human IL-33 (Adipogen, AG-40B-0038), 2.5 nM biotinylated mouse IL-33 FLAG®His or 12 nM biotinylated cynomolgus IL-33 FLAG® His combined with 4.6 nM streptavidin cryptate detection (Cisbio International, 610SAKLB). All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 4 hour at room temperature followed by 16 hour at 4 degrees Celsius and time resolved fluorescence was read at 620 nm and 665 nm emission wavelengths using an EnVision plate reader (Perkin Elmer). Data were analysed by calculating the 665/620 nm ratio followed by the % Delta F values for each sample. The 665/620 nm ratio was used to correct for sample interference using Equation 1. The % Delta F for each sample was then calculated using Equation 2. The negative control (non-specific binding) was defined by replacing biotinylated IL-33 combined with streptavidin cryptate detection with streptavidin cryptate detection only. The % Delta F values were subsequently used to calculate % specific binding as described in Equation 3.

FIG. 14A: shows inhibition of the FRET signal, produced by biotinylated human IL-33 binding to IL330101 with increasing concentrations of IL-33 IgG1 antibodies IL330101, IL330259, wherein the x-axis is the concentration of antibody in molar concentration and the y-axis is percent specific binding.

As the epitope competition assay reached its limit of sensitivity an assay using an intermediate optimised mAb IL330259 was used for testing purified IgG samples. This is as described for testing purified scFv.

As the IL330259 epitope competition assay reached its limit of sensitivity, a third assay using an optimised mAb (H338L293) was used for testing purified IgG samples. Purified anti-IL-33 antibody samples were tested for inhibition of biotinylated human IL-33, biotinylated cynomolgus IL-33 FLAG®His or biotinylated mouse IL-33 FLAG®His binding DyLight labelled H338L293 by adding 5 microlitres of each sample to a 384 well low volume assay plate (Costar, 3673). Next, a solution containing 20 nM DyLight labelled H338L293 was prepared and 2.5 microlitres added to the assay plates (labelled using kit (Thermo Scientific, 53051) as per manufacturer's instructions). This was followed by the addition of 2.5 microlitres of a solution containing 4 nM biotinylated human IL-33 (Adipogen, AG-40B-0038), 0.8 nM biotinylated mouse IL-33 FLAG®His or 1.6 nM biotinylated cynomolgus IL-33 FLAG®His combined with 4.6 nM streptavidin cryptate detection (Cisbio International, 610SAKLB). All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 4 hour at room temperature followed by 16 hour at 4° C. and time resolved fluorescence was read at 620 nm and 665 nm emission wavelengths using an EnVision plate reader (Perkin Elmer). Data were analysed by calculating the 665/620 nm ratio followed by the % Delta F values for each sample. The 665/620 nm ratio was used to correct for sample interference using Equation 1. The % Delta F for each sample was then calculated using Equation 2. The negative control (non-specific binding) was defined by replacing biotinylated IL-33 combined with streptavidin cryptate detection with streptavidin cryptate detection only. The % Delta F values were subsequently used to calculate % specific binding as described in Equation 3.

FIG. 14B: shows inhibition of the FRET signal, produced by biotinylated human IL-33 binding to H338L293 with increasing concentrations of IgG1 antibodies H338L293, IL330396 and IL330388 wherein the x-axis is the concentration of antibody in molar concentration and the y-axis is percent specific binding.

Inhibition of Huvec IL-6 Production by IL-33 Antibodies

Antibodies were assessed for ability to inhibit IL-33-stimulated IL-6 production from Huvecs as described in Example 2

Figure 15:
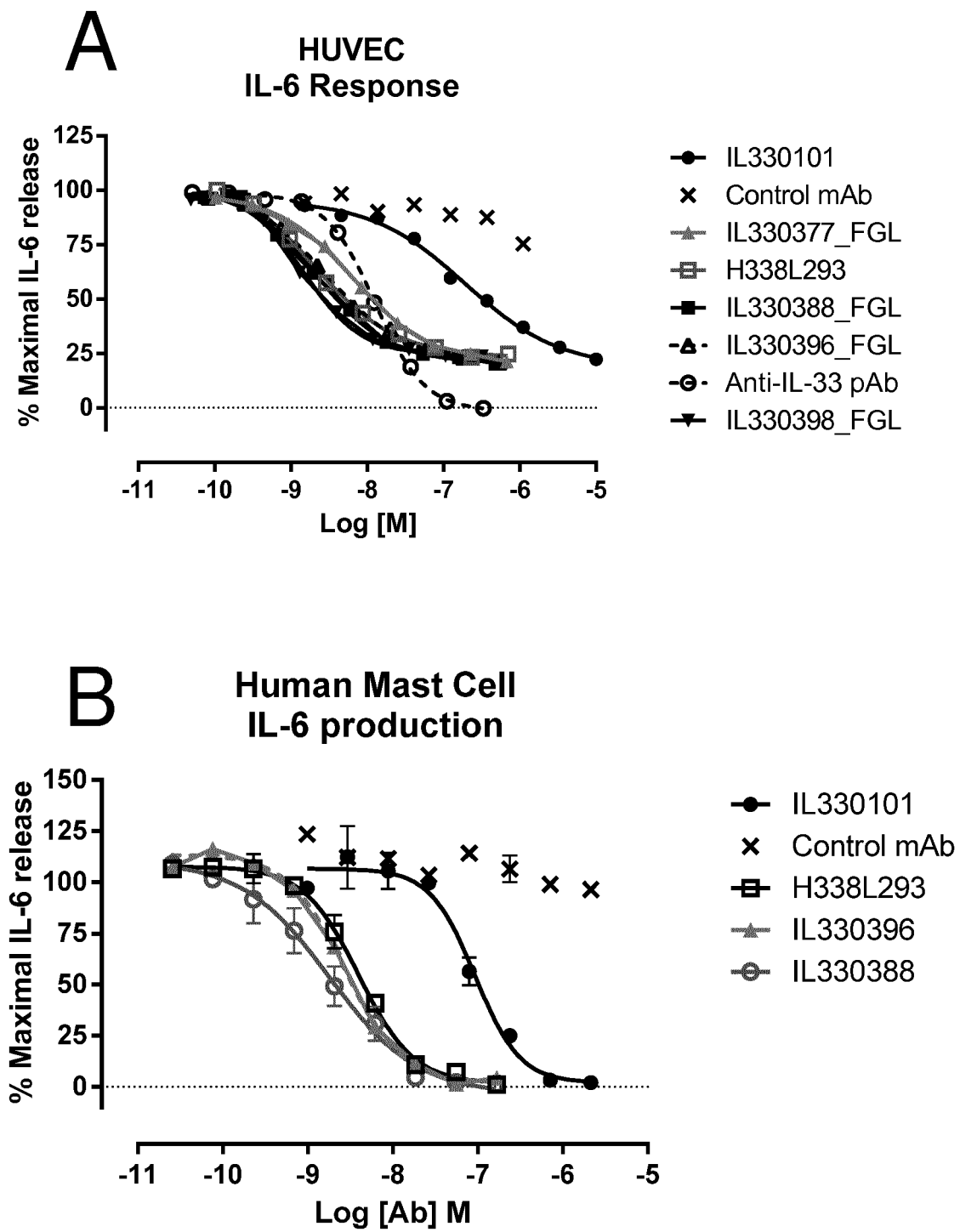
FIG. 15 Shows neutralizing activity of antibodies in HUVEC (FIG. 15A) or mast cell (FIG. 15B) IL-6 production assays.

FIG. 15A shows the reduction of IL-6 production by increasing concentrations of antibodies (IL330101, IL330377, H338L293, IL330388, IL330396, IL330398) wherein the x-axis is the concentration of antibody in molar concentration and the y-axis is % maximum response. Purified IgG preparations of antibodies inhibited the IL-6 activity by a maximum of ~70%, compared to a commercial polyclonal antibody which inhibited 100%.

Inhibition of Mast Cell IL-6 Production by IL-33 Antibodies

Antibodies were assessed for ability to inhibit IL-33-stimulated IL-6 production from human cord blood derived mast cells as described in Example 2

FIG. 15B shows the reduction of IL-6 production by increasing concentrations of antibodies (IL330101, H338L293, IL330388, IL330396) wherein the x-axis is the concentration of antibody in molar concentration and the y-axis is % maximum response. Purified IgG preparations of antibodies inhibited the IL-6 activity by 100%, compared to the negative control antibody.

IC50 results for HUVEC IL-6 production and mast cell IL-6 production are shown in Table 14.

TABLE 14

Example potencies of optimised antibodies

| Clone | IgG1 Geomean (95% CI) IC50 (nM) | |
| --- | --- | --- |
| | Huvec IL-6 production | Mast cell IL-6 production |
| IL330101 | 193 | 93 |
| IL330377_FGL | 6.6 | 1.3 |
| H338L293 | 1.9 | 1.7 |
| IL330388_FGL | 2.1 | 1.2 |
| IL330396_FGL | 2.8 | 1.5 |
| IL330398_FGL | 1.5 | 0.9 |

Antibody Pharmacology

IL-6 production from cord blood-derived mast cells was induced by increasing concentrations of IL-33 (Adipogen) using the method described in Example 2. This dose-response was carried out in the presence of increasing concentrations of H338L293 or IL330388 to produce a rightward shift of the IL-33 dose-response curve. $EC_{50}$ values for IL-33 in the absence and presence of antibody were calculated using GraphPad PRISM software (La Jolla, Calif., USA), and the dose ratio (DR) was calculated. Data were plotted as log [Antibody] M (x-axis) versus log [DR−1] (y-axis). This clearly shows a non-competitive profile (curved plot), characteristic of an allosteric modulator. To investigate this, data from each experiment were normalised and combined into a single data set. An allosteric model was fitted using Prism Graphpad Software and the $K_b$ and value of alpha determined. Values of alpha were similar for both leads examined, indicating a value for alpha of ~0.02 (i.e. the maximum reduction in IL-33 affinity/potency when antibody is bound is ~50-fold). Functional affinity ($K_b$) can be estimated for H338L293 (~4.2 nM) and IL330388 ~1.7 nM).

Figure 16:
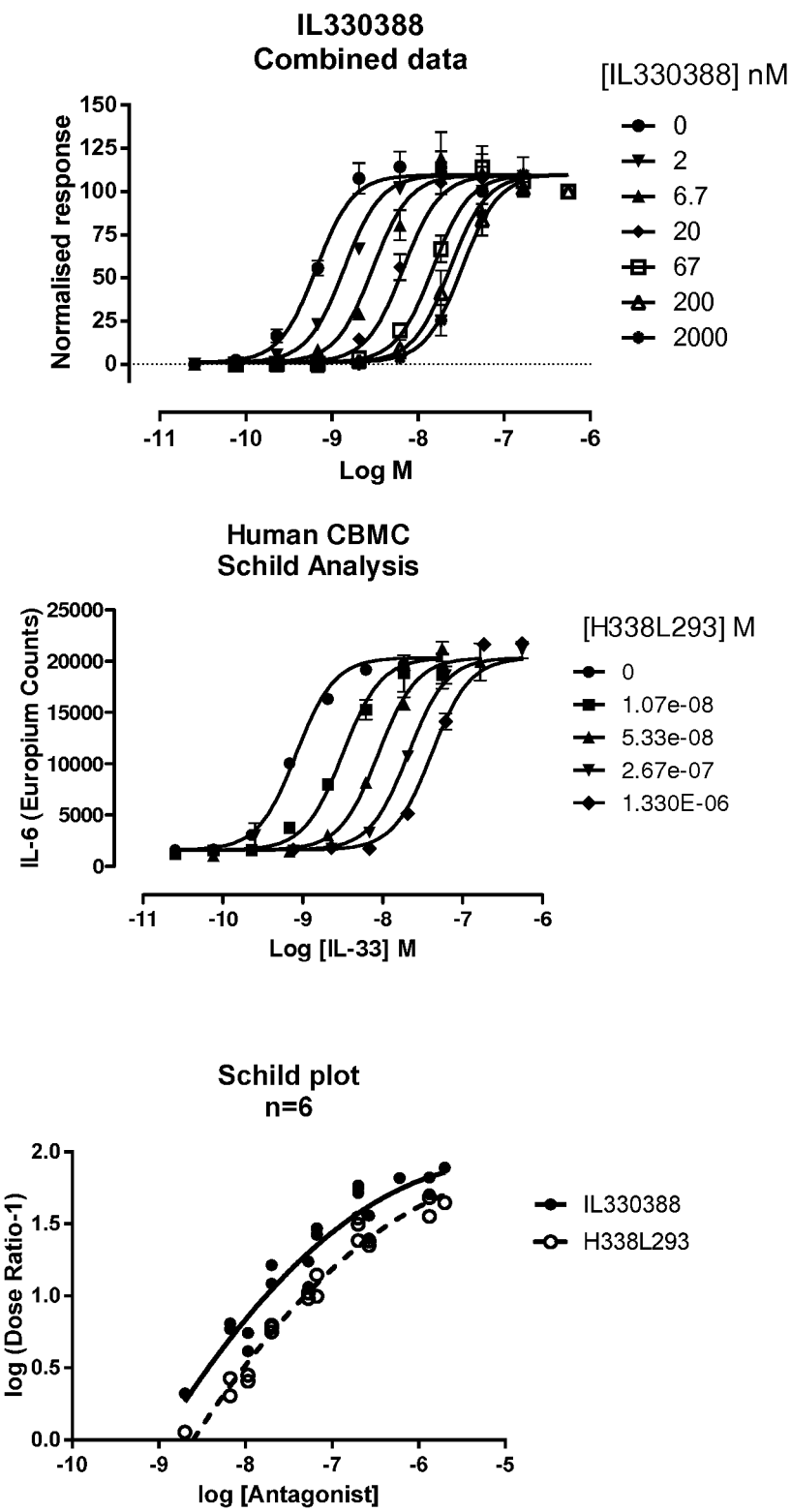
FIG. 16 Shows a Schild analysis of IL330388 and H338L293 in a mast cell IL-6 production assay.

FIG. 16 shows a Schild analysis of IL330388 and H338L293 in a mast cell IL-6 production assay. Both antibodies display the profile of an allosteric modulator.

Binding Affinity Calculation for IL-33 Antibodies using BIAcore

The binding affinity of purified IgG samples of exemplary binding members to human, cynomolgus or mouse IL-33 was determined by solution affinity using a BIAcore 2000 (GE healthcare). A biotinylated-IL33 surface was immobilised on a streptavin coated sensor chip (GE healthcare cat. No. BR-1000-32). Anti-IL33 antibodies were incubated with various concentrations of unlabelled IL33 and equilibrated at 25° C. for 48 hours. The amount of free antibody was determined by flowing the samples over the IL33 chip and measuring the response compared to a standard curve of antibody. Affinities were determined using the solution affinity fit in BIAevaluation software. The affinities for antibodies IL330101, H338L293, IL330388, IL330396 binding to human, cynomolgus or mouse IL-33 are shown in Table 15.

TABLE 15

BIAcore solution affinity of exemplary binding members

| Antibody | Antigen | KD (nM) |
| --- | --- | --- |
| IL3300101 | Human IL-33 FLAG ®-His | 3.20E−06 |
| H338L293 | Human IL-33 FLAG ®-His | 5.90E−10 |
| H338L293 | Cynomolgus IL-33 FLAG ®-His | 5.45E−10 |
| H338L293 | Mouse IL-33 FLAG ®-His | 4.52E−10 |
| IL3300388 | Human IL-33 FLAG ®-His | 3.00E−10 |
| IL3300388 | Cynomolgus IL-33 FLAG ®-His | 2.92E−10 |
| IL3300388 | Mouse IL-33 FLAG ®-His | 8.82E−11 |
| IL3300396 | Human IL-33 FLAG ®-His | 5.93E−10 |

Example 4 Redox Regulation of IL-33

Reagents cDNA encoding the mature component of Human IL-33 (amino acids 112-270); accession number (Swiss-Prot) O95760 was synthesized by primer extension PCR and cloned into pJexpress404 (DNA 2.0). The coding sequence was modified to contain a 10× his, Avitag, and Factor-Xa protease cleavage site (MHHHHHHHHHHAAGLN-DIFEAQKIEWHEAAIEGR) at the N-terminus of the protein. N-terminal tagged His10/Avitag IL33-01 (WT, SEQ ID 632) was generated by transforming *E. coli* BL21(DE3) cells. Transformed cells were cultured in autoinduction media (Overnight Express™ Autoinduction System 1, Merck Millipore, 71300-4) at 37° C. for 18 hours before cells were harvested by centrifugation and stored at −20° C. Cells were resuspended in BugBuster (Merck Millipore, 70921-5), containing complete protease inhibitor cocktail tablets (Roche, 11697498001), 2.5 u/ml Benzonase nuclease (merck Millipore, 70746-3) and 1 mg/ml recombinant lysozyme. Cell lysate was clarified by centrifugation at 75,000×g for 2 hours at 4° C. IL-33 proteins were purified from the supernatant by Nickel affinity chromatography in 50 mM Sodium phosphate, pH 8.0, 300 mM NaCl, 20 mM Imidazole, eluting in 50 mM Sodium phosphate, pH 8.0, 300 mM NaCl, 250 mM Imidazole. IL-33 was further purified by size exclusion chromatography using a Superdex 75 10/300 GL column in Phosphate Buffered Saline pH 7.4. Peak fractions were analysed by SDS PAGE. Fractions containing pure IL-33 were pooled and the concentration measured by Nanodrop A280 measurement. Final samples were analysed by SDS PAGE.

To generate detagged IL-33 (BK349), N-terminal tagged His10/Avitag IL33-01 was incubated with 10 units of Factor Xa (GE healthcare 27-0849-01) per mg of protein in 2×DPBS buffer at RT for 1 hour. Untagged IL33 was purified using SEC chromatography in 2×DPBS on a S75 column (GE healthcare 28-9893-33) with a flow rate of 1 ml/min.

Other reagents outlined in Table 16 were generated as described in Example 1.

TABLE 16

IL-33 reagents

| Reagent | Supplier | Catalogue Number/ Designation | SEQ ID |
| --- | --- | --- | --- |
| Human IL-33 Flag ®His | In house | | SEQ ID NO: 627 |

TABLE 16-continued

IL-33 reagents

| Reagent | Supplier | Catalogue Number/ Designation | SEQ ID |
|---|---|---|---|
| Mouse IL-33 Flag®His | In house | | SEQ ID NO. 628 |
| Human His10/Avitag IL33-01 | In house | | SEQ ID NO. 632 |
| Human IL33-01 detagged | In house | BK349 | |
| Human IL-33 | Axxora/Alexis | ALX-522-098 | |
| Mouse IL-33 | Peprotech | 210-33 | |
| Mouse IL-33 | R&D systems | 3626/ML | |

Protein Modifications

IgGs and modified receptor proteins used herein were biotinylated via free amines using EZ link Sulfo-NHS-LC-Biotin (Thermo/Pierce, 21335) as described in Example 1. IL-33 proteins used herein were biotinylated via free cysteines using EZ link Biotin-BMCC (Perbio/Pierce, product no. 21900).

IL-33 Loses Activity Rapidly In Vitro

IL-33 activity was measured in HUVEC signaling assays (30 minutes) and IL-6 production assay (18-24 hours), the methods of which are described in Examples 1 and 2 respectively.

Figure 17:
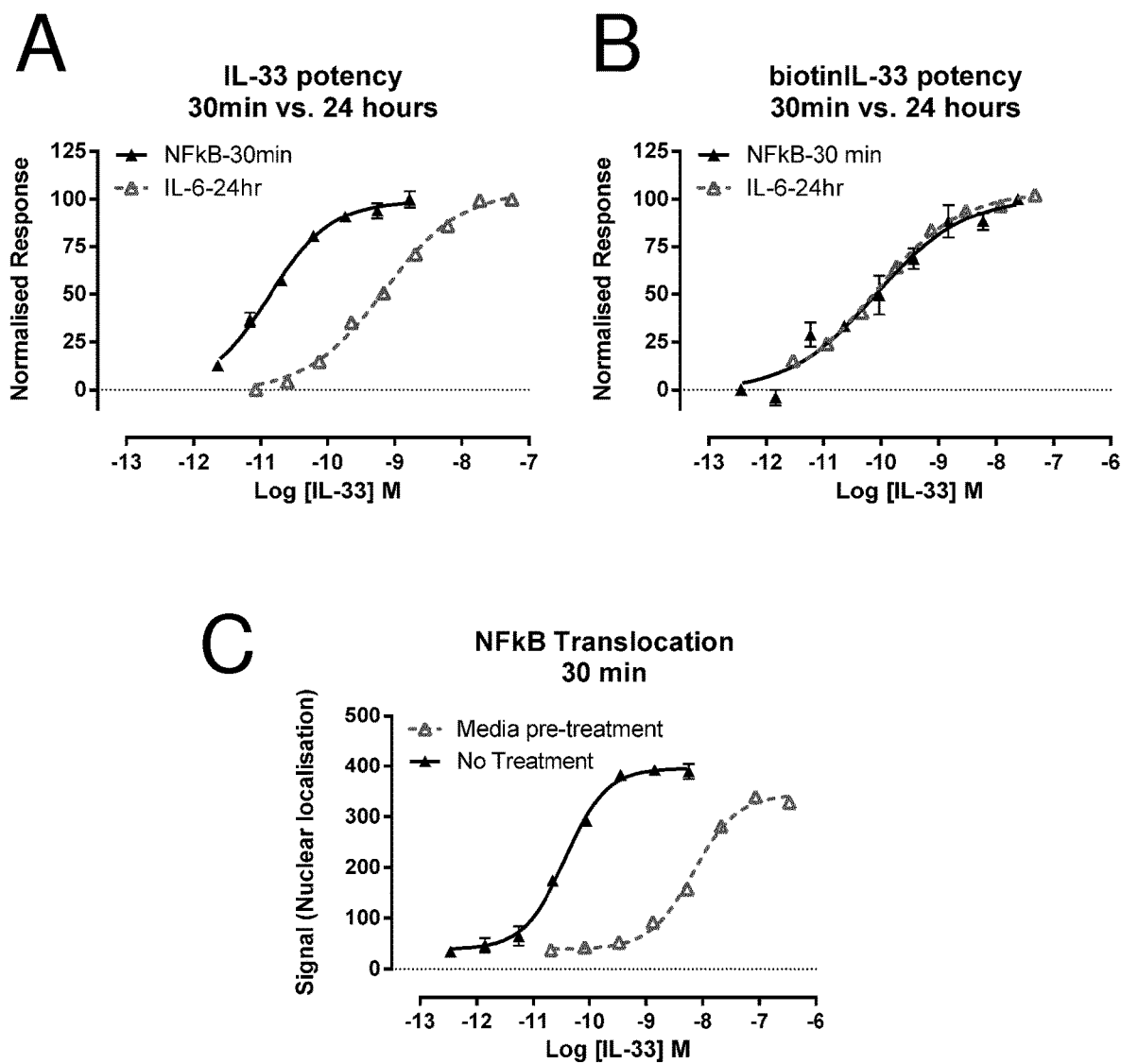
FIG. 17 Shows the activity of human IL-33 (FIG. 17A), cysteine-biotinylated IL-33 (FIG. 17B) or cell culture media-pretreated IL-33 (FIG. 17C), measured in HUVEC signaling assays (30 minutes) and IL-6 production assay (18-24 hours).

FIG. 17 shows the activity of human IL-33, cysteine-biotinylated IL-33 or cell culture media-pretreated IL-33, measured in HUVEC signaling assays (30 minutes) and IL-6 production assay (18-24 hours). FIG. 17A shows the comparison of human IL-33 activity (Adipogen) as measured by the NFkB or IL-6 assays wherein the x-axis is the concentration of human IL-33 in molar concentration and the y-axis is percent maximal response. IL-33 was significantly less potent in overnight compared with short (30 minute) assays. Human IL-33 Flag®His biotinylated via cysteine residues did not lose activity between short (30 minute) and longer (overnight) assays (FIG. 17B). To investigate this phenomenon, IL-33 (BK349) was pretreated for 18 hours in cell culture media (EBM-2 (Lonza, # CC-3156) with EGM-2 SingleQuot Kit Suppl. & Growth Factors (Lonza, # CC-4176)) and then compared with untreated IL-33 for ability to induce NFkB signaling. IL-33 that has been pre-treated with culture media displayed a significant loss of activity (FIG. 17C).

SDS-PAGE Analysis of IL-33

To investigate potential changes to the IL-33 protein, PBS/0.1% bovine serum albumin (BSA) or Iscoves Modified Dulbeccos Medium (IMDM)-treated human IL-33 (BK349 or human IL-33 Flag®His) and mouse IL-33 Flag®His were analysed by SDS PAGE electrophoresis under reducing or non-reducing conditions. Samples were made up in 1× NuPAGE gel loading buffer (Invitrogen) and denatured at 90° C. for 3 min. Reduced samples contained 2% beta-mercaptoethanol. Samples were run on NuPAGE Novex 12% Bis-Tris mini gels (Invitrogen) with MOPS running buffer (Invitrogen) according to manufacturer's instructions. Reduced and non-reduced samples were run on separate gels. 500 ng of IL-33 was loaded per lane. Gels were washed 3×5 min on shaking platform in ddH20 and then stained for 1 hour using EzBlue (Coomassie brilliant blue G-250 based gel staining reagent, Sigma G1041). Gels were destained in dH2O and scanned using an Epsom Scanner.

Figure 18:
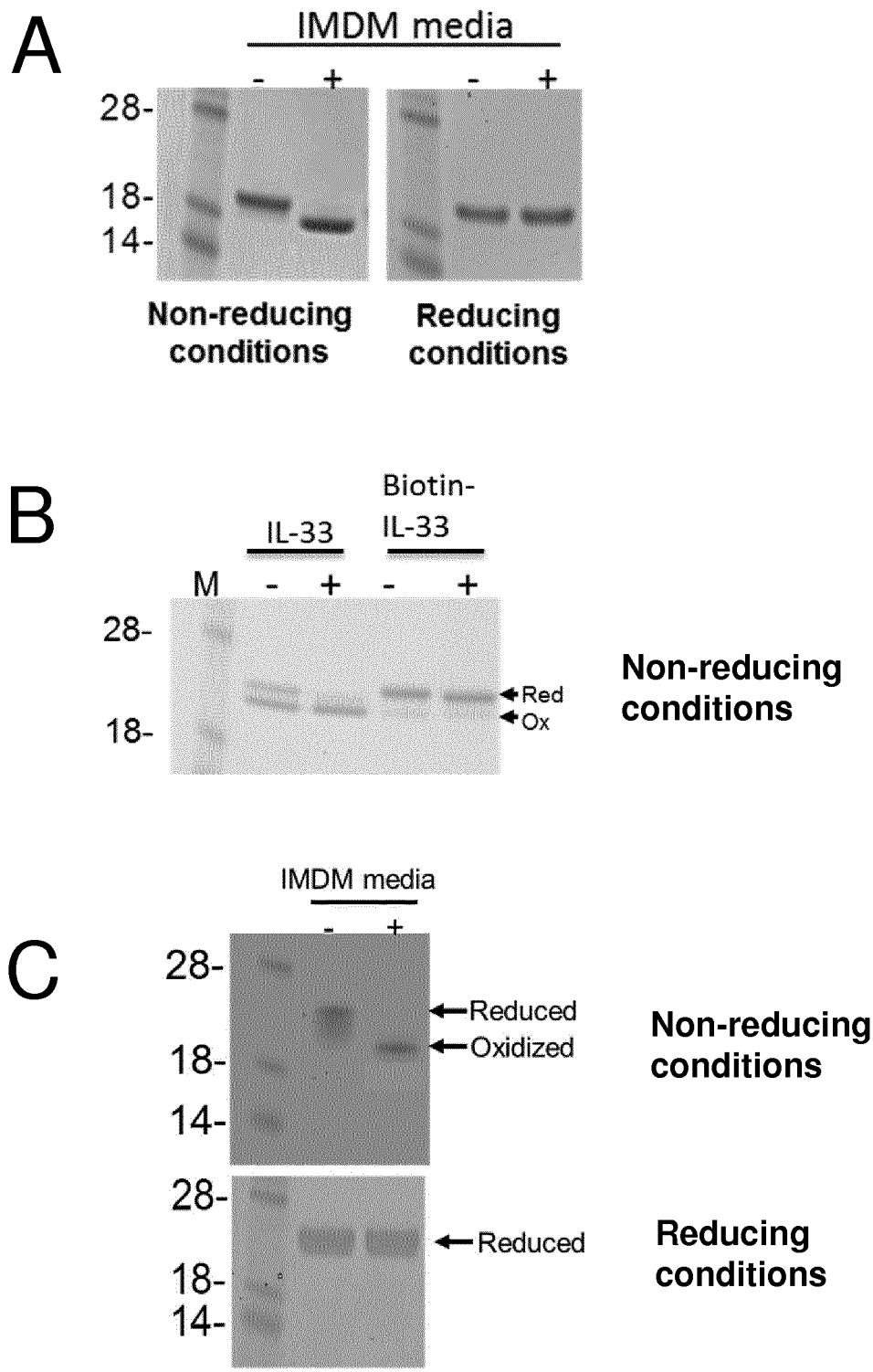
FIG. 18 Shows SDS-PAGE of: human IL-33 (BK349) before or after treatment with Iscoves Modified Dulbeccos Medium (IMDM) (FIG. 18A), of human IL-33 Flag®His, non-biotinylated versus biotinylated under non-reducing conditions (FIG. 18B), of the mouse IL-33 Flag®His after treatment with IMDM (FIG. 18C).

FIG. 18 shows SDS-PAGE of human or mouse IL-33 under reducing or non-reducing conditions, before or after treatment with Iscoves Modified Dulbeccos Medium (IMDM). Differences in apparent molecular weight of IL-33 after treatment with IMDM were observed only under non-reducing conditions implying the presence of redox-related modifications for both human and mouse IL-33. FIG. 18A shows difference in apparent molecular weight of the human IL-33 (BK349) after treatment with IMDM that was observed only under non-reducing conditions. FIG. 18B shows human IL-33 Flag®His, non-biotinylated versus biotinylated under non-reducing conditions. Difference in apparent molecular weight was observed for IL-33 Flag®His, but not cysteine biotnylated IL-33 Flag®His after IMDM treatment. FIG. 18C shows difference in apparent molecular weight of the mouse IL-33 Flag®His after treatment with IMDM that was observed only under non-reducing conditions.

Mass Spectrometry Analysis and Disulphide Mapping

The media-treated form of human IL-33 was purified for further analysis. Human IL-33 (BK349) was incubated with 60% IMDM media or in PBS at a final protein concentration of 300 ug/ml for 18 hours at 37° C. After 18 hours, media-treated IL33 was purified from media components using Size Exclusion Chromatography (SEC) on an S75 16:600 Superdex column (GE healthcare 28-9893-33) in 2×DPBS using an AKTAxpress FPLC system (GE healthcare). Peak fractions were analysed by SDS PAGE, and the non-aggregated, pure fractions were pooled and analysed by LC-MS.

FIG. 19 shows the purification of IMDM-treated human IL-33 by SEC. The monomer fraction was collected for further analysis.

LC-MS

Reverse phase (RP) LC-MS analysis was performed using an Acquity UPLC coupled to a Synapt G1 quadrupole time of flight (QToF) mass spectrometer (Waters, Milford, US). 1 µg of purified protein diluted in 10 mM Tris HCl pH 8 at 1 mg/ml was injected onto a 50 mm×2.1 mm, 1.7 µm particle size BEH300 C4 analytical column held at 65° C. (Waters, Milford, US). Protein was eluted at a constant flow rate of 0.15 mL/min using a 5 minute binary gradient; solvent B was initially increased from 5 to 95% over 1 minute, reduced to 20% over 2 minutes and returned to 5% over a further 2 minutes. The column was cleaned prior to the subsequent injection by oscillating between high (95%) and low (5%) solvent B for 5 minutes. Solvent A (water) and B (acetonitrile) were supplemented with 0.01% (v/v) trifluoroacetic acid and 0.1% (v/v) formic acid. Spectra were acquired between 500-4500 m/z. Key instrument parameters included +ve ionisation mode, source voltage: 3.4 kV, sample cone voltage: 50 V, source temperature: 140° C., desolvation temperature: 400° C. BioPharmaLynx (Waters, Milford, US) was used to deconvolute the charge envelopes.

Figure 20:
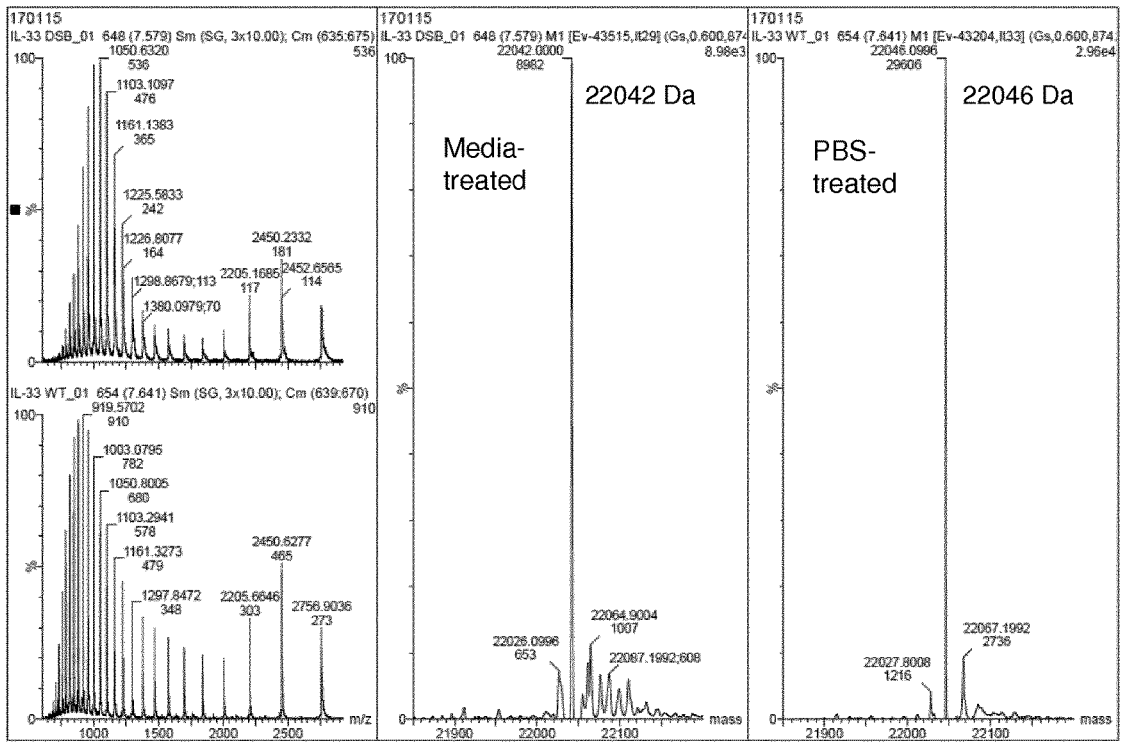
FIG. 20 Shows the intact mass of PBS versus media-treated IL-33 determined by LC-MS. IMDM-treated IL-33 displayed a 4 Da loss compared with PBS-treated compatible with the formation of two disulphide bonds.

FIG. 20 shows the intact mass of PBS versus IMDM treated IL-33 determined by LC-MS. IMDM-treated IL-33 displayed a 4 Da loss compared with PBS-treated IL-33 compatible with the formation of two disulphide bonds.

Disulphide Bond Mapping

For each sample, 50 µg of protein was prepared at 3 mg/ml in 100 mM sodium phosphate, 1 mM N-ethylmaleimide, pH 7.0 buffer and incubated for 20 minutes at room temperature. Dried samples were resuspended in 7 M Guanidine HCl, 100 mM NaCl, 10 mM sodium phosphate and incubated at 37° C. for 30 minutes. Denatured protein was diluted to 0.3 mg/ml and digested with Glu-C at an E:S ratio of 1:50 in 2 M Guanadine, 100 mM sodium phosphate, 0.1 mM EDTA, pH7.0 at 37° C. After 2 hours a second, equal aliquot of Lys-C was added. After a further 2 hours the digest was split; for the reduced analysis the digest was incubated with 50 mM Dithiothreitol for 15 min at room temperature. Reduced and non-reduced samples were analysed by RP LC-MS using an Acquity UPLC coupled to a Synapt G2 QToF mass spectrometer (Waters, Milford, US). For each sample, 5 ug of Lys-C digest was injected onto a 150 mm×2.1 mm, 1.7 µm particle size BEH300 C18 analytical column held at 55° C. (Waters, Milford, US). Peptides were eluted at a constant flow rate of 0.2 mL/min using a 75 minute binary gradient; solvent B was increased from 0% to 35%. The column was cleaned prior to the subsequent injection by oscillating between high (95%) and low (5%) solvent B for 5 minutes. Solvent A (water) and B (acetonitrile) were supplemented with 0.02% (v/v) trifluoroacetic acid. Spectra were acquired between 50-2000 m/z using a data independent mode of acquisition. Low and high energy spectra were processed using BioPharmaLynx (Waters, Milford, US).

FIG. 21 shows the disulphide mapping of IMDM-treated human IL-33. FIG. 21A shows combined, deconvoluted mass spectra from non-reduced and reduced Lys-C peptide mapping analysis of DSB IL-33. FIG. 21B shows isolated spectra for cysteine containing peptides. Peptides unique to reduced and non-reduced samples are highlighted in green and blue, respectively. Data were consistent with the formation of two disulphide bridges. One species identified had bridges between cysteines C208-C249 and C227-C232, respectively. However, the predominant peak was not resolved and other species may exist. FIG. 21C shows sequences of disulphide bonded peptides identified by non-reduced and reduced Lys-C peptide mapping analysis of disulphide bonded IL-33. Disulphide linkages are represented by two hyphens (- -). Lys-C miscleavages are represented by square brackets.

NMR Analysis of the Disulphide Bonded IL-33

Based on the reported structure of IL-33 (Lingel, A. et al. *Structure* 17, 1398-1410 (2009); Liu, X. et al. *Proc. Natl. Acad. Sci. U.S.A.* 110, 14918-14923 (2013)), cysteine residues are not in sufficiently close proximity for disulphide bonding to occur without significant conformational change. To investigate this NMR heteronuclear multiple quantum coherence (HMQC) analysis was performed.

Production of $^{15}$N-IL-33 Proteins

DNA encoding wild type IL-33 with an N-terminal 6His tag and TEV protease cleavage site (SEQ ID. 633) was used to transform *E. coli* BL21 Gold cells. Transformed cells were cultured at 37° C. in M9 minimal media supplemented with 5 g/L of $^{15}$N-IsoGro™ powder until they reached an OD600 nm of 0.6 to 0.8, when protein expression was induced by addition of 100 mM IPTG. Cultures were continued at 18° C. for a further 20 hours before cells were harvested by centrifugation and stored at −80° C. Cells were resuspended in 50 mM Sodium phosphate, pH 8.0, 300 mM NaCl, 20 mM Imidazole, 5 mM BetaMercaptoethanol containing Complete protease inhibitor tablets (Roche, 11697498001), 2.5 U/ml Benzonase nuclease (merck Millipore, 70746-3) and 1 mg/ml recombinant lysozyme. Resuspended cells were lysed using a Constant Systems cell disruptor at 25 kpsi and clarified by centrifugation at 75,000×g for 2 hours at 4° C. IL-33 was purified from the supernatant by Nickel affinity chromatography in 50 mM Sodium phosphate, pH 8.0, 300 mM NaCl, 20 mM Imidazole, 5 mM BetaMercaptoethanol, eluting in 50 mM Sodium phosphate, pH 8.0, 300 mM NaCl, 250 mM Imidazole, 5 mM BetaMercaptoethanol. Eluted protein was incubated with TEV protease and dialysed into 50 mM Sodium phosphate, pH 8.0, 300 mM NaCl, 20 mM Imidazole, 5 mM BetaMercaptoethanol at 4° C. De-tagged protein was separated from uncleaved IL-33 by Nickel affinity chromatography in 50 mM Sodium phosphate, pH 8.0, 300 mM NaCl, 20 mM Imidazole, 5 mM BetaMercaptoethanol. IL-33 was further purified by size exclusion chromatography using a HiLoad 16/60 Superdex 75 column (GE healthcare) in 20 mM Sodium phosphate pH 6.5, 100 mM NaCl, 5 mM BetaMercaptoethanol, using an AKTAxpress FPLC system (GE healthcare). Peak fractions were analysed by SDS PAGE.

Fractions containing pure IL-33 were pooled and the concentration measured by Nanodrop A280 measurement. Protein was concentrated using an Amicon 10,000 molecular weight cut-off spin concentrator to a final concentration of 9.5 mg/ml for NMR analysis.

Purified $^{15}$N labelled protein in PBS pH7.4 was incubated with 60% IMDM media at a final protein concentration of 0.28 mg/ml for 18 hours at 37° C. After 18 hours, the protein was concentrated using an Amicon 10,000 molecular weight cut-off spin concentrator to a concentration of 0.8 mg/ml. The protein was then purified by size exclusion chromatography using a HiLoad 16/60 Superdex 75 in PBS pH 7.4. Peak fractions were analysed by SDS PAGE, and the non-aggregated, pure fractions were pooled. Finally protein was concentrated using an Amicon 10,000 molecular weight cut-off spin concentrator to a concentration of 1.8 mg/ml (100 µM) for NMR analysis.

NMR Analysis

NMR spectra were recorded at 298 K on a Bruker Avance 600 MHz spectrometer running Topspin 2.3 equipped with a 5 mm TCI Cryoprobe with Z-axis gradients. The $^{15}$N-labelled IL33 WT sample was prepared as described with the addition of 5% deuterium oxide to allow sample locking. The exemplified $^{1}$H-$^{15}$N correlation spectra were acquired employing the sofast HMQC pulse sequence (Schanda, P; Brutscher, B; *Very fast two-dimensional NMR spectroscopy for real-time investigation of dynamic events in proteins on the time scale of seconds, J. Am. Chem. Soc.* (2005) 127, 8014-5) with (F2×F1) 1024×64 complex points (in states-TPPI mode), 9615×1460 Hz sweep width, 53.4 ms×43.8 ms acquisition times.

Figure 22:
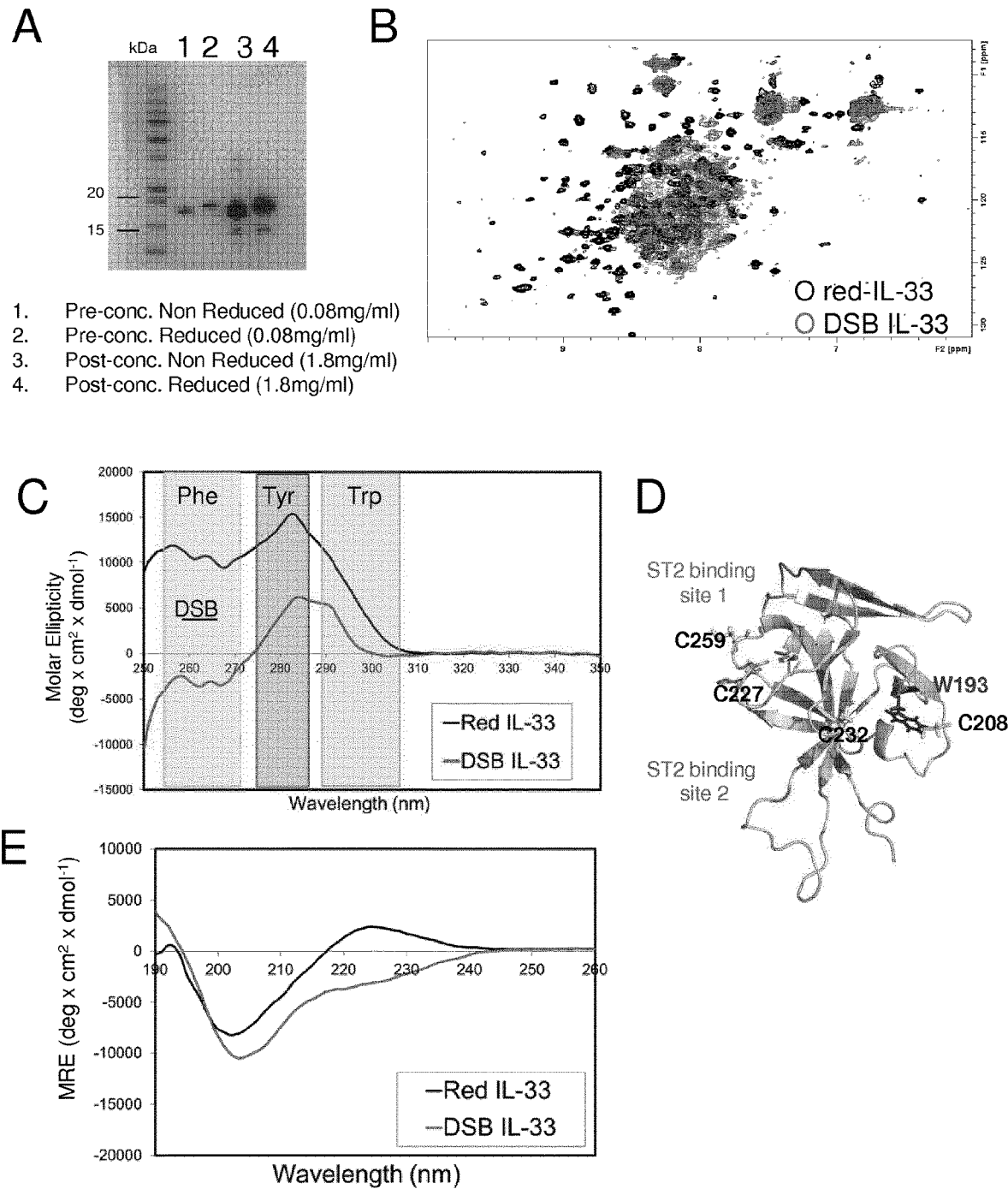
FIG. 22A Shows SDS-PAGE analysis of high concentration redIL-33 and DSB IL-33 for NMR analysis FIG. 22B Shows NMR heteronuclear multiple quantum coherence (HMQC) analysis with overlay of the $^1$H-$^{15}$N HMQC spectra for $^{15}$N-labeled human IL-33 for redIL-33 and DSB IL-33.
FIG. 22C Near-UV circular dichroism (CD) Spectrum
FIG. 22D Shows key features of IL-33 (Trp193, cysteines, and ST2 binding site) indicated within the solved IL-33 structure.
FIG. 22E Shows Far-UV circular dichroism (CD) Spectrum

FIG. 22A shows SDS PAGE analysis of IMDM treated WT IL33. SDS PAGE showing reduced and non-reduced IMDM treated WT IL33 before and after concentration for NMR.

FIG. 22B shows NMR analysis of WT IL33. Overlay of the $^{1}$H-$^{15}$N HMQC spectra for 0.1 mM $^{15}$N-labeled IL33 WT before and after IMDM media treatment plotted in black and red, respectively. Comparison of the two spectra indicate an entirely different, and less ordered, structure after IMDM treatment.

Circular Dichroism (CD) Spectroscopy.

To confirm conformational change and investigate further, Circular Dichroism (CD) Spectroscopy analysis was performed.

Far-UV and near-UV CD analysis were performed on a Jasco-815 instrument (Easton, Md.). For Far-UV CD the spectra were recorded over wavelength range 180-260 nm in a 1 mm pathlength cuvette at sample concentration of 0.14 mg/mL and 0.12 mg/mL for respectively redIL-33 and DSB IL-33 at 20° C. in buffer solution 10 mM Phosphate pH=6.9. For near-UV CD the spectra were recorded over wavelength range 260-350 nm in a 10 mm pathlength cuvette at sample concentration of 1.38 mg/mL and 0.89 mg/mL for respectively redIL-33 and DSB IL-33 at 20° C. in buffer solution DPBS. CD spectra of the buffer solution were recorded and subtracted from all sample spectra to correct for instrument, cuvette and baseline effects. CD Pro software was employed for the deconvolution of spectra into secondary structure elements.

FIG. 22C: Near-UV circular dichroism (CD) Spectroscopy. Spectra were recorded over wavelength range 260-350 nm. The final spectra were the average of 4 scans. Aromatic amino-acids and disulphide absorption bands are adapted from Kelly (Kelly S. M. et al. *How to study proteins by Circular Dichroism. Biochimica et Biophysica Acta*, 1751, 119-139 (2005)) The difference observed in ellipticity around Trp absorption is consistent with change in environment of the sole Tryptophan (W193) demonstrating changes to tertiary structure in this region between reduced and DSB IL-33. The difference in intensity around 260 nm is consistent with the introduction of additional chromophores from disulphide bond formation.

FIG. 22D: Key features of IL-33. Trp193, cysteines, and ST2 binding site (Liu, X. et al. *Structural insights into the interaction of IL-33 with its receptors. Proc. Natl. Acad. Sci. U.S.A.* 110, 14918-14923 (2013)) are indicated within the solved IL-33 structure (Lingel 2009)

FIG. 22E: Far-UV circular dichroism (CD) Spectroscopy. Spectra were recorded over wavelength range 190-260 nm. The final spectra were the average of 8 scans. Far-UV spectra are consistent with predominantly β-sheet secondary structures as seen previously with this family of proteins (Chang B. S. et al, *Formation of an active dimer during storage of interleukin-1 receptor antagonist in aqueous solution. Biophysical Journal.* 71, 3399-3406 (1996); Craig S. et al. *Conformation, Stability and folding of Interleukin*1β. *Biochemistry.* 26, 3570-3576 (1987); Hailey K. L. et al. *Pro-interleukin (IL)-1β shares a core region of stability as compared with mature IL-1β while maintaining a distinctly different configurational landscape. J. Biol. Chem.* 284. 26137-26148 (2009); Hazudat D. et al. *Purification and characterisation of Human Recombinant Precursor Interleukin* 1β. *J. Biol. Chem.* 264, 1689-1693 (1989); Meyers C. A. et al, *Purification and characterization of Human recombinant interleukin-1β. J. Biol. Chem.* 262, 11176-11181 (1987)). Spectra are significantly different demonstrating a change in secondary structure in DSB IL-33, relative to reduced IL-33.

CD spectra indicated a significant conformatonal change between the IL-33 forms. redIL-33 spectra were consistent with published data. DSB-IL-33 spectra were consistent with a structured protein that was different to the reduced form. To map the areas that may be most altered between reduced and DSB-IL-33, we performed hydrogen/deuterium-exchange mass spectrometry.

Hydrogen/Deuterium-Exchange Mass Spectrometry (HDX-MS).

Proteins were diluted to 3.5 uM in phosphate buffered saline, pH 7.4. This stock was used to initiate labeling experiments by diluting 10-fold with deuterated (10 mM sodium phosphate, pD 6.6) aqueous solvent. Initial mapping experiments were done to assign species from the mass spectra to peptic peptide sequences from IL33. This was done largely as described[21]. Briefly, protonated diluted protein was mixed 1:1 with a quench solution (100 mM potassium phosphate, pH 2.55, 0.1 M TCEP, 1° C.), such that the final mixture pH was 2.55. The quenched protein was injected into a Waters HDX Manager with an immobilized pepsin column (2.0×30 mm; Poroszyme, Life Technologies), C18 trapping column (VanGuard ACQUITY BEH 2.1×5 mm; Waters) and analytical C18 column (1.0×100 mm ACQUITY BEH; Waters). Mobile phases were 0.1% formic acid in H2O (A) and 0.1% formic acid in ACN (B), such that their pH was 2.55. Protein was applied to the pepsin and trapping columns in 100 μL/min buffer A and eluted from the analytical column in a linear gradient of 3-40% B at 40 μL/min. Peptide sequences were assigned from MSE fragment data with Protein Lynx Global Server (Waters) 3.0.2 and DynamX 3.0 (Waters). Labeling data was acquired as for sequencing, except the mass spectrometer was set to MS scans only. Peptide-level data were analyzed in DynamX and MatLab (Mathworks).

Figure 23:
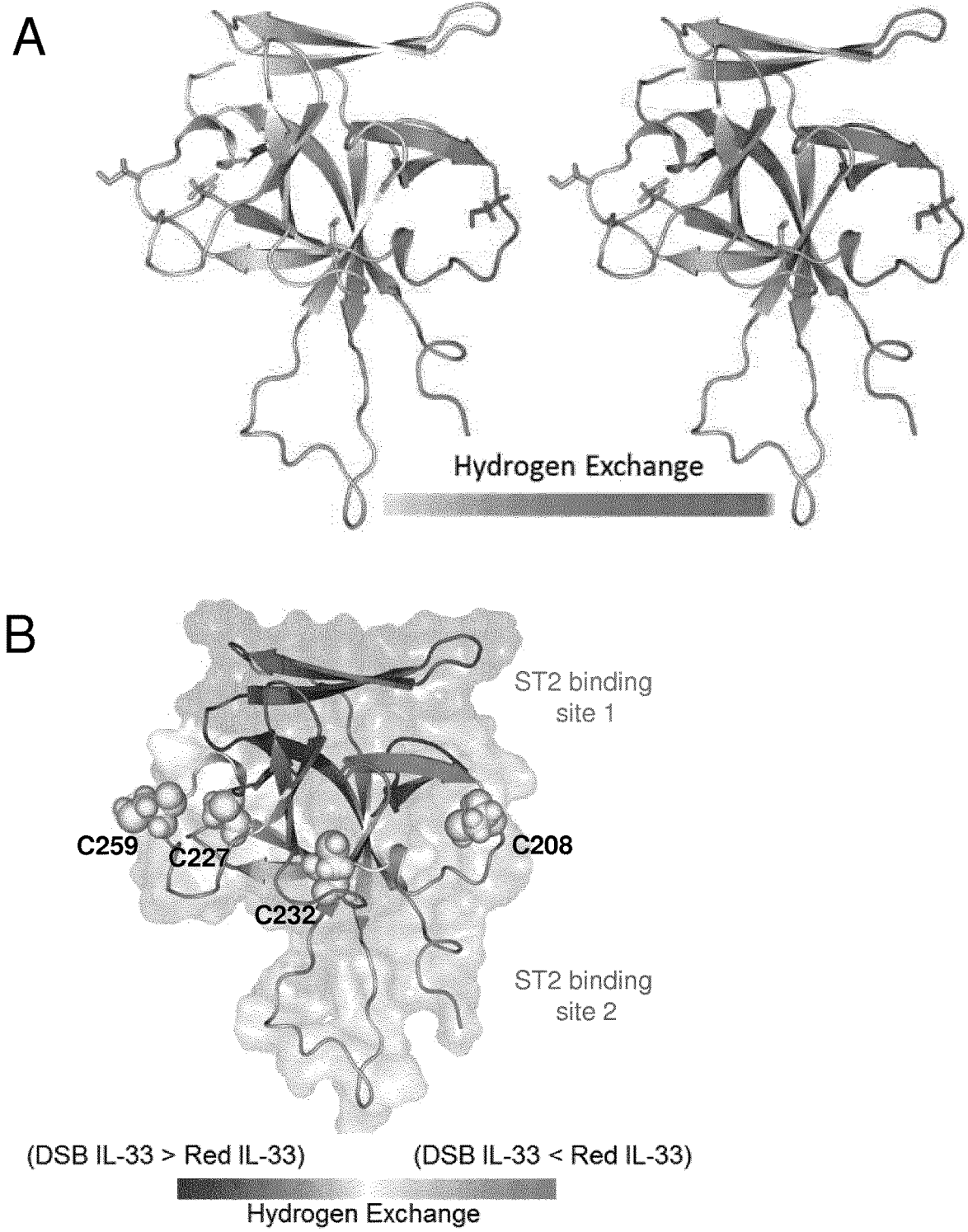
FIG. 23 Shows hydrogen-deuterium exchange analysis of redIL-33 and DSB IL-33. Differences in deuterium incorporation are mapped onto the published IL-33 structure.

FIG. 23 shows hydrogen-exchange mass spectrometry (HX-MS) analysis of reduced and DSB IL-33. FIG. 23A Comparison of fractional hydrogen exchange (for deuterium) in reduced IL-33 (left panel) and DSB IL-33 (right panel). Data are mapped onto the published IL-33 structure [lingel 2009] in both cases for comparison purposes. Gaps in sequence coverage where no data HX-MS data could be obtained are highlighted in slate blue. Side chains of cysteine residues are displayed as sticks. FIG. 23B shows a structural model of differential HX-MS data overlaid with the ST2 binding site (red and magenta).[Liu 2013] Dark blue indicates regions of increased hydrogen exchange in DSB IL-33 relative to reduced IL-33. The ST2 binding site 1 is in the area of greatest difference in H/D exchange and has likely been altered in structure.

Binding of Reduced vs DSB IL-33 to ST2 (BIAcore)

The disulphide bonded IL-33 is likely a very different structure to the reduced, ST2-binding IL-33 form (FIG. 22, 23), and conversion to the disulphide bonded form was associated with loss of functional activity (FIG. 17C). To investigate this, the disulphide bonded form of IL-33 was tested for ability to bind ST2 by BIAcore analysis. Direct binding of IL-33 to the extracellular domain of ST2 was determined by Surface Plasmon Resonance using a BIAcore 2000 (GE healthcare). ST2 was immobilised via the Fc-tag using an anti-human Fc capture (GE healthcare BR-1003-39) on a CM5 sensor chip (GE healthcare BR-1003-99) to give a stable surface of approximately 150 RU. IL-33 was flowed over the surface at 30 ul/min for three minutes to determine association rates. Dissociation was measured by flowing buffer at 30 ul/min for 15 minutes. Sensorgrams were interpreted using BIAevaluation software and kinetics were determined using double reference subtracted sensorgrams using a 1:1 (Langmuir) binding model.

FIG. 24A shows redIL-33 binding to ST2. Sensorgrams from 7.8 nM to 0.24 nM are shown, giving a KD of 0.2 nM.

FIG. 24B shows disulphide bonded IL-33 (IL33-DSB) binding to ST2. Sensorgrams from 500 nM to 0.24 nM are shown with no obvious binding observed.

Loss of ST2 binding and activity led us to hypothesise that oxidation could be a mechanism to terminate IL-33 activity and limit duration of ST2-dependent immunological responses in vivo.

Detection of IL-33 Forms

To ascertain that the disulphide-bonded form of IL-33 indeed exists in vivo, we used three different commercial IL-33 detection assays (2 human IL-33 and one mouse IL-33). Human and mouse IL-33 Duoset ELISAs (RnD Systems) were converted to MSD format (Meso Scale Discovery, Rockville, Md.). Coating concentrations of capture antibodies were as follows: anti-mouse IL-33 pAb 37.5 ug/ml; anti-human IL-33 pAb 18 ug/mL. Capture antibody was diluted in PBS with 0.03% Triton X-100 and 5 μl was spot coated onto standard bind plates (Meso Scale Discovery, Rockville, Md.) into the centre of each well and left to dry overnight at room temperature. Plates were washed ×3 in PBS-Tween and blocked with 25 μl Assay Diluent by sealing plates and incubating for 30 minutes at room temperature with shaking (450 rpm). 25 µl of samples or calibrator diluted in Assay Diluent were transferred to the blocked assay plates, which were incubated for 2 hours at room temperature with shaking (450 rpm). Plates were washed ×3 in PBS-Tween and 25 µl of detection reagent (detection antibody plus streptavidin SulfoTag both diluted to 1 µg/ml in antibody diluent). Plates were sealed and incubated for 1 hour at RT with shaking. Plates were washed ×3 in PBS-Tween. 150 µl of Read Buffer T diluted to 2× in distilled water was added. Plates were read within 15 minutes (Meso Scale Discovery, Rockville, Md.).

The Millipore human IL-33 assay (Cat # HTH17MAG-14K lot 2159117) was performed according to manufacturer's instructions. Briefly, IL-33 standards and samples were diluted in assay buffer and incubated with beads for 1 hour at room temperature with shaking (500 rpm), protected from light. Well contents were removed and washed ×2 with 200 uL of wash buffer. 25 uL of detection antibody was added per well and plates incubated for 1 hour at room temperature. 25 uL streptavidin-PE was added (without washing) and plates incubated for a further 30 minutes, shaking (850 rpm) and protected from light. Well contents were removed and washed ×2 with 200 uL of wash buffer. Samples were resuspended in 125 uL assay buffer, covered and shaken at 850 rpm for 30 seconds. Samples were analysed on Bio-Plex 200 (BioRad). Plate was read at low RP1, counting 50 beads per region (region 44) with doublet detection gates set to 5000 (low) and 25000 (high).

Figure 25:
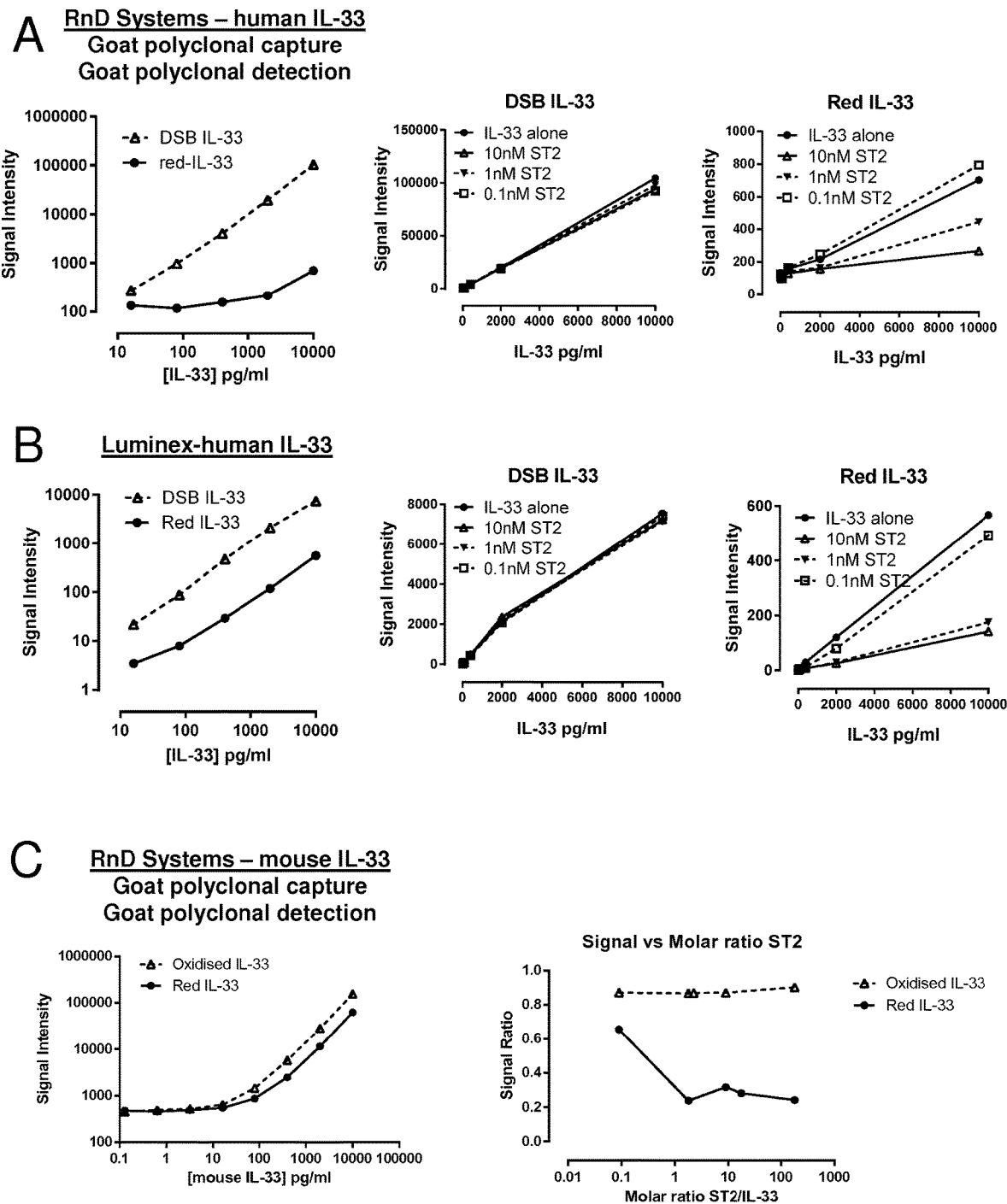
FIG. 25 Shows analysis of three commercial IL-33 ELISA assays for detection of redIL-33 and DSB IL-33 forms.

FIG. 25 shows analysis of three commercial IL-33 ELISA assays for detection of reduced and disulphide bonded IL-33 forms. The effect of ST2 on interference with the assay signal for both reduced and disulphide bonded forms is also shown. FIGS. 25A and B shows that the two commercial human IL-33 assays predominantly detect the disulphide-bonded form of IL-33 (IL33-DSB), suggesting that this is the main species that others have measured to date in human ex vivo samples. The 'reduced' but not oxidized/disulphide bonded IL-33 assay signal can be eliminated by addition of sST2. FIG. 25C shows the mouse IL-33 assay which detects both reduced and oxidized forms of mouse IL-33. The 'reduced' but not oxidized IL-33 assay signal can be eliminated by addition of sST2.

As we were unable to identify a commercial assay specific for the reduced, ST2-active form of human IL-33, we developed our own novel assays. IL330425 mAb (SEQ ID NOs. 62 and 67) or IL330004 mAb (SEQ ID NOs. 12 and 17) were used as capture antibodies. Captured IL-33 was detected with biotinylated sST2.Fc (R&D systems) or biotinylated IL330425 (SEQ ID NOs. 62 and 67) respectively. Capture antibody was diluted to 150 ug/mL in PBS with 0.03% Triton X-100 and 5 µl was spot coated onto standard bind plates (Meso Scale Discovery, Rockville, Md.) into the centre of each well and left to dry overnight at room temperature. Plates were washed ×3 in PBS-Tween and blocked with 25 µl Assay Diluent by sealing plates and incubating for 30 minutes at room temperature with shaking (450 rpm). 25 µl of samples or calibrator diluted in Assay Diluent were transferred to the blocked assay plates, which were incubated for 2 hours at room temperature with shaking (450 rpm). Plates were washed 3× in PBS-Tween and 25 µl of detection reagent (detection antibody plus streptavidin SulfoTag both diluted to 1 µg/ml in antibody diluent). Plates were sealed and incubated for 1 hour at RT with shaking. Plates were washed ×3 in PBS-Tween. 150 µl of Read Buffer T diluted to 2× in distilled water was added. Plates were read within 15 minutes (Meso Scale Discovery, Rockville, Md.).

Figure 26:
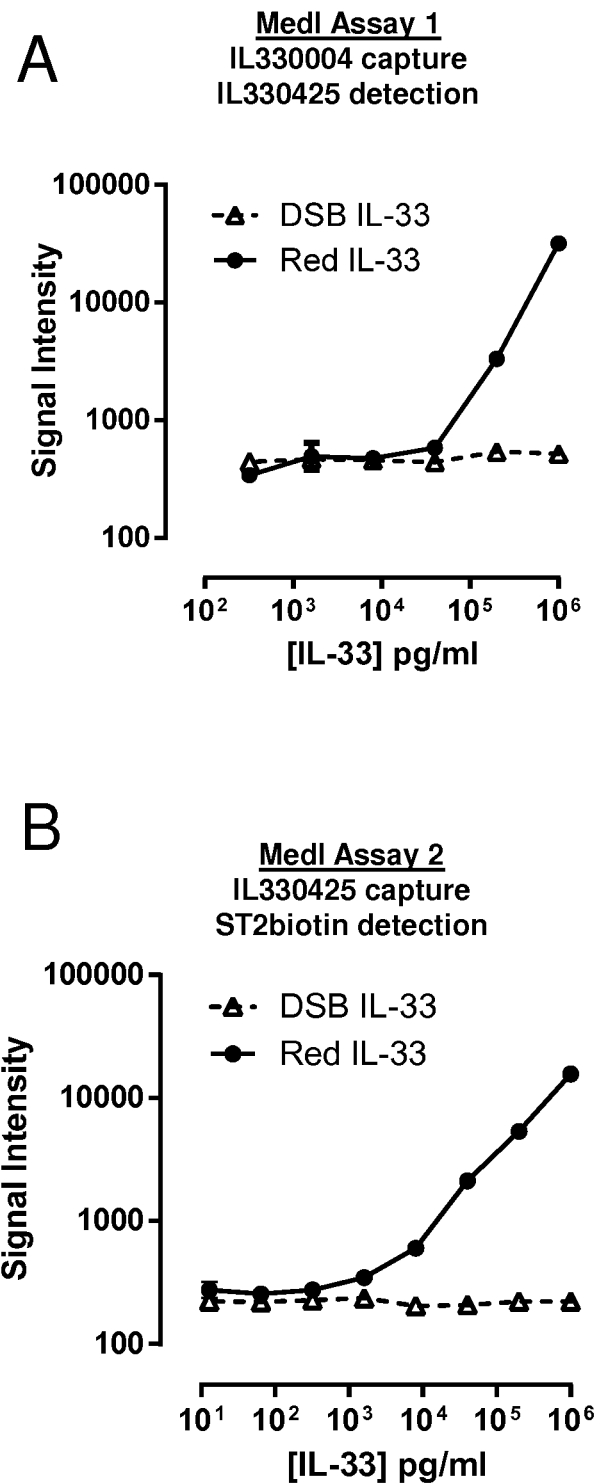
FIG. 26 Shows ELISA assays that are specific for detection of redIL-33.

FIG. 26A, B shows ELISA assays that are specific for detection of reduced IL-33. No detection of the disulphide bonded form is observed.

Timecourse of Conversion to Disulphide Bonded Form of IL-33

Assays detecting different IL-33 forms as described above were used to monitor a time course of conversion from redIL-33 to its disulphide bonded form. 10 ug/mL of detagged redIL-33 was incubated in 100% human serum, PBS/1% BSA or IMDM/1% BSA at 37° C. At timepoints t=0, 15 minutes, 30 minutes, 1 hour, 2 hours, 4 hours, 6 hours, 8 hours and 24 hours a 10 ul aliquot was removed and added to 90 ul PBS/1% BSA (1 in 10 dilution to 1 ug/ml), this was divided into 3×30 ul aliquots and snap frozen on dry ice before storage at −80° C. A t=0 sample was also prepared fresh immediately prior to the ELISA analysis as a control for the freeze/thaw cycle. Samples were analysed using the human MSD (R&D Systems) and the IL33004/IL330425-biotin assays described above to measure disulphide bonded and reduced IL-33 respectively. Together, these assays allowed monitoring of the conversion from the reduced to the disulphide-bonded form of IL-33.

To confirm the result from the ELISAs, IL-33 in the timecourse samples was analysed by Western blot. Samples were subjected to SDS-PAGE under reducing or non-reducing conditions. Samples were made up in 1× NuPAGE gel loading buffer (Invitrogen) and denatured at 90° C. for 3 minutes. Reduced samples contained 2% beta-mercaptoethanol. Samples were run on NuPAGE Novex 12% Bis-Tris mini gels (Invitrogen) with MOPS running buffer (Invitrogen) according to manufacturer's instructions. Reduced and non-reduced samples were run on separate gels. 100 pg of IL-33 was loaded per lane. Proteins were transferred to Nitrocellulose membranes (Invitrogen cat. no. IB3010-02) and detected by Western blotting with anti-IL-33 pAb (R&D systems).

Figure 27:
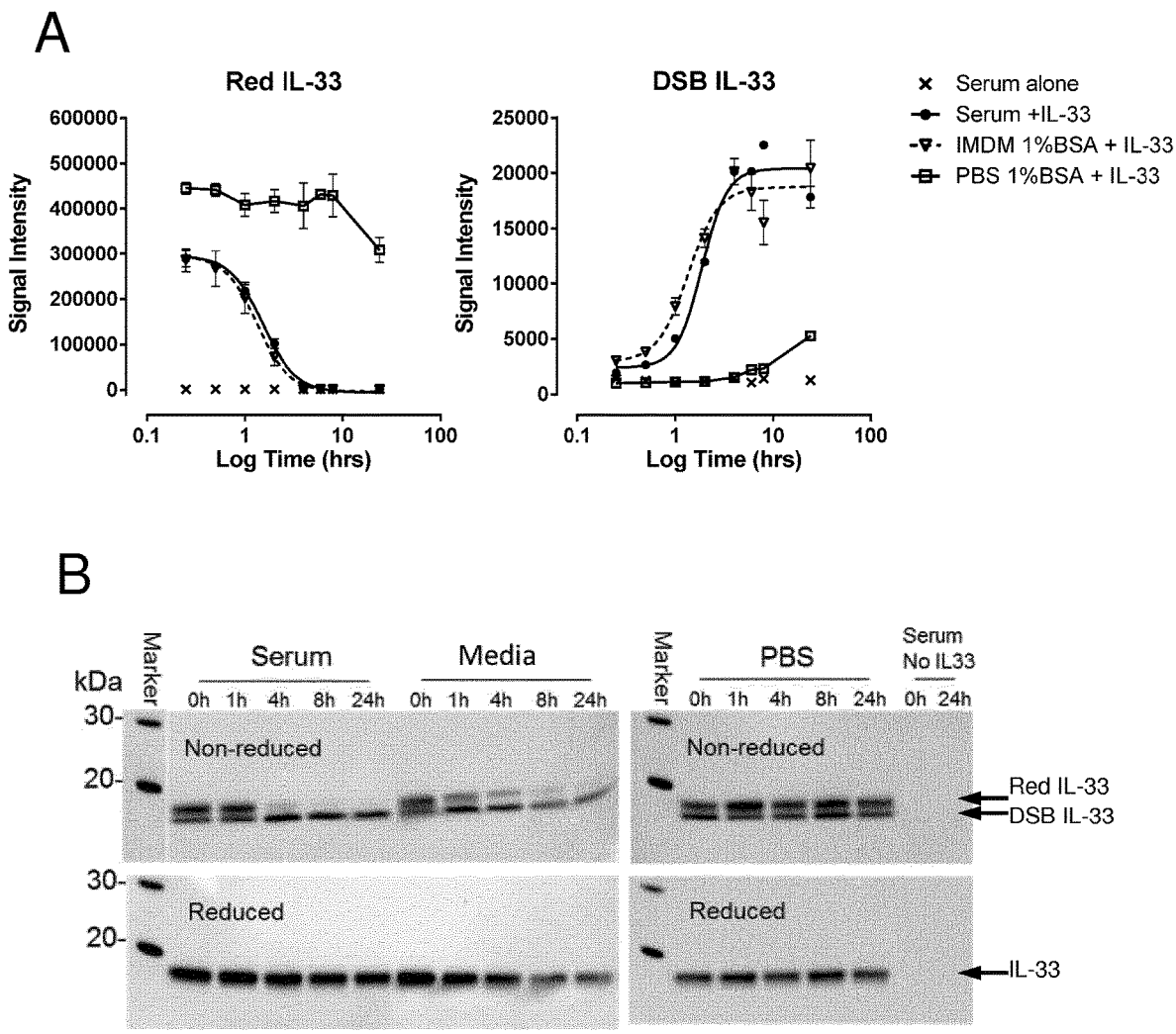
FIG. 27 Shows a time course of human IL-33 incubated in cell culture media (IMDM) or human serum. redIL-33 or DSB IL-33 forms are measured by ELISA (FIG. 27A) or Western blot (FIG. 27B).

FIG. 27 shows a time course of human IL-33 incubated in IMDM or human serum. FIG. 27A: IL-33 ELISAs (IL33004/IL330425-biotin and human R&D systems MSD assays) were used to detect reduced and disulphide bonded IL-33 respectively. FIG. 27B: Western blot analysis was used to detect reduced and disulphide bonded IL-33 forms. The conversion to the disulphide bonded form of IL-33 occurred rapidly with a 50% conversion in 1-2 hours. The disappearance of reduced IL-33 correlated well with the appearance of oxidised IL-33 in both ELISA and Western blot analysis.

Generation of a Humanized IL-33 Transgenic Mouse

To study the behaviour and lifecycle of endogenous IL-33, we used a transgenic mouse with the gene for mouse IL-33 replaced with the human IL-33 gene. A humanized IL-33 transgenic mouse were generated as described below. Briefly, mouse genomic fragments (obtained from the C57BL/6J RPCIB-731 BAC library), a human genomic fragment (obtained from the human RPCIB-753 BAC library) and selected features (such as recombination sites and selection markers) were combined to make the targeting vector (data not shown).

The targeting vector was linearized with BstBI and electroporated into TaconicArtemis Balb/cJ ES cell line (Balb/c.2) and ES cell clones were selected with Puromycin (positive selection) and Gancyclovir (negative selection). The resultant puromycin-resistant ES cell clones were then screened by a combination of PCR and Southern analyses to identify correctly targeted ES clones. These were expanded and frozen in liquid nitrogen.

After administration of hormones, superovulated C57BL/6 females were mated with C57BL/6 males. Blastocysts were isolated from the uterus at dpc 3.5. For microinjection, blastocysts were placed in a drop of DMEM with 15% FCS under mineral oil. A flat tip, piezo actuated microinjection-pipette with an internal diameter of 12-15 micrometer was used to inject 10-15 targeted BALB/c ES cells into each blastocyst. After recovery, 8 injected blastocysts were transferred to each uterine horn of 2.5 days post coitum, pseudopregnant NMRI females. Chimerism was measured in chimeras (G0) by coat colour contribution of ES cells to the C57BL/6 host (white/black). Highly chimeric mice were bred to strain BALB/cJBomTac females mutant for the presence of a Flp recombinase gene (Flp-Deleter strain). Germline transmission by coat colour was identified by the presence of white, strain BALB/c, offspring (G1). Actual germline transmission was confirmed by PCR genotyping using primers specific for the targeted allele (data not shown).

Existence of Redox Forms of IL-33 In Vivo.

Models of *Alternaria alternata* induced airway inflammation in mice have been previously described (Kouzaki et al. *J. Immunol.* 2011, 186: 4375-4387; Bartemes et al *J Immunol*, 2012, 188: 1503-1513). Male or female wildtype or humanized IL-33 mice (6-10 weeks) were anaesthetized briefly with isofluorane and administered either 25 μg of *Alternaria alternata* (ALT) extract (Greer, Lenoir, N.C.) or vehicle intranasally in a total volume of 50 μl. At multiple timepoints after ALT challenge, mice were terminally anaesthetised with pentobarbital sodium prior to bronchoalveolar lavage (BAL). Bronchoalveolar lavage fluid (BALF) was collected by lavage (0.3 ml, 0.3 ml & 0.4 ml) via tracheal cannula. BALF was centrifuged and supernatant was analysed for presence of redox forms of IL-33 using assays described above. All work was carried out to UK Home Office ethical and husbandry standards under the authority of an appropriate project license.

FIG. 28 shows analysis of BALF from humanized IL-33 mice collected at varying timepoints following ALT intranasal challenge, using a combination of multiple ELISA assays. (A) Millipore, (B) R&D systems and (C) IL330425/sST2-biotin assays were used to measure IL-33 in the presence or absence of sST2 (left hand graphs). Signals in the presence of sST2 (signal from the reduced IL-33 fraction eliminated) were compared with a disulphide bonded IL-33 standard to quantify the levels of disulphide bonded IL-33. The reduced IL-33 signal was calculated as the difference in signal between IL-33 measurements in the presence and absence of ST2, quantified against a reduced IL-33 standard. Estimations for reduced IL-33 are shown on the right hand graphs. All assays show that the released IL-33 was predominantly in its reduced form with a maximum between 5 and 30 min, followed by a rapid decline becoming undetectable by 120 minutes. Conversely, IL-33-DSB gradually increased from time 0, peaking at 30-120 minutes and disappearing by 24 hours. These data are consistent with a model where IL-33 is released in reduced form and then rapidly oxidised in vivo to IL33-DSB.

FIG. 29 shows analysis of BALF from wild type BALB/c mice collected at varying timepoints following ALT intranasal challenge. FIG. 29A Mouse IL-33 ELISA (R&D systems) was used to measure IL-33 in the presence or absence of sST2 (media-treated mouse IL-33 used as standard curve). FIG. 29B Signals in the presence of sST2 (signal from the reduced IL-33 fraction eliminated) were compared with a media-treated mouse IL-33 standard to quantify the levels of oxidised IL-33. The reduced IL-33 signal was calculated as the difference in signal between IL-33 measurements in the presence and absence of ST2, quantified against a reduced mouse IL-33 standard. Data show that the released IL-33 was predominantly in its reduced form peaking at 15 minutes, followed by a rapid decline becoming undetectable by 120 minutes. Conversely, IL-33-DSB gradually increased from time 0, peaking at 45-60 minutes and disappearing by 24 hours. These data are consistent with a model where IL-33 is released in reduced form and then rapidly oxidised in vivo to IL33-DSB.

Example 5 Characterisation of Anti-IL-33 Antibodies

H338L293 Causes a Conformational Change

Monoclonal antibody H338L293 (SEQ ID NOs 182 and 187), the generation of which is described in examples 2 and 3, is an allosteric modulator of IL-33. IL-33 can significantly change conformation into a disulfide bonded form (as described in Example 4). The following experiments demonstrate that H338L293 mAb appears to destabilize the IL-33 molecule, promoting its unfolding and accelerating conversion to the disulfide bonded form. Reagents and protein modifications used herein were as described in previous examples.

Sypro Orange Assay

Sypro orange binds nonspecifically to hydrophobic surfaces, and water strongly quenches the fluorescence of Sypro Orange. When a protein unfolds, the exposed hydrophobic surfaces bind the dye, resulting in an increase in fluorescence. 5 uM of antibody was incubated with 20 uM redIL-33 at 25° C. in the presence of 8×SYPRO orange dye diluted from a 5000× stock (Life technologies S-6650) in 1×DPBS. Fluorescence (excitation 490 nm and emission 575 nm) was measured every minute using a Chromo4 Real Time detector (Bio-rad). We observed that incubating redIL-33 with H338L293 antibody, and not redIL-33 or antibody alone, there was an increase in the fluorescence signal indicative of protein unfolding.

Figure 30:
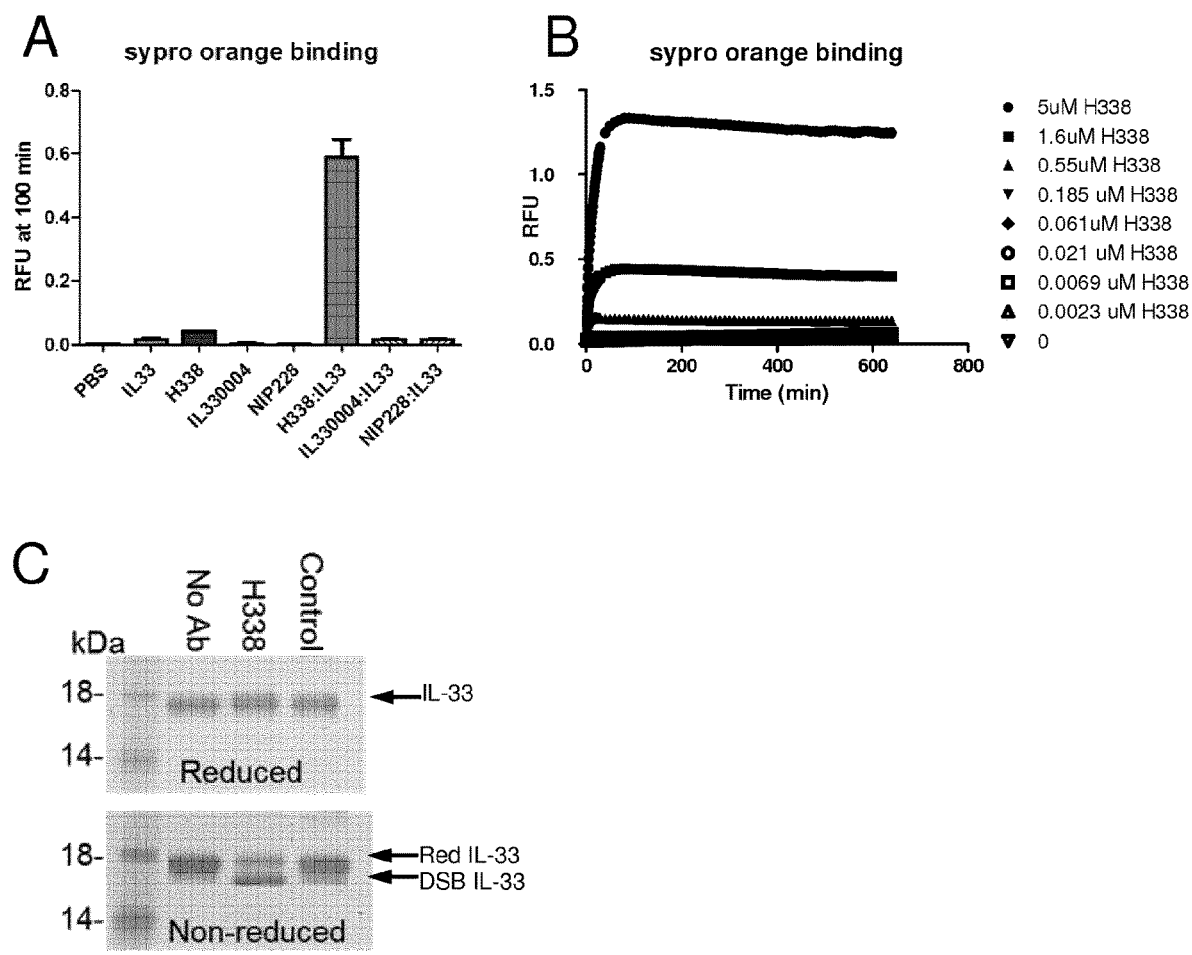
FIG. 30A Shows relative fluorescence units at 100 minutes following incubation of 5 uM antibody with 20 uM IL33 at 25° C. in the presence of 8xSYPRO orange dye. In the presence of IL-33 H338L293, but not IL330004 or the control mAb, the increased fluorescent signal is indicative of protein unfolding.
FIG. 30B Shows relative fluorescence units over time following incubation of varying concentrations of H338L293 with 20 uM IL33 at 25° C. in the presence of 8xSYPRO orange dye. Fluorescent signal increased with increasing antibody concentration FIG. 30C Shows SDS-PAGE analysis of IL-33. Preincubation of IL-33 with H338L293, but not control mAb or no mAb, increased the presence of the faster migrating, disulfide bonded form of IL-33 under non-reducing conditions.

FIG. 30A shows relative fluorescence units at 100 minutes following incubation of 5 uM antibody with 20 uM redIL33 at 25° C. in the presence of 8×SYPRO orange dye. In the presence of redIL-33 H338L293, but not IL330004 or the control mAb, increased the fluorescent signal indicative of protein unfolding.

FIG. 30B shows relative fluorescence units over time following incubation of varying concentrations of H338L293 with 20 uM redIL33 at 25° C. in the presence of 8×SYPRO orange dye. Fluorescent signal increased with increasing antibody concentration.

SDS-PAGE Electrophoresis

To determine if H338L293 could influence disulfide bonding of IL-33, IL-33 was monitored in the presence of H338L293 by comparing reduced and non-reduced SDS-PAGE analysis. 100 ug/ml recombinant human IL-33$^{112\text{-}270}$ (BK349) was incubated in PBS/0.1% BSA containing either 1.5 mg/ml H338L293 mAb, NIP228 mAb or without addition of a mAb. Samples were incubated for 20 h at 37 C in a standard tissue culture incubator. Samples containing 1 ug of IL-33 were analysed by SDS-PAGE on Novex 12% Bis-Tris mini NuPAGE gels (Invitrogen) under reducing and non-reducing conditions. Following SDS-PAGE gels were washed 3×5 min in ddH20, incubated in EzBlue (Sigma G1041, a coomassie brilliant blue G-250 based protein stain) for 1 h, and destained in ddH20 until background of gel was clear. All gel staining steps performed at room temperature on a rocking platform. Gels were visualised using Epsom digital scanner.

FIG. 30C shows SDS-PAGE analysis of IL-33. Preincubation of IL-33 with H338L293, but not control mAb or no mAb, increased the presence of the faster migrating, disulfide bonded form of IL-33 under non-reducing conditions.

Inhibition of NFkB Signaling in Huvec by IgG

NFkB signaling in human umbilical vein endothelial cells in response to IL-33 was assessed by nuclear translocation of the p65/RelA NFkB subunit, detected by immunofluorecence staining as described in Example 1. Cells were stimulated with varying IL-33 concentrations in the presence of multiple concentrations of test antibody H338L293 for either 30 minutes or 6 hours.

Figure 31:
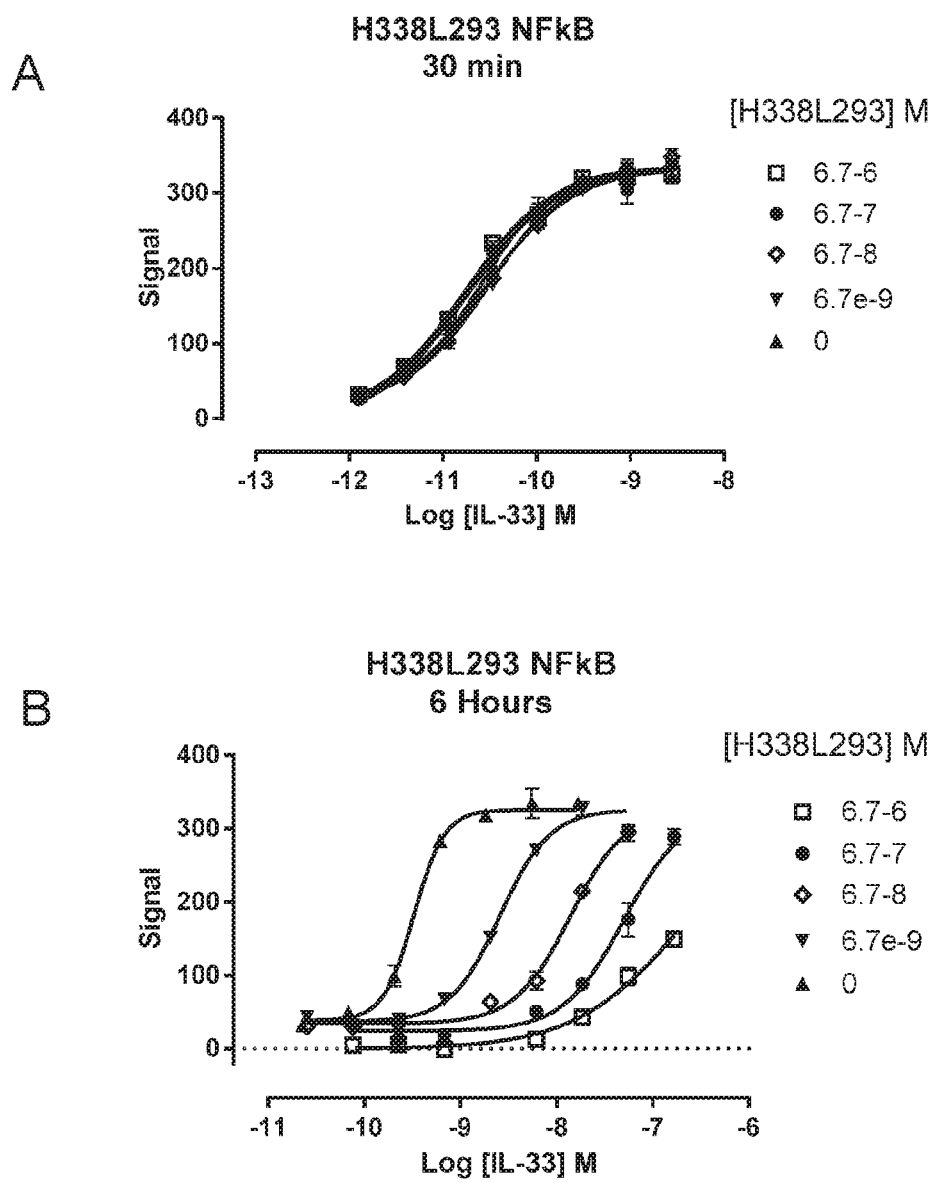
FIG. 31 Shows a timecourse of neutralization of IL-33 stimulated NFkB signaling in HUVECs with mAb H338L293.

FIG. 31 shows the effect of H338L293 on IL-33 stimulated NFkB translocation on HUVECs. These results show that, as seen previously, H338L293 did not inhibit nuclear translocation of p65/RelA NFkB in IL-33-stimulated Huvecs 30 minutes following stimulation. However, after 6 hours, inhibition is seen. The results are consistent with failure of H338L293 to inhibit IL-33 binding to ST2 directly but ability to convert IL-33 to a non-ST2 binding form within hours.

Inhibition of IL-33 Binding to ST2 by Purified IgG

The ability of H338L293 to inhibit the binding of FLAG®His tagged IL-33 to the ST2 receptor was assessed in a biochemical HTRF® (Homogeneous Time-Resolved Fluorescence, Cisbio International) competition assay as described in Example 1. Two conditions were tested. Firstly the antibody and IL-33 were added simultaneously to the assay exactly as in Example 1. As previously, purified IgG preparations were not able to inhibit the IL-33:ST2 interaction at concentrations tested. Secondly, H338L293 was preincubated with the IL-33FLAG®His for 18 hours prior to addition to the assay. In this case concentration-dependent inhibition of IL-33:ST2 binding was observed. Taken together these data are consistent with H338L293 converting IL-33 to a non-ST2 binding form over time.

FIG. 32 shows the inhibition of the FRET signal, produced by human IL-33 binding to human ST2 with increasing concentrations of H338L293, wherein the x-axis is the concentration of antibody in molar concentration and the y-axis is percent specific binding. These results show that H338L293 inhibits IL-33 binding to ST2 only after prolonged pre-incubation with the ligand.

Epitope Mapping

Epitope mapping of H338L293 IgG was attempted in order to clarify the mode of IL-33 binding to this IgG. Size Exclusion Chromatography (SEC) experiments were performed in order to observe the formation of IL-33:IgG complexes. A BioSep-SES-S 2000 column (300×7.4 mm, s/n 550331-4) was equilibrated with Dulbecco's PBS at 0.5 mL min$^{-1}$ on an Agilent HP1100 HPLC. Peaks were detected using the 280 nm signal from a Diode Array Detector (DAD). These studies confirmed that antibody-antigen complex formation was fairly slow taking at least several hours. Once sufficient time for full complex formation had been allowed, trypsin was added to pre-formed IL-33:IgG complexes, followed by SEC analysis. 36 min trypsin digest led to an increase in the retention time of the main peak to 14.1 minutes (intermediate between the untreated complex peak elution time (13.6 min) and the intact H338L292 IgG elution (14.4 min)). Mass spectrometry methods were then used to identify the minimal H338L293 IgG epitope. The Shimadzu MALDI-TOF MS observed masses from captured 14.1 min peak were 3,209 and 4,485.3 Da. ABI4800 MALDI-TOF MS observed masses were 3,208.9 Da peak at high intensity with a secondary 4,486.4 Da peak also present. The observed precursor ion mass of 3206-3208 Da and ABI4800 MS/MS fragmentation analysis of the 3,206 Da precursor ions matched the predicted tryptic IL-33 fragment MLMVTL-SPTKDFWLHANNKEHSVELHK. This lies within the overall primary sequence of r Human IL-33-Flag His10 (SEQ ID NO. 627) as shown below: MSITGISPITEY-LASLSTYNDQSITFALEDESYEIYVEDLKKDEKKDK-VLLSYYESQHPSNE SGDGVDGK MLMVTLSPTKDFWLHANNKEHSVELHKCEKPLPDQ AFFVLHNMHSNCVS FECKTDPGVFIGVKDNHLA-LIKVDSSENLCTENILFKLSETNPAFLYKV-VGAADYKDDDD KAAHHHHHHHHHH The identified peptide together with a truncate (LSPTKD-FWLHANNKEHSVELHK) and scrambled variants of both, were then chemically synthesised and used in confirmatory T100 Biacore (GE Healthcare) binding studies. Protein G' (Sigma Aldrich, P4689) was covalently coupled to the surface of a CM5 sensor chip (GE Healthcare) using standard amine coupling reagents according to manufacturer's instructions. The protein G' surface was used to capture H338L293 or ST2-Fc via the Fc domain to provide a surface density of approximately 290RU per cycle. IL33 peptides prepared in HBS-EP+ buffer, at a range of concentrations were passed over the sensor chip surface. The surface was regenerated using two 10 mM Glycine washes of pH 1.7 and pH 1.5 between each injection of antibody. The resulting sensorgrams were evaluated using Biacore T100 evaluation software 2.0.3 (GE Healthcare) and fitted to a 1:1 Langmuir binding model, to provide relative binding data.

The full length synthetic epitope peptide bound strongly to H338L293 IgG but not the IL-33 receptor (ST2-Fc). Both the full length and the truncated synthetic peptide bound strongly to H338L293 but the scrambled full length and truncated versions did not. This is strong evidence that IL-33 fragment identified by peptide excision is not an artefact and represents the core of the H338L293 epitope. 0.625-20 nM of the truncated peptide was flowed over H338L293 IgG to estimate affinity. Good quality 1:1 fits were obtained giving a $K_D$ value of 2.36 nM.

Figure 33A:
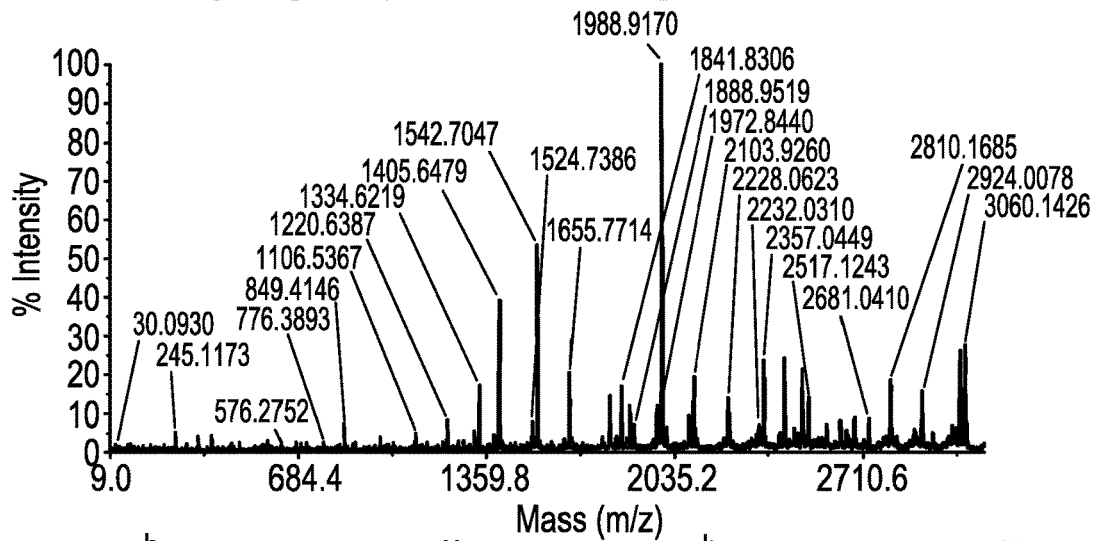
FIG. 33A shows SEC analysis of IL33:IgG complexes with H338L293 pre and post digestion with trypsin.
Figure 33B:
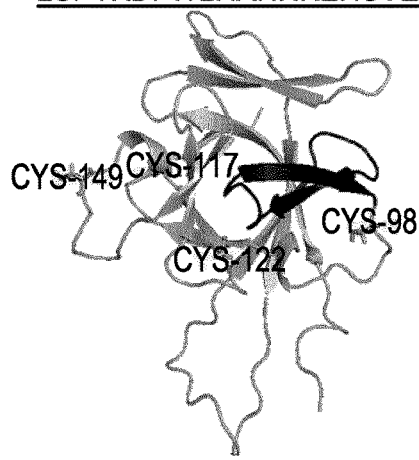
FIG. 33B shows the truncate peptide that was determined to bind strongly to H338L293 coloured black within the IL-33 structure described by Lingel et al 2009.

FIG. 33 shows epitope mapping of H338L293. The top panel shows SEC analysis of IL33:IgG complexes with H338L293 pre and post digestion with trypsin. The lower panel shows the truncate peptide that was determined to bind strongly to H338L293 coloured black within the IL-33 structure described by Lingel et al 2009.

Example 6 Cys→Ser IL-33 Mutants

To understand the role of the four free cysteines of human IL-33 in its conversion to the disulphide bonded form, we generated a full panel of all possible Cys-to-Ser mutants. Most of these mutant IL-33 molecules showed similar initial activity through ST2 compared with wild type IL-33. Following incubation in media mutants did not display faster gel migration, consistent with lack of ability to form 2 disulfide bonds. However, loss of potency after media treatment varied between mutants.

Generation of IL-33 Cysteine to Serine Mutant Panel cDNA molecules encoding the mature component of Human IL-33 (112-270); accession number (Swiss-Prot) O95760, and a series of variants with 1, 2, 3 or 4 cysteine residues mutated to serine in all combinations (15 in total) were synthesized by primer extension PCR and cloned into pJexpress404 (DNA 2.0). The wild-type (WT) and mutant IL-33 coding sequences were modified to contain a 10× his, Avitag, and Factor-Xa protease cleavage site (MHHHHH-HHHHHAAGLNDIFEAQKIEWHEAAIEGR) at the N-terminus of the proteins.

DNA encoding the IL-33 mutants was used to transform E. coli BL21 Gold cells. Transformed cells were cultured at 37° C. until they reached an OD600 nm of 0.3 to 0.5. Cultures were then grown at 18° C. until they reached an OD600 nm of 0.6 to 0.8, when protein expression was induced by addition of 100 mM IPTG. Cultures were continued at 18° C. for a further 20 hours before cells were harvested by centrifugation and stored at −80° C.

Cells were resuspended in 50 mM Sodium phosphate, pH 8.0, 300 mM NaCl, 20 mM Imidazole, 5 mM BetaMercaptoethanol containing complete protease inhibitor tablets (Roche, 11697498001), 2.5 u/ml Benzonase nuclease (merck Millipore, 70746-3) and 1 mg/ml recombinant lysozyme. Resuspended cells were lysed using a Constant Systems cell disruptor at 25 kpsi and clarified by centrifugation at 75,000×g for 2 hours at 4° C. IL33 was purified from the supernatant by Nickel affinity chromatography in 50 mM Sodium phosphate, pH 8.0, 300 mM NaCl, 20 mM Imidazole, 5 mM BetaMercaptoethanol, eluting in 50 mM Sodium phosphate, pH 8.0, 300 mM NaCl, 250 mM Imidazole, 5 mM BetaMercaptoethanol. IL33 was further purified by size exclusion chromatography using a Superdex 75 10/300 GL column (GE Healthcare) in Phosphate Buffered Saline pH 7.4. Peak fractions were analysed by SDS PAGE. Fractions containing pure IL33 were pooled and the concentration measured by Nanodrop A280 measurement. Final samples were analysed by SDS PAGE and intact mass spectrometry. Protein was snap frozen in liquid nitrogen.

TABLE 17

IL-33 mutant sequences

| Mutant | Position 208 | Position 227 | Position 232 | Position 259 | AA.112-270 |
|---|---|---|---|---|---|
| IL33-01 | C | C | C | C | SEQ ID NO: 632 |
| IL33-02 | S | C | C | C | SEQ ID NO: 634 |
| IL33-03 | C | S | C | C | SEQ ID NO: 635 |
| IL33-04 | C | C | S | C | SEQ ID NO: 636 |
| IL33-05 | C | C | C | S | SEQ ID NO: 637 |
| IL33-06 | S | S | C | C | SEQ ID NO: 638 |
| IL33-07 | C | C | S | S | SEQ ID NO: 639 |
| IL33-08 | S | C | S | C | SEQ ID NO: 640 |
| IL33-09 | C | S | C | S | SEQ ID NO: 641 |
| IL33-10 | C | S | S | C | SEQ ID NO: 642 |
| IL33-11 | S | C | C | S | SEQ ID NO: 643 |
| IL33-12 | S | S | S | C | SEQ ID NO: 644 |
| IL33-13 | S | S | C | S | SEQ ID NO: 645 |
| IL33-14 | S | C | S | S | SEQ ID NO: 646 |
| IL33-15 | C | S | S | S | SEQ ID NO: 647 |
| IL33-16 | S | S | S | S | SEQ ID NO: 648 |

Activity of IL-33 Cys→Ser Mutants

To check protein integrity, activity of untreated wild type IL-33 (IL33-01) and the IL-33 mutants were measured in a ST2-dependent signaling assay. NFκB signaling in Human umbilical vein endothelial cells (Huvecs) in response to IL-33 was assessed by nuclear translocation of the p65/RelA NFkB subunit detected by immunofluorecence staining as described in Example 1. To investigate loss of activity after cell culture media treatment, IL-33 proteins 01-16 were incubated overnight in Iscoves Modified Dulbeccos Medium (IMDM) and assessed in comparison with the untreated proteins.

TABLE 18

Activity of IL-33 mutants in HUVEC NFkB translocation assay

| Name | Sequence | IC50 (nM) Untreated | Loss of activity after IMDM treatment | SEQUENCE |
|---|---|---|---|---|
| IL33-01 (WT) | CCCC | 0.13 | +++ | SEQ ID NO: 632 |
| IL33-02 | SCCC | 0.19 | ++ | SEQ ID NO: 634 |
| IL33-03 | CSCC | 0.16 | ++ | SEQ ID NO: 635 |
| IL33-04 | CCSC | 0.17 | + | SEQ ID NO: 636 |
| IL33-05 | CCCS | 0.10 | ++ | SEQ ID NO: 637 |
| IL33-06 | SSCC | 0.28 | + | SEQ ID NO: 638 |
| IL33-07 | CCSS | 0.22 | + | SEQ ID NO: 639 |
| IL33-08 | SCSC | 0.21 | − | SEQ ID NO: 640 |
| IL33-09 | CSCS | 0.20 | ++ | SEQ ID NO: 641 |
| IL33-10 | CSSC | 0.61 | + | SEQ ID NO: 642 |
| IL33-11 | SCCS | 0.49 | + | SEQ ID NO: 643 |
| IL33-12 | SSSC | 0.39 | − | SEQ ID NO: 644 |
| IL33-13 | SSCS | 0.08 | + | SEQ ID NO: 645 |
| IL33-14 | SCSS | 0.14 | − | SEQ ID NO: 646 |
| IL33-15 | CSSS | 0.12 | − | SEQ ID NO: 647 |
| IL33-16 | SSSS | 0.17 | − | SEQ ID NO: 648 |

Figure 34:
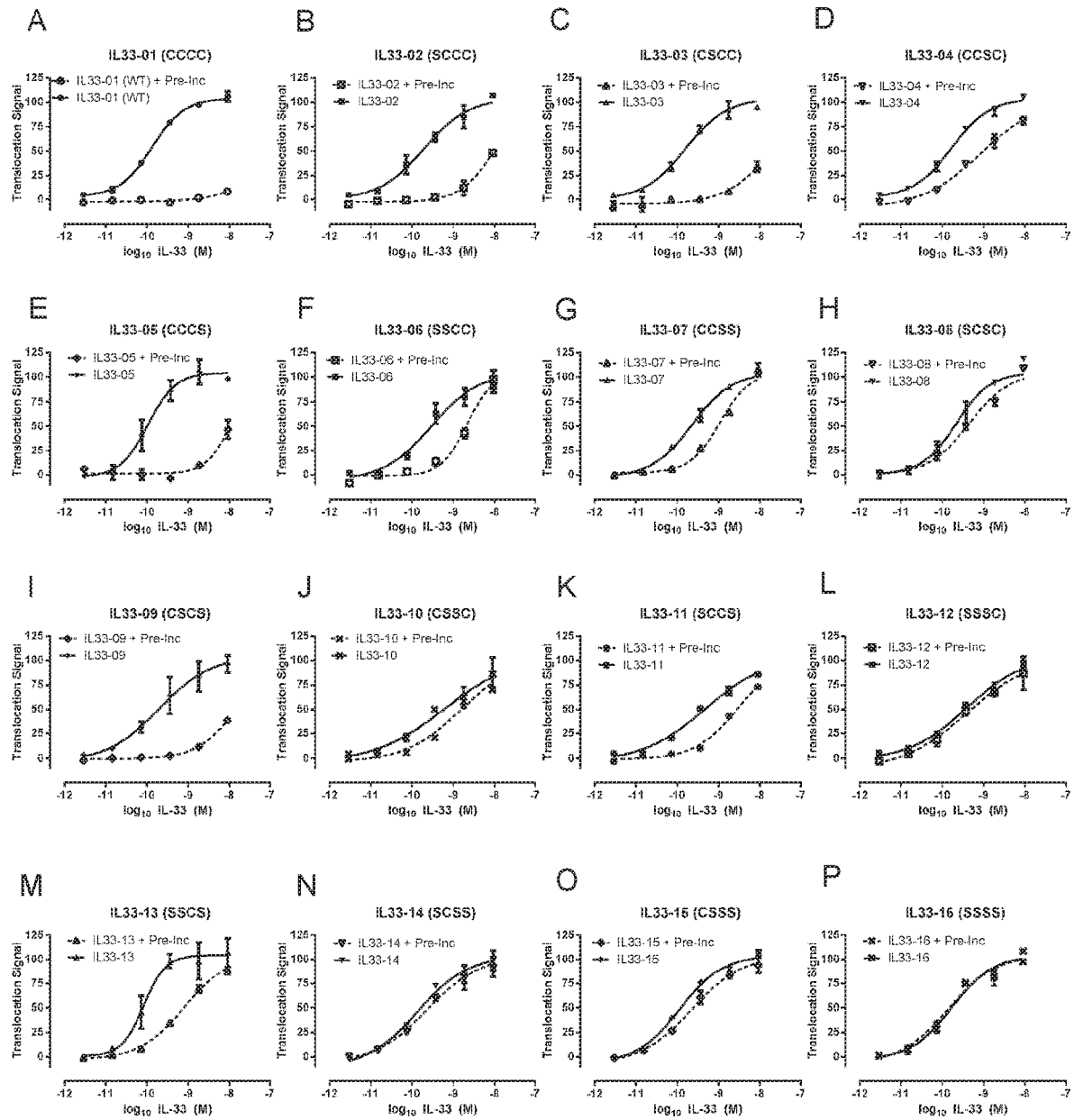
FIG. 34 Shows NFkB signaling activity of wild type IL-33 (IL33-01—FIG. 34A) and IL-33 cysteine to serine mutants (IL33-02—FIG. 34B, IL33-03—FIG. 34C, IL33-04—FIG. 34D, IL33-05—FIG. 34E, IL33-06—FIG. 34F, IL33-07—FIG. 34G, IL33-08—FIG. 34H, IL33-09—FIG. 34I, IL33-10—FIG. 34J, IL33-11—FIG. 34K, IL33-12—FIG. 34L, IL33-13—FIG. 34M, IL33-14—FIG. 34N, IL33-15—FIG. 34O, IL33-16—FIG. 34P) before and after treatment for 18 hours with IMDM cell culture media.

FIG. 34 shows activity of the IL-33 mutants before and after treatment for 18 hours with IMDM. Wild type IL-33 (IL33-01) that has been pre-treated with culture media completely lost detectable activity. All mutants displayed less potency loss than WT. Some mutants were completely protected from potency loss.

Human Mast Cell Cytokine Release

To see if mutants were more potent at stimulating downstream responses at longer timepoints in vitro, an overnight mast cell IL-6 production assay was used to measure activity of human IL-33 wild type and selected mutants. Assay methods are described in Example 2. Data are exemplified by IL33-11.

FIG. 35A shows that IL33-11 has greater potency than IL-33 WT at stimulating human mast cell IL-6 production. IL33-01 (WT) and IL33-11 without prior treatment were used to stimulate IL-6 production from human cord blood derived mast cells at varying concentrations, wherein the x-axis is the concentration of IL-33 in molar concentration and the y-axis is the level of IL-6 detected in the supernatants after 18 hours.

In Vivo Potency of Mutant IL-33

Female BALB/c mice (6-8 weeks) were anaesthetized briefly with isofluorane and administered either 0.1-10 ug of wild type human IL-33 (IL33-01, SEQ ID NO: 632), IL33-11 (SEQ ID NO: 643) or vehicle intranasally in a total volume of 50 μl. 24 hours after challenge, mice were terminally anaesthetised with pentobarbital sodium prior to bronchoalveolar lavage (BAL). BALF was collected and analysed as described in Example 4.

FIG. 35B shows that intranasal administration of IL33-11 double mutant required only a tenth as much protein for an equivalent ST2-dependent IL-5 response compared to native IL-33. This is consistent with prolonged activity of the mutant in contrast to the more rapid inactivation of the wild type IL-33 in the mouse lung environment.

NMR Analysis of IL33-11

To investigate conformational differences between IL33-11 and wild type human IL-33 protein (IL33-01), NMR analysis was performed.

Production of $^{15}$N-IL-33 Proteins

DNA encoding wild type IL-33 with an N-terminal 6His tag and TEV protease cleavage site (SEQ ID. 633) was used to transform E. coli BL21 Gold cells. Transformed cells were cultured at 37° C. in M9 minimal media supplemented with 5 g/L of $^{15}$N-IsoGro™ powder until they reached an OD600 nm of 0.6 to 0.8, when protein expression was induced by addition of 100 mM IPTG. Cultures were continued at 18° C. for a further 20 hours before cells were harvested by centrifugation and stored at −80° C. Cells were resuspended in 50 mM Sodium phosphate, pH 8.0, 300 mM NaCl, 20 mM Imidazole, 5 mM BetaMercaptoethanol containing Complete protease inhibitor tablets (Roche, 11697498001), 2.5 U/ml Benzonase nuclease (merck Millipore, 70746-3) and 1 mg/ml recombinant lysozyme. Resuspended cells were lysed using a Constant Systems cell disruptor at 25 kpsi and clarified by centrifugation at 75,000×g for 2 hours at 4° C. IL-33 was purified from the supernatant by Nickel affinity chromatography in 50 mM Sodium phosphate, pH 8.0, 300 mM NaCl, 20 mM Imidazole, 5 mM BetaMercaptoethanol, eluting in 50 mM Sodium phosphate, pH 8.0, 300 mM NaCl, 250 mM Imidazole, 5 mM BetaMercaptoethanol. Eluted protein was incubated with TEV protease and dialysed into 50 mM Sodium phosphate, pH 8.0, 300 mM NaCl, 20 mM Imidazole, 5 mM BetaMercaptoethanol at 4° C. De-tagged protein was separated from uncleaved IL-33 by Nickel affinity chromatography in 50 mM Sodium phosphate, pH 8.0, 300 mM NaCl, 20 mM Imidazole, 5 mM BetaMercaptoethanol. IL-33 was further purified by size exclusion chromatography using a HiLoad 16/60 Superdex 75 column (GE healthcare) in 20 mM Sodium phosphate pH 6.5, 100 mM NaCl, 5 mM BetaMercaptoethanol, using an AKTAxpress FPLC system (GE healthcare). Peak fractions were analysed by SDS PAGE. Fractions containing pure IL-33 were pooled and the concentration measured by Nanodrop A280 measurement. Protein was concentrated using an Amicon 10,000 molecular weight cut-off spin concentrator to a final concentration of 1.8 mg/ml (100 μM) for NMR analysis.

NMR Analysis

NMR spectra were recorded at 298 K on a Bruker Avance 600 MHz spectrometer running Topspin 2.3 equipped with a 5 mm TCI Cryoprobe with Z-axis gradients. The $^{15}$N-labelled IL33 WT sample was prepared as described with the addition of 5% deuterium oxide to allow sample locking. The exemplified $^{1}$H-$^{15}$N correlation spectra were acquired employing the sofast HMQC pulse sequence (Schanda, P; Brutscher, B; *Very fast two-dimensional NMR spectroscopy for real-time investigation of dynamic events in proteins on the time scale of seconds*, J. Am. Chem. Soc. (2005) 127, 8014-5) with (F2×F1) 1024×64 complex points (in states-TPPI mode), 9615×1460 Hz sweep width, 53.4 ms×43.8 ms acquisition times.

Figure 36:
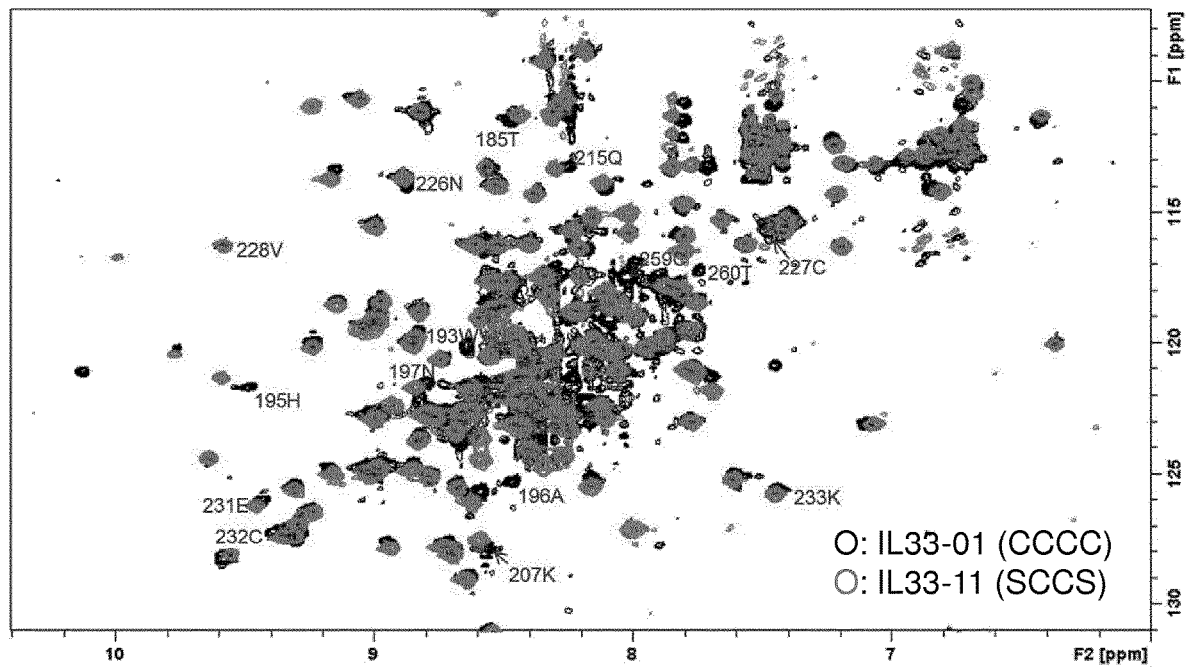
FIG. 36 Shows overlay of the $^1$H-$^{15}$N HMQC spectra for 0.1 mM $^{15}$N-labeled IL33-01 and IL33-11 plotted in black and red, respectively. Assignment for relevant residues are indicated. Data show peak shifts around C208 and C259 as expected. However, there are more more peak shifts than expected from T185 to A196 which might indicate a conformation change.

FIG. 36 shows overlay of the $^{1}$H-$^{15}$N HMQC spectra for 0.1 mM $^{15}$N-labeled IL33-01 and IL33-11 plotted in black and red, respectively. Assignment for relevant residues are indicated. Data show peak shifts around C208 and C259 as expected. However, there are more peak shifts than expected from T185 to A196 which might indicate a conformation change.

Example 7 Isolation and Identification of Anti-IL-33 Antibodies Using IL33-11

Cys→Ser mutant IL-33 proteins stabilise IL-33 in its reduced form and have different conformations to wild type (as described in Example 6). Mutant proteins may provide availability of different antibody epitopes or greater longevity/stability of epitopes and may therefore be useful for isolating neutralizing IL-33 antibodies, in particular to the reduced form of IL-33. This example uses oxidation-resistant mutant IL33-11 protein to isolate IL-33 antibodies by phage display.

Recombinant Proteins

N-terminal tagged His10/Avitag IL33-01 (WT, SEQ ID NO. 632), N-terminal tagged His10/Avitag IL33-11 (C208S, C259S, SEQ ID 643) and N-terminal tagged His10/Avitag cyno IL-33 (SEQ ID 649), were generated by transforming E. coli BL21(DE3) cells. Transformed cells were cultured in autoinduction media (Overnight Express™ Autoinduction System 1, Merck Millipore, 71300-4) at 37° C. for 18 hours before cells were harvested by centrifugation and stored at −20° C. Cells were resuspended in BugBuster (Merck Millipore, 70921-5), containing complete protease inhibitor cocktail tablets (Roche, 11697498001), 2.5 u/ml Benzonase nuclease (merck Millipore, 70746-3) and 1 mg/ml recombinant lysozyme. Cell lysate was clarified by centrifugation at 75,000×g for 2 hours at 4° C. IL-33 proteins were purified from the supernatant by Nickel affinity chromatography in 50 mM Sodium phosphate, pH 8.0, 300 mM NaCl, 20 mM Imidazole, eluting in 50 mM Sodium phosphate, pH 8.0, 300 mM NaCl, 250 mM Imidazole. IL-33 was further purified by size exclusion chromatography using a Superdex 75 10/300 GL column in Phosphate Buffered Saline pH 7.4. Peak fractions were analysed by SDS PAGE. Fractions containing pure IL-33 were pooled and the concentration measured by Nanodrop A280 measurement. Final samples were analysed by SDS PAGE.

The human ST2 vector described in Example 1 was modified to contain human ST2 ECD with a C-terminal Flag-His tag (SEQ ID NO 650).

TABLE 19

Reagents

| Reagent | Supplier | Catalogue Number/ Designation | SEQ |
|---|---|---|---|
| His10/Avi Human IL33-01 | In house | PS-937 | SEQ ID NO. 632 |
| His10/Avi Human IL33-11 | In house | PS-938 | SEQ ID NO. 643 |

TABLE 19-continued

| Reagent | Supplier | Catalogue Number/ Designation | SEQ |
|---|---|---|---|
| His10/Avi Cyno IL-33 | In House | CCH 3$^{rd}$ Apr. 2014 | SEQ ID NO. 649 |
| IL-4Rα Flag ®His | In house | 020629080 | |
| Bovine insulin - biotin | Sigma | I2258 | |
| Human ST2 Flag His | In house | BK282 | SEQ ID NO. 650 |
| Human ST2.Fc | R&D Systems | | |

Protein Modifications

Proteins containing the Avitag sequence motif (GLN-DIFEAQKIEWHE) were biotinylated using the biotin ligase (BirA) enzyme (Avidty, Bulk BirA) following the manufacturer's protocol. All IgGs and modified proteins without Avitag used herein were biotinylated via free amines using EZ link Sulfo-NHS-LC-Biotin (Thermo/Pierce, 21335) as described in Example 1.

Selections

Selections were performed essentially as described in Example 1 but using the IL33-11 C208S, C259S mutant protein. In brief, the scFv-phage particles were incubated with biotinylated recombinant IL-33-11 in solution (biotinylated via Avi tag). Particles were incubated with 100 nM biotinylated recombinant IL33-11 for 2 hours. ScFv bound to antigen were then captured on streptavidin-coated paramagnetic beads (Dynabeads®, M-280) following manufacturer's recommendations. Unbound phage was washed away in a series of wash cycles using PBS-Tween. The phage particles retained on the antigen were eluted, infected into bacteria and rescued for the next round of selection. Two more rounds of selections were carried out in the presence of decreasing concentrations of biotinylated IL33-11 (50 nM and 25 nM).

Inhibition of IL-33 Binding to ST2 by Unpurified scFv

A representative number of individual clones from the selection outputs after two or three rounds of selection described above were grown up in 96-well plates. ScFv were expressed in the bacterial periplasm (Kipriyanov, et al. *J Immunol Methods* 200(1-2): 69-77 (1997)) and screened for their inhibitory activity in a homogeneous FRET (fluorescence resonance energy transfer) HTRF® (Homogeneous Time-Resolved Fluorescence, Cisbio International) based IL-33:ST2-binding assay. Essentially methods were similar to those described in Example 1. In this assay, samples competed with FLAG®His-tagged human ST2 for binding to biotinylated human IL33-01 (IL33-01, SEQ ID No. 632) (wild type) or biotinylated human IL33-11 (IL33-11, SEQ ID No. 643).

Unpurified anti-IL-33 antibody samples were tested for inhibition of biotinylated IL-33 binding FLAG®His-tagged ST2 by adding 5 microlitres of each dilution of antibody test sample to a 384 well low volume assay plate (Costar, 3673). Next, a solution containing 4 nM human FLAG®His-tagged ST2 and 5 nM anti-FLAG® XL665 detection (Cisbio International, 61FG2XLB) was prepared and 2.5 microlitres of the mix added to the assay plate. This was followed by the addition of 2.5 microlitres of a solution containing 2.4 nM biotinylated human IL33-01 or IL33-11 combined with 1.5 nM streptavidin cryptate detection (Cisbio International, 610SAKLB). All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 1 hour at room temperature and time resolved fluorescence was read at 620 nm and 665 nm emission wavelengths using an EnVision plate reader (Perkin Elmer). Plates were incubated for a further 16 hour (overnight) at 4 degrees Celsius and time resolved fluorescence read again. The negative control (non-specific binding) was defined by replacing biotinylated human IL33-01 or IL33-11 combined with streptavidin cryptate detection with streptavidin cryptate detection only. Data were analysed as described in Example 1.

Inhibition of IL-33 Binding to ST2 by Purified scFv

Single chain Fv clones which showed an inhibitory effect on IL-33:ST2 interaction as unpurified periplasmic extracts at both time points were subjected to DNA sequencing (Osbourn, et al. *Immunotechnology* 2(3):181-96 (1996); Vaughan, et al. *Nat Biotechnol* 14(3):309-14 (1996)). Unique scFv were expressed again in bacteria and purified by affinity chromatography (as described in WO01/66754). The potencies of these samples were determined by competing a dilution series of the purified preparation against FLAG®His-tagged human ST2 for binding to biotinylated IL33-01 or biotinylated IL33-11 as described above. Assay plates were incubated for 1 hour at room temperature (1 hour incubation), or assay plates were incubated for 1 hour at room temperature followed by 16 hour at 4 degrees Celsius (overnight incubation). Purified scFv preparations that were capable of inhibiting the IL-33:ST2 interaction at both timepoints were selected for conversion to IgG format.

Figure 37:
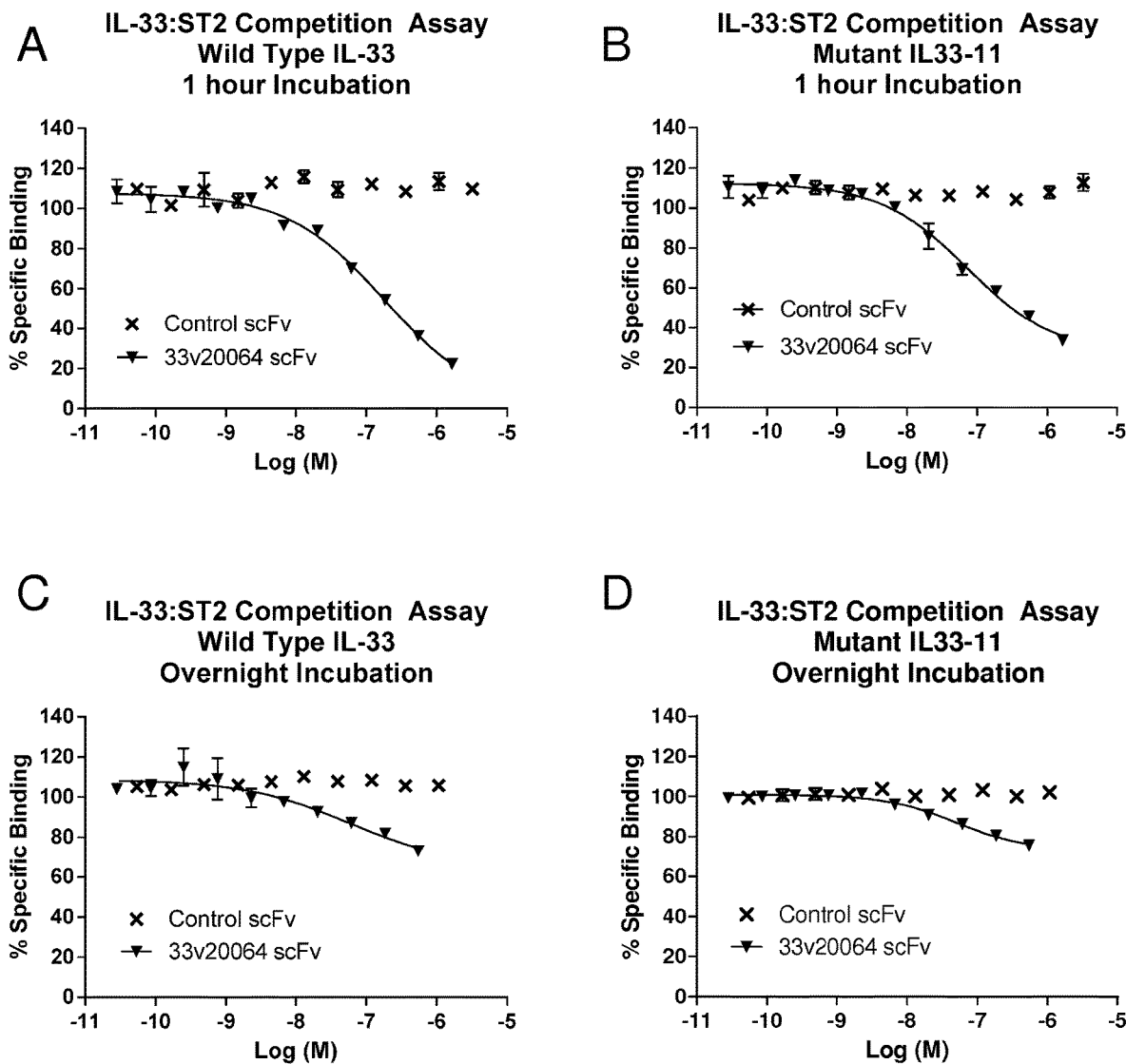
FIG. 37 Shows a timecourse of IL-33 neutralizing activity of 33v20064 scFv in an IL33-ST2 HTRF binding assay.

FIG. 37A: shows the inhibition of the FRET signal after 1 hour incubation, produced by human IL-33-01 binding to human ST2 with increasing concentrations of IL-33 scFv antibody 33v20064, wherein the x-axis is the concentration of antibody in molar concentration and the y-axis is percent specific binding.

FIG. 37B: shows the inhibition of the FRET signal after 1 hour incubation, produced by IL33-11 binding to human ST2 with increasing concentrations of IL-33 scFv antibody 33v20064, wherein the x-axis is the concentration of antibody in molar concentration and the y-axis is percent specific binding.

FIG. 37C: shows the inhibition of the FRET signal after overnight incubation, produced by human IL-33-01 binding to human ST2 with increasing concentrations of IL-33 scFv antibody 33v20064, wherein the x-axis is the concentration of antibody in molar concentration and the y-axis is percent specific binding.

FIG. 37D: shows the inhibition of the FRET signal after overnight incubation, produced by IL33-11 binding to human ST2 with increasing concentrations of IL-33 scFv antibody 33v20064, wherein the x-axis is the concentration of antibody in molar concentration and the y-axis is percent specific binding.

Reformatting of scFv to IgG1

Purified scFv preparations that were capable of inhibiting the IL-33:ST2 interaction were converted to whole immunoglobulin G1 (IgG1) antibody format as described in Example 1. Antibodies that inhibited to a similar or greater extent then IL330004 (Example 1, SEQ ID Nos. 12 and 17) were taken forward for further analysis. Such antibodies are exemplified by 33v20064. SEQ ID NOs. corresponding to the various regions of antibody 33v20064 are shown in Table 20.

TABLE 20

Anti-IL-33 Antibody Sequences

| IgG1 | VH Sequence | VL Sequence | VH CDRs 1, 2, 3 | VL CDRs 1, 2, 3 |
|---|---|---|---|---|
| 33v20064 | SEQ ID NO: 272 | SEQ ID NO: 277 | SEQ ID NO: 273 SEQ ID NO: 274 SEQ ID NO: 275 | SEQ ID NO: 278 SEQ ID NO: 279 SEQ ID NO: 280 |

Inhibition of IL-33 Binding to ST2 by Purified IgG

The ability of anti-IL-33 antibodies to inhibit the binding of biotinylated IL-33-01 to the FLAG®-His tagged ST2 receptor was assessed in a biochemical HTRF® (Homogeneous Time-Resolved Fluorescence, Cisbio International) competition assay, the principles of which are described above. Activity of purified IgG preparations were determined by competing a dilution series of the purified IgG against human FLAG®-His tagged ST2 for binding to human biotinylated human IL-33-01 (SEQ ID No. 632).

Figure 38:
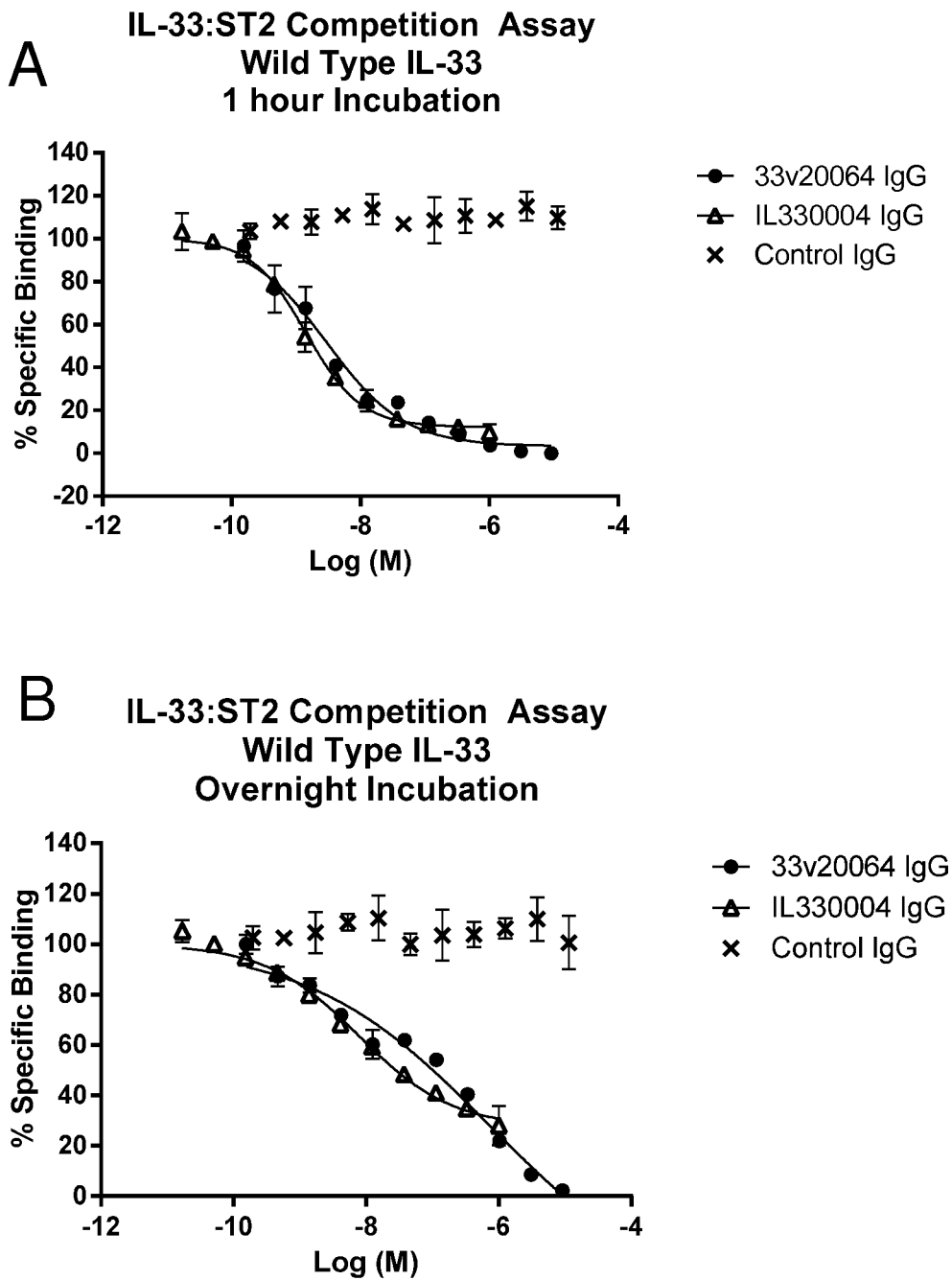
FIG. 38 Shows a timecourse of IL-33 neutralizing activity of 33v20064 IgG in an IL33-ST2 HTRF binding assay.

FIG. 38A: shows the inhibition of the FRET signal after 1 hour incubation, produced by human IL-33 binding to human ST2 with increasing concentrations of 33v20064 IgG1 antibody, wherein the x-axis is the concentration of antibody in molar concentration and the y-axis is percent specific binding.

FIG. 38B: shows the inhibition of the FRET signal after overnight incubation, produced by human IL-33 binding to human ST2 with increasing concentrations of 33v20064 IgG1 antibody, wherein the x-axis is the concentration of antibody in molar concentration and the y-axis is percent specific binding.

Inhibition of IL-6 Production in Huvec by IgG

33v20064 was assessed for inhibition of IL-33 stimulated IL-6 production in HUVECs, the methods of which are described in Example 2. His-Avi human IL-33 wild type (IL33-01, SEQ ID No. 632) (30 ng/mL) or His-Avi mutant IL-33 (IL33-11, SEQ ID No. 643) (30 ng/mL) were used to stimulate HUVECs in the presence of varying concentrations of test antibodies.

Figure 39:
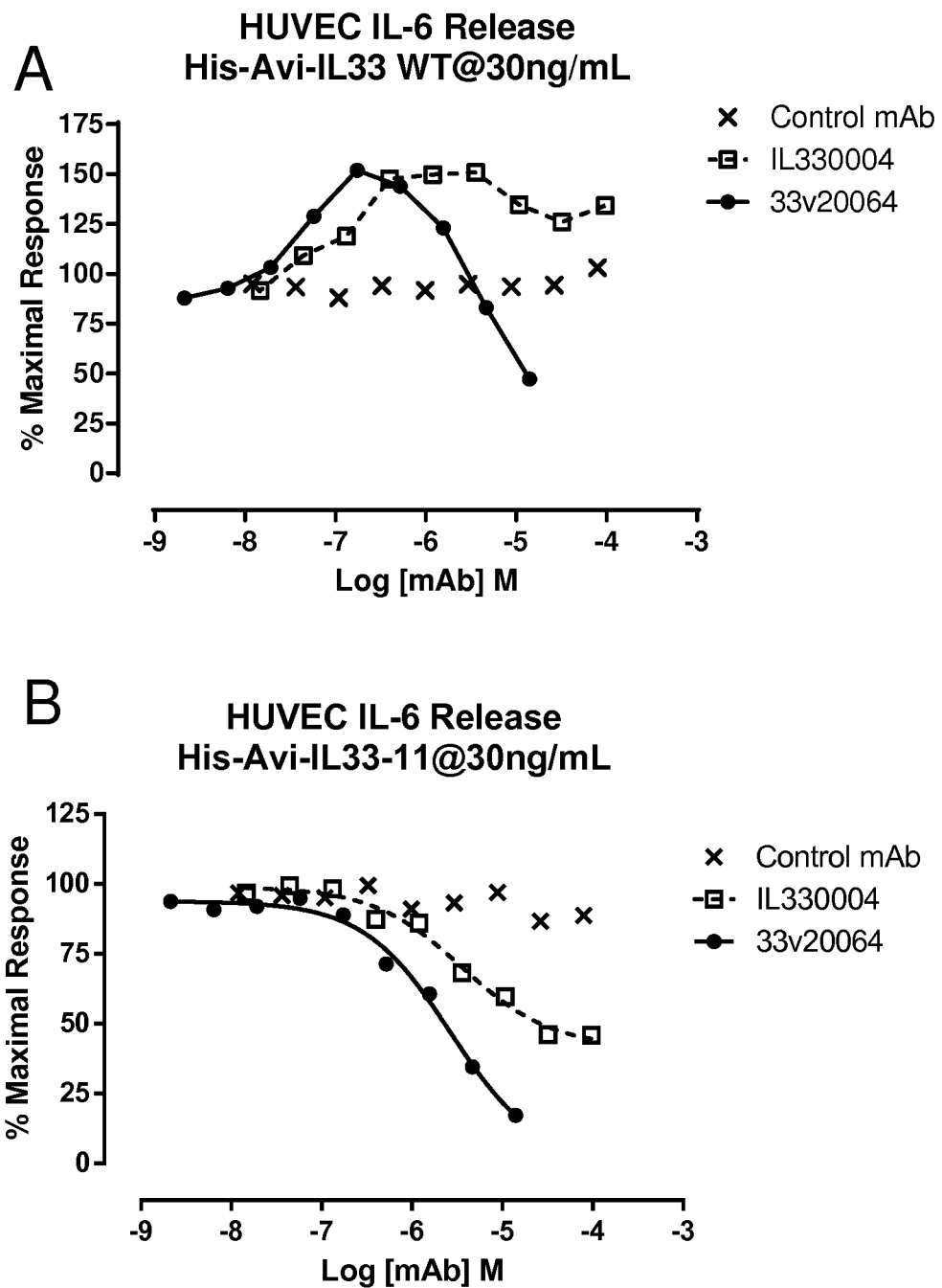
FIG. 39 Shows antibody neutralization of IL-6 production in HUVECs stimulated by wild type (FIG. 39A) or mutant IL-33 (FIG. 39B).

FIG. 39A: shows the inhibition of IL-6 production from IL33-01 (WT) stimulated HUVECs by antibody 33v20064 compared with IL330004 and anti-NIP IgG1 negative control antibody, NIP228, wherein the x-axis is the concentration of antibody in molar concentration and the y-axis is percent maximal response. 33v20064 showed partial inhibition of the response to WT IL-33 at high antibody concentrations, whereas IL330004 showed no effect.

FIG. 39B: shows the inhibition of IL-6 production from IL33-11 stimulated HUVECs by antibody 33v20064 compared with IL330004 and anti-NIP IgG1 negative control antibody, NIP228, wherein the x-axis is the concentration of antibody in molar concentration and the y-axis is percent maximal response. 33v20064 showed a more complete inhibition of IL-6 production stimulated by IL33-11 mutant compared with IL330004.

Cross-Reactivity of Anti-IL-33 Antibodies

Cross-reactivity of anti IL-33 antibody 33v20064 was determined using a homogeneous FRET (fluorescence resonance energy transfer) HTRF® (Homogeneous Time-Resolved Fluorescence, Cisbio International) based IL-33:mAb-binding assay. In this assay, samples competed with biotinylated human IL-33-01 (SEQ ID No. 632) for binding to DyLight labelled 33v20064 IgG.

TABLE 21

FRET Assay Reagents

| Reagent | Supplier | Catalogue Number/ Designation | SEQUENCE |
|---|---|---|---|
| Human IL-33 Flag ®His | In house | PS-582 | SEQ ID No. 627 |
| Mouse IL-33 Flag ®His | In house | BK-265 | SEQ ID No. 628 |
| Cynomolgus IL-33 Flag ®His | In house | PS-368 | SEQ ID No. 629 |
| B7H3 Avi-His | In house | DBPur125 | |
| Human IL-1 alpha | R&D Systems | 201-LB/CF | |
| Human IL-1 beta | R&D Systems | 200-LA/CF | |

Human, cyno and mouse IL-33 FLAG®His (described in Example 1) were tested for inhibition of human IL-33 binding to DyLight labelled 33v20064 by adding 5 microlitres of each dilution of IL-33 sample to a 384 well low volume assay plate (Costar, 3673). Next, a solution containing 20 nM DyLight labelled 33v20064 was prepared and 2.5 microlitres added to the assay plate (labelled using kit (Innova Biosciences, 326-0010) as per manufacturer's instructions). This was followed by the addition of 2.5 microlitres of a solution containing 1.2 nM biotinylated human IL-33-01 combined with 1.5 nM streptavidin cryptate detection (Cisbio International, 610SAKLB). All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 1 hour at room temperature and time resolved fluorescence was read at 620 nm and 665 nm emission wavelengths using an EnVision plate reader (Perkin Elmer). Data were analysed by calculating the 665/620 nm ratio followed by the % Delta F values for each sample. The 665/620 nm ratio was used to correct for sample interference using Equation 1. The % Delta F for each sample was then calculated using Equation 2. The negative control (non-specific binding) was defined by replacing biotinylated human IL-33 combined with streptavidin cryptate detection with streptavidin cryptate detection only. The % Delta F values were subsequently used to calculate % specific binding as described in Equation 3. $IC_{50}$ values were determined using GraphPad Prism software by curve fitting using a four-parameter logistic equation (Equation 4). These results demonstrated that 33v20064 cross reacts with cynomolgus IL-33. 33v20064 but did not show competition with mouse IL-33.

FIG. 40A: shows the inhibition of the FRET signal, produced by biotinylated human IL-33-01 binding to DyLight labelled 33v20064, with increasing concentrations of test proteins, wherein the x-axis is the concentration of test sample in molar concentration and the y-axis is percent specific binding. Inhibition of the FRET signal was observed with human and cynomolgus, but not mouse, IL-33.

Selectivity of Anti-IL-33 Antibodies

Selectivity of anti IL-33 antibody 33v20064 was determined using a homogeneous FRET (fluorescence resonance energy transfer) HTRF® (Homogeneous Time-Resolved Fluorescence, Cisbio International) based IL-33:mAb-binding assay. In this assay, samples competed with biotinylated His-Avi human IL-33 (IL33-01, SEQ ID No. 632) for binding to wild type DyLight labelled 33v20064 IgG. Human IL-1 alpha and human IL-1 beta were tested for inhibition of biotinylated IL-33-01 binding DyLight labelled 33v20064 as described above. These results demonstrated that 33v20064 did not show competition with human IL-1 alpha or IL-1 beta.

FIG. 40B: shows the inhibition of the FRET signal, produced by biotinylated human IL-33-01 binding to DyLight labelled 33v20064, with increasing concentrations of test proteins, wherein the x-axis is the concentration of test sample in molar concentration and the y-axis is percent specific binding. Inhibition of the FRET signal was not observed with human IL-1 alpha or IL-1 beta.

Example 8 Optimization of Anti-IL-33 Ab 33v20064

Germlining Framework Regions of 33v20064

The amino acid sequences of the $V_H$ and $V_L$ domains of the parent antibody 33v20064 were aligned to the known human germline sequences in the IMGT database (Lefranc, M. P. et al. *Nucl. Acids Res.* 2009. 37(Database issue): D1006-D1012), and the closest germline was identified by sequence similarity. For the $V_H$ domains of the 33v20064 antibody lineage this was IGHV3-23*01. For the $V_L$ domains it was IGLV3-1. Germlining was carried out on 33v20064 prior to the affinity maturation process. Without considering the Vernier residues (Foote 1992), which were left unchanged, there were 6 residues in the frameworks of the $V_L$ domains of 33v20064 which differed from germline, 5 of which were reverted to the closest germline sequence using the Kunkel mutagenesis method (Clackson, T. and Lowman, H. B. *Phage Display—A Practical Approach*, 2004. Oxford University Press) with the appropriate mutagenic primers. The product of this germlining was 33_640001. Sequence ID Numbers are described in Table 22.

TABLE 22

Antibody 33v20064 Germline Sequences

| IgG1 | VH Sequence | VL Sequence | VH CDRs 1, 2, 3 | VL CDRs 1, 2, 3 |
|---|---|---|---|---|
| 33_640001 | SEQ ID NO: 282 | SEQ ID NO: 287 | SEQ ID NO: 283 SEQ ID NO: 284 SEQ ID NO: 285 | SEQ ID NO: 288 SEQ ID NO: 289 SEQ ID NO: 290 |

Inhibition of IL-33 Binding to ST2 by Purified scFv

Activity of 33_640001 was compared with its non-germlined parent, 33v20064. The ability of scFv antibodies to inhibit the binding of biotinylated His Avi human IL-33 (IL33-01, SEQ ID No. 632) to the FLAG®-His tagged ST2 receptor was assessed in a biochemical HTRF® (Homogeneous Time-Resolved Fluorescence, Cisbio International) competition assay as described in Example 7.

Figure 41:
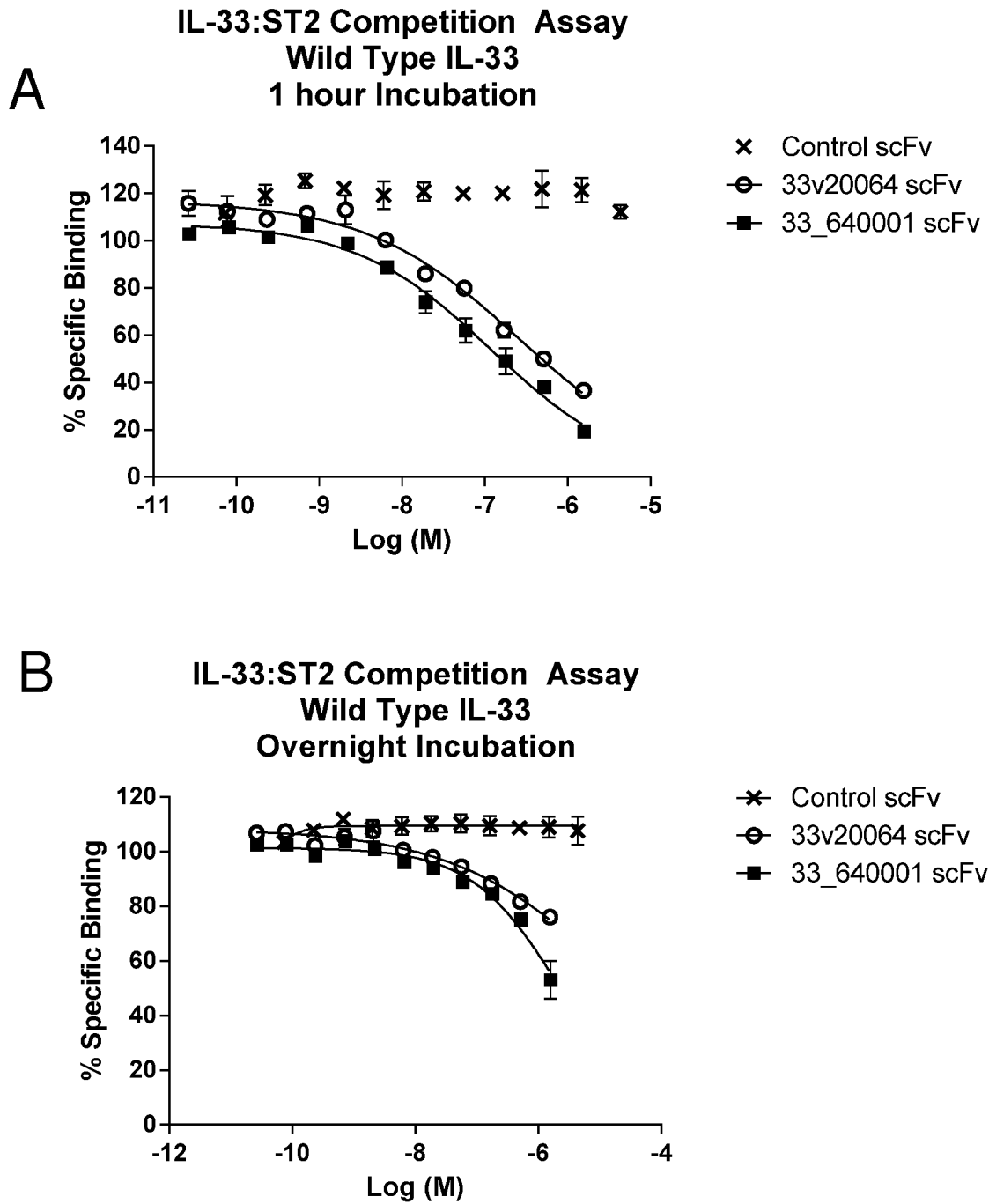
FIG. 41 Shows a timecourse of IL-33 neutralizing activity in an IL33-ST2 HTRF binding assay of germline variant 33_640001 compared with parent 33v20064 scFv.

FIG. 41A: shows the inhibition of the FRET signal after 1 hour incubation, produced by human IL-33 binding to human ST2 with increasing concentrations of scFv antibodies, wherein the x-axis is the concentration of antibody in molar concentration and the y-axis is percent specific binding. 33_640001 had equivalent activity to its non-germlined parent.

FIG. 41B: shows the inhibition of the FRET signal after overnight incubation, produced by human IL-33 binding to human ST2 with increasing concentrations of scFv antibodies, wherein the x-axis is the concentration of antibody in molar concentration and the y-axis is percent specific binding. 33_640001 had equivalent activity to its non-germlined parent.

Affinity Maturation

33v20064 was optimised using a targeted mutagenesis approach and affinity-based phage display selections. Large scFv-phage libraries derived from the germlined parent (33_640001) were created by oligonucleotide-directed mutagenesis of the variable heavy ($V_H$) complementarity determining region 3 (CDR3) and light ($V_L$) chain CDR3 using standard molecular biology techniques as described (Clackson 2004). For the $V_H$ CDR3, the two Vernier positions preceding the Kabat-defined CDRs (i.e. $V_H$ positions 93 and 94) were also included for potential optimisation in the targeted mutagenesis approach. The libraries were subjected to affinity-based phage display selections in order to select variants with higher affinity for human IL-33. These selections were carried out by either alternating the biotinylated His-Avi human IL-33 wild type (IL33-01, SEQ ID NO. 632) and biotinylated His Avi mutant IL-33 (IL33-11, SEQ ID NO. 643) antigens in sequential rounds, or with the biotinylated IL33-11 antigen only in all rounds. The selections were performed essentially as described previously (Thompson 1996). In brief, the scFv-phage particles were incubated with the recombinant biotinylated antigen in solution. ScFv-phage bound to antigen were then captured on streptavidin-coated paramagnetic beads (Dynabeads® M-280) following the manufacturer's recommendations. The selected scFv-phage particles were then rescued as described previously (Osbourn, J. K., et al. *Immunotechnology*, 1996. 2(3): p. 181-96), and the selection process was repeated in the presence of decreasing concentrations of biotinylated antigen—typically from 50 nM to 10 pM over five rounds of selection.

33v20064 was also optimised using ribosome display technology essentially as described by Hanes et al. (Hanes, J., et al. *Methods in Enzymology*, 2000. 328: p. 404-30). The parent scFv clone 33v20064 was used as a template for library construction and conversion to a ribosome display format for subsequent selections. On the DNA level, a T7 promoter was added at the 5'-end for efficient transcription to mRNA. On the mRNA level, the construct contained a prokaryotic ribosome-binding site (Shine-Dalgarno sequence). At the 3'-end of the single chain, the stop codon was removed and a portion of M13 bacteriophage gIII (gene III) was added to act as a spacer between the nascent scFv polypeptide and the ribosome (Hanes 2000).

A ribosome display library derived from the parent (33v20064) scFv construct was created by random mutagenesis using the Diversify™ PCR (polymerase chain reaction) Random Mutagenesis Kit (BD Biosciences) following the manufacturer's recommendations. The conditions for this error-prone PCR (EP) were chosen to introduce on average 8.1 nucleotide changes per 1000 basepairs (according to the manufacturer). The resulting EP library was then used in affinity-based ribosome display selections (Hanes 2000). The scFvs were expressed in vitro using the RiboMAX™ Large Scale RNA Production System (T7) (Promega) following the manufacturer's protocol and an *E. coli*-based prokaryotic cell-free translation system. The produced scFv antibody-ribosome-mRNA (ARM) complexes were incubated in solution with biotinylated human IL-33 antigen, with either alternating the biotinylated IL33-01 and biotinylated IL33-11 antigens in sequential rounds, or with the biotinylated IL-33-11 antigen only in all rounds. The specifically bound tertiary complexes (IL-33:ARM) were captured on streptavidin-coated paramagnetic beads (Dynabeads® M-280) following the manufacturer's recommendations (Dynal) whilst unbound ARMs were washed away. The mRNA encoding the bound scFvs were then recovered by reverse transcription-PCR (RT-PCR). The selection process was repeated on the obtained population for further rounds of selections with decreasing concentrations of biotinylated human IL-33 (100 nM to 100 pM over 5 rounds), in order to enrich and thereby select clones with higher affinity for IL-33. The outputs from selection rounds 3, 4 and 5 were sub-cloned into pCantab6 (McCafferty, J., et al. *Appl Biochem Biotechnol*, 1994. 47(2-3): p. 157.), and improved clones were identified as described below.

Inhibition of IL-33 Binding to mAb by Unpurified scFv

A representative number of individual clones from the selection outputs were grown up in 96-well plates. ScFv were expressed in the bacterial periplasm (Kipriyanov, et al. *J Immunol Methods* 200(1-2): 69-77 (1997)) and screened for their inhibitory activity in a homogeneous FRET (fluorescence resonance energy transfer) HTRF® (Homogeneous Time-Resolved Fluorescence, Cisbio International) based IL-33:mAb-binding assay. In this assay, samples competed with DyLight labelled 33v20064 IgG for binding to biotinylated His Avi IL-33-01 (SEQ ID NO. 632) or biotinylated His Avi cynomolgus IL-33 (SEQ ID NO. 649). Such epitope competition assays are based on the principle that a test antibody sample, which recognizes a similar epitope to the labelled anti IL-33 IgG, will compete with the labelled IgG for binding to biotinylated IL-33 resulting in a reduction in assay signal.

Unpurified anti-IL-33 antibody samples were tested for inhibition of biotinylated His Avi IL33-01 (human) or biotinylated His Avi cynomolgus IL-33 binding DyLight labelled 33v20064 by adding 5 microlitres of sample to a 384 well low volume assay plate (Costar, 3673). Next, a solution containing 2.4 nM DyLight labelled 33v20064 was prepared for the human IL-33 assay and 6 nM DyLight labelled 33v20064 was prepared for the cynomolgus assay and 2.5 microlitres added to the assay plates (labelled using kit (Innova Biosciences, 326-0010) as per manufacturer's instructions). This was followed by the addition of 2.5 microlitres of a solution containing 0.8 nM biotinylated human IL-33-01 combined with 0.75 nM streptavidin cryptate detection (Cisbio International, 610SAKLB) for the human assay or a solution containing 4 nM biotinylated cynomolgus IL-33 combined with 1.5 nM streptavidin cryptate detection (Cisbio International, 610SAKLB) for the cynomolgus assay. All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 1 hour at room temperature and time resolved fluorescence was read at 620 nm and 665 nm emission wavelengths using an EnVision plate reader (Perkin Elmer). Data were analysed by calculating the 665/620 nm ratio followed by the % Delta F values for each sample. The 665/620 nm ratio was used to correct for sample interference using Equation 1. The % Delta F for each sample was then calculated using Equation 2. The negative control (non-specific binding) was defined by replacing biotinylated IL-33 combined with streptavidin cryptate detection with streptavidin cryptate detection only. The % Delta F values were subsequently used to calculate % specific binding as described in Equation 3.

As the epitope competition assay reached its limit of sensitivity an assay using an intermediate optimised mAb 33_640027 was used for testing unpurified scFv samples. The assay was essentially as described for the 33v20064 competition assay with the following modifications: 20 nM DyLight labelled 33_640027 was prepared and 2.5 microlitres added to the assay plates. This was followed by the addition of 2.5 microlitres of a solution containing 0.32 nM biotinylated human IL-33-01 combined with 0.75 nM streptavidin cryptate detection (Cisbio International, 610SAKLB) for the human assay or a solution containing 0.8 nM biotinylated cynomolgus IL-33 combined with 1.5 nM streptavidin cryptate detection (Cisbio International, 610SAKLB) for the cynomolgus assay.

Inhibition of IL-33 Binding to mAb by Purified scFv

Single chain Fv clones which showed an inhibitory effect on IL-33:mAb interaction as unpurified periplasmic extracts were subjected to DNA sequencing (Osbourn, et al. *Immunotechnology* 2(3):181-96 (1996); Vaughan, et al. *Nat Biotechnol* 14(3):309-14 (1996).). Unique scFv were expressed again in bacteria and purified by affinity chromatography (as described in WO01/66754). Purified anti-IL-33 antibody samples were tested for potency of inhibition by competing a dilution series of the purified preparation against DyLight labelled 33v20064 IgG or DyLight labelled 33_640027 IgG for binding to biotinylated His Avi IL33-01, biotinylated His Avi IL33-11 or biotinylated His Avi cynomolgus IL-33. Methods are as described in the previous section.

TABLE 23

Activity of scFv antibodies in epitope competition assays

| Assay | | Potency IC50 (nM) | | | |
| --- | --- | --- | --- | --- | --- |
| | | 33v20064 | 33_640027 | 33_640047 | 33_640050 |
| 33v20064 | IL33-01 | 12 | 0.4 | 0.4 | 0.2 |
| | IL33-11 | 26 | 0.6 | 0.5 | 0.4 |
| | Cyno IL-33 | 103 | 8.2 | 2.7 | 1.4 |
| 33_640027 | IL33-01 | 1498 | 3.8 | 2.3 | 2.5 |
| | IL33-11 | 1467 | 2.9 | Not determined | 2.4 |
| | Cyno IL-33 | 3433 | 38 | 8.8 | 4.1 |

Reformatting of scFv to IgG1

Single chain Fv clones with desirable properties from the IL-33:mAb binding assays were converted to whole immunoglobulin G1 (IgG1) antibody format as described in Example 1. These include antibodies 33_640027 (derived from the EP library selections), and 33_640047, 33_640050 (derived from the $V_H$ CDR3 block mutagenesis library selections) SEQ ID NOs corresponding to the various regions of these antibodies are shown in Table 24

TABLE 24

Sequences of IL33 antibodies

| IgG1 | VH Sequence | VL Sequence | VH CDRs 1, 2, 3 | VL CDRs 1, 2, 3 |
|---|---|---|---|---|
| 33_640027 | SEQ ID NO: 292 | SEQ ID NO: 297 | SEQ ID NO: 293  SEQ ID NO: 294  SEQ ID NO: 295 | SEQ ID NO: 298  SEQ ID NO: 299  SEQ ID NO: 300 |
| 33_640047 | SEQ ID NO: 312 | SEQ ID NO: 317 | SEQ ID NO: 313  SEQ ID NO: 314  SEQ ID NO: 315 | SEQ ID NO: 318  SEQ ID NO: 319  SEQ ID NO: 320 |
| 33_640050 | SEQ ID NO: 302 | SEQ ID NO: 307 | SEQ ID NO: 303  SEQ ID NO: 304  SEQ ID NO: 305 | SEQ ID NO: 308  SEQ ID NO: 309  SEQ ID NO: 310 |

Inhibition of IL-33 Binding to mAb by Purified IgG

The ability of anti-IL-33 antibodies to inhibit the binding of biotinylated His Avi IL33-01, biotinylated His Avi IL33-11 or biotinylated His Avi cynomolgus IL-33 to the DyLight labelled 33v20064 IgG or DyLight labelled 33_640027 IgG was assessed in a biochemical HTRF® (Homogeneous Time-Resolved Fluorescence, Cisbio International) competition assay as described. IgGs with desirable properties from the IL-33:mAb binding assays were selected for further analysis.

Inhibition of IL-8 Production in Huvec by IgG

A cytokine release assay was used to assess the inhibition of IL-33 induced IL-8 production from human umbilical vein endothelial cells (Huvec) by anti-IL-33 antibodies. Cells were exposed to IL-33 in the presence or absence of test antibody or ST2.Fc (R&D systems) essentially as described in Example 2 with minor modifications. Test solutions of purified IgG (in duplicate) were diluted to the desired concentration in complete culture media. N-terminal His Avi IL-33 (IL33-01, SEQ ID NO 632) was prepared in complete culture media mixed with appropriate test antibody to give a final IL-33 concentration of 2 ng/mL. All samples were incubated for 30 minutes at room temperature, prior to transfer of IL-33/antibody mixture to the assay plate. Following 18-24 hour incubation, IL-8 was measured in cell supernatants by ELISA (R&D Systems, DY208) adapted for europium readout as described in Example 2. Data were analyzed using Graphpad Prism software. $IC_{50}$ values were determined by curve fitting using a four-parameter logistic equation. $IC_{50}$ values were calculated and are summarized in Table 25 below.

Figure 42:
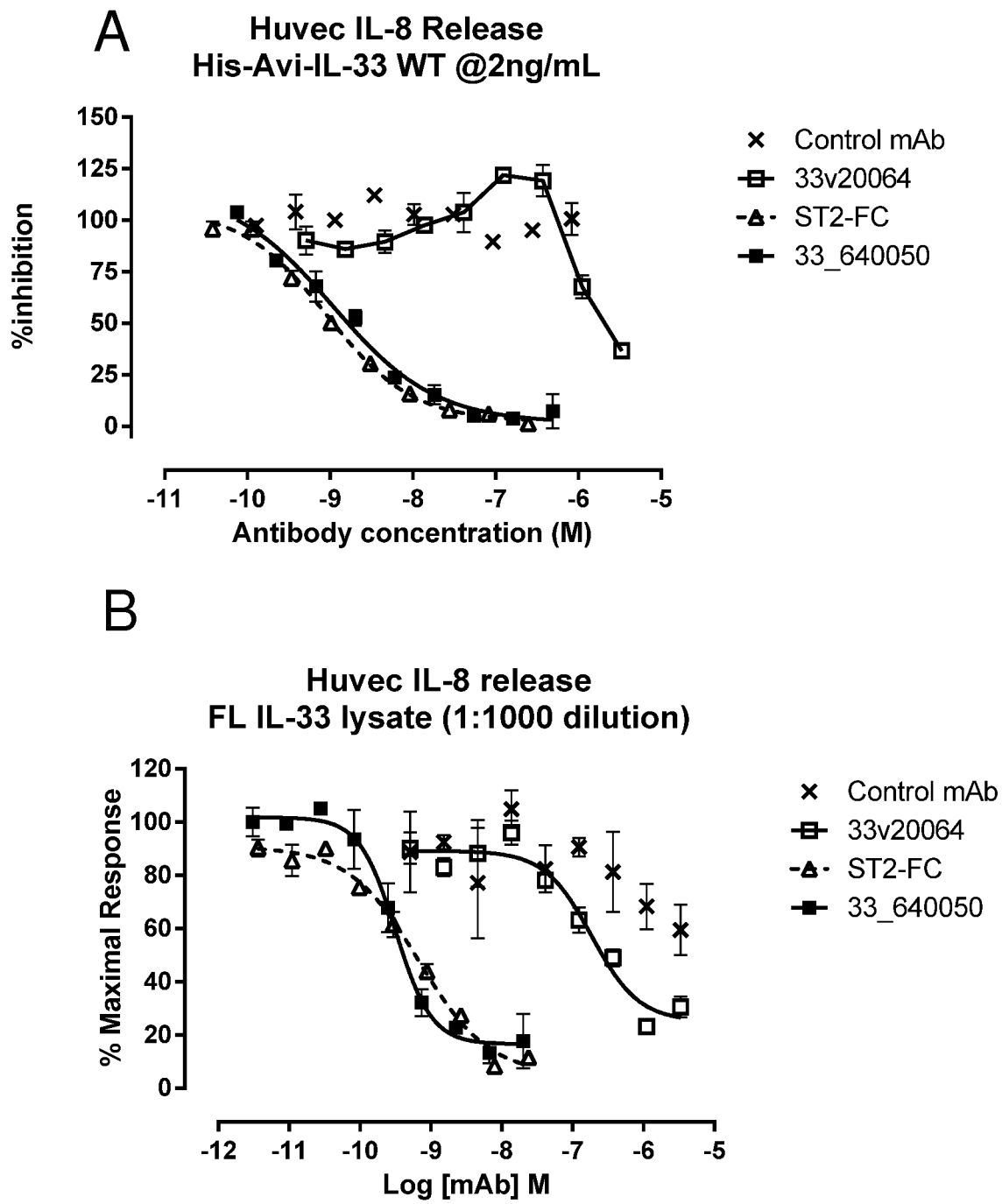
FIG. 42 Shows antibody neutralization of IL-8 production in HUVECs stimulated by truncated (112-270) (FIG. 42A) or full length (1-270) IL-33, (FIG. 42B).

FIG. 42A shows HUVECs stimulated with IL33-01 in the presence of 33v20064, 33_640050, human ST2-Fc or control mAb, wherein the x-axis is the concentration of antibody in molar concentration and the y-axis is a percentage of the maximum response (IL-8 production).

Neutralization of Mammalian Full Length IL-33

Full length IL-33 is also active (Cayrol et al., *Proc Natl Acad Sci USA* 106(22):9021-6 (2009); Hayakawa et al., *Biochem Biophys Res Commun* 387(1):218-22 (2009); Talabot-Ayer et al., *J Biol Chem.* 284(29):19420-6 (2009)).

To evaluate the ability of antibodies to neutralize full length IL-33, HEK293-EBNA cells expressing full length (FL) HuIL-33 (and mock-transfected controls) were harvested 24 hours following transfection with accutase (PAA, # L11-007). Cells were diluted to $1 \times 10^8$/mL with PBS and homogenized for 30 seconds using a tissue homogenizer. Cell debris was removed by centrifugation. HUVECs were stimulated with cell lysates at varying concentrations. Stimulation of cytokine production was only observed with full length IL-33-transfected cell lysate and not with mock transfected cell lysate. A 1:1000 concentration of lysate that stimulated a sub-maximal cytokine release (approx $EC_{50}$) was selected for antibody neutralization studies. Experiments were performed as described above. $IC_{50}$ values were calculated and are summarized in Table 25 below.

FIG. 42B shows HUVECs stimulated with full length IL-33 cell lysate in the presence of 33v20064, 33_640050, human ST2-Fc or control mAb, wherein the x-axis is the concentration of antibody in molar concentration and the y-axis is a percentage of the maximum response (IL-8 production).

TABLE 25

IC50 values in the Huvec IL-8 assay

| | Geomean IC50 (95% CI) (nM) | |
|---|---|---|
| Antibody | vs. His Avi IL-33 | vs. full length IL-33 cell lysate |
| 33v20064 | Partial inhibition | 185 |
| 33_640050 | 0.7 (0.3-1.5) | 0.32 |
| ST2.Fc | 0.3 (0.1-0.9) | 0.67 |

Prevention of Disulphide Bonded Form of IL-33 by IgG

IL-33-01 (0.14 nM or 3 ng/mL) was incubated in IMDM or PBS, both containing 1% BSA in the presence of absence of antibodies (25 ug/mL) or human ST2-Fc (105 ug/mL) for 0-24 hours at 37° C., 5% $CO_2$. At various time points aliquots were removed and added to a pre-chilled plate containing PBS or sST2 (final concentration 10.5 ug/mL). sST2 was spiked into control mAb and untreated samples at harvesting to stop the IL-33 oxidation reaction continuing. Samples were aliquoted into pre-frozen 96 well plates and stored at −80° C. The human IL-33 ELISA was performed according to manufacturer's instructions (R&D Systems, Cat # DY3625, Lot #1362797) with the substitution of DELFIA detection system (Perkin Elmer) in place of streptavidin-HRP and onwards. Briefly, black 96 well Maxisorp plates were coated with 50 uL per well of capture antibody overnight at room temperature. Plates were washed 3× with 300 uL 0.05% Tween-20 in PBS and blocked with 150 uL 1% BSA in PBS for 1 hour at room temperature. Plates were washed 3× and 50 uL per well of samples or standards were added to the plate for 2 hours at room temperature with shaking (400 rpm). Plates were washed 3× and 50 uL per well of detection antibody was added to the plate for 2 hours at room temperature with shaking (400 rpm). Plates were washed as previously stated and 50 uL per well of streptavidin-europium diluted 1 in 1000 in DELFIA Assay Buffer was added to the plate for 40 minutes at room temperature, protected from light, with shaking (400 rpm). Plates were washed 7× with 300 uL per well of DELFIA Wash Buffer. 50 uL per well of DELFIA Enhancement Solution (pre-warmed to room temperature) was added to the plate. After 10 minutes incubation at room temperature protected from the light, fluorescence was measured using an EnVision plate reader (PerkinElmer). Standards and data interpolation were performed in Microsoft Excel with subsequent analysis performed in GraphPad Prism software.

As discussed in Example 4, FIG. 24A, this ELISA detects predominantly disulphide bonded IL-33 (IL33-DSB) within the range of IL-33 concentrations measured in this experiment. The ELISA is used here to monitor the conversion of IL-33 to its disulphide bonded form in the presence of test antibodies.

FIG. 43 shows conversion of IL33-01 to its disulphide bonded form (IL33-DSB) during incubation in IMDM (FIG. 43A) or PBS (FIG. 43B) in the presence or absence of test antibodies, wherein the x-axis is time in hours and the y-axis is the concentration of IL-33-DSB. IL330004 and 33v20064 slow the rate of IL-33 conversion to IL33-DSB. 33_640050 and ST2.Fc prevent conversion to IL-33-DSB over the time course tested.

Recombination of Beneficial Mutations and Further Optimization

With the aim of generating further affinity improvements, beneficial mutations identified from previous selection and screening cascades were recombined in a number of different ways, either by a simple additive approach or via a recombination library approach with further selections.

Sequence analyses suggested that there were two single-point mutational 'hotspots' which were prevalent in many of the lead antibody sequences; I98M in $V_H$ CDR3 and Q50R in $V_L$ CDR2 (Kabat numbering). These two mutations were grafted onto the 33_640001 construct to generate a new antibody, 33_640036, using standard molecular biology techniques. In a further recombination, the $V_H$ of 33_640047 was paired with the $V_L$ of 33_640036 to generate antibody 33_640117. These are examples of sequence recombination using an additive approach. SEQ ID NOs are shown in Table 26.

TABLE 26

Sequences of IL33 antibodies

| IgG1 | VH Sequence | VL Sequence | VH CDRs 1, 2, 3 | VL CDRs 1, 2, 3 |
|---|---|---|---|---|
| 33_640036 | SEQ ID NO: 352 | SEQ ID NO: 357 | SEQ ID NO: 353 SEQ ID NO: 354 SEQ ID NO: 355 | SEQ ID NO: 358 SEQ ID NO: 359 SEQ ID NO: 360 |
| 33_640117 | SEQ ID NO: 362 | SEQ ID NO: 367 | SEQ ID NO: 363 SEQ ID NO: 364 SEQ ID NO: 365 | SEQ ID NO: 368 SEQ ID NO: 369 SEQ ID NO: 370 |

In addition, selection outputs from block mutagenesis libraries covering the $V_H$ CDR3 and $V_L$ CDR3 regions had shown affinity improvements and good sequence diversity and were thus recombined using a population cloning approach. Round 3 selection outputs were recombined to form libraries in which clones contained randomly paired, individually randomised $V_H$ CDR3 and $V_L$ CDR3 sequences. These recombined $V_H$ CDR3/$V_L$ CDR3 libraries were then used in ribosome display selections with either alternating the biotinylated His Avi human IL-33 wild type (IL33-01, SEQ ID NO. 632) and biotinylated His Avi mutant IL-33 (IL33-11, SEQ ID NO. 643) antigens in sequential rounds, or with the biotinylated His Avi IL33-11 antigen only in all rounds. The selections were performed essentially as described for the individual CDR3 libraries, in the presence of decreasing concentrations of biotinylated antigen—from 50 nM to 30 pM over five rounds of selection.

Crude scFv-containing periplasmic extracts were prepared of a representative number of individual scFv's from the selection outputs of the recombined $V_H$ CDR3/$V_L$ CDR3 libraries. The ability of anti-IL-33 antibodies to inhibit the binding of biotinylated His Avi IL33-01 or biotinylated His Avi cynomolgus IL-33 to the DyLight labelled 33v20064 IgG or DyLight labelled 33_640027 IgG was assessed in a biochemical HTRF® (Homogeneous Time-Resolved Fluorescence, Cisbio International) competition assay as described. ScFv variants which showed a significantly improved inhibitory effect when compared to parent scFv and leads generated pre-recombination, were subjected to DNA sequencing, and unique recombined variants were produced as purified scFv and tested as described in the previous section.

Optimised antibodies obtained from these recombined libraries are exemplified by 33_640076, 33_640081, 33_640082, 33_640084, 33_640086 and 33_640087. The SEQ ID NOs. of these antibodies are shown in Table 27.

TABLE 27

Sequences of IL33 antibodies

| IgG1 | VH Sequence | VL Sequence | VH CDRs 1, 2, 3 | VL CDRs 1, 2, 3 |
|---|---|---|---|---|
| 33_640076 | SEQ ID NO: 372 | SEQ ID NO: 377 | SEQ ID NO: 373 SEQ ID NO: 374 SEQ ID NO: 375 | SEQ ID NO: 378 SEQ ID NO: 379 SEQ ID NO: 380 |
| 33_640081 | SEQ ID NO: 382 | SEQ ID NO: 387 | SEQ ID NO: 383 SEQ ID NO: 384 SEQ ID NO: 385 | SEQ ID NO: 388 SEQ ID NO: 389 SEQ ID NO: 390 |
| 33_640082 | SEQ ID NO: 392 | SEQ ID NO: 397 | SEQ ID NO: 393 SEQ ID NO: 394 SEQ ID NO: 395 | SEQ ID NO: 398 SEQ ID NO: 399 SEQ ID NO: 400 |
| 33_640084 | SEQ ID NO: 402 | SEQ ID NO: 407 | SEQ ID NO: 403 SEQ ID NO: 404 SEQ ID NO: 405 | SEQ ID NO: 408 SEQ ID NO: 409 SEQ ID NO: 410 |
| 33_640086 | SEQ ID NO: 412 | SEQ ID NO: 417 | SEQ ID NO: 413 SEQ ID NO: 414 SEQ ID NO: 415 | SEQ ID NO: 418 SEQ ID NO: 419 SEQ ID NO: 420 |
| 33_640087 | SEQ ID NO: 422 | SEQ ID NO: 427 | SEQ ID NO: 423 SEQ ID NO: 424 SEQ ID NO: 425 | SEQ ID NO: 428 SEQ ID NO: 429 SEQ ID NO: 430 |

Additional spontaneous mutations were introduced into the variable regions of these antibodies in scFv format during the ribosome display selection procedures as a result of repeated rounds of PCR amplifications. These events add to the sequence diversity of the outputs but are often undesirable when they occur in the framework regions. Hence the spontaneous mutations which occurred in the framework regions of 33_640076, 33_640081, 33_640082, 33_640084, 33_640086 and 33_640087 were reverted back to germline on the IgG constructs as described in Example 3 using standard molecular biology techniques. Such spontaneous mutations which occurred in any of the CDRs or in the Vernier residues adjacent to the CDRs (e.g. $V_H$ positions 27, 28, 29, 30, 93 and 94 by Kabat numbering) were left unchanged. As an additional strategy to increase affinity, a previously identified 'hotspot' (the Q05R mutation in $V_L$ CDR2) was also grafted onto the constructs at the same time. The antibodies resulting from these germlining and hotspot grafting modifications were named 33_640076-1, 33_640081-A, 33_640082-2, 33_640084-2, 33_640086-2 and 33_640087-2, corresponding to their parental antibodies of 33_640076, 33_640081, 33_640082, 33_640084, 33_640086 and 33_640087 respectively. The SEQ ID NO. of these antibodies are shown in Table 28.

germlined parent (33_640001) were created by oligonucleotide-directed mutagenesis of the variable heavy ($V_H$) CDR1 and CDR2 and light ($V_L$) chain CDR1 and CDR2 using standard molecular biology techniques as described (Clackson 2004). Selections and screening were performed as described for $V_H V_L$ CDR3 libraries. The most improved antibody variants were obtained from the $V_H$ CDR2 library. These are exemplified by 33_640166, 33_640169, 33_640170. The SEQ ID NOs. of these antibodies are shown in Table 29.

TABLE 28

Sequences of IL33 antibodies

| IgG1 | VH Sequence | VL Sequence | VH CDRs 1, 2, 3 | VL CDRs 1, 2, 3 |
|---|---|---|---|---|
| 33_640076-1 | SEQ ID NO: 432 | SEQ ID NO: 437 | SEQ ID NO: 433 | SEQ ID NO: 438 |
| | | | SEQ ID NO: 434 | SEQ ID NO: 439 |
| | | | SEQ ID NO: 435 | SEQ ID NO: 440 |
| 33_640081-A | SEQ ID NO: 442 | SEQ ID NO: 447 | SEQ ID NO: 443 | SEQ ID NO: 448 |
| | | | SEQ ID NO: 444 | SEQ ID NO: 449 |
| | | | SEQ ID NO: 445 | SEQ ID NO: 450 |
| 33_640082-2 | SEQ ID NO: 452 | SEQ ID NO: 457 | SEQ ID NO: 453 | SEQ ID NO: 458 |
| | | | SEQ ID NO: 454 | SEQ ID NO: 459 |
| | | | SEQ ID NO: 455 | SEQ ID NO: 460 |
| 33_640084-2 | SEQ ID NO: 462 | SEQ ID NO: 467 | SEQ ID NO: 463 | SEQ ID NO: 468 |
| | | | SEQ ID NO: 464 | SEQ ID NO: 469 |
| | | | SEQ ID NO: 465 | SEQ ID NO: 470 |
| 33_640086-2 | SEQ ID NO: 472 | SEQ ID NO: 477 | SEQ ID NO: 473 | SEQ ID NO: 478 |
| | | | SEQ ID NO: 474 | SEQ ID NO: 479 |
| | | | SEQ ID NO: 475 | SEQ ID NO: 480 |
| 33_640087-2 | SEQ ID NO: 482 | SEQ ID NO: 487 | SEQ ID NO: 483 | SEQ ID NO: 488 |
| | | | SEQ ID NO: 484 | SEQ ID NO: 489 |
| | | | SEQ ID NO: 485 | SEQ ID NO: 490 |

Optimisation of Additional CDRs

As a further strategy to increase affinity, additional CDRs were optimised. Large scFv-phage libraries derived from the

TABLE 29

Sequences of IL33 antibodies

| IgG1 | VH Sequence | VL Sequence | VH CDRs 1, 2, 3 | VL CDRs 1, 2, 3 |
|---|---|---|---|---|
| 33_640166 | SEQ ID NO: 322 | SEQ ID NO: 327 | SEQ ID NO: 323 | SEQ ID NO: 328 |
| | | | SEQ ID NO: 324 | SEQ ID NO: 329 |
| | | | SEQ ID NO: 325 | SEQ ID NO: 330 |
| 33_640169 | SEQ ID NO: 332 | SEQ ID NO: 337 | SEQ ID NO: 333 | SEQ ID NO: 338 |
| | | | SEQ ID NO: 334 | SEQ ID NO: 339 |
| | | | SEQ ID NO: 335 | SEQ ID NO: 340 |
| 33_640170 | SEQ ID NO: 342 | SEQ ID NO: 347 | SEQ ID NO: 343 | SEQ ID NO: 348 |
| | | | SEQ ID NO: 344 | SEQ ID NO: 349 |
| | | | SEQ ID NO: 345 | SEQ ID NO: 350 |

As an additive strategy to achieve further improvements in affinity, the $V_H$ CDR2 sequences of 33_640166, 33_640169 and 33_640170 were grafted onto the IgG constructs of 33_640076-1, 33_640082-2, 33_640086-2 and 33_640087-2, using standard molecular biology methods. Antibodies resulting from these recombinations were exemplified by 33_640076-4, 33_640082-4, 33_640082-6, 33_640082-7, 33_640086-6 and 33_640087-7. The sequence origins and SEQ ID NO are shown in Table 30.

TABLE 30

Sequence origin and SEQ ID numbers of IL33 antibodies

| IgG1 | Origin | VH Sequence | VL Sequence | VH CDRs 1, 2, 3 | VL CDRs 1, 2, 3 |
|---|---|---|---|---|---|
| 33_640076-4 | Grafting of the $V_H$ CDR2 sequence of 33_640170 onto 33_640076-1 | SEQ ID NO: 492 | SEQ ID NO: 497 | SEQ ID NO: 493 | SEQ ID NO: 498 |
| | | | | SEQ ID NO: 494 | SEQ ID NO: 499 |
| | | | | SEQ ID NO: 495 | SEQ ID NO: 500 |
| 33_640082-4 | Grafting of the $V_H$ CDR2 | SEQ ID NO: 502 | SEQ ID NO: 507 | SEQ ID NO: 503 | SEQ ID NO: 508 |

TABLE 30-continued

Sequence origin and SEQ ID numbers of IL33 antibodies

| IgG1 | Origin | VH Sequence | VL Sequence | VH CDRs 1, 2, 3 | VL CDRs 1, 2, 3 |
|---|---|---|---|---|---|
| | sequence of 33_640166 onto 33_640082-2 | | | SEQ ID NO: 504 SEQ ID NO: 505 | SEQ ID NO: 509 SEQ ID NO: 510 |
| 33_640082-6 | Grafting of the V$_H$ CDR2 sequence of 33_640169 onto 33_640082-2 | SEQ ID NO: 512 | SEQ ID NO: 517 | SEQ ID NO: 513 SEQ ID NO: 514 SEQ ID NO: 515 | SEQ ID NO: 518 SEQ ID NO: 519 SEQ ID NO: 520 |
| 33_640082-7 | Grafting of the V$_H$ CDR2 sequence of 33_640170 onto 33_640082-2 | SEQ ID NO: 522 | SEQ ID NO: 527 | SEQ ID NO: 523 SEQ ID NO: 524 SEQ ID NO: 525 | SEQ ID NO: 528 SEQ ID NO: 529 SEQ ID NO: 530 |
| 33_640086-6 | Grafting of the V$_H$ CDR2 sequence of 33_640169 onto 33_640086-2 | SEQ ID NO: 532 | SEQ ID NO: 537 | SEQ ID NO: 533 SEQ ID NO: 534 SEQ ID NO: 535 | SEQ ID NO: 538 SEQ ID NO: 539 SEQ ID NO: 540 |
| 33_640087-7 | Grafting of the V$_H$ CDR2 sequence of 33_640170 onto 33_640087-2 | SEQ ID NO: 542 | SEQ ID NO: 547 | SEQ ID NO: 543 SEQ ID NO: 544 SEQ ID NO: 545 | SEQ ID NO: 548 SEQ ID NO: 549 SEQ ID NO: 550 |

The recombination of beneficial V$_H$ CDR3/V$_L$ CDR3 and V$_H$ CDR2 sequences was also carried out using a population cloning and selection approach. The round 3 selection outputs from the block mutagenesis libraries covering the V$_H$ CDR2 region was recombined with the round 3 selection outputs of the recombined V$_H$ CDR3/V$_L$ CDR3 library in a population cloning approach using standard molecular biology techniques. Selection outputs comprising of large numbers of scFv variants were recombined to form libraries in which clones contained randomly paired sequences derived from the V$_H$ CDR3/V$_L$ CDR3 and V$_H$ CDR2 selections. Selections were performed as described for V$_H$V$_L$ CDR3 libraries in the presence of decreasing concentrations of biotinylated antigen—typically from 3 nM to 3 pM over five rounds of selection. Crude scFv-containing periplasmic extracts from a representative number of individual scFv's from the selection outputs were screened in biochemical HTRF® assays as described for V$_H$V$_L$ CDR3 libraries. ScFv variants which showed a significantly improved inhibitory effect when compared to parent scFv and leads generated pre-recombination, were subjected to DNA sequencing.

As the epitope competition assay utilising 33_640027 reached its limit of sensitivity, an assay using 33_640117 was used for testing purified scFv samples. The assay was essentially as described for the 33v20064 competition assay with the following modifications: 2.5 nM DyLight labelled 33_640117 was prepared and 2.5 microlitres added to the assay plates. This was followed by the addition of 2.5 microlitres of a solution containing 0.12 nM biotinylated human IL-33-01 combined with 0.75 nM streptavidin cryptate detection (Cisbio International, 610SAKLB) for the human assay or a solution containing 0.24 nM biotinylated cynomolgus IL-33 combined with 1.5 nM streptavidin cryptate detection (Cisbio International, 610SAKLB) for the cynomolgus assay. Fluorescence was read after one hour and overnight incubation. The most potent samples at both time points were taken forward for reformatting to IgG.

Unique recombed variants were evaluated as purified scFv and the most active scFv's were then selected and converted to IgG1 format as described in Example 1. Antibodies obtained from these recombed libraries are exemplified by 33_640201 and 33_640237. The spontaneous mutations which were introduced into the framework regions of 33_640201 and 33_640237 during ribosome display selections were reverted back to germline sequences as described previously in this section, and their germlined counterparts were named 33_640201-2 and 33_640237-2 respectively. The SEQ IDs of these antibodies are shown in Table 31.

TABLE 31

Sequences of IL33 antibodies

| IgG1 | VH Sequence | VL Sequence | VH CDRs 1, 2, 3 | VL CDRs 1, 2, 3 |
|---|---|---|---|---|
| 33_640201 | SEQ ID NO: 552 | SEQ ID NO: 557 | SEQ ID NO: 553 SEQ ID NO: 554 SEQ ID NO: 555 | SEQ ID NO: 558 SEQ ID NO: 559 SEQ ID NO: 560 |
| 33_640237 | SEQ ID NO: 562 | SEQ ID NO: 567 | SEQ ID NO: 563 SEQ ID NO: 564 SEQ ID NO: 565 | SEQ ID NO: 568 SEQ ID NO: 569 SEQ ID NO: 570 |
| 33_640201-2 | SEQ ID NO: 572 | SEQ ID NO: 577 | SEQ ID NO: 573 SEQ ID NO: 574 SEQ ID NO: 575 | SEQ ID NO: 578 SEQ ID NO: 579 SEQ ID NO: 580 |

TABLE 31-continued

Sequences of IL33 antibodies

| IgG1 | VH Sequence | VL Sequence | VH CDRs 1, 2, 3 | VL CDRs 1, 2, 3 |
|---|---|---|---|---|
| 33_640237-2 | SEQ ID NO: 582 | SEQ ID NO: 587 | SEQ ID NO: 583 SEQ ID NO: 584 SEQ ID NO: 585 | SEQ ID NO: 588 SEQ ID NO: 589 SEQ ID NO: 590 |

Figure 44:
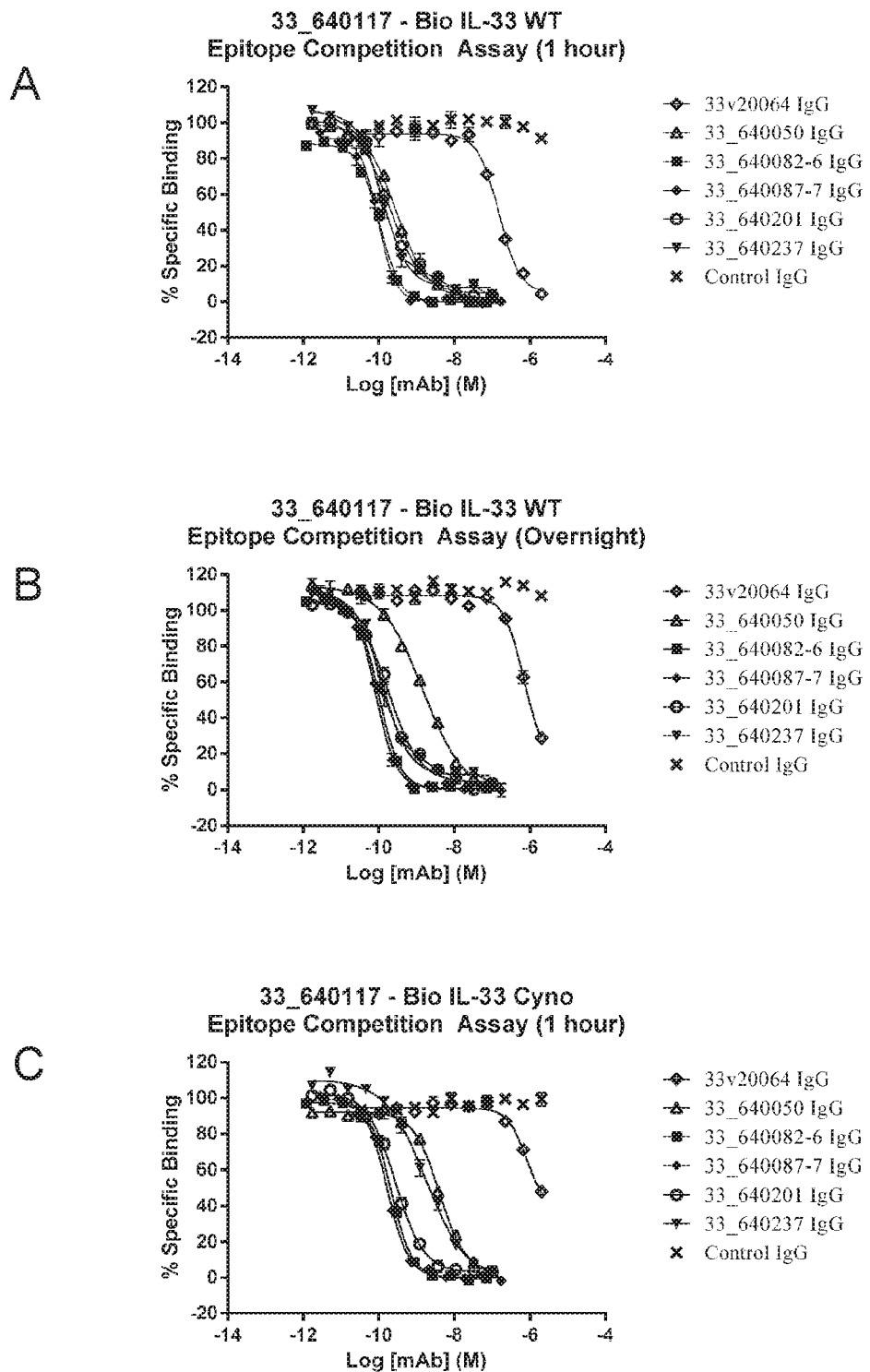
FIG. 44 Shows the inhibition of the FRET signal, produced by biotinylated human IL-33 after 1 hour incubation (FIG. 44A) or after overnight incubation (FIG. 44B), or cynomolgus IL-33 binding to 33_640117 mAb (FIG. 44C), with increasing concentrations of test proteins. Inhibition of the signal corresponds with relative binding affinity of 33v20064 to the test protein.

Data for antibodies optimised for $V_H$ CDR3/$V_L$ CDR3 and $V_H$ CDR2 by rational recombination or population approaches are exemplified by 33_640082-6, 33_640087-7, 33_640201 and 33_640237 in FIGS. 44 and 45.

Inhibition of IL-33 Binding to mAb by Purified IgG

The ability of anti-IL-33 antibodies to inhibit the binding of biotinylated His Avi human IL-33 or cynomolgus His Avi IL-33 to the DyLight labelled 33_640117 IgG was assessed in a biochemical HTRF® (Homogeneous Time-Resolved Fluorescence, Cisbio International) competition assays as described above.

FIG. 44A shows inhibition of the FRET signal after 1 hour incubation, produced by biotinylated human IL-33 (IL33-01) binding to DyLight-labeled 33_640117 IgG with increasing concentrations of antibodies 33v20064, 33_640050, 33_640082-6, 33_640087-7, 33_640201 and 33_640237, wherein the x-axis is the concentration of antibody in molar concentration and the y-axis is percent specific binding.

FIG. 44B shows inhibition of the FRET signal after overnight incubation, produced by biotinylated human IL-33 (IL33-01) binding to DyLight-labeled 33_640117 IgG with increasing concentrations of antibodies 33v20064, 33_640050, 33_640082-6, 33_640087-7, 33_640201 and 33_640237, wherein the x-axis is the concentration of antibody in molar concentration and the y-axis is percent specific binding.

FIG. 44C shows inhibition of the FRET signal after 1 hour incubation, produced by biotinylated cynomolgus His Avi IL-33 binding to DyLight-labeled 33_640117 IgG with increasing concentrations of antibodies 33v20064, 33_640050, 33_640082-6, 33_640087-7, 33_640201 and 33_640237, wherein the x-axis is the concentration of antibody in molar concentration and the y-axis is percent specific binding.

TABLE 32

IC50 values of IgG1 antibodies in 117 epitope competition assays

| | IC50 (nM) | | |
|---|---|---|---|
| Antibody | 117-WT 1 hour | 117-WT Overnight | 117-cyno 1 hour |
| 33v20064 IgG | 150 | 689 | 788 |
| 33_640050 IgG | 0.3 | 1.5 | 4.1 |
| 33_640076-4 IgG | 0.1 | 0.1 | 0.6 |
| 33-640081 IgG | 0.3 | 0.6 | 10 |
| 33_640082-6 IgG | 0.1 | 0.1 | 0.2 |
| 33_640082-7 IgG | 0.1 | 0.1 | 0.2 |
| 33_640084-2 IgG | 0.3 | 0.3 | 0.8 |
| 33_640086-6 IgG | 0.1 | 0.1 | 0.2 |
| 33_640087-7 IgG | 0.1 | 0.1 | 0.2 |
| 33_640201 IgG | 0.2 | 0.2 | 0.3 |
| 33_640237 IgG | 0.1 | 0.1 | 1.8 |

Inhibition of IL-8 Production in Huvec by IgG

IgGs were tested in a Huvec IL-8 production assay. Cells were exposed to N-terminal His Avi IL-33 (IL33-01, SEQ ID NO 632) or mammalian full length IL-33 cell lysate (FL-IL33 lysate) in the presence or absence of test antibody as previously described. $IC_{50}$ values were calculated and are summarized in Table 33 below.

FIG. 45A shows HUVECs stimulated with IL33-01 in the presence of test antibodies 33_640050, 33_640082-6, 33_640087-7, 33_640201 and 33_640237, wherein the x-axis is the concentration of antibody in molar concentration and the y-axis is a percentage of the maximum response (IL-8 production).

FIG. 45B shows HUVECs stimulated with full length IL-33 cell lysate in the presence of test antibodies 33_640050, 33_640082-6, 33_640087-7, 33_640201 and 33_640237, wherein the x-axis is the concentration of antibody in molar concentration and the y-axis is a percentage of the maximum response (IL-8 production).

TABLE 33

IC50 values in the Huvec IL-8 assay

| | IC50 (nM) | |
|---|---|---|
| Antibody | vs. His Avi IL-33 | vs. full length IL-33 cell lysate |
| 33_640076-4 | 0.032 | 0.095 |
| 33_640082-6 | 0.030 | 0.097 |
| 33_640082-7 | 0.031 | 0.095 |
| 33_640084-2 | 0.036 | 0.132 |
| 33_640086-6 | 0.026 | 0.081 |
| 33_640087-7 | 0.025 | 0.073 |
| 33_640201 | 0.046 | 0.101 |
| 33_640237 | 0.056 | 0.091 |

Germlining IGLJ Sequence

The amino acid sequences of the $V_L$ framework regions of antibodies 33_640076-4, 33_640081-A, 33_640082-6, 33_640082-7, 33_640084-2, 33_640086-6, 33_640087-7, 33_640201-2 and 33_640237-2 were aligned to known human IGLJ germline sequences in the IMGT database (Lefranc, M. P. et al. *Nucl. Acids Res.* 2009. 37(Database issue): D1006-D1012), and the closest germline was identified by sequence similarity. For all of these antibodies this was IGLJ2, which has a single amino acid difference to the antibodies at position 104 of the $V_L$ region (Kabat numbering). This residue was reverted to germline as described in Example 3 using standard molecular biology methods. The resulting antibodies were named 33_640076-4B, 33_640081-AB, 33_640082-6B, 33_640082-7B, 33_640084-2B, 33_640086-6B, 33_640087-7B, 33_640201-2B and 33_640237-2B corresponding to their parental lineage of 33_640076-4, 33_640081-A, 33_640082-6, 33_640082-7, 33_640084-2, 33_640086-6, 33_640087-7, 33_640201-2 and 33_640237-2 respectively. The SEQ IDs of the $V_H$ and $V_L$ regions of these antibodies are shown in Table 34.

TABLE 34

Sequences of germlined IL33 antibodies

| IgG1 | VH Sequence | VL Sequence |
|---|---|---|
| 33_640076-4B | SEQ ID NO: 592 | SEQ ID NO: 594 |
| 33_640081-AB | SEQ ID NO: 596 | SEQ ID NO: 598 |
| 33_640082-6B | SEQ ID NO: 600 | SEQ ID NO: 602 |
| 33_640082-7B | SEQ ID NO: 604 | SEQ ID NO: 606 |

TABLE 34-continued

Sequences of germlined IL33 antibodies

| IgG1 | VH Sequence | VL Sequence |
|---|---|---|
| 33_640084-2B | SEQ ID NO: 608 | SEQ ID NO: 610 |
| 33_640086-6B | SEQ ID NO: 612 | SEQ ID NO: 614 |
| 33_640087-7B | SEQ ID NO: 616 | SEQ ID NO: 618 |
| 33_640201-2B | SEQ ID NO: 620 | SEQ ID NO: 622 |
| 33_640237-2B | SEQ ID NO: 624 | SEQ ID NO: 626 |

Example 9 In Vivo Airway Inflammation Model

Cloning, Expression and Purification of IL-33 Cytokine Trap

Protein sequences for mouse IL-1RAcP and mouse ST2 were obtained from Swiss Prot (accession numbers Q61730 and P14719 respectively). Mouse IL-33 cytokine trap was designed based on Economides et al 2003 and consisted of amino acids 1-359 Q61730 and amino acids 27-332 P14719 fused to the Fc portion of human IgG1. Protein sequences were codon optimised (Geneart) and cloned into pDEST12.2 OriP proteins were secreted from cells into the media utilizing the native signal peptides from IL-1RAcP. For expression in CHO cells, the gateway linker was removed by overlapping primer PCR. Trap expression vector was transfected into CHO-transient mammalian cells. Mouse IL-33 trap was expressed and secreted into the medium. Harvests were pooled and filtered prior to purification using Protein A chromatography. Culture supernatants were loaded onto a 5 ml Hitrap Protein A column (GE Healthcare) and washed with 1×DPBS, bound Trap was eluted from the column using 0.1 M Sodium Citrate (pH 3.0) and neutralized by the addition of Tris-HCl (pH 9.0). The eluted material was further purified by SEC in 1×DPBS using a S200 16:600 Superdex column (GE healthcare) and the concentration determined spectrophotometrically using an extinction coefficient based on the amino acid sequence (Mach et al., *Anal. Biochem.* 200(1):74-80 (1992)).

Humanized IL-33 Mice

Methods for generation of humanized IL-33 mice have been previously described in Example 4. The humanized mice are used in models of airways and/or allergic inflammation to assess the effect of anti-human IL-33 antibodies.

In Vivo Airway Inflammation Model

Models of *Alternaria alternata* (ALT) induced airway inflammation in mice have been previously described (Kouzaki et al. *J. Immunol.* 2011, 186: 4375-4387; Bartemes et al *J Immunol*, 2012, 188: 1503-1513). Endogenous IL-33 is released rapidly following ALT exposure and drives IL-33-dependent IL-5 production and eosinphilia in the lung. Male or female wildtype or humanized IL-33 mice (6-10 weeks) were anaesthetized briefly with isofluorane and administered either 25 µg of ALT extract (Greer, Lenoir, N.C.) or vehicle intranasally in a total volume of 50 µl. Mice were treated intraperitoneally or intranasally with test substances: IL330004 IgG (SEQ ID Nos. 12 and 17), H338L293 IgG (SEQ ID Nos. 182 and 187), mouse IL-33 Trap, 33_640050 (SEQ ID nos. 302 and 307), isotype control IgG (NIP228) or vehicle (PBS, 10 ml/kg) at 24 hours prior (for intraperitoneal treatment) or 2 hours prior (for intranasal treatment) to intranasal challenge with ALT. At 24 hours after challenge, mice were terminally anaesthetised with pentobarbital sodium prior to exsanguination and bronchoalveolar lavage (BAL). Bronchoalveolar lavage fluid (BALF) was collected by lavage (0.3 ml, 0.3 ml & 0.4 ml) via tracheal cannula. BALF was centrifuged, cells counted (total cells by FACS (FacsCALIBER, BD)) and supernatant was analysed for cytokines by ELISA (Meso Scale Discovery, Rockville, Md.). Differential cell counts (200 cells/slide) were performed on cytospin preparations stained with Diff-Quik (Fisher Scientific, UK). All work was carried out to UK Home Office ethical and husbandry standards under the authority of an appropriate project licence.

Figure 46:
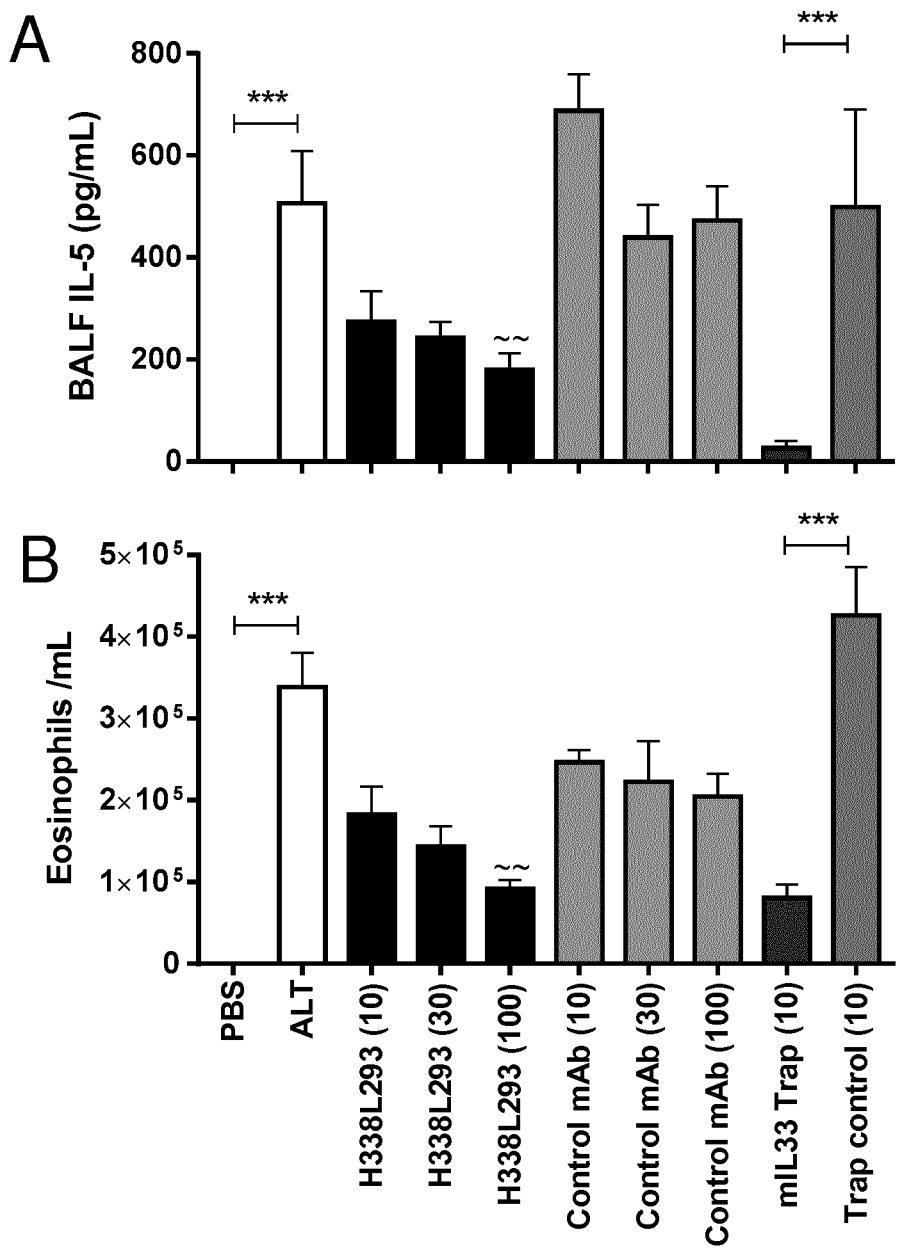
FIG. 46 Shows that H338L293 dose-dependently inhibits *Alternaria* (ALT)-induced BAL IL-5 and eosinophilia in wild type BALB/c mice. Test substances were dosed intranasally (10, 30 or 100 mg/kg as indicated in brackets) at −2 hours prior to challenge with 25 ug of ALT. BALF was harvested at 24 hours post ALT challenge and analysed for presence of IL-5 (FIG. 46A) and eosinophils (FIG. 46B). Significant effect of test substances was determined using one-way ANOVA with Bonferroni's multiple comparisons test. ***p<0.001, ~~p<0.01 compared to control mAb (n=4-8). Mouse IL-33 Trap was used as a positive control.

FIG. 46 shows that H338L293 dose-dependently inhibits ALT-induced BAL IL-5 and eosinophilia in wild type BALB/c mice. Test substances were dosed intranasally (10, 30 or 100 mg/kg as indicated in brackets) at −2 hours prior to challenge with 25 ug of ALT. BALF was harvested at 24 hours post ALT challenge and analysed for presence of IL-5 (FIG. 46A) and eosinophils (FIG. 46B). Significant effect of test substances was determined using one-way ANOVA with Bonferroni's multiple comparisons test. ***$p<0.001$, --$p<0.01$ compared to control mAb (n=4-8). Mouse IL-33 Trap was used as a positive control.

Figure 47:
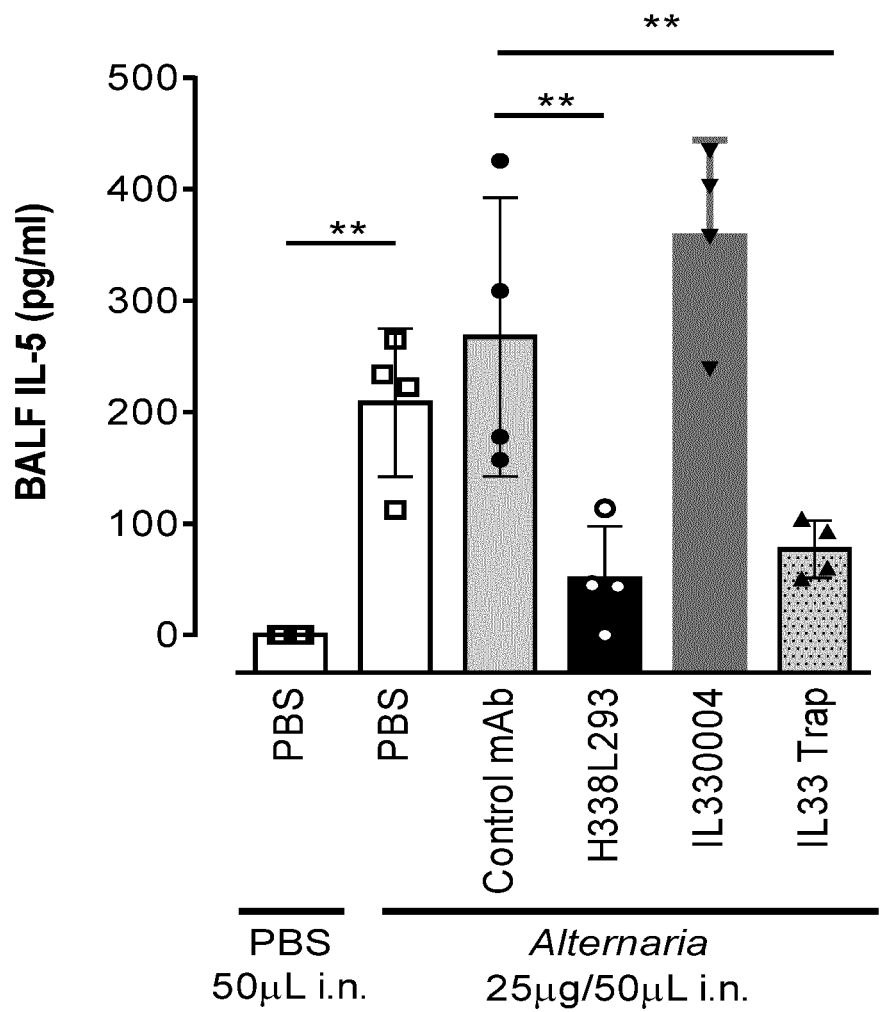
FIG. 47 Shows that H338L293 (30 mg/kg) and mouse IL-33 Trap (10 mg/kg), but not IL330004 (30 mg/kg), inhibit ALT-induced BAL IL-5 in humanized 1L-33 mice. Test substances were dosed intranasally at −2 hours prior to challenge with 25 ug of ALT. BALF was harvested at 24 hours post ALT challenge and analysed for presence of IL-5. Significant effect of test substances was determined using one-way ANOVA with Bonferroni's multiple comparisons test. *p<0.001, p<0.01 (n=4).

FIG. 47 shows that H338L293 (30 mg/kg) and mouse IL-33 Trap (10 mg/kg), but not IL330004 (30 mg/kg), inhibit ALT-induced BAL IL-5 in humanized IL-33 mice. Test substances were dosed intranasally at −2 hours prior to challenge with 25 ug of ALT. BALF was harvested at 24 hours post ALT challenge and analysed for presence of IL-5. Significant effect of test substances was determined using one-way ANOVA with Bonferroni's multiple comparisons test. *$p<0.001$, $p<0.01$ (n=4).

Figure 48:
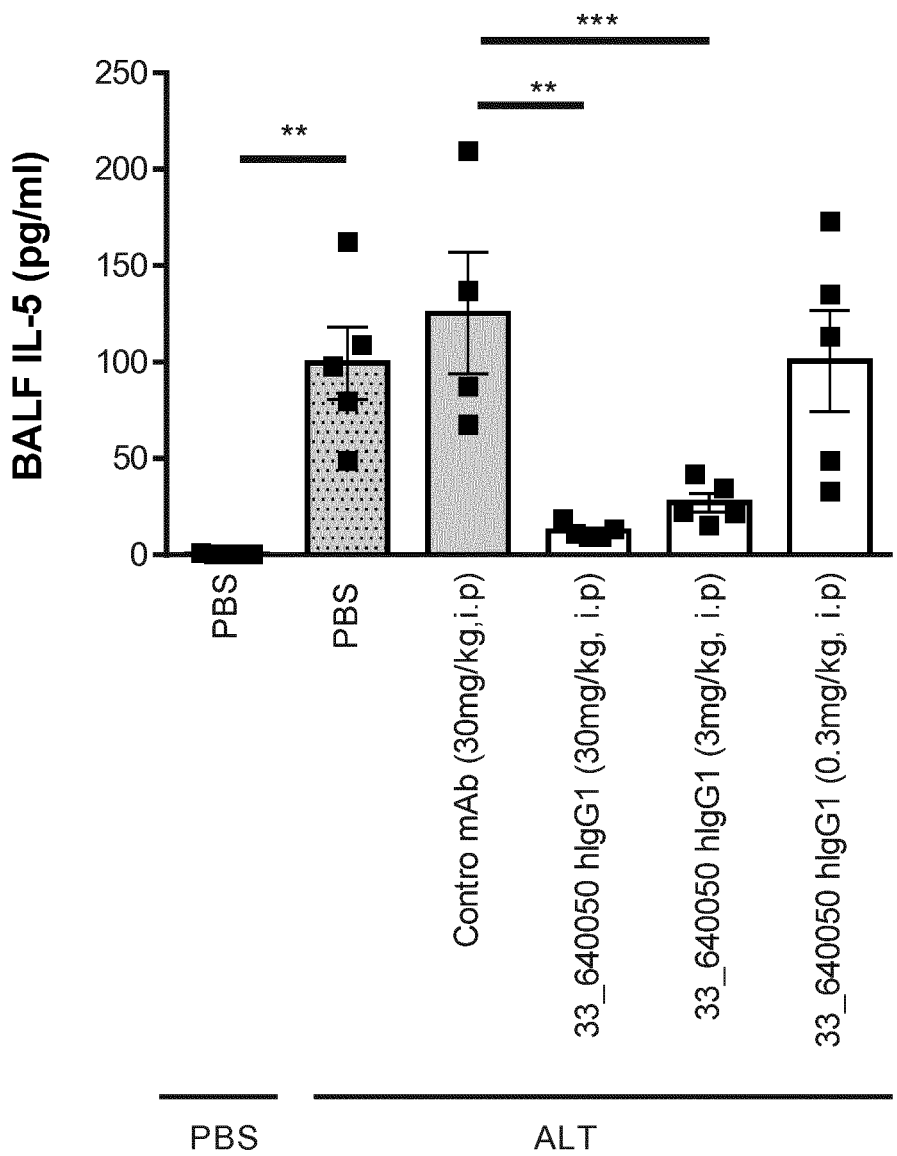
FIG. 48 Shows that 33_640050 dose dependently inhibits *Alternaria*-induced BAL IL-5 in humanized IL-33 mice. Test substances were dosed intraperitoneally (0.3, 3 or 30 mg/kg as indicated in brackets) at −24 hours prior to challenge with 25 ug of *Alternaria*. BALF was harvested at 24 hours post ALT challenge and analysed for presence of IL-5. Significant effect of test substances was determined using one-way ANOVA with Bonferroni's multiple comparisons test. *p<0.001, p<0.01 (n=4-5).

FIG. 48 shows that 33_640050 dose dependently inhibits *Alternaria*-induced BAL IL-5 in humanized IL-33 mice. Test substances were dosed intraperitoneally (0.3, 3 or 30 mg/kg as indicated in brackets) at −24 hours prior to challenge with 25 ug of *Alternaria*. BALF was harvested at 24 hours post ALT challenge and analysed for presence of IL-5. Significant effect of test substances was determined using one-way ANOVA with Bonferroni's multiple comparisons test. *$p<0.001$, $p<0.01$ (n=4-5).

Example 10 Characterization of Anti-IL-33 Antibodies

Inhibition of IL-33 Binding to ST2 by Purified IgG

The ability of anti-IL-33 antibodies to inhibit the binding of biotinylated IL33-01 to the FLAG®-His tagged ST2 receptor was assessed in a biochemical HTRF® (Homogeneous Time-Resolved Fluorescence, Cisbio International) competition assay, the principles of which are described above. Activity of purified IgG preparations were determined by competing a dilution series of the purified IgG against human FLAG®-His tagged ST2 for binding to human biotinylated human IL33-01 (SEQ ID No. 632).

Figure 49:
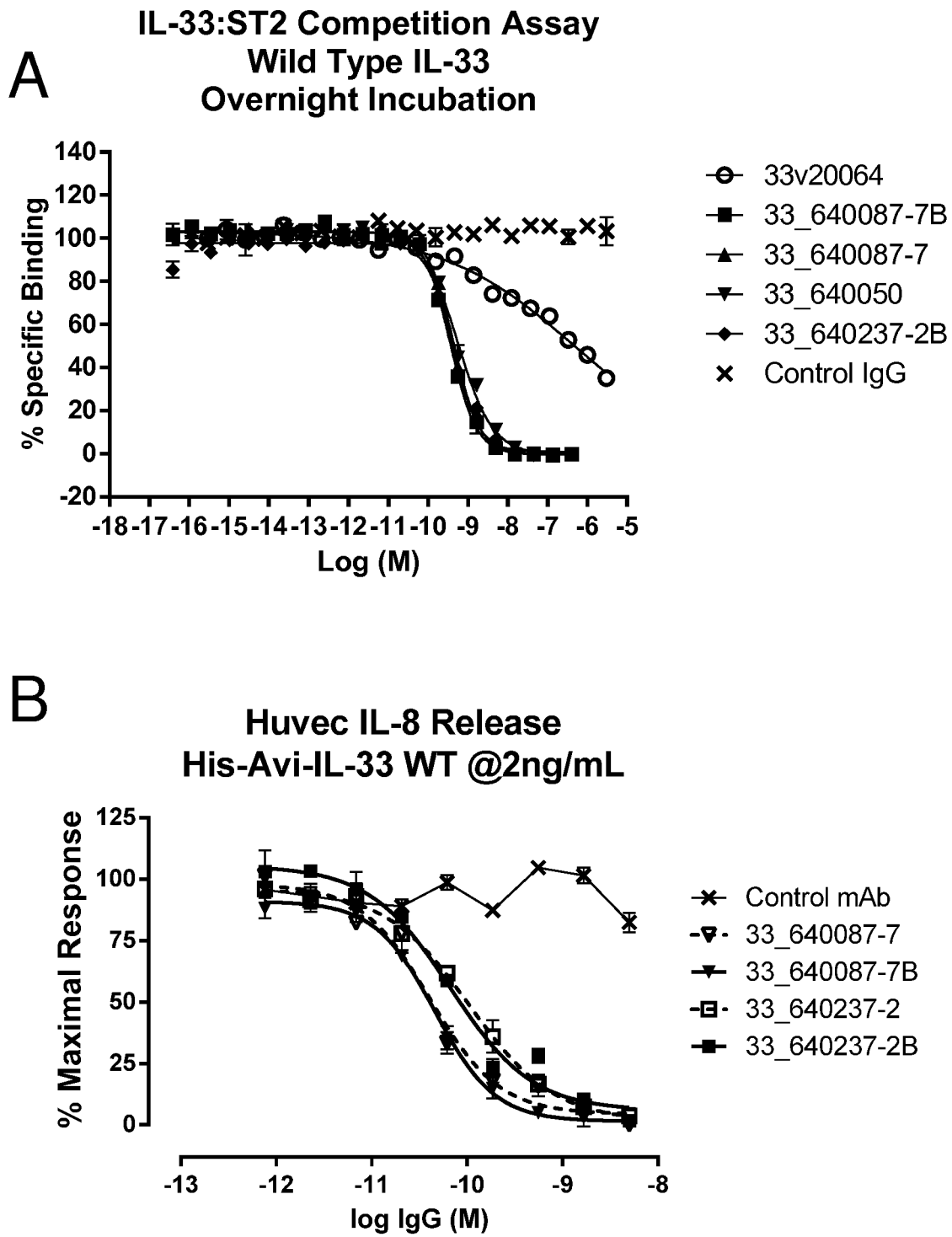
FIG. 49A Shows effect of antibodies in an IL33-ST2 FRET binding assay.
FIG. 49B Shows effect of antibodies on IL-33 stimulated IL-8 release from Huvecs.

FIG. 49A: shows the inhibition of the FRET signal after overnight incubation, produced by human IL-33 binding to human ST2 with increasing concentrations of antibodies 33v20064, 33_640087-7, 33_640087-7B, 33_640050 and 33_640237-2B, wherein the x-axis is the concentration of antibody in molar concentration and the y-axis is percent specific binding.

Inhibition of IL-8 Production in Huvec by IgG

IgGs were tested in a Huvec IL-8 production assay. Cells were exposed to N-terminal His Avi IL-33 (IL33-01, SEQ ID NO 632) in the presence or absence of test antibody as previously described. $IC_{50}$ values were calculated and are summarized in Table 35 below. Data shows that germlining of the IGLJ Sequence did not have any effect on antibody potency.

FIG. 49B shows HUVECs stimulated with IL33-01 in the presence of test antibodies 33_640087-7, 33_640087-7B, 33_640237-2 and 33_640237-2B, wherein the x-axis is the concentration of antibody in molar concentration and the y-axis is a percentage of the maximum response (IL-8 production).

TABLE 35

IC50 values in the Huvec IL-8 assay

| Antibody | IC50 (nM) vs. His Avi IL-33 |
| --- | --- |
| 33_640087-7 | 0.041 |
| 33_640087-7B | 0.046 |
| 33_640237-2 | 0.105 |
| 33_640237-2B | 0.067 |

Selectivity and Cross-Reactivity of Anti-IL-33 Antibodies

Selectivity and cross-reactivity of germlined anti-IL-33 antibodies was determined using a homogeneous FRET (fluorescence resonance energy transfer) HTRF® (Homogeneous Time-Resolved Fluorescence, Cisbio International) based IL-33:mAb-binding assay. In this assay, samples competed with biotinylated human IL-33-01 (SEQ ID No. 632) for binding to DyLight labelled 33_640087-7B IgG (SEQ ID Nos. 618 and 618) or 33_640237-2B IgG (SEQ ID Nos. 624 and 626).

Human, cyno and mouse IL-33 FLAG®His (described in Example 1 and Table 21), Human IL-1 alpha and IL-1 beta (R&D Systems) (Table 21) or rat IL-33 (GenScript) were tested for inhibition of human IL-33 binding to DyLight650 labelled 33_640087-7B or DyLight650 labelled 33_640237-2B by adding 5 microlitres of each dilution of sample to a 384 well low volume assay plate (Costar, 3673). Next, a solution containing 1.2 nM DyLight650 labelled 33_640087-7B or 33_640237-2B was prepared and 2.5 microlitres added to the assay plate (labelled using kit (Innova Biosciences, 326-0010) as per manufacturer's instructions). This was followed by the addition of 2.5 microlitres of a solution containing 0.12 nM biotinylated human IL-33-01 combined with 0.75 nM streptavidin cryptate detection (Cisbio International, 610SAKLB). All dilutions were performed in assay buffer containing 0.8 M potassium fluoride (VWR, 26820.236) and 0.1% bovine serum albumin (BSA, PAA, K05-013) in Dulbeccos PBS (Invitrogen, 14190185). Assay plates were incubated for 4 hours at room temperature followed by 18 hours at 4 degrees Celsius and time resolved fluorescence was read at 620 nm and 665 nm emission wavelengths using an EnVision plate reader (Perkin Elmer). Data were analysed by calculating the 665/620 nm ratio followed by the % Delta F values for each sample. The 665/620 nm ratio was used to correct for sample interference using Equation 1. The % Delta F for each sample was then calculated using Equation 2. The negative control (non-specific binding) was defined by replacing biotinylated human IL-33 combined with streptavidin cryptate detection with streptavidin cryptate detection only. The % Delta F values were subsequently used to calculate % specific binding as described in Equation 3. $IC_{50}$ values were determined using GraphPad Prism software by curve fitting using a four-parameter logistic equation (Equation 4). These results demonstrated that 33_640087-7B and 33_640237-2B cross react with cynomolgus IL-33 but not mouse IL-33, rat IL-33, human IL-1 alpha or human IL-1 beta.

FIG. 50A: shows the inhibition of the FRET signal, produced by biotinylated human IL-33-01 binding to DyLight labelled 33_640087-7B (SEQ ID Nos. 618 and 618), with increasing concentrations of test proteins, wherein the x-axis is the concentration of test sample in molar concentration and the y-axis is percent specific binding. Inhibition of the FRET signal was observed with human and cynomolgus, but not mouse or rat IL-33, human IL-1 alpha or human IL-1 beta.

FIG. 50B: shows the inhibition of the FRET signal, produced by biotinylated human IL-33-01 binding to DyLight labelled 33_640237-2B (SEQ ID Nos. 624 and 626), with increasing concentrations of test proteins, wherein the x-axis is the concentration of test sample in molar concentration and the y-axis is percent specific binding. Inhibition of the FRET signal was observed with human and cynomolgus, but not mouse or rat IL-33, human IL-1 alpha or human IL-1 beta.

Neutralisation of Endogenous IL-33 in the HUVEC IL-8 Assay

Figure 51:
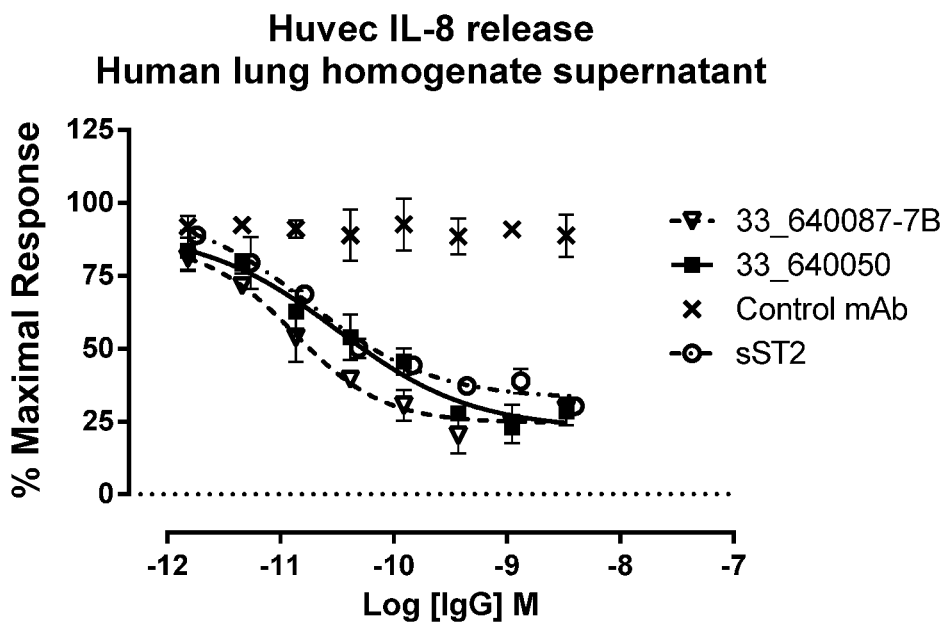
FIG. 51 Shows effect of antibodies on IL-8 release from Huvecs stimulated by human lung lysate.

In order to determine whether antibodies were able to neutralize endogenous IL-33, human lung tissue was used to provide a source of endogenous IL-33 protein. The study was approved by the NRES East of England (Cambridge East) Research Ethics Committee (reference number 08/H0304/56Þ5) and tissue was donated with the informed consent of patients. Non-cancerous adjacent tissue from lung cancer patients and from lung transplant surgeries were supplied in Aqix RS-I medium (Aqix Ltd) on ice by Papworth Hospital NHS Trust Research Tissue Bank. Tissue was diluted with 400 mg/mL in PBS and homogenized for 30 seconds using a tissue homogenizer. Cell debris was removed by centrifugation. HUVECs were stimulated with lung lysates at varying concentrations. An $EC_{50}$ concentration of lysate that stimulated IL-8 release was selected for antibody neutralization studies. Cells were exposed to lung lysate in the presence or absence of test antibody as previously described. sST2 inhibited the IL-8 response by a maximum of approximately 70%, suggesting that most, but not all, of the IL-8 production was driven by endogenous IL-33 within the lung lysate. 33_640050 and 33_640087-7B IgG inhibited the IL-8 response to a similar extent as sST2, demonstrating their ability to bind and neutralize endogenous IL-33. 33_640050 IgG neutralized the lung lysate with an IC50 of 0.032 nM. 33_640087-7B neutralized the lung lysate with an $IC_{50}$ of 0.013 nM. sST2 neutralized the lung lysate with an IC50 of 0.019 nM FIG. 51 shows HUVECs stimulated with human lung lysate in the presence of test antibodies 33_640050 and 33_640087-7B in comparison with sST2, wherein the x-axis is the concentration of antibody in molar concentration and the y-axis is a percentage of the maximum response (IL-8 production). sST2 inhibited the IL-8 response by a maximum of approximately 70%, suggesting that most, but not all, of the IL-8 production was driven by endogenous IL-33 within the lung lysate. Both antibodies inhibited the IL-8 response to a similar extent as sST2, demonstrating their ability to bind and neutralize endogenous IL-33.

In Vivo Airway Inflammation Model

Methods for generation of humanized IL-33 mice have been previously described in Example 4. Humanized mice were used in a model of *Alternaria alternata* (ALT) induced airway inflammation as described in Example 9 to assess the effect of 33_640087-7B. Male or female wild type or humanized IL-33 mice (6-10 weeks) were anaesthetized briefly with isofluorane and administered either 25 µg of ALT extract (Greer, Lenoir, N.C.) or vehicle intranasally in a total volume of 50 µl. Mice were treated intraperitoneally with test substances: 33_640087-7B IgG (SEQ ID Nos. 618 and 618), isotype control IgG (NIP228) or vehicle (PBS, 10 ml/kg) at 24 hours prior to intranasal challenge with ALT. At 24 hours after challenge, mice were terminally anaesthetised with pentobarbital sodium prior to exsanguination and bronchoalveolar lavage (BAL). Bronchoalveolar lavage fluid (BALF) was collected by lavage (0.3 ml, 0.3 ml & 0.4 ml) via tracheal cannula. BALF was centrifuged and supernatant was analysed for cytokines by ELISA (Meso Scale Discovery, Rockville, Md.). All work was carried out to UK Home Office ethical and husbandry standards under the authority of an appropriate project licence.

Figure 52:
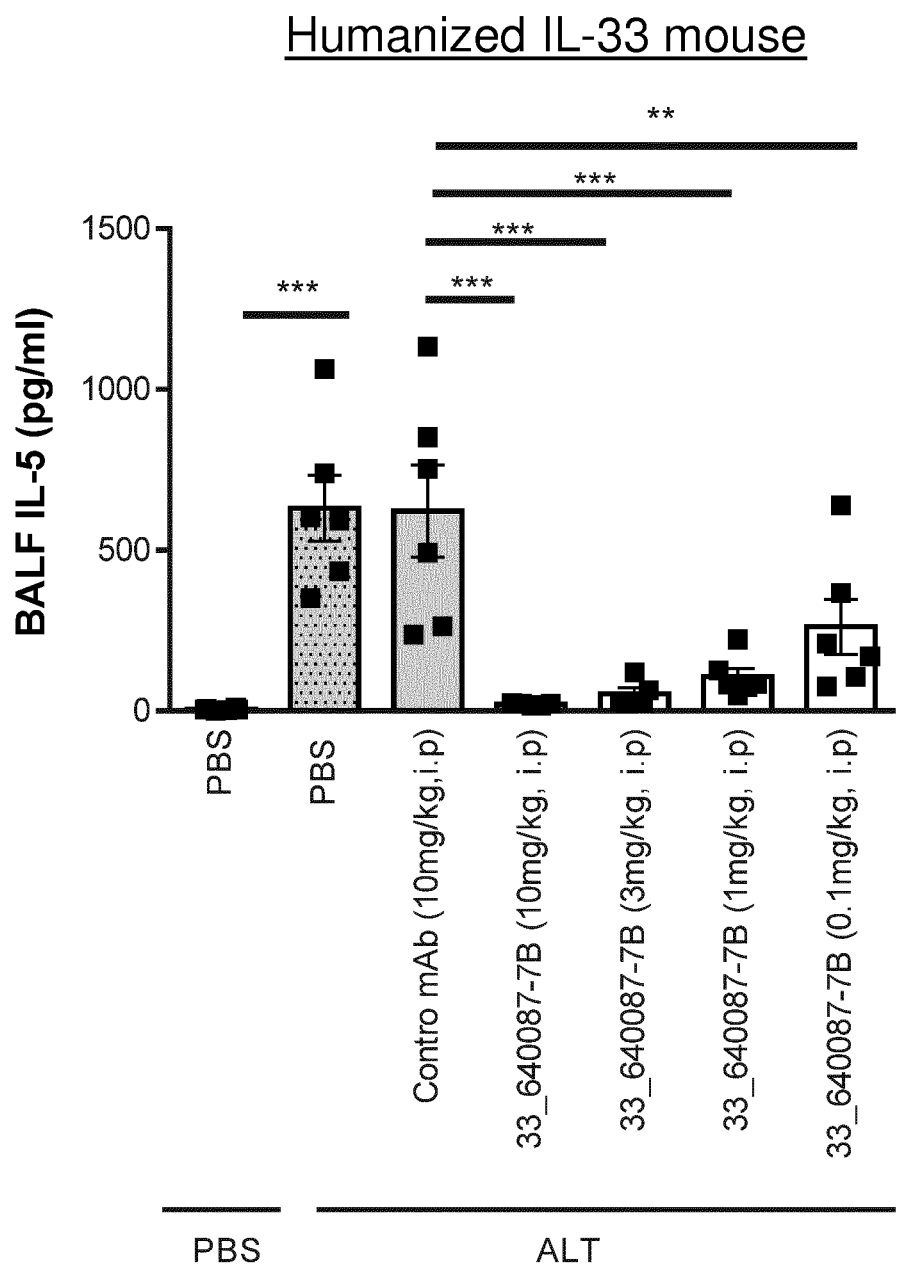
FIG. 52 Shows that 33_640087-7B dose dependently inhibits *Alternaria*-induced BAL 1L-5 in humanized IL-33 mice.

FIG. 52 shows that 33_640087-7B dose dependently inhibits *Alternaria*-induced BAL IL-5 in humanized IL-33 mice. Test substances were dosed intraperitoneally (0.1, 1, 3 or 10 mg/kg as indicated in brackets) at −24 hours prior to challenge with 25 ug of *Alternaria*. BALF was harvested at 24 hours post ALT challenge and analysed for presence of IL-5. Significant effect of test substances was determined using one-way ANOVA with Bonferroni's multiple comparisons test. *$p<0.001$, $p<0.01$ (n=5-6).

Example 11 Affinity of Anti-IL-33 Antibodies

The affinity of the anti-IL-33 antibody fragment (Fab) for recombinant human IL33 was determined using real time interaction monitoring by BIACORE™ and at equilibrium using KinExA™ for 33_640087-7B. For both methodologies the human IL33 protein was purified by SEC-HPLC to ensure quality of the antigen and also of the Fab for the biacore analysis.

Biacore Affinity Analysis

Fab fragments were generated by papain cleavage from full length IgG1 and purified by SEC. The affinity of the antibody fragment (Fab) was measured using the Biacore T100 at 25° C. Streptavidin was covalently immobilised to a C1 chip surface using standard amine coupling techniques at a concentration of 4 μg/ml in 10 mM Sodium acetate pH 4.5. Typical final streptavidin surface densities in the range 115-170 RUs were achieved. Recombinant, enzymatically biotinylated human IL-33 (produced in-house) was titrated onto the streptavidin chip surface at 4 μg/ml in HBS-EP+ buffer to enable ~30 RUs of Fab binding at saturation (Rmax). This low level of analyte binding ensured minimal mass transport effects.

The IL-33 Fab was serially diluted from 5 nM to 78 pM in HBS-EP+ buffer and flowed over the chip at 50 μl/min, with 3 minutes association and up to 30 minutes dissociation. Multiple buffer only injections were made under the same conditions to allow for double reference subtraction of the final sensorgram sets, which were analysed using the BiaEval software (version 2.0.1). The chip surface was fully regenerated with pulses of 3M $MgCl_2$.

The affinity of ST2-Flag-His10 (SEQ. ID no. 650) expressed in HEK-EBNA cells for human IL-33 was determined by BIACORE™ using the same methods described above.

KinExA Affinity Analysis

In order to confirm the high affinity found with the SPR assay we turned to Kinetic Exclusion Assays (KinExA). KinExA is increasingly finding favour for resolving higher-affinity protein:protein interactions, especially those in the pM to sub-pM ranges where surface based biosensor techniques reach their practical limits (Rathanaswami P, Roalstad S, Roskos L, Qiaojuan J S, Lackie S, Babcook J. *Demonstration of an in vivo generated sub-picomolar affinity fully human monoclonal antibody to interleukin-8*. Biochemical and Biophysical Research Communications. 2005; 334: 1004-1013).

The affinity of the antibody 33_640087-7B was measured by kinetic exclusion assays performed on the KinExA 3200. The sampling beads were prepared by mixing 200 mg of dry UltraLink Biosupport Azlactone beads with 110 μg of IL-33 (as mentioned previously) in 2.5 ml of 50 mM sodium hydrogen bicarbonate pH 8.4 at room temperature for 2 hours with constant agitation. The beads were rinsed and blocked with 10 mg/ml BSA in 1M Tris pH 8.7. Prior to use, the beads were resuspended into D-PBS, 0.02% sodium azide. 33_640087-7B/IL-33 equilibrium mixtures were prepared in sample buffer composed of 1 mg/ml BSA, 0.02% sodium azide in DPBS (Dulbecco's PBS). Two different IgG concentrations were used with varying IL-33 concentrations, 5 pM of 33_640087-7B with IL-33 serially diluted from 125 pM to 61 fM and 500 fM 33_640087-7B with IL-33 serially diluted from 62.5 pM to 15 fM, both were carried out with zero IL-33 controls. The fluorescent secondary detection reagent was Alexa Fluor 647 goat anti-human-Fc diluted in 1 mg/ml BSA, 0.02% sodium azide, 0.1% Tween 20 in DPBS. The samples were run on the KinExA whilst housed in a temperature controlled cabinet set at 25° C. The data was analysed using the KinExA Pro software version 4.1.11.

KinExA assays indicate that 33_640087-7B has a $K_D$ of <142 fM (femtomolar) for human IL-33 (Table 37).

TABLE 37

KinExA Affinity Results for 33_640087-7B IgG

| Analyte | Estimated $K_D$ (pM) | Upper 95% confidence interval $K_D$ (pM) | Lower 95% confidence interval $K_D$ (pM) |
|---|---|---|---|
| 33_640087-7B | 0.03 | 0.142 | undefined |

Example 12 Activity of Oxidized IL-33

In Vivo Pilot Study to Explore Activity of Oxidized IL-33

In Example 4 (see also Cohen, E. S. et al. *Oxidation of the alarmin IL-33 regulates ST2-dependent inflammation*. Nat. Commun. 6:8327 doi: 10.1038/ncomms9327 (2015)) we describe the discovery of an oxidized, disulphide bonded form of IL-33 (DSB IL-33) and showed that this form does

TABLE 36

Biacore Affinity Results for anti-IL-33 Fab

| Analyte | Fit setting | $k_a$ $(M^{-1}s^{-1})$ | $k_d$ $(s^{-1})$ | $K_D$ (pM) | $R_{max}$ | $Chi^2$ |
|---|---|---|---|---|---|---|
| 33_640001 Fab | Rmax global | 9.76E+6 | 3.26E−2 | 3340 | 27.0 | 0.022 |
| 33_640050 Fab | Rmax local | 3.08E+7 | 1.05E−4 | 3.4 | 48.9 | 0.022 |
| 33_640087-7B Fab | Rmax local | 2.20E+7 | 9.42E−6 | 0.43 | 30.7-32.8 | 0.010 |
| ST2-FH monomer | Rmax local | 1.52E+7 | 4.35E−5 | 2.9 | 23.4 | 0.022 | not bind ST2. To investigate if oxidized IL-33 had an alternative activity independent of ST2, ST2-deficient mice were treated intraperitoneally or intranasally with repeated doses of human IL-33 for 2, 4 or 6 weeks. Histological analysis was performed on multiple tissues.

ST2-deficient mice were generated as previously described (Townsend, M. J., Fallon, P. G., Matthews, D. J., John, H. E., and McKenzie, A. N. J. (2000). *T1/ST2-deficient mice demonstrate the importance of T1/ST2 in developing primary T helper cell type 2 responses. J. Exp. Med.* 191, 1069-1076). Female ST2-deficient mice (12 weeks) were anaesthetized briefly with isofluorane and administered either 10 μg of N-terminal His Avi IL-33 (IL33-01, SEQ ID NO 632; lot number CCH168, endotoxin levels 0.03 EU/mg), or vehicle (PBS) intranasally in a total volume of 50 μl. Alternatively, the IL-33 or vehicle was administered by i.p. injection. This process was repeated 3× weekly for a total 18 treatments. Mice that received only 2 or 4 weeks treatment with IL-33 were administered PBS for the first 4 or 2 weeks of dosing, prior to receiving IL-33.

At 24 hours after the last treatment, mice were terminally anaesthetised with pentobarbital sodium prior to exsanguination and bronchoalveolar lavage (BAL). Blood was collected by cardiac bleed using an EDTA flushed syringe. Blood haematology was done using Sysmex XTVet haematology analyser. The remaining blood was centrifuged and plasma extracted. Bronchoalveolar lavage fluid (BALF) was collected by lavage (0.3 ml, 0.3 ml & 0.4 ml) via tracheal cannula. BAL cells were counted (BAL total cells by flow-cytometer (MACSquant, Miltenye Biotec) and BALF was centrifuged to separate supernatant, that was analysed for cytokines by ELISA (Meso Scale Discovery, Rockville, Md.). Differential cell counts (200 cells/slide) were performed on cytospin preparations stained with Diff-Quik (Fisher Scientific, UK). Following PBS lavage lungs were inflated with 10% neutral buffered formalin (NBF) via a tracheal infusion to maintain lung architecture and immerse-fixed in NBF for 24-48 hours. Fixed lung samples were then cut transversely into 4 equal cross-sections before being processed through a series of alcohols, xylene and into paraffin wax. Finally the lung cross-sections were then embedded into paraffin wax blocks. 4 μm histological sections were cut and stained with haematoxylin and eosin (H&E) for analysis and inflammation scoring assessment.

All work was carried out to UK Home Office ethical and husbandry standards under the authority of an appropriate project licence.

To investigate IL-33 exposure via intraperitoneal or intranasal routes, human IL-33 was measured in BALF and plasma using Millipore human IL-33 assay (Cat # HTH17MAG-14K lot 2159117) as described in Example 4. Ability of sST2-Fc to reduce the assay signal was used to determine the presence of ST2-binding (reduced) vs non-ST2-binding (oxidized) IL-33. Following intranasal administrations, IL-33 was consistently detected in BALF and plasma at 2, 4 and 6 week endpoints. The majority of the IL-33 detected was oxidised. Following a single intraperitoneal administration, IL-33 was detected transiently in the plasma 5 hours after dosing but was undetectable by 24 hours. Following repeated IL-33 administrations, human IL-33 was not consistently detected in BALF or plasma at the 2, 4 or 6 week endpoints. These data indicated that the best systemic exposure of oxidized IL-33 is achieved through intranasal dosing.

FIG. 53A. Experimental design of in vivo pilot study. ST2-deficient mice were treated intraperitoneally or intranasally with repeated administration of human IL-33 or vehicle (PBS) for 6 weeks (n=3-4 per group). Tissues, BALF and serum were collected 24 hours following the final IL-33 administration.

FIG. 53B. Analysis of human IL-33 exposure in BAL fluid following repeated administration of human IL-33 to BALB/c mice. Human IL-33 was measured in BALF from mice treated as described in FIG. 53A, wherein the x-axis shows the treatment group and the y-axis shows the human IL-33 assay signal in arbitrary units. IL-33 was only detected in BALF after intra-nasal dosing. The IL-33 detected was found to be predominantly oxidized (non-ST2 binding).

FIG. 53C Analysis of IL-33 exposure in plasma following a single intraperitoneal administration of human IL-33 (10 ug). Human IL-33 was measured in plasma at 2, 5, 24 and 48 hours after administration, wherein the x-axis shows the time point of analysis and the y-axis shows the human IL-33 assay signal in arbitrary units. IL-33 was detected transiently in the plasma 5 hours after dosing but was undetectable by 24-48 hours.

FIG. 53D Analysis of IL-33 exposure in plasma following repeated administration of human IL-33 to BALB/c mice. Human IL-33 was measured in plasma from mice treated as described in FIG. 53A, wherein the x-axis shows the treatment group and the y-axis shows the human IL-33 assay signal in arbitrary units. IL-33 was only detected in plasma after intra-nasal dosing. The IL-33 detected was found to be predominantly oxidized (non-ST2 binding).

Histological analysis was performed on multiple tissues. No relevant abnormalities in human IL-33 treated mice compared to controls in liver, brain, spleen, skin, stomach, lymph node or heart. In the lung, increased lymphocytic perivascular inflammation was present in IL-33 treated mice compared to controls only in the intranasal group and only after 6 weeks of treatment. This is consistent with the highest exposure to oxidized IL-33 (FIG. 53). In conclusion, the treatment of ST2 KO mice with IL-33 increases the presence of perivascular lymphocytic infiltrate in lungs of IL-33 treated mice compared to controls. This pathology may be mediated through oxidized IL-33.

FIG. 54A shows representative H&E stained paraffin sections of lung tissue from mice administered PBS intranasally for 6 weeks (n=3)

FIG. 54B shows representative H&E stained paraffin sections of lung tissue from mice administered IL-33 intranasally for 6 weeks (n=4).

Pathway Analysis of IL-33 Treated Mouse Lung

To gain insight into the pathways modulated by oxidized IL-33 in the mouse lung leading to the inflammatory response observed, microarray analysis was performed on lung tissue from 6 week PBS treated versus 6 week IL-33-treated animals.

Lung tissues from 7 ST2KO mice (3 dosed with PBS and 4 dosed with IL33-01 as described above) were collected and directly placed into 350 uL of RLT buffer (Qiagen #79216). Tissue was then disrupted using a Qiagen TissueLyser (Qiagen #85300) according to manufacturer's protocol and RNA was purified using the RNeasy Fibrous Tissue kit (Qiagen #74704). Purified RNA from this kit was then concentrated using RNeasy Micro Columns (Qiagen #74004) according to manufacturer's protocol. RNA was then amplified to single stranded DNA using Affymetrix's GeneChip WT Plus Reagent kit (Affymetrix #902513) and hybridised onto Mouse Transcriptome 1.0 (MTA1.0) genechips (Affymetrix #900720), washed in Affymetrix Fluidics Station and scanned on the Affymetrix Genechip Scanner 3000 7G. Data was then processed in Affymetrix Expression console. Data were analysed in Microsoft Excel and sorted for genes where at least 2 out of 4 IL33-treated mice had greater than ±1.2-fold change in signal from the control group average. The sorted gene list were converted to KEGG IDs using Biological Database Network (BioDB-net v2.1) and analysed in KEGG pathway analysis (www.kegg.jp; KEGG Mapper v2.5). The same genes that were analysed in KEGG pathway were also analysed using Ingenuity Pathway Analysis (IPA) (Qiagen). IPA analysis suggested pathways relating to cell cycle appeared modulated. Example genes are listed in Table 38.

TABLE 38

Genes modulated in ST2-deficient mice by intranasal IL-33 treatment

| | Gene Symbols |
|---|---|
| Upregulated genes relating to cell cycle (>1.2 average fold change) | HSPA1A, CEBP, CDKN1A, JUNB, AHCY, SOX2, MYC, ID2, HRAS, EGR1, WT1, JUND, COX4I1 |
| Downregulated genes relating to cell cycle (>-1.2 average fold change) | IL1A, HGF, ERG, ZEB1, P10, DMTF1, ARHGAP18, PLA2R1, NSMCE2, CAV1 |

Signaling of DSB IL-33 in Huvecs

To acertain whether a response to oxidized (DSB) human IL-33 could be observed on human cells, stimulation of human cells in vitro was explored. The mouse microarray analysis indicated activation of pathways relating to cell cycle and therefore p38 MAP Kinase and JAK-STAT signaling were investigated. Human umbilical vein endothelial cells (Huvecs) were cultured according to manufacturer's instructions and stimulated with reduced or DSB IL-33. Nuclear translocation of p-p38 MAPK or p-STAT5 was detected by immunofluorecence staining. Imaging and quantification of the nuclear staining intensity was performed on ArrayScan VTi HCS Reader (Cellomics). The assay was essentially the same as that described for NFkB p65/RelA nuclear translocation but with the following modifications.

For p-p38 MAPK assay, Huvecs were seeded at $1 \times 10^4/75$ μl/well in culture media [EBM-2 (Lonza, # CC-3156) with EGM-2 SingleQuot Kit Suppl. & Growth Factors (Lonza, # CC-4176)] into 96-well black walled, clear flat-bottomed Collagen I coated plates (Greiner #655956) and incubated at 37° C., 5% $CO_2$ for 18-24 hours. Test samples of reduced or DSB IL-33 (in duplicate) were diluted to the desired concentration in complete culture media in 96 well U-bottom polypropylene plates (Greiner, 650201) and 75 uL added to the Huvec plates to initiate the stimulation. Following 15 or 30 minute assay incubation at 37° C., cells were fixed for 15 minutes in 3.7% formaldehyde solution (by addition of 50 uL of 16% solution that had been pre-warmed to 37° C.). Fixative was aspirated and cells were washed twice with 100 μL/well of PBS. Cells were stained for p-p38 with Phospho-p38 antibody (Cell signaling #9211S) at 1:250 dilution. Briefly, cells were permeabilised for 15 minutes at room temperature, blocked for 15 minutes and stained for 1 hour with primary antibody solution in a volume of 50 μL. Plates were washed ×2 in blocking buffer and stained for 1 hour at room temperature with secondary antibody solution (DyLight 488-labelled goat anti-rabbit IgG; ThermoFisher Scientific #35552 at 1:400 dilution) and Hoechst nuclear stain (ThermoFisher Scientific #62249 at 1:10000 dilution). Plates were washed ×2 in PBS. Cells were stored in a final volume of 150 μL/well PBS and covered with a black, light-blocking seal (Perkin Elmer, #6005189) before reading on ArrayScan VTi HCS Reader. The intensity of nuclear staining was calculated using a suitable algorithm. Data were analysed using Graphpad Prism software.

For pSTAT5 assay, Huvecs were seeded at $1 \times 10^4/75$ μl/well in culture media [EBM-2 (Lonza, # CC-3156) with EGM-2 SingleQuot Kit Suppl. & Growth Factors (Lonza, # CC-4176)] into 96-well black walled, clear flat-bottomed Collagen I coated plates (Greiner, #655956) and incubated at 37° C., 5% $CO_2$ for 18-24 hours. Following this complete media was aspirated, the cells were washed 2× in 100 uL PBS/well, the PBS was aspirated and 75 uL of Starve media [EBM-2 (Lonza, # CC-3156) with pen/strep] was added to each well. Cells were then were incubated at 37° C., 5% $CO_2$ for 18 hours. Test samples of reduced or DSB IL-33 (in duplicate) were diluted to the desired concentration in starve media in 96 well U-bottom polypropylene plates (Greiner, 650201) and 75 uL added to the Huvec plates to initiate the stimulation. Following 15 or 30 minute assay incubation at 37° C., cells were fixed for 15 minutes in 3.7% formaldehyde solution (by addition of 50 uL of 16% solution that had been pre-warmed to 37° C.). Fixative was aspirated and cells were washed twice with 100 μL/well of PBS. Cells were stained for p-STAT5 with Phospho-STAT5 rabbit antibody C71E5 (Cell Signaling #9314S) at 1:250 dilution, which was detected as described above.

Reduced IL-33 triggered p-p38 MAPK signaling, which was lost upon oxidation to the DSB form (FIG. 55A), similar to that previously described for NFkB signaling (Examples 4-6). However DSB IL-33, but not reduced IL-33, triggered p-STAT5 signaling (FIG. 55B). Thus a clear switch in signaling pathway activation was observed upon conversion of human IL-33 from the reduced to the DSB form, suggesting that DSB IL-33 may have activity distinct of known IL-33 pathways.

To confirm the result from the nuclear translocation assays, IL-33 signaling was determined by Western blot analysis. Huvecs were stimulated as above with reduced or DSB IL-33 (3 ng/mL) for 15 minutes. Cells were then washed twice in ice cold PBS and lysed with 250 uL RIPA Buffer (Pierce #89901) containing HALT protease inhibitors (Pierce #78430). Samples were subjected to SDS-PAGE under reducing conditions. Samples were mixed 3:1 with 4× NuPAGE gel loading buffer (Invitrogen) and denatured at 90° C. for 3 minutes. Reduced samples contained 2% beta-mercaptoethanol. Samples were run on NuPAGE Novex 4-12% Bis-Tris mini gels (Invitrogen) with MOPS running buffer (Invitrogen) according to manufacturer's instructions. Proteins were transferred to Nitrocellulose membranes (Invitrogen cat. no. IB3010-02) and detected by western blotting with rabbit phospho-p38 MAPK antibody (Cell signaling #9211S), rabbit phospho-STAT5 antibody C71E5 (Cell Signaling #9314S) or rabbit p-JAK2 antibody (Cell Signaling #3771S). Primary antibodies were detected with anti-rabbit-HRP (Cell Signaling #7074) and visualized using ECL reagent (Thermo Scientific #34096).

FIG. 55A shows p-p38 MAPK nuclear translocation activity in Huvecs in response to reduced IL-33 or DSB IL-33 (IL33-01 pre-treated with IMDM media), wherein the x-axis shows the IL-33 concentration and the y-axis shows the nuclear translocation signal in arbitrary units. A concentration dependent signal was observed for reduced but not oxidized IL-33.

FIG. 55B shows p-STAT5 nuclear translocation in Huvecs in response to reduced IL-33 or DSB IL-33 (IL33-01 pre-treated with IMDM media), wherein the x-axis shows the IL-33 concentration and the y-axis shows the nuclear translocation signal in arbitrary units. A concentration dependent signal was observed for DSB but not reduced IL-33.

FIG. 55C. Western blot analysis of for p-p38 MAPK, p-JAK2 and p-STAT5 in Huvecs stimulated for 15 minutes with reduced IL-33 or DSB IL-33 (IL33-01 pre-treated with IMDM media). Activation of p-p38 MAPK was detected following stimulation with reduced but not DSB IL-33. Activation of p-JAK2 and p-STAT5 was detected following stimulation with DSB IL-33 but not reduced IL-33.

Signaling of DSB IL-33 is Mediated via the Receptor for Advanced Glycation End Products (RAGE)

To gain insight into the pathways modulated by DSB IL-33 in Huvecs, Huvecs were cultured as described previously, plated at 1×10$^6$ cells/well in a 6 well tissue culture treated plate (Nunc 140675). Following overnight incubation, cells were stimulated with DSB IL-33 for 2 or 6 hours. Cells were collected in 350 uL of RLT buffer (Qiagen #79216). RNA was purified using the RNeasy Micro Kit (Qiagen #74004) according to manufacturer's protocol. RNA was then amplified to single stranded DNA using Affymetrix's GeneChip WT Plus Reagent kit (Affymetrix #902513) and hybridised onto Human Genome U133A 2.0 (U133A 2.0) genechips (Affymetrix #900469), washed in Affymetrix Fluidics Station and scanned on the Affymetrix Genechip Scanner 3000 7G. Data was then processed in Affymetrix Expression console and sorted for genes with greater than ±1.8-fold change in signal from the untreated control. Very few gene expression changes were observed (Table 39). Nevertheless, the limited gene panel were analyzed using Ingenuity Pathway Analysis (IPA) (Qiagen), which suggested EIF2 signaling pathway at 2 hours and AGER signaling at 6 hours. Potentially these suggested scavenging/receptor for advanced glycation endproducts (RAGE) pathway activation.

TABLE 39

Genes modulated in DSB-IL-33 stimulated Huvecs.

| Timepoint | Gene Symbols Regulated genes >±1.8 fold change |
|---|---|
| 2 hours | EIF3F, RPL14, RPL38, RPL27A, RPL37A, RPS10, RPS27L |
| 6 hours | IFIT1, S100A8 |

The receptor for advanced glycation end-products (RAGE) is a multi-ligand receptor that belongs to the immunoglobulin superfamily, and recognizes a variety of ligands, including high-mobility group box 1 (HMGB-1), S100 family of proteins, advanced glycation end-products (AGE) and β-sheet fibrillar materials. It is thought to be involved in oxidative stress and has been linked to the pathogenesis of numerous diseases.

To assess whether DSB directly interacted with RAGE, an ELISA format was used to explore RAGE binding to reduced IL-33 versus DSB IL-33 (FIG. 56A). Reduced or DSB N-terminal His Avi IL-33 (IL33-01, SEQ ID NO 632) were biotinylated as described in Example 7. Streptavidin plates (Thermo Scientific, AB-1226) were coated with biotinylated antigen at 50 μg/ml in PBS and incubated at room temperature for 1 hour. Plates were washed 3× with PBS-T (PBS+1% (v/v) Tween-20) and blocked with 300 μl/well blocking buffer (PBS with 1% BSA (Sigma, A9576)) for 1 hour. Plates were washed 3× with PBS-T. RAGE-Fc (R&D Systems #1145-RG) was diluted in blocking buffer, added to the IL-33-coated or control (no IL-33) wells and incubated at room temperature for 1 hour. RAGE-Fc was detected with anti-human IgG HRP (Sigma, A0170) diluted 1:5000 in blocking buffer, 50 μl/well for 1 hour at room temperature. Plates were washed 3× with PBS-T and developed with TMB, 50 μl/well (Sigma, T0440). The reaction was quenched with 50 μl/well 0.1M H$_2$SO$_4$ before reading on an EnVision™ plate reader, or similar equipment, at 450 nm.

To further confirm the interaction of DSB IL-33 with RAGE, the ability of RAGE-Fc or anti-RAGE antibodies to inhibit the ST2-independent pSTAT5 signaling in Huvecs was evaluated. To this purpose, varying concentrations of DSB IL-33 (IMDM-treated IL33-01) were used to stimulate Huvecs according to the protocol described above in the presence or absence of RAGE-Fc (R&D Systems #1145-RG), ST2-Fc (R&D Systems #523-ST), anti-RAGE mAb (from WO 2008137552) or control reagents. Neutralisation of DSB IL-33 with RAGE-Fc (FIG. 56B), or neutralization of the receptor with anti-RAGE mAb (FIG. 56C) were able to completely inhibit the pSTAT5 signal.

FIG. 56A. Binding of RAGE-Fc to reduced IL-33 or DSB plate surface by ELISA, wherein the x-axis shows the RAGE-Fc concentration and the y-axis shows the absorbance@450 nM. Data showed increased binding of RAGE to DSB IL-33 compared with reduced IL-33.

FIG. 56B shows the pSTAT5 response to DSB IL-33 in Huvec in the presence of RAGE-Fc (50 ug/mL), ST2-Fc (50 ug/mL) or anti-NIP IgG1 negative control antibody, NIP228 (50 ug/mL). pSTAT5 signaling was completely inhibited by RAGE-Fc but not ST2-Fc or NIP228.

FIG. 56C shows the pSTAT5 response to DSB IL-33 in Huvec in the presence of anti-RAGE mAb, m4F4 (10 ug/mL), or mouse IgG1 negative control antibody (10 ug/mL). pSTAT5 signaling was completely inhibited by m4F4 but not control mAb.

Prevention of DSB IL-33 Activity with Anti-IL-33 Antibodies

As described in Example 8, antibodies that bind IL-33 may prevent oxidation of IL-33 to the DSB form (FIG. 43A). The ability of IL-33 antibodies to prevent pSTAT5 signaling in Huvecs was evaluated.

Fixed concentrations of 33_640087-7B (SEQ ID Nos 616 and 618), Anti-ST2 (from WO 2013/173761 Ab2; SEQ ID 85 and SEQ ID 19) and isotype control mAbs were prepared in IMDM and then combined (100 uL with 100 uL) with a titration of WT IL-33 (also prepared in IMDM) in 96 well U-bottom plates. Plates were incubated at 37° C. and 5% CO2 overnight. 75 uL from each well of these 'preincubation treatment' plates was added to 'starved' cells prepared as described above for pSTAT5 assay and incubated at 37° C. for 15 mins. Cells were then washed twice in ice cold PBS and 100 uL Lysis Buffer from the eBioscience Phospho-STAT5A/B Instant One ELISA (eBioscience #85-86112-11) was added to each well. pSTAT5 activity in cell lysates was then measured according to manufacturers instructions.

Figure 57:
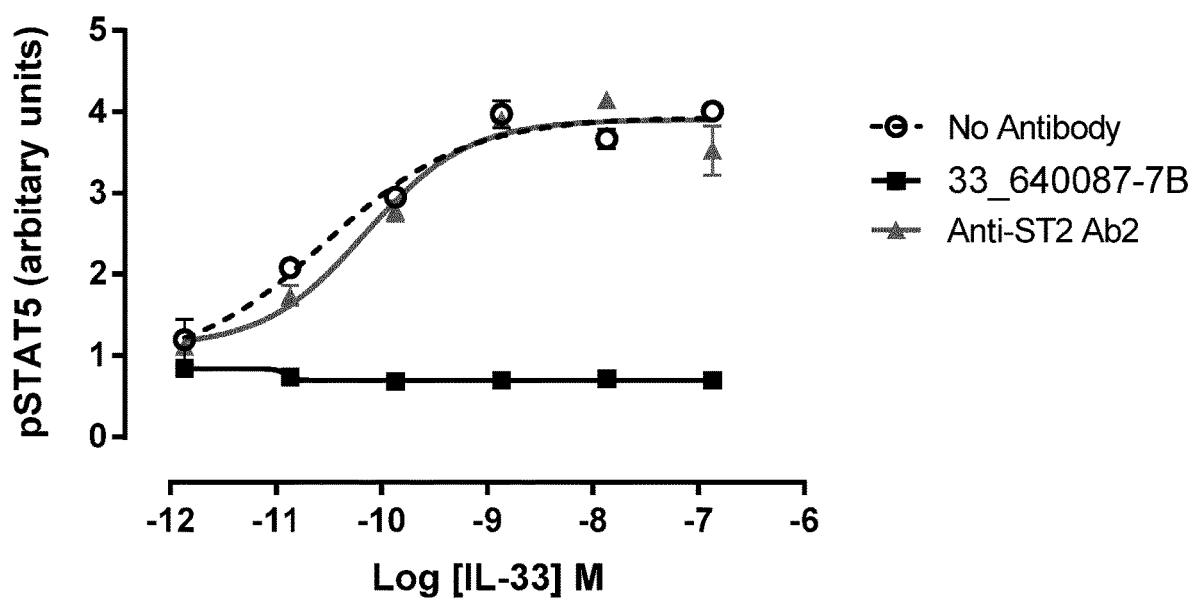
FIG. 57 Shows the effect of anti-IL-33 versus anti-ST2 on the pSTAT5 response in Huvecs.

FIG. 57 shows the pSTAT5 response in Huvecs to IL-33 treated with IMDM in the presence of 33_640087-7B (10 ug/mL) or Anti-ST2 mAb, Ab2, (10 ug/mL), wherein the x-axis is the concentration of IL-33 and the y axis is the pSTAT5 signal. pSTAT5 signaling was completely inhibited by 33_640087-7B but not anti-ST2, confirming that this response is ST2-independent.

Anti-IL-33 Antibodies Inhibit RAGE-Dependent Response in Epithelial Cells

RAGE is expressed highly in lung epithelial cells. Lung epithelial cell lines were evaluated for DSB IL-33 dependent responses. To this purpose, A549 cells were cultured in F12K Media (Gibco #21127022) supplemented with 1% Penicillin/Streptomycin and 10% FBS. Cells were harvested with 0.5% Trypsin-EDTA (Gibco, #15400-054), washed and seeded in 96 well plates at 1×10$^5$/cells/well in culture media. Cells were then were incubated at 37° C., 5% CO$_2$ for 24 hours. The following day complete media was removed, cells were washed twice in PBS and media replaced with 'starve' media (F12K media with 1% Pen/Strep) and plates incubated for 24 hours at 37° C. and 5% $CO_2$.

Fixed concentrations of 33_640087-7B (SEQ ID Nos 616 and 618), Anti-ST2 (WO 2013/173761 Ab2 (SEQ ID 85 and SEQ ID 19)), anti-RAGE m4F4 (from WO 2008137552) and isotype control mAbs were prepared in IMDM and then combined (100 uL with 100 uL) with WT IL-33 (also prepared in IMDM) in 96 well U-bottom plates. Both cell and treatment plates were incubated at 37° C. and 5% $CO_2$ overnight. 75 uL from each well of these 'preincubation treatment' plates was added to 'starved' cells prepared as described above and plates incubated for 24 hours at 37° C. and 5% $CO_2$. The 96 well transwell system (Corning # CLS3422-48EA) is then set up by adding a 96 well transwell plate to a low binding 96 well receiver plate. 235 uL of complete media (F12K media supplemented with 10% FBS and 1% Pen/Strep) was added to the bottom chamber of the transwell system. Each well of the 96 well treated A549 cells were then washed in PBS, trypsinised to detach, centrifuged at 1000 rpm for 5 min, resuspended in 75 uL 'starve' media and added to the top chamber of the transwell system. The transwell plate was then incubated at 37° C., 5% $CO_2$ for 16 hours. Media was then removed from both top and bottom chambers and cells removed from the bottom chamber using 235 uL trypsin. 100 uL of the trypsin/cell suspension was then added to 100 uL of Cell Titer Glo (Promega # G7571). A titration of fresh A549 cells is prepared in trypsin and added 50:50 to Cell Titer Glo to create a standard curve of cell number. Plates were then incubated and read according to manufacturer's instructions.

FIG. 58A shows the migration of A549 cells after treatment with IL33-01 incubated in the presence of 33_640087-7B (10 ug/mL), Anti-ST2 mAb, Ab2, (10 ug/mL), or anti-RAGE mAb 4F4, wherein the x-axis shows the cell pre-treatment condition and the y axis is the number of cells migrated. Data demonstrate that pre-treatment of A549 cells with DSB IL-33 reduces subsequent cell migration. This inhibition of migration was reversed by anti-RAGE mAb and 33_640087-7B but not by anti-ST2.

FIG. 58B shows the migration of A549 cells after treatment with DSB IL33-01 incubated in the presence of 33_640087-7B (10 ug/mL) or Anti-ST2 mAb, Ab2, (10 ug/mL, wherein the x-axis shows the cell pre-treatment condition and the y axis is the number of cells migrated. Data demonstrate that pre-treatment of A549 cells with DSB IL-33 reduces subsequent cell migration. This inhibition of migration was not reversed by 33_640087-7B or anti-ST2

Together, these data confirm that 33_640087-7B inhibits DSB-IL_33 activity by preventing the conversion of reduced IL-33 to DSB IL-33 rather than neutralizing DSB IL-33 directly, consistent with its ability to bind only the reduced, ST2-active form of IL-33.

What is claimed is:

1. An isolated antibody or antigen-binding fragment thereof which specifically binds to IL-33, comprising a VHCDR1 having the sequence of SEQ ID NO: 183, a VHCDR2 having the sequence of SEQ ID NO: 184, a VHCDR3 having the sequence of SEQ ID NO: 185, a VLCDR1 having the sequence of SEQ ID NO: 188, a VLCDR2 having the sequence of SEQ ID NO: 189, and a VLCDR3 having the sequence of SEQ ID NO: 190.

2. The isolated antibody or antigen-binding fragment thereof of claim 1, wherein the VH and VL of said antibody or antigen-binding fragment thereof comprise amino acid sequences at least 95%, 90%, or 85% identical to SEQ ID NO: 182 and SEQ ID NO: 187, respectively.

3. The antibody or antigen-binding fragment thereof according to claim 2, comprising a VH having the sequence of SEQ ID NO: 182 and a VL having the sequence of SEQ ID NO: 187.

4. An isolated antibody or antigen-binding fragment thereof which specifically binds to IL 33, comprising a VHCDR1 having the sequence of SEQ ID NO: 543, a VHCDR2 having the sequence of SEQ ID NO: 544, a VHCDR3 having the sequence of SEQ ID NO: 545, a VLCDR1 having the sequence of SEQ ID NO: 548, a VLCDR2 having the sequence of SEQ ID NO: 549, and a VLCDR3 having the sequence of SEQ ID NO: 550.

5. An isolated antibody or antigen-binding fragment thereof according to claim 4 which specifically binds to IL-33, wherein the VH and VL of said antibody or antigen-binding fragment thereof comprise amino acid sequences at least 95%, 90%, or 85% identical to SEQ ID NO: 542 and SEQ ID NO: 547, respectively.

6. The antibody or antigen-binding fragment thereof according to claim 5, comprising a VH having the sequence of SEQ ID NO: 542 and a VL having the sequence of SEQ ID NO: 547.

7. The antibody or antigen-binding fragment thereof according to claim 4, comprising a VH having the sequence of SEQ ID NO: 616 and a VL having the sequence of SEQ ID NO: 618.

8. The antibody of either of claim 1 or 4 or an antigen-binding fragment thereof, which is selected from the group consisting of a human antibody, a chimeric antibody, and a humanized antibody.

9. The antibody of either of claim 1 or 4 or an antigen-binding fragment thereof, which is selected from the group consisting of a naturally-occurring antibody, an scFv fragment, an Fab fragment, an F(ab')2 fragment, a minibody, a diabody, a triabody, a tetrabody, and a single chain antibody.

10. The antibody of either of claim 1 or 4, or an antigen-binding fragment thereof, which is a monoclonal antibody.

11. A pharmaceutical composition comprising the antibody of either of claim 1 or 4 or an antigen-binding fragment thereof and a carrier.

12. A combination product comprising the antibody of either of claim 1 or 4 or an antigen-binding fragment thereof and a second therapeutic agent.

13. A method for detecting reduced IL-33 expression in a sample comprising:
   (a) isolating a cell-containing sample;
   (b) contacting said sample with the antibody of either of claim 1 or 4, or an antigen-binding fragment thereof; and
   (c) detecting binding of said binding molecule in said sample.

\* \* \* \* \*